United States Patent
Charrier et al.

(10) Patent No.: US 8,410,112 B2
(45) Date of Patent: Apr. 2, 2013

(54) COMPOUNDS USEFUL AS INHIBITORS OF ATR KINASE

(75) Inventors: Jean-Damien Charrier, Wantage (GB); Steven John Durrant, Abingdon (GB); David Kay, Purton (GB); Michael O'Donnell, Abingdon (GB); Ronald Marcellus Alphonsus Knegtel, Abingdon (GB); Somhairle MacCormick, Reading (GB); Joanne Pinder, Didcot (GB); Stephen Clinton Young, Oxford (GB); Hayley Marie Binch, Encinitas, CA (US); Thomas Cleveland, San Diego, CA (US); Lev Tyler Dewey Fanning, San Marcos, CA (US); Dennis James Hurley, San Marcos, CA (US); Pramod Joshi, San Diego, CA (US); Urvi Jagdishbhai Sheth, San Diego, CA (US); Alina Silina, San Diego, CA (US); Philip Michael Reaper, Shillingford (GB); Anisa Nizarali Virani, Thatcham (GB)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 0 days.

(21) Appl. No.: 13/104,291

(22) Filed: Oct. 27, 2011

(65) Prior Publication Data
US 2012/0040020 A1 Feb. 16, 2012

Related U.S. Application Data

(63) Continuation of application No. PCT/US2009/063922, filed on Nov. 10, 2009.

(60) Provisional application No. 61/163,655, filed on Mar. 26, 2009, provisional application No. 61/146,463, filed on Jan. 22, 2009, provisional application No. 61/114,204, filed on Nov. 13, 2008, provisional application No. 61/112,906, filed on Nov. 10, 2008.

(51) Int. Cl.
*A61K 31/4965* (2006.01)
*C07D 403/00* (2006.01)

(52) U.S. Cl. ............... 514/255.05; 514/255.06; 544/405
(58) Field of Classification Search ............. 514/255.05, 514/255.06; 544/405
See application file for complete search history.

(56) References Cited

U.S. PATENT DOCUMENTS

| | | | |
|---|---|---|---|
| 4,309,430 A | 1/1982 | Bock et al. |
| 5,143,824 A | 9/1992 | Yamakawa et al. |
| 6,660,753 B2 | 12/2003 | Van Wagenen et al. |
| 6,858,600 B2 | 2/2005 | Hamilton et al. |
| 6,992,087 B2 | 1/2006 | Verhoest et al. |
| 7,041,672 B2 | 5/2006 | Verhoest et al. |
| 7,199,123 B2 | 4/2007 | Munchhof |
| 7,452,993 B2 | 11/2008 | Arnold et al. |
| 7,622,583 B2 | 11/2009 | Ungashe et al. |
| 7,626,021 B2 | 12/2009 | Arnold et al. |
| 7,704,995 B2 | 4/2010 | Buhr et al. |
| 7,829,558 B2 | 11/2010 | Arnold et al. |
| 7,872,031 B2 | 1/2011 | Lauffer et al. |
| 7,902,197 B2 | 3/2011 | Elworthy et al. |
| 7,932,254 B2 | 4/2011 | DuBois et al. |
| 7,939,531 B2 | 5/2011 | Bamberg et al. |
| 8,063,032 B2 | 11/2011 | Chytil et al. |
| 2003/0008882 A1 | 1/2003 | Hamilton et al. |
| 2003/0055085 A1 | 3/2003 | Wagenen et al. |
| 2004/0034037 A1 | 2/2004 | Harbeson et al. |
| 2004/0180905 A1 | 9/2004 | Munchhof |
| 2006/0211709 A1 | 9/2006 | Buhr et al. |
| 2007/0037794 A1 | 2/2007 | Ungashe et al. |
| 2007/0254868 A1 | 11/2007 | Lauffer et al. |
| 2007/0270420 A1 | 11/2007 | Harbeson et al. |
| 2007/0287711 A1 | 12/2007 | Arnold et al. |
| 2009/0005381 A1 | 1/2009 | Brown et al. |
| 2009/0215724 A1 | 8/2009 | DuBois et al. |
| 2009/0215750 A1 | 8/2009 | Bamberg et al. |
| 2009/0215785 A1 | 8/2009 | DuBois et al. |
| 2009/0215788 A1 | 8/2009 | Elworthy et al. |
| 2009/0306087 A1 | 12/2009 | Ibrahim et al. |

(Continued)

FOREIGN PATENT DOCUMENTS

| EP | 313724 A2 | 5/1989 |
|---|---|---|
| EP | 1217000 A1 | 6/2002 |

(Continued)

OTHER PUBLICATIONS

Ammar, et al., "3-Ethoxycarbonylmethylenequinoxalin-2-one in Heterocyclic Synthesis. Part 1: Synthesis of New Substituted and Condensed Quinoxalines", Afinidad (2005), 62, pp. 151-160.

(Continued)

*Primary Examiner* — Erich A Leeser
(74) *Attorney, Agent, or Firm* — Jennifer G. Che

(57) ABSTRACT

The present disclosure relates to pyrazine compounds of formula I:

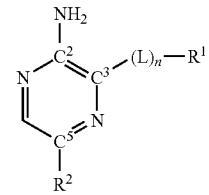

wherein L, n, $R^1$, and $R^2$ are as described in the specification. These compounds are useful as inhibitors of ATR protein kinase. The disclosure also relates to pharmaceutically acceptable compositions comprising the compounds of the disclosure; methods of treating of various diseases, disorders, and conditions using the compounds of the disclosure; processes for preparing the compounds of the disclosure; intermediates for the preparation of the compounds of the disclosure; and methods of using the compounds in in vitro applications, such as the study of kinases in biological and pathological phenomena; the study of intracellular signal transduction pathways mediated by such kinases; and the comparative evaluation of new kinase inhibitors.

71 Claims, 1 Drawing Sheet

U.S. PATENT DOCUMENTS

| | | | |
|---|---|---|---|
| 2010/0036118 A1 | 2/2010 | Arnold et al. |
| 2010/0168138 A1 | 7/2010 | DeGoey et al. |
| 2010/0204214 A1 | 8/2010 | Chytil et al. |
| 2010/0222318 A1 | 9/2010 | Charrier et al. |
| 2010/0233091 A1 | 9/2010 | Neumann et al. |
| 2011/0015231 A1 | 1/2011 | Al-Abed et al. |
| 2012/0027874 A1 | 2/2012 | Charrier et al. |
| 2012/0035407 A1 | 2/2012 | Charrier et al. |
| 2012/0035408 A1 | 2/2012 | Charrier et al. |
| 2012/0065247 A1 | 3/2012 | Thompson et al. |
| 2012/0115874 A1 | 5/2012 | Wang et al. |
| 2012/0122884 A1 | 5/2012 | Charrier et al. |
| 2012/0177748 A1 | 7/2012 | Charrier et al. |
| 2012/0178756 A1 | 7/2012 | Charrier et al. |

FOREIGN PATENT DOCUMENTS

| | | | |
|---|---|---|---|
| EP | 2157090 A1 | 2/2010 |
| WO | 9842701 A1 | 10/1998 |
| WO | 0004014 A1 | 1/2000 |
| WO | 0144206 A1 | 6/2001 |
| WO | 0209648 A2 | 2/2002 |
| WO | 03/004475 | * | 1/2003 |
| WO | 03004472 A1 | 1/2003 |
| WO | 03004475 | * | 1/2003 |
| WO | 03004475 A1 | 1/2003 |
| WO | 03045924 A1 | 6/2003 |
| WO | 03076422 A1 | 9/2003 |
| WO | 03080610 A1 | 10/2003 |
| WO | 03087057 A1 | 10/2003 |
| WO | 03092686 A1 | 11/2003 |
| WO | 03093297 A2 | 11/2003 |
| WO | 03101968 A1 | 12/2003 |
| WO | 04000318 A2 | 12/2003 |
| WO | 2004033431 A2 | 4/2004 |
| WO | 2004055005 A1 | 7/2004 |
| WO | 2004055006 A1 | 7/2004 |
| WO | 2004084813 A2 | 10/2004 |
| WO | 2004084824 A2 | 10/2004 |
| WO | 2004085409 A2 | 10/2004 |
| WO | 2004103279 A2 | 12/2004 |
| WO | 2005028475 A2 | 3/2005 |
| WO | 2005079802 A1 | 9/2005 |
| WO | 2005123672 A2 | 12/2005 |
| WO | 2006015124 A2 | 2/2006 |
| WO | 2006053342 A2 | 5/2006 |
| WO | 2006058074 A1 | 6/2006 |
| WO | 2006067462 A1 | 6/2006 |
| WO | 2006071548 A2 | 7/2006 |
| WO | 2006075152 A1 | 7/2006 |
| WO | 2006088837 A2 | 8/2006 |
| WO | 2006114180 A1 | 11/2006 |
| WO | 2006120573 A2 | 11/2006 |
| WO | 2007015632 A1 | 2/2007 |
| WO | 2007058850 A2 | 5/2007 |
| WO | 2007063012 A1 | 6/2007 |
| WO | 2007066805 A1 | 6/2007 |
| WO | 2007076360 A1 | 7/2007 |
| WO | 2007096151 A2 | 8/2007 |
| WO | 2007096764 | 8/2007 |
| WO | 2007096765 A1 | 8/2007 |
| WO | 2007102770 A1 | 9/2007 |
| WO | 2007111904 A2 | 10/2007 |
| WO | 2007126964 A2 | 11/2007 |
| WO | 2007147874 A1 | 12/2007 |
| WO | 2008037477 A1 | 4/2008 |
| WO | 2008038010 A1 | 4/2008 |
| WO | 2008040651 A1 | 4/2008 |
| WO | 2008060907 A2 | 5/2008 |
| WO | 2008071456 A2 | 6/2008 |
| WO | 2008074997 A1 | 6/2008 |
| WO | 2008079291 A2 | 7/2008 |
| WO | 2008079903 A1 | 7/2008 |
| WO | 2008079906 A1 | 7/2008 |
| WO | 2008103277 A2 | 8/2008 |
| WO | 2008106692 A1 | 9/2008 |
| WO | 2008124850 A1 | 10/2008 |
| WO | 2008141065 A1 | 11/2008 |
| WO | 2008144463 A1 | 11/2008 |
| WO | 2008144464 A1 | 11/2008 |
| WO | 2008157191 A2 | 12/2008 |
| WO | 2009007390 A2 | 1/2009 |
| WO | 2009012482 A2 | 1/2009 |
| WO | 2009014637 A2 | 1/2009 |
| WO | 2009016460 A2 | 2/2009 |
| WO | 2009024825 A1 | 2/2009 |
| WO | 2009037247 A1 | 3/2009 |
| WO | 2009053737 A2 | 4/2009 |
| WO | 2009106885 A1 | 9/2009 |
| WO | 2010015803 A1 | 2/2010 |
| WO | 2010048131 A1 | 4/2010 |
| WO | 2010054398 A1 | 5/2010 |
| WO | 2010063634 A1 | 6/2010 |
| WO | 2010068483 A2 | 6/2010 |
| WO | 2010071837 A1 | 6/2010 |
| WO | 2011143399 A1 | 11/2011 |
| WO | 2011143419 A1 | 11/2011 |
| WO | 2011143422 A1 | 11/2011 |
| WO | 2011143423 A2 | 11/2011 |
| WO | 2011143425 A2 | 11/2011 |
| WO | 2011143426 A1 | 11/2011 |

OTHER PUBLICATIONS

Charrier, et al, "Discovery of Potent and Selective Inhibitors of Ataxia Telangiesctasia Mutated and Rad3 Related (ATR) Protein Kinase as Potential Anticancer Agents" J. Med. Chem. (Apr. 14, 2011) 54(7), pp. 2320-2330.

El-Emary, "Synthesis and Biological Activity of Some New Pyrazolo[3,4-b]pyrazines", J. Chin. Chem. Soc. (2006), 53, pp. 391-401.

Fernandes, et al., "Synthesis and Biological Activity of Heterocyclic Derivatives derived from Ethyl-2-hydroxy-quinoxaline-3-carboxylate", J. Indian Chem. Soc. (1986), 63, pp. 427-429.

Hickson, et al., "Identification and Characterization of a Novel and Specific Inhibitor of the Ataxia-Telangiectasia Mutated Kinase ATM", Cancer Research (2004), 64, pp. 9152-9159.

Hilton, et al., "Identification and characterisation of 2-aminopyridine inhibitors of checkpoint kinase 2", Bioorg. Med. Chem., (2010) 18, pp. 707-718.

Klicnar, et al., "Studien in der Chinoxalinreihe III. Syntheses, Reaktionen und ir-spektren einiger 3-hydroxy-2-carboxymethylchinoxalin-derivative", Collection Czechoslav. Chem. Commun. (1965), 30, pp. 3092-3101.

Kim, et al., "Substrate Specificities and Identification of Putative Substrates of ATM Kinase Family Members", J. Biol. Chem. (1999) 274, pp. 37538-37543.

Kurasawa, et al., "Revised Structure for the Product from the Reaction of 3-Hydrazinocarbonylmethylene-2-oxo-1,2,3,4-tetrahydroquinoxaline with Nitrous Acid", Chem. Pharm. Bull. (1984), 32(10), pp. 4140-4143.

Reaper, et al, "Selective Killing of ATM- or p53-deficient cancer cells through inhibition of ATR" Nature Communications (2011), 7, pp. 428-430.

Sarkaria, et al., "Inhibition of ATM and ATR Kinase Activities by the Radiosensitizing Agent, Caffeine", Cancer Research (1999) 59, pp. 4375-4382.

Sugimoto, et al., "Imidazopteridines. I. Synthesis of Imidazo[1,2-c]pteridine and its Alkyl Derivatives", Bull. Chem. Soc. Japan (1977) 50(10), pp. 2744-2747.

Ward and Chen, "Histone H2AX is Phosphorylated in an ATR-dependent Manner in Response to Replicational Stress", J. Biol. Chem. (2001), 51, pp. 47759-47762.

Charrier, JD, "Discovery of potent and selective inhibitors of Ataxia Telangiectasia mutated and Rad3 related (ATR) protein kinase as potential anticancer agents", Presentation, ACS Denver 2011, Aug. 28, 2011.

Charrier, Jean-Damien et al., "Discovery of Potent and Selective Inhibitors of Ataxia Telangiectasia Mutated and Rad3 Related (ATR) Protein Kinase as Potential Anticancer Agents", Journal of Medicinal Chemistry, Mar. 17, 2011, 54, pp. 2320-2330.

Charrier, Jean-Damien et al., "Discovery of Potent and Selective Inhibitors of ATR (Ataxia Telangiectasia Mutated and Rad3 Related) as Potential Anticancer Agents", Supplementary Information, Apr. 14, 2011.

McKenna, Gillies et al., "Evaluation of the first potent and highly selective inhibitor of ATR kinase: an approach to selectively sensitize cancer cells to ionizing radiation and hypoxia", Abstract, Mar. 31, 2012.

McKenna, Gillies et al., "Evaluation of the first potent and highly selective ATR inhibitor, VE-821: an approach to selectively sensitize cancer cells to ionizing radiation and hypoxia", Poster, Mar. 31, 2012.

Pires, IM et al., "Targeting radiation-resistant hypoxic tumour cells through ATR inhibition", British Journal of Cancer, Jun. 19, 2012, pp. 1-9.

Pollard, John, "Inhibition of the DNA Damage Response Kinase, ATR, as a Promising Anti-Cancer Approach", Presentation, Mar. 8, 2012.

Reaper, Philip M. et al., "Selective killing of ATM- or p53-deficient cancer cells through inhibition of ATR", Supplementary Information, Apr. 13, 2011.

Reaper, Philip M. et al., "Selective killing of ATM- or p53-deficient cancer cells through inhibition of ATR", Nature Chemical Biology, Apr. 13, 2011, pp. 1-3.

Reaper, Philip M. et al., "Selective killing of ATM- or p53-deficient cancer cells through inhibition of ATR", Presentation, Nov. 21, 2011.

Reaper, Philip M. et al., "Selective killing of ATM- or p53-deficient cancer cells through inhibition of ATR", Presentation, Nov. 29, 2011.

Reaper, Philip M. et al., "Evaluation of a potent and highly selective inhibitor of ATR kinase: an approach to selectively sensitize cancer cells to genotoxic drugs", Abstract, Mar. 31, 2012.

Reaper, Philip M. et al., "Evaluation of a Potent and Highly Selective Inhibitor of ATR Kinase: An Approach to Selectively Sensitize Cancer Cells to Genotoxic Drugs", Poster, Mar. 31, 2012.

Fokas, E. et al., "Targeting ATR in vivo using the novel inhibitor VE-822 results in selective sensitization of pancreatic tumors to radiation", Cell Death and Disease (2012), 3, pp. 1-5.

* cited by examiner

Below is a pictorial representation illustrating the position of the hydrogen bond acceptor of J. The hydrogen bond acceptor is located in a sphere wherein the center of the sphere is located 6Å from $C^5$ on the line defined by the $C^2$-$C^5$ axis in the direction away from $C^2$ and the radius of the sphere is 4Å.

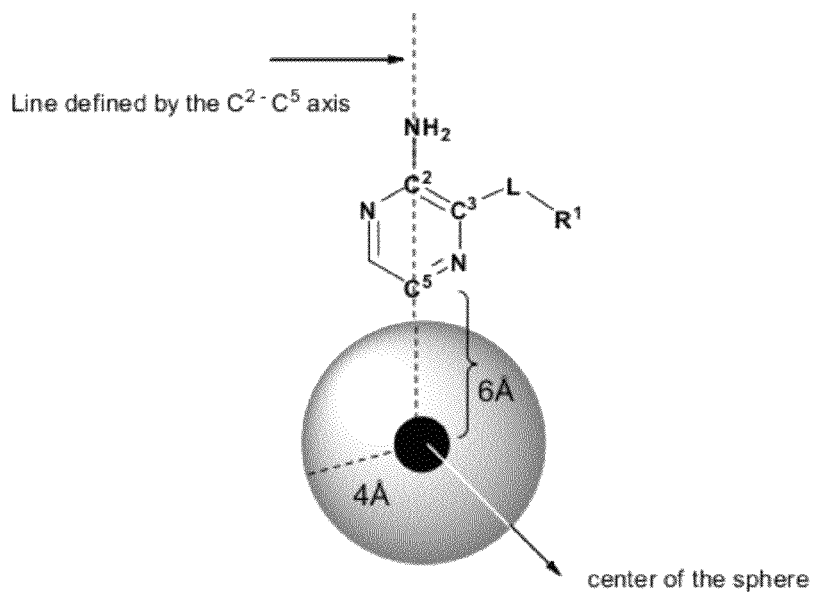

*note: structure may not be drawn to actual relative scale*

COMPOUNDS USEFUL AS INHIBITORS OF ATR KINASE

BACKGROUND OF THE INVENTION

ATR ("ATM and Rad3 related") kinase is a protein kinase involved in cellular responses to DNA damage. ATR kinase acts with ATM ("ataxia telangiectasia mutated") kinase and many other proteins to regulate a cell's response to DNA damage, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinase ATR. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR. In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells. In fact, ATR inhibition has been shown to be effective in cancer cells as single agents and as potent sensitizers to radiotherapy and genotoxic chemotherapy.

Additionally, ATR is also implicated in other diseases, such as HIV1: (see Ward et al, 2009 PLOS Pathogens 5:e1000613, Lai et al, 2005 J Virol 79:1544, and Daniel et al 2003 PNAS 100:4778); Hepatitis B (see e.g., Zhao et al, 2008 World J Gastroenterol 14:6163, Wang et al 2008 JBC 283:25455); Adenovirus (see e.g., Nichols et al, 2009 J Virol 83: 5987), and Psoriasis (see e.g., Derheimer et al., 2009 Mol Pharmacol 75:599).

Accordingly, there is a need for the development of potent and selective ATR inhibitors to treat these diseases. More specifically, there is a need for the development of potent and selective ATR inhibitors for the treatment of cancer, either as single agents or as combination therapies with radiotherapy or genotoxic chemotherapy.

BRIEF DESCRIPTION OF THE DRAWINGS

FIG. 1

FIG. 1 is a pictorial representation illustrating the position of the hydrogen bond acceptor of J. The hydrogen bond acceptor is located in a sphere wherein the center of the sphere is located 6 Å from $C^5$ on the line defined by the $C^2$-$C^5$ axis in the direction away from $C^2$ and the radius of the sphere is 4 Å.

SUMMARY OF THE INVENTION

The present invention relates to pyrazine compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of this invention have formula I:

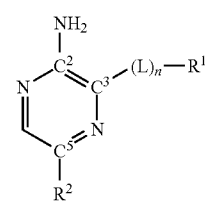

I wherein the variables are as defined herein.

DETAILED DESCRIPTION OF THE INVENTION

One aspect of this invention provides a compound of formula I:

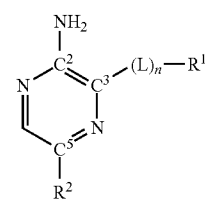

I or a pharmaceutically acceptable salt thereof wherein:

$R^1$ is a 5-6 membered monocyclic aryl or heteroaryl ring having 0-3 heteroatoms independently selected from nitrogen, oxygen, or sulfur; wherein said monocyclic aryl or heteroaryl ring is optionally fused to another ring to form a 8-10 membered bicyclic aryl or heteroaryl ring having 0-4 heteroatoms independently selected from nitrogen, oxygen, or sulfur; $R^1$ is optionally substituted with 1-5 $J^1$ groups;

$C^2$, $C^3$ and $C^5$ are carbon;

$R^2$ is -Q or -Q-$Q^1$;

Q is a 3-7 membered monocyclic saturated or partially unsaturated non-aromatic ring having 0-4 heteroatoms independently selected from nitrogen, oxygen, or sulfur; Q can be optionally fused to $Q^1$; each Q is independently and optionally substituted with 1-4 $J^Q$ groups; Q is substituted with one to two occurrences of J or contains J as a ring member;

$Q^1$ is a 5-8 membered monocyclic saturated or unsaturated ring having 0-4 heteroatoms independently selected from nitrogen, oxygen, or sulfur; each $Q^1$ is independently and optionally substituted with 1-4 $J^{Q1}$ groups;

J is fluoro or a moiety containing a hydrogen bond acceptor: wherein the hydrogen bond acceptor is located in a sphere wherein
  a) the center of the sphere is located 6 Å from $C^5$ on the line defined by the $C^2$-$C^5$ axis in the direction away from $C^2$ and b) the radius of the sphere is 4 Å;

L is —C(O)NH—;

n is 0 or 1;

Each $J^1$, $J^Q$, and $J^{Q1}$ is independently halo, —CN, —NO$_2$, V—R, or —(V)$_m$-Q$^2$;

V is a C$_{1-10}$aliphatic chain wherein 0-3 methylene units are optionally replaced with oxygen, nitrogen, sulfur, C(O), S(O), or S(O)$_2$; V is optionally substituted with 1-6 occurrences of $J^V$;

m is 0 or 1;

$Q^2$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^2$ is optionally substituted with 1-5 $J^{Q2}$;

each $J^V$ is independently NH$_2$, NH(C$_{1-4}$aliphatic), N(C$_{1-4}$aliphatic)$_2$, halogen, C$_{1-4}$aliphatic, OH, (C$_{1-4}$aliphatic), NO$_2$, CN, CO$_2$H, CO$_2$ (C$_{1-4}$aliphatic), O(haloC$_{1-4}$aliphatic), or haloC$_{1-4}$aliphatic;

each $J^{Q2}$ is independently halogen, NO$_2$, CN, or C$_{1-6}$aliphatic wherein up to 1 methylene unit is optionally replaced with N(R)$_2$, OR, SR, COR, CO$_2$R, CON(R)$_2$, SOR, SO$_2$R, SO$_2$N(R)$_2$, OCOR, NRCOR, NRCOOR, NRSOR, NRSO$_2$R, NRSO$_2$N(R)$_2$, OCON(R)$_2$, or NRCON(R)$_2$; wherein said C$_{1-6}$aliphatic is optionally substituted with 1-4 substituents selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic;

R is H or C$_{1-4}$alkyl wherein said C$_{1-6}$alkyl is optionally substituted with 1-4 halo.

DESCRIPTION OF FIGURES

FIG. 1: A pictorial representation illustrating the position of the hydrogen bond acceptor of J. The hydrogen bond acceptor is located in a sphere wherein the center of the sphere is located 6 Å from $C^5$ on the line defined by the $C^2$-$C^5$ axis in the direction away from $C^2$ and the radius of the sphere is 4 Å.

In one aspect of the invention, Q is substituted with one occurrence of J. In some embodiments, J is oxo or (V$^1$)—R''; V$^1$ is C$_{1-6}$ aliphatic chain wherein up to three methylene unit of the aliphatic chain may be optionally replaced with —NR'—, —O—, —S—, —C(O)—, —S(O)—, or —S (O)$_2$— wherein the first or second methylene group away from the point of attachment is replaced with CO, SO, SO$_2$, S, or O; R' is H or C$_{1-4}$alkyl; and R'' is H or a 5-6 membered monocyclic ring containing 0-2 heteroatoms selected from O, N, or S; wherein said R'' is optionally substituted with 1-3 occurrences of halo, C$_{1-3}$alkyl, CN, OH, O(C$_{1-3}$alkyl), NH$_2$, NH(C$_{1-3}$alkyl), N(C$_{1-3}$alkyl)$_2$, or acetyl. In some embodiments, up to 2 methylene units of the aliphatic chain are optionally replaced with heteroatom selected from O, N, or S.

In another aspect of the invention, Q contains J as a ring member. In some embodiment, J is selected from sulfur, nitrogen, or oxygen. Examples of such Q rings include, but are not limited to, morpholinyl and thiomorpholinyl.

In some embodiments, n is 1; in other embodiments, n is 0.

In some embodiments, $R^1$ is a monocyclic 6-membered ring, such as phenyl or pyridyl. In other embodiments, $R^1$ is a 5-6 membered monocyclic heteroaryl ring having 1-4 heteroatoms independently selected from nitrogen, oxygen, or sulfur, or a 8-10 membered bicyclic heteroaryl ring having 1-6 heteroatoms independently selected from nitrogen, oxygen, or sulfur; each $R^1$ is optionally substituted with 1-5 $J^1$ groups.

In some embodiments, n is 1 and $R^1$ is a monocyclic 6-membered ring. In some embodiments, said 6-membered ring is phenyl or pyridyl.

In other embodiments, n is 0 and $R^1$ is a 5-6 membered monocyclic heteroaryl ring having 1-4 heteroatoms independently selected from nitrogen, oxygen, or sulfur, or a 8-10 membered bicyclic heteroaryl ring having 1-6 heteroatoms independently selected from nitrogen, oxygen, or sulfur; each $R^1$ is optionally substituted with 1-5 $J^1$ groups. In some embodiments, $R^1$ is a monocyclic 5-membered heteroaryl ring containing 1-3 heteroatoms selected from oxygen, nitrogen, or sulfur; or $R^1$ is a 5-membered heteroaryl ring containing 1-2 heteroatoms selected from oxygen, nitrogen, or sulfur fused to a 6-membered aryl or heteroaryl ring containing 0-4 nitrogen atoms.

In some embodiments, $R^1$ is bonded to $C^3$ via a carbon atom and wherein $R^1$ contains at least one ring heteroatom. In some embodiments, said ring heteroatom (shown as G) is located next to the carbon atom bonded to $C^3$ as shown below in formula II:

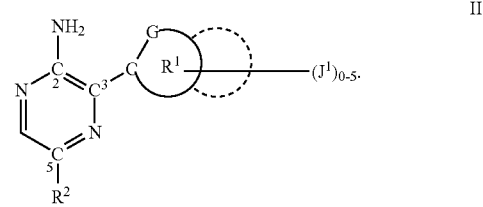

In some embodiments, $R^1$ is a 5-membered ring optionally fused to another ring. In some embodiments, $R^1$ is a monocyclic 5-membered ring containing 1-3 heteroatoms selected from oxygen, nitrogen, or sulfur. In some embodiments, $R^1$ is a 5-membered ring and is selected from the following:

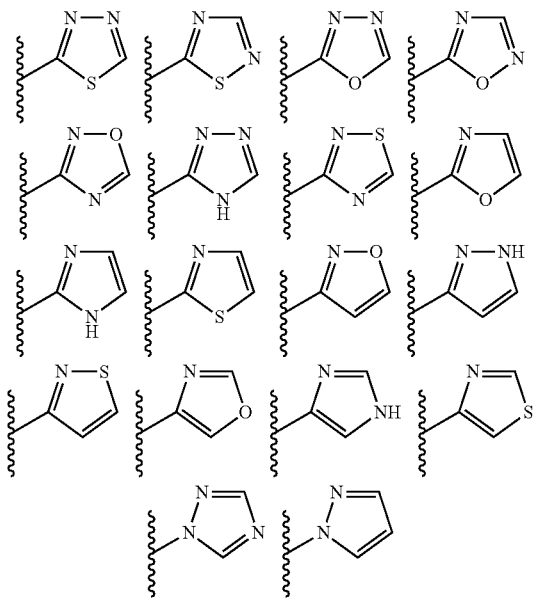

wherein each $R^1$ is optionally substituted with 1-2 occurrences of $J^1$.

In some embodiments, $R^1$ is

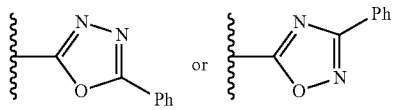

In other embodiments, $R^1$ is a 5-membered ring fused to another ring. In some embodiments, $R^1$ is selected from the following:

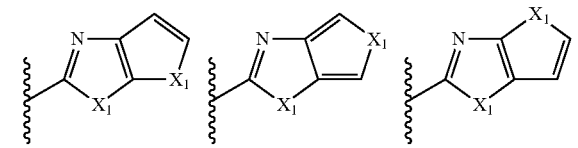

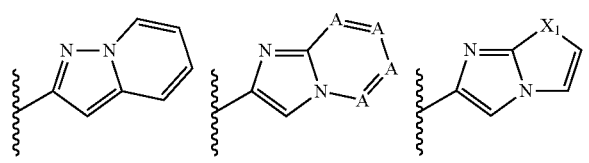

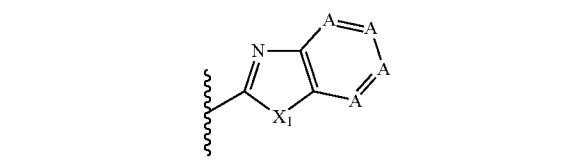

wherein each $R^1$ is optionally substituted with 1-2 occurrences of $J^1$; A is carbon or nitrogen, provided that at least two occurrences of A are carbon; and $X_1$ is O, N, or S. In some embodiments, $R^1$ is

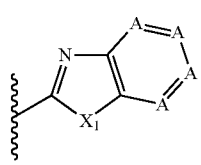

wherein each $R^1$ is optionally substituted with 1-2 occurrences of $J^1$; A is carbon; and $X_1$ is selected from O, N, or S.

In another aspect of this invention, $R^2$ can be -Q or -Q-$Q^1$. In one embodiment, $R^2$ is Q (i.e. monocyclic ring). In some embodiments, Q is a 6 membered ring and can contain 0, 1, or 2 double bonds. In some embodiments, Q is $C_{3-7}$ cycloalkyl, pyrrolidinyl, piperidinyl, piperazinyl, homopiperazinyl, homopiperidinyl, morpholinyl, or thiomorpholinyl. In some embodiments, Q is selected from the following:

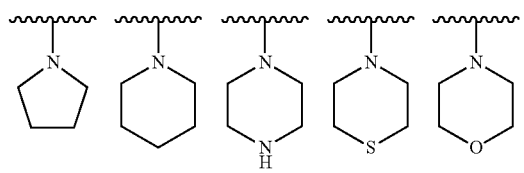

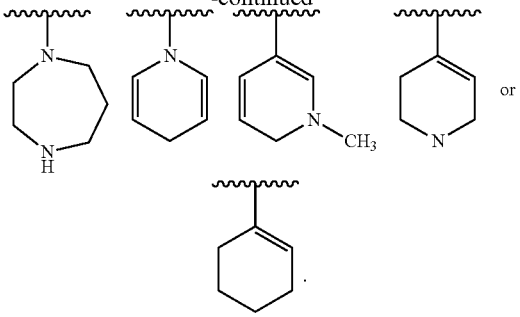

In some embodiments, Q is

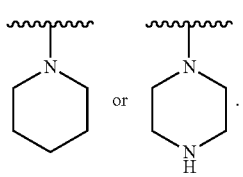 [SMILES: *N1CCCCC1 ; *N1CCNCC1]

In other embodiments, Q is

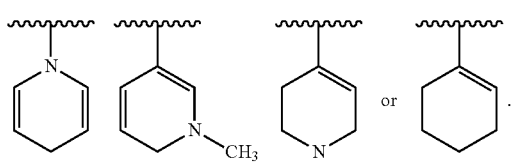

In some embodiments, when J is oxo, $R^2$ is

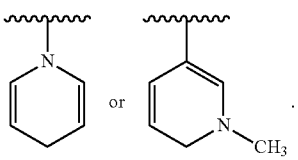

In another aspect of this invention, J is bonded in the position of Q as shown below:

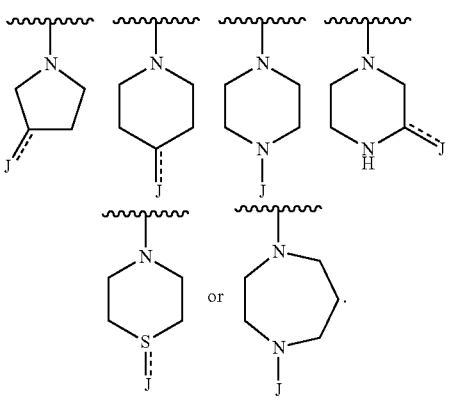

In some embodiments, J is a $C_{1-6}$aliphatic chain wherein up to 2 methylene units of $C_{1-6}$aliphatic are optionally replaced with a heteroatom selected from O, N, or S. In other embodiments, J is selected from oxo, —OH, —O($C_{1-6}$aliphatic), CN, $CH_2CN$, —C(O)($C_{1-6}$aliphatic), —C(O)(phenyl), —C(O)(benzyl), —C(O)$CH_2$O(benzyl), —C(O)(pyridyl), —C(O)(pyrrolidinyl), —C(O)(piperidinyl), —C(O)(piperazinyl), —C(O)(morpholinyl), —C(O)(tetrahydropyranyl), —C(O)O($C_{1-6}$aliphatic), —C(O)O(phenyl), —C(O)O(benzyl), —C(O)$NH_2$, —C(O)NH($C_{1-6}$aliphatic), —C(O)NH($C_{1-6}$aliphatic)$_2$, —C(O)NH(phenyl), —C(O)NH(benzyl), —S(O)$_2$($C_{1-6}$aliphatic), —S(O)$_2$(phenyl), —S(O)$_2$(benzyl), —S(O)$_2$(pyridyl), —S(O)$_2$(furanyl), —S(O)$_2$(imidazole), —S(O)$_2$(thienyl), —S(O)$_2$NH($C_{1-6}$aliphatic), —S(O)$_2$N($C_{1-6}$aliphatic)$_2$, —S(O)$_2$NH(phenyl), —S(O)$_2$NH(benzyl), —NHC(O)($C_{1-6}$aliphatic); wherein said phenyl, benzyl, pyrrolidinyl, piperidinyl, piperazinyl, morpholinyl, tetrahydropyranyl, or $C_{1-6}$aliphatic is optionally substituted with halo, $C_{1-3}$alkyl, CN, OH, O($C_{1-3}$alkyl), $NH_2$, NH($C_{1-3}$alkyl), N($C_{1-3}$ alkyl)$_2$, acetyl. In yet other embodiments, J is selected from, oxo, —OH, —NHC(O)($C_{1-4}$alkyl), —C(O)($C_{1-4}$alkyl), —C(O)$NH_2$, —C(O)NH($C_{1-4}$alkyl), —C(O)NH($C_{1-4}$alkyl)$_2$, —S(O)$_2$($C_{1-4}$alkyl), —S(O)$_2$NH($C_{1-4}$alkyl), or —S(O)$_2$N($C_{1-4}$alkyl)$_2$.

Another embodiment provides a compound of formula I:

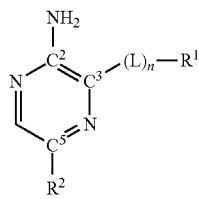

I or a pharmaceutically acceptable salt thereof wherein:
$R^1$ is a 5-6 membered monocyclic aryl or heteroaryl ring having 0-4 heteroatoms independently selected from nitrogen, oxygen, or sulfur; wherein said monocyclic aryl or heteroaryl ring is optionally fused to another ring to form a 8-10 membered bicyclic aryl or heteroaryl ring having 0-6 heteroatoms independently selected from nitrogen, oxygen, or sulfur; $R^1$ is optionally substituted with 1-5 $J^1$ groups;
$C^2$, $C^3$ and $C^5$ are carbon;
$R^2$ is -Q or -Q-$Q^1$;
Q is a 3-7 membered monocyclic saturated or unsaturated non-aromatic ring having 0-4 heteroatoms independently selected from nitrogen, oxygen, or sulfur; each Q is independently and optionally substituted with 1-4 $J^Q$ groups; Q is substituted with zero to two occurrences of J or contains J as a ring member;
Q is optionally fused to $Q^1$ to form a fused bicyclic ring Q-$Q^1$; or Q and $Q^1$ are optionally joined together at a carbon atom to form a spirocyclic bicyclic ring Q-$Q^1$; or Q and $Q^1$, taken together, form a bridged bicyclic ring Q-$Q^1$ wherein said bridge is 1-3 atoms long; Q-$Q^1$ can be optionally substituted with 1-2 J groups; wherein J can be bonded to either Q or $Q^1$;
$Q^1$ is a 3-8 membered monocyclic saturated or unsaturated ring having 0-4 heteroatoms independently selected from nitrogen, oxygen, or sulfur; each $Q^1$ is independently and optionally substituted with 1-4 $J^{Q1}$ groups;
J is fluoro, oxo, or a moiety containing a hydrogen bond acceptor:
  wherein the hydrogen bond acceptor is located in a sphere wherein
  a) the center of the sphere is located 6 Å from $C^5$ on the line defined by the $C^2$-$C^5$ axis in the direction away from $C^2$ and
  b) the radius of the sphere is 4 Å;
L is —C(O)NH— or —C(O)N($C_{1-6}$alkyl)-;
n is 0 or 1;
each $J^Q$ and $J^{Q1}$ is independently halo, oxo, —CN, —$NO_2$, V—R, or —(V)$_m$-$Q^2$;
$J^1$ is halo, —CN, —$NO_2$, V—R, or —($V^2$)$_m$-$Q^3$;
V is a $C_{1-10}$aliphatic chain wherein 0-3 methylene units are optionally and independently replaced with oxygen, nitrogen, sulfur, C(O), S(O), or S(O)$_2$; V is optionally substituted with 1-6 occurrences of $J^V$;
$V^2$ is a $C_{1-10}$aliphatic chain wherein 0-3 methylene units are optionally and independently replaced with oxygen, nitrogen, sulfur, C(O), S(O), or S(O)$_2$; V is optionally substituted with 1-6 occurrences of $J^{V2}$;
m is 0 or 1;
$Q^2$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^2$ is optionally substituted with 1-5 $J^{Q2}$;
$Q^3$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^3$ is optionally substituted with 1-5 $J^{Q3}$;
each $J^V$ and $J^{V2}$ is independently halogen, CN, $NH_2$, $NO_2$, $C_{1-4}$aliphatic, NH($C_{1-4}$aliphatic), N($C_{1-4}$aliphatic)$_2$, OH, O($C_{1-4}$aliphatic), $CO_2$H, $CO_2$($C_{1-4}$aliphatic), C(O)$NH_2$, C(O)NH($C_{1-4}$aliphatic), C(O)N($C_{1-4}$aliphatic)$_2$, NHCO($C_{1-4}$aliphatic), N($C_{1-4}$aliphatic)CO($C_{1-4}$aliphatic), $SO_2$($C_{1-4}$aliphatic), $NHSO_2$($C_{1-4}$aliphatic), or N($C_{1-4}$aliphatic)$SO_2$($C_{1-4}$aliphatic), wherein said $C_{1-4}$aliphatic is optionally substituted with halo;
each $J^{Q2}$ and $J^{Q3}$ is independently halo, oxo, CN, $NO_2$X—R, or —(X)$_p$-$Q^4$,
p is 0 or 1;
X is $C_{1-10}$aliphatic; wherein 1-3 methylene units of said $C_{1-6}$aliphatic are optionally replaced with —NR, —O—, —S—, C(O), S(O)$_2$, or S(O); wherein X is optionally and independently substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2$H, $CO_2$($C_{1-4}$aliphatic), C(O)$NH_2$, C(O)NH($C_{1-4}$aliphatic), C(O)N($C_{1-4}$aliphatic)$_2$, SO($C_{1-4}$aliphatic), $SO_2$($C_{1-4}$aliphatic), $SO_2$NH($C_{1-4}$aliphatic), $SO_2$NH($C_{1-4}$aliphatic), NHC(O)($C_{1-4}$aliphatic), N($C_{1-4}$aliphatic)C(O)($C_{1-4}$aliphatic), wherein said $C_{1-4}$aliphatic is optionally substituted with 1-3 occurrences of halo;
$Q^4$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^4$ is optionally substituted with 1-5 $J^{Q4}$;
$J^{Q4}$ is halo, CN, or $C_{1-4}$alkyl wherein up to 2 methylene units are optionally replaced with O, N,
S, C(O), S(O), or S(O)$_2$;
R is H or $C_{1-4}$alkyl wherein said $C_{1-4}$alkyl is optionally substituted with 1-4 halo.

In some embodiments,
$R^1$ is a 5-6 membered monocyclic aryl or heteroaryl ring having 0-3 heteroatoms independently selected from nitrogen, oxygen, or sulfur; wherein said monocyclic aryl or heteroaryl ring is optionally fused to another ring to form a 8-10 membered bicyclic aryl or heteroaryl ring having 0-4 heteroatoms independently selected from nitrogen, oxygen, or sulfur; $R^1$ is optionally substituted with 1-5 $J^1$ groups;

Q is a 3-7 membered monocyclic saturated or partially unsaturated non-aromatic ring having 0-4 heteroatoms independently selected from nitrogen, oxygen, or sulfur; Q can be optionally fused to $Q^1$; each Q is independently and optionally substituted with 1-4 $J^Q$ groups; Q is substituted with one to two occurrences of J or contains J as a ring member;

$Q^1$ is a 5-8 membered monocyclic saturated or unsaturated ring having 0-4 heteroatoms independently selected from nitrogen, oxygen, or sulfur; each $Q^1$ is independently and optionally substituted with 1-4 $J^{Q1}$ groups;

J is fluoro or a moiety containing a hydrogen bond acceptor;

L is —C(O)NH—;

each $J^Q$ and $J^{Q1}$ is independently halo, —CN, —NO$_2$, V—R, or —(V)$_m$-Q$^2$;

each $J^{Q2}$ and $J^{Q3}$ is independently halogen, NO$_2$, CN, or C$_{1-6}$aliphatic wherein up to 1 methylene unit is optionally replaced with N(R)$_2$, OR, SR, COR, CO$_2$R, CON(R)$_2$, SOR, SO$_2$R, SO$_2$N(R)$_2$, OCOR, NRCOR, NRCOOR, NRSOR, NRSO$_2$R, NRSO$_2$N(R)$_2$, OCON(R)$_2$, or NRCON(R)$_2$; wherein said C$_{1-6}$aliphatic is optionally substituted with 1-4 substituents selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$ (C$_{1-4}$aliphatic), O(haloC$_{1-4}$aliphatic), or haloC$_{1-4}$aliphatic;

each $J^V$ is independently NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$ (C$_{1-4}$aliphatic), O(haloC$_{1-4}$aliphatic), or haloC$_{1-4}$aliphatic.

In other embodiments, J is halo, oxo, —CN, —NO$_2$, V$^1$—R″, or —(V)$_m$—R*. In other embodiments, the moiety containing a hydrogen-bond acceptor is selected from oxo or (V$^1$)—R″.

In some embodiments,

J is oxo or (V$^1$)—R″;

V$^1$ is C$_{1-6}$ aliphatic chain wherein up to three methylene unit of the aliphatic chain may be optionally replaced with —NR′—, —O—, —S—, —C(O)—, —S(O)—, or —S(O)$_2$—; wherein the first or second methylene group away from the point of attachment is replaced with CO, SO, SO$_2$, S, or O;

R′ is H or C$_{1-4}$alkyl;

R″ is H or a 5-6 membered monocyclic ring containing 0-2 heteroatoms selected from O, N, or S; wherein said R″ is optionally substituted with 1-3 occurrences of halo, C$_{1-3}$alkyl, CN, OH, O(C$_{1-3}$alkyl), NH$_2$, NH(C$_{1-3}$alkyl), N(C$_{1-3}$alkyl)$_2$, or acetyl.

In other embodiments, $R^1$ is

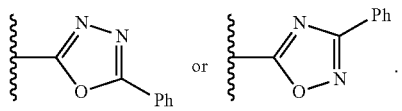 [SMILES: *c1nnc(-c2ccccc2)o1 ; *c1nc(-c2ccccc2)no1]

In some embodiments, Q is C$_{3-7}$ cycloalkyl, pyrrolidinyl, piperidinyl, piperazinyl, homopiperazinyl, homopiperidinyl, morpholinyl, or thiomorpholinyl. In some embodiments, Q is

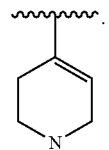 [SMILES: *C1=CCNCC1]

In other embodiments, J is C$_{1-6}$aliphatic chain wherein up to 2 methylene units of C$_{1-6}$aliphatic optionally replaced with heteroatom selected from O, N, or S.

Another embodiment provides a compound of formula Ia:

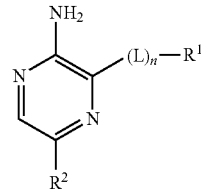

Ia or a pharmaceutically acceptable salt thereof wherein:

$R^1$ is a 5-6 membered monocyclic aryl or heteroaryl ring having 0-4 heteroatoms independently selected from nitrogen, oxygen, or sulfur; wherein said monocyclic aryl or heteroaryl ring is optionally fused to another ring to form a 8-10 membered bicyclic aryl or heteroaryl ring having 0-6 heteroatoms independently selected from nitrogen, oxygen, or sulfur; $R^1$ is optionally substituted with 1-5 $J^1$ groups;

$R^2$ is -Q or -Q-Q$^1$;

Q is a 3-7 membered monocyclic saturated or unsaturated non-aromatic ring having 0-4 heteroatoms independently selected from nitrogen, oxygen, or sulfur; Q is optionally substituted with 1-4 $J^Q$ groups; Q is optionally substituted with 1-2 J groups;

$Q^1$ is a 3-8 membered monocyclic saturated or unsaturated ring having 0-4 heteroatoms independently selected from nitrogen, oxygen, or sulfur; each $Q^1$ is independently and optionally substituted with 1-4 $J^{Q1}$ groups;

Q is optionally fused to $Q^1$ to form a fused bicyclic ring Q-Q$^1$; or Q and $Q^1$ are optionally joined together at a carbon atom to form a spirocyclic bicyclic ring Q-Q$^1$; or Q and $Q^1$, taken together, form a bridged bicyclic ring Q-Q$^1$ wherein said bridge is 1-3 atoms long; Q-Q$^1$ can be optionally substituted with 1-2 J groups; wherein J can be bonded to either Q or $Q^1$;

each $J^Q$ and $J^{Q1}$ is independently halo, oxo, —CN, —NO$_2$, V—R, or —(V)$_m$-Q$^2$;

J is halo, oxo, —CN, —NO$_2$, V$^1$—R″, or —(V)$_m$—R*;

L is —C(O)NH— or —C(O)N(C$_{1-6}$alkyl)-;

n is 0 or 1;

$J^1$ is halo, —CN, —NO$_2$, V—R, or —(V$^2$)$_m$-Q$^3$;

V is a C$_{1-10}$aliphatic chain wherein 0-3 methylene units are optionally replaced with —NR—, —O—, —S—, C(O), S(O), or S(O)$_2$; V is optionally substituted with 1-6 occurrences of $J^V$;

V$^1$ is a C$_{1-10}$aliphatic chain wherein 0-3 methylene units are optionally replaced with —NR′—, —O—, —S—, C(O), S(O), or S(O)$_2$; V$^1$ is optionally substituted with 1-6 occurrences of $J^{V1}$;

V$^2$ is a C$_{1-10}$aliphatic chain wherein 0-3 methylene units are optionally and independently replaced with —NR—, —O—, —S—, C(O), S(O), or S(O)$_2$; V$^2$ is optionally substituted with 1-6 occurrences of J$^{V2}$;

m is 0 or 1;

Q$^2$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each Q$^2$ is optionally substituted with 1-5 J$^{Q2}$;

Q$^3$ is a 3-8 membered saturated or unsaturated monocyclic ring having 0-4 heteroatoms independently selected from nitrogen, oxygen, or sulfur, or a 8-10 membered saturated or unsaturated bicyclic ring having heteroatoms independently selected from nitrogen, oxygen, or sulfur; each Q$^3$ is optionally substituted with 1-5 J$^{Q3}$;

R" is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each R" is optionally substituted with 1-5 J';

each J$^V$, J$^{V1}$, and J$^{V2}$ is independently halogen, CN, NH$_2$, NO$_2$, C$_{1-4}$aliphatic, NH(C$_{1-4}$aliphatic), N(C$_{1-4}$aliphatic)$_2$, OH, O(C$_{1-4}$aliphatic), CO$_2$H, CO$_2$(C$_{1-4}$aliphatic), C(O)NH$_2$, C(O)NH(C$_{1-4}$aliphatic), C(O)N(C$_{1-4}$aliphatic)$_2$, NHCO(C$_{1-4}$aliphatic), N(C$_{1-4}$aliphatic)CO(C$_{1-4}$aliphatic), SO$_2$(C$_{1-4}$aliphatic), NHSO$_2$(C$_{1-4}$aliphatic), or N(C$_{1-4}$aliphatic)SO$_2$(C$_{1-4}$aliphatic), wherein said C$_{1-4}$aliphatic is optionally substituted with halo;

each J$^{Q2}$, J$^{Q3}$, and J' is independently halo, oxo, CN, NO$_2$, X—R, or —(X)$_p$-Q$^4$, p is 0 or 1;

X is a C$_{1-10}$aliphatic; wherein 1-3 methylene units of said C$_{1-6}$aliphatic are optionally replaced with —NR, —O—, —S—, C(O), S(O)$_2$, or S(O); wherein X is optionally and independently substituted with 1-4 occurrences of NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), C(O)NH$_2$, C(O)NH(C$_{1-4}$aliphatic), C(O)N(C$_{1-4}$aliphatic)$_2$, SO(C$_{1-4}$aliphatic), SO$_2$(C$_{1-4}$aliphatic), SO$_2$NH(C$_{1-4}$aliphatic), SO$_2$N(C$_{1-4}$aliphatic)$_2$, NHC(O)(C$_{1-4}$aliphatic), or N(C$_{1-4}$aliphatic)C(O)(C$_{1-4}$aliphatic), wherein said C$_{1-4}$aliphatic is optionally substituted with 1-3 occurrences of halo;

Q$^4$ is a 3-6 membered monocyclic ring containing 0-2 heteroatoms selected from O, N, or S;

each Q$^4$ is optionally substituted with halo, CN, or C$_{1-4}$alkyl wherein up to 2 methylene units are optionally replaced with O, N, S, C(O), S(O), or S(O)$_2$;

each R*, R', and R is independently H or C$_{1-4}$alkyl wherein said C$_{1-4}$alkyl is optionally substituted with 1-4 halo.

In one embodiment, Q is an unsubstituted ring and Q$^1$ does not exist. In some embodiments, Q is pyrrolidinyl or piperidinyl. In some embodiments, each J$^Q$ and J$^{Q1}$ is independently halo, oxo, —CN, —NO$_2$, or V—R.

In some embodiments, Q or Q$^1$ is substituted with 1-2 occurrences of J. In other embodiments, Q or Q$^1$ is substituted with 1 occurrence of J. In other embodiments, Q or Q$^1$ is substituted with zero occurrences of J$^Q$ and J$^{Q1}$ and 1 occurrence of J. In some embodiments, Q-Q$^1$ is substituted with 1 occurrence of J.

In one embodiment, each J is independently oxo, (V$^1$)—R" or —(V)$_m$—R*;

each V and V$^1$ is independently a C$_{1-6}$ aliphatic chain wherein up to three methylene unit of the aliphatic chain may be optionally replaced with —NR'—, —O—, —S—, —C(O)—, —S(O)—, or —S(O)$_2$—; wherein the first or second methylene group away from the point of attachment is replaced with —C(O)—, —S(O)—, —S(O)$_2$—, —S—, or —O—;

each J$^V$ and J$^{V1}$ is independently halo or C$_{1-4}$alkyl;

R' is H or C$_{1-4}$alkyl;

R* is H or C$_{1-4}$alkyl;

R" is a 3-7 membered monocyclic ring containing 0-2 heteroatoms selected from O, N, or S; wherein said R" is optionally substituted with 1-3 occurrences of J';

J' is oxo, halo, C$_{1-3}$alkyl, haloC$_{1-3}$alkyl, CN, OH, O(C$_{1-3}$alkyl), NH$_2$, NH(C$_{1-3}$alkyl), N(C$_{1-3}$alkyl)$_2$, or acetyl.

In some embodiments, Q contains sulfur, nitrogen, or oxygen as a ring member. In some embodiments, Q contains nitrogen as a ring member. In some embodiments, said nitrogen of Q is substituted with one occurrence of J$^Q$; wherein J$^Q$ is phenyl, pyridyl, pyrimidyl, thiazolyl, C$_{1-6}$aliphatic, or benzyl; and wherein J$^Q$ is optionally substituted with 1-3 occurrences of J$^{Q2}$; and J$^{Q2}$ is halo, haloC$_{1-6}$aliphatic, CN, NO$_2$, or C$_{1-6}$aliphatic, wherein 1-3 methylene units of said C$_{1-6}$aliphatic are optionally replaced with —NH—, —O—, —S—, C(O), S(O)$_2$, or S(O).

One aspect provides compounds wherein n is 1.

In some embodiments, R$^1$ is a bicyclic ring, according to some embodiments, said bicyclic ring is a 8-9 membered ring. In other embodiments, said ring is a 8-9 membered heteroaryl containing 1-4 heteroatoms selected from O, N, or S. In yet other embodiments, said ring is selected from benzimidazolyl, benzoxazolyl, indazolyl, benzothiazolyl, indolyl, benzotriazolyl, pyrrolopyridyl, imidazopyridyl, or triazolopyridyl. In other embodiments, said ring is a 8-9 membered heteroaryl containing 1-4 nitrogen atoms. In some embodiments, said ring is selected from benzimidazolyl or indazolyl.

In other embodiments, R$^1$ is a monocyclic 5-6-membered ring. In some embodiments, R$^1$ is pyrazolyl, phenyl, pyridyl, or pyrazinyl. In other embodiments, R$^1$ is 2-pyridyl, 3-pyridyl, or 4-pyridyl.

Another aspect provides compounds wherein n is 0. In some embodiments, R$^1$ is a 5-6 membered monocyclic heteroaryl ring having 1-4 heteroatoms independently selected from nitrogen, oxygen, or sulfur, or a 8-10 membered bicyclic heteroaryl ring having 1-6 heteroatoms independently selected from nitrogen, oxygen, or sulfur; each R$^1$ is optionally substituted with 1-5 J$^1$ groups.

In some embodiments, R$^1$ is a 6-membered monocyclic ring selected from pyrimidyl or pyridyl. In other embodiments, R$^1$ is a monocyclic 5-membered heteroaryl ring containing 1-3 heteroatoms selected from oxygen, nitrogen, or sulfur; or R$^1$ is a 5-membered heteroaryl ring containing 1-2 heteroatoms selected from oxygen, nitrogen, or sulfur fused to a 6-membered aryl or heteroaryl ring containing 0-4 nitrogen atoms. In some embodiments, R$^1$ is bonded to C$^3$ via a carbon atom and wherein R$^1$ contains at least one ring heteroatom.

According to one embodiment, said ring heteroatom (shown as G) is located next to the carbon atom bonded to $C^3$ as shown below in formula II:

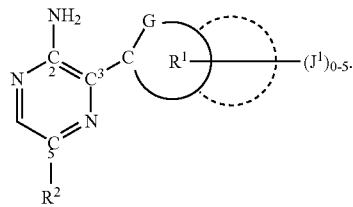

II

In some embodiments, $R^1$ is a 5-membered ring optionally fused to another ring.

In other embodiments, $R^1$ is a monocyclic 5-membered ring containing 1-3 heteroatoms selected from oxygen, nitrogen, or sulfur.

In some embodiments, $R^1$ is a 5-membered ring and is selected from the following:

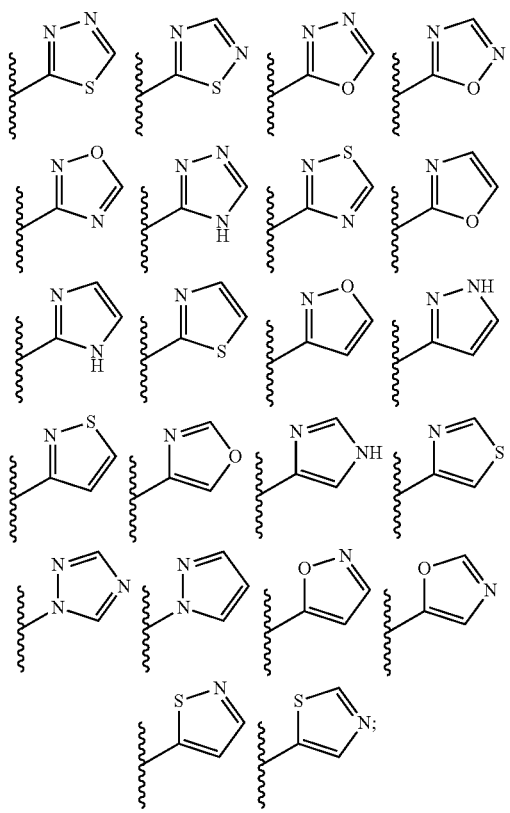

wherein each $R^1$ is optionally substituted with 1-2 occurrences of $J^1$.

In other embodiments, $R^1$ is selected from the following:

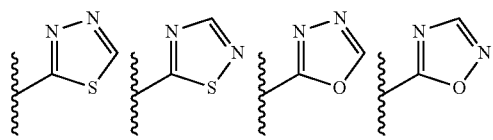

-continued

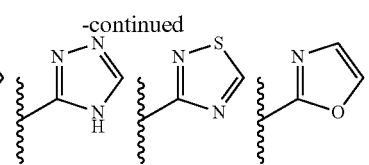

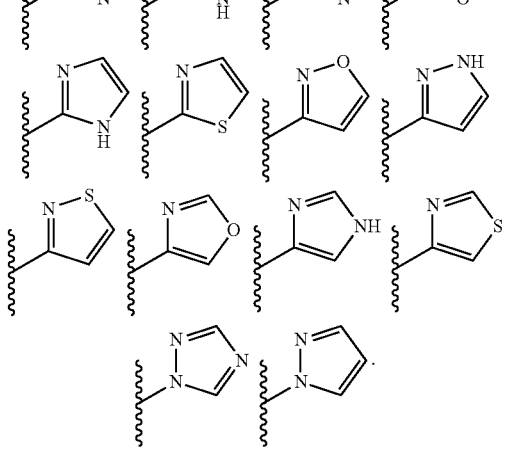

In some embodiments, $R^1$ is

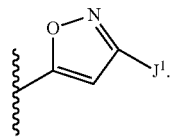

In other embodiments, $R^1$ is

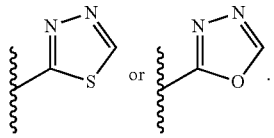 [SMILES: *c1nncs1 ; *c1nnco1]

In yet other embodiments, $R^1$ is

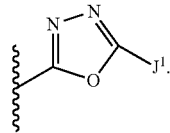

In some embodiments, $J^1$ is $C_{1-4}$alkyl, cyclohexyl, phenyl, thienyl, furanyl, or NH-phenyl. In certain embodiments, $J^1$ is phenyl.

In some embodiments, the phenyl of $J^1$ is optionally substituted with 1-3 occurrences of $J^{Q3}$; wherein $J^{Q3}$ is selected from halo, CN, $NO_2$, X—R, or —$(X)_p$-$Q^4$; p is 0-1; and X is a $C_{1-10}$-aliphatic; wherein 1-3 methylene units of said $C_{1-6}$aliphatic are optionally replaced with —NR—, —O—, —S—, C(O), $S(O)_2$, or S(O); R is H; and $Q^4$ is a 3-6 membered monocyclic ring containing 0-2 heteroatoms selected from O or N, wherein X is optionally substituted with 1-3 occurrences of halo or CN.

In some embodiments, $J^{Q3}$ is a $C_{1-10}$aliphatic chain wherein 1-2 methylene units of X are replaced with —O— or —NR—. In some embodiments, $Q^4$ is a 3-6 membered cycloaliphatic ring. In some embodiments, $Q^4$ is cyclopropyl.

In another embodiment, $J^{Q3}$ is halo, OH, $NH_2$, $CH_2NH_2$, $CH(CH_3)NH_2$, $CH(CH_3)NHCH_3$, $C(CH_3)_2NH_2$, $CH_2CH_2NH_2$, $CH_2NHCH_3$, $CH_2N(CH_3)_2$, $CH(CH_3)NH_2$, $CH_2NHC(CH_3)_2$, $CH_2NHCH_2CHF_2$, $CH_2NHCH_2CH(CH_3)OH$, $CH_2NHCH_2N(CH_3)_2$, $CH_2NHCH(CH_2CH_3)_3$, $CH_2NHCH_3$, $CH_2NHCH_2CH_3$, $CH_2NHCH_2CH_2CH_3$, $CH_2NH$-cyclopropyl, $CH_2NHCH_2CH_2OH$, $CH_2NHCH_2CH_2OCH_3$, $CH_2NHCH_2CH_2—OCH_2CH_2OH$, azetidinyl, or pyrrolidinyl.

In another embodiment, $R^1$ is

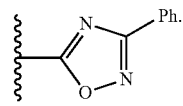

In yet another embodiment, $R^1$ is selected from benzimidazolyl, imidazopyridyl, triazolopyridyl, benzofuranyl, or benzothiazolyl.

In some embodiments, $R^1$ is selected from:

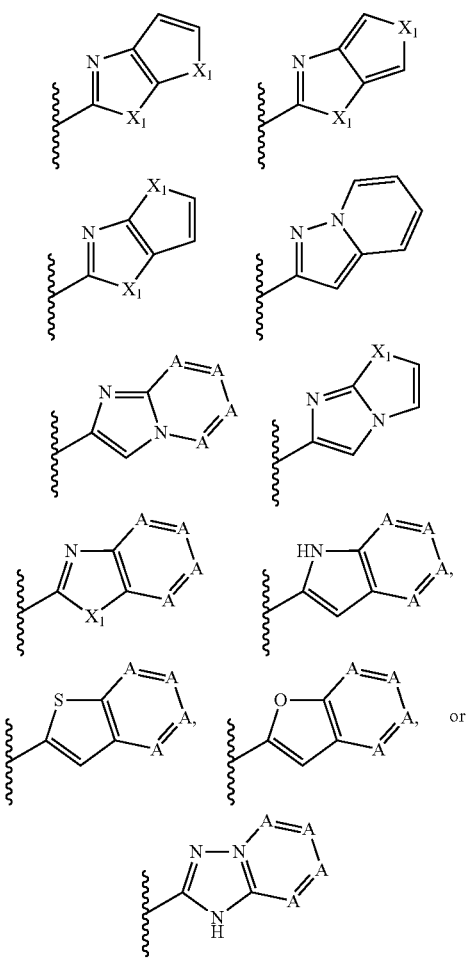

wherein each $R^1$ is optionally substituted with 1-2 occurrences of J';
A is C or N, provided that at least two occurrence of A are carbon; and
$X_1$ is O, N, or S.

In other embodiments, $R^1$ is

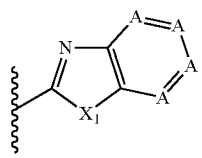

wherein each $R^1$ is optionally substituted with 1-2 occurrences of $J^1$; A is carbon or nitrogen; and $X_1$ is selected from O, N, or S.

In certain embodiments, $R^1$ is benzimidazolyl.

Another aspect provides compounds wherein $R^2$ is Q (i.e. monocyclic ring). Each Q is optionally substituted with 1-4 $J^Q$ groups and 1-2 J groups. It should be understood that Q, $Q^1$, or Q-$Q^1$ structures depicted herein showing no substituents or showing only J-substituents, are also intended to be optionally substituted with 1-4 occurrences of $J^Q$ or $J^{Q1}$.

In some embodiments, Q is selected from the following:

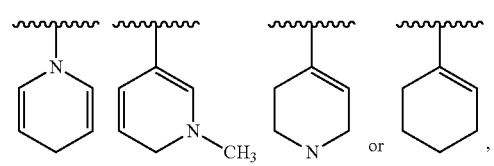

wherein each Q is optionally substituted with 1-4 $J^Q$ groups and 1-2 J groups.

In other embodiments, Q is selected from the following:

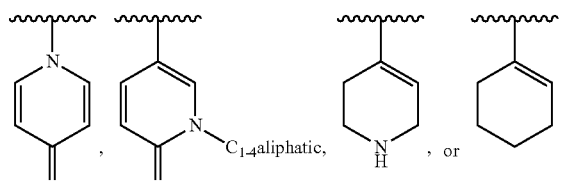

wherein each Q is optionally substituted with 1-4 $J^Q$ groups and 1-2 J groups. In yet another embodiment, Q is selected from the following:

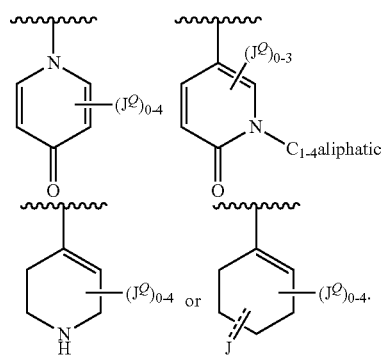

In yet another embodiment, Q is

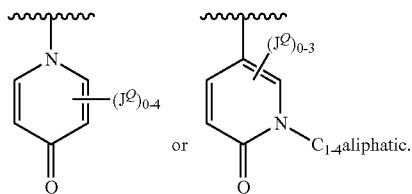

In yet other embodiments, Q is $C_{3-7}$ cycloalkyl, pyrrolidinyl, piperidinyl, piperazinyl, homopiperazinyl, homopiperidinyl, morpholinyl, or thiomorpholinyl.

According to one embodiment, Q is bonded through a carbon atom. In some embodiments, Q, $Q^1$, or Q-$Q^1$ is optionally substituted with 1-2 occurrences of $J^Q$ or $J^{Q1}$ respectively and optionally with 1 occurrence of J.

In some embodiments, Q or Q-$Q^1$ is selected from the following: $C_{3-8}$cycloaliphatic ring,

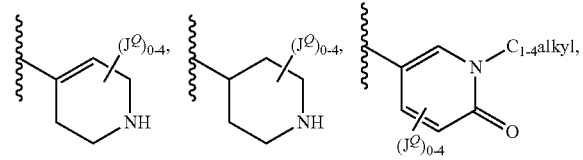

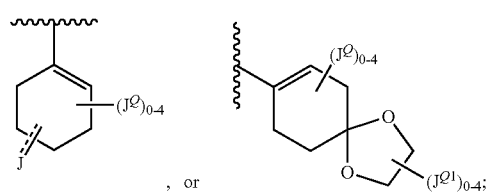

wherein said $C_{1-4}$aliphatic bonded to the pyridone is optionally substituted with halo, halo$C_{1-3}$alkyl, CN, OH, O($C_{1-3}$ alkyl), $NH_2$, NH($C_{1-3}$alkyl), N($C_{1-3}$alkyl)$_2$, or acetyl.

In some embodiments, Q is

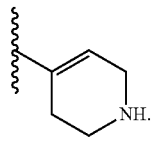 [SMILES: *C1=CCNCC1]

According to another embodiment, Q is bonded through a nitrogen atom.

In some embodiments, Q is azetidinyl, pyrrolidinyl, piperidinyl, piperazinyl, homopiperazinyl, homopiperidinyl, morpholinyl, or thiomorpholinyl, wherein said Q is optionally fused to $Q^1$; or Q and $Q^1$ optionally joined together at a carbon atom to form a spirocyclic bicyclic ring, or Q and $Q^1$, taken together, form a bridged bicyclic ring Q-$Q^1$ wherein said bridge is 1-3 atoms long; wherein Q-$Q^1$ is optionally substituted with 1-2 J groups; wherein J can be bonded to either Q or $Q^1$.

In other embodiments, Q is selected from the following:

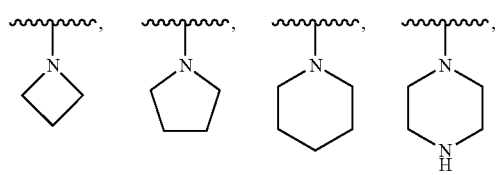

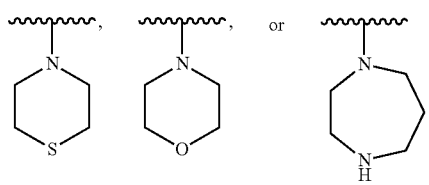

In yet other embodiments, Q and $Q^1$ together combine to form a bicyclic ring selected from the group consisting of

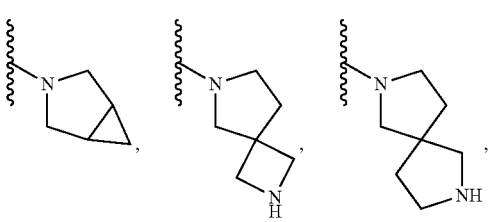

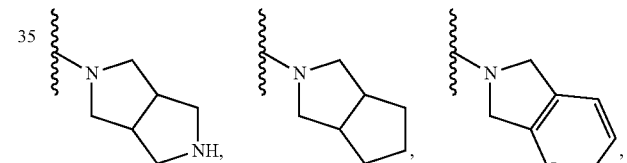

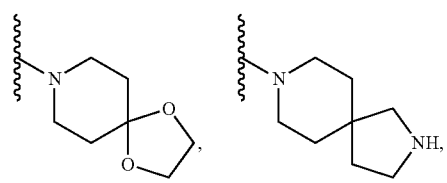

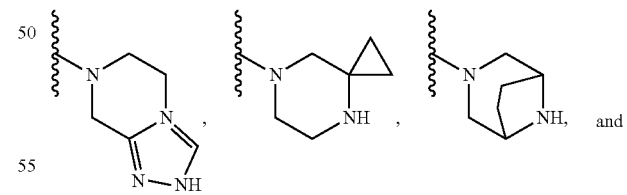

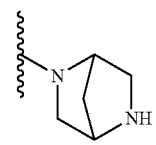

wherein each Q or $Q^1$ is optionally substituted with 1-2 occurrences of $J^Q$ or $J^{Q1}$ respectively and optionally with 1 occurrence of J.

In some embodiments, J is bonded in the position of Q as shown below:

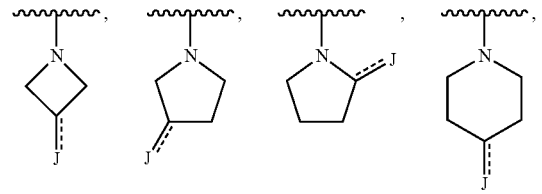

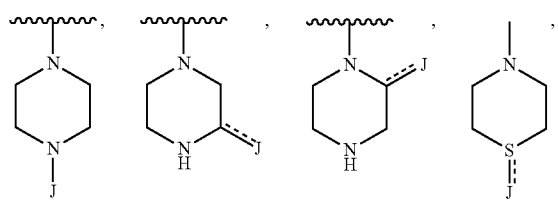

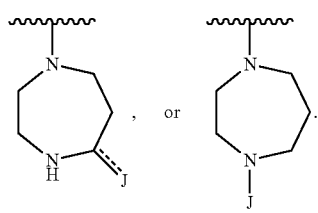

In other embodiments, J is bonded in the position of Q or $Q^1$ as shown below:

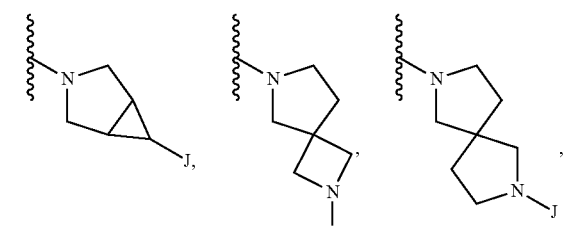

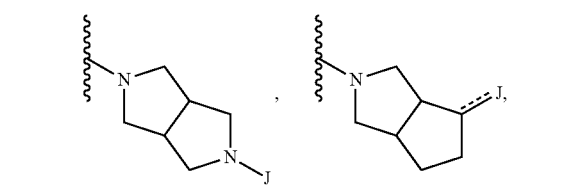

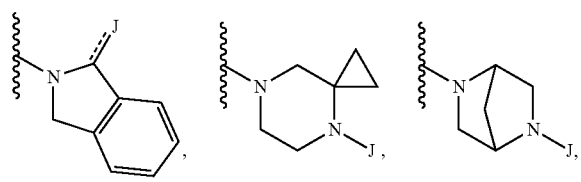

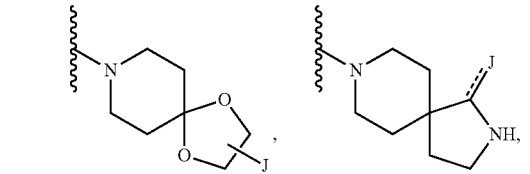

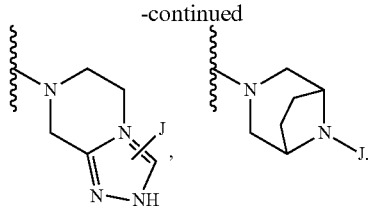

In some embodiments, J is $C_{1-6}$ aliphatic chain wherein up to 2 methylene units of $C_{1-6}$ aliphatic optionally replaced with heteroatom selected from O, N, or S.

In yet another embodiment, J is oxo, $V^1$—R", or —(V)$_m$—R*; wherein
each V and $V^1$ is independently a $C_{1-6}$ alkylidene chain wherein 0-3 methylene units are replaced with O, N, S, CO, SO, or $SO_2$;
R* is H or $C_{1-6}$alkyl;
m is 0-1, and
R" is a 3-7 membered saturated or unsaturated monocyclic ring having 0-3 heteroatoms independently selected from nitrogen, oxygen, or sulfur.

In some embodiments, $R^2$ is piperazine or tetrahydropyridinyl; m is 0; and J is oxo, $V^1$—R", or —(V)$_m$—R* wherein R" is thiazolyl, pyridyl, pyrimidyl, phenyl; and R* is optionally substituted with halo, O($C_{1-4}$alkyl), halo$C_{1-4}$alkyl, or CN.

In yet another embodiment, V is O, O($C_{1-6}$alkyl), ($C_{1-4}$ alkyl)O, C(O)O, C(O)O($C_{1-6}$alkyl), C(O)O($C_{1-6}$alkyl)O ($C_{1-6}$ alkyl), C(O)($C_{1-6}$alkyl), C(O)($C_{1-6}$alkyl)N, C(O)($C_{1-6}$ alkyl)NH($C_{1-6}$alkyl), C(O)($C_{1-6}$alkyl)C(O)O, C(O)($C_{1-6}$ alkyl)O, C(O)($C_{1-6}$alkyl)O($C_{1-6}$alkyl), C(O)($C_{1-6}$alkyl)NH ($C_{1-6}$alkyl), C(O)($C_{1-6}$alkyl)O($C_{1-4}$alkyl)O($C_{1-6}$alkyl), C(O) NH, C(O)NH($C_{1-6}$alkyl), C(O)N($C_{1-6}$alkyl), NH, N($C_{1-6}$ alkyl), N($C_{1-6}$alkyl)$_2$, NHC(O), NHC(O)$C_{1-6}$alkyl, NHC(O) ($C_{1-6}$alkyl)O, NHC(O)($C_{1-6}$alkyl)O($C_{1-6}$alkyl), NHC(O) ($C_{1-6}$ alkyl)O($C_{1-6}$alkyl)O($C_{1-6}$alkyl), NHC(O)($C_{1-6}$alkyl) NH($C_{1-6}$alkyl), C(O)N($C_{1-6}$alkyl)-, C(O)N($C_{1-6}$alkyl)$_2$, $SO_2$, $S(O)_2$($C_{1-6}$alkyl)-, $S(O)_2$($C_{1-6}$alkyl)NH, $S(O)_2$NH($C_{1-6}$ alkyl)-, $S(O)_2$N($C_{1-6}$alkyl)$_2$, $NHSO_2$, or $NHSO_2$N($C_{1-6}$ alkyl)$_2$;
R* is H or $C_{1-6}$alkyl; and
R" is $C_3$-$C_8$ cycloaliphatic, imidazolyl, thienyl, thiazolyl, furanyl, pyrazolyl, triazolyl, pyrrolyl, phenyl, pyridyl, pyrimidyl, pyrazinyl, pyrrolidinyl, piperidinyl, piperazinyl, homopiperidinyl, homopiperazinyl, morpholinyl, thiomorpholinyl, or tetrahydropyranyl.

In yet another embodiment V is O, $OCH_2$, $CH_2O$, C(O), $C(O)CH_2$, $C(O)CH_2CH_2NH$, $C(O)CH_2CH_2NHCH_2$, C(O) $CH_2CH_2C(O)O$, $C(O)CH_2O$, $C(O)CH_2OCH_2$, $C(O)CH_2N$ ($CH_3)CH_2$, $C(O)CH_2OCH_2CH_2OCH_2$, $C(O)CH(CH_3)CH_2$, $C(O)CH(CH_2CH_3)CH_2CH_2$, C(O)O, $C(O)OCH_2$, C(O) $OCH_2CH_2$, $C(O)OCH_2CH_2OCH_2$, $C(O)OCH_2C\equiv C$—$CH_2$, C(O)NH, $C(O)NHCH_2$, $C(O)N(CH_3)$—, $C(O)N(CH_3)$ $CH_2$—, NH, N($C_{1-6}$aliphatic), $N(CH_3)CH_2$, NHC(O), NHC (O)$CH_2$, $NHC(O)CH_2O$, $NHC(O)CH_2OCH_2$, NHC(O) $CH_2OCH_2CH_2OCH_2$, $NHC(O)CH_2N(CH_3)CH_2$, NHC(O)C $(CH_3)_2CH_2$, $NHC(O)CH(CH_2CH_3)CH_2CH_2$, $SO_2$, $S(O)_2$ $CH_2$, $S(O)_2CH_2CH_2$, $S(O)_2CH_2CH_2NH$, $S(O)_2$ $CH_2CH_2CH_2NH$, $S(O)_2CH_2CH_2CH_2$, $S(O)_2CH(CH_3)CH_2$, $S(O)_2N(CH_3)CH_2$, $NHSO_2$, or $NHSO_2N(CH_3)CH_2$;
R is H or $C_{1-6}$alkyl; and
$Q^2$ is cyclopropyl, cyclobutyl, cyclopentyl, cyclohexyl, phenyl, imidazolyl, thienyl, thiazolyl, furanyl, pyrazolyl, triazolyl, tetrazolyl, pyrrolyl, phenyl, pyridyl, pyrimidyl, pyrazinyl, pyrrolidinyl, piperidinyl, piperazinyl, homopiperidinyl, homopiperazinyl, morpholinyl, thiomorpholinyl, or tetrahydropyranyl; wherein said $Q^2$ is optionally substituted with $C_{1-6}$alkyl, CN, halo, halo$C_{1-4}$alkyl, NH($C_{1-4}$alkyl), N($C_{1-4}$alkyl)$_2$, or O($C_{1-6}$ alkyl).

In some embodiments, J is selected from $C_{1-6}$aliphatic, oxo, —OH, —O($C_{1-6}$aliphatic), CN, —C(O)($C_{1-6}$aliphatic), —C(O)(phenyl), —C(O)(benzyl), —C(O)CH$_2$O(phenyl), —C(O)CH$_2$O($C_{1-6}$aliphatic), —C(O)CH$_2$O(benzyl), —C(O)(pyridyl), —C(O)(pyrrolidinyl), —C(O)(piperidinyl), —C(O)(piperazinyl), —C(O)(homopiperazinyl), —C(O)(morpholinyl), —C(O)(tetrahydropyranyl), —C(O)O($C_{1-6}$aliphatic), —C(O)O(phenyl), —C(O)O(benzyl), —C(O)NH$_2$, —C(O)NH($C_{1-6}$aliphatic), —C(O)N($C_{1-6}$aliphatic)$_2$, —C(O)NH(phenyl), —C(O)NH(benzyl), —S(O)$_2$($C_{1-6}$aliphatic), —S(O)$_2$(phenyl), —S(O)$_2$(benzyl), —S(O)$_2$(pyridyl), —S(O)$_2$(furanyl), —S(O)$_2$(imidazolyl), —S(O)$_2$(thienyl), —S(O)$_2$NH($C_{1-6}$aliphatic), —S(O)$_2$N($C_{1-6}$aliphatic)$_2$, —S(O)$_2$NH(phenyl), —S(O)$_2$NH(benzyl), —NHC(O)($C_{1-6}$aliphatic), —NHC(O)(pyridyl), NHS(O)$_2$N($C_{1-6}$aliphatic)$_2$, NH$_2$, NH($C_{1-6}$aliphatic), N($C_{1-6}$aliphatic)$_2$; wherein said phenyl, benzyl, pyrrolidinyl, piperidinyl, piperazinyl, morpholinyl, tetrahydropyranyl, or $C_{1-6}$aliphatic is optionally substituted with halo, $C_{1-3}$alkyl, CN, OH, O($C_{1-3}$alkyl), NH$_2$, NH($C_{1-3}$alkyl), N($C_{1-3}$alkyl)$_2$, acetyl, SO$_2$($C_{1-3}$alkyl).

In other embodiments J is selected from, oxo, —OH, —NHC(O)($C_{1-4}$alkyl), —C(O)($C_{1-4}$alkyl), —C(O)NH$_2$, —C(O)NH($C_{1-4}$alkyl), —C(O)NH($C_{1-4}$alkyl)$_2$, —S(O)$_2$($C_{1-4}$ alkyl), —S(O)$_2$NH($C_{1-4}$alkyl), or —S(O)$_2$N($C_{1-4}$ alkyl)$_2$.

In yet other embodiments J is selected from —C(O)CH$_2$(phenyl), NH$_2$, NH($C_{1-3}$alkyl), N($C_{1-3}$alkyl)$_2$, —NHS(O)$_2$(phenyl), —NHC(O)(phenyl), —NHC(O)(pyridyl), —C(O)CH$_2$O(phenyl), —C(O)CH$_2$O($C_{1-3}$alkyl), —NHC(O)CH$_2$O($C_{1-3}$alkyl), —NHC(O)CH$_2$O(phenyl), —C(O)CH$_2$N($C_{1-3}$alkyl)$_2$, —NHC(O)CH$_2$N($C_{1-3}$alkyl)$_2$, —C(O)CH$_2$O($C_{1-3}$alkyl)O($C_{1-3}$alkyl), —NHC(O)CH$_2$O($C_{1-3}$alkyl)O($C_{1-3}$alkyl), —C(O)O($C_{1-3}$alkyl)O($C_{1-3}$alkyl), phenyl, pyridyl, thiazolyl, CF$_3$, pyrimidyl, wherein said phenyl, pyridyl, or pyrimidyl group is optionally substituted with halo, O($C_{1-6}$aliphatic), CN, CF$_3$, C(O)(furanyl).

In one embodiment, two J groups, attached to the same carbon atom, taken together form 1,3 dioxalane.

In some embodiments, the variables are as depicted in the compounds of the following Tables. Another embodiment provides a compound selected from the following tables:

TABLE 1

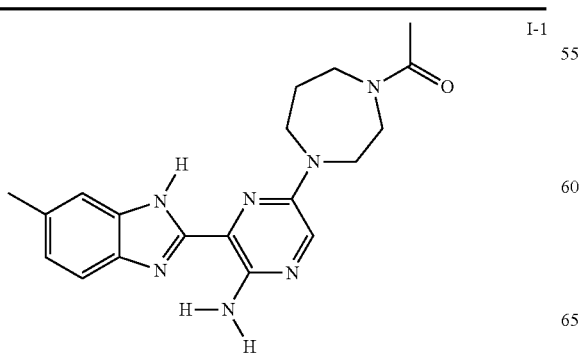

I-1

TABLE 1-continued

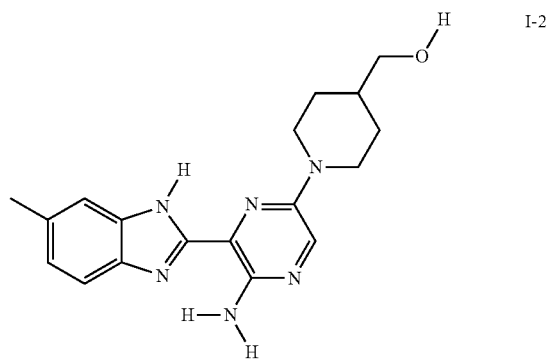

I-2

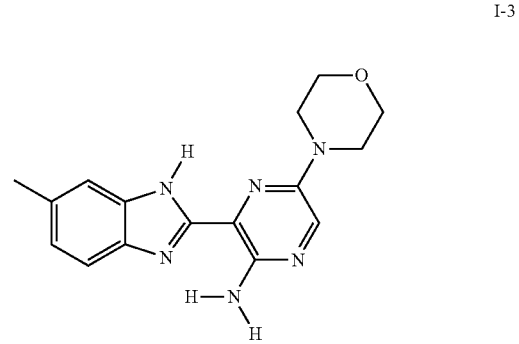

I-3

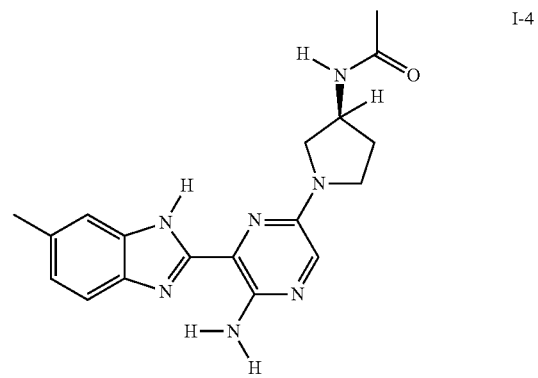

I-4

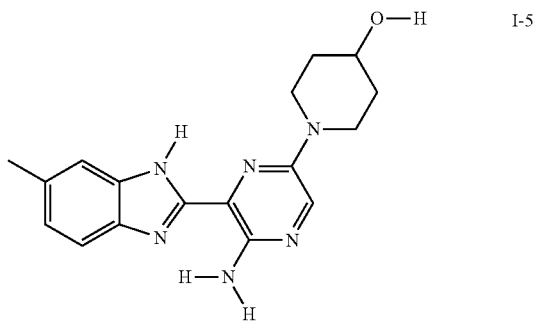

I-5

TABLE 1-continued
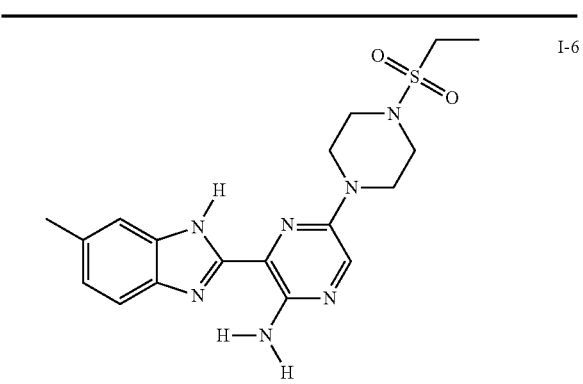
I-6
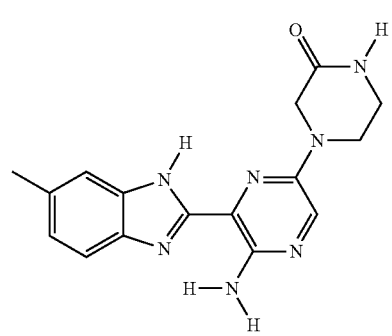
I-7
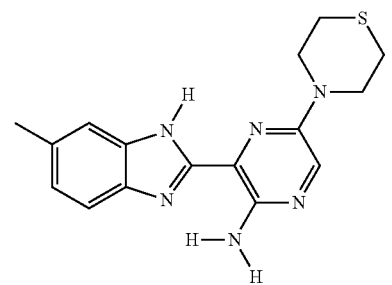 [SMILES: Cc1ccc2nc(-c3nc(N4CCOCC4)cnc3N)[nH]c2c1]
I-8
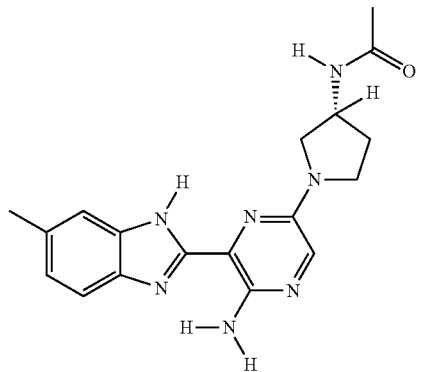 [SMILES: CC(=O)N[C@@H]1CCN(c2cnc(N)c(-c3nc4ccc(C)cc4[nH]3)n2)C1]
I-9
TABLE 1-continued
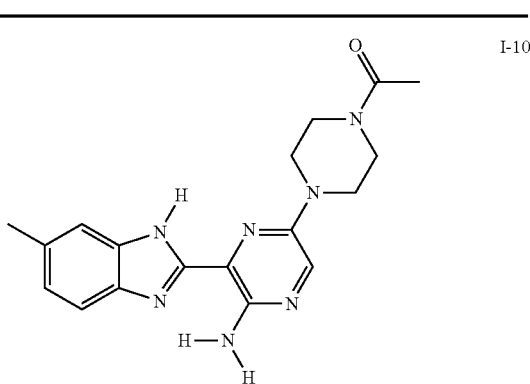
I-10
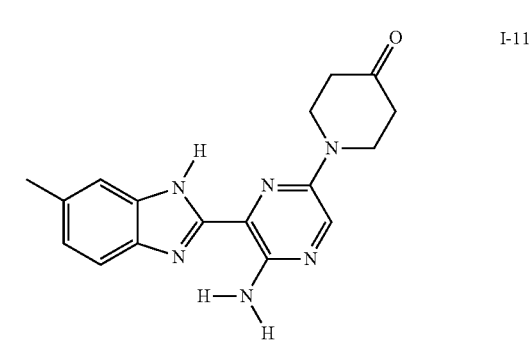
I-11
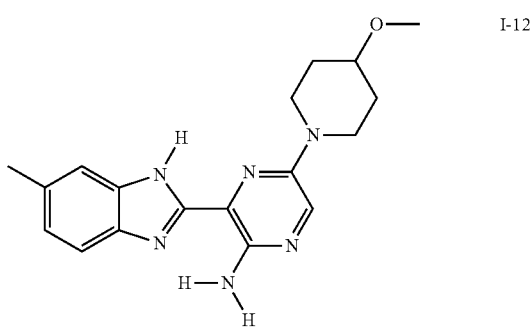
I-12
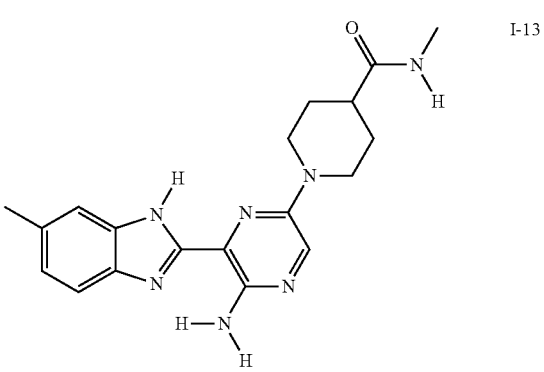
I-13

TABLE 1-continued
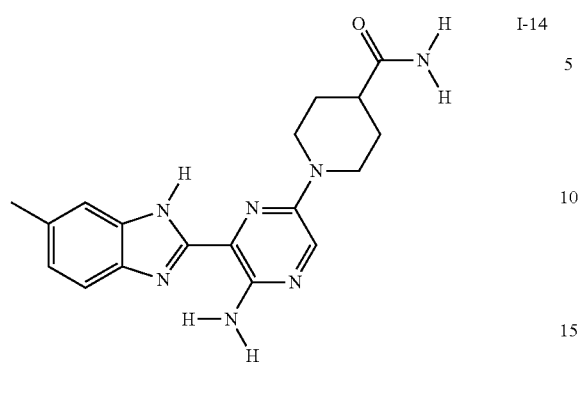
I-14
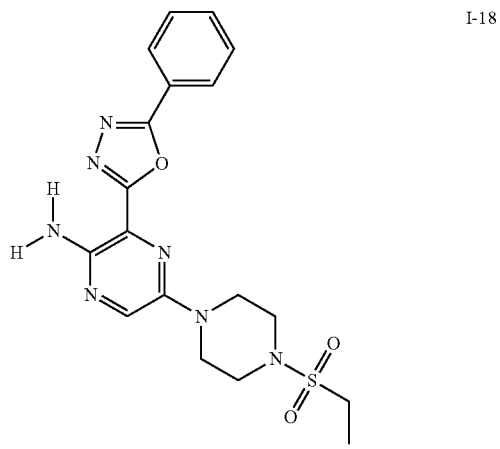
I-18
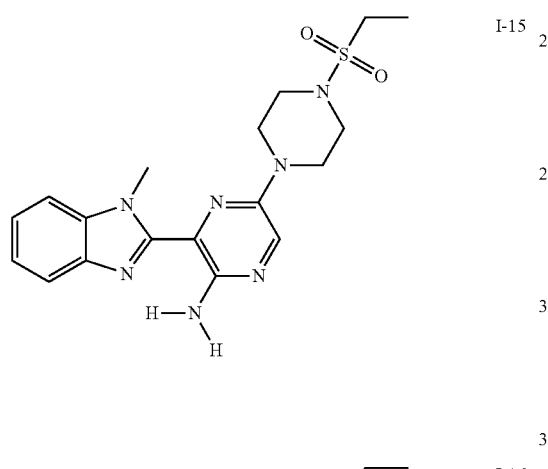
I-15
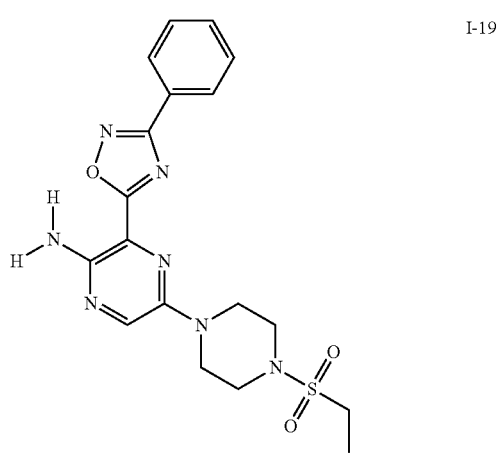
I-19
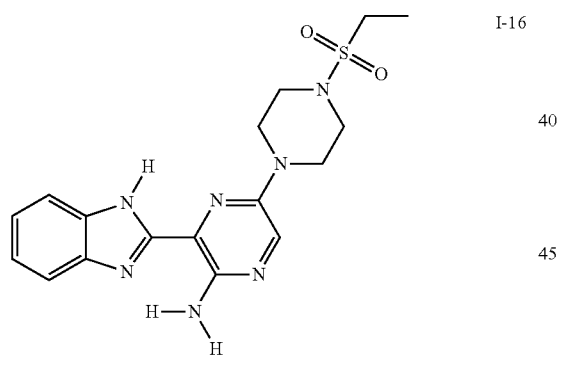
I-16
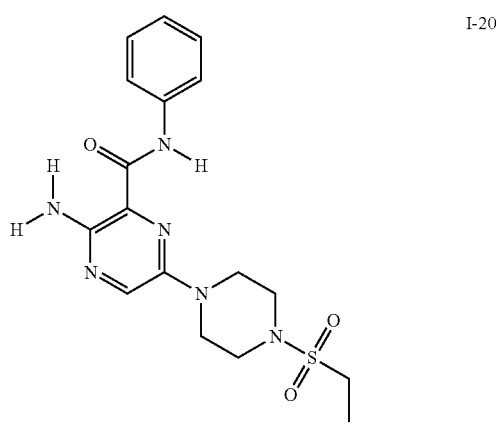
I-20
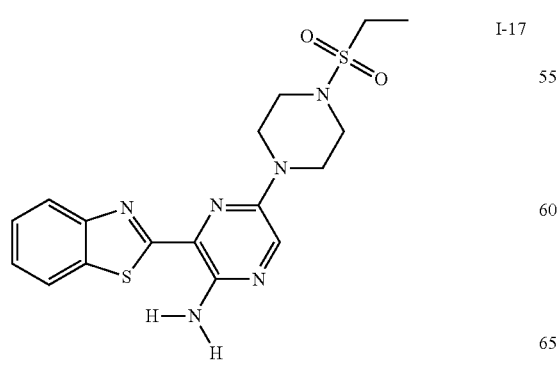
I-17
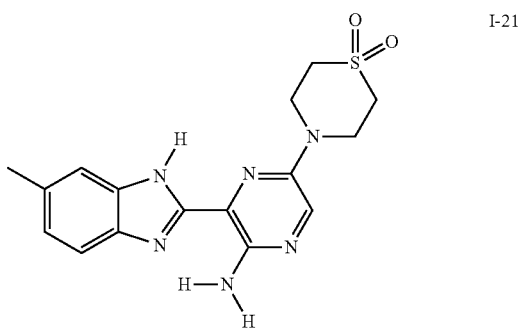
I-21

TABLE 1-continued
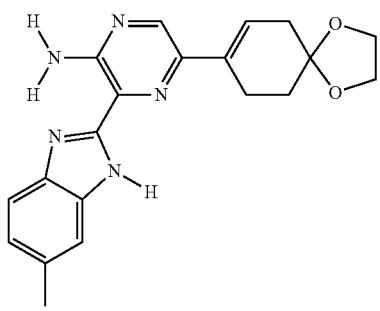 [SMILES: Cc1ccc2nc(-c3nc(C4=CCC5(CC4)OCCO5)cnc3N)[nH]c2c1] I-22
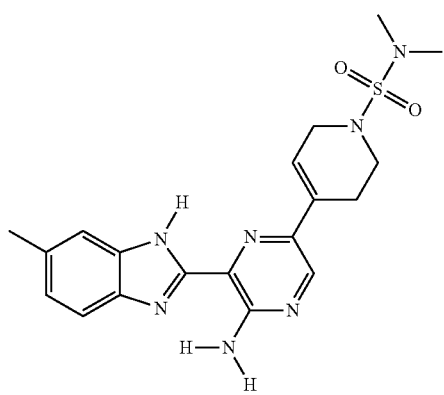 I-23
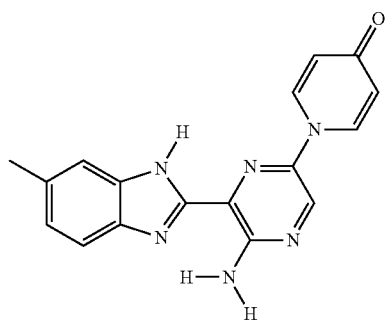 [SMILES: Cc1ccc2nc(-c3nc(-n4ccc(=O)cc4)cnc3N)[nH]c2c1] I-24
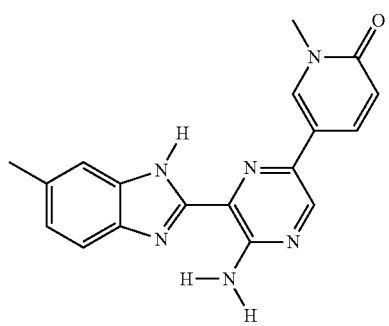 [SMILES: Cc1ccc2nc(-c3nc(-c4ccc(=O)n(C)c4)cnc3N)[nH]c2c1] I-25
TABLE 2
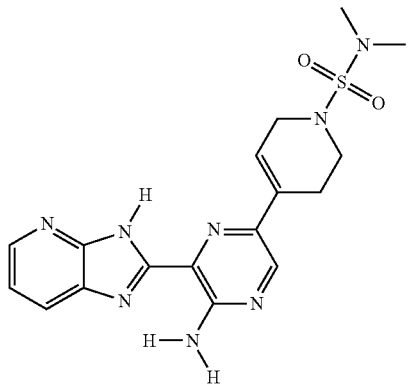 [SMILES: CN(C)S(=O)(=O)N1CC=C(c2cnc(N)c(-c3nc4cccnc4[nH]3)n2)CC1] I-26
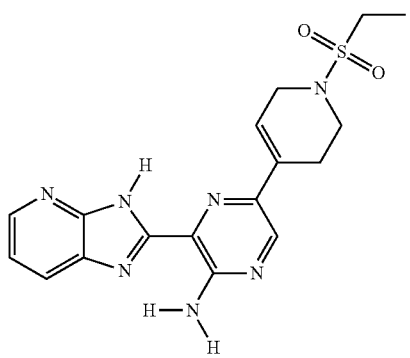 [SMILES: CCS(=O)(=O)N1CC=C(c2cnc(N)c(-c3nc4cccnc4[nH]3)n2)CC1] I-27
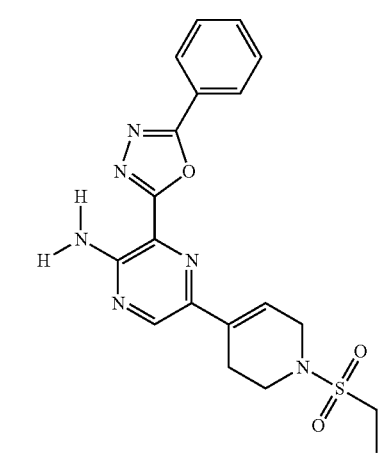 [SMILES: CCS(=O)(=O)N1CC=C(c2cnc(N)c(-c3nnc(-c4ccccc4)o3)n2)CC1] I-28
TABLE 3
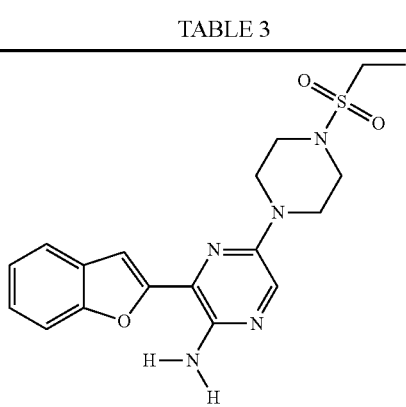 I-29

TABLE 3-continued
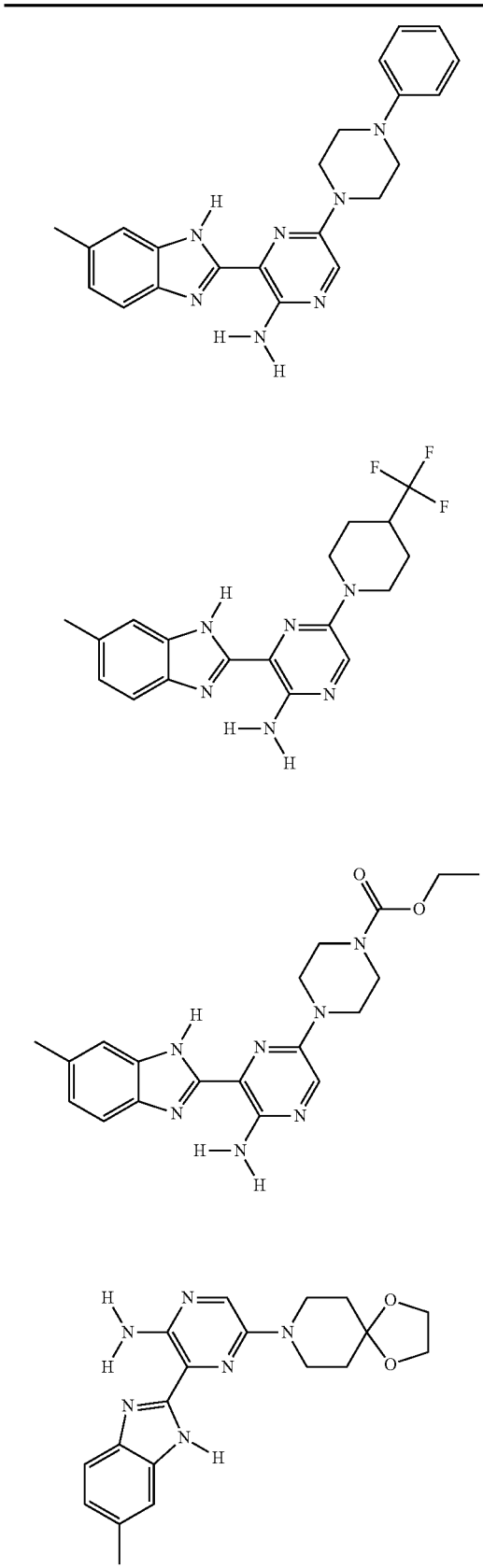
I-30
I-31
I-32
I-33
TABLE 3-continued
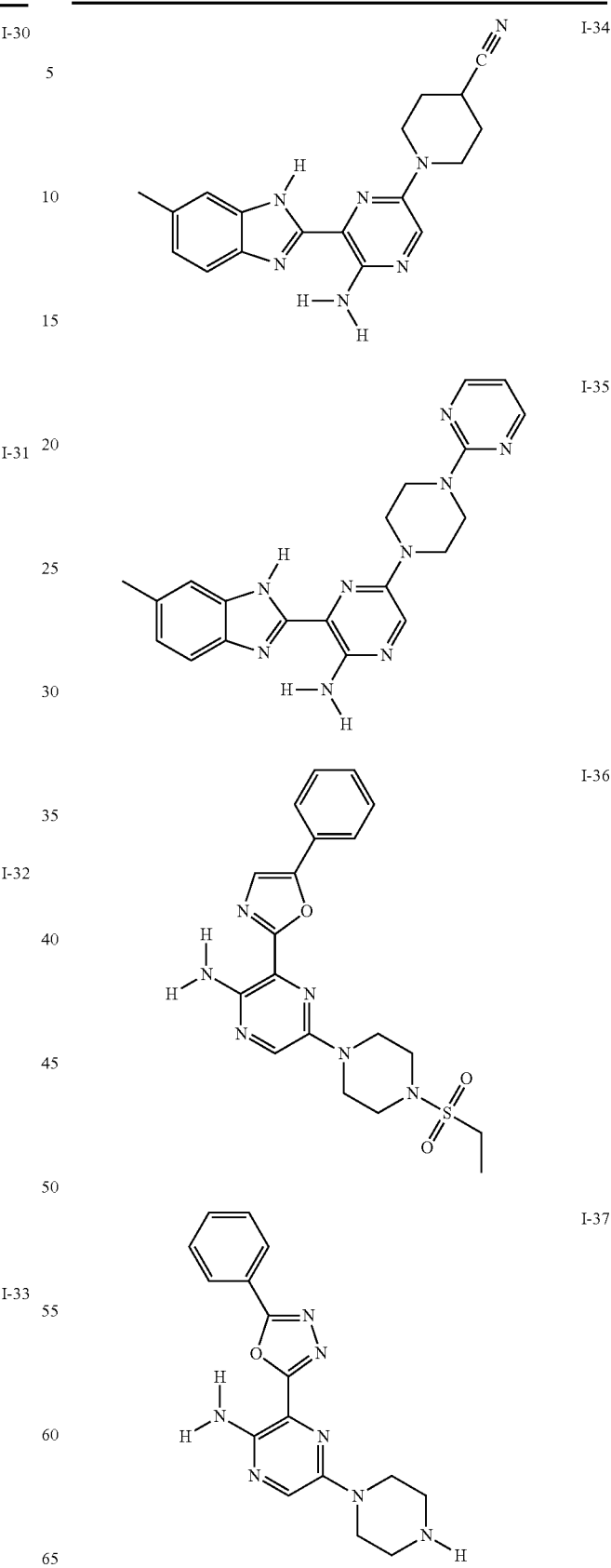
I-34
I-35
I-36
I-37

TABLE 3-continued
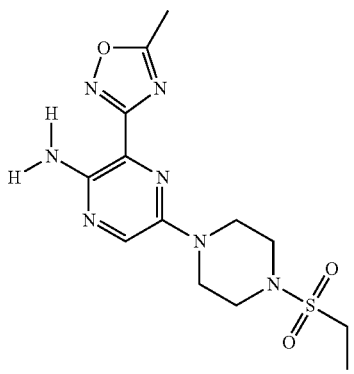 [SMILES: CCS(=O)(=O)N1CCN(c2cnc(N)c(-c3noc(C)n3)n2)CC1]
I-38
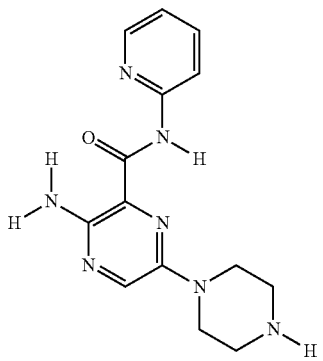 [SMILES: Nc1ncc(N2CCNCC2)nc1C(=O)Nc1ccccn1]
I-42

I-39
I-43

I-40
I-44
I-41
I-45

TABLE 3-continued
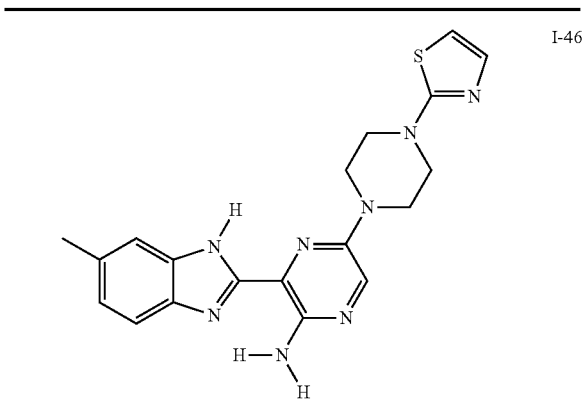
I-46
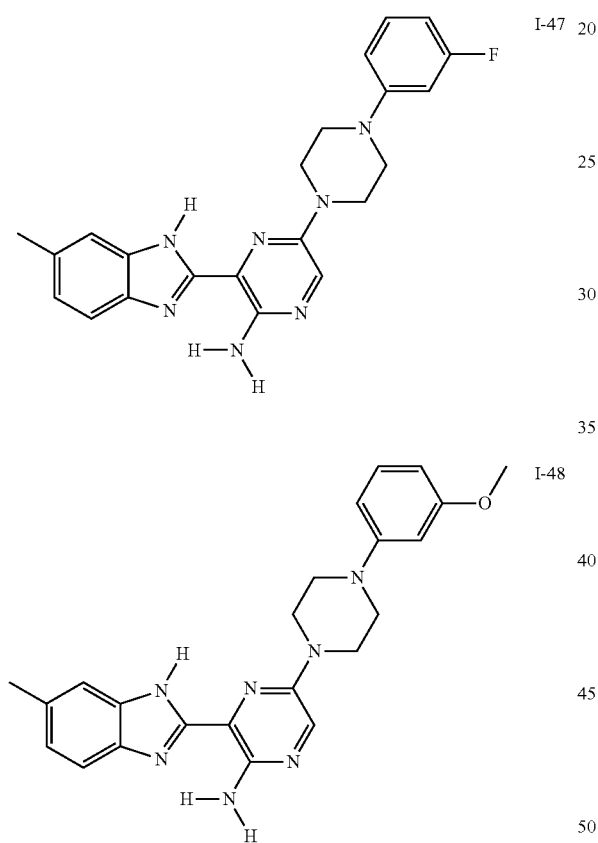
I-47
I-48
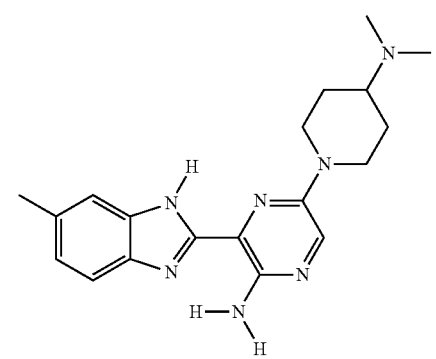
I-49
TABLE 3-continued
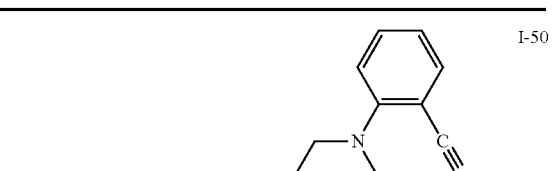
I-50
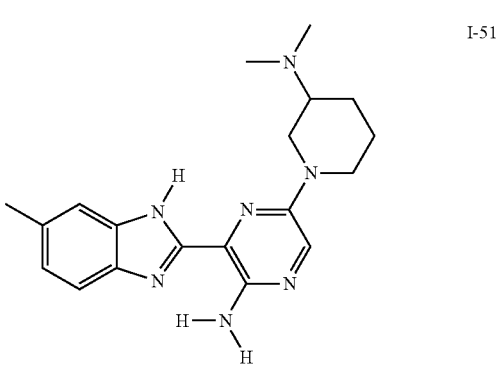
I-51
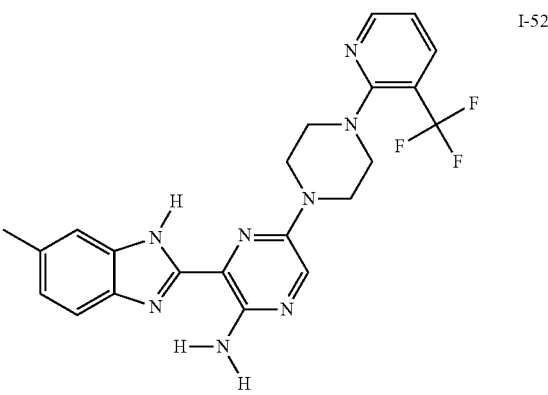
I-52
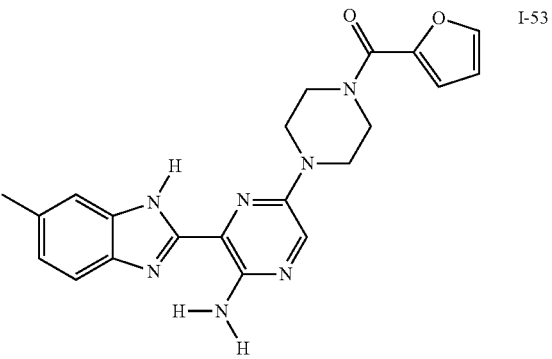
I-53

TABLE 3-continued
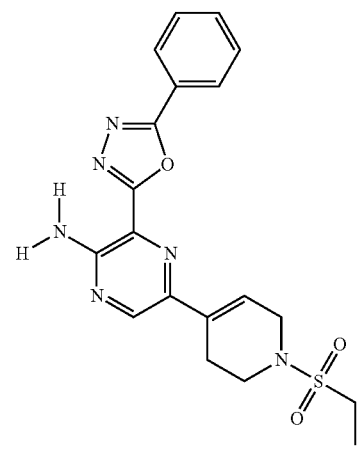 [SMILES: CCS(=O)(=O)N1CC=C(c2cnc(N)c(-c3nnc(-c4ccccc4)o3)n2)CC1]
I-54
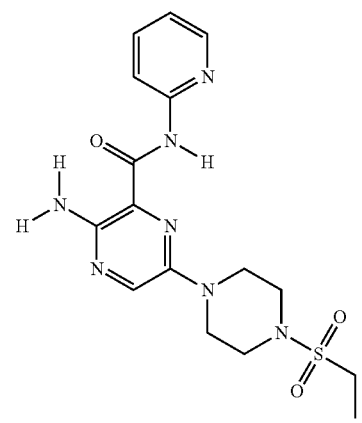 [SMILES: CCS(=O)(=O)N1CCN(c2cnc(N)c(C(=O)Nc3ccccn3)n2)CC1]
I-55
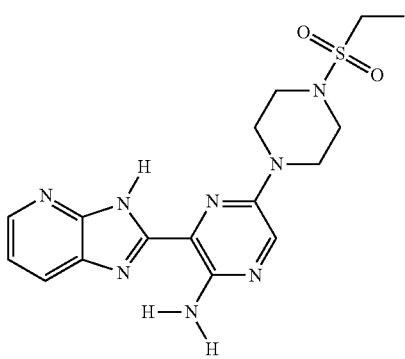 [SMILES: CCS(=O)(=O)N1CCN(c2cnc(N)c(-c3nc4cccnc4[nH]3)n2)CC1]
I-56
TABLE 3-continued
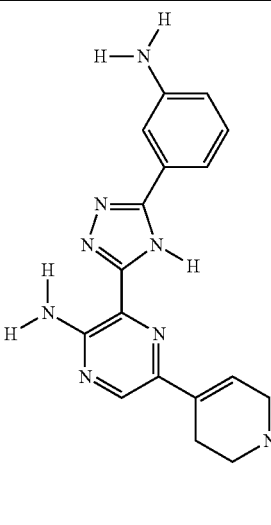
I-57
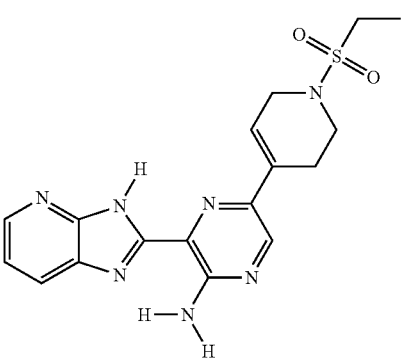 [SMILES: CCS(=O)(=O)N1CC=C(c2cnc(N)c(-c3nc4cccnc4[nH]3)n2)CC1]
I-58
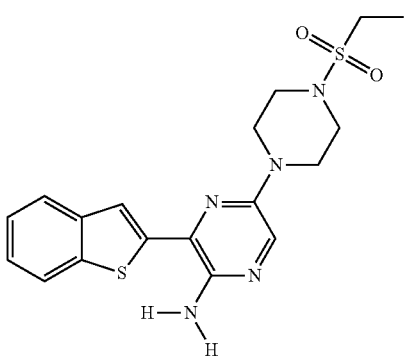 [SMILES: CCS(=O)(=O)N1CCN(c2cnc(N)c(-c3cc4ccccc4s3)n2)CC1]
I-59
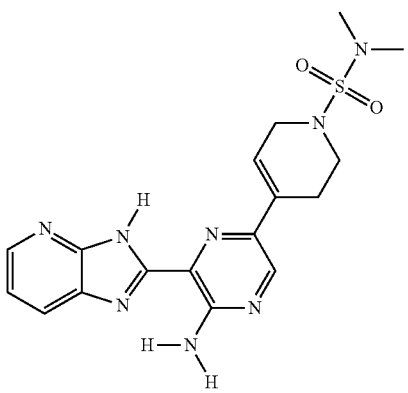 [SMILES: CN(C)S(=O)(=O)N1CC=C(c2cnc(N)c(-c3nc4cccnc4[nH]3)n2)CC1]
I-60

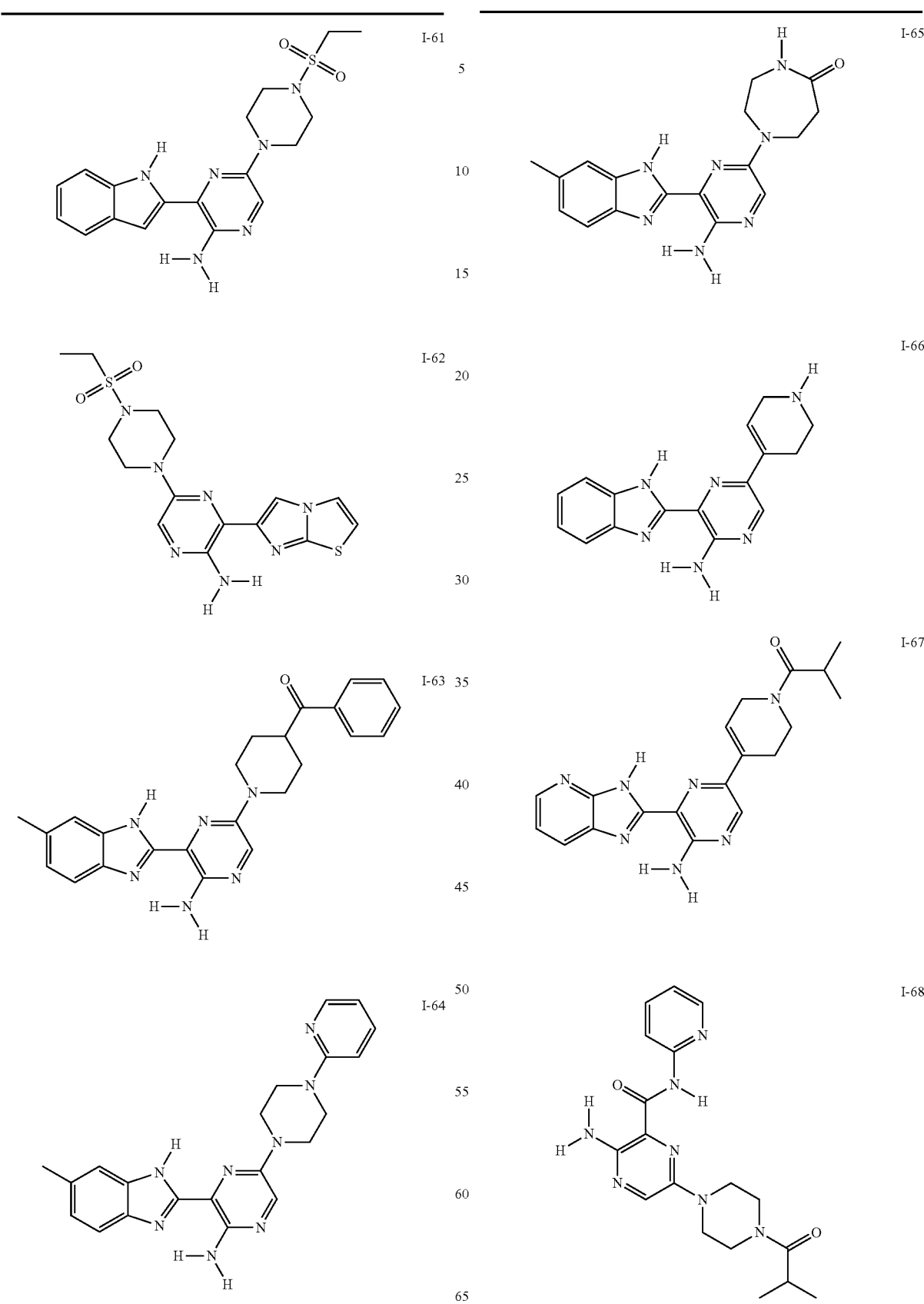

TABLE 3-continued
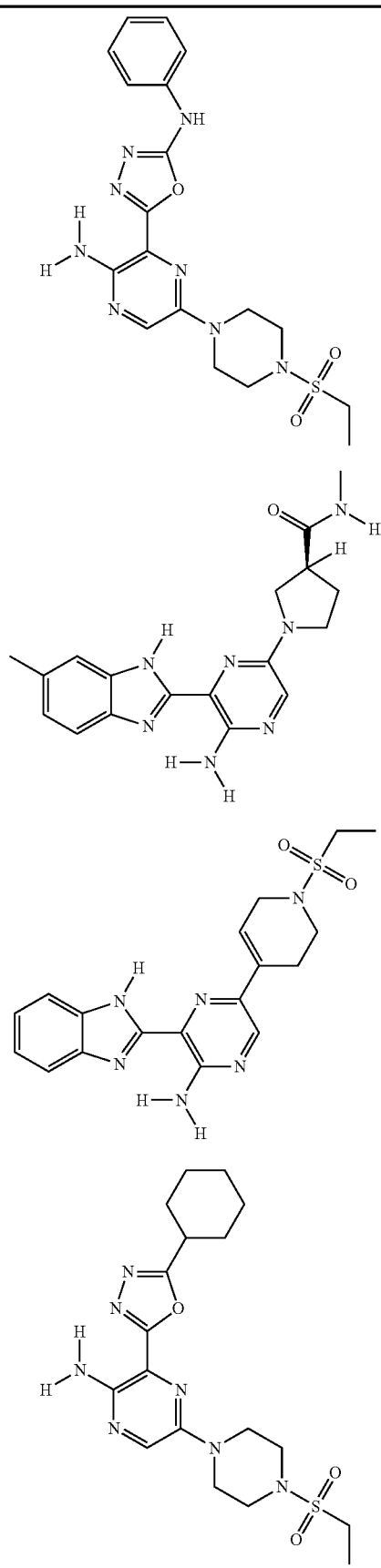
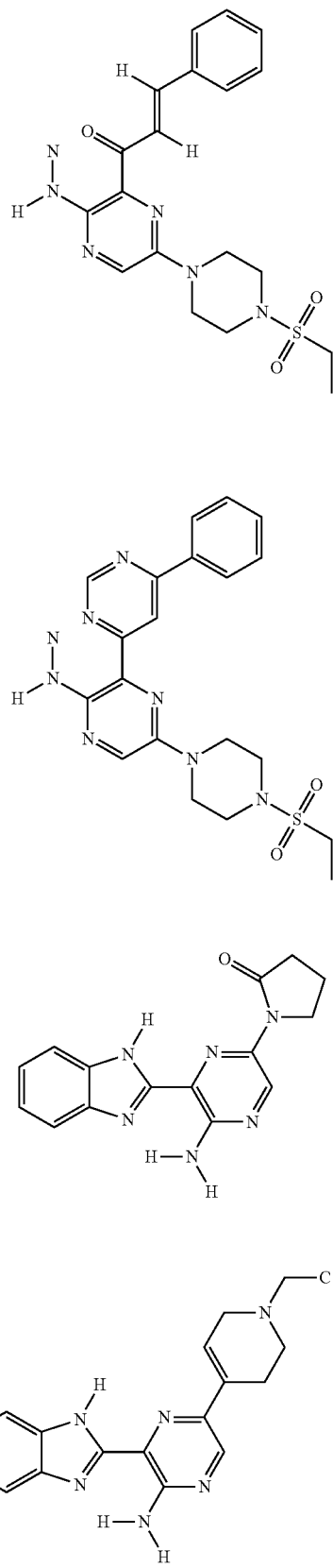

TABLE 3-continued
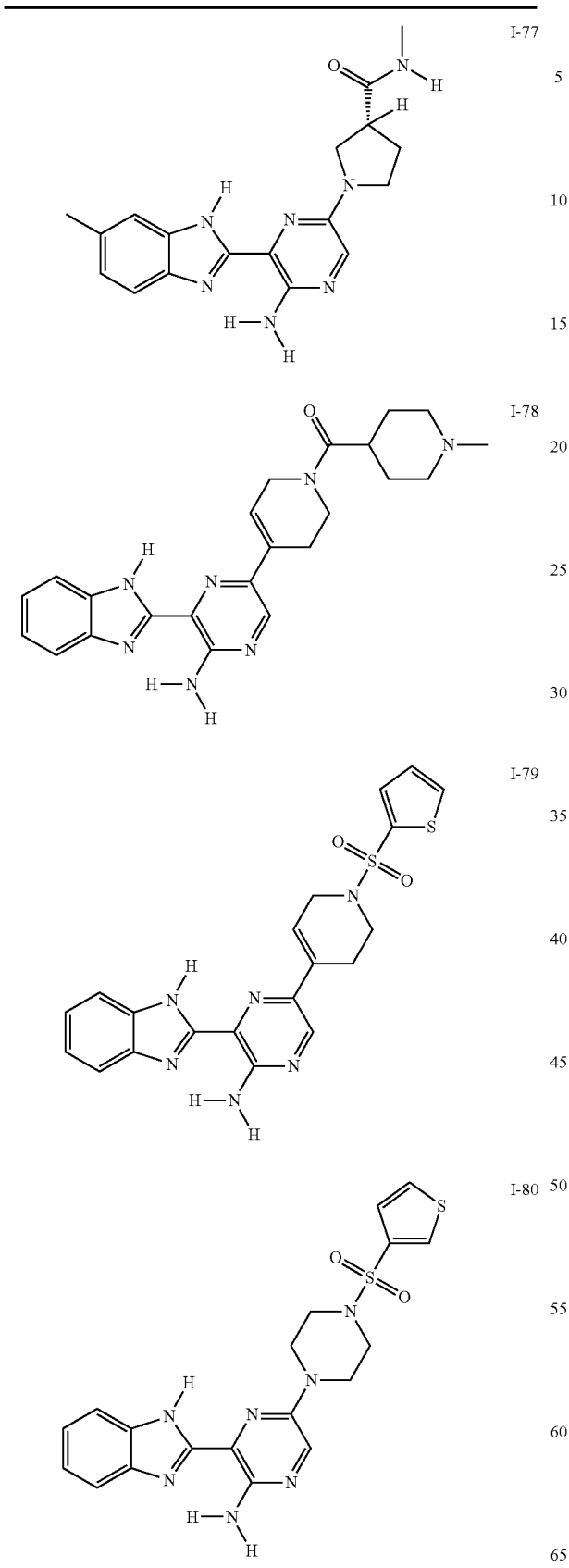
I-77
I-78
I-79
I-80
TABLE 3-continued
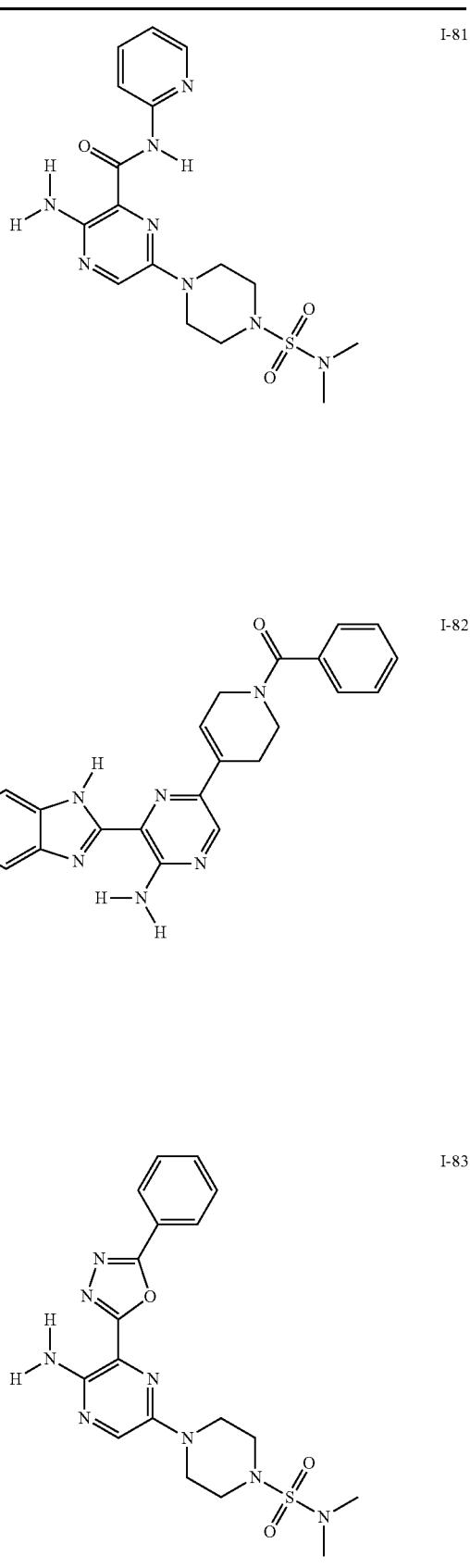
I-81
I-82
I-83

TABLE 3-continued
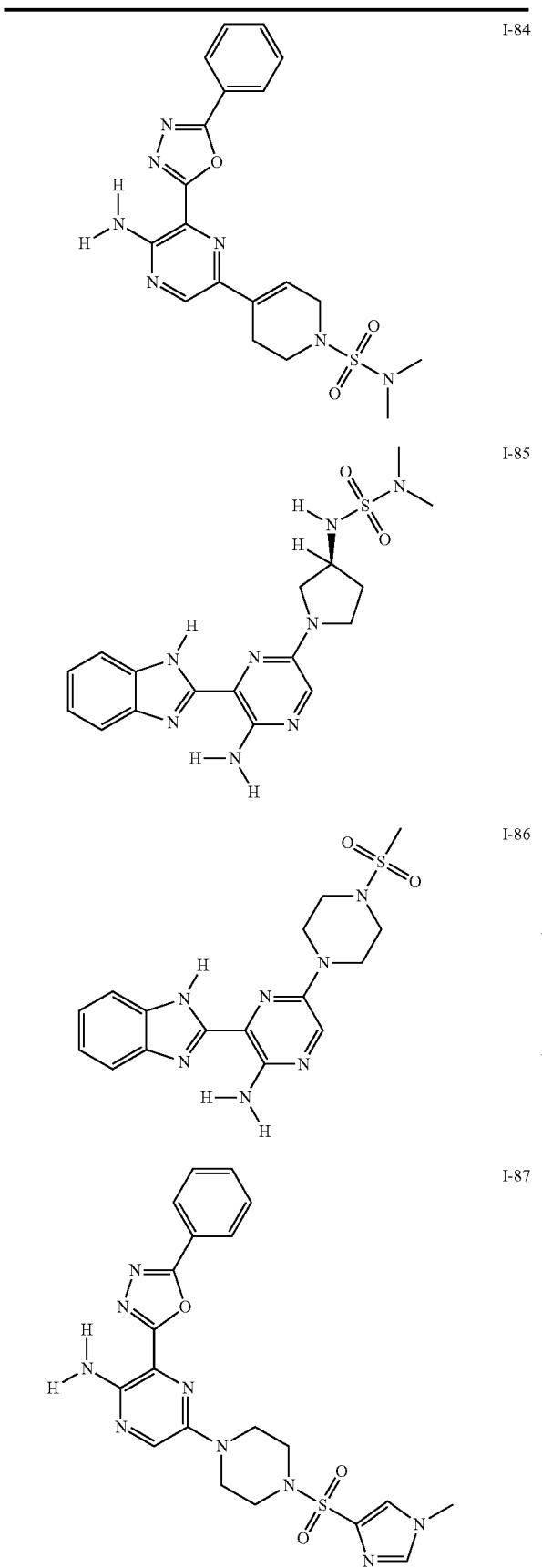
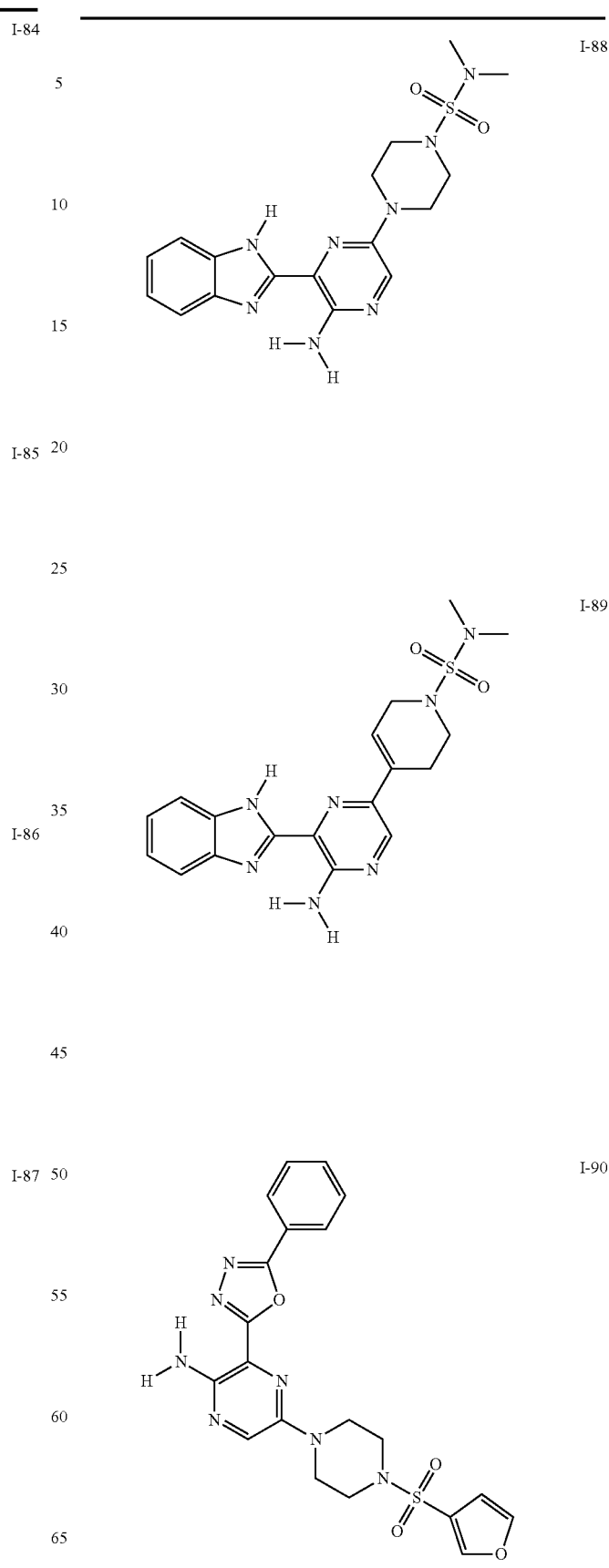

TABLE 3-continued
I-91
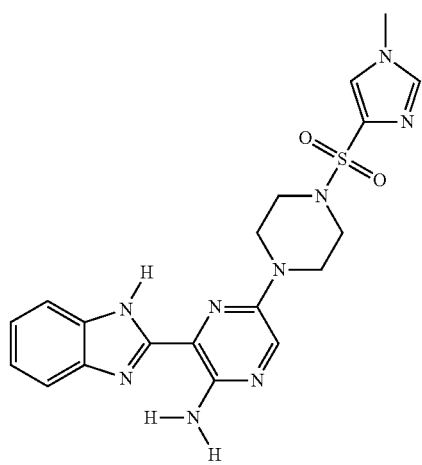 [SMILES: Cn1cnc(S(=O)(=O)N2CCN(c3cnc(N)c(-c4nc5ccccc5[nH]4)n3)CC2)c1]
I-92
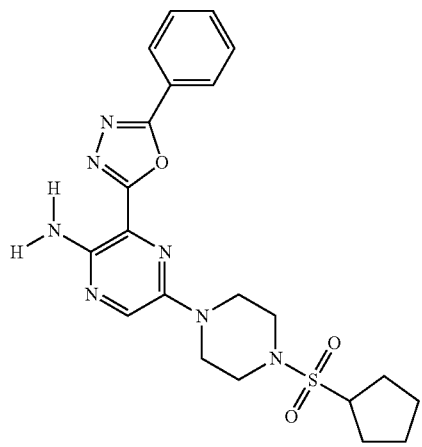 [SMILES: Nc1ncc(N2CCN(S(=O)(=O)C3CCCC3)CC2)nc1-c1nnc(-c2ccccc2)o1]
I-93
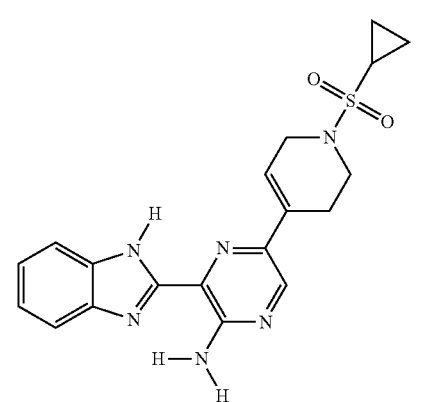 [SMILES: Nc1ncc(C2=CCN(S(=O)(=O)C3CC3)CC2)nc1-c1nc2ccccc2[nH]1]
TABLE 3-continued
I-94
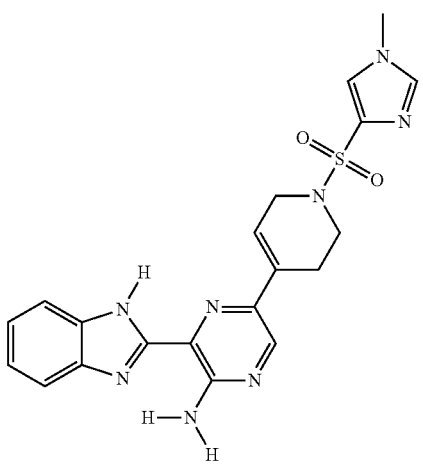 [SMILES: Cn1cnc(S(=O)(=O)N2CC=C(c3cnc(N)c(-c4nc5ccccc5[nH]4)n3)CC2)c1]
I-95
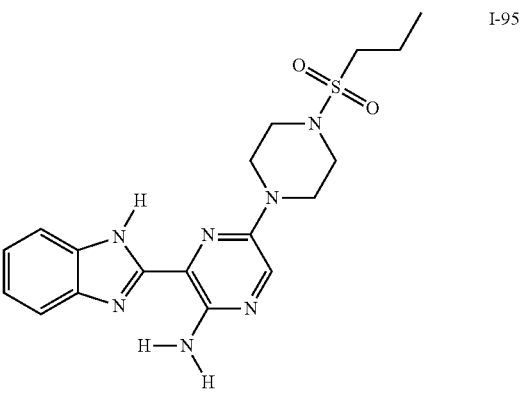
I-96
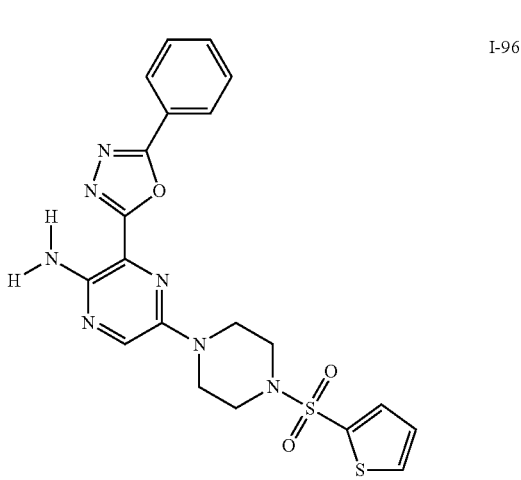

TABLE 3-continued
I-97
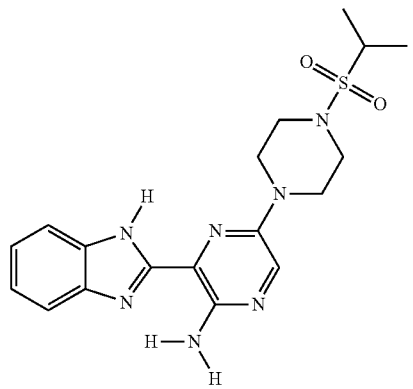 [SMILES: CC(C)S(=O)(=O)N1CCN(c2cnc(N)c(-c3nc4ccccc4[nH]3)n2)CC1]
I-98
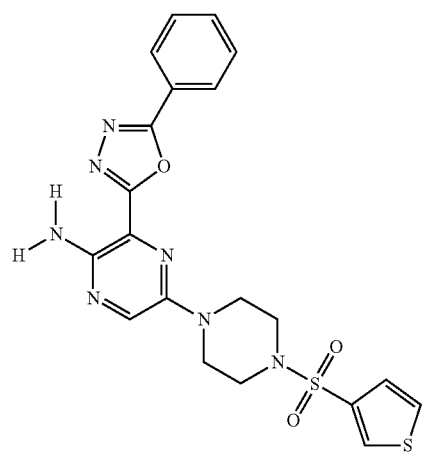 [SMILES: Nc1ncc(N2CCN(S(=O)(=O)c3ccsc3)CC2)nc1-c1nnc(-c2ccccc2)o1]
I-99
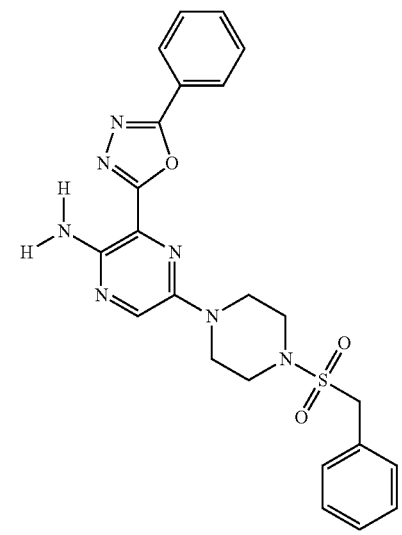 [SMILES: Nc1ncc(N2CCN(S(=O)(=O)Cc3ccccc3)CC2)nc1-c1nnc(-c2ccccc2)o1]
TABLE 3-continued
I-100
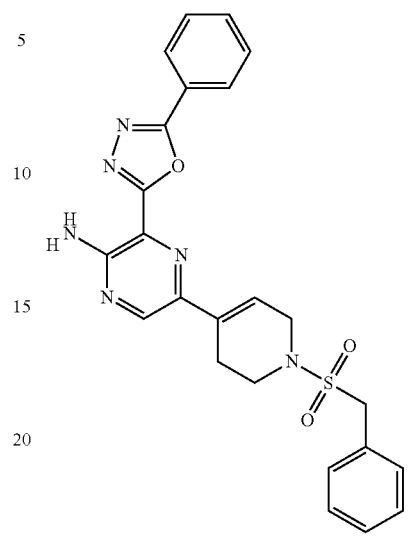
I-101
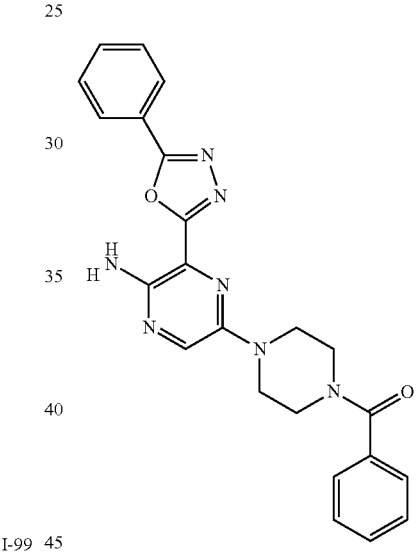
I-102
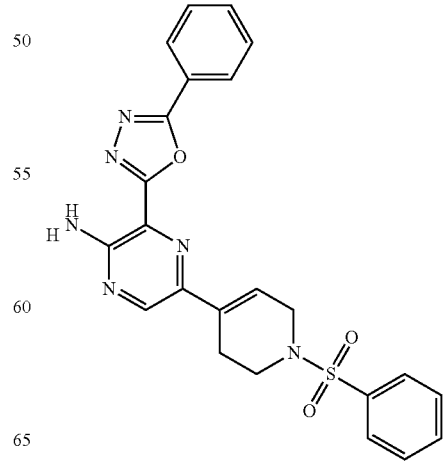

TABLE 3-continued
I-103
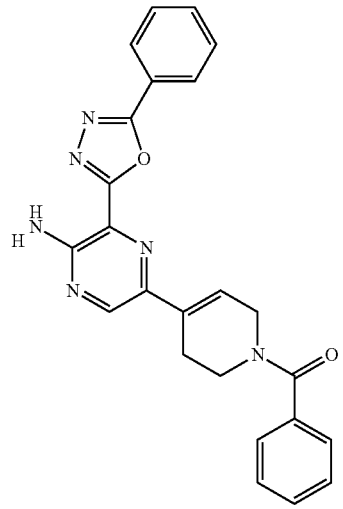
I-106
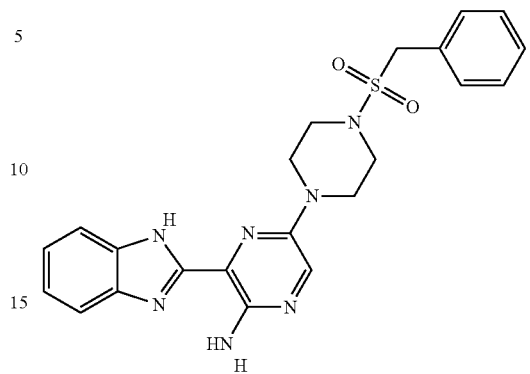
I-104
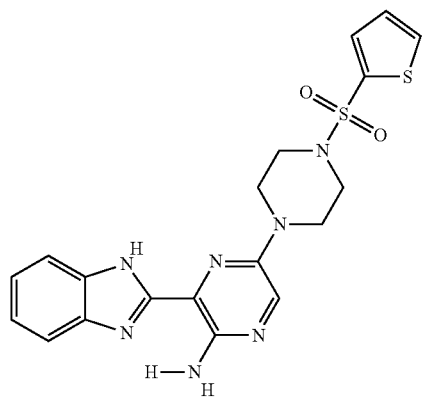
I-107
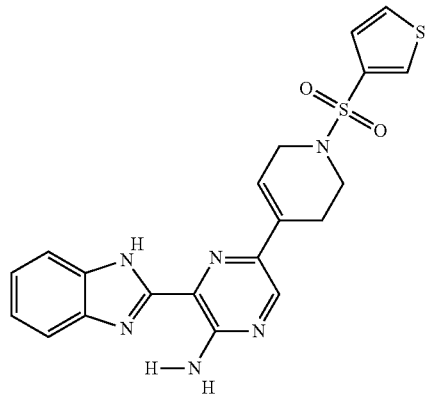
I-105
I-108
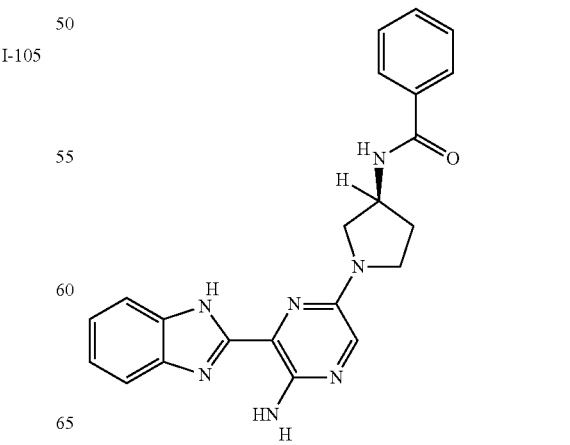

TABLE 3-continued
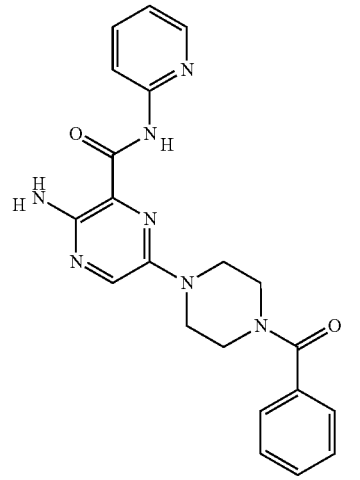
I-109
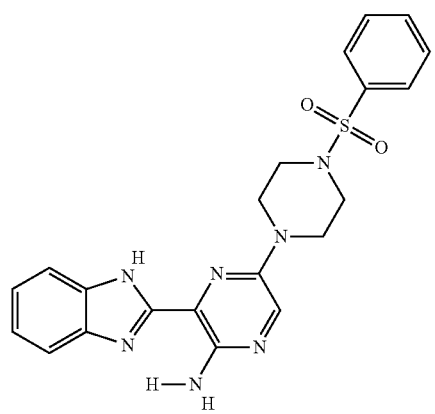
I-110
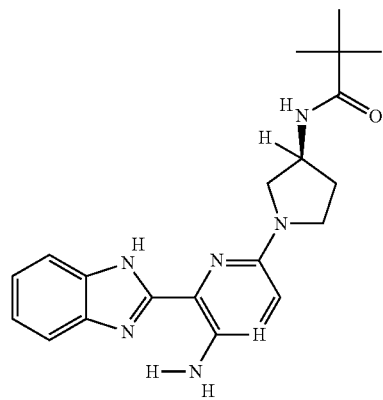
I-111
TABLE 3-continued
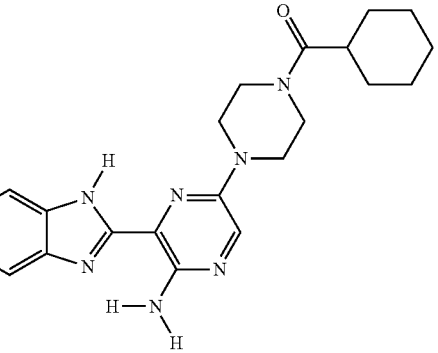
I-112
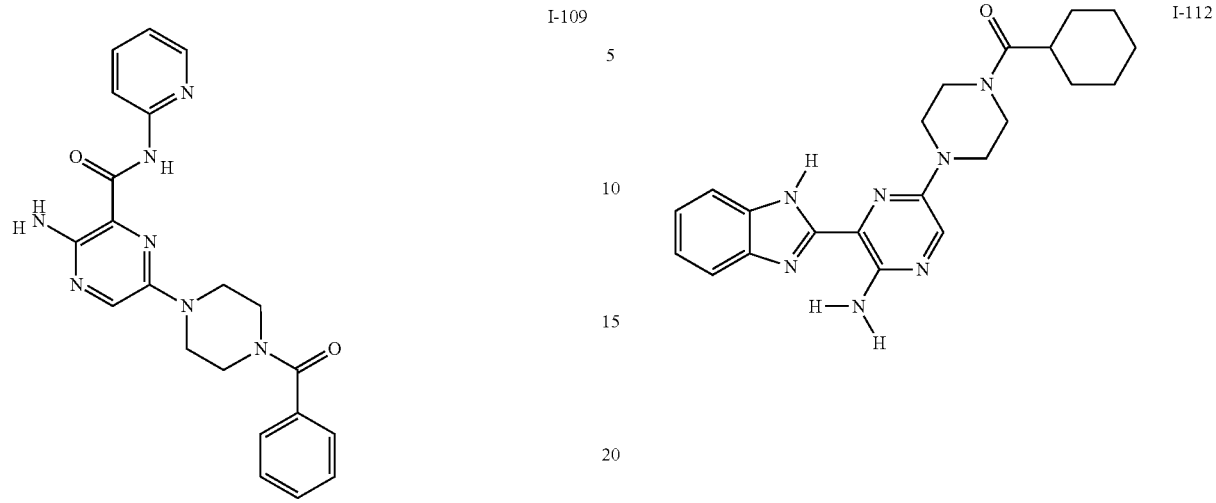
I-113
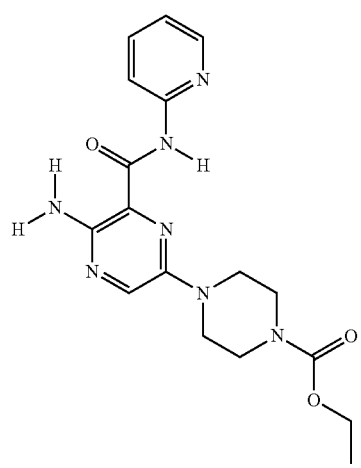 [SMILES: CCOC(=O)N1CCN(c2cnc(N)c(C(=O)Nc3ccccn3)n2)CC1]
I-114

TABLE 3-continued
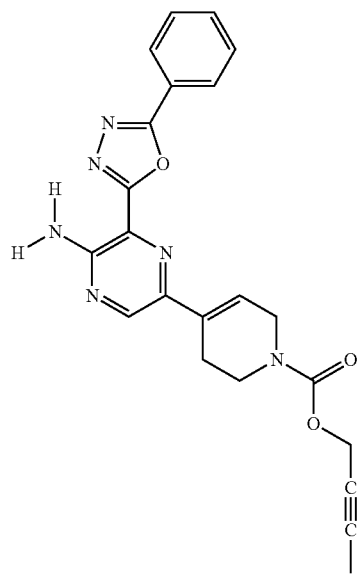 [SMILES: CC#CCOC(=O)N1CC=C(c2cnc(N)c(-c3nnc(-c4ccccc4)o3)n2)CC1]
I-115
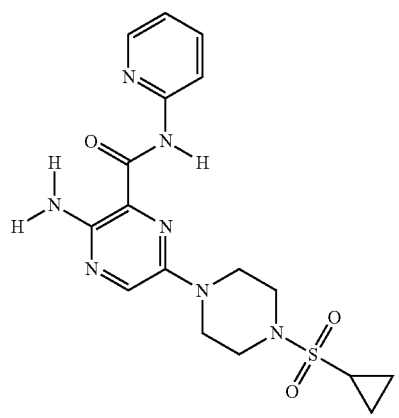
I-118
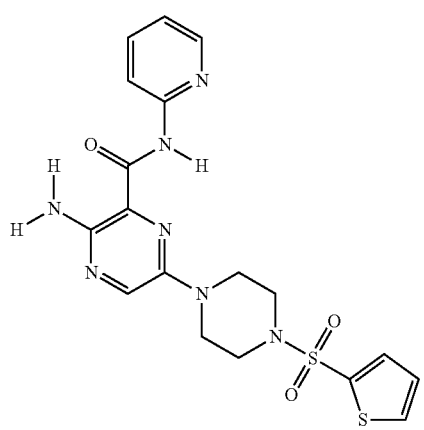 [SMILES: Nc1ncc(N2CCN(S(=O)(=O)c3cccs3)CC2)nc1C(=O)Nc1ccccn1]
I-116
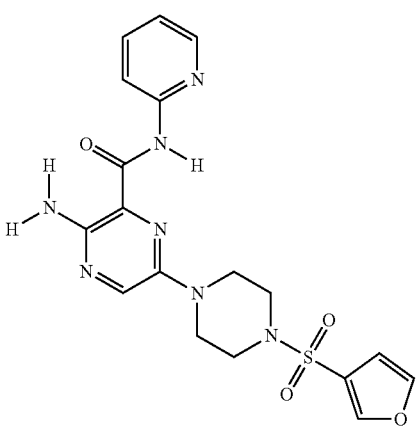
I-119
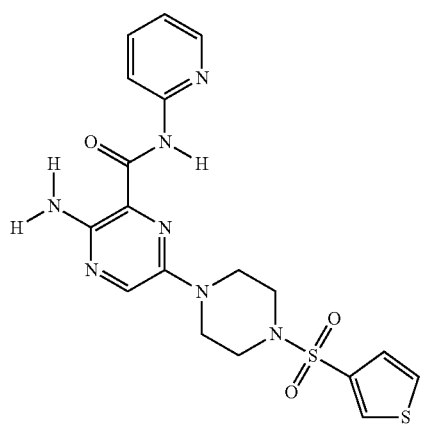 [SMILES: Nc1ncc(N2CCN(S(=O)(=O)c3ccsc3)CC2)nc1C(=O)Nc1ccccn1]
I-117
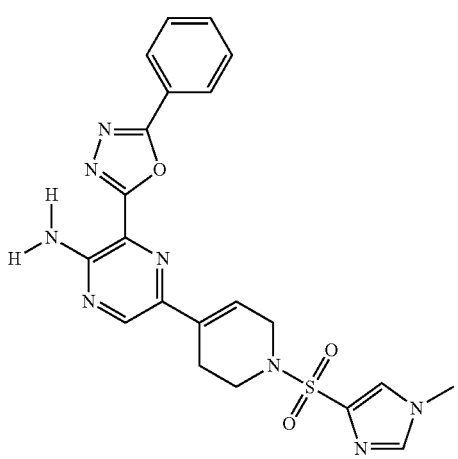 [SMILES: Cn1cnc(S(=O)(=O)N2CC=C(c3cnc(N)c(-c4nnc(-c5ccccc5)o4)n3)CC2)c1]
I-120

TABLE 3-continued
I-121
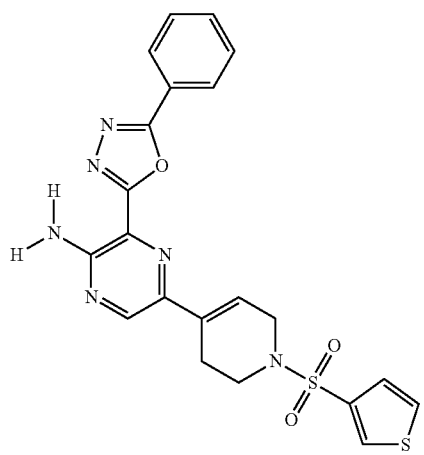 [SMILES: Nc1ncc(C2=CCN(S(=O)(=O)c3ccsc3)CC2)nc1-c1nnc(-c2ccccc2)o1]
I-122
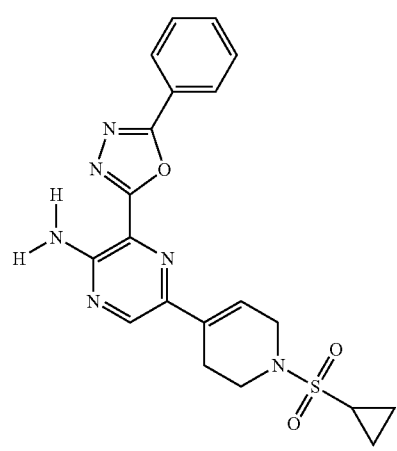 [SMILES: Nc1ncc(C2=CCN(S(=O)(=O)C3CC3)CC2)nc1-c1nnc(-c2ccccc2)o1]
I-123
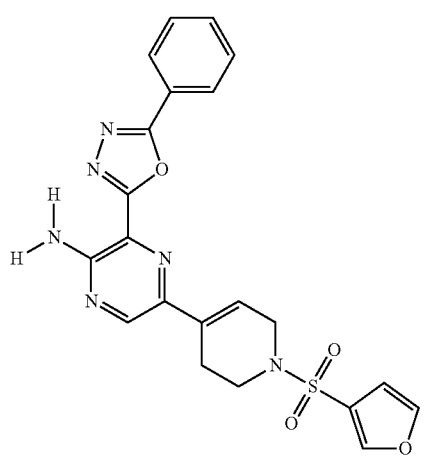
TABLE 3-continued
I-124
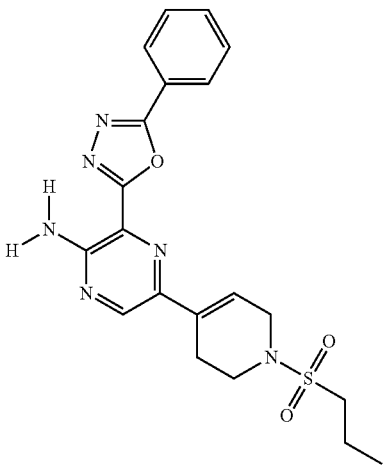 [SMILES: CCCS(=O)(=O)N1CC=C(c2cnc(N)c(-c3nnc(-c4ccccc4)o3)n2)CC1]
I-125
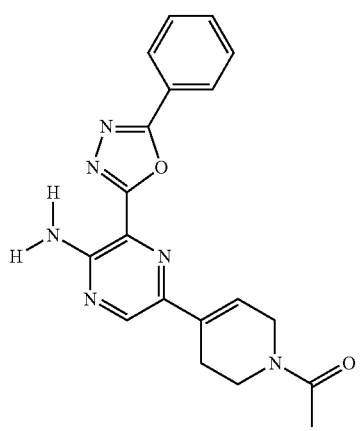 [SMILES: CC(=O)N1CC=C(c2cnc(N)c(-c3nnc(-c4ccccc4)o3)n2)CC1]
I-126
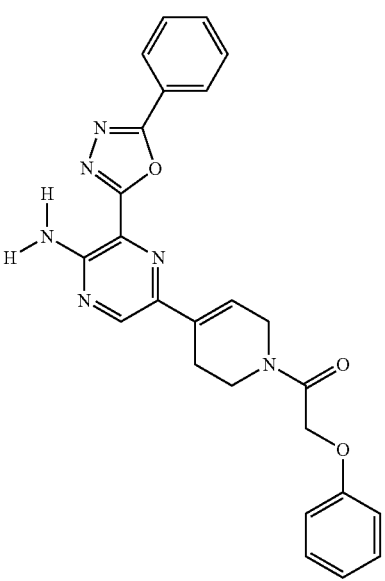 [SMILES: Nc1ncc(C2=CCN(C(=O)COc3ccccc3)CC2)nc1-c1nnc(-c2ccccc2)o1]

TABLE 3-continued
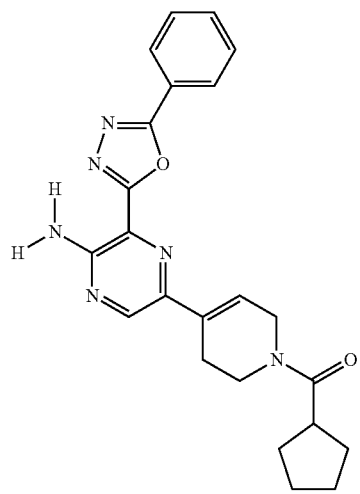 [SMILES: Nc1ncc(C2=CCN(C(=O)C3CCCC3)CC2)nc1-c1nnc(-c2ccccc2)o1]
I-127
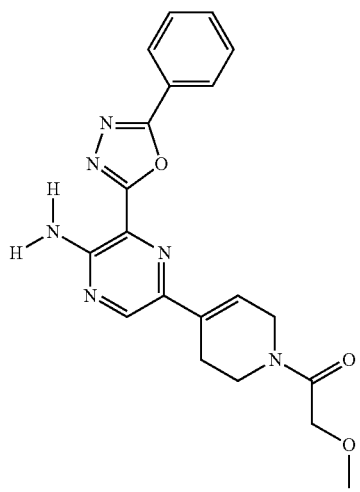 [SMILES: COCC(=O)N1CC=C(c2cnc(N)c(-c3nnc(-c4ccccc4)o3)n2)CC1]
I-130
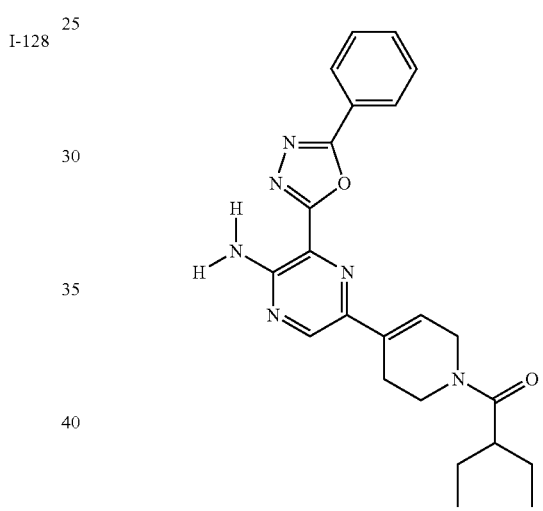
I-128
I-131
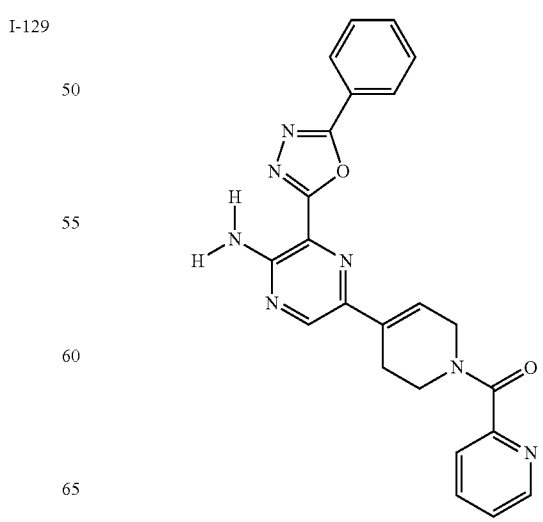
I-129
I-132

TABLE 3-continued
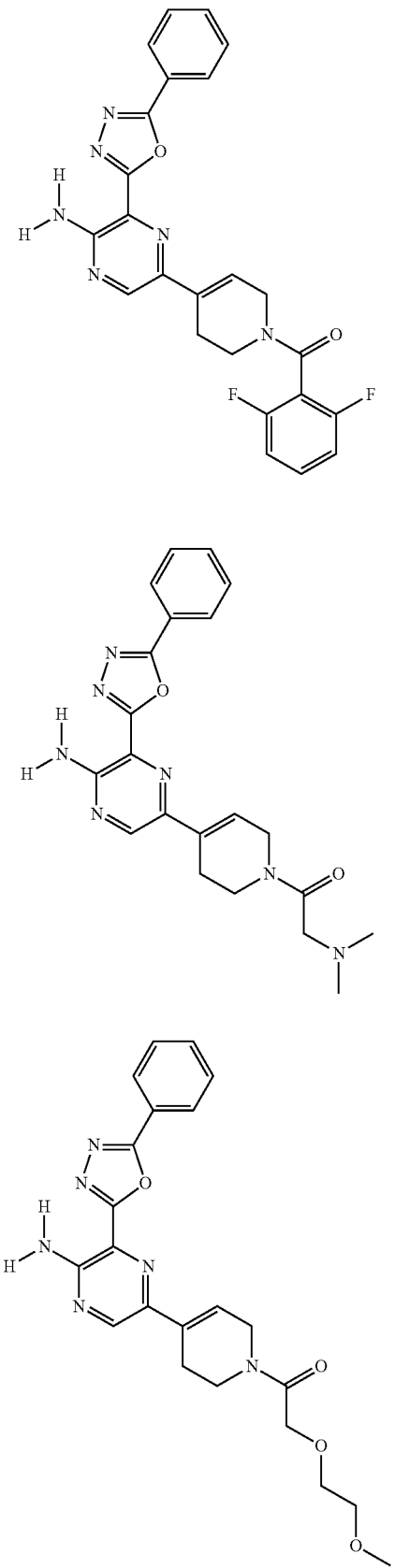
I-133
I-134
I-135
TABLE 3-continued
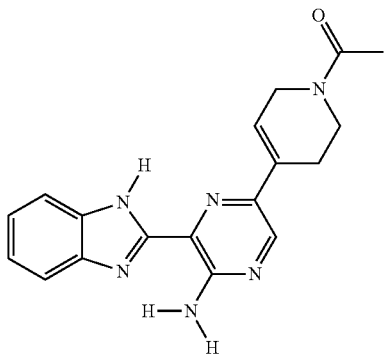 [SMILES: CC(=O)N1CC=C(c2cnc(N)c(-c3nc4ccccc4[nH]3)n2)CC1]
I-136
I-137
I-138
I-139

TABLE 3-continued
I-140
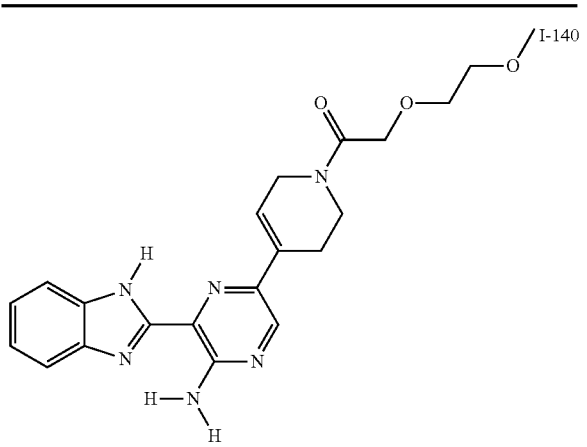
I-143
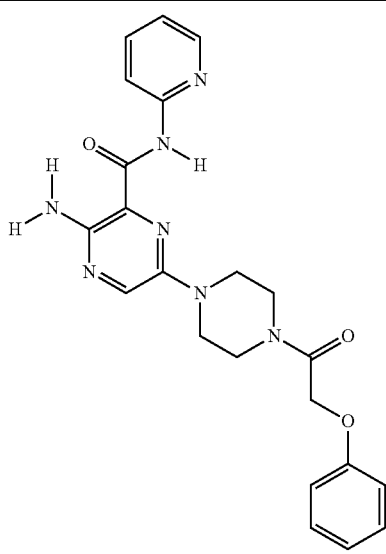
I-141
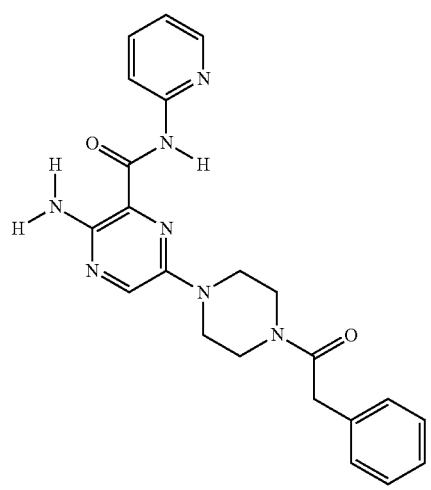 [SMILES: Nc1ncc(N2CCN(C(=O)Cc3ccccc3)CC2)nc1C(=O)Nc1ccccn1]
I-144
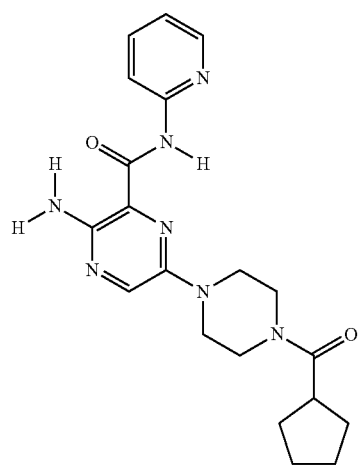
I-142
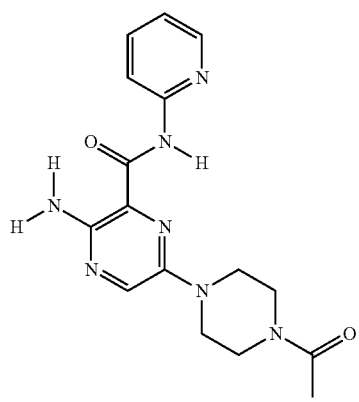 [SMILES: CC(=O)N1CCN(c2cnc(N)c(C(=O)Nc3ccccn3)n2)CC1]
I-145
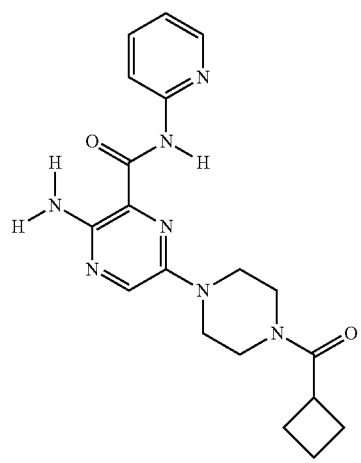 [SMILES: Nc1ncc(N2CCN(C(=O)C3CCC3)CC2)nc1C(=O)Nc1ccccn1]

TABLE 3-continued
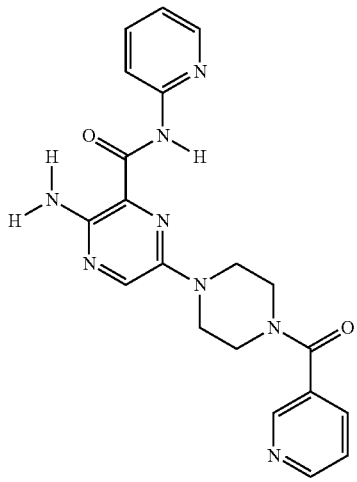 [SMILES: Nc1ncc(N2CCN(C(=O)c3cccnc3)CC2)nc1C(=O)Nc1ccccn1]
I-146
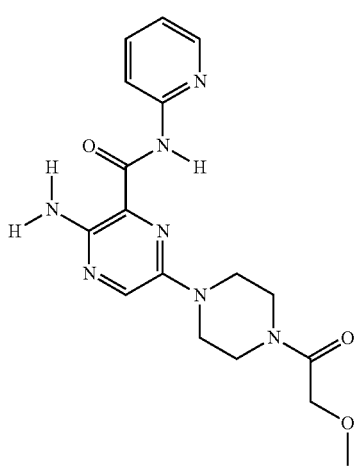 [SMILES: COCC(=O)N1CCN(c2cnc(N)c(C(=O)Nc3ccccn3)n2)CC1]
I-147
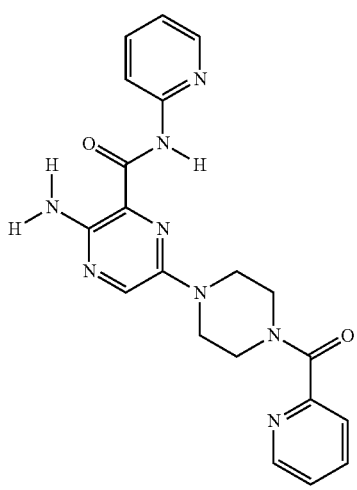 [SMILES: Nc1ncc(N2CCN(C(=O)c3ccccn3)CC2)nc1C(=O)Nc1ccccn1]
I-148
TABLE 3-continued
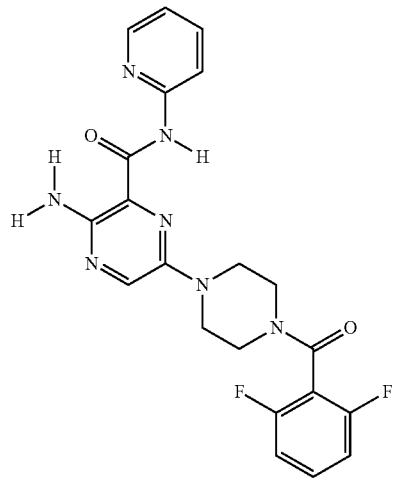 [SMILES: Nc1ncc(N2CCN(C(=O)c3c(F)cccc3F)CC2)nc1C(=O)Nc1ccccn1]
I-149
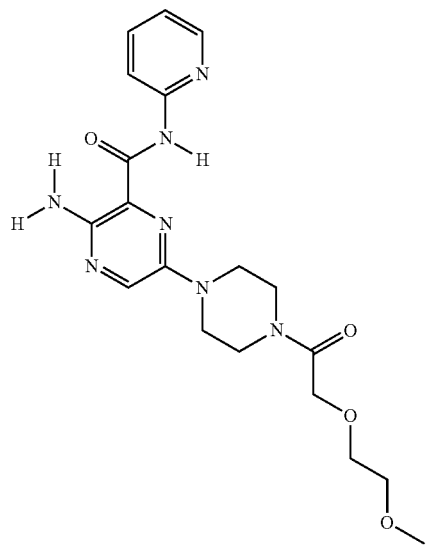 [SMILES: COCCOCC(=O)N1CCN(c2cnc(N)c(C(=O)Nc3ccccn3)n2)CC1]
I-150
I-151

TABLE 3-continued
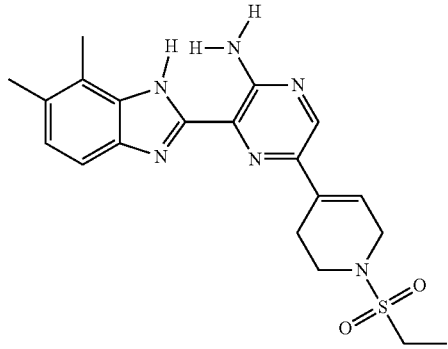 [SMILES: CCS(=O)(=O)N1CC=C(c2cnc(N)c(-c3nc4ccc(C)c(C)c4[nH]3)n2)CC1]
I-152
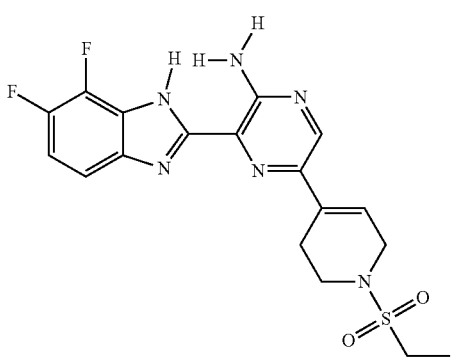 [SMILES: CCS(=O)(=O)N1CC=C(c2cnc(N)c(-c3nc4ccc(F)c(F)c4[nH]3)n2)CC1]
I-153
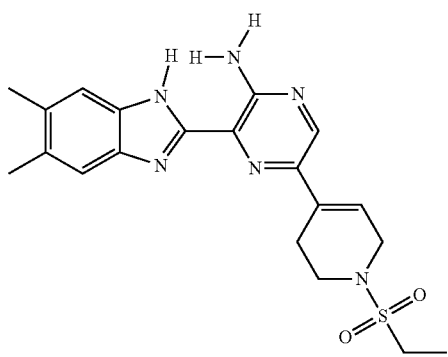 [SMILES: CCS(=O)(=O)N1CC=C(c2cnc(N)c(-c3nc4cc(C)c(C)cc4[nH]3)n2)CC1]
I-154
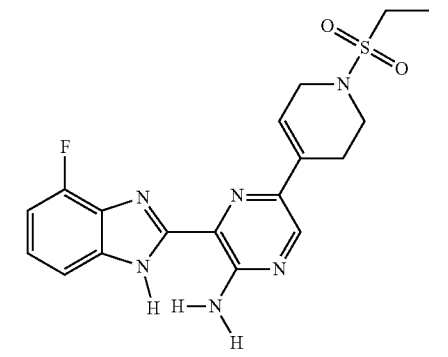 [SMILES: CCS(=O)(=O)N1CC=C(c2cnc(N)c(-c3nc4c(F)cccc4[nH]3)n2)CC1]
I-155
TABLE 3-continued
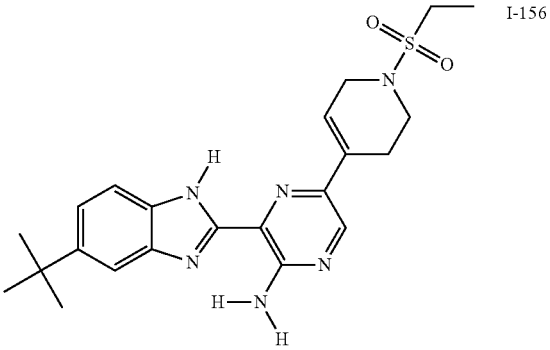
I-156
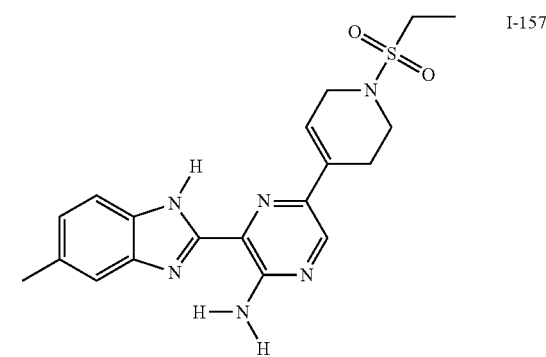
I-157
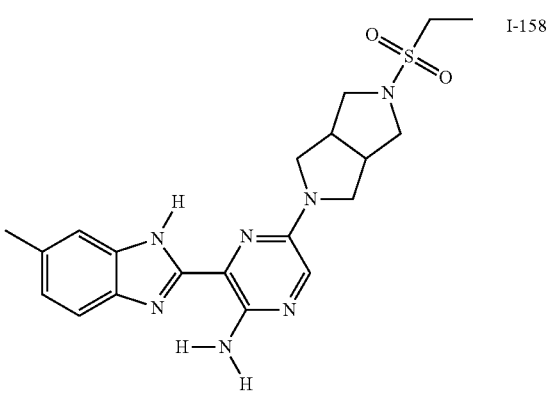
I-158
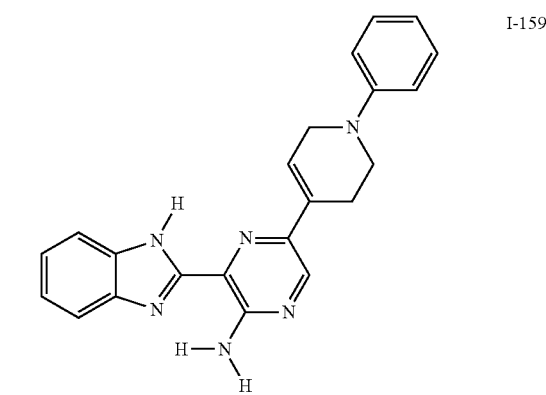
I-159

TABLE 3-continued
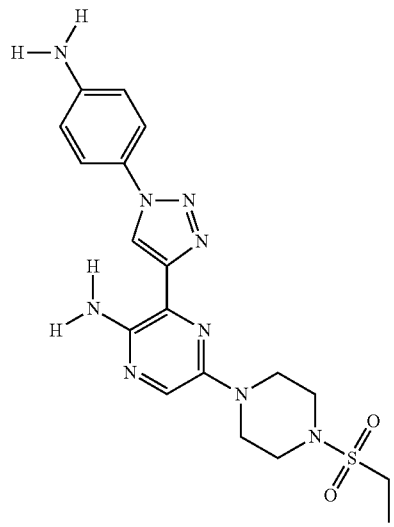 [SMILES: CCS(=O)(=O)N1CCN(c2cnc(N)c(-c3cn(-c4ccc(N)cc4)nn3)n2)CC1]
I-160
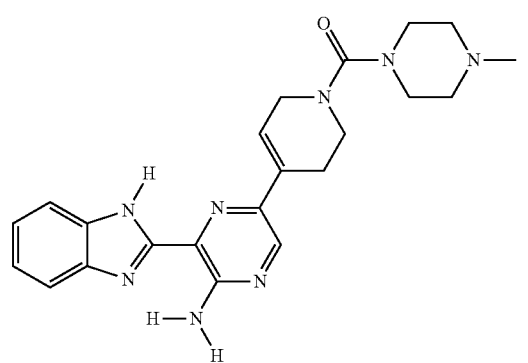
I-161
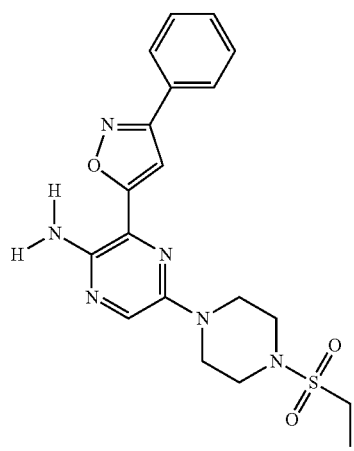 [SMILES: CCS(=O)(=O)N1CCN(c2cnc(N)c(-c3cc(-c4ccccc4)no3)n2)CC1]
I-162
TABLE 3-continued
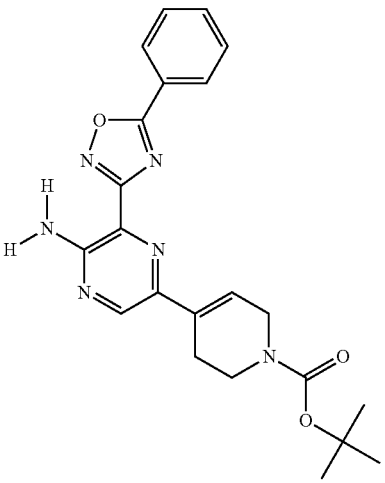 [SMILES: CC(C)(C)OC(=O)N1CC=C(c2cnc(N)c(-c3noc(-c4ccccc4)n3)n2)CC1]
I-163
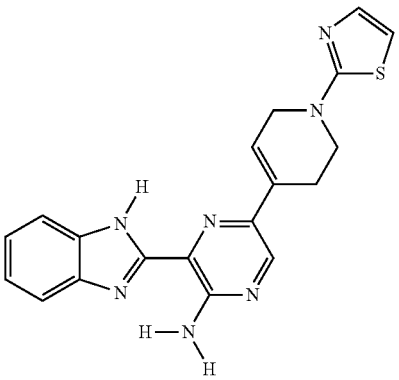 [SMILES: Nc1ncc(C2=CCN(c3nccs3)CC2)nc1-c1nc2ccccc2[nH]1]
I-164
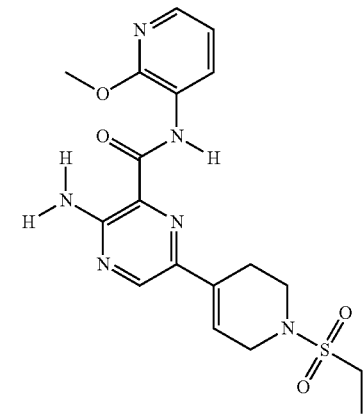 [SMILES: CCS(=O)(=O)N1CC=C(c2cnc(N)c(C(=O)Nc3cccnc3OC)n2)CC1]
I-165

TABLE 3-continued
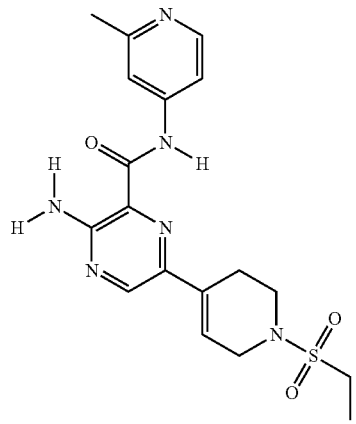 [SMILES: CCS(=O)(=O)N1CC=C(c2cnc(N)c(C(=O)Nc3ccnc(C)c3)n2)CC1]
I-166
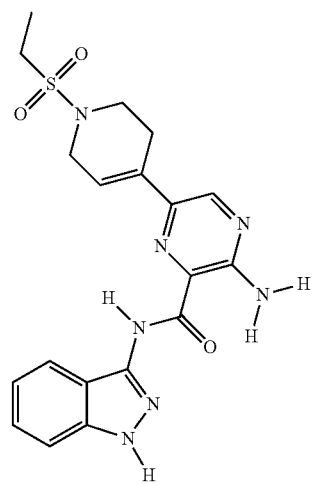
I-169
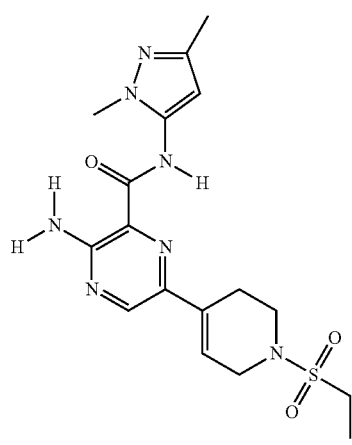 [SMILES: CCS(=O)(=O)N1CC=C(c2cnc(N)c(C(=O)Nc3cc(C)nn3C)n2)CC1]
I-167
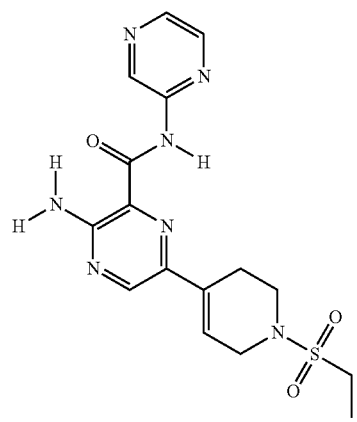 [SMILES: CCS(=O)(=O)N1CC=C(c2cnc(N)c(C(=O)Nc3cnccn3)n2)CC1]
I-170
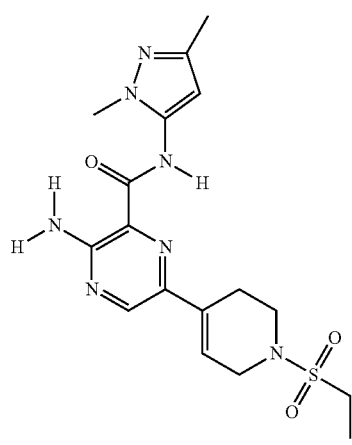 [SMILES: CCS(=O)(=O)N1CC=C(c2cnc(N)c(C(=O)Nc3cc(C)nn3C)n2)CC1]
I-168
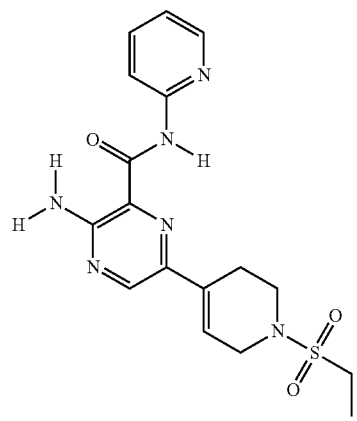 [SMILES: CCS(=O)(=O)N1CC=C(c2cnc(N)c(C(=O)Nc3ccccn3)n2)CC1]
I-171

TABLE 3-continued
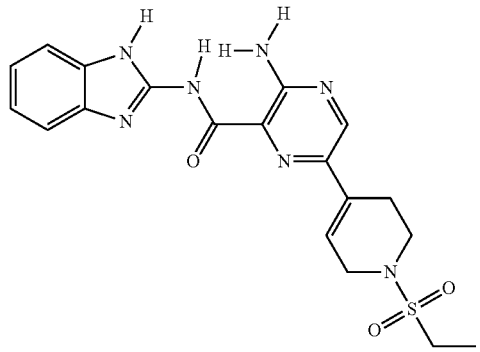 [SMILES: CCS(=O)(=O)N1CC=C(c2cnc(N)c(C(=O)Nc3nc4ccccc4[nH]3)n2)CC1]
I-172
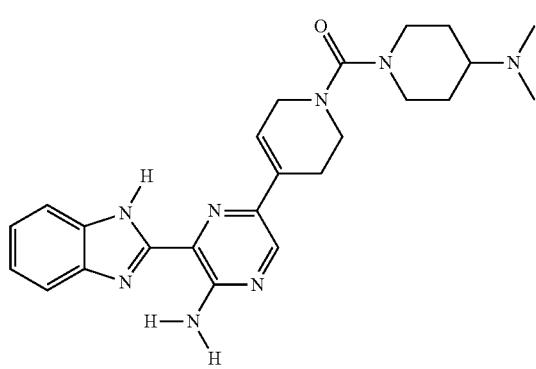 [SMILES: CN(C)C1CCN(C(=O)N2CC=C(c3cnc(N)c(-c4nc5ccccc5[nH]4)n3)CC2)CC1]
I-173
TABLE 4
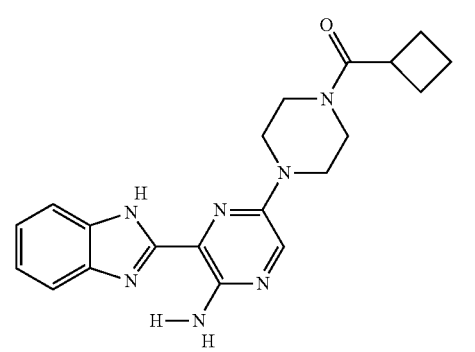
I-174
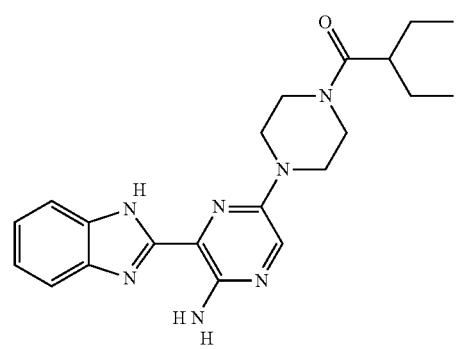
I-175
TABLE 4-continued
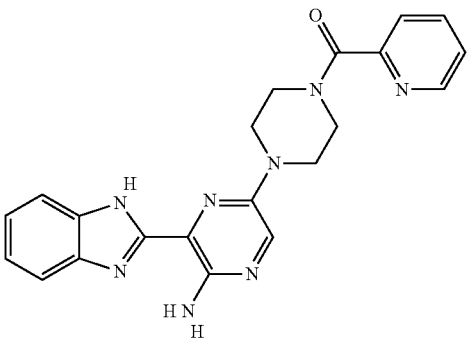
I-176
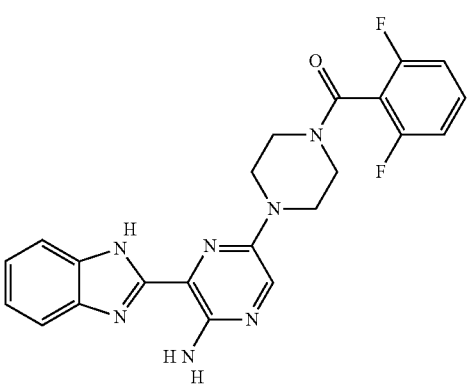
I-177
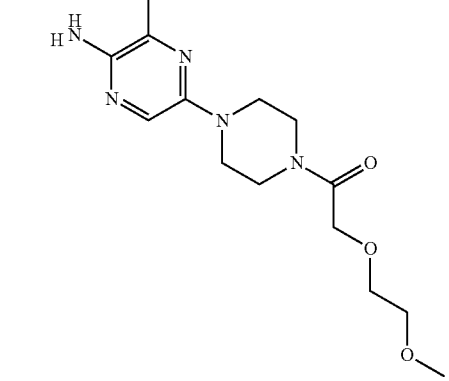
I-178

TABLE 4-continued
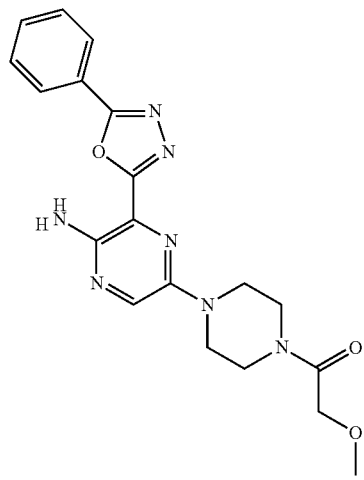
I-179
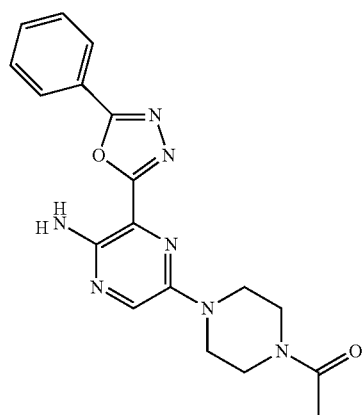
I-180
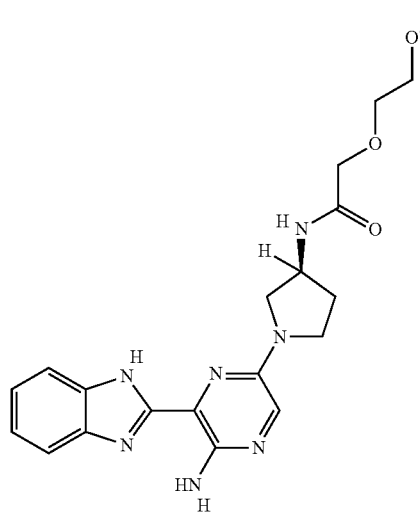
I-181
TABLE 4-continued
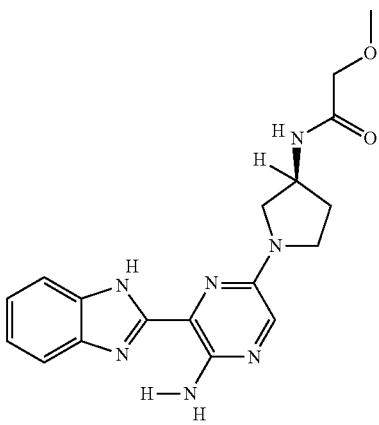
I-182
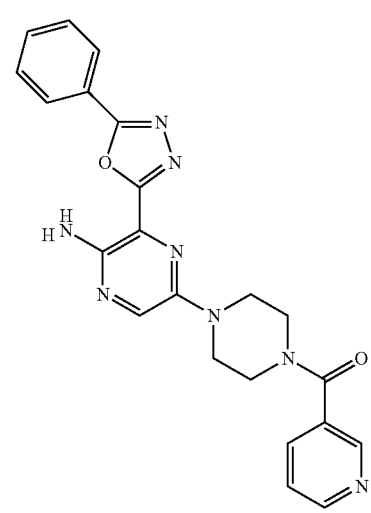
I-183
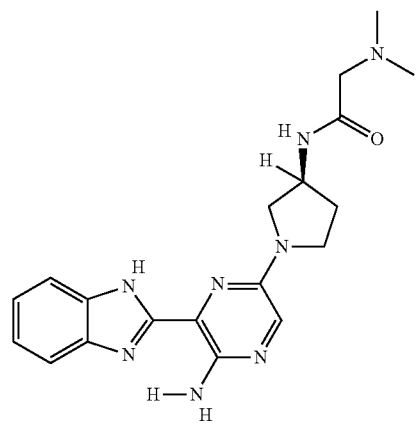
I-184

TABLE 4-continued
I-185
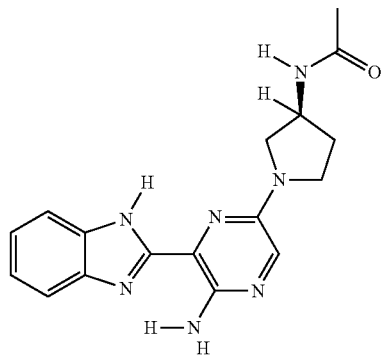
I-186
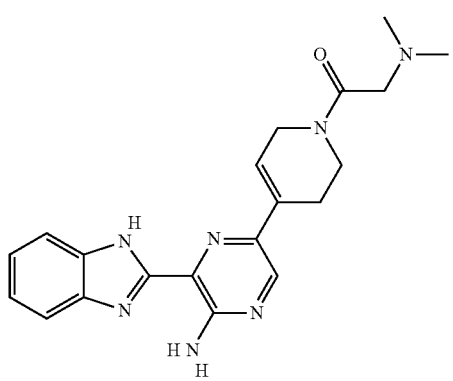
I-187
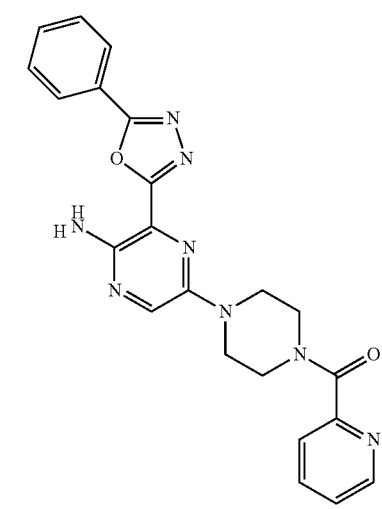
TABLE 4-continued
I-188
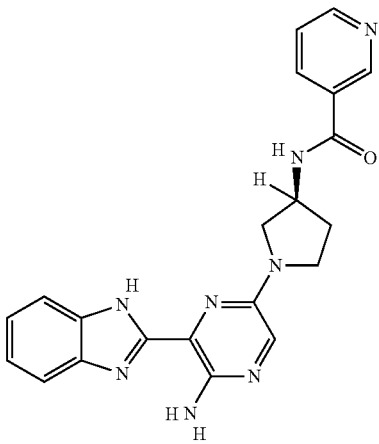
I-189
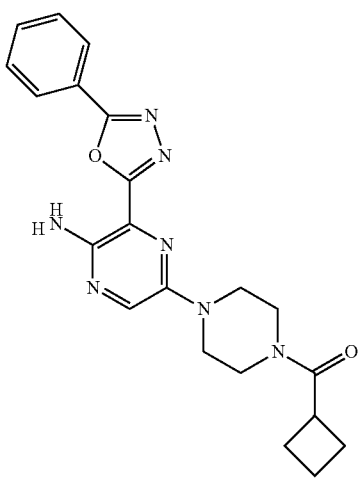
I-190
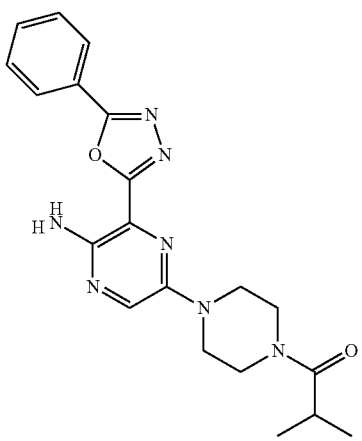

TABLE 4-continued
I-191
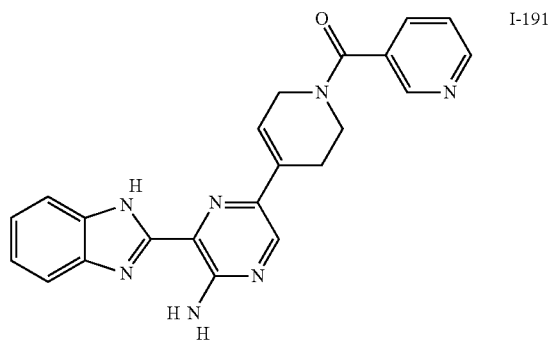
I-192
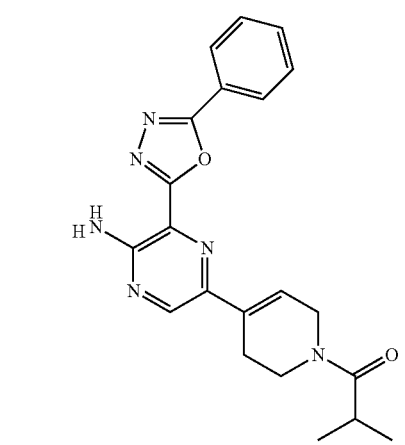
I-193
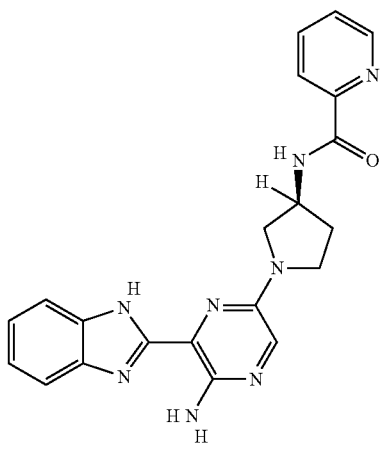
TABLE 4-continued
I-194
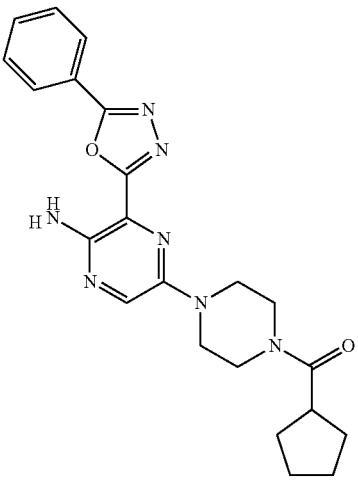
I-195
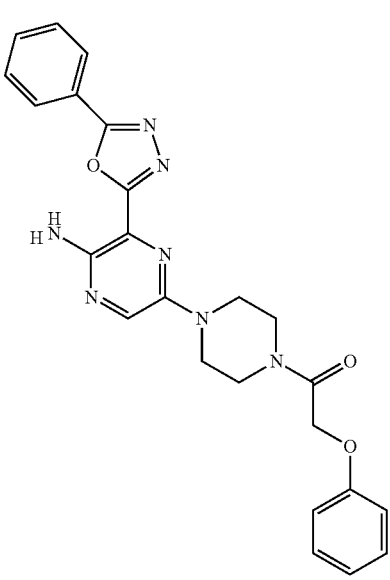
I-196
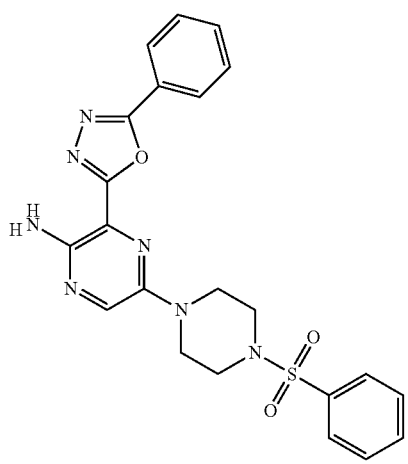

TABLE 4-continued
I-197
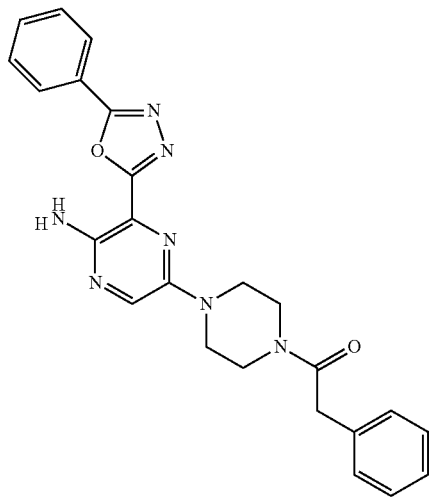
I-198
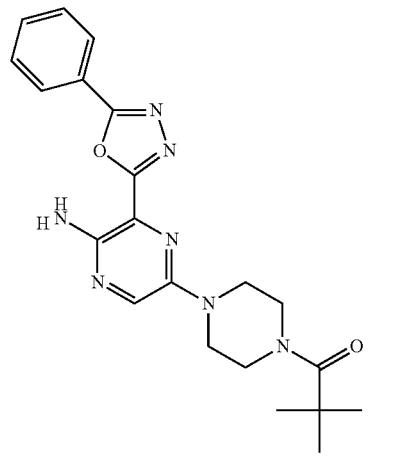
I-199
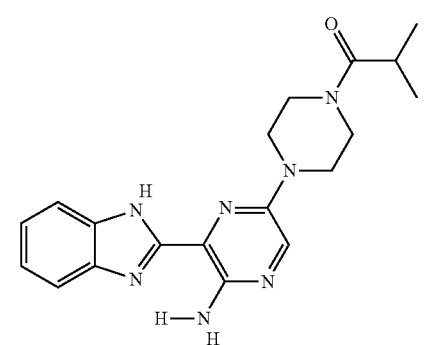
I-200
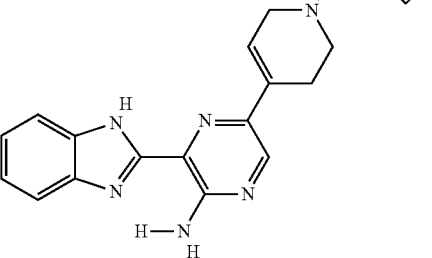
TABLE 4-continued
I-201
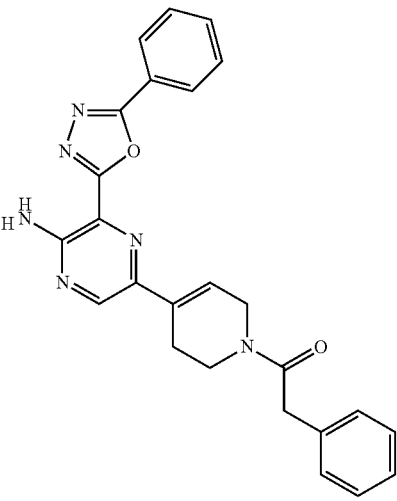
I-202
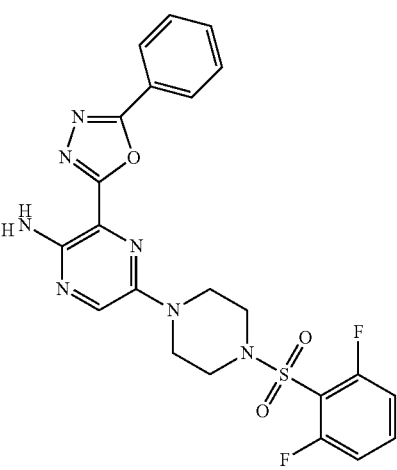
I-203
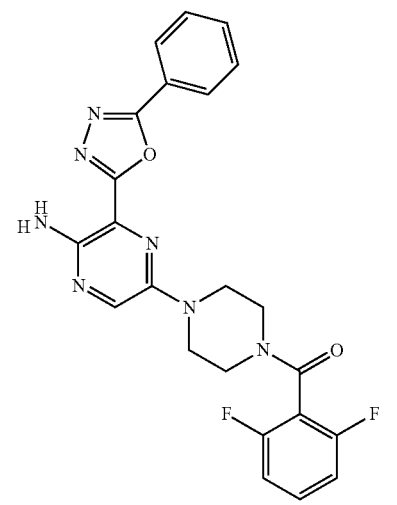

TABLE 4-continued
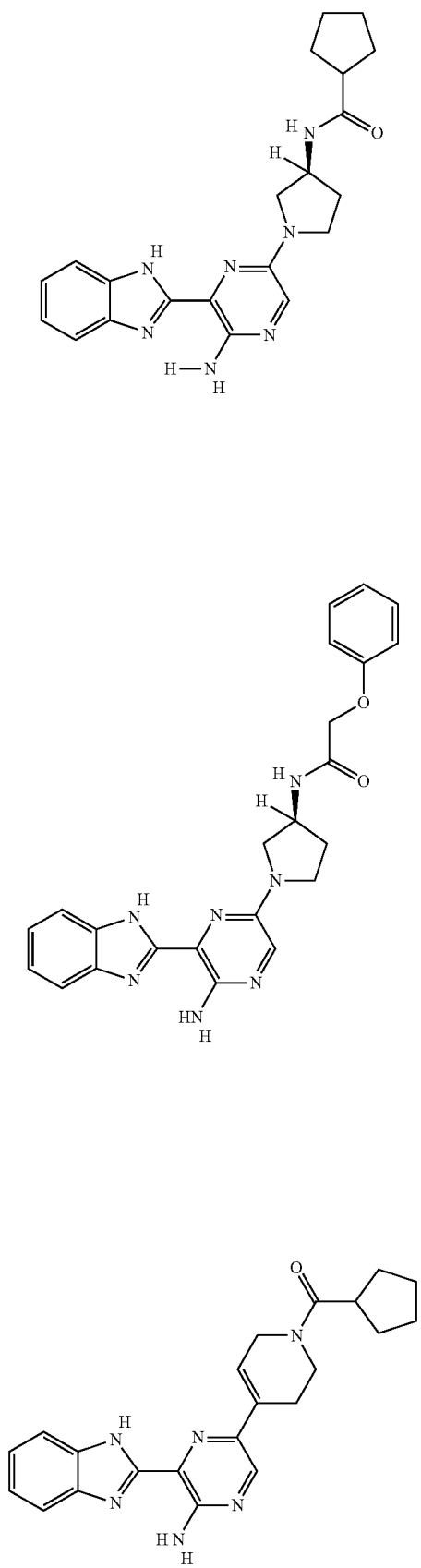
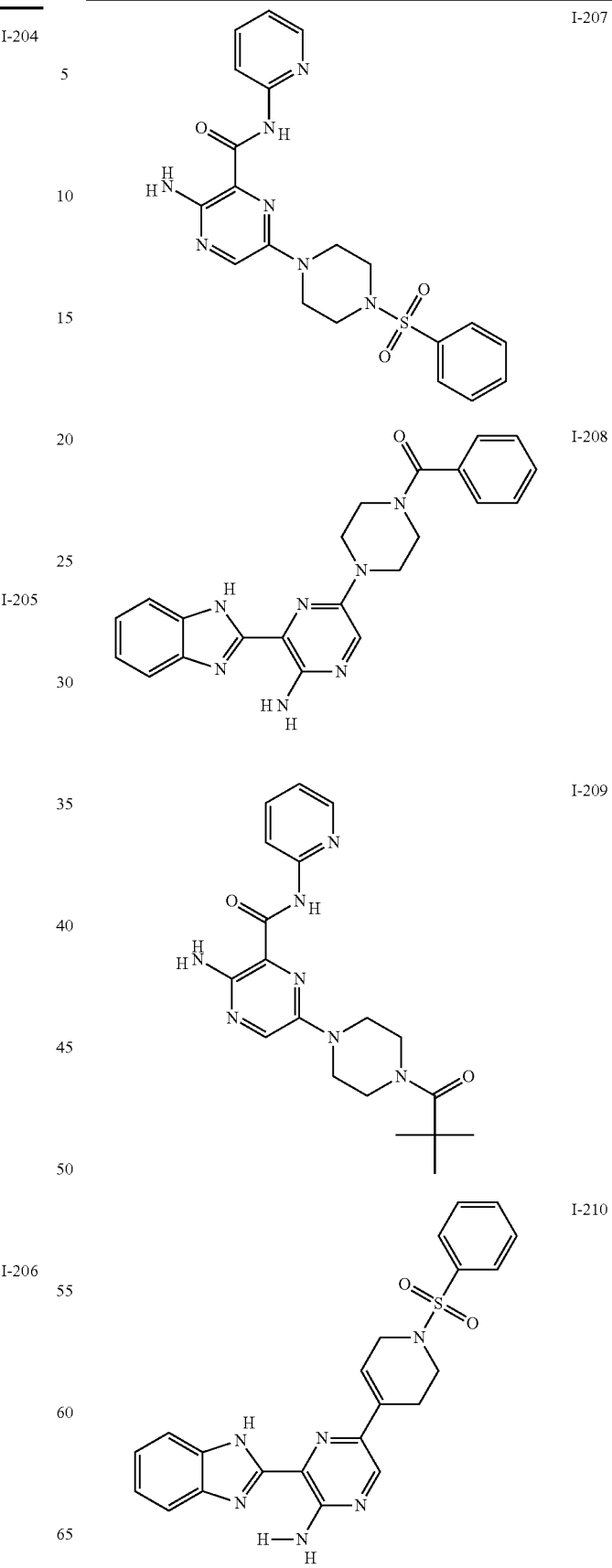

TABLE 4-continued
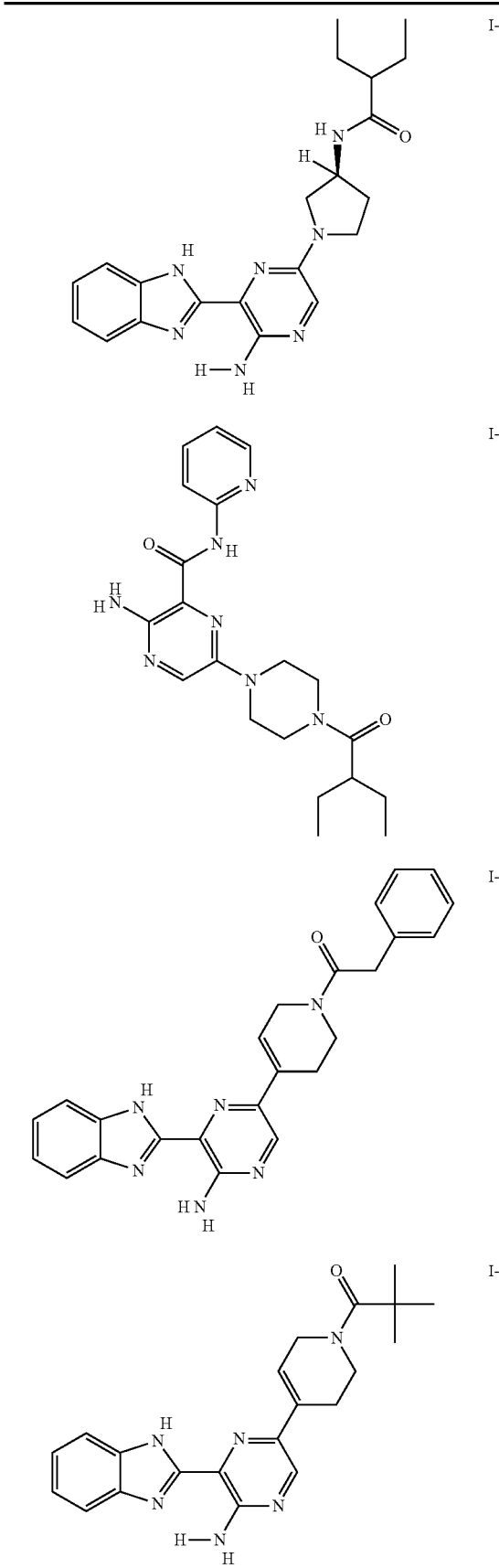
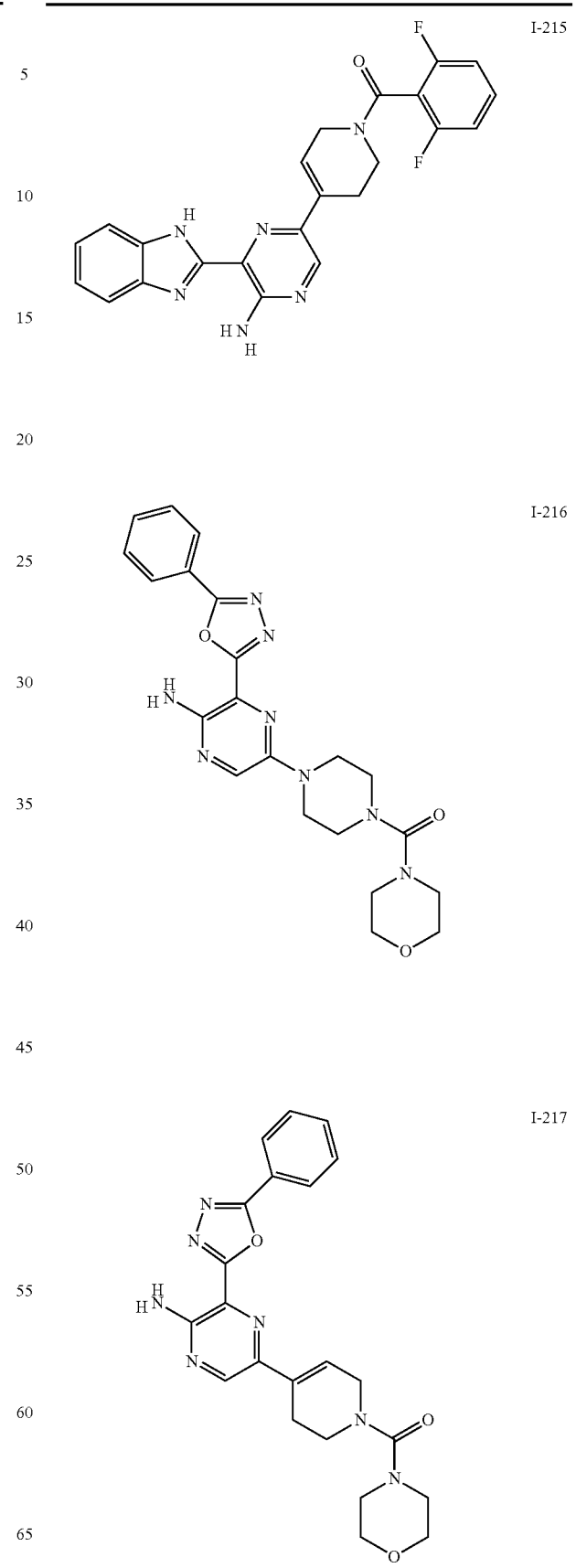

TABLE 4-continued
I-218
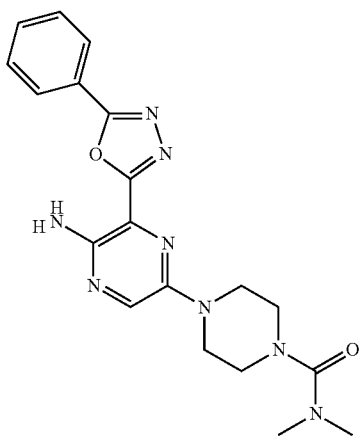
I-219
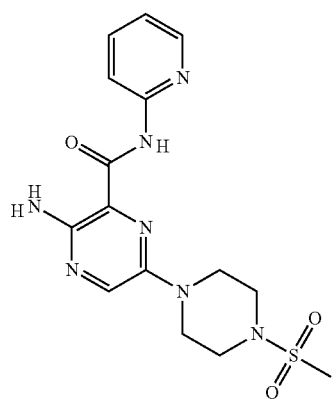
I-220
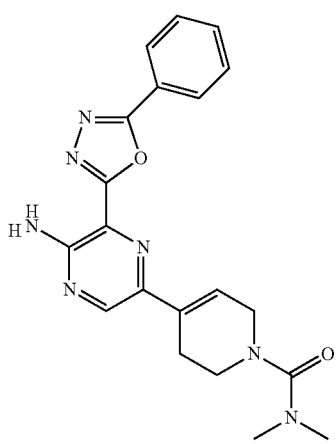
TABLE 4-continued
I-221
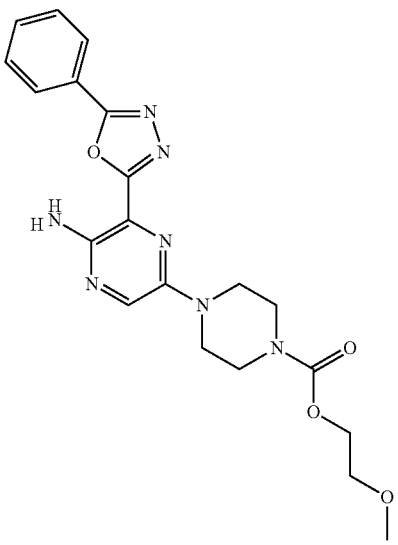
I-222
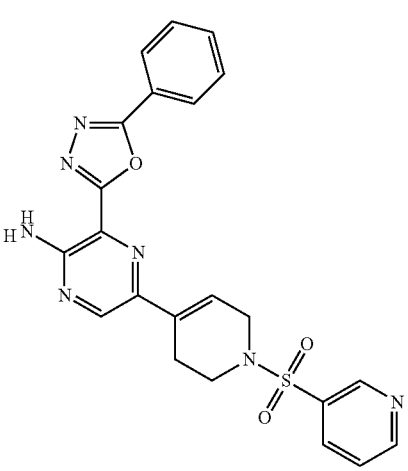
I-223
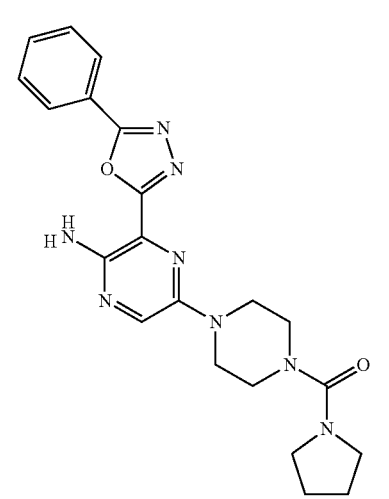

TABLE 4-continued
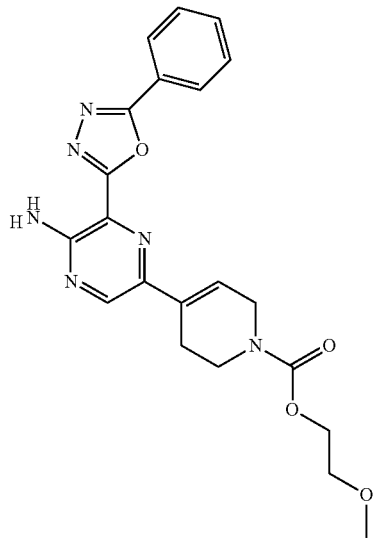
I-224
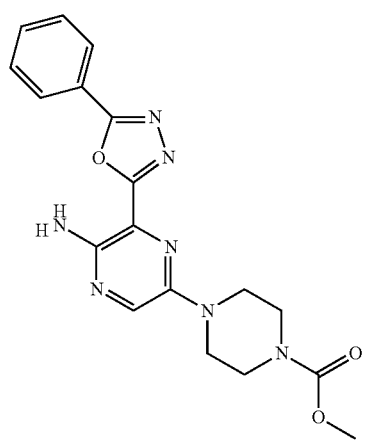
I-225
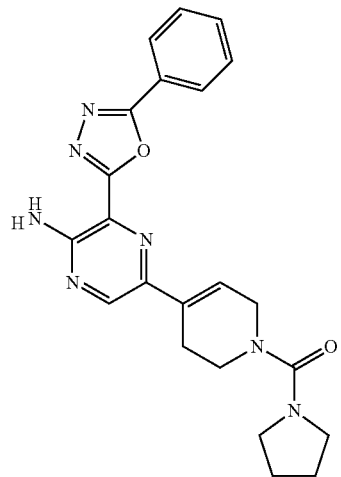
I-226
TABLE 4-continued
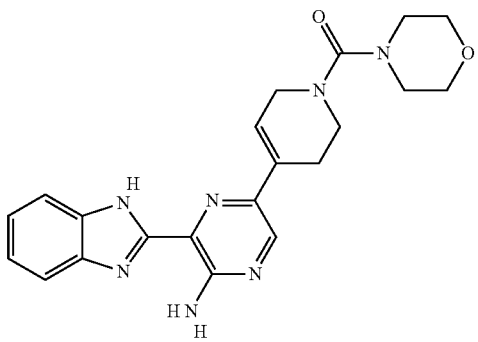
I-227
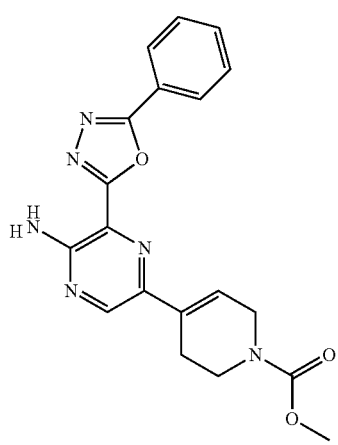
I-228
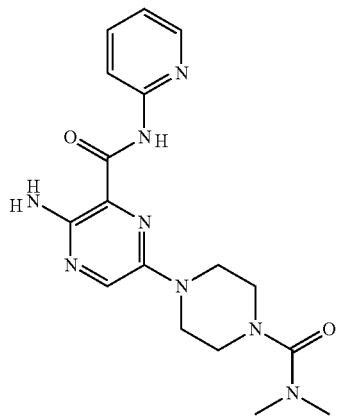
I-229

TABLE 4-continued
I-230
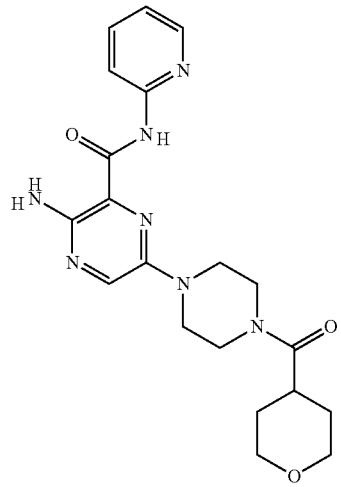
I-231
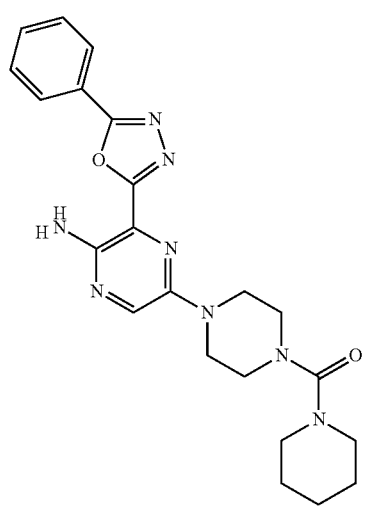
I-232
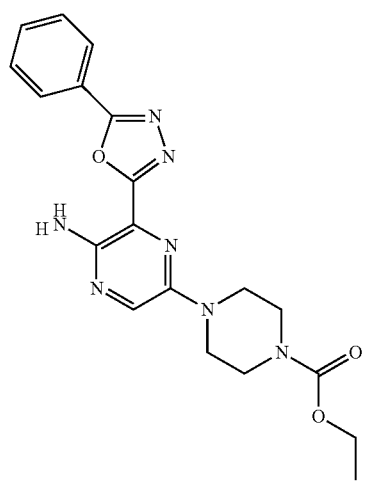
TABLE 4-continued
I-233
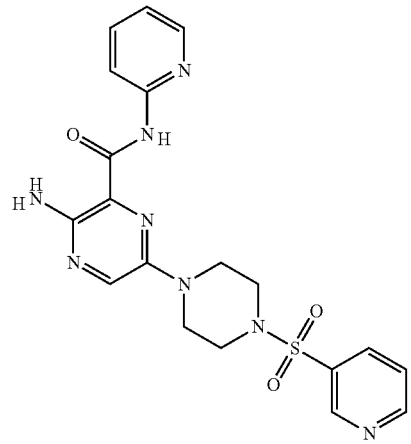
I-234
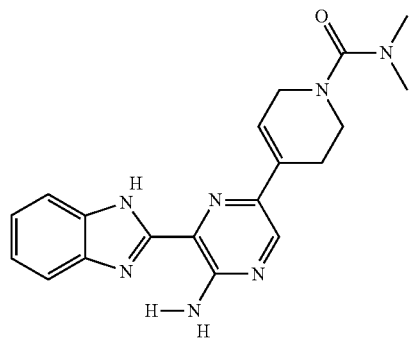
I-235
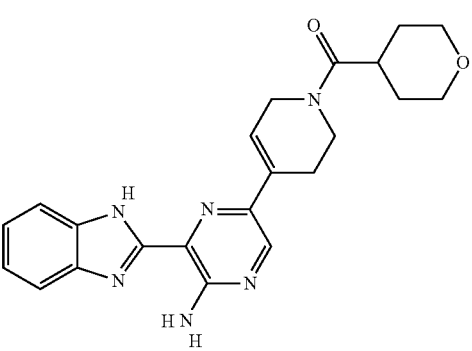
I-236
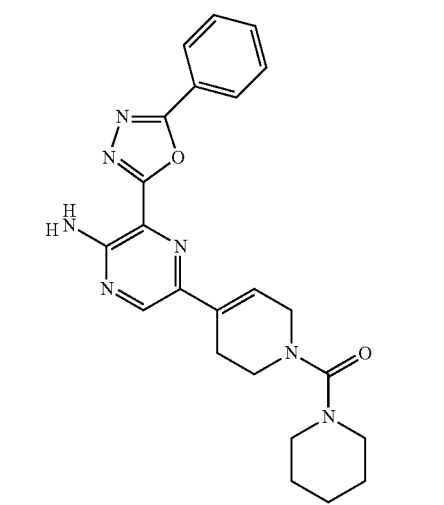

TABLE 4-continued
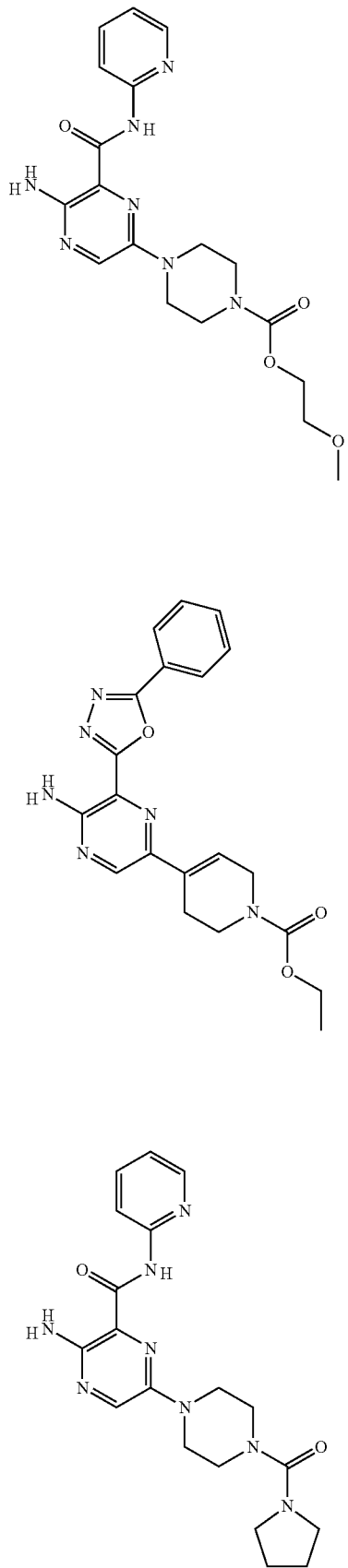
I-237
I-238
I-239
TABLE 4-continued
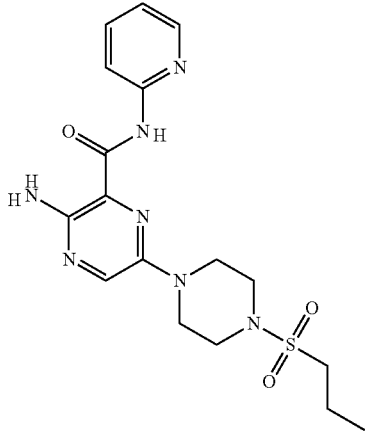
I-240
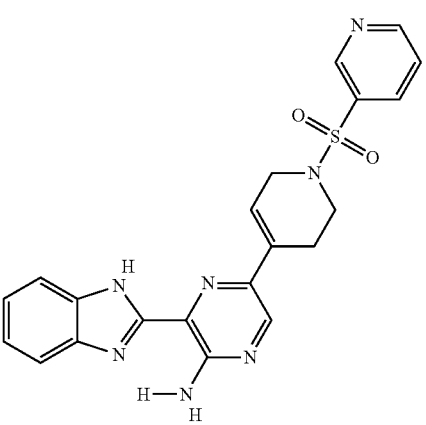
I-241
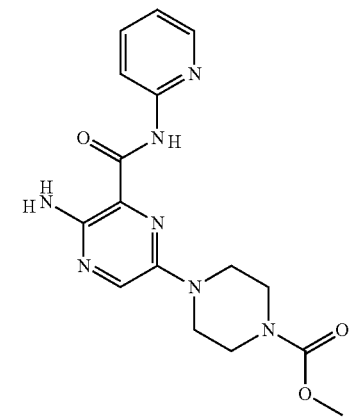
I-242
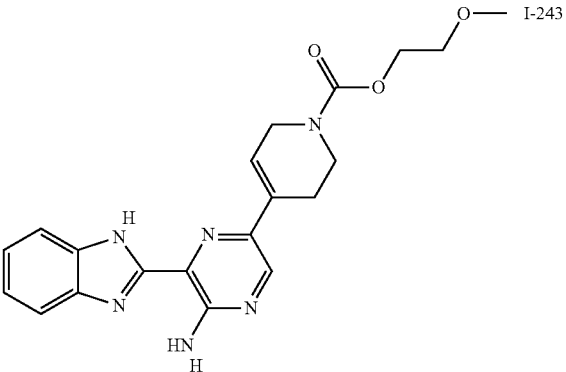
I-243

TABLE 4-continued
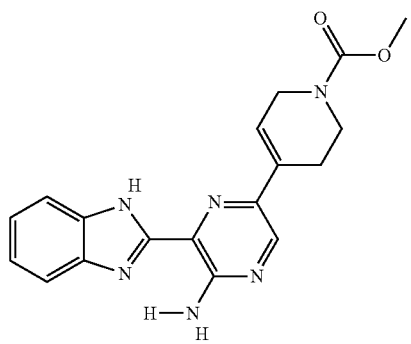
I-244
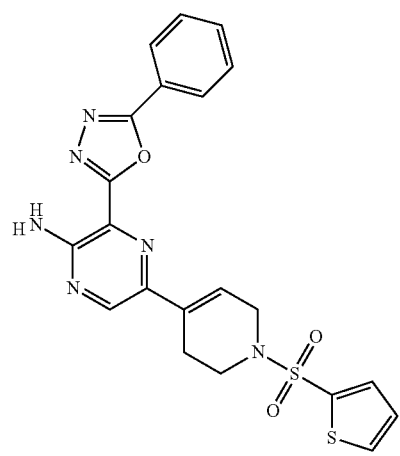
I-245
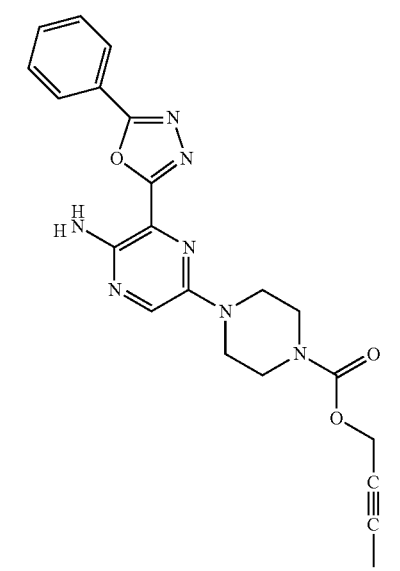
I-246
TABLE 4-continued
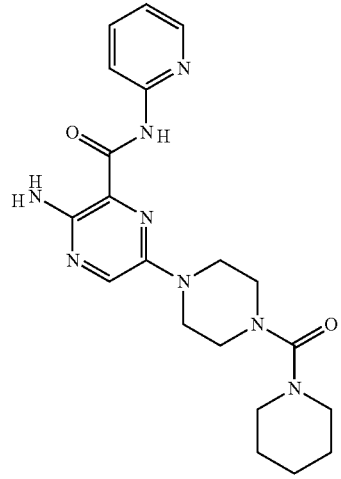
I-247
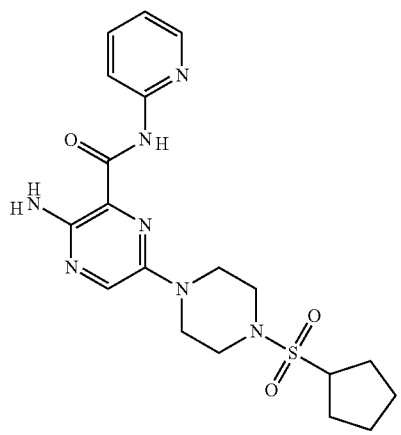
I-248
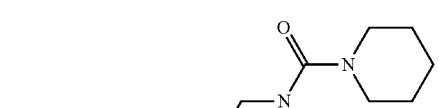
I-249
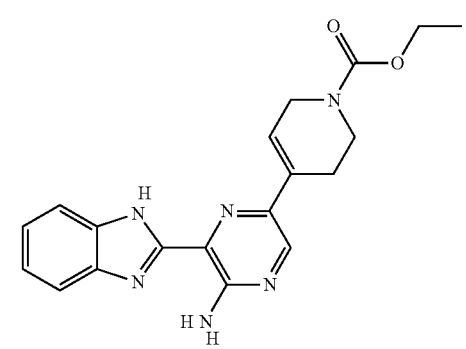
I-250

TABLE 4-continued
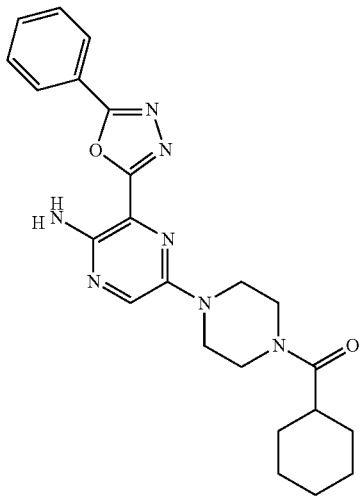
I-251
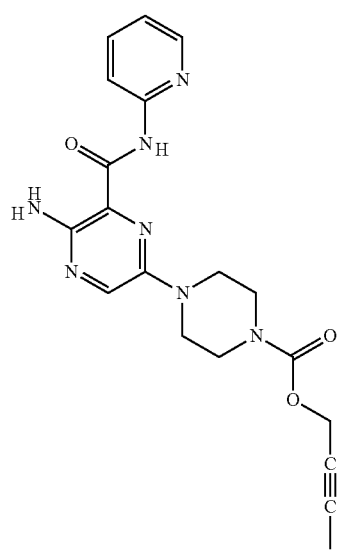
I-252
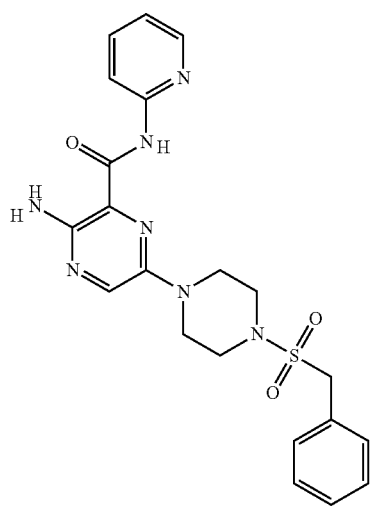
I-253
TABLE 4-continued
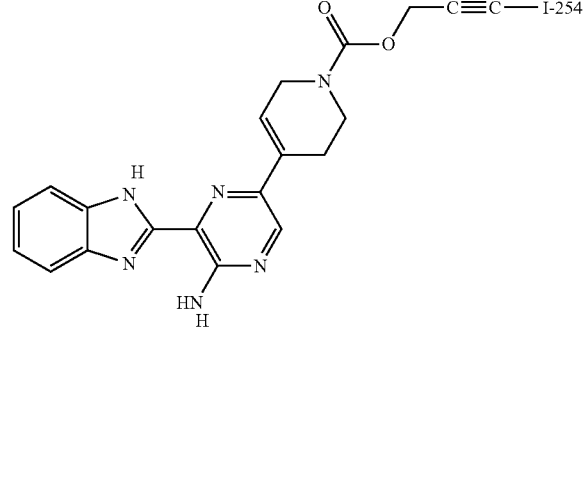
I-254
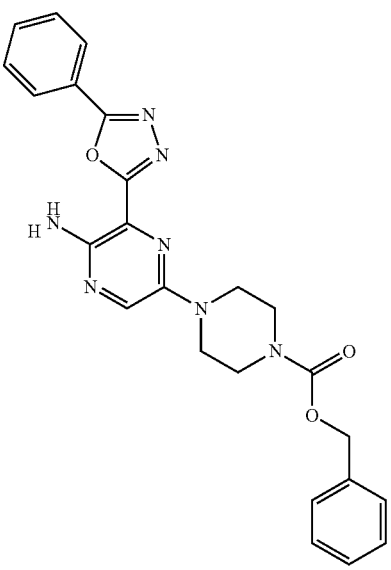
I-255
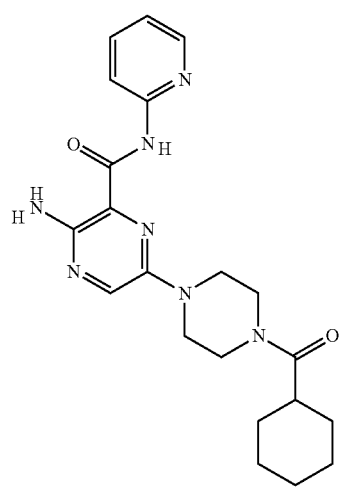
I-256

TABLE 4-continued
I-257
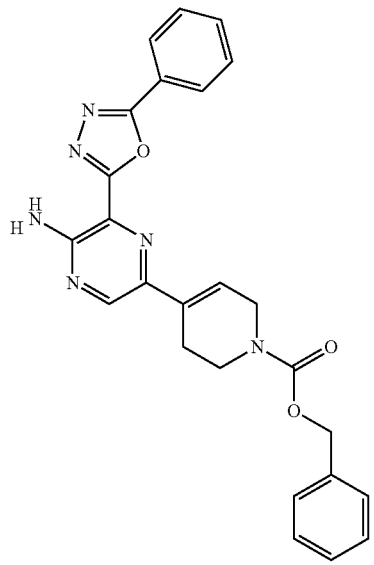
I-260
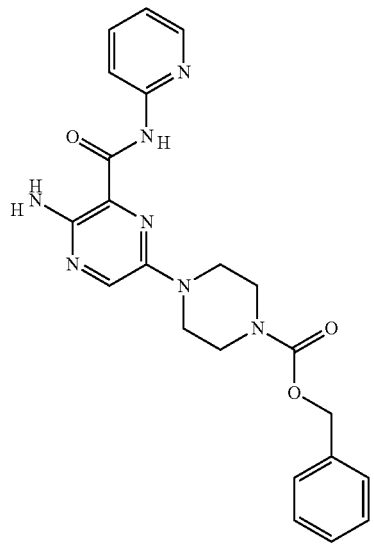
I-258
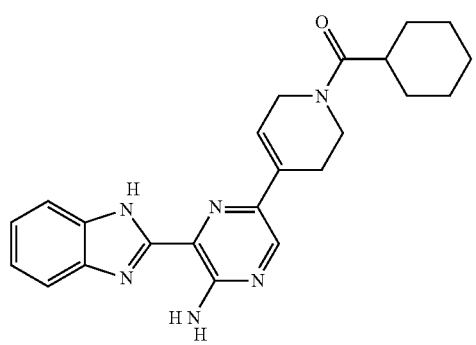
I-261
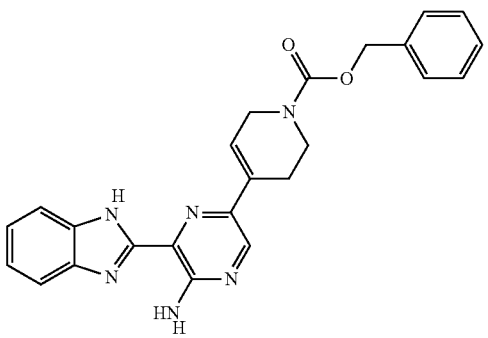
I-259
I-262
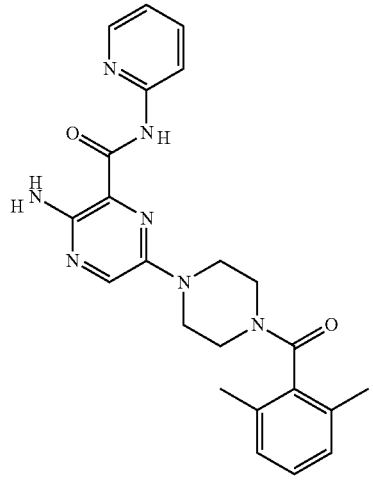

TABLE 4-continued
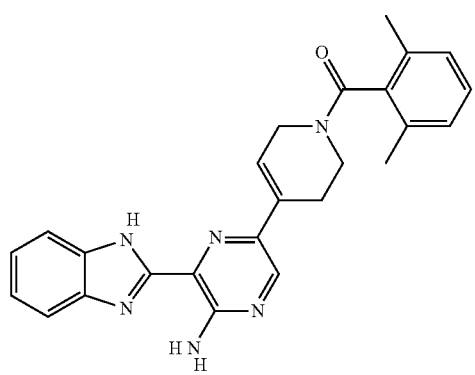
I-263
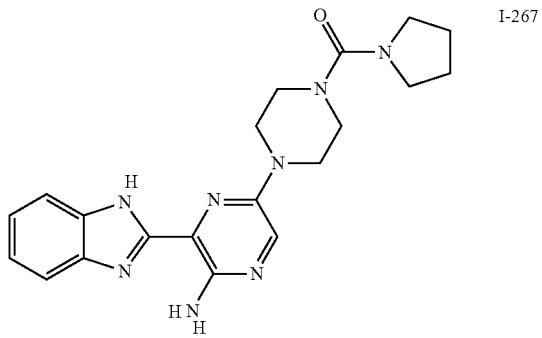
I-267
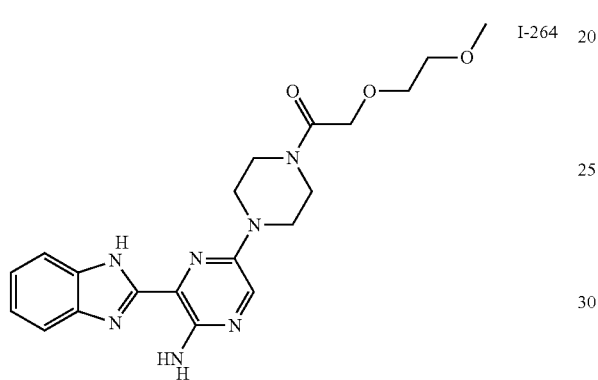
I-264
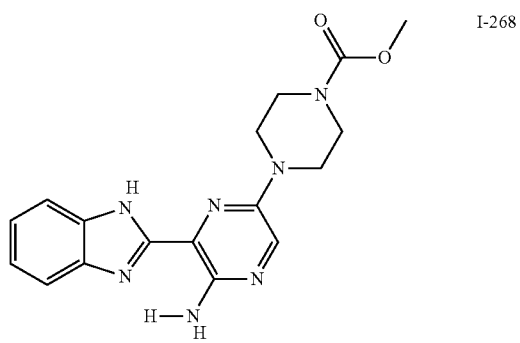
I-268
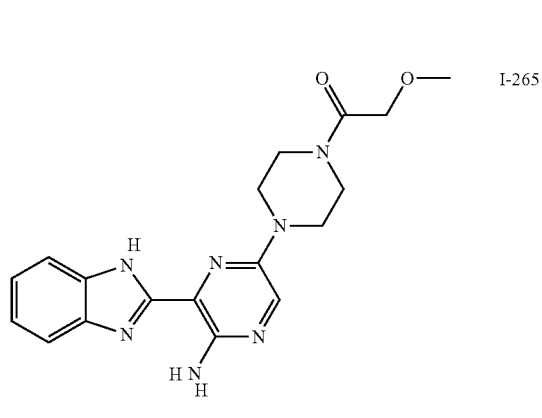
I-265
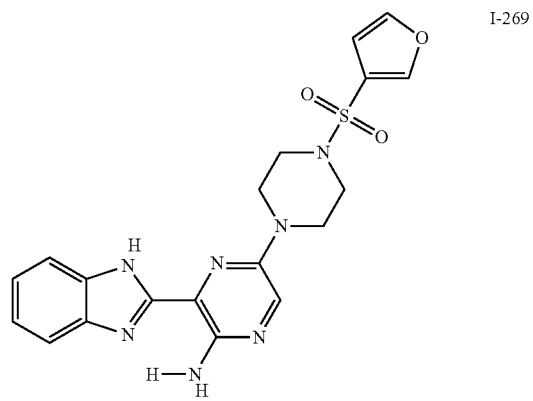
I-269
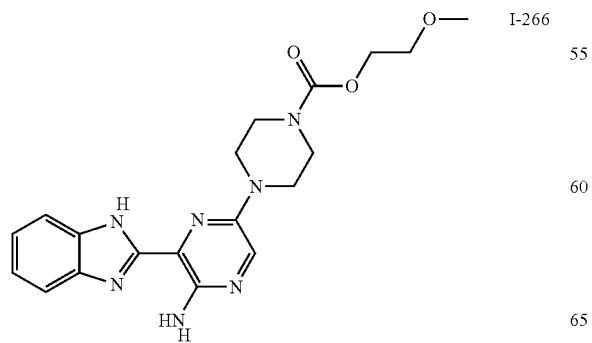
I-266
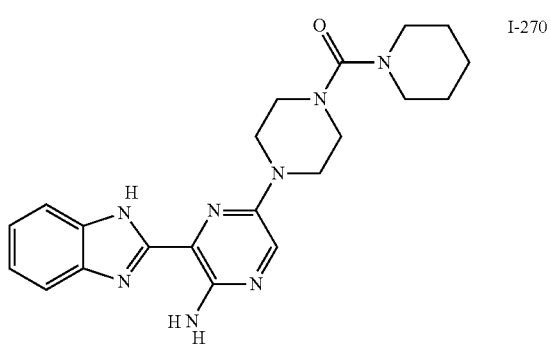
I-270

TABLE 4-continued
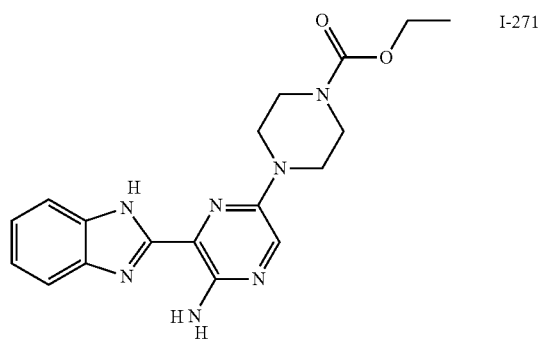
I-271
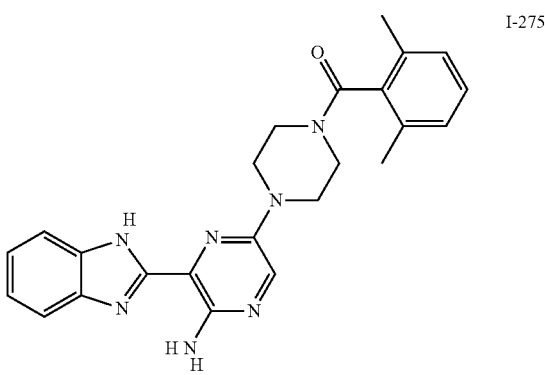
I-275
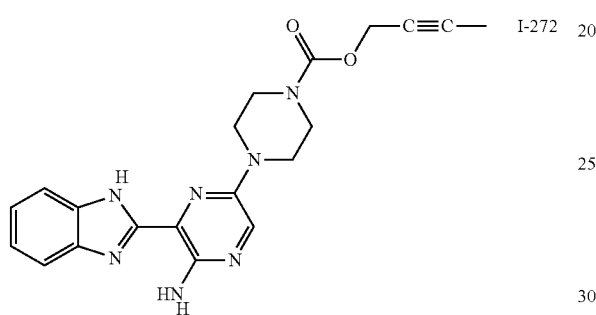
I-272
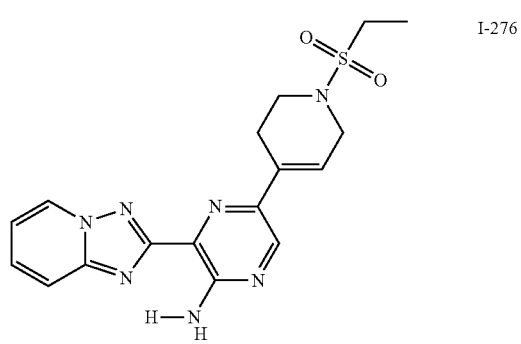
I-276
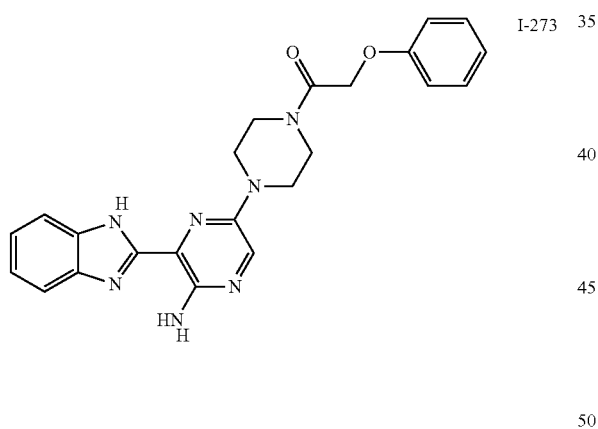
I-273
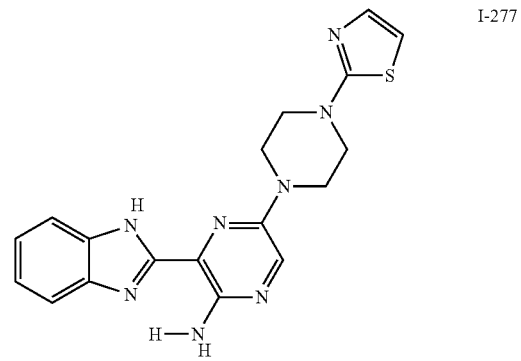
I-277
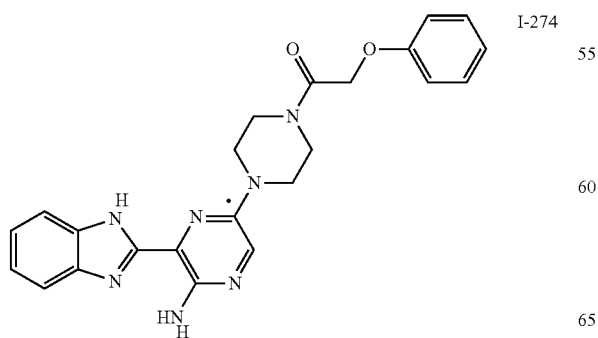
I-274
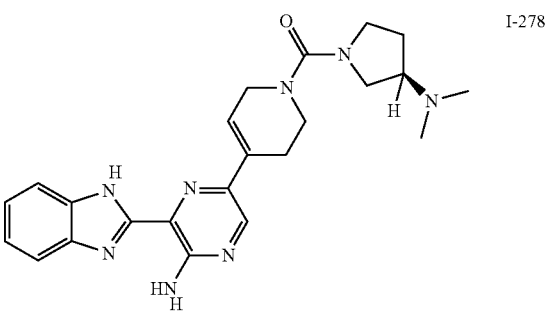
I-278

TABLE 4-continued
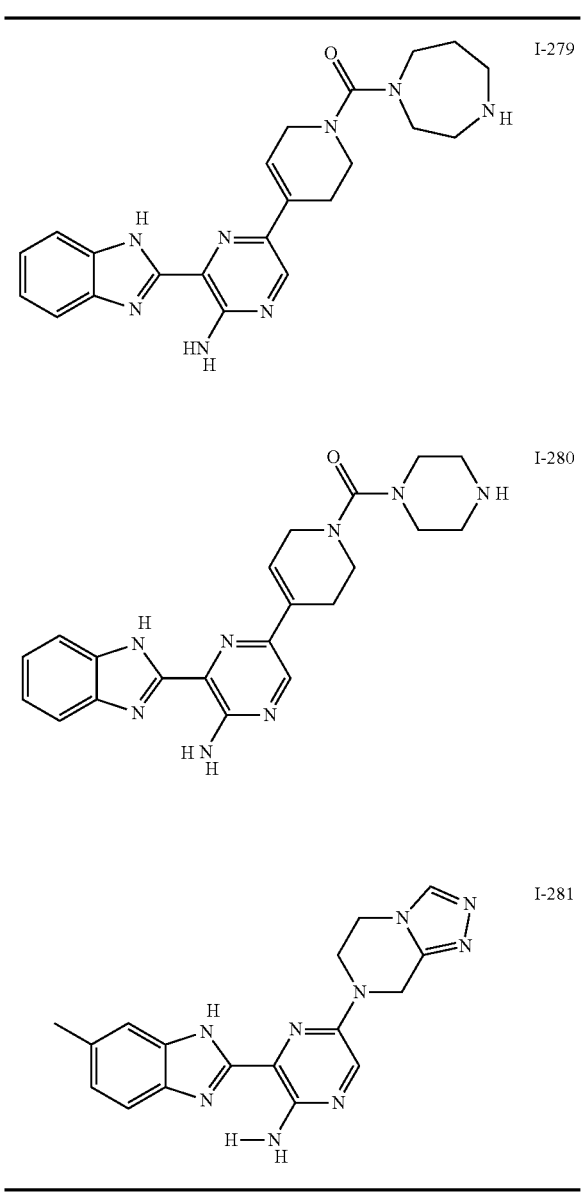
TABLE 5
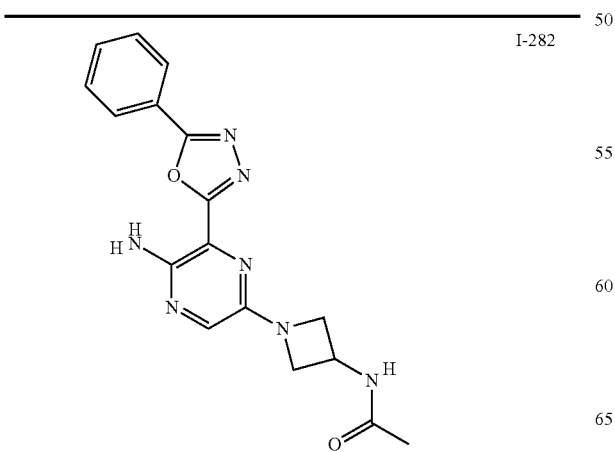
TABLE 5-continued
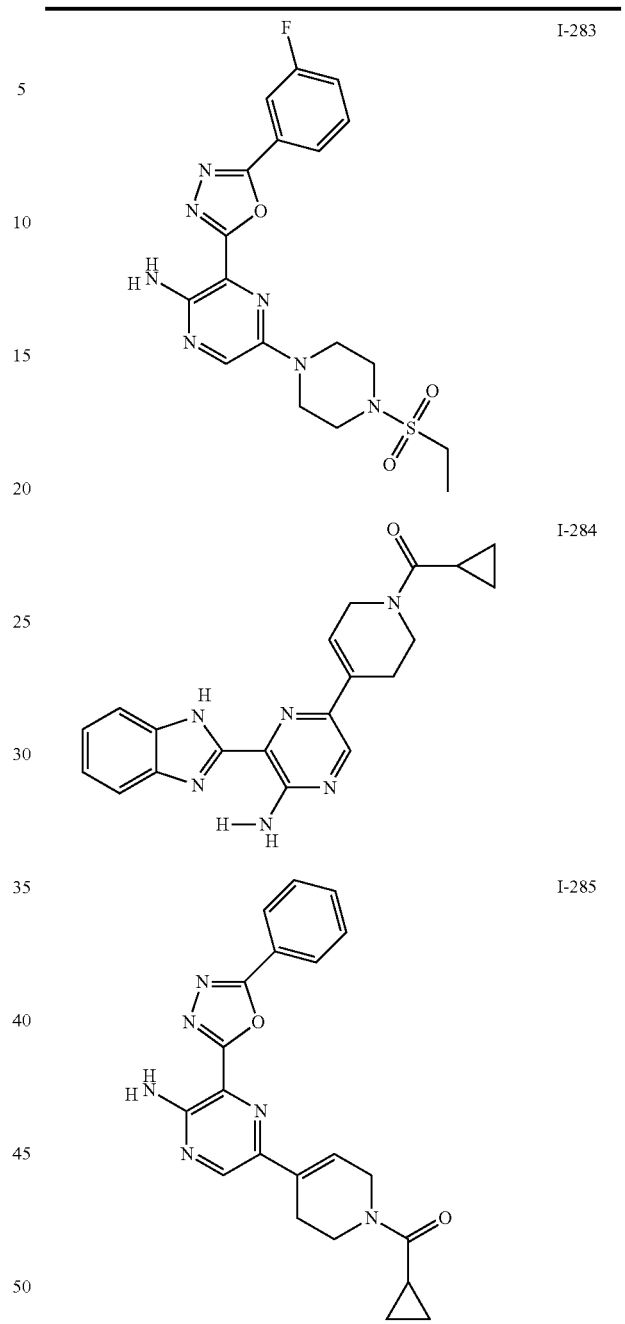

TABLE 5-continued
I-287
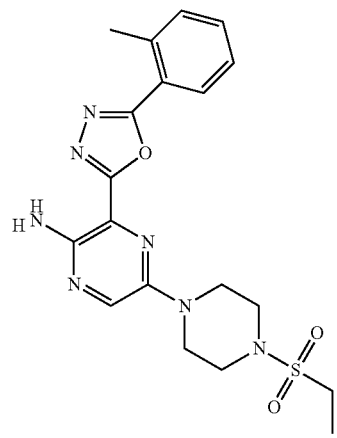
I-288
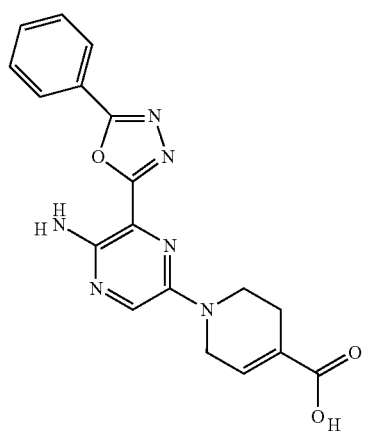
I-289
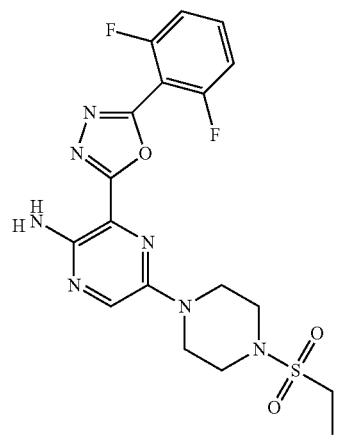
TABLE 5-continued
I-290
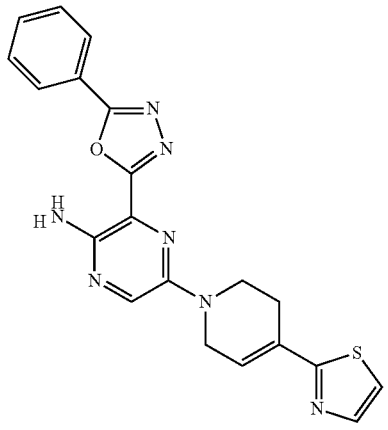
I-291
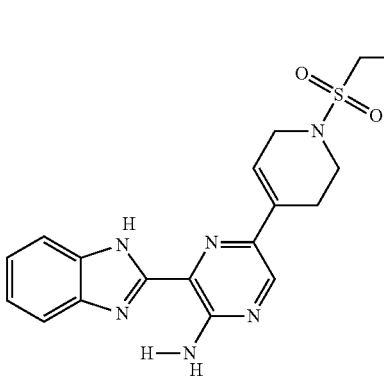
I-292
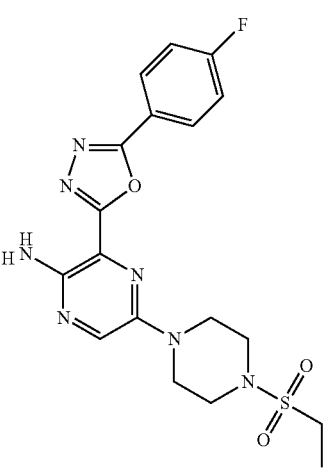
I-293
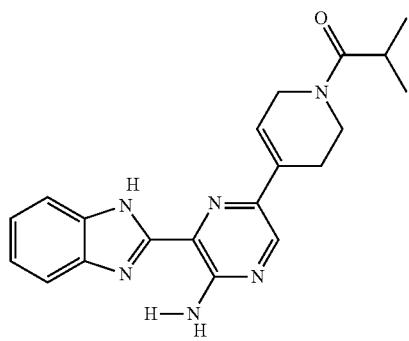

107
TABLE 5-continued
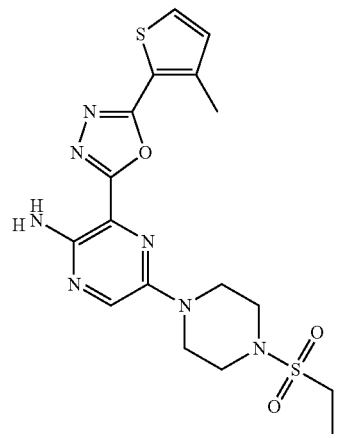
I-294
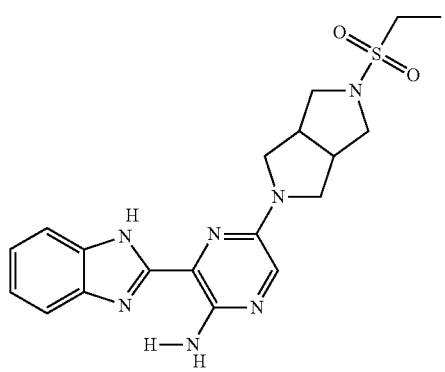
I-295
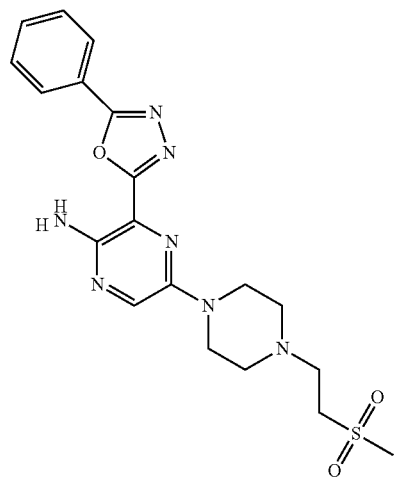
I-296
108
TABLE 5-continued
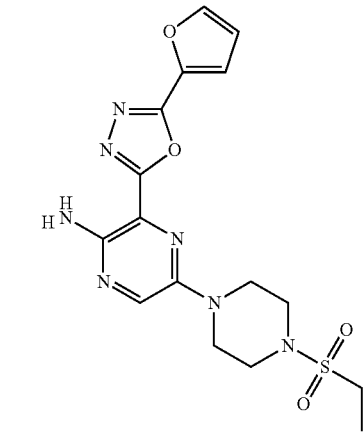
I-297
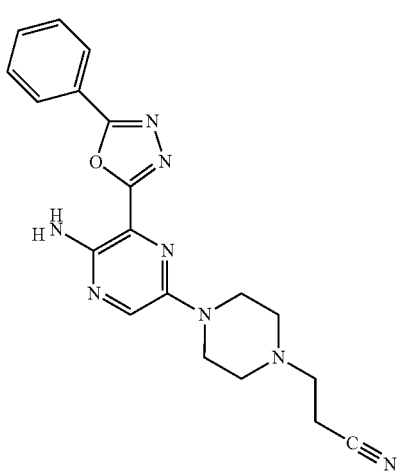
I-298
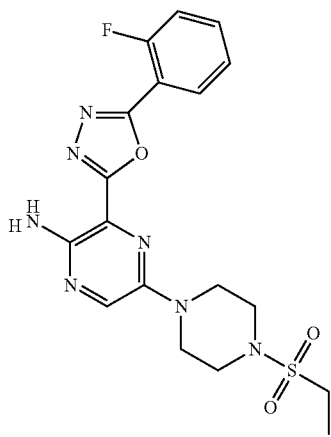
I-299

TABLE 5-continued
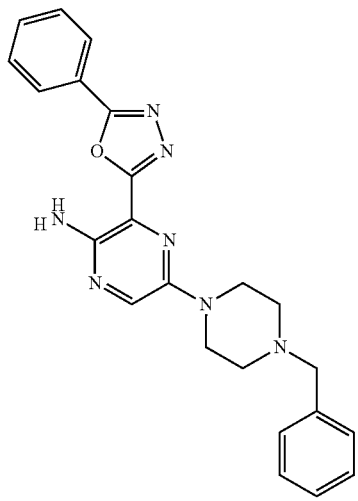
I-300
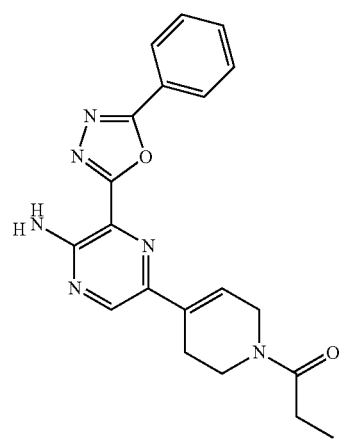
I-301
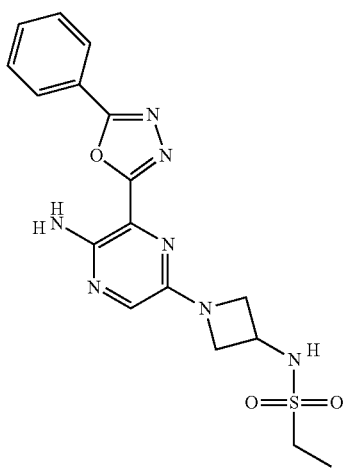
I-302
TABLE 5-continued
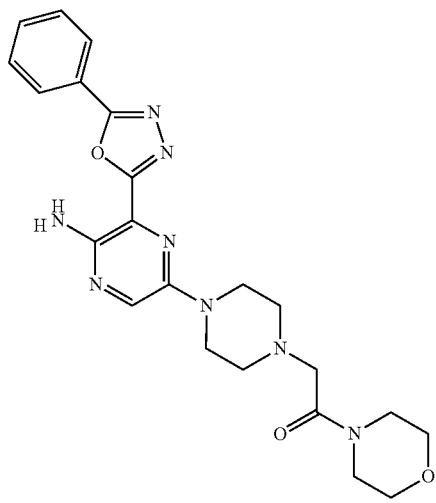
I-303
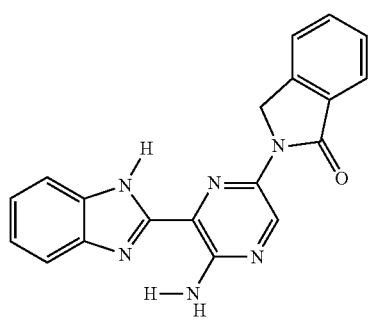
I-304
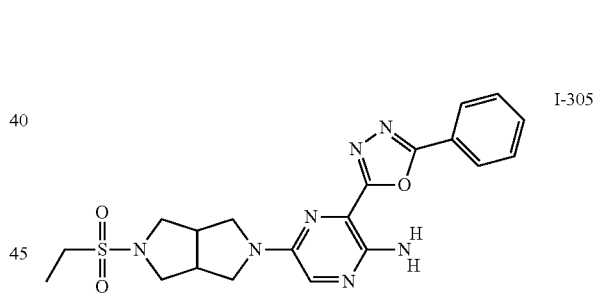
I-305
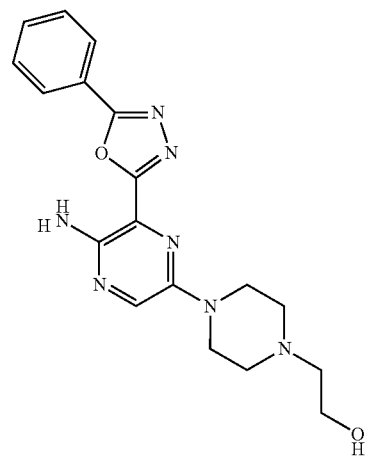
I-306

TABLE 5-continued
I-307
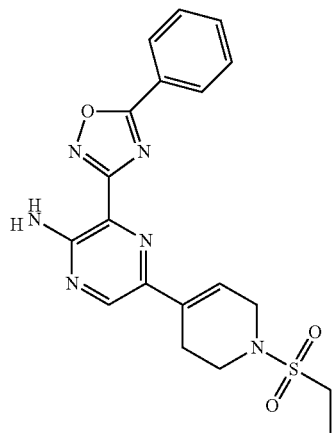
I-308
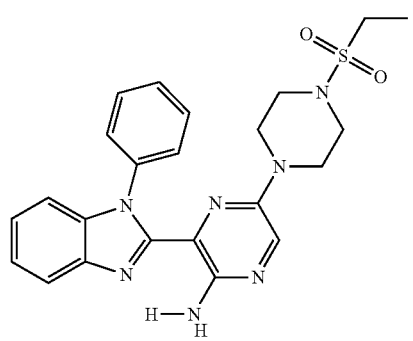
I-309
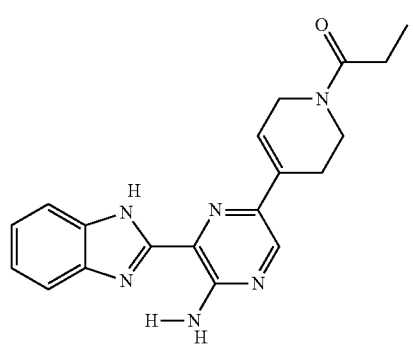
I-310
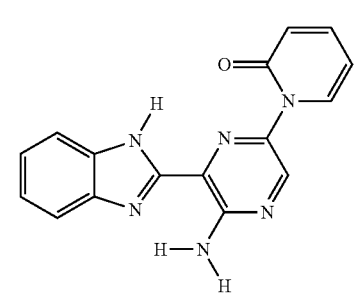 [SMILES: Nc1ncc(-n2ccccc2=O)nc1-c1nc2ccccc2[nH]1]
TABLE 5-continued
I-311
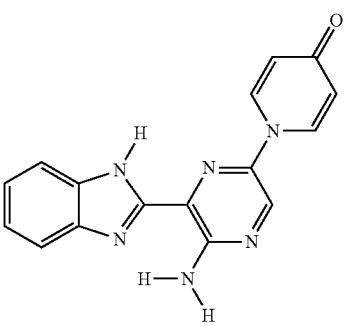 [SMILES: Nc1ncc(-n2ccc(=O)cc2)nc1-c1nc2ccccc2[nH]1]
I-312
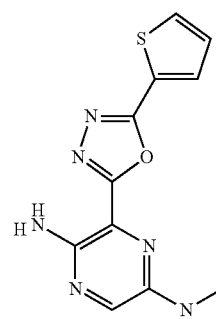
I-313
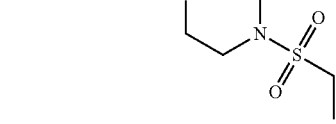

TABLE 5-continued
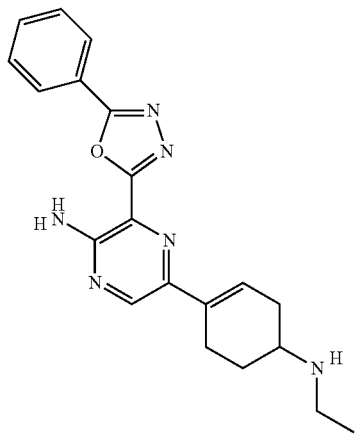 I-314
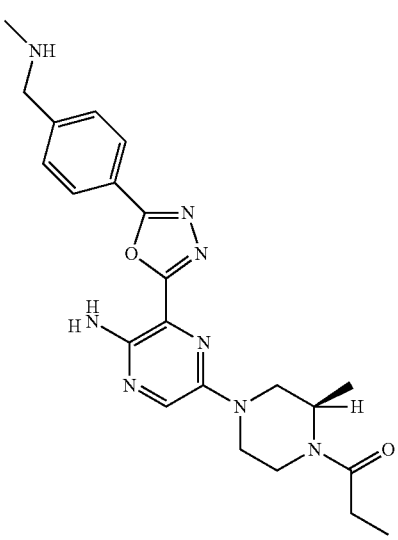 I-315
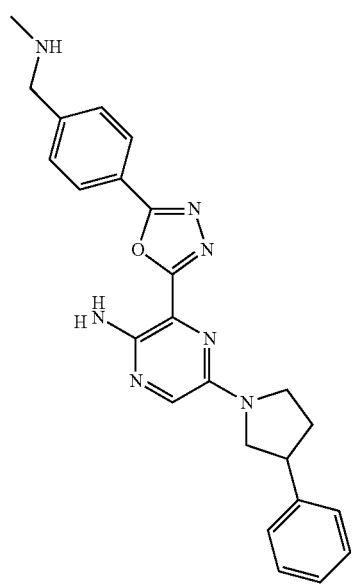 I-316
TABLE 5-continued
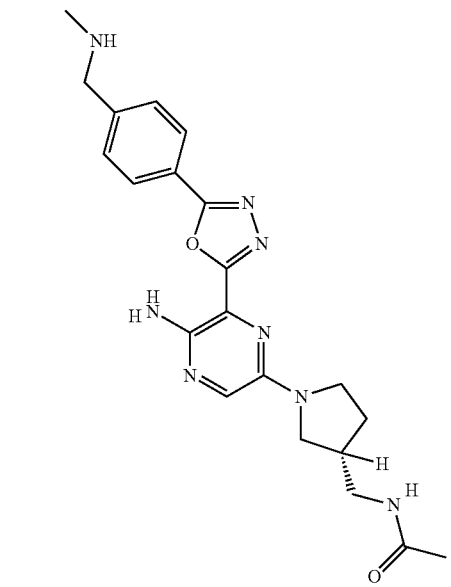 I-317
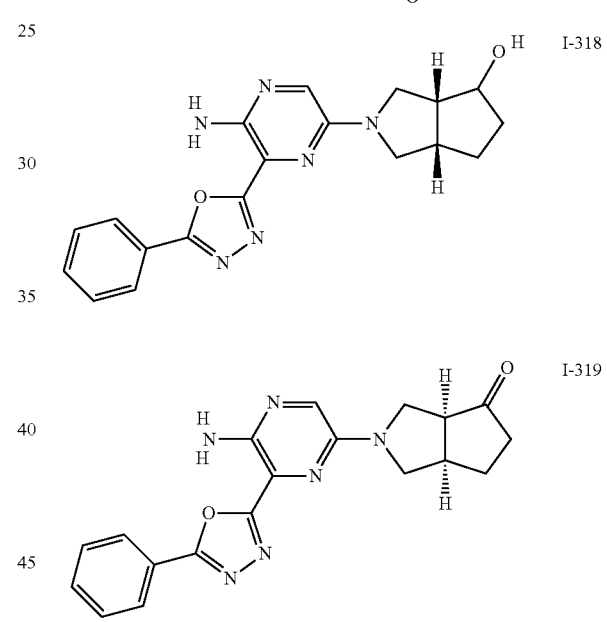 I-318
I-319
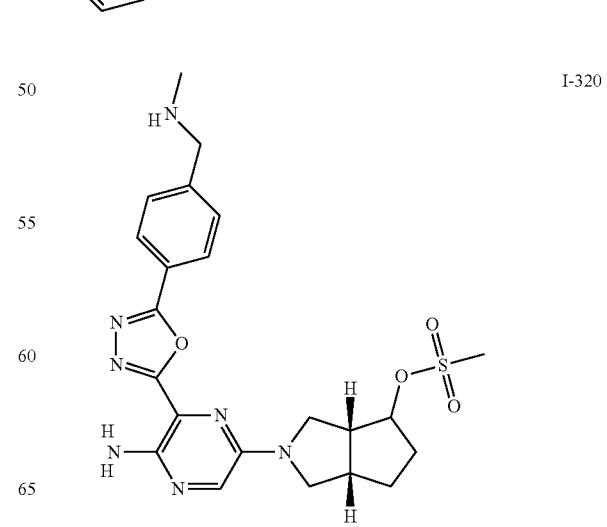 I-320

TABLE 5-continued
I-321
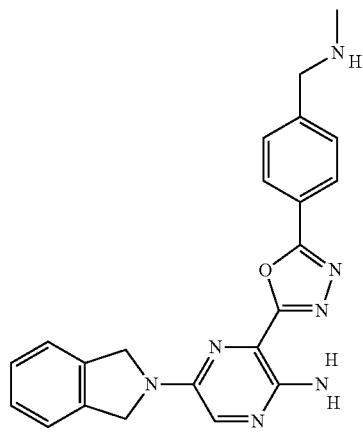
I-322
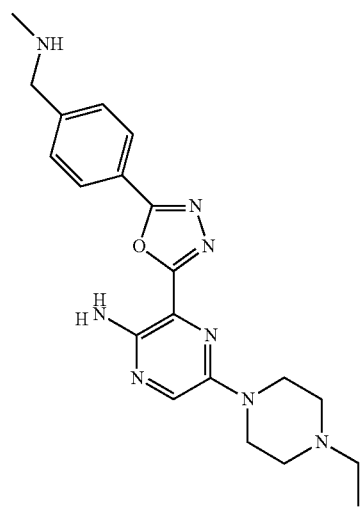
I-323
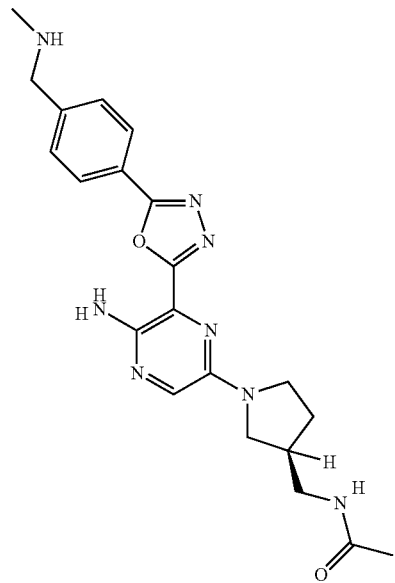
TABLE 5-continued
I-324
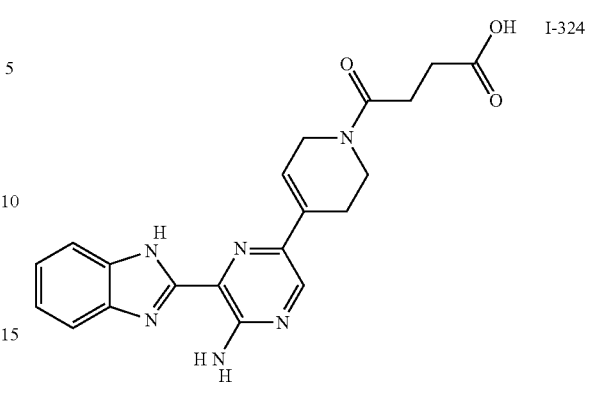
I-325
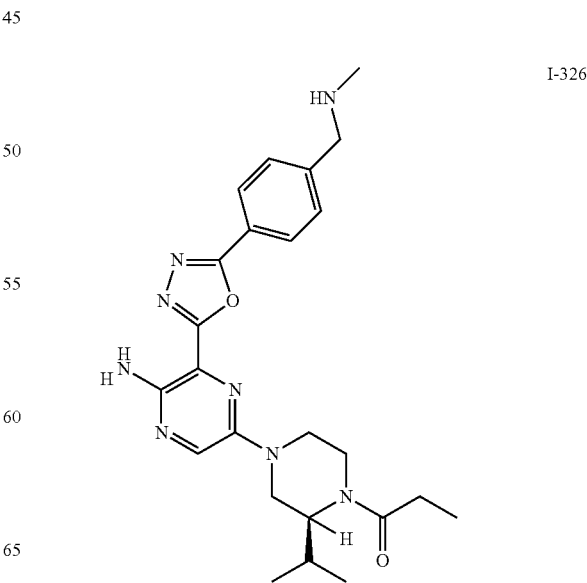
I-326

TABLE 5-continued
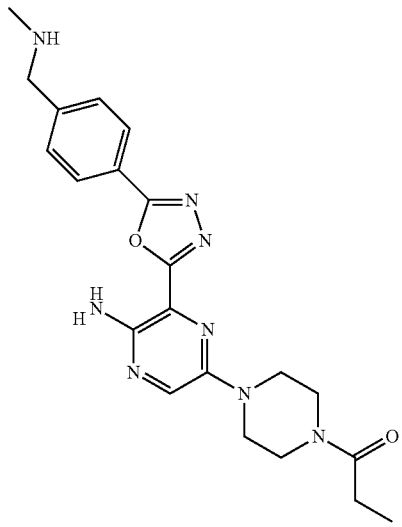
I-327
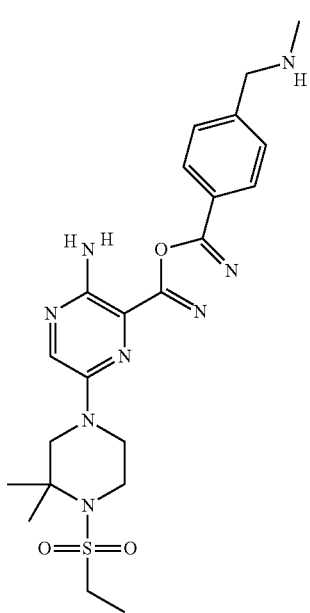
I-328
TABLE 5-continued
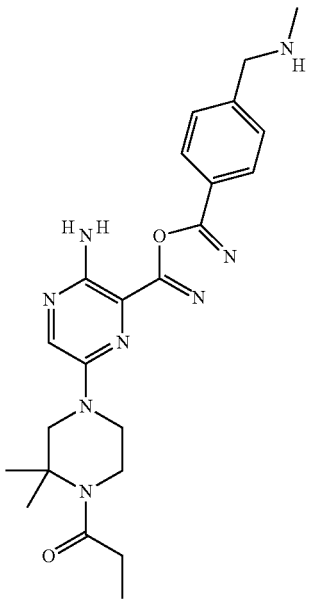
I-29
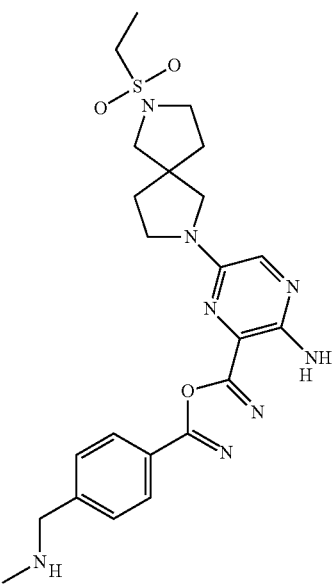
I-330
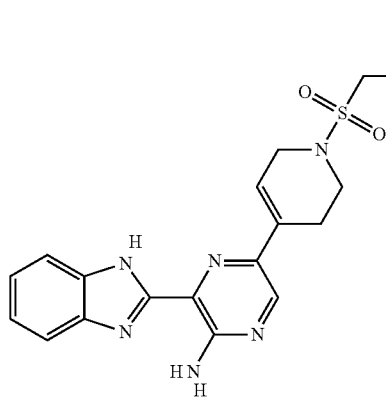
I-331

TABLE 5-continued
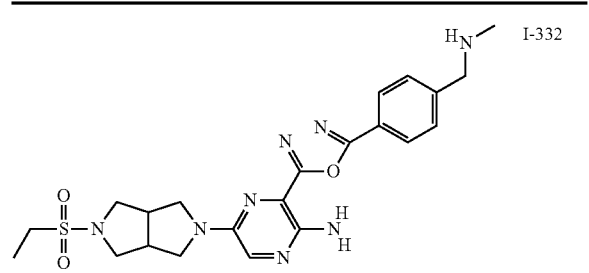
I-332
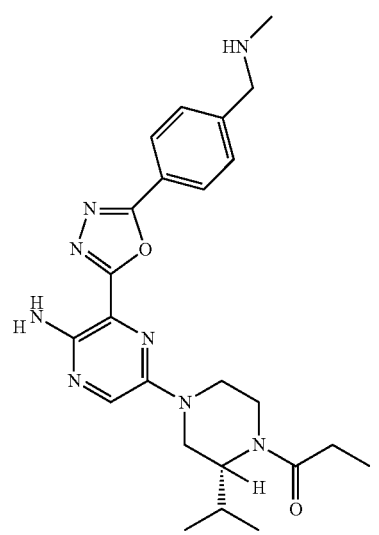
I-333
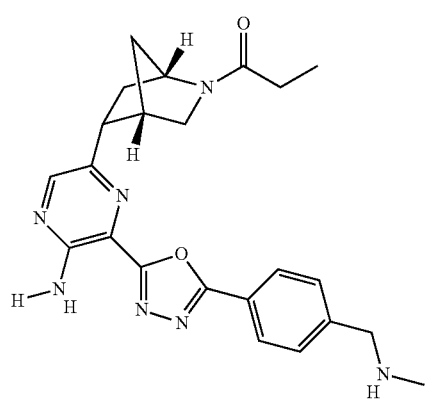
I-334
TABLE 5-continued
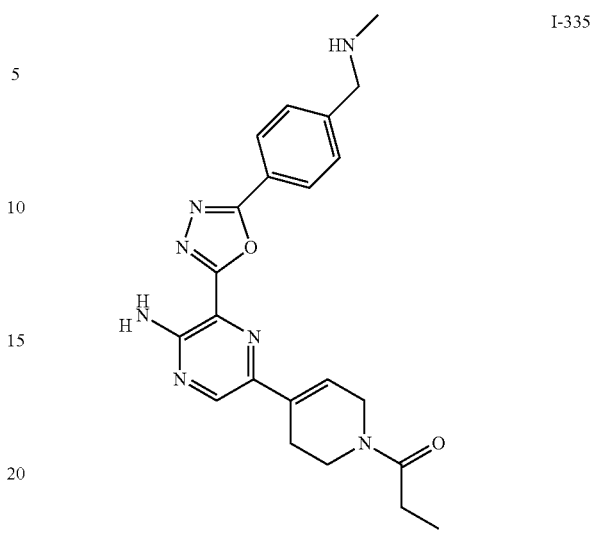
I-335
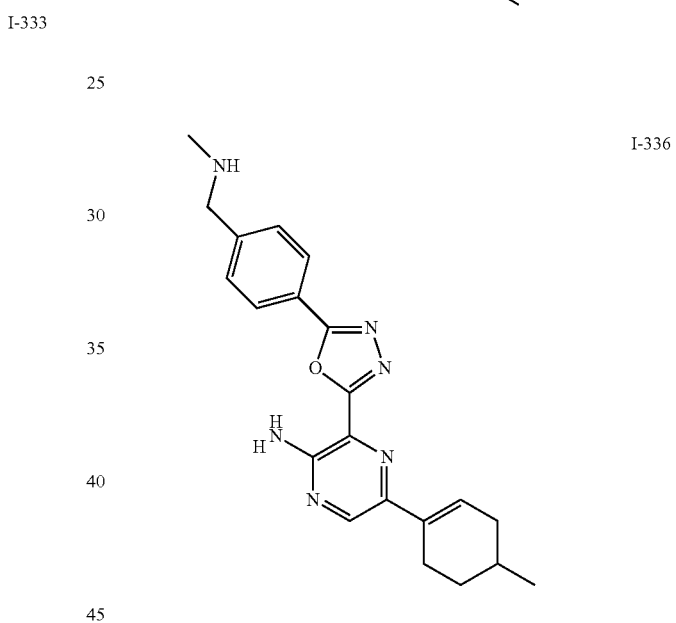
I-336
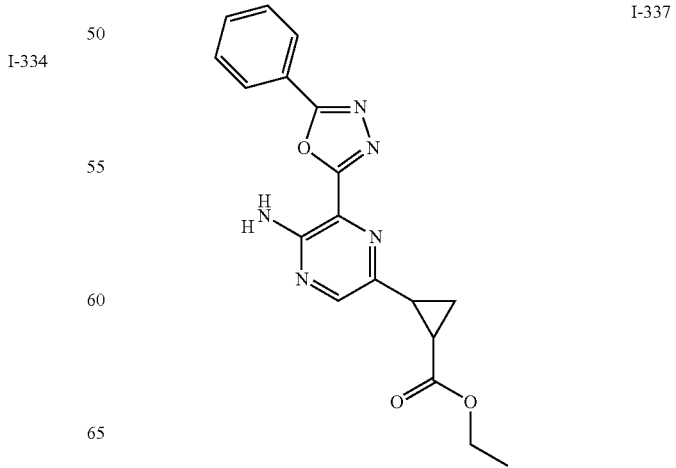
I-337

TABLE 5-continued
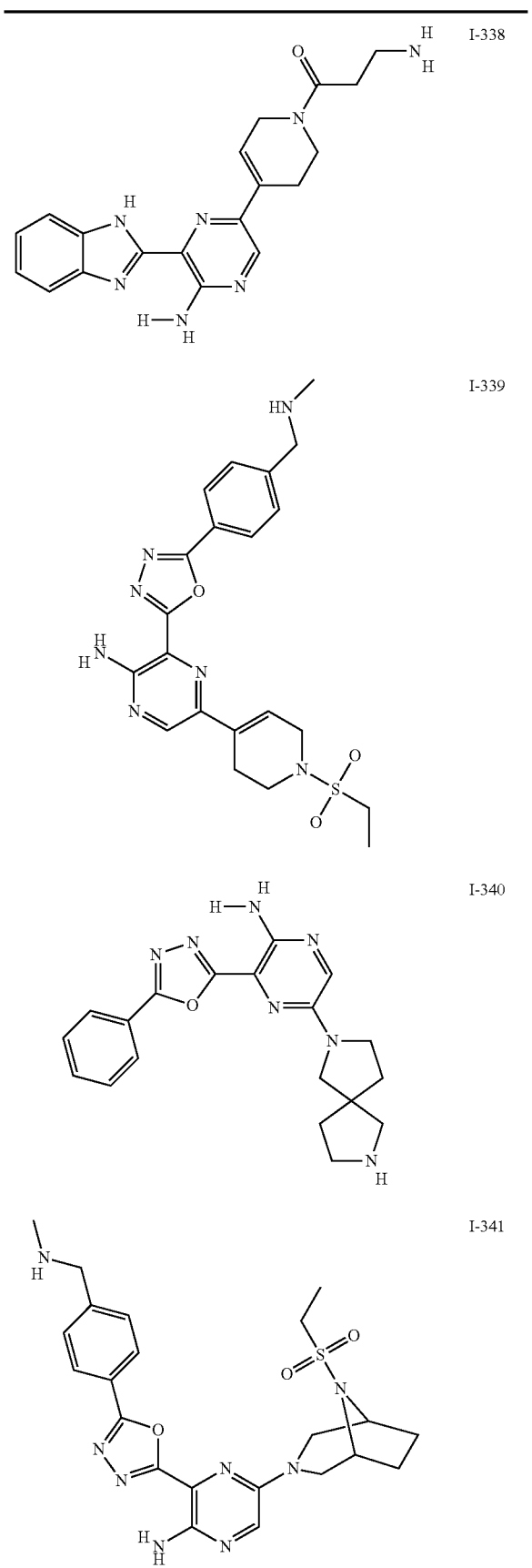
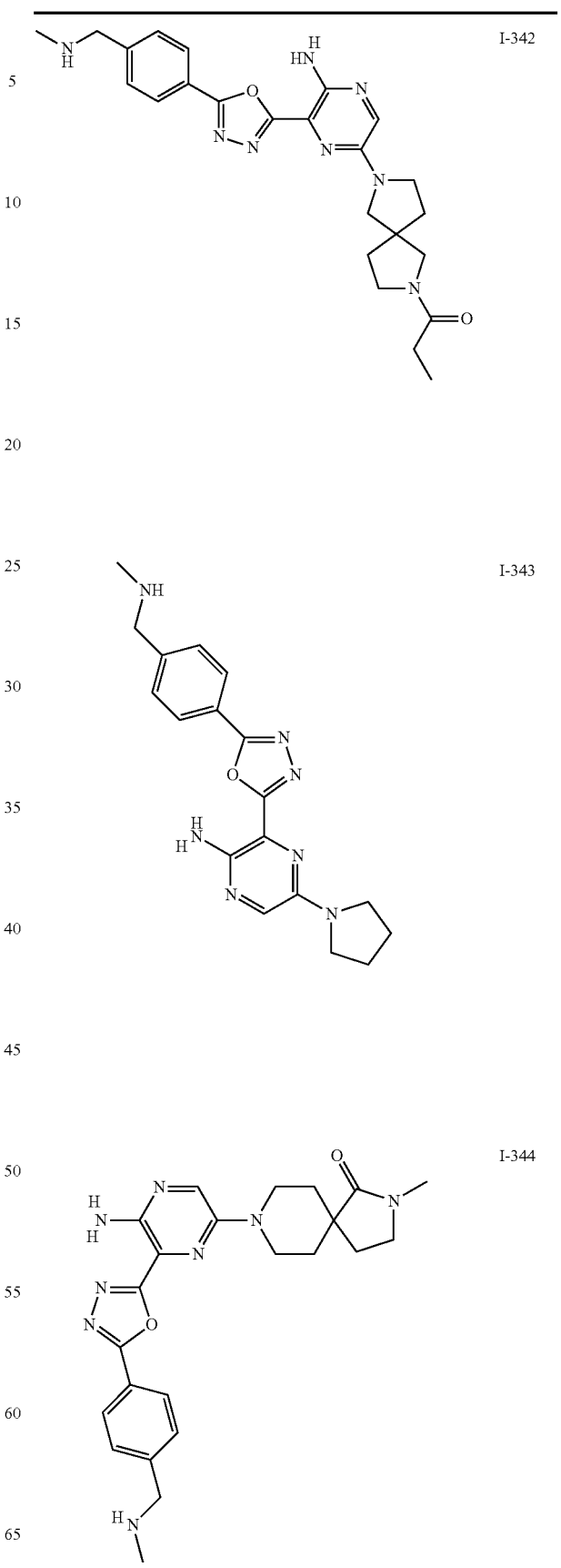

TABLE 5-continued
I-345
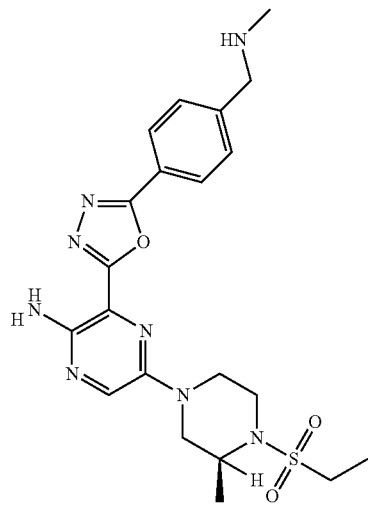
I-346
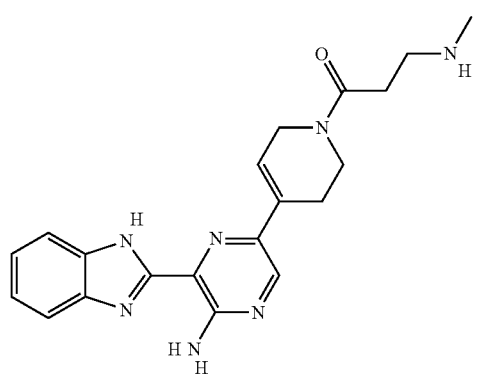
I-347
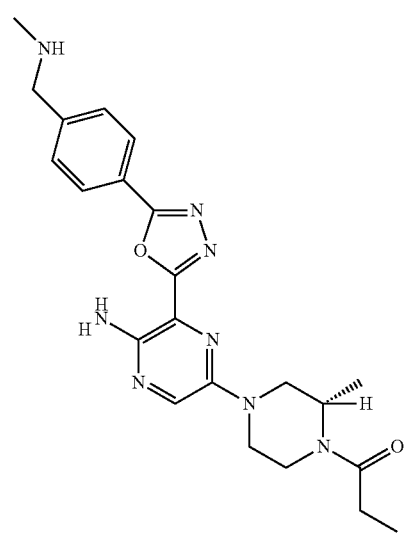
TABLE 6
I-348
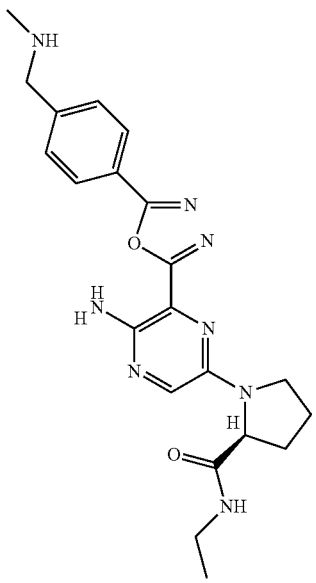
I-349
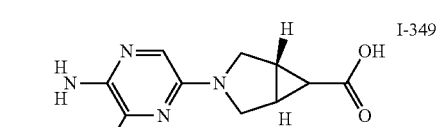
I-350
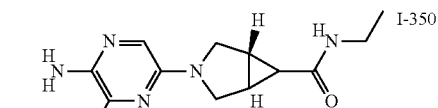
I-351
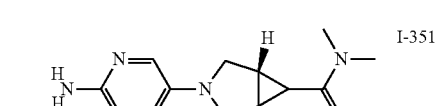

TABLE 6-continued
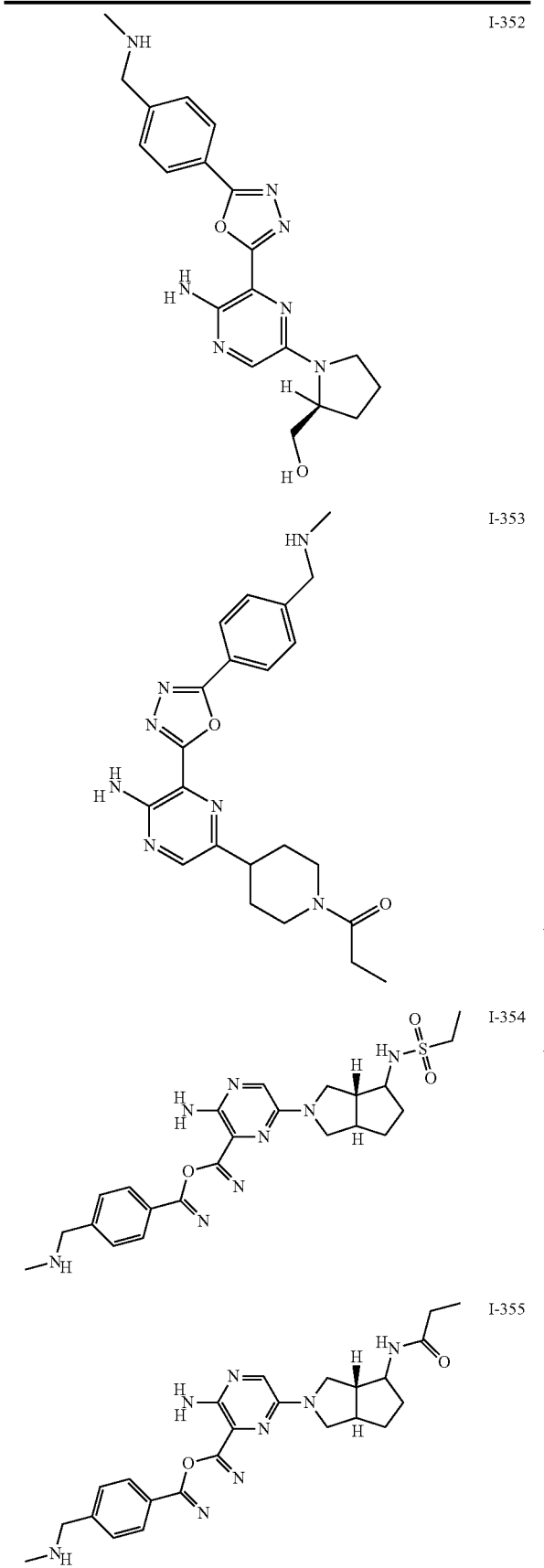
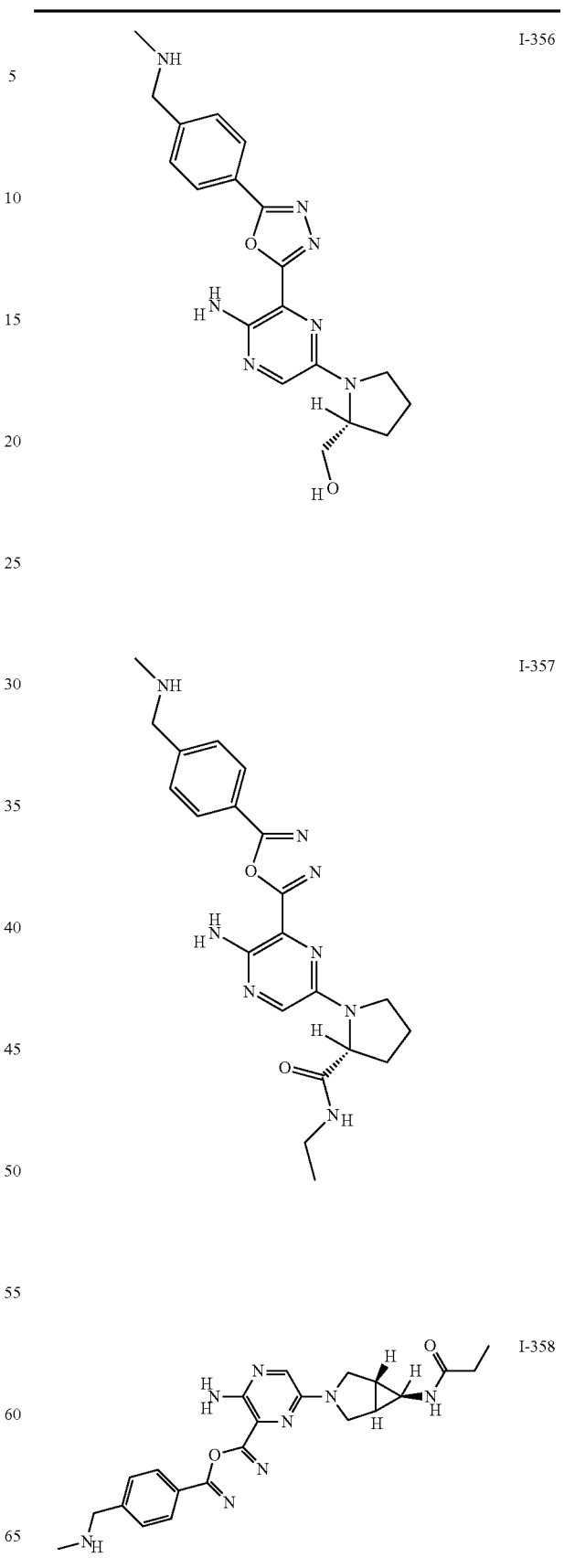

TABLE 6-continued
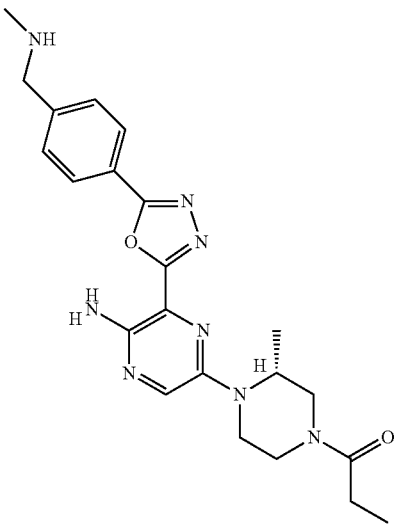
I-359
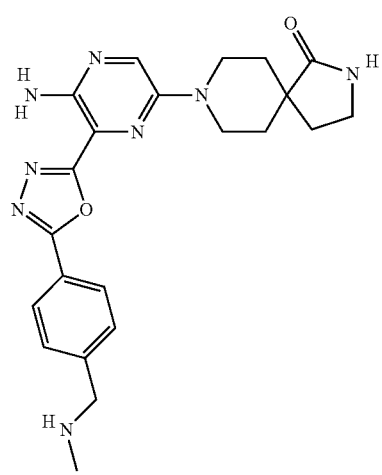
I-360
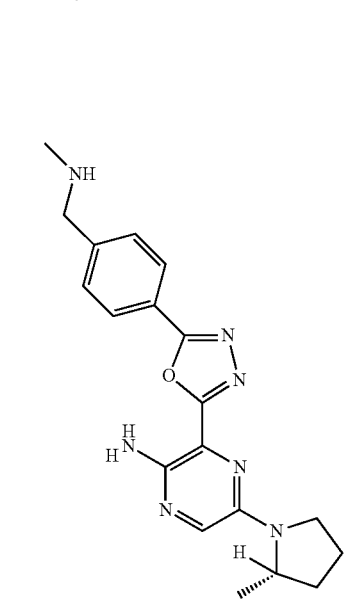
I-361
TABLE 6-continued
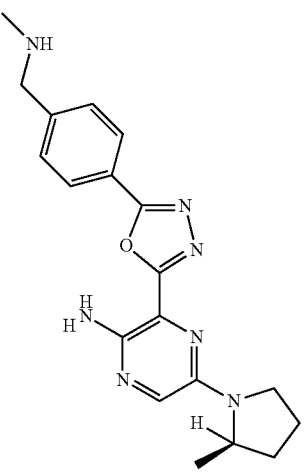
I-362
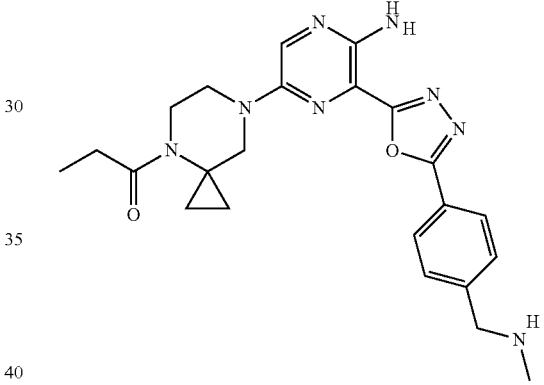
I-363
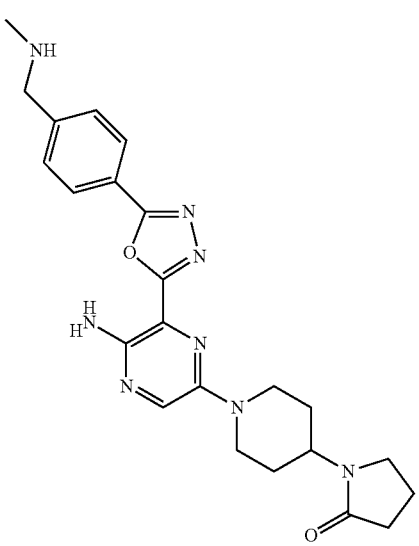
I-364

TABLE 6-continued
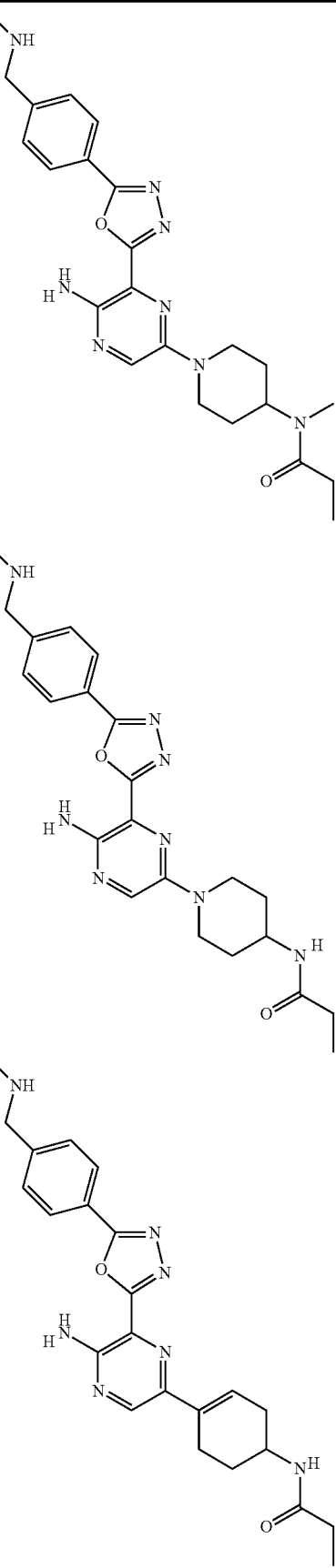
I-365
I-366
I-367
TABLE 6-continued
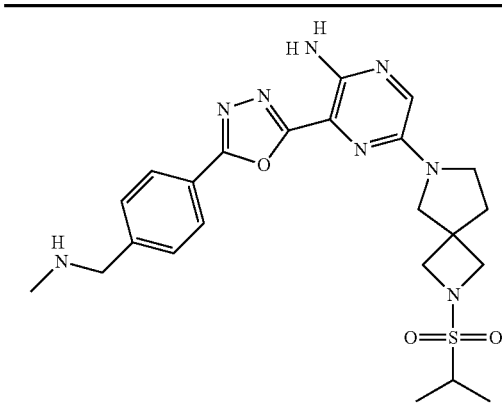
I-368
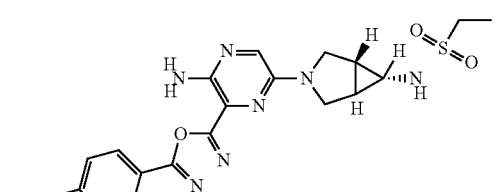
I-369
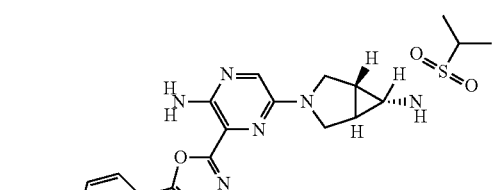
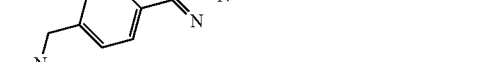
I-370

TABLE 6-continued
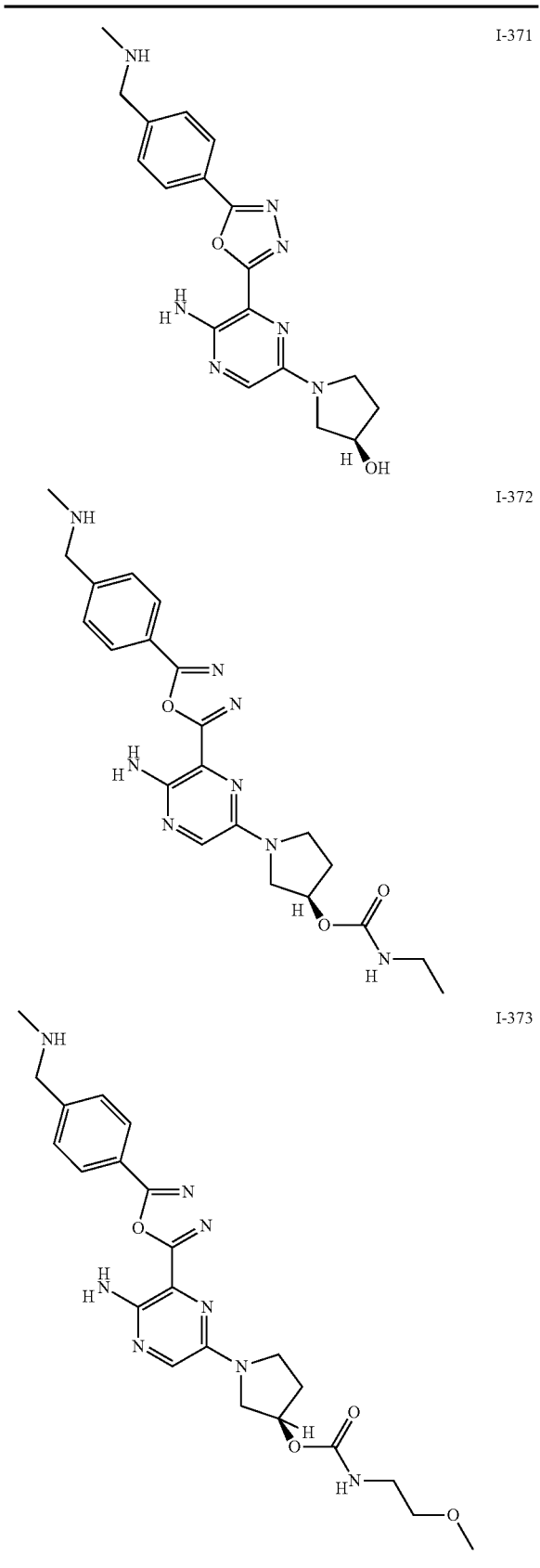
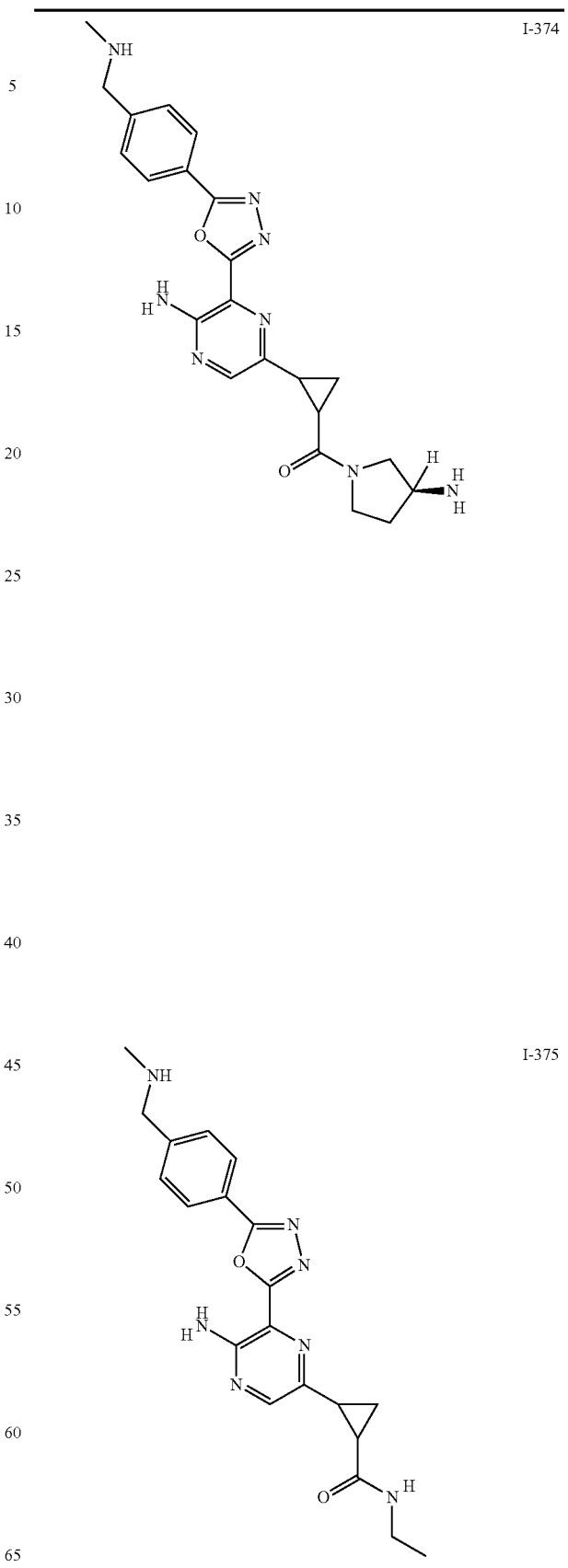

TABLE 6-continued

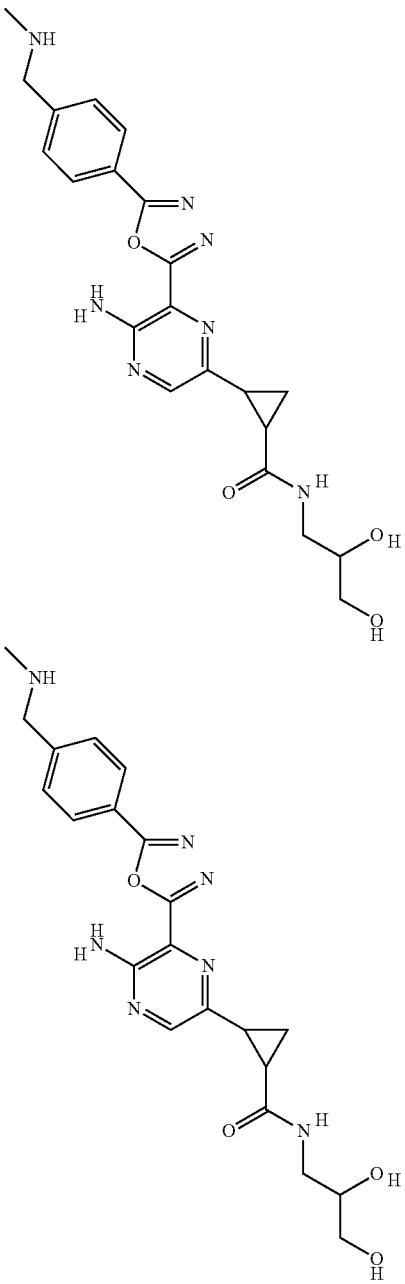

I-376

I-377

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, J$^1$ can be bonded to any position on the pyridyl ring. For bicyclic rings, a bond drawn through both rings indicates that the substituent can be bonded from any position of the bicyclic ring. In example ii below, for instance, J$^1$ can be bonded to the 5-membered ring (on the nitrogen atom, for instance), and to the 6-membered ring.

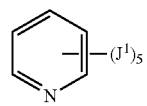

i

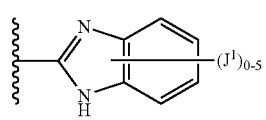

ii

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one. For the avoidance of doubt, it should be understood that rings such as phenyl, pyridyl, and thienyl are aromatic, while rings such as cyclooctatetraene and 1-methylpyridin-2(1H)-one are not aromatic.

The term "aromatic" as used herein, is used to describe a moiety that satisfies Hückel's rule, having 4n+2 electrons in a delocalized cloud.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —$CF_3$ and —$CF_2CF_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "hydrogen bond acceptor" refers to a relatively electronegative atom that can form a hydrogen bond with a hydrogen atom. Examples of hydrogen bond acceptors include, but are not limited to, fluorine, oxygen, nitrogen, and sulfur.

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N=N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

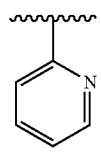

also represents

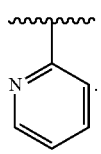

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Pharmaceutically Acceptable Salts

The compounds of this invention can exist in free form for treatment, or where appropriate, as a pharmaceutically acceptable salt.

A "pharmaceutically acceptable salt" means any non-toxic salt of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of the ATR protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenyl-propionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and N$^+$(C$_{1-4}$alkyl)$_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Abbreviations

The following abbreviations are used:
DMSO dimethyl sulfoxide
ATP adenosine triphosphate
DTT dithiothreitol
$^1$HNMR proton nuclear magnetic resonance
HPLC high performance liquid chromatography
LCMS liquid chromatography-mass spectrometry
TLC thin layer chromatography
Rt retention time
Compound Uses One aspect of this invention provides compounds that are inhibitors of ATR kinase, and thus are useful for treating or lessening the severity of a disease, condition, or disorder where ATR is implicated in the disease, condition, or disorder.

Another aspect of this invention provides compounds that are useful for the treatment of diseases, disorders, and conditions characterized by excessive or abnormal cell proliferation. Such diseases include, a proliferative or hyperproliferative disease. Examples of proliferative and hyperproliferative diseases include, without limitation, cancer and myeloproliferative disorders.

The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

Thus, the term "cancerous cell" as provided herein, includes a cell afflicted by any one of the above-identified conditions. In some embodiments, the cancer is selected from colorectal, thyroid, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutically Acceptable Derivatives or Prodrugs

In addition to the compounds of this invention, pharmaceutically acceptable derivatives or prodrugs of the compounds of this invention may also be employed in compositions to treat or prevent the herein identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds of this invention include, but are not limited to radiation, radiomimetic neocarzinostatin, Platinating agents, such as Cisplatin, Oxaliplatin, Carboplatin, Nedaplatin, Lobaplatin, Triplatin Tetranitrate, Picoplatin, Satraplatin, ProLindac, Aroplatin and other derivatives; Topo I inhibitors, such as Camptothecin, Topotecan, Irinotecan/SN38, Rubitecan, Belotecan, and other derivatives; Topo II inhibitors, such as Etoposide, Daunorubicin, Doxorubicin, Aclarubicin, Epirubicin, Idarubicin, Amrubicin, Pirarubicin, Valrubicin, Zorubicin and Teniposide; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Some other examples of antimetabolites: (Aminopterin, Raltitrexed, Pentostatin, Cladribine, Clofarabine, Fludarabine, Mercaptopurine, Fluorouracil, Capecitabine, Tegafur, Carmofur, Floxuridine, Azacitidine and Hydroxyurea); Alkylating agents, such as Nitrogen mustards (Cyclophosphamide, Melphalan, Chlorambucil, mechlorethamine, Ifosfamide and relatives); nitrosoureas (eg Carmustine); Triazenes (Dacarbazine, temozolomide); Alkyl sulphonates (eg Busulfan); Procarbazine and Aziridines; Some other examples of alkylating agents: (Mechlorethamine, Cyclophosphamide, Ifosfamide, Trofosfamide, Chlorambucil, Melphalan, Prednimustine, Bendamustine, Uramustine, Estramustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Altretamine, Mitobronitol, Actinomycin, Bleomycin, Mitomycin and Plicamycin). Antibiotics, such as Hydroxyurea, Anthracyclines (doxorubicin, daunorubicin, epirubicin and other derivatives); Anthracenediones (Mitoxantrone and relatives); *Streptomyces* family (Bleomycin, Mitomycin C, actinomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Compositions for Administration into a Subject

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies"

section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular protein kinase-mediated conditions to be treated or prevented, additional drugs, which are normally administered to treat or prevent that condition, may be administered together with the compounds of this invention.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satraplatin and other derivatives; Topo I inhibitors, such as Camptothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); *Streptomyces* family (Bleomycin, Mitomycin C, actinomycin) and Ultraviolet light.

Biological Samples

As inhibitors of ATR kinase, the compounds and compositions of this invention are also useful in biological samples. One aspect of the invention relates to inhibiting ATR kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of ATR kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability, of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Another aspect of the invention provides a method for modulating enzyme activity by contacting a compound of formula I with ATR kinase.

Methods of Treatment

In one aspect, the present invention provides a method for treating or lessening the severity of a disease, condition, or disorder where ATR kinase is implicated in the disease state. In another aspect, the present invention provides a method for treating or lessening the severity of an ATR kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the ATR kinase. Another aspect provides a method for treating or lessening the severity of a kinase disease, condition, or disorder by inhibiting enzymatic activity of ATR kinase with an ATR kinase inhibitor.

One aspect of the invention relates to a method of inhibiting ATR kinase activity in a patient, which method comprises administering to the patient a compound of formula I, or a composition comprising said compound. In some embodiments, said method is used to treat or prevent a condition selected from proliferative and hyperproliferative diseases, such as cancer. In another embodiment, said method is used to treat or prevent HIV, hepatitis, adenovirus, or psoriasis. In some embodiments, said method is used to treat or prevent HIV1, hepatitis B, adenovirus, or psoriasis.

Another aspect of this invention provides a method for treating, preventing, or lessening the severity of proliferative or hyperproliferative diseases comprising administering an effective amount of a compound, or a pharmaceutically acceptable composition comprising a compound, to a subject in need thereof. In some embodiments, said subject is a patient. The term "patient", as used herein, means an animal, preferably a human.

In some embodiments, said method is used to treat or prevent cancer. In some embodiments, said method is used to treat or prevent a type of cancer with solid tumors. In yet another embodiment, said cancer is selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma. In some embodiments, the cancer is selected from the cancers described herein. In some embodiments, said cancer is lung cancer, head and neck cancer, pancreatic cancer, gastric cancer, or brain cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound of formula I as described herein. Another embodiment provides a method of treating cancer comprising administering to a patient a compound of formula I, wherein the variables are as defined herein.

Some embodiments comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

In some embodiments, said DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, or an antibiotic. In yet other embodiments, said DNA-damaging agent is a platinating agent or ionizing radiation.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives; examples of the Pyrimidine family include Cytarabine, gemcitabine, 5-Fluorouracil (5FU) and relatives. Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines. Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan. Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, *Streptomyces* family. Examples of Anthracyclines include doxorubicin, daunorubicin, epirubicin and other derivatives; examples of Anthracenediones include Mitoxantrone and relatives; examples of *Streptomyces* family include Bleomycin, Mitomycin C, and actinomycin.

In certain embodiments, said platinating agent is Cisplatin or Oxaliplatin; said Topo I inhibitor is Camptothecin; said Topo II inhibitor is Etoposide; and said antibiotic is Mitomycin. In other embodiments, said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from a member of the Folic Family, the Purine Family, or the Pyrimidine Family; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or *Streptomyces* family.

Another embodiment provides a method of promoting cell death in cancer cells comprising administering to a patient a compound of formula I, or a composition comprising said compound.

Yet another embodiment provides a method of preventing cell repair of DNA damage in cancer cells comprising administering to a patient a compound of formula I, or a composition comprising said compound. Yet another embodiment provides a method of preventing cell repair caused by of DNA damage in cancer cells comprising administering to a patient a compound of formula I, or composition comprising said compound.

Another embodiment provides a method of sensitizing cells to DNA damaging agents comprising administering to a patient a compound of formula I, or a composition comprising said compound.

In some embodiments, said cell is a cancer cell having defects in the ATM signaling cascade. In some embodiments, said defect is altered expression or activity of one or more of the following: ATM, p53, CHK2, MRE11, RAD50, NBS1, 53BP1, MDC1 or H2AX. In other embodiments, said cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

Yet another embodiment provides use of a compound of formula I as a radio-sensitizer or a chemo-sensitizer. Yet other embodiment provides use of a compound of formula I as a single agent (monotherapy) for treating cancer. In some embodiments, the compounds of formula I are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

Synthetic Methodology

GENERAL SCHEME A

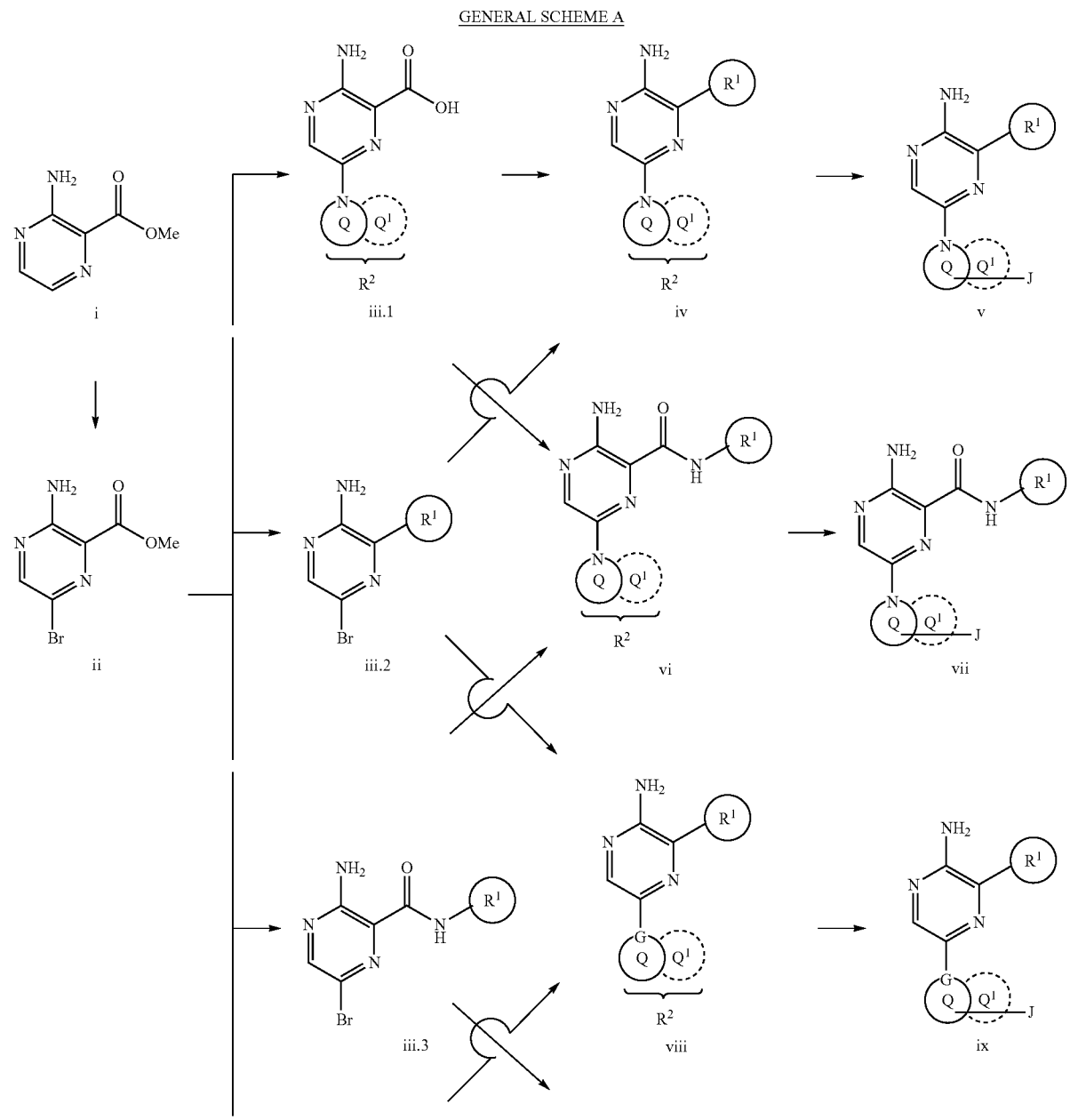

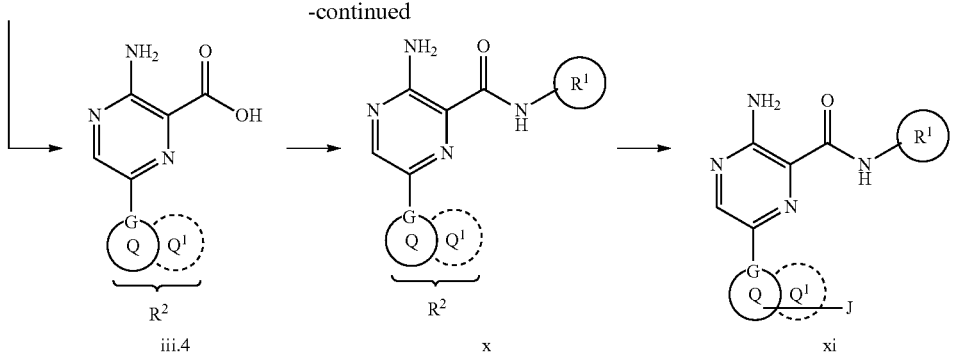

The compounds of this invention may be made according to the general schemes shown above. Unless otherwise indicated, all variables in the schemes are as defined herein.

Intermediate ii, rapidly obtained by bromination of aminoester i, can be used as a building block to generate various advanced intermediates iii.1-iii.4 useful for the preparation of the compounds of this invention. Compound ii can be used to generate advanced intermediate iii.1 to make compounds wherein $R^2$ is linked to the aminopyrazine moiety through a nitrogen atom. This can be done by (a) using the bromine atom as a handle for nucleophilic displacement with a cyclic amine followed by (b) an ester hydrolysis to generate acid iii.1. The carboxylic acid moiety can be manipulated in multiple ways, using methodology known in the art to generate compounds Iv of this invention where n is 0 and $R^1$ is a monocyclic or bicyclic (hetero)aromatic ring. For compounds Iv where an H-bond acceptor is not yet present, ring Q can be further manipulated and derivatised into compounds v of this invention that bear a H-bond acceptor feature. Additionally, the carboxylic acid group in iii.1 can be transformed into amides vi of this invention where n is 1 and $R^1$ is a monocyclic or bicyclic (hetero)aromatic ring. This can be done using methods known in the art for amide bond formation. For compounds vi where an H-bond acceptor is not yet present, ring Q can be further manipulated and derivatised into compounds vii of this invention that bear a H-bond acceptor feature.

In a similar step sequence compound ii can be used to generate advanced intermediate iii.4 to make compounds where $R^2$ is linked to the aminopyrazine moiety through a carbon atom. This can be done by (a) using the bromine atom as a handle for metal-catalysed cross-coupling (eg palladium catalysed coupling with a boronic acid) followed by (b) an ester hydrolysis to generate acid iii.4. The carboxylic acid moiety can be manipulated in multiple ways, using methodology known in the art to generate compounds viii of this invention where n is 0 and $R^1$ is a monocyclic or bicyclic (hetero)aromatic ring. For compounds viii where an H-bond acceptor is not yet present, ring Q can be further manipulated and derivatised into compounds ix of this invention that bear a H-bond acceptor feature. Additionally, the carboxylic acid group in iii.4 can be transformed into amides x of this invention where n is 1 and $R^1$ is a monocyclic or bicyclic (hetero) aromatic ring; This has been performed using methods known in the art for amide bond formation. For compounds x where an H-bond acceptor is not yet present, ring Q can be further manipulated and derivatised into compounds xi of this invention that bear a H-bond acceptor feature.

Alternatively, the synthetic sequence can be modified and compound ii can be used to prepare advanced intermediate iii.2 and iii.3;

Compound iii.2 is prepared by hydrolysis of the ester in ii, followed by a variety of methodologies known in the art to transform the carboxylic acid moiety into advanced intermediate iii.2 where n is 0 and $R^1$ is a monocyclic or bicyclic (hetero)aromatic ring. The bromine atom in iii.2 can then be used as a handle for nucleophilic displacement with a cyclic amine to generate compounds iv of this invention where $R^2$ is linked to the aminopyrazine moiety through a nitrogen atom. The bromine atom in iii.2 can also be used as a handle for metal-catalysed cross-coupling (e.g., palladium-catalyzed coupling with a boronic acid) to generate compounds viii of this invention where $R^2$ is linked to the aminopyrazine moiety through a carbon atom Hydrolysis of the ester in ii, followed by amide bond formation using methods known in the art afforded advanced intermediate iii.3 where n is 1 and $R^1$ is a monocyclic or bicyclic (hetero)aromatic ring. The bromine atom in iii.3 can then be used as a handle for nucleophilic displacement with a cyclic amine to generate compounds vi of this invention where $R^2$ is linked to the aminopyrazine moiety through a nitrogen atom. The bromine atom in iii.3 can also be used as a handle for metal-catalyzed cross-coupling (e.g., palladium catalyzed coupling with a boronic acid) to generate compounds x of this invention where $R^2$ is linked to the aminopyrazine moiety through a carbon atom.

SCHEME B

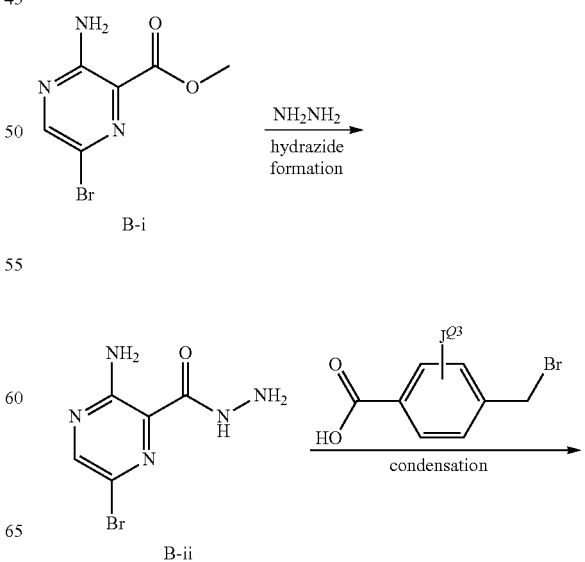

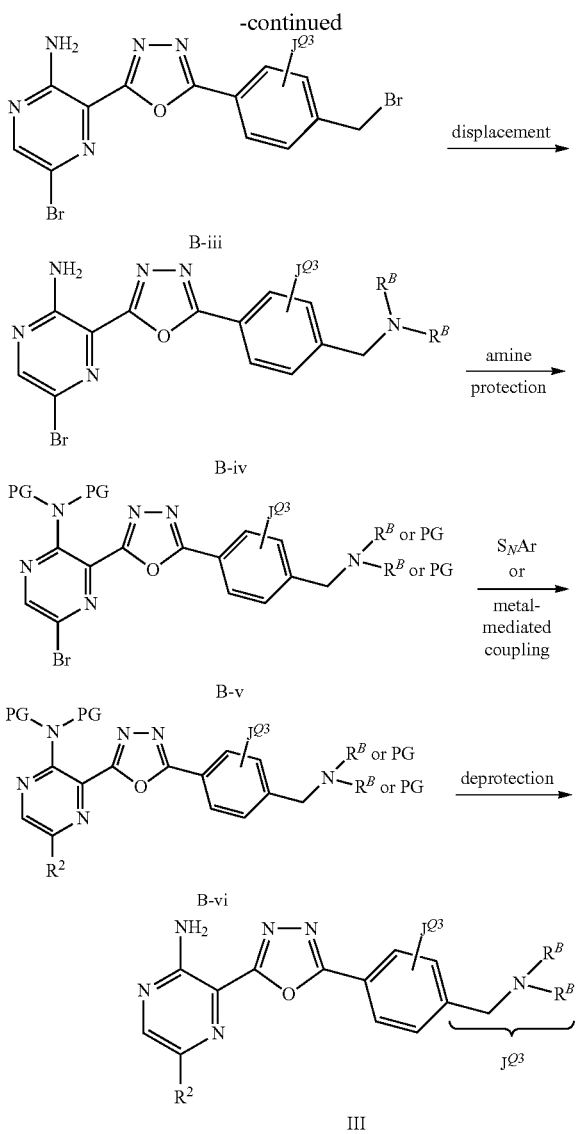

Scheme B depicts a general method for making compounds of formula III wherein one of the $J^1$ groups is $CH_2N(R^B)_2$, wherein $R^B$ is defined such that $CH_2N(R^B)_2$ is within the scope of $J^{Q3}$ as defined herein. The hydrazide of formula B-ii is formed from an ester of formula B-i in the presence of $NH_2NH_2$ and a suitable solvent. The result carbohydrazide of formula B-ii can then be combined with a variety of different carboxylic acids to form oxadiazoles of formula B-iii, which can undergo a displacement reaction to form amines of formula B-iv. The amines of formula B-iv can then be protected with suitable amine protecting groups ("PG") to form compounds of formula B-v, which can either undergo an SNAr reaction or a metal-mediated coupling reaction to form compounds of formula B-vi. Deprotection of the nitrogen protecting group is then done under suitable deprotecting conditions to form compounds of formula III.

Suitable hydrazide formation solvents include, but are not limited to alcohol solvents, such as EtOH and MeOH. Suitable condensation reaction conditions include, but are not limited to the following: $PPh_3Br_2$ in the presence of $CH_3CN$ and DIEA.

The SNAr reaction is used to prepare compounds wherein $R^2$ is bonded to the pyrazine via a nitrogen atom. The bromo-aminopyrazine of B-v is combined with suitable $R^2$ cyclic amines under suitable reduction SNAr conditions to form compounds of formula B-v. Suitable reduction SNAr conditions include, but are not limited to a suitable solvent (e.g., DMSO or DMF), a suitable base (e.g., TEA), and heat.

Metal-mediated coupling conditions are used to prepare compounds wherein $R^2$ is bonded to the pyrazine via a carbon atom. The bromo-aminopyrazine of B-v is combined with suitable $R^2$ boronic acids or esters under suitable metal-mediated coupling conditions to form compounds of formula B-v. Suitable metal-mediated coupling conditions include, but are not limited to, a catalyst (such as $Pd(PPh_3)_4$) a salt (such as $Na_2CO_3$), and suitable solvents (such as $CH_3CN$, DMF, DME, or water).

Suitable deprotection conditions, include, but are not limited to TFA/DCM or dioxane/HCl for a BOC protecting group.

EXAMPLES

The compounds of this invention may be prepared in light of the specification using steps generally known to those of ordinary skill in the art. Those compounds may be analyzed by known methods, including but not limited to LCMS (liquid chromatography mass spectrometry) and NMR (nuclear magnetic resonance). Compounds of this invention may be also tested according to these examples. It should be understood that the specific conditions shown below are only examples, and are not meant to limit the scope of the conditions that can be used for making, analyzing, or testing the compounds of this invention. Instead, this invention also includes conditions known to those skilled in that art for making, analyzing, and testing the compounds of this invention.

HPLC Methods

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm

Gradient: 0-100% acetonitrile+methanol 60:40 (20 mM Tris phosphate)

Flow rate: 1.5 mL/minute

Detection: 225 nm.

HNMR Methods $^1$H-NMR spectra were recorded at 400 MHz using a Bruker DPX 400 instrument.

Mass Spectrometry Methods

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions are 5%-100% acetonitrile-methanol over 3.5 mins gradient time and 5 mins run time on an ACE C8 3.0×75 mm column. Flow rate is 1.2 ml/min.

The following compounds of formula I were prepared and analyzed as follows.

Example 1

1-(4-(5-amino-6-(6-methyl-1H-benzo[d]imidazol-2-yl)pyrazin-2-yl)-1,4-diazepan-1-yl)ethanone (Compound I-1)

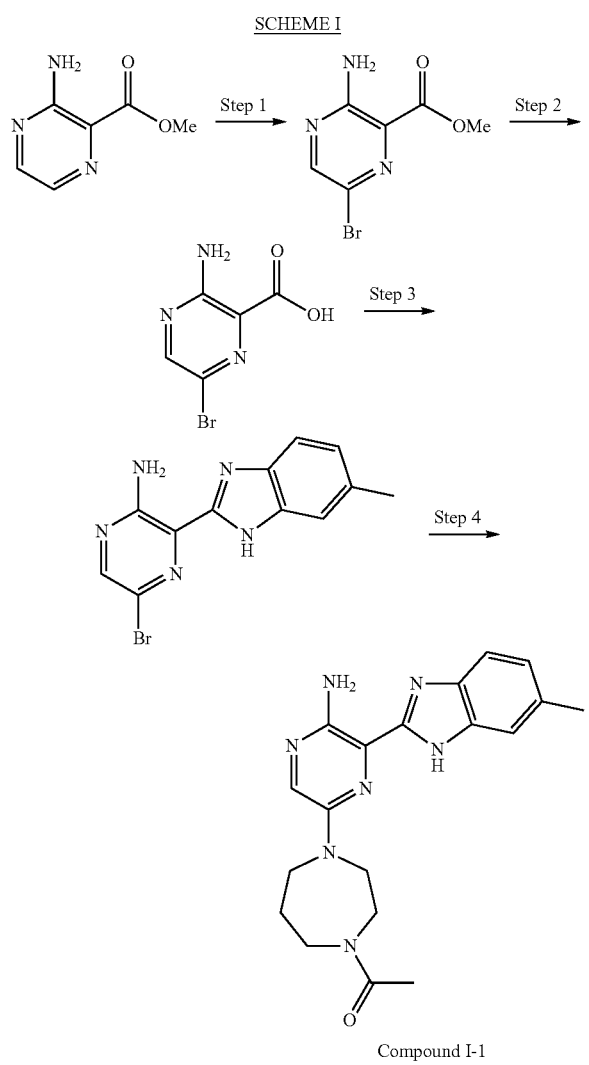

Compound I-1

Method A

Step 1: Methyl 3-amino-6-bromopyrazine-2-carboxylate

A mixture of methyl 3-aminopyrazine-2-carboxylate (8.35 g, 54.53 mmol) and N-bromo-succinimide (9.705 g, 54.53 mmol) was stirred in MeCN (100 mL) at room temp overnight. The resultant precipitate was filtered, washed with MeCN and dried to give the desired product as a yellow solid (11.68 g, 92% Yield) $^1$H NMR (400.0 MHz, DMSO) 3.85 (s, 3H), 7.55 (br s, 2H) and 8.42 (s, 1H) ppm; MS (ES$^+$) 233

Step 2: 3-amino-6-bromopyrazine-2-carboxylic acid

A mixture of methyl 3-amino-6-bromo-pyrazine-2-carboxylate (3 g, 12.93 mmol) and lithium hydroxide (1.548 g, 64.65 mmol) in MeOH (11.74 mL) and H2O (11.74 mL) was heated to 90° C. for 2 hours. The reaction mixture was allowed to cool, neutralised with HCl and diluted with water, and the resultant precipitate collected by filtration (2.2 g, 78% Yield). $^1$H NMR (400.0 MHz, DMSO) 7.57 (br s, 2H) and 8.39 (s, 1H), 13.41 (br s, 1H) ppm.

Step 3: 5-bromo-3-(6-methyl-1H-benzo[d]imidazol-2-yl)pyrazin-2-amine

A mixture of 3-amino-6-bromo-pyrazine-2-carboxylic acid (2.5 g, 11.47 mmol), 4-methylbenzene-1,2-diamine (1.401 g, 11.47 mmol), diethoxyphosphoryl-formonitrile (2.058 g, 1.871 mL, 12.62 mmol) and triethylamine (2.321 g, 3.197 mL, 22.94 mmol) was heated in DME (75.00 mL) at 170° C. in the microwave for 1 hour. The reaction mixture was diluted with EtOAc, filtered and washed with water and brine, dried over MgSO$_4$ and concentrated to a brown solid. The mixture was slurried in DCM and treated with diethyl ether/petroleum ether. The resultant solid was washed with ether and dried to afford the product as an orange/brown solid (1.6 g, 46% Yield). MS (ES$^+$) 305.

Step 4: 1-(4-(5-amino-6-(6-methyl-1H-benzo[d]imidazol-2-yl)pyrazin-2-yl)-1,4-diazepan-1-yl)ethanone (Compound I-1)

A mixture of 5-bromo-3-(6-methyl-1H-benzimidazol-2-yl)pyrazin-2-amine (100 mg, 0.3288 mmol) and 1-(1,4-diazepan-1-yl)ethanone (701 mg, 4.932 mmol) in NMP (200.0 µL) was heated at 190° C. in the microwave for 2 hours. The reaction mixture was partitioned between DCM and water and the organics separated and concentrated to dryness. The resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected, passed through a sodium bicarbonate cartridge and freeze-dried to give the title compound (67.7 mg, 54% Yield). 1H NMR (400.0 MHz, DMSO) d 1.80-1.94 (2H, m), 1.78 (3H, s), 2.43-2.46 (3H, s), 3.40 (2H, m), 3.63-3.83 (5H, m), 3.92 (1H, m), 7.04-7.11 (3H, m), 7.38-7.59 (2H, m), 7.90 (1H, m), 12.37 (1H, m) ppm; MS (ES$^+$) 366

The following compounds were all prepared using Method A.

Compound I-2 (1-(5-amino-6-(6-methyl-1H-benzo[d]imidazol-2-yl)pyrazin-2-yl)piperidin-4-yl)methanol 1H NMR (400.0 MHz, DMSO) d 1.22 (2H, m), 1.59 (1H, m), 1.79 (2H, m), 2.45 (3H, s), 2.72 (2H, m), 3.31 (1H, m), 4.30 (2H, d), 4.52 (1H, s), 7.04 (1H, m), 7.18 (2H, s), 7.37-7.57 (3H, m), 7.98 (1H, s), 12.44 (1H, s) ppm; MS (ES+) 339

Compound I-3 3-(6-methyl-1H-benzo[d]imidazol-2-yl)-5-morpholinopyrazin-2-amine 1H NMR (400.0 MHz, DMSO) d 2.45 (3H, s), 3.45 (4H, m), 3.79 (4H, m), 7.08 (1H, s), 7.27-7.58 (4H, m), 7.98 (1H, s), 12.50 (1H, s) ppm; MS (ES+) 311

Compound I-4 (S)-N-(1-(5-amino-6-(6-methyl-1H-benzo[d]imidazol-2-yl)pyrazin-2-yl)pyrrolidin-3-yl)ethanamide 1H NMR (400.0 MHz, DMSO) d 1.22 (2H, m), 1.59 (1H, m), 1.79 (2H, m), 2.45 (3H, s), 2.72 (2H, m), 3.31 (1H, m), 4.30 (2H, d), 4.52 (1H, s), 7.04 (1H, m), 7.18 (2H, s), 7.37-7.57 (3H, m), 7.98 (1H, s), 12.44 (1H, s) ppm; MS (ES+) 352

Compound I-5 1-(5-amino-6-(6-methyl-1H-benzo[d]imidazol-2-yl)pyrazin-2-yl)piperidin-4-ol 1H NMR (400.0 MHz, DMSO) 1.48 (2H, m), 1.86 (2H, m), 2.43, 2.45 (3H, s), 3.02 (2H, m), 3.69 (1H, m), 4.02 (2H, m), 4.72 (1H, s), 7.09 (1H, d), 7.18 (2H, s), 7.36-7.57 (2H, m), 7.99 (1H, s), 12.45 (1H, s) ppm; MS (ES+) 325

Compound I-6 5-(4-(ethylsulfonyl)piperazin-1-yl)-3-(6-methyl-1H-benzo[d]imidazol-2-yl)pyrazin-2-amine; 1H NMR (400.0 MHz, DMSO) d 1.31 (3H, t), 2.50 (3H, s), 3.20 (2H, m), 3.35 (4H, m), 3.66 (4H, m), 7.12 (1H, m), 7.35-7.66 (4H, m), 8.09 (1H, s), 12.61 (1H, m) ppm; MS (ES+) 402

Compound I-7 4-(5-amino-6-(6-methyl-1H-benzo[d]imidazol-2-yl)pyrazin-2-yl)piperazin-2-one; MS (ES+) 324

Compound I-8 3-(6-methyl-1H-benzo[d]imidazol-2-yl)-5-thiomorpholinopyrazin-2-amine; MS (ES+) 327

Compound I-9 (R)-N-(1-(5-amino-6-(6-methyl-1H-benzo[d]imidazol-2-yl)pyrazin-2-yl)pyrrolidin-3-yl)ethanamide; MS (ES+) 352

Compound I-10 1-(4-(5-amino-6-(6-methyl-1H-benzo[d]imidazol-2-yl)pyrazin-2-yl)piperazin-1-yl)ethanone; MS (ES+) 352

Compound I-11 1-(5-amino-6-(6-methyl-1H-benzo[d]imidazol-2-yl)pyrazin-2-yl)piperidin-4-one; MS (ES+) 323

Compound I-12 5-(4-methoxypiperidin-1-yl)-3-(6-methyl-1H-benzo[d]imidazol-2-yl)pyrazin-2-amine; MS (ES+) 339

Compound I-13 1-(5-amino-6-(6-methyl-1H-benzo[d]imidazol-2-yl)pyrazin-2-yl)-N-methylpiperidine-4-carboxamide; MS (ES+) 366

Compound I-14 1-(5-amino-6-(6-methyl-1H-benzo[d]imidazol-2-yl)pyrazin-2-yl)piperidine-4-carboxamide; MS (ES+) 352

Compound I-30 3-(6-methyl-1H-benzo[d]imidazol-2-yl)-5-(4-phenylpiperazin-1-yl)pyrazin-2-amine 1H NMR (400.0 MHz, DMSO) d 2.49, 2.50 (3H, 2×s), 3.31 (4H, m), 3.64 (4H, m), 6.91 (1H, m), 7.05, 7.07 (2H, 2×s), 7.17.25 (4H, m), 7.35-7.60 (2H, m), 8.05 (1H, 2×s), 12.55, 12.58 ppm; MS (ES+) 386.06

Compound I-31 3-(6-methyl-1H-benzo[d]imidazol-2-yl)-5-(4-(trifluoromethyl)piperidin-1-yl)pyrazin-2-amine; MS (ES+) 377.05

Compound I-32 ethyl 4-(5-amino-6-(6-methyl-1H-benzo[d]imidazol-2-yl)pyrazin-2-yl)piperazine-1-carboxylate; MS (ES+) 382.05

Compound I-33 3-(6-methyl-1H-benzo[d]imidazol-2-yl)-5-(1,4-dioxa-8-azaspiro[4.5]decan-8-yl)pyrazin-2-amine; MS (ES+) 367.14

Compound I-34 1-(5-amino-6-(6-methyl-1H-benzo[d]imidazol-2-yl)pyrazin-2-yl)piperidine-4-carbonitrile 1H NMR (400.0 MHz, DMSO) d 1.90 (2H, m), 2.07 (2H, m), 2.49, 2.52 (3H, 2×s), 3.16 (1H, m), 3.37 (2H, m), 3.86 (2H, m), 7.10, 7.16 (1H, 2×d), 7.31 (2H, br s), 7.42, 7.56 (1H, 2×s), 7.52, 7.64 (1H, 2×d), 8.07 (1H, s), 12.54 (1H, 2×s) ppm; MS (ES+) 334.09

Compound I-35 3-(6-methyl-1H-benzo[d]imidazol-2-yl)-5-(4-(pyrimidin-2-yl)piperazin-1-yl)pyrazin-2-amine; MS (ES+) 388.17

Compound I-43 N-(1-(5-amino-6-(6-methyl-1H-benzo[d]imidazol-2-yl)pyrazin-2-yl)piperidin-4-yl)ethanamide; MS (ES+) 366.08

Compound I-44 1-(1-(5-amino-6-(6-methyl-1H-benzo[d]imidazol-2-yl)pyrazin-2-yl)-4-phenylpiperidin-4-yl)ethanone; MS (ES+) 427.2

Compound I-45 5-(4-(2-fluorophenyl)piperazin-1-yl)-3-(6-methyl-1H-benzo[d]imidazol-2-yl)pyrazin-2-amine; MS (ES+) 404.16

Compound I-46 3-(6-methyl-1H-benzo[d]imidazol-2-yl)-5-(4-(thiazol-2-yl)piperazin-1-yl)pyrazin-2-amine; MS (ES+) 393.1

Compound I-47 5-(4-(3-fluorophenyl)piperazin-1-yl)-3-(6-methyl-1H-benzo[d]imidazol-2-yl)pyrazin-2-amine; MS (ES+) 404.16

Compound I-48 5-(4-(3-methoxyphenyl)piperazin-1-yl)-3-(6-methyl-1H-benzo[d]imidazol-2-yl)pyrazin-2-amine; 1H NMR (400.0 MHz, DMSO) d 2.44+2.45 (3H, 2×s), 3.32 (4H, m), 3.63 (4H, m), 3.75 (3H, s), 6.41(1H, dd), 6.56 (1H, s), 6.65 (1H, d), 7.06+7.11 (1H, 2×d), 7.16 (1H, t), 7.28 (2H, br s), 7.37+7.51 (1H, 2×s), 7.47+7.59 (1H, 2×d), 8.05, 8.06 (1H, 2×s), 12.12 (1H, 2×s); MS (ES+) 416.17

Compound I-49 5-(4-(dimethylamino)piperidin-1-yl)-3-(6-methyl-1H-benzo[d]imidazol-2-yl)pyrazin-2-amine; MS (ES+) 352.11

Compound I-50 2-(4-(5-amino-6-(6-methyl-1H-benzo[d]imidazol-2-yl)pyrazin-2-yl)piperazin-1-yl)benzonitrile; MS (ES+) 411.13

Compound I-51 5-(3-(dimethylamino)piperidin-1-yl)-3-(6-methyl-1H-benzo[d]imidazol-2-yl)pyrazin-2-amine; MS (ES+) 352.11

Compound I-52 3-(6-methyl-1H-benzo[d]imidazol-2-yl)-5-(4-(3-(trifluoromethyl)pyridin-2-yl)piperazin-1-yl)pyrazin-2-amine; MS (ES+) 455.04

Compound I-53 (4-(5-amino-6-(6-methyl-1H-benzo[d]imidazol-2-yl)pyrazin-2-yl)piperazin-1-yl)(furan-2-yl)methanone; MS (ES+) 404.13

Compound I-56 5-(4-(ethylsulfonyl)piperazin-1-yl)-3-(3H-imidazo[4,5-b]pyridin-2-yl)pyrazin-2-amine; $^1$H NMR (400.0 MHz, DMSO) d 1.45 (3H, t), 3.17 (2H, q), 3.37-3.4 (4H, m), 3.65-3.7 (4H, m), 7.3-7.35 (1H, m), 8.12 (1H, d), 8.15 (1H, s), 8.42-8.45 (1H, m) ppm; MS (ES+) 389

Compound I-63 (1-(5-amino-6-(6-methyl-1H-benzo[d]imidazol-2-yl)pyrazin-2-yl)piperidin-4-yl)(phenyl)methanone; 1H NMR (400.0 MHz, DMSO) d 1.70 (2H, m), 1.92 (2H, m), 2.43+2.45 (3H, 2×s), 2.99 (2H, m), 2.72 (1H, m), 4.34 (2H, m), 7.07 (1H, dd), 7.23 (2H, br s), 7.35-7.67 (5H, m), 8.03 (3H, m), 12.50 (1H, d) ppm; MS (ES+) 413.1

Compound I-64 3-(6-methyl-1H-benzo[d]imidazol-2-yl)-5-(4-(pyridin-2-yl)piperazin-1-yl)pyrazin-2-amine; 1H NMR (400.0 MHz, DMSO) d 2.43+2.46 (3H, 2×s), 3.60 (4H, m), 3.68 (4H, m), 6.68 (1H, m), 6.95 (1H, d), 7.09 (1H, dd), 7.28 (2H, br s), 7.51-7.61 (3H, m), 8.06 (1H, d), 8.17 (1h, d), 12.50 (1h, d) ppm; MS (ES+) 387.06

Compound I-65 1-(5-amino-6-(6-methyl-1H-benzo[d]imidazol-2-yl)pyrazin-2-yl)-1,4-diazepan-5-one; 1H NMR (400.0 MHz, DMSO) d 2.43+2.46 (3H, 2×s), 2.55 (2H, m), 3.24 (2H, m), 3.80 (4H, m), 7.06 (1H, dd), 7.12 (2H, br s), 7.36-7.65 (3H, m), 7.99 (1H, s), 12.40 (1H, s) ppm; MS (ES+) 338.03

Compound I-70 (S)-1-(5-amino-6-(6-methyl-1H-benzo[d]imidazol-2-yl)pyrazin-2-yl)-N-methylpyrrolidine-3-carboxamide; 1H NMR (400.0 MHz, DMSO) d 2.15 m), 2.43+ 2.45 (3H, 2×s), 2.63+2.65 (3H, 2×s), 3.06 (1H, m), 3.46 (2H, m), 3.63 (1H, m), 3.77 (1H, m), 7.01 (3H, m), 7.35-7.64 (2H, m), 7.69 (1H, s), 8.05 (1H, m), 12.35 (1H, m) ppm; MS (ES+) 352.03

Compound I-75 1-(5-amino-6-(1H-benzo[d]imidazol-2-yl)pyrazin-2-yl)pyrrolidin-2-one 1H NMR (400.0 MHz, DMSO) d 2.05-2.15 (2H, m), 2.62 (2H, t), 4.18 (2H, t), 7.25-7.3 (2H, m), 7.7-7.75 (2H, m), 9.03 (1H, s), 13.15 (1H, vbrs) ppm; MS (ES+) 295

Compound I-77 (R)-1-(5-amino-6-(6-methyl-1H-benzo[d]imidazol-2-yl)pyrazin-2-yl)-N-methylpyrrolidine-3-carboxamide; MS (ES+) 352.08

Compound I-158 5-(5-(ethylsulfonyl)hexahydropyrrolo[3,4-c]pyrrol-2(1H)-yl)-3-(6-methyl-1H-benzo[d]imidazol-2-yl)pyrazin-2-amine 1H NMR (400.0 MHz, DMSO) d 1.23 (3H, m), 2.43+2.46 (3H, 2×s), 3.11-3.20 (6H, m), 3.34-3.47 (2H, m), 3.61 (4H, m), 7.00-7.10 (3H, m), 7.35-7.59 (2H, m), 7.73 (1H, br s), 12.37+12.40 (1H, 2×s) ppm; MS (ES+) 428.01

For compound I-281 below, please see Tables 7 and 8 for analytical data.

Compound I-281 5-(5,6-dihydro-[1,2,4]triazolo[4,3-a]pyrazin-7(8H)-yl)-3-(6-methyl-1H-benzo[d]imidazol-2-yl)pyrazin-2-amine

Example 2

5-(4-(ethylsulfonyl)piperazin-1-yl)-3-(1-methyl-1H-benzo[d]imidazol-2-yl)pyrazin-2-amine (Compound I-15)

SCHEME II

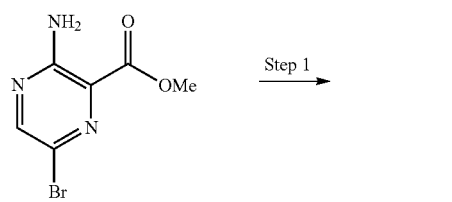

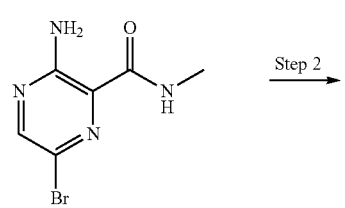

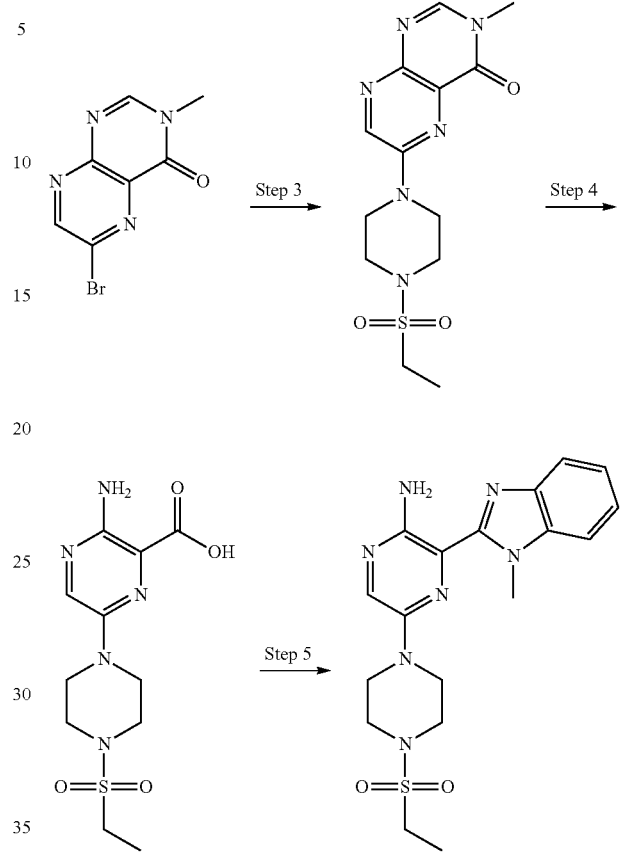

Method B

Step 1:
3-amino-6-bromo-N-methylpyrazine-2-carboxamide

Methyl 3-amino-6-bromo-pyrazine-2-carboxylate (7.5 g, 32.32 mmol) was suspended in 40% aqueous methylamine and the resulting mixture stirred vigorously at RT for 4 hours. The resultant precipitate was collected, washed with water and dried to give the desired product (6.73 g, 90% Yield). 1H NMR (400.0 MHz, DMSO) d 2.76 (s, 3H), 7.75 (br s, 2H), 8.34 (s, 1H), 8.58 (b rs, 1H) ppm; MS (ES+) 232.

Step 2: 6-bromo-3-methylpteridin-4(3H)-one

A mixture of triethyl orthoformate (32.23 g, 36.17 mL, 217.5 mmol) and acetic anhydride (38.49 g, 35.57 mL, 377.0 mmol) was treated with 3-amino-6-bromo-N-methyl-pyrazine-2-carboxamide (6.7 g, 29.00 mmol) and the resulting solution was heated at reflux for 2 hours. After cooling to RT, the resultant precipitate was collected, washed with EtOAc and dried to give the product as a beige solid (5.52 g, 79% Yield). 1H NMR (400.0 MHz, DMSO) d 3.54 (s, 3H), 8.72 (s, 1H); 9.17 (s, 1H) ppm; MS (ES+) 242.

Step 3: 6-(4-(ethylsulfonyl)piperazin-1-yl)-3-methylpteridin-4(3H)-one

A solution of 6-bromo-3-methyl-pteridin-4-one (5.516 g, 22.88 mmol) in 2-methoxyethanol (50.81 mL) was treated with 1-ethylsulfonylpiperazine (6.118 g, 34.32 mmol) and the resulting suspension heated for 2 hours at 100° C. The reaction mixture was cooled in an ice-water bath and resultant precipitate collected and washed with cold methanol to give the product as a yellow solid (5.02 g, 65% Yield). 1H NMR (400.0 MHz, DMSO) d 1.25 (t, 3H), 3.10 (q, 2H), 3.34 (m, 4H), 3.49 (s, 3H), 3.85 (m, 4H), 8.37 (s, 1H), 8.84 (s, 1H) ppm; MS (ES+) 339

Step 4: 3-amino-6-(4-(ethylsulfonyl)piperazin-1-yl)pyrazine-2-carboxylic acid A solution of 6-(4-ethylsulfonylpiperazin-1-yl)-3-methyl-pteridin-4-one (5 g, 14.78 mmol) in methanol (51.00 mL) was treated with sodium hydroxide (45.92 mL of 10% w/v, 114.8 mmol) and the reaction mixture stirred at RT overnight. The reaction mixture was concentrated in vacuo and the residue diluted with water and neutralised with formic acid. The resulting precipitate was filtered off and the filtrate acidified to pH4 by the addition of formic acid and extracted with dichloromethane. The combined organics were washed with brine, dried over MgSO$_4$ and concentrated in vacuo to give the product as a bright yellow solid (4.66 g, 52% Yield). 1H NMR (400.0 MHz, CDCl$_3$) d 1.45 (3H, t), 3.05 (2H, q), 3.54 (8H, m), 6.05 (2H, br s), 8.21 (1H, s) ppm; MS (ES+) 316

Step 5: 5-(4-(ethylsulfonyl)piperazin-1-yl)-3-(1-methyl-1H-benzo[d]imidazol-2-yl)pyrazin-2-amine (Compound I-15)

A mixture of 3-amino-6-(4-ethylsulfonylpiperazin-1-yl)pyrazine-2-carboxylic acid (100 mg, 0.3171 mmol), N-methylbenzene-1,2-diamine (42.61 mg, 39.64 μL, 0.3488 mmol), diethoxyphosphorylformonitrile (56.89 mg, 51.72 μL, 0.3488 mmol) and triethylamine (64.17 mg, 88.39 μL, 0.6342 mmol) in DME (3.000 mL) was heated in the microwave at 150° C. for 20 mins. The reaction mixture was allowed to cool and concentrated in vacuo. The resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected, passed through a sodium bicarbonate cartridge and freeze-dried to give the title compound as a yellow solid (79 mg, 60% Yield).

1H NMR (400.0 MHz, DMSO) d 1.24 (3H, t), 3.13 (2H, q), 3.31 masked signal, 3.50 (4H, m), 4.23 (3H, s), 7.30 (1H, m), 7.36 (1H, m), 7.44 (2H, br s), 7.67 (1H, m), 7.73 (1H, m), 8.10 (1H, s) ppm; MS (ES+) 402

The following compounds were all prepared using the method described for Compound I-15 above.

Compound I-16 3-(1H-benzo[d]imidazol-2-yl)-5-(4-(ethylsulfonyl)piperazin-1-yl)pyrazin-2-amine was also prepared using Method B, Steps 1-5. $^1$H NMR (400.0 MHz, DMSO) d 1.25 (3H, t), 3.12 (2H, q), 3.34 (4H, m), 3.60 (4H, m), 7.25 (2H, m), 7.66 (2H, m), 8.06 (1H, s) ppm; MS (ES+) 388

Compound I-308 5-(4-ethylsulfonylpiperazin-1-yl)-3-(1-phenylbenzimidazol-2-yl)pyrazin-2-amine 1H NMR (400.0 MHz, CDCl$_3$) d 1.37 (t, 3H), 2.76 (t, 4H), 2.93 (q, 2H), 3.11-3.14 (m, 4H), 7.04 (d, 1H), 7.24-7.28 (m, 3H), 7.32-7.35 (m, 3H), 7.43-7.54 (m, 3H), 7.64 (s, 1H) and 7.83 (d, 1H); MS (ES+) 464.0

Example 3

3-(benzo[d]thiazol-2-yl)-5-(4-(ethylsulfonyl)piperazin-1-yl)pyrazin-2-amine (Compound I-17)

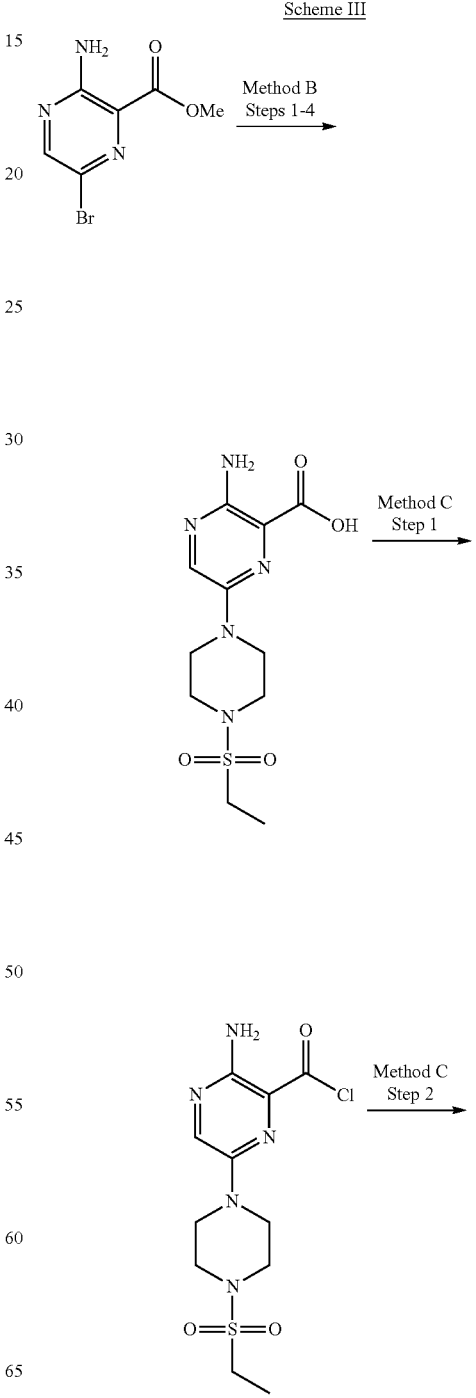

Scheme III

167
-continued

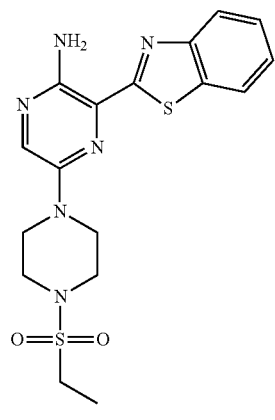

Compound I-17

Compound I-17 was prepared using Method B, Steps 1-4 followed by Method C, Steps 1 and 2.

Method C

Step 1: 3-amino-6-(4-(ethylsulfonyl)piperazin-1-yl)pyrazine-2-carbonyl chloride Thionyl chloride (1.887 g, 1.157 mL, 15.86 mmol) was added to a solution of 3-amino-6-(4-ethylsulfonylpiperazin-1-yl)pyrazine-2-carboxylic acid (1.25 g, 3.964 mmol) in chloroform (50 mL) and DMF (1 mL) and the resulting dark solution heated under reflux for 1 hour. The reaction mixture was allowed to cool to RT, concentrated in vacuo and taken through crude to the next stage.

Step 2: 3-(benzo[d]thiazol-2-yl)-5-(4-(ethylsulfonyl)piperazin-1-yl)pyrazin-2-amine (Compound I-17)

A mixture of 3-amino-6-(4-ethylsulfonylpiperazin-1-yl)pyrazine-2-carbonyl chloride (100 mg, 0.2996 mmol) and 2-aminobenzenethiol (112.5 mg, 96.98 µL, 0.8988 mmol) in acetonitrile was heated at 70° C. overnight. The reaction mixture was allowed to cool to RT, filtered and the resultant residue was purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were combined but still contained an impurity. The mixture was therefore purified on silica gel by flash column chromatography (50% EtOAc/Hexanes) to afford the title compound as a bright orange solid (23.2 mg, 20% Yield). 1H NMR (400.0 MHz, DMSO) d 1.24 (3H, t), 3.12 (2H, q), 3.36 masked signal, 3.54 (4H, m), 7.39 (2H, br s), 7.44-7.48 (1H, d), 7.52-7.57 (1H, d), 8.06 (1H, m), 8.11 (1H, m), 8.24 (1H, s) ppm; MS (ES⁺) 405

168
Example 4

5-(4-(ethylsulfonyl)piperazin-1-yl)-3-(3-phenyl-1,2,4-oxadiazol-5-yl)pyrazin-2-amine (Compound I-19)

Scheme IV

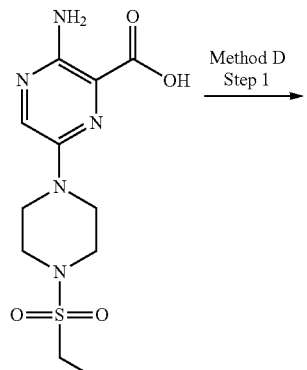

Method B
Steps 1-4

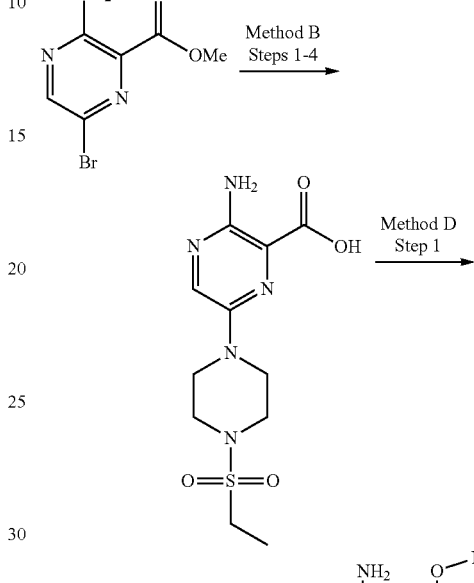

Method D
Step 1

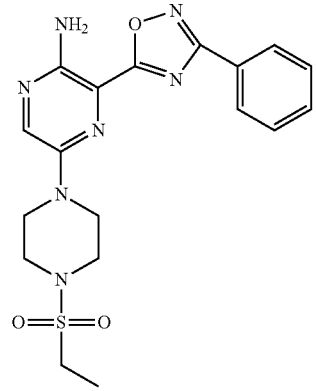

Compound I-19

Compound I-19 was prepared using Method B, Steps 1-4 followed by Method D, Step 1.

Method D

Step 1: 5-(4-(ethylsulfonyl)piperazin-1-yl)-3-(5-phenyl-1,3,4-oxadiazol-2-yl)pyrazin-2-amine (Compound I-19) CDI (102.8 mg, 0.6342 mmol) was added to a solution of 3-amino-6-(4-ethylsulfonylpiperazin-1-yl)pyrazine-2-carboxylic acid (100 mg, 0.3171 mmol) and N'-hydroxybenzamidine (86.35 mg, 0.6342 mmol) in DMF (3.000 mL) and the resulting solution stirred at RT for 3 hours and then heated at 100° C. overnight. The mixture was allowed to cool, poured in water and extracted with EtOAc. The organic extract was washed with water (2×), brine, dried over Na₂SO₄, filtered and concentrated in vacuo. The resultant residue was purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were collected and freeze-dried to give the title compound as a bright yellow solid (53.6 mg, 30% Yield). 1H NMR (400.0 MHz, DMSO) d 1.24 (3H, t), 3.11 (2H, q), 3.33 (4H, m), 3.55 (4H, m), 7.18 (2H, br s), 7.59-7.66 (3H, m), 8.19 (2H, m), 8.42 (1H, s) ppm; MS (ES⁺) 416

Example 5

5-(4-(ethylsulfonyl)piperazin-1-yl)-3-(5-phenyl-1,3,4-oxadiazol-2-yl)pyrazin-2-amine (Compound I-18)

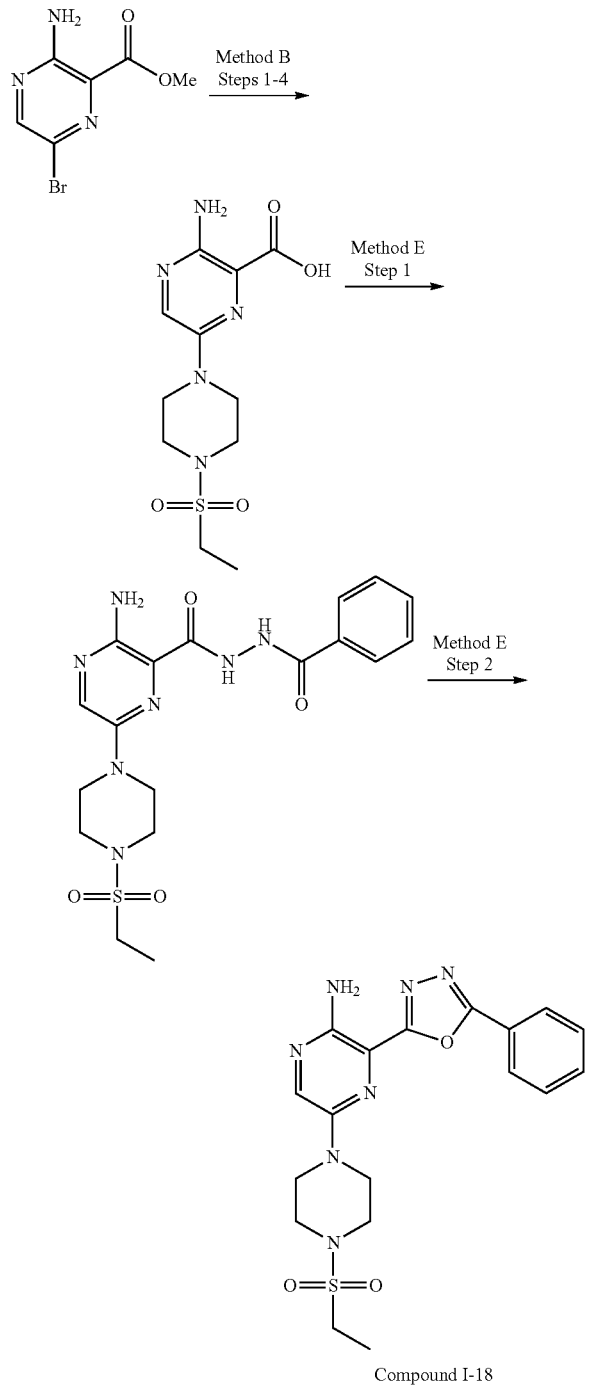

Compound I-18 was prepared using Method B, Steps 1-4 followed by Method E, Steps 1-2.

Method E

Step 1: 3-amino-N'-benzoyl-6-(4-ethylsulfonylpiperazin-1-yl)pyrazine-2-carbohydrazide TBTU (763.9 mg, 2.379 mmol) and triethylamine (160.5 mg, 221.1 μL, 1.586 mmol) were added to a solution of 3-amino-6-(4-ethylsulfonylpiperazin-1-yl)pyrazine-2-carboxylic acid (500 mg, 1.586 mmol) and benzohydrazide (259.1 mg, 1.903 mmol) in DMF and the resulting solution stirred overnight at RT. The mixture was diluted with EtOAc and water and the layers separated. Aqueous layer extracted further with ethyl acetate (2×20 mL) and combined organics washed with water (3×20 mL), dried (MgSO₄) and concentrated in vacuo. Purified by column chromatography on silica eluting with ethyl acetate. Product fractions combined and concentrated in vacuo to leave the product as a yellow solid (522 mg, 76% Yield).

1H NMR (400.0 MHz, DMSO) d 1.36 (3H, t), 3.24 (2H, q), 3.41 (4H, m), 3.65 (4H, m), 6.95 (2H, br s), 7.58 (2H, m), 7.65 (1H, m), 8.05 (2H, m), 8.45 (1H, m), 10.41 (1H, s), 10.55 (1H, s) ppm; MS (ES⁺) 434

Step 2: 5-(4-(ethylsulfonyl)piperazin-1-yl)-3-(5-phenyl-1,3,4-oxadiazol-2-yl)pyrazin-2-amine (Compound I-18)

A mixture of 3-amino-N'-benzoyl-6-(4-ethylsulfonylpiperazin-1-yl)pyrazine-2-carbohydrazide (50 mg, 0.1153 mmol) in phosphorus oxychloride (884.0 mg, 537.4 μL, 5.765 mmol) was heated at 100° C. for 3 hours. The mixture was allowed to cool to RT and added carefully to ice water. The mixture was extracted with EtOAc (3×10 mL) and the combined organics washed with 1N NaOH and brine, dried (MgSO₄) and concentrated in vacuo. The resultant residue was purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were collected and freeze-dried to give the title compound (48.8 mg, 80% Yield).

1H NMR (400.0 MHz, DMSO) d 1.24 (3H, t), 3.11 (2H, q), 3.33-3.36 (4H, m), 3.56 (4H, masked signal), 6.95 (2H, br s), 7.63-7.69 (3H, m), 8.11-8.13 (2H, m), 8.28 (1H, s) ppm; MS (ES⁺) 416.01

The following compounds were all prepared using the same method or a similar method to the one described for Compound I-18 above.

Compound I-69 5-(3-amino-6-(4-(ethylsulfonyl)piperazin-1-yl)pyrazin-2-yl)-N-phenyl-1,3,4-oxadiazol-2-amine 1H NMR (400.0 MHz, DMSO) d 1.24 (t, 3H), 3.17 (d, J=5.2 Hz, 2H), 3.35 (br s, 4H), 3.48-3.50 (m, 4H), 6.87 (s, 2H), 7.03 (t, 1H), 7.35-7.39 (m, 2H), 7.65-7.67 (m, 2H), 8.14 (s, 1H) and 10.89 (s, 1H) ppm; MS (ES⁺) 430.99

Compound I-283 5-(4-ethylsulfonylpiperazin-1-yl)-3-[5-(3-fluorophenyl)-1,3,4-oxadiazol-2-yl]pyrazin-2-amine 1H NMR (400 MHz, DMSO) d 1.24 (t, 3H), 3.11 (q, 2H), 3.33 (m, 4H), 3.56 (m, 4H), 6.97 (br s, 2H), 7.53-7.58 (m, 1H), 7.69-7.75 (m, 1H), 7.86-7.90 (m, 1H), 7.96-7.98 (m, 1H) and 8.29 (1H, s) ppm; MS (ES⁺) 434.16

Compound I-287 5-(4-ethylsulfonylpiperazin-1-yl)-3-[5-(o-tolyl)-1,3,4-oxadiazol-2-yl]pyrazin-2-amine 1H NMR (400 MHz, DMSO) d 1.24 (t, 3H), 2.70 (s, 3H), 3.10 (q, 2H), 3.30 (m, 4H) 3.54 (m, 4H), 6.96 (br s, 2H), 7.45-7.50 (m, 2H), 7.57 (m, 1H), 8.03 (m, 1H) and 8.28 (s, 1H) ppm; MS (ES⁺) 430.20

Compound I-289 3-[5-(2,6-difluorophenyl)-1,3,4-oxadiazol-2-yl]-5-(4-ethylsulfonylpiperazin-1-yl)pyrazin-2-amine 1H NMR (400 MHz, DMSO) d 1.23 (t, 3H), 3.10 (q, 2H), 3.32

(m, 4H), 3.52 (m, 4H), 6.98 (br s, 2H), 7.45 (m, 1H), 7.77-7.85 (m, 1H) and 8.31 (s, 1H) ppm; MS (ES+) 452.12

Compound I-292 5-(4-ethylsulfonylpiperazin-1-yl)-3-[5-(4-fluorophenyl)-1,3,4-oxadiazol-2-yl]pyrazin-2-amine 1H NMR (400 MHz, DMSO) d 1.24 (m, 3H), 3.11 (t, 2H), 3.31 masked signal, 3.56 (m, 4H), 6.96 (br s, 2H), 7.50 (m, 2H), 8.18 (m, 2H) and 8.28 (1H, s) ppm; MS (ES+) 434.12

Compound I-294 5-(4-ethylsulfonylpiperazin-1-yl)-3-[5-(3-methyl-2-thienyl)-1,3,4-oxadiazol-2-yl]pyrazin-2-amine 1H NMR (400 MHz, DMSO) d 1.23 (t, 3H), 2.63 (s, 3H), 3.10 (q, 2H), 3.30 (m, 4H), 3.54 (m, 4H), 6.92 (br s, 2H), 7.19 (d, 1H), 7.87 (d, 1H) and 8.27 (s, 1H) ppm; MS (ES+) 436.11

Compound I-297 5-(4-ethylsulfonylpiperazin-1-yl)-3-[5-(2-furyl)-1,3,4-oxadiazol-2-yl]pyrazin-2-amine 1H NMR (400 MHz, DMSO) d 1.24 (t, 3H), 3.11 (q, 2H), 3.30 (m, 4H), 3.52 (m, 4H), 6.85 (m, 1H), 6.95 (br s, 2H), 7.47 (m, 1H), 8.12 (m, 1H) and 8.27 (1H, s) ppm; MS (ES+) 406.15

Compound I-299 5-(4-ethylsulfonylpiperazin-1-yl)-3-[5-(2-fluorophenyl)-1,3,4-oxadiazol-2-yl]pyrazin-2-amine 1H NMR (400 MHz, DMSO) d 1.24 (t, 3H), 3.11 (t, 2H), 3.30 (m, 4H), 3.53 (m, 4H), 6.97 (br s, 2H), 7.47-7.56 (m, 2H), 7.75 (m, 1H), 8.11 (m, 1H) and 8.29 (1H, s) ppm; MS (ES+) 434.15

Compound I-312 5-(4-ethylsulfonylpiperazin-1-yl)-3-[5-(2-thienyl)-1,3,4-oxadiazol-2-yl]pyrazin-2-amine 1H NMR (400 MHz, DMSO) d 1.24 (t, 3H), 3.11 (q, 2H), 3.34 (m, 4H), 3.55 (m, 4H), 6.93 (br s, 2H), 7.35 (m, 1H), 7.94 (dd, 1H), 8.01 (dd, 1H) and 8.27 (1H, s) ppm; MS (ES+) 422.10

Example 6

3-amino-6-(4-(ethylsulfonyl)piperazin-1-yl)-N-phenylpyrazine-2-carboxamide (Compound I-20)

Scheme VI

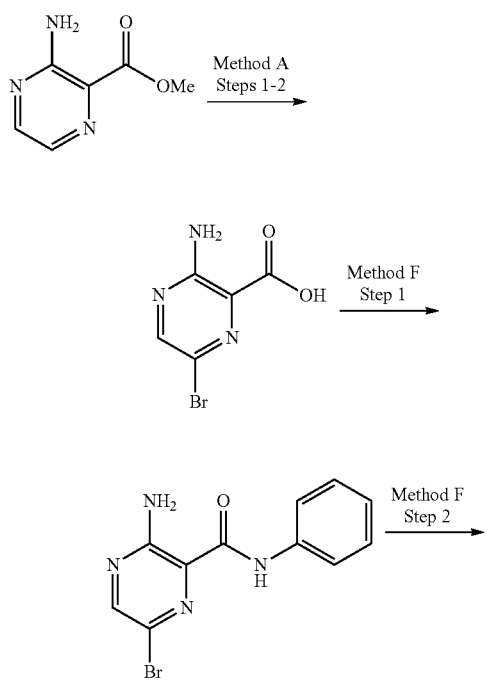

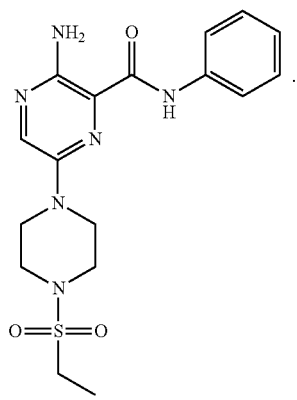

Compound I-20

Compound I-20 was prepared using Method A, Steps 1-2 followed by Method F, Steps 1-2.

Method F

Step 1:
3-amino-6-bromo-N-phenylpyrazine-2-carboxamide

A mixture of 3-amino-6-bromo-pyrazine-2-carboxylic acid (3.5 g, 16.05 mmol), 1,1'-carbonyldiimidazole (5.205 g, 32.10 mmol), DIPEA (2.282 g, 3.075 mL, 17.66 mmol) and DMAP (98.04 mg, 0.8025 mmol) were combined in DMSO (131.2 mL) and stirred for 30 min. Aniline (1.495 g, 1.463 mL, 16.05 mmol) was then added and the resulting solution stirred at RT for 18 hours. After this time water was added and the product collected by filtration to give a brown powder (3.5 g, 74% Yield).

1H NMR (400.0 MHz, DMSO) d 7.04 (1H, m), 7.29 (2H, m), 7.72 (4H, m), 8.36 (1H, s), 10.22 (2H) ppm; MS (ES+) 295.

Step 2: 3-amino-6-(4-(ethylsulfonyl)piperazin-1-yl)-N-phenylpyrazine-2-carboxamide 3-amino-6-bromo-N-phenyl-pyrazine-2-carboxamide (50 mg, 0.1706 mmol) was heated in neat 1-ethylsulfonylpiperazine (excess) at 190° C. for 115 mins in the microwave. The mixture was partitioned between water and EtOAc and the aqueous layer separated. The organic phase was dried (MgSO4) and concentrated in vacuo. The resultant residue was purified by reverse phase preparative HPLC [Waters Sunfire C18, 10 uM, 100A column, gradient 10%-95% B (solvent A: 0.05% TFA in water, solvent B: CH3CN) over 16 minutes at 25 mL/min]. The fractions were collected and freeze-dried to give the title compound (41.2 mg, 58% Yield).

1H NMR (400.0 MHz, DMSO) d 1.24 (t, J=7.4 Hz, 3H), 3.11 (t, J=7.3 Hz, 2H), 3.34-3.31 (m, 4H), 3.58-3.56 (m, 4H), 6.94 (s, 2H), 7.13 (s, 1H), 7.40-7.36 (m, 2H), 7.77-7.75 (m, 2H), 8.29 (s, 1H) and 9.99 (s, 1H) ppm; MS (ES+) 391

Example 7

5-(1,1-dioxo-1,4-thiazinan-4-yl)-3-(6-methyl-1H-benzimidazol-2-yl)pyrazin-2-amine (Compound I-21)

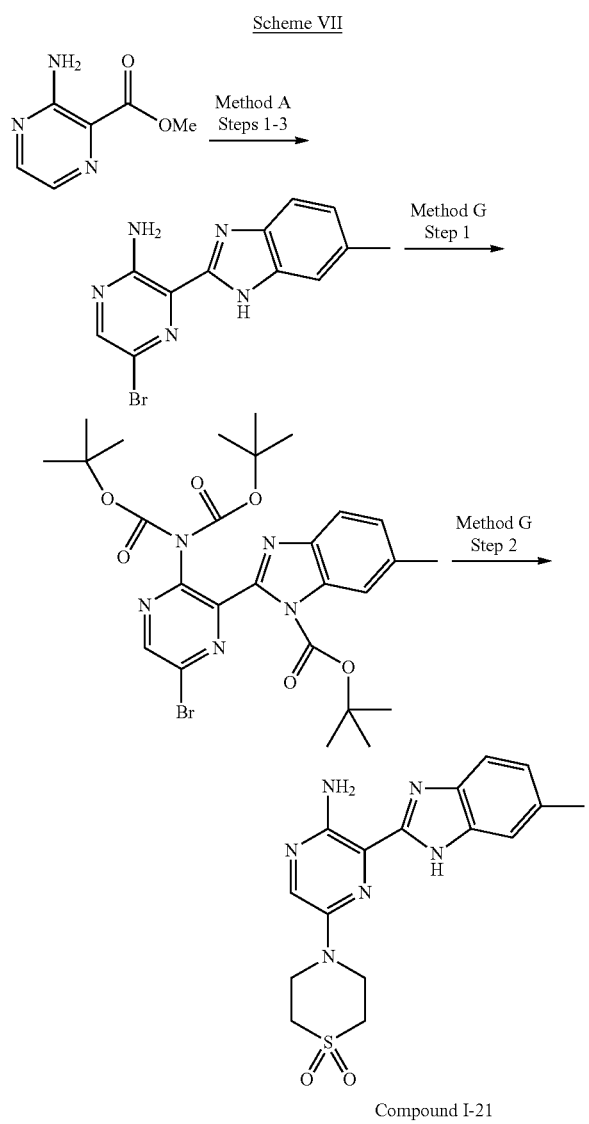

Compound I-21

Compound I-21 was prepared using Method A, Steps 1-3 followed by Method G, Steps 1-2.

Method G

Step 1: Tert-butyl 2-(3-(bis(tert-butoxycarbonyl)amino)-6-bromopyrazin-2-yl)-1H-benzo[d]imidazole-1-carboxylate A mixture of 5-bromo-3-(6-methyl-1H-benzimidazol-2-yl)pyrazin-2-amine (800 mg, 2.630 mmol), di-tert-butyl dicarbonate (2.584 g, 2.720 mL, 11.84 mmol) and DMAP (32.13 mg, 0.2630 mmol) in a mixture of acetonitrile (15 ml) and THF (10 ml) was allowed to stir overnight at RT. The mixture was concentrated in vacuo and purified on silica gel by flash column chromatography (30% EtOAc/Hexanes) to afford the title compound as a light yellow solid (1.10 g, 69% Yield). MS (ES+) 606

Step 2: 5-(1,1-dioxo-1,4-thiazinan-4-yl)-3-(6-methyl-1H-benzimidazol-2-yl)pyrazin-2-amine A solution of tert-butyl 2-[3-[bis(tert-butoxycarbonyl)amino]-6-bromo-pyrazin-2-yl]-6-methyl-benzimidazole-1-carboxylate (70 mg, 0.1158 mmol) in DMF (2 mL) was treated with thiomorpholine (59.74 mg, 0.5790 mmol) and heated to 60° C. for 3 hours. The mixture was then diluted with EtOAc, washed with water, brine, dried (MgSO$_4$) and concentrated in vacuo. The residue was dissolved in DCM (10 mL), treated with mCPBA (59.95 mg, 0.3474 mmol) and stirred at RT for 1 hour. After washing with a 1:1 Na$_2$CO$_3$/Na$_2$S$_2$O$_3$ solution, TFA (264.1 mg, 178.4 µL, 2.316 mmol) was added and the mixture stirred at RT for 1 hour. This was concentrated in vacuo and the resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected and freeze-dried to give the title compound (13.1 mg, 31% Yield).

$^1$H NMR (400.0 MHz, DMSO) d 2.45 (3H, s), 3.15-3.2 (4H, m), 4.15-4.2 (4H, m), 7.1-7.15 (1H, m), 7.4-7.45 (1H, m), 7.5-7.55 (1H, m), 8.15 (1H, s) ppm; MS (ES+) 359

Example 8

3-(6-methyl-1H-benzo[d]imidazol-2-yl)-5-(1,4-dioxaspiro[4.5]dec-7-en-8-yl)pyrazin-2-amine (Compound I-22)

Scheme VIII

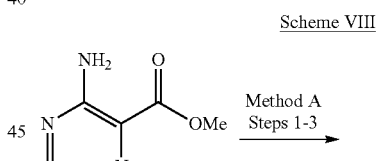

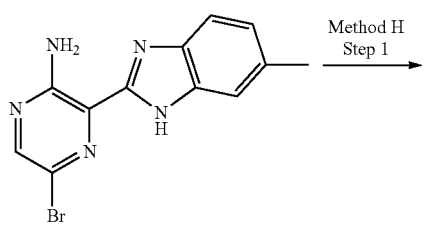

175

-continued

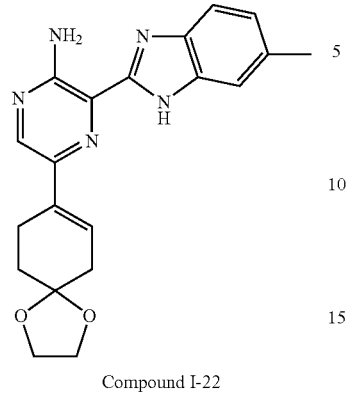

Compound I-22

Compound I-22 was prepared using Method A, Steps 1-3 followed by Method H, Step 1.

Method H: Step 1: 3-(6-methyl-1H-benzo[d]imidazol-2-yl)-5-(1,4-dioxaspiro[4.5]dec-7-en-8-yl)pyrazin-2-amine A mixture of 5-bromo-3-(6-methyl-1H-benzimidazol-2-yl)pyrazin-2-amine (150 mg, 0.4932 mmol), 1,4-dioxaspiro[4.5]dec-7-en-8-ylboronic acid (181.5 mg, 0.9864 mmol), dichloropalladium; triethylphosphane (10.20 mg, 0.02466 mmol) and $Na_2CO_3$ (740.0 µL of 2 M, 1.480 mmol) were heated in DMF (1.500 mL) at 130° C. in a microwave for 30 min. EtOAc was added and the organic phase washed with saturated aqueous $Na_2CO_3$, dried ($MgSO_4$) and concentrated in vacuo. The resulting oil was purified by reverse phase preparative HPLC [Waters Sunfire C18, 10 uM, 100A column, gradient 10%-95% B (solvent A: 0.05% TFA in water, solvent B: $CH_3CN$) over 16 minutes at 25 mL/min]. The fractions were collected and freeze-dried to give the title compound as a yellow solid (113 mg, 63% Yield). $^1$H NMR (400.0 MHz, DMSO) d 1.86 (t, J=6.4 Hz, 2H), 2.45 (m, 5H), 2.76 (s, 2H), 3.95 (s, 4H), 6.61 (t, J=3.9 Hz, 1H), 7.07 (dd, J=1.3, 8.3 Hz, 1H), 7.38 (s, 1H), 7.48 (d, J=8.2 Hz, 1H), 7.54 (s, 1H), 7.62 (d, J=8.3 Hz, 1H), 8.31 (d, J=4.0 Hz, 1H) and 8.37 (s, 1H) ppm; MS (ES$^+$) 364

Example 9

4-(5-amino-6-(6-methyl-1H-benzo[d]imidazol-2-yl)pyrazin-2-yl)-N,N-dimethyl-5,6-dihydropyridine-1(2H)-sulfonamide (Compound I-23)

Scheme IX

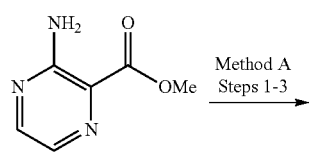

176

-continued

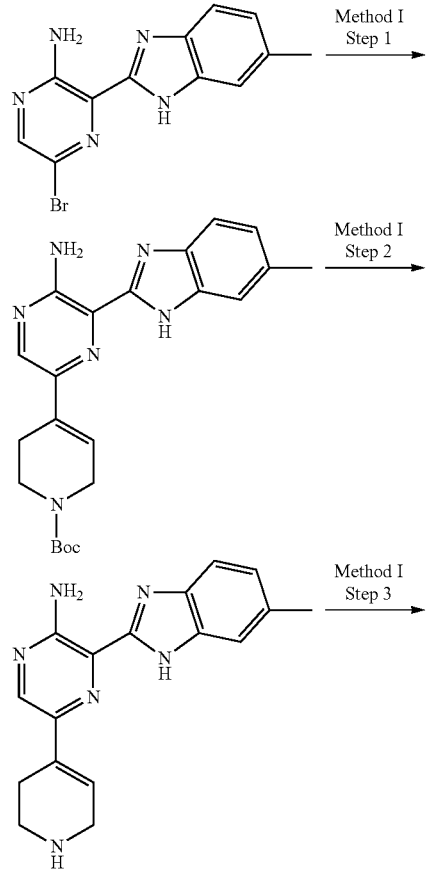

Compound I-23

Compound I-23 was prepared using Method A, Steps 1-3 followed by Method I, Steps 1-3.

Method I:

Step 1: Tert-butyl 4-(5-amino-6-(6-methyl-1H-benzo[d]imidazol-2-yl)pyrazin-2-yl)-5,6-dihydropyridine-1(2H)-carboxylate A mixture of 5-bromo-3-(6-methyl-1H-benzimidazol-2-yl)pyrazin-2-amine (500 mg, 1.644 mmol), tert-butyl 4-(4,4,5,5-tetramethyl-1,3,2-dioxaborolan-2-yl)-3,6-dihydro-2H-pyridine-1-carboxylate (660.8 mg, 2.137 mmol), dichloropalladium; triethylphosphane (34.00 mg, 0.08220 mmol) and $Na_2CO_3$ (2.466 mL of 2 M, 4.932 mmol) in DMF (5.000 mL) were heated to 130° C. for 60 min in a microwave.

EtOAc was added and the organic phase washed with saturated aqueous Na$_2$CO$_3$, dried (MgSO$_4$) and concentrated in vacuo. The mixture was taken through crude to the next stage. MS (ES$^+$) 407

Step 2: 3-(6-methyl-1H-benzo[d]imidazol-2-yl)-5-(1,2,3,6-tetrahydropyridin-4-yl)pyrazin-2-amine Tert-butyl 4-[5-amino-6-(6-methyl-1H-benzimidazol-2-yl)pyrazin-2-yl]-3,6-dihydro-2H-pyridine-1-carboxylate (620 mg, 1.525 mmol) was stirred in DCM (20 mL) with TFA (4 mL) for 2 hours. The solvent was removed in vacuo and the residue taken up in EtOAc and washed with saturated aqueous Na$_2$CO$_3$. DCM was added and the resultant solid was collected by filtration and taken through to the next stage. MS (ES$^+$) 307

Step 3: 4-(5-amino-6-(6-methyl-1H-benzo[d]imidazol-2-yl)pyrazin-2-yl)-N,N-dimethyl-5,6-dihydropyridine-1(2H)-sulfonamide (Compound I-23)

A solution of 3-(6-methyl-1H-benzimidazol-2-yl)-5-(1,2,3,6-tetrahydropyridin-4-yl)pyrazin-2-amine (58 mg, 0.1893 mmol) and triethylamine (38.31 mg, 52.77 µL, 0.3786 mmol) in DMSO (1.450 mL) was treated with N,N-dimethylsulfamoyl chloride (35.34 mg, 26.43 µL, 0.2461 mmol). The solution was stirred at RT for 16 hours and then partitioned between EtOAc and water. The aqueous layer was separated, organics dried over MgSO$_4$ and concentrated in vacuo to give a yellow solid which was washed with MeOH and filtered to give the desired product (47 mg, 57% Yield). 1H NMR (400.0 MHz, DMSO) d 2.46 (s, 3H), 2.77 (s, 2H), 2.80 (s, 6H), 3.48 (s, 2H), 3.96 (d, J=3.0 Hz, 2H), 6.76 (s, 1H), 7.10 (s, 1H), 7.61-7.40 (m, 3H) and 8.34 (s, 1H) ppm; MS (ES$^+$) 414

Example 10

1-(5-amino-6-(6-methyl-1H-benzo[d]imidazol-2-yl)pyrazin-2-yl)pyridin-4(1H)-one (Compound I-24)

Scheme X

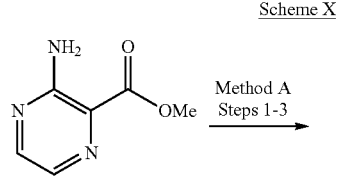

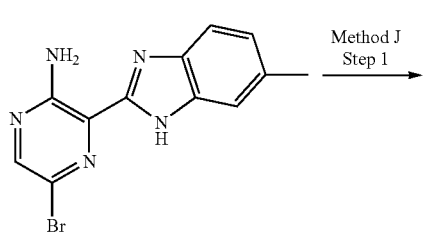

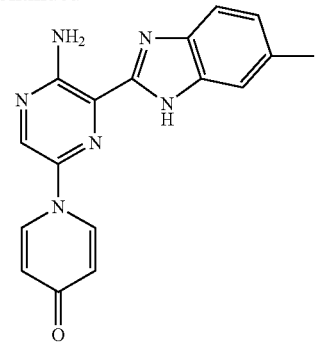

Compound I-24

Compound I-24 was prepared using Method A, Steps 1-3 followed by Method J, Step 1.

Method J: 1-(5-amino-6-(6-methyl-1H-benzo[d]imidazol-2-yl)pyrazin-2-yl)pyridin-4(1H)-one A mixture of 5-bromo-3-(6-methyl-1H-benzimidazol-2-yl)pyrazin-2-amine (80 mg, 0.263 mmol), pyridin-4(1H)-one (287 mg, 2.63 mmol), cesium carbonate (257 mg, 0.8 mmol) and copper (5 mg, 0.08 mmol) were heated in NMP (2 mL) at 150° C. for 1 hour. The reaction mixture was diluted with EtOAc, washed with 1N NaOH, and the organic layer filtered through a pad of celite and concentrated in vacuo. The resulting solid was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected and freeze-dried to give the title compound (24.7 mg, 30% Yield).

1H NMR (400.0 MHz, MeOD) d 2.5 (3H, s), 6.65 (2H, d), 7.1-7.2 (1H, m), 7.4-7.5 (1H, m), 7.5-7.6 (1H, m), 8.45 (1H, s), 8.6 (2H, d) ppm; MS (ES$^+$) 319

The following compounds were all prepared using a similar method to the one described for Compound I-24 in Example 10 above.

Compound I-310 1-(5-amino-6-(1H-benzo[d]imidazol-2-yl)pyrazin-2-yl)pyridin-2(1H)-one 1H NMR (400 MHz, DMSO) d 6.45 (t, 1H), 6.55 (d, 1H), 7.3-7.35 (m, 2H), 7.5-7.55 (m, 1H), 7.6-7.7 (br s, 2H), 8.05-8.1 (m, 1H), 8.55 (s, 1H) and 13.15 (br s, 1H) ppm; MS (ES$^+$) 305.1

Compound I-311 1-[5-amino-6-(1H-benzimidazol-2-yl)pyrazin-2-yl]pyridin-4-one

1H NMR (400 MHz, DMSO) d 6.34 (d, 2H), 7.26-7.37 (m, 2H), 7.62 (d, 1H), 7.80 (d, 1H), 8.56 (d, 2H), 8.64 (s, 1H) and 13.17 (s, 1H) ppm; MS (ES$^+$) 305.15

Example 11

5-(5-amino-6-(1-methyl-1H-benzo[d]imidazol-2-yl)pyrazin-2-yl)-1-methylpyridin-2(1H)-one (Compound I-25)

Scheme XI

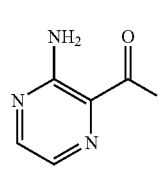

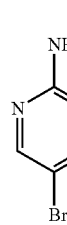

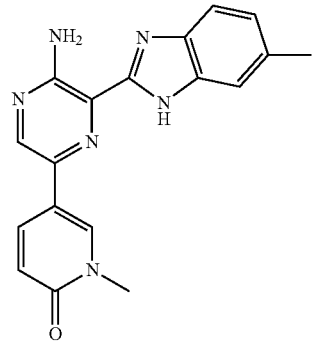

Compound I-25

Compound I-25 was prepared using Method A, Steps 1-3 followed by Method K, Step 1.

Method K: Step 1: 5-(5-amino-6-(6-methyl-1H-benzo[d]imidazol-2-yl)pyrazin-2-yl)-1-methylpyridin-2(1H)-one A mixture of 5-bromo-3-(6-methyl-1H-benzimidazol-2-yl)pyrazin-2-amine (100 mg, 0.3288 mmol), 1-methyl-5-(4,4,5,5-tetramethyl-1,3,2-dioxaborolan-2-yl)pyridin-2(1H)-one (154.6 mg, 0.6578 mmol), potassium carbonate (136.4 mg, 0.9867 mmol) and [1,1-bis(diphenylphosphino)ferrocene]dichloropalladium (26.86 mg, 0.03289 mmol) in DMF (3 mL) were heated to 110° C. for 2 hours. The mixture was diluted with EtOAc, washed with water, and the organic layer concentrated in vacuo. The resulting residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected and freeze-dried to give the title compound (47.4 mg, 40% Yield). MS (ES$^+$) 333

Example 12

3-(1H-benzo[d]imidazol-2-yl)-5-(1-(ethylsulfonyl)-1,2,3,6-tetrahydropyridin-4-yl)pyrazin-2-amine (Compound I-71)

Scheme XII

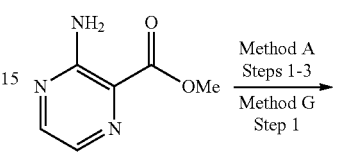

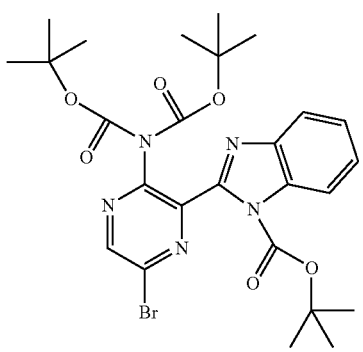

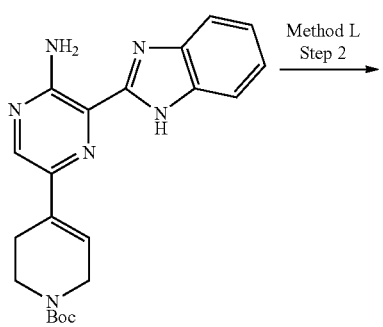

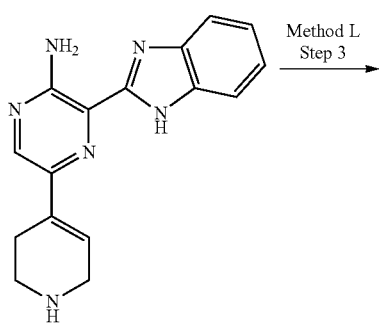

-continued

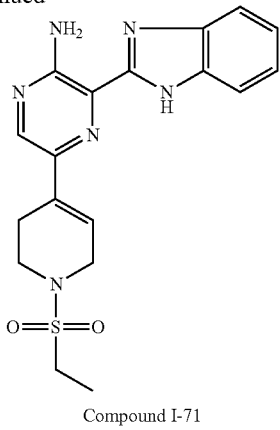

Compound I-71

Compound I-71 was, prepared using Method A, Steps 1-3 followed by Method G, Step 1 followed by Method L, Steps 1-3.

Method L: Step 1: Tert-butyl 4-(5-amino-6-(1H-benzo[d]imidazol-2-yl)pyrazin-2-yl)-5,6-dihydropyridine-1(2H)-carboxylate A mixture of tert-butyl 243-[bis(tert-butoxycarbonyl)amino]-6-bromo-pyrazin-2-yl)benzimidazole-1-carboxylate (5 g, 8.468 mmol), tert-butyl 4-(4,4,5,5-tetramethyl-1,3,2-dioxaborolan-2-yl)-3,6-dihydro-2H-pyridine-1-carboxylate (3.142 g, 10.16 mmol), 4-ditert-butylphosphanyl-N,N-dimethyl-aniline; dichloropalladium (59.96 mg, 0.08468 mmol) and $K_2CO_3$ (2.341 g, 16.94 mmol) in toluene (45.00 mL) and water (5.000 mL) was heated to 100° C. overnight. The reaction mixture was allowed to cool to RT and diluted with DCM and water. The DCM layer was separated, washed with 1M NaOH solution, dried ($Na_2SO_4$), filtered and evaporated to dryness to give a brown oil. This was purified on silica gel by flash column chromatography (0-30% EtOAc/hexanes) to afford the title compound (4.818 g, 82% Yield).

1H NMR (400.0 MHz, DMSO) d 1.16 (18H, s), 1.38 (9H, s), 1.43 (9H, s), 2.63 (2H, m), 3.61 (2H, m), 4.02 (2H, m), 7.01 (1H, m), 7.49 (1H, m), 7.52 (1H, m), 7.70 (1H, m), 8.05 (1H, m), 9.02 (1H, m) ppm; MS (ES$^+$) 693.38

Method L: Step 2: 3-(1H-benzo[d]imidazol-2-yl)-5-(1,2,3,6-tetrahydropyridin-4-yl)pyrazin-2-amine To a solution of tert-butyl 243-(bis(tert-butoxycarbonyl)amino)-6-(1-tert-butoxycarbonyl-3,6-dihydro-2H-pyridin-4-yl)pyrazin-2-yl)benzimidazole-1-carboxylate (5.808 g, 8.383 mmol) in DCM (58.08 mL) was added TFA (7.646 g, 5.166 mL, 67.06 mmol) and the mixture allowed to stir at RT for 30 minutes. Analysis showed there was SM remaining therefore a further 10 mL of TFA was added and reaction mixture left to stir for 24 hours. The reaction mixture was evaporated in vacuo to obtain the product as a yellow solid (4.362 g, 84% Yield).

1H NMR (400.0 MHz, DMSO) d 2.90 (s, 2H), 3.39 (s, 2H), 3.87 (s, 2H), 6.80 (s, 1H), 7.30 (s, 2H), 7.70 (s, 2H), 8.44 (s, 1H), 8.88 (s, 2H) and 12.90 (br s, 1H) ppm; MS (ES$^+$) 293.0

Method L: Step 3: 3-(1H-benzo[d]imidazol-2-yl)-5-(1-(ethylsulfonyl)-1,2,3,6-tetrahydropyridin-4-yl)pyrazin-2-amine Ethanesulfonyl chloride (16.30 mg, 12.01 µL, 0.1268 mmol) was added to a solution of 3-(1H-benzimidazol-2-yl)-5-(1,2,3,6-tetrahydropyridin-4-yl)pyrazin-2-amine (60 mg, 0.1153 mmol) and DIPEA (44.71 mg, 60.26 µL, 0.3459 mmol) in N,N-dimethylformamide (1 mL) and the resulting solution stirred at ambient temperature. Analysis after 30 minutes showed SM still remaining therefore the reaction was treated with further ethanesulfonyl chloride (4 µL, 0.04222 mmol). The mixture was allowed to stir for a further 10 minutes and then partitioned between EtOAc and water. The aqueous layer was extracted with EtOAc (2×), DCM (2×), dried (MgSO$_4$), filtered and concentrated. The mixture was triturated with DCM and the resultant yellow solid dried under vacuum at 50° C. (44.33 mg, 57% Yield).

1H NMR (400.0 MHz, DMSO) d 1.25 (t, J=7.3 Hz, 3H), 2.79 (br s, 2H), 3.16 (q, 2H), 3.51 (t, J=5.6 Hz, 2H), 4.01 (br d, 2H), 6.79 (s, 1H), 7.26 (t, 1H), 7.32 (t, 1H), 7.62 (d, J=7.8 Hz, 1H), 7.76 (d, J=7.9 Hz, 1H), 8.37 (s, 1H) and 12.85 (s, 1H) ppm; MS (ES$^+$) 385.0

The following compounds were all prepared using same method or a method similar to the one described for Compound I-71 in Example 12 above.

Compound I-26 4-(5-amino-6-(3H-imidazo[4,5-b]pyridin-2-yl)pyrazin-2-yl)-N,N-dimethyl-5,6-dihydropyridine-1(2H)-sulfonamide 1H NMR (400.0 MHz, DMSO) d 8.48-8.44 (m, 2H), 8.13 (d, J=7.9 Hz, 1H), 7.38 (dd, J=4.9, 7.6 Hz, 1H), 6.84 (s, 1H), 3.96 (d, J=2.8 Hz, 2H), 3.47 (s, 2H), 3.47 (s, 6H) ppm; MS (ES$^+$) 401

Compound I-27 5-(1-(ethylsulfonyl)-1,2,3,6-tetrahydropyridin-4-yl)-3-(3H-imidazo[4,5-b]pyridin-2-yl)pyrazin-2-amine 1H NMR (400.0 MHz, DMSO) d 8.48-8.44 (m, 2H), 8.13 (d, J=7.9 Hz, 1H), 7.38 (dd, J=4.9, 7.6 Hz, 1H), 6.84 (s, 1H), 4.00 (d, J=2.8 Hz, 2H), 3.50 (t, J=5.7 Hz, 2H), 3.16 (q, J=7.4 Hz, 2H), 2.81 (d, J=1.5 Hz, 2H) and 1.25 (t, J=7.3 Hz, 3H) ppm; MS (ES$^+$) 386

Compound I-58 5-(1-(ethylsulfonyl)-1,2,3,6-tetrahydropyridin-4-yl)-3-(3H-imidazo[4,5-b]pyridin-2-yl)pyrazin-2-amine; MS (ES$^+$) 386

Compound I-60 4-(5-amino-6-(3H-imidazo[4,5-b]pyridin-2-yl)pyrazin-2-yl)-N,N-dimethyl-5,6-dihydropyridine-1(2H)-sulfonamide

MS (ES$^+$) 401

Compound I-66 3-(1H-benzo[d]imidazol-2-yl)-5-(1,2,3,6-tetrahydropyridin-4-yl)pyrazin-2-amine 1H NMR (400.0 MHz, DMSO) d 2.90 (s, 2H), 3.39 (s, 2H), 3.87 (s, 2H), 6.80 (s, 1H), 7.30 (s, 2H), 7.70 (s, 2H), 8.44 (s, 1H), 8.88 (s, 2H) and 12.90 (br s, 1H) ppm; MS (ES$^+$) 293

Compound I-67 1-(4-(5-amino-6-(3H-imidazo[4,5-b]pyridin-2-yl)pyrazin-2-yl)-5,6-dihydropyridin-1(2H)-yl)-2-methylpropan-1-one H NMR (400.0 MHz, MeOH) d 8.51 (d, J=5.6 Hz, 1H), 8.42-8.38 (m, 1H), 8.34 (s, 1H), 7.66-7.63 (m, 1H), 6.61 (s, 1H), 4.35 (s, 1H), 4.24 (d, J=1.2 Hz, 1H), 3.83 (dd, J=5.8, 13.7 Hz, 2H), 3.05 (dt, J=23.4, 7.5 Hz, 1H), 2.74 (s, 1H), 2.68 (s, 1H) and 1.17 (dd, J=6.8, 12.1 Hz, 6H) ppm; MS (ES$^+$) 364

Compound I-76 2-(4-(5-amino-6-(1H-benzo[d]imidazol-2-yl)pyrazin-2-yl)-5,6-dihydropyridin-1(2H)-yl)ethanenitrile 1H NMR (400.0 MHz, DMSO) d 2.78-2.82 (2H, m), 2.95-3.0 (2H, m), 3.42-3.45 (2H, m), 4.05 (2H, s), 6.8-6.83 (1H, m), 7.3-7.33 (2H, m), 7.65-7.7 (2H, m), 8.19 (1H, s) ppm; MS (ES$^+$) 332.1

Compound I-78 (4-(5-amino-6-(1H-benzo[d]imidazol-2-yl)pyrazin-2-yl)-5,6-dihydropyridin-1(2H)-yl)(1-methylpiperidin-4-yl)methanone $^1$HNMR (400.0 MHz, DMSO) d 1.65 (4H, m), 2.06 (2H, m), 2.23 (3H, s), 2.67-2.85 (4H, m), 3.73 (2H, m), 4.19, 4.29 (2H, 2×m), 6.75 (1H, d), 7.27 (2H, m), 7.61 (1H, d), 7.75 (1H, d), 8.24 (1H, s), 8.36 (1H, d), 12.85 (1H, br s) ppm; MS (ES$^+$) 418.05

Compound I-79 3-(1H-benzo[d]imidazol-2-yl)-5-(1-(thiophen-2-ylsulfonyl)-1,2,3,6-tetrahydropyridin-4-yl)pyrazin-2-amine; MS (ES$^+$) 439.1

Compound I-82 (4-(5-amino-6-(1H-benzo[d]imidazol-2-yl)pyrazin-2-yl)-5,6-dihydropyridin-1(2H)-yl)(phenyl)methanone; MS (ES$^+$) 396.2

Compound I-89 4-(5-amino-6-(1H-benzo[d]imidazol-2-yl)pyrazin-2-yl)-N,N-dimethyl-5,6-dihydropyridine-1(2H)-sulfonamide; MS (ES$^+$) 399.2

Compound I-93 3-(1H-benzo[d]imidazol-2-yl)-5-(1-(cyclopropylsulfonyl)-1,2,3,6-tetrahydropyridin-4-yl)pyrazin-2-amine; MS (ES$^+$) 396.1

Compound I-94 3-(1H-benzo[d]imidazol-2-yl)-5-(1-(1-methyl-1H-imidazol-4-ylsulfonyl)-1,2,3,6-tetrahydropyridin-4-yl)pyrazin-2-amine; MS (ES$^+$) 436.1

Compound I-105 3-(1H-benzo[d]imidazol-2-yl)-5-(1-(thiophen-3-ylsulfonyl)-1,2,3,6-tetrahydropyridin-4-yl)pyrazin-2-amine; MS (ES$^+$) 438.1

Compound I-136 1-(4-(5-amino-6-(1H-benzo[d]imidazol-2-yl)pyrazin-2-yl)-5,6-dihydropyridin-1(2H)-yl)ethanone; MS (ES$^+$) 334.2

Compound I-137 1-(4-(5-amino-6-(1H-benzo[d]imidazol-2-yl)pyrazin-2-yl)-5,6-dihydropyridin-1(2H)-yl)-2-phenoxyethanone; MS (ES$^+$) 426.2

Compound I-138 1-(4-(5-amino-6-(1H-benzo[d]imidazol-2-yl)pyrazin-2-yl)-5,6-dihydropyridin-1(2H)-yl)-2-methoxyethanone; MS (ES$^+$) 364.2

Compound I-139 (4-(5-amino-6-(1H-benzo[d]imidazol-2-yl)pyrazin-2-yl)-5,6-dihydropyridin-1(2H)-yl)(pyridin-2-yl)methanone; MS (ES$^+$) 397.2

Compound I-140 1-(4-(5-amino-6-(1H-benzo[d]imidazol-2-yl)pyrazin-2-yl)-5,6-dihydropyridin-1(2H)-yl)-2-(2-methoxyethoxy)ethanone; MS (ES$^+$) 408.2

Compound I-161 (4-(5-amino-6-(1H-benzo[d]imidazol-2-yl)pyrazin-2-yl)-5,6-dihydropyridin-1(2H)-yl)(4-methylpiperazin-1-yl)methanone 1H NMR (400.0 MHz, DMSO) d 2.19 (3H, s), 2.32 (4H, m), 2.73 (2H, m), 3.19 (4H, m), 3.42 (2H, m), 3.96 (2H, m), 6.74 (1H, s), 7.30 (2H, m), 7.61 (1H, d), 7.75 (1H, d), 8.36 (1H, s), 12.82 (1H, s) ppm; MS (ES$^+$) 419.06

Compound I-173 (4-(5-amino-6-(1H-benzo[d]imidazol-2-yl)pyrazin-2-yl)-5,6-dihydropyridin-1(2H)-yl)(4-(dimethylamino)piperidin-1-yl)methanone 1H NMR (400.0 MHz, DMSO) d 1.35 (2H, m), 1.76 (2H, d), 2.19 (6H, s), 2.26 (1H, m), 2.74 (4H, m), 3.41 (2H, m), 3.64 (2H, d), 3.94 (2H, s), 6.74 (1H, s), 7.29 (2H, dt), 7.61 (1H, d), 7.75 (1H, d), 8.36 (1H, s), 12.82 (1H, s) ppm; MS (ES$^+$) 447.09

For compounds I-186 to I-280 below, please see Tables 7 and 8 for analytical data.

Compound I-186 1-(4-(5-amino-6-(1H-benzo[d]imidazol-2-yl)pyrazin-2-yl)-5,6-dihydropyridin-1(2H)-yl)-2-(dimethylamino)ethanone Compound I-191 4-(5-amino-6-(1H-benzo[d]imidazol-2-yl)pyrazin-2-yl)-5,6-dihydropyridin-1(2H)-yl)(pyridin-3-yl)methanone Compound I-200 (4-(5-amino-6-(1H-benzo[d]imidazol-2-yl)pyrazin-2-yl)-5,6-dihydropyridin-1(2H)-yl)(cyclobutyl)methanone Compound I-206 (4-(5-amino-6-(1H-benzo[d]imidazol-2-yl)pyrazin-2-yl)-5,6-dihydropyridin-1(2H)-yl)(cyclopentyl)methanone Compound I-210 3-(1H-benzo[d]imidazol-2-yl)-5-(1-(phenylsulfonyl)-1,2,3,6-tetrahydropyridin-4-yl)pyrazin-2-amine Compound I-213 1-(4-(5-amino-6-(1H-benzo[d]imidazol-2-yl)pyrazin-2-yl)-5,6-dihydropyridin-1(2H)-yl)-2-phenylethanone Compound I-214 1-(4-(5-amino-6-(1H-benzo[d]imidazol-2-yl)pyrazin-2-yl)-5,6-dihydropyridin-1(2H)-yl)-2,2-dimethylpropan-1-one Compound I-215 (4-(5-amino-6-(1H-benzo[d]imidazol-2-yl)pyrazin-2-yl)-5,6-dihydropyridin-1(2H)-yl)(2,6-difluorophenyl)methanone Compound I-227 (4-(5-amino-6-(1H-benzo[d]imidazol-2-yl)pyrazin-2-yl)-5,6-dihydropyridin-1(2H)-yl)(morpholino)methanone Compound I-234 4-(5-amino-6-(1H-benzo[d]imidazol-2-yl)pyrazin-2-yl)-N,N-dimethyl-5,6-dihydropyridine-1(2H)-carboxamide Compound I-235 (4-(5-amino-6-(1H-benzo[d]imidazol-2-yl)pyrazin-2-yl)-5,6-dihydropyridin-1(2H)-yl)(tetrahydro-2H-pyran-4-yl)methanone Compound I-241 3-(1H-benzo[d]imidazol-2-yl)-5-(1-(pyridin-3-ylsulfonyl)-1,2,3,6-tetrahydropyridin-4-yl)pyrazin-2-amine Compound I-243 2-methoxyethyl 4-(5-amino-6-(1H-benzo[d]imidazol-2-yl)pyrazin-2-yl)-5,6-dihydropyridine-1(2H)-carboxylate Compound I-244 methyl 4-(5-amino-6-(1H-benzo[d]imidazol-2-yl)pyrazin-2-yl)-5,6-dihydropyridine-1(2H)-carboxylate Compound I-249 (4-(5-amino-6-(1H-benzo[d]imidazol-2-yl)pyrazin-2-yl)-5,6-dihydropyridin-1(2H)-yl)(piperidin-1-yl)methanone Compound I-250 ethyl 4-(5-amino-6-(1H-benzo[d]imidazol-2-yl)pyrazin-2-yl)-5,6-dihydropyridine-1(2H)-carboxylate Compound I-254 but-2-ynyl 4-(5-amino-6-(1H-benzo[d]imidazol-2-yl)pyrazin-2-yl)-5,6-dihydropyridine-1(2H)-carboxylate Compound I-259 (4-(5-amino-6-(1H-benzo[d]imidazol-2-yl)pyrazin-2-yl)-5,6-dihydropyridin-1(2H)-yl)(cyclohexyl)methanone Compound I-261 benzyl 4-(5-amino-6-(1H-benzo[d]imidazol-2-yl)pyrazin-2-yl)-5,6-dihydropyridine-1(2H)-carboxylate Compound I-263 (4-(5-amino-6-(1H-benzo[d]imidazol-2-yl)pyrazin-2-yl)-5,6-dihydropyridin-1(2H)-yl)(2,6-dimethylphenyl)methanone Compound I-278 (R)-(4-(5-amino-6-(1H-benzo[d]imidazol-2-yl)pyrazin-2-yl)-5,6-dihydropyridin-1(2H)-yl)(3-(dimethylamino)pyrrolidin-1-yl)methanone Compound I-279 (4-(5-amino-6-(1H-benzo[d]imidazol-2-yl)pyrazin-2-yl)-5,6-dihydropyridin-1(2H)-yl)(1,4-diazepan-1-yl)methanone Compound I-280 (4-(5-amino-6-(1H-benzo[d]imidazol-2-yl)pyrazin-2-yl)-5,6-dihydropyridin-1(2H)-yl)(piperazin-1-yl)methanone Compound I-284 [4-[5-amino-6-(1H-benzimidazol-2-yl)pyrazin-2-yl]-3,6-dihydro-2H-pyridin-1-yl]-cyclopropyl-methanone 1H NMR (400.0 MHz, DMSO) d 0.75-0.78 (m, 4H), 2.00-2.05 (m, 1H), 2.67 (s, 1H), 2.80 (s, 1H), 3.75 (s, 1H), 3.94 (s, 1H), 4.21 (s, 1H), 4.47 (s, 1H), 6.78 (s, 1H), 7.24 (s, 2H), 7.62 (d, 1H), 7.76 (d, 1H), 8.37 (d, 1H) and 12.85 (s, 1H) ppm; MS (ES+) 361.21

Compound I-291 3-(1H-benzimidazol-2-yl)-5-(1-propylsulfonyl-3,6-dihydro-2H-pyridin-4-yl)pyrazin-2-amine 1H NMR (400.0 MHz, DMSO) d 0.99-1.03 (m, 3H), 1.69-1.79 (m, 2H), 2.80 (br s, 2H), 3.10-3.20 (m, 2H), 3.49-3.50 (m, 2H), 3.95 (s, 2H), 6.79 (s, 1H), 7.24-7.34 (m, 2H), 7.62 (d, 1H), 7.76 (d, 1H), 8.37 (s, 1H) and 12.85 (s, 1H) ppm; MS (ES+) 399.14

Compound I-293 1-[4-[5-amino-6-(1H-benzimidazol-2-yl)pyrazin-2-yl]-3,6-dihydro-2H-pyridin-1-yl]-2-methyl-propan-1-one 1H NMR (400.0 MHz, DMSO) d 1.04-1.07 (m, 6H), 2.67 (br s, 1H), 2.73 (br s, 1H), 2.89-3.04 (m, 1H), 3.75 (s, 2H), 4.20 (s, 1H), 4.30 (s, 1H), 6.76 (br s, 1H), 7.24-7.33 (m, 2H), 7.62 (d, 1H), 7.76 (d, 1H), 8.36 (s, 1H) and 12.84 (s, 1H) ppm; MS (ES+) 363.22

Compound I-309 1-[4-[5-amino-6-(1H-benzimidazol-2-yl)pyrazin-2-yl]-3,6-dihydro-2H-pyridin-1-yl]propan-1-one 1H NMR (400.0 MHz, DMSO) d 1.01-1.06 (m, 3H), 2.33-2.47 (m, 2H), 2.67 (s, 1H), 2.76 (s, 1H), 3.67-3.75 (m, 2H), 4.19-4.23 (m, 2H), 6.76 (d, 1H), 7.24-7.33 (m, 2H), 7.62 (d, 1H), 7.76 (d, 1H), 8.36 (d, 1H) and 12.84 (s, 1H) ppm; MS (ES+) 349.19

Example 13

3-amino-6-(4-(ethylsulfonyl)piperazin-1-yl)-N-(pyridin-2-yl)pyrazine-2-carboxamide (Compound I-55)

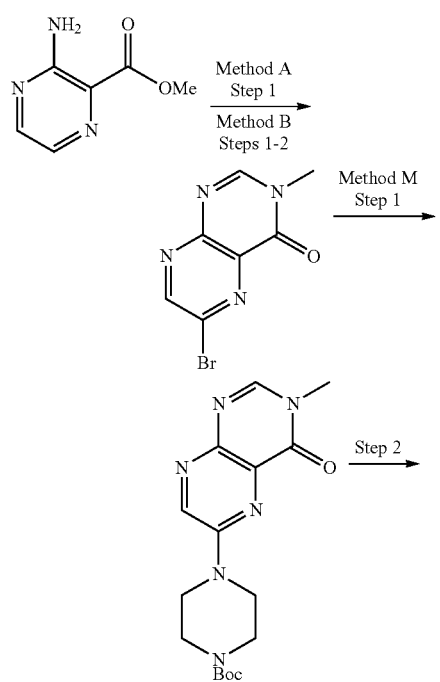

Scheme XIII

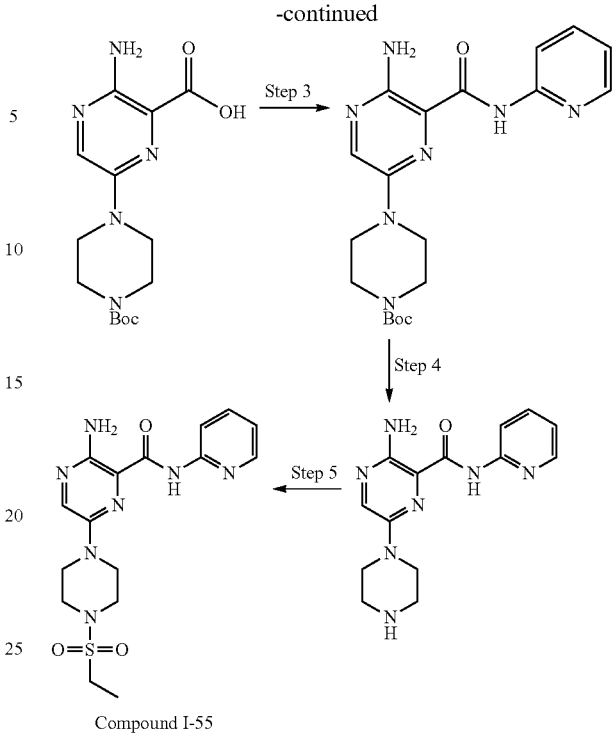

Compound I-55

Compound I-55 was prepared using Method A, Step 1 followed by Method M, Steps 1-5.

Method M: Step 1: Tert-butyl 4-(3-methyl-4-oxo-3,4-dihydropteridin-6-yl)piperazine-1-carboxylate To a solution of 6-bromo-3-methyl-pteridin-4-one (17.75 g, 73.64 mmol) in 2-methoxyethanol (163.5 mL) was added tert-butyl piperazine-1-carboxylate (24.70 g, 132.6 mmol) and the resulting suspension heated for 2 hours at 100° C. The reaction mixture was allowed to cool in an ice-water bath and the precipitate that formed collected and washed with cold methanol to give the desired product as a yellow solid (25.08 g, 98% Yield).

1H NMR (400.0 MHz, CDCl₃) d 1.50 (9H, m), 3.49 (3H, s), 3.62 (4H, br m), 3.83 (4H, br m), 8.09 (1H, s), 8.58 (1H, s) ppm; MS (ES+) 347.08

Method M: Step 2: 3-amino-6-(4-(tert-butoxycarbonyl)piperazin-1-yl)pyrazine-2-carboxylic acid Tert-butyl 4-(3-methyl-4-oxo-pteridin-6-yl)piperazine-1-carboxylate (25 g, 72.17 mmol) was stirred in NaOH (250 mL of 10% w/w,) and MeOH (250 mL) overnight at RT. The resulting suspension was concentrated and then acidified with formic acid followed by extraction of the aqueous with DCM. The mixture was treated with water, taken to pH 10 and filtered. The aqueous layer was reacidified and the resulting precipitated product was extracted into DCM and concentrated to give the product as a yellow solid (8 g, 24.74 mmol, 34% Yield).

MS (ES+) 324.02

Method M: Step 3: Tert-butyl 4-(5-amino-6-(pyridin-2-ylcarbamoyl)pyrazin-2-yl)piperazine-1-carboxylate To a mixture of 3-amino-6-(4-tert-butoxycarbonylpiperazin-1-yl)pyrazine-2-carboxylic acid (8.08 g, 24.99 mmol), di(imidazol-1-yl)methanone (4.863 g, 29.99 mmol), DMAP (152.7 mg, 1.250 mmol) and N-ethyl-N-isopropyl-propan-2-amine (8.074 g, 10.88 mL, 62.47 mmol) in DMSO (80.80 mL) was added pyridin-2-amine (4.704 g, 49.98 mmol) and the resulting solution stirred at 110° C. for 20 hours. Water (500 mL) was added and the mixture extracted into EtOAc (3×300 mL), dried and concentrated to give a residue which was triturated with EtOAc and filtered to give the required product as a yellow solid (5.48 g, 55% Yield).

1H NMR (400.0 MHz, DMSO) d 10.08 (s, 1H), 8.38 (dd, J=0.9, 5.0 Hz, 1H), 8.36 (s, 1H), 8.21 (d, J=8.3 Hz, 1H), 7.88 (s, 1H), 7.20-7.17 (m, 1H), 7.01 (s, 2H), 3.50 (s, 4H), 3.41 (d, J=5.2 Hz, 4H) and 1.43 (s, 9H) ppm; MS (ES$^+$) 400.08

Method M: Step 4: 3-amino-6-(piperazin-1-yl)-N-(pyridin-2-yl)pyrazine-2-carboxamide Tert-butyl-4-[5-amino-6-(2-pyridylcarbamoyl)pyrazin-2-yl]piperazine-1-carboxylate (5.43 g, 13.59 mmol) was suspended in DCM (50 mL) and stirred at 0° C. during addition of TFA (10 ml). The reaction mixture was warmed to RT over 2 hours but analysis showed little deprotection. The reaction was treated with a further 30 ml of TFA and stirred at RT for 15 minutes. The mixture was concentrated under reduced pressure to give a dark red oil which was dissolved in MeOH/DCM and azeotroped with toluene to give an intense orange solid which was filtered, washed with ether and dried under high vacuum (5.41 g, 73% Yield).

1H NMR (400.0 MHz, DMSO) d 3.29 (4H, m), 3.65 (4H, m), 7.21 (1H, m), 7.89 (1H, m), 8.21 (1H, d), 8.38 (2H, m), 8.88 (2H, br s), 10.10 (1H, s) ppm; MS (ES$^+$) 300.0

Method M: Step 5: 3-amino-6-(4-(ethylsulfonyl)piperazin-1-yl)-N-(pyridin-2-yl)pyrazine-2-carboxamide 3-amino-6-piperazin-1-yl-N-(2-pyridyl)pyrazine-2-carboxamide (100 mg, 0.1896 mmol) was dissolved in DCM (5 mL) and treated with Et$_3$N (57.56 mg, 79.28 µL, 0.5688 mmol) followed by ethanesulfonyl chloride (26.82 mg, 19.76 µL, 0.2086 mmol). The reaction mixture was allowed to stir for 2 hours and then diluted with dichloromethane and washed with water. The aqueous layer was extracted further with dichloromethane and the organics washed with saturated aqueous NaHCO$_3$, dried and concentrated in vacuo. The residue was purified on silica gel by flash column chromatography (0-5% MeOH/DCM) to afford the title compound (74.2 mg, 37% Yield). 1H NMR (400.0 MHz, DMSO) d 1.24 (t, J=7.3 Hz, 3H), 3.13 (q, J=7.4 Hz, 2H), 3.34-3.38 (m, 4H), 3.52-3.54 (m, 4H), 7.04 (s, 2H), 7.18-7.21 (m, 1H), 7.88 (s, 1H), 8.21 (d, J=8.4 Hz, 1H), 8.38 (d, J=3.2 Hz, 2H) and 10.08 (s, 1H) ppm; MS (ES$^+$) 392.0

The following compounds were all prepared using the same method or a method similar to the one described for Compound I-55 in Example 13 above.

Compound I-42 3-amino-6-(piperazin-1-yl)-N-(pyridin-2-yl)pyrazine-2-carboxamide 1H NMR (400.0 MHz, DMSO) d 3.29 (4H, m), 3.65 (4H, m), 7.21 (1H, m), 7.89 (1H, m), 8.21 (1H, d), 8.38 (2H, m), 8.88 (2H, br s), 10.10 1H, s); MS (ES) 300

Compound I-68 3-amino-6-(4-(2-methylpropanoyl)piperazin-1-yl)-N-(pyridin-2-yl)pyrazine-2-carboxamide 1H NMR (400.0 MHz, DMSO) d 1.03 (d, J=6.7 Hz, 6H), 2.96 (m, 1H), 3.40-3.48 (m, 4H), 3.62-3.71 (m, 4H), 7.02 (s, 2H), 7.18-7.21 (m, 1H), 7.86-7.90 (m, 1H), 8.22 (d, 1H), 8.38 (s, 2H) and 10.09 (s, 1H) ppm; MS (ES$^+$) 370.1

Compound I-81 3-amino-6-(4-(N,N-dimethylsulfamoyl)piperazin-1-yl)-N-(pyridin-2-yl)pyrazine-2-carboxamide; MS (ES$^+$) 406.2

Compound I-109 3-amino-6-(4-(phenylcarbonyl)piperazin-1-yl)-N-(pyridin-2-yl)pyrazine-2-carboxamide; MS (ES$^+$) 403.2

Compound I-113 ethyl 4-(5-amino-6-(pyridin-2-ylcarbamoyl)pyrazin-2-yl)piperazine-1-carboxylate; MS (ES$^+$) 371.2

Compound I-114 3-amino-6-(4-(morpholine-4-carbonyl)piperazin-1-yl)-N-(pyridin-2-yl)pyrazine-2-carboxamide; MS (ES$^+$) 412.2

Compound I-116 3-amino-N-(pyridin-2-yl)-6-(4-(thiophen-2-ylsulfonyl)piperazin-1-yl)pyrazine-2-carboxamide; MS (ES$^+$) 445.1

Compound I-117 3-amino-N-(pyridin-2-yl)-6-(4-(thiophen-3-ylsulfonyl)piperazin-1-yl)pyrazine-2-carboxamide; MS (ES$^+$) 445.1

Compound I-118 3-amino-6-(4-(cyclopropylsulfonyl)piperazin-1-yl)-N-(pyridin-2-yl)pyrazine-2-carboxamide; MS (ES$^+$) 403.1

Compound I-119 3-amino-6-(4-(furan-3-ylsulfonyl)piperazin-1-yl)-N-(pyridin-2-yl)pyrazine-2-carboxamide MS (ES$^+$) 429.1

Compound I-141 3-amino-6-(4-(2-phenylethanoyl)piperazin-1-yl)-N-(pyridin-2-yl)pyrazine-2-carboxamide; MS (ES$^+$) 417.2

Compound I-142 3-amino-6-(4-ethanoylpiperazin-1-yl)-N-(pyridin-2-yl)pyrazine-2-carboxamide; MS (ES$^+$) 341.2

Compound I-143 3-amino-6-(4-(2-phenoxyethanoyl)piperazin-1-yl)-N-(pyridin-2-yl)pyrazine-2-carboxamide; MS (ES$^+$) 433.2

Compound I-144 3-amino-6-(4-(cyclopentanecarbonyl)piperazin-1-yl)-N-(pyridin-2-yl)pyrazine-2-carboxamide; MS (ES$^+$) 395.2

Compound I-145 3-amino-6-(4-(cyclobutanecarbonyl)piperazin-1-yl)-N-(pyridin-2-yl)pyrazine-2-carboxamide; MS (ES$^+$) 381.2

Compound I-146 3-amino-N-(pyridin-2-yl)-6-(4-(pyridine-3-carbonyl)piperazin-1-yl)pyrazine-2-carboxamide; MS (ES$^+$) 404.2

Compound I-147 3-amino-6-(4-(2-methoxyethanoyl)piperazin-1-yl)-N-(pyridin-2-yl)pyrazine-2-carboxamide; MS (ES$^+$) 371.2

Compound I-148 3-amino-N-(pyridin-2-yl)-6-(4-(pyridine-2-carbonyl)piperazin-1-yl)pyrazine-2-carboxamide; MS (ES$^+$) 404.2

Compound I-149 3-amino-6-(4-(2,6-difluorophenylcarbonyl)piperazin-1-yl)-N-(pyridin-2-yl)pyrazine-2-carboxamide; MS (ES$^+$) 439.2

Compound I-150 3-amino-6-(4-(2-(dimethylamino)ethanoyl)piperazin-1-yl)-N-(pyridin-2-yl)pyrazine-2-carboxamide; MS (ES$^+$) 384.2

Compound I-151 3-amino-6-(4-(2-(2-methoxyethoxy)ethanoyl)piperazin-1-yl)-N-(pyridin-2-yl)pyrazine-2-carboxamide; MS (ES$^+$) 415.2

For compounds I-207 to I-262 below, please see Tables 7 and 8 for analytical data.

Compound I-207 3-amino-6-(4-(phenylsulfonyl)piperazin-1-yl)-N-(pyridin-2-yl)pyrazine-2-carboxamide Compound I-209 3-amino-6-(4-(2,2-dimethylpropanoyl)piperazin-1-yl)-N-(pyridin-2-yl)pyrazine-2-carboxamide Compound I-212 3-amino-6-(4-(2-ethylbutanoyl)piperazin-1-yl)-N-(pyridin-2-yl)pyrazine-2-carboxamide Compound I-219 3-amino-6-(4-(methylsulfonyl)piperazin-1-yl)-N-(pyridin-2-yl)pyrazine-2-carboxamide Compound I-229 3-amino-6-(4-(dimethylcarbamoyl)piperazin-1-yl)-N-(pyridin-2-yl)pyrazine-2-carboxamide
Compound I-230 3-amino-N-(pyridin-2-yl)-6-(4-(tetrahydro-2H-pyran-4-carbonyl)piperazin-1-yl)pyrazine-2-carboxamide
Compound I-233 3-amino-N-(pyridin-2-yl)-6-(4-(pyridin-3-ylsulfonyl)piperazin-1-yl)pyrazine-2-carboxamide
Compound I-237 2-methoxyethyl 4-(5-amino-6-(pyridin-2-ylcarbamoyl)pyrazin-2-yl)piperazine-1-carboxylate
Compound I-239 3-amino-N-(pyridin-2-yl)-6-(4-(pyrrolidine-1-carbonyl)piperazin-1-yl)pyrazine-2-carboxamide
Compound I-240 3-amino-6-(4-(propylsulfonyl)piperazin-1-yl)-N-(pyridin-2-yl)pyrazine-2-carboxamide
Compound I-242 methyl 4-(5-amino-6-(pyridin-2-ylcarbamoyl)pyrazin-2-yl)piperazine-1-carboxylate
Compound I-247 3-amino-6-(4-(piperidine-1-carbonyl)piperazin-1-yl)-N-(pyridin-2-yl)pyrazine-2-carboxamide
Compound I-248 3-amino-6-(4-(cyclopentylsulfonyl)piperazin-1-yl)-N-(pyridin-2-yl)pyrazine-2-carboxamide
Compound I-252 but-2-ynyl 4-(5-amino-6-(pyridin-2-ylcarbamoyl)pyrazin-2-yl)piperazine-1-carboxylate
Compound I-253 3-amino-6-(4-(benzylsulfonyl)piperazin-1-yl)-N-(pyridin-2-yl)pyrazine-2-carboxamide
Compound I-256 3-amino-6-(4-(cyclohexanecarbonyl)piperazin-1-yl)-N-(pyridin-2-yl)pyrazine-2-carboxamide
Compound I-260 benzyl 4-(5-amino-6-(pyridin-2-ylcarbamoyl)pyrazin-2-yl)piperazine-1-carboxylate
Compound I-262 3-amino-6-(4-(2,6-dimethylphenylcarbonyl)piperazin-1-yl)-N-(pyridin-2-yl)pyrazine-2-carboxamide Example 14

5-(4-(ethylsulfonyl)piperazin-1-yl)-3-(5-phenyl-1,3,4-oxadiazol-2-yl)pyrazin-2-amine (Compound I-18)

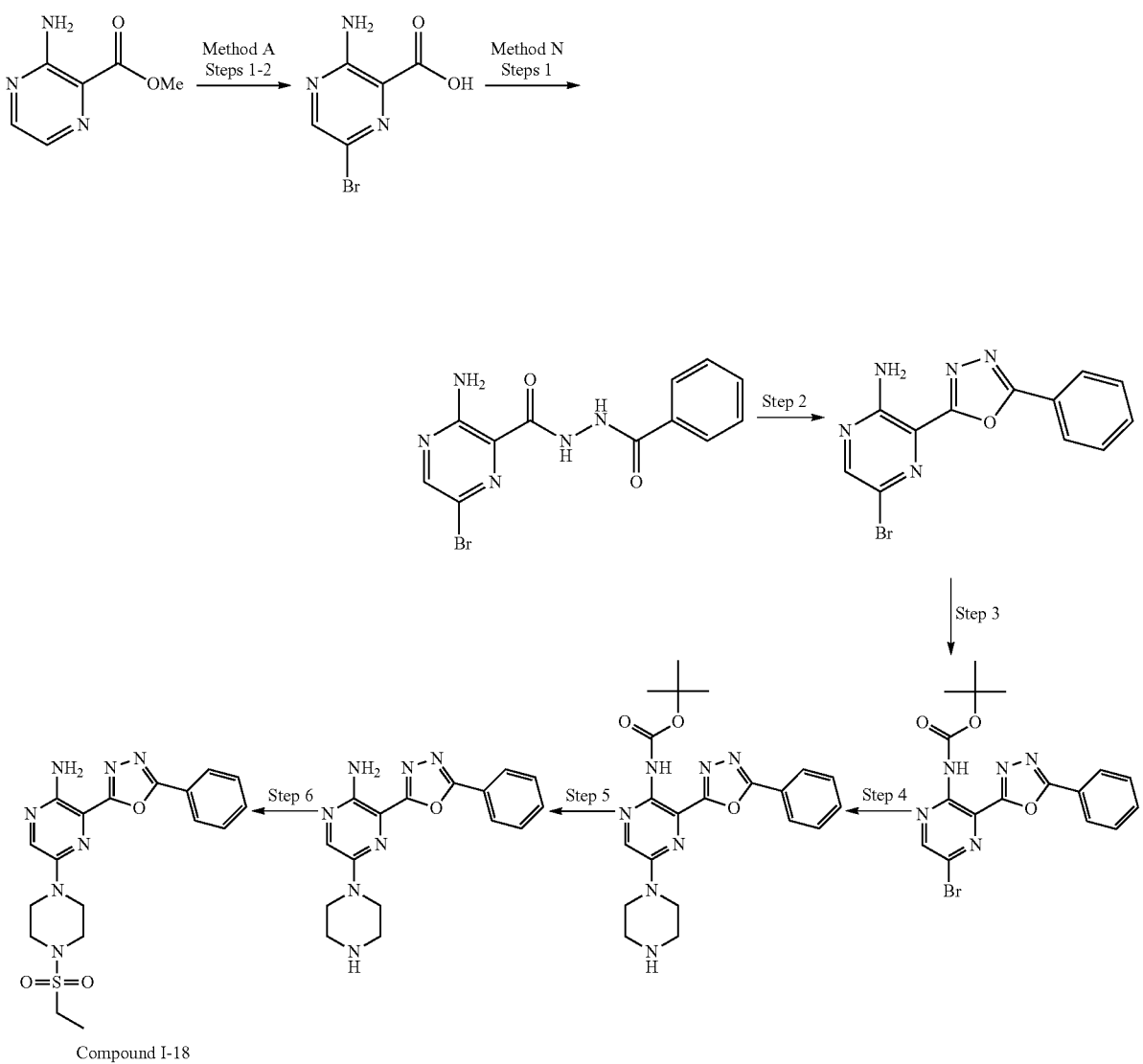

Compound I-18 was also prepared using Method A, Steps 1-2 followed by Method N, Steps 1-6.

Method N: Step 1: 3-amino-6-bromo-N-(phenylcarbonyl)pyrazine-2-carbohydrazide TBTU (22.09 g, 68.80 mmol) and Et₃N (4.642 g, 6.394 mL, 45.87 mmol) were added to a solution of 3-amino-6-bromo-pyrazine-2-carboxylic acid (10 g, 45.87 mmol) and benzohydrazide (7.494 g, 55.04 mmol) in DMF (100.0 mL) and the resulting solution stirred at ambient temperature overnight. The reaction mixture was poured into water and the resultant precipitate was filtered and dried under vacuum. This was triturated with hot EtOAc and the resulting precipitate filtered and dried to give the desired product (13.11 g, 85% Yield).
1H NMR (400.0 MHz, DMSO) d 7.53 (t, 2H), 7.60 (d, 1H), 7.69 (br s, 2H), 7.91 (d, 2H), 8.44 (s, 1H), 10.48 (s, 1H) and 10.55 (s, 1H) ppm; MS (ES⁺) 338.92

Method N: Step 2: 5-bromo-3-(5-phenyl-1,3,4-oxadiazol-2-yl)pyrazin-2-amine

Polyphosphonic acid (25 mL of 84% w/v, 256.1 mmol) was heated to 100° C. and treated with 3-amino-N'-benzoyl-6-bromo-pyrazine-2-carbohydrazide (6.82 g, 20.29 mmol) in portions. Analysis after 1 hour showed SM remaining therefore further polyphosphonic acid was added (25 mL of 84% w/v, 256.1 mmol). The reaction was heated for a total of 3 hours and then allowed to cool. Water was added and the mixture allowed to stir to obtain a precipitate which was filtered and dried under vacuum (5.02 g, 78% Yield). MS (ES⁺) 317.86

Method N: Step 3: Tert-butyl 5-bromo-3-(5-phenyl-1,3,4-oxadiazol-2-yl)pyrazin-2-ylcarbamate 5-bromo-3-(5-phenyl-1,3,4-oxadiazol-2-yl)pyrazin-2-amine (5.02 g, 15.78 mmol) was suspended in DCM (75 mL) and DMAP (192.8 mg, 1.578 mmol) was added. BOC anhydride (10.33 g, 10.87 mL, 47.34 mmol) was added in portions and the reaction allowed to stir at ambient temperature. Further BOC anhydride (3.444 g, 3.625 mL, 15.78 mmol) was added followed by triethylamine (2.395 g, 3.299 mL, 23.67 mmol) and the mixture heated to 60° C. The reaction was allowed to cool to ambient temperature and the solvent removed in vacuo. The mixture was redissolved in DCM, washed with 1M HCl, NaHCO₃, brine, dried over MgSO₄, filtered and concentrated to dryness. The resultant residue was purified on silica gel by flash column chromatography (0-40% EtOAc/Petrol) to afford the title compound as a yellow solid (5.12 g, 78% Yield); 1H NMR (400.0 MHz, DMSO) d 1.29 (s, 9H), 7.57-7.75 (m, 4H), 8.12-8.14 (m, 2H) and 9.16 (s, 1H) ppm; MS (ES⁺) 420.01

Method N: Step 4: Tert-butyl 3-(5-phenyl-1,3,4-oxadiazol-2-yl)-5-(piperazin-1-yl)pyrazin-2-ylcarbamate Tert-butyl 5-bromo-3-(5-phenyl-1,3,4-oxadiazol-2-yl)pyrazin-2-ylcarbamate (2.56 g, 6.121 mmol) was dissolved in DMF (20 mL) and piperazine (5.272 g, 61.21 mmol) was added. The mixture was heated to 100° C. for 30 minutes, allowed to cool to ambient temperature and the solvent removed in vacuo. The mixture was partitioned between DCM/Water and the organic layer washed with brine, dried over MgSO₄, filtered and concentrated to give a yellow oil. The resultant residue was purified on silica gel by flash column chromatography (0-10% MeOH/DCM) to afford the title compound (2.29 g, 89% Yield).
1H NMR (400.0 MHz, DMSO) d 1.30 (s, 9H), 2.60 (t, J=5.0 Hz, 2H), 2.83 (d, J=5.0 Hz, 2H), 3.21 (t, J=4.7 Hz, 2H), 3.55 (d, J=5.1 Hz, 2H), 7.63-7.69 (m, 3H), 8.06-8.07 (m, 2H), 8.35 (s, 1H) and 9.55 (s, 1H) ppm; MS (ES⁺) 424.17

Method N: Step 5: 3-(5-phenyl-1,3,4-oxadiazol-2-yl)-5-(piperazin-1-yl)pyrazin-2-amine Tert-butyl 3-(5-phenyl-1,3,4-oxadiazol-2-yl)-5-(piperazin-1-yl)pyrazin-2-ylcarbamate (2.29 g, 5.408 mmol) was dissolved in DCM (20 mL) and treated with TFA (5 mL, 64.90 mmol) was added. The reaction was allowed to stir for 1 hour at ambient temperature and then the solvent removed in vacuo. The mixture was treated with NaHCO₃/brine and EtOAc and the 2 layers separated layers. The aqueous layer was extracted with EtOAc, followed by DCM and CHCl₃. The mixture was dried over MgSO₄, filtered and concentrated to give the product as an orange solid (1.44 g, 82% Yield). ¹H NMR (400.0 MHz, DMSO) d 3.00 (4H, br m), 3.43 (4H, br m), 6.05 (2H, br s), 7.20 (1H, m), 7.34 (2H, m), 7.90 (1H, m), 8.13 (2H, m) ppm; (ES⁺) 324.03

Method N: Step 6: 5-(4-(ethylsulfonyl)piperazin-1-yl)-3-(5-phenyl-1,3,4-oxadiazol-2-yl)pyrazin-2-amine Ethanesulfonyl chloride (37.51 mg, 27.64 µL, 0.2917 mmol) was added to a solution of 3-(5-phenyl-1,3,4-oxadiazol-2-yl)-5-piperazin-1-yl-pyrazin-2-amine (116 mg, 0.2652 mmol) and triethylamine (53.67 mg, 73.93 µL, 0.5304 mmol) in dichloromethane (5 mL) at 0° C. and the resulting solution stirred at room temperature for 1.5 hours. The mixture was diluted with dichloromethane, washed with water and the aqueous layer extracted further with dichloromethane. The organics were washed with saturated aqueous NaHCO₃, dried over MgSO₄ and concentrated in vacuo. The resultant residue was purified on silica gel by flash column chromatography (3% MeOH/DCM) to afford the title compound still impure. This was purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were collected and freeze-dried to give the title compound (25.2 mg, 18% Yield).
1H NMR (400.0 MHz, DMSO) d 1.24 (3H, t), 3.11 (2H, q), 3.33-3.36 (4H, m), 3.56 (4H, m), 6.97 (2H, br s), 7.63-7.68 (3H, m), 8.11-8.13 (2H, m), 8.28 (1H, s) ppm; MS (ES⁺) 416.01

The following compounds were all prepared using the same method or a method similar to the one described for Compound I-18 in Example 14 above.

Compound I-37 3-(5-phenyl-1,3,4-oxadiazol-2-yl)-5-(piperazin-1-yl)pyrazin-2-amine 1H NMR (400.0 MHz, DMSO) d 3.27 (s, 4H), 3.67-3.69 (m, 4H), 7.03 (s, 1H), 7.64-7.70 (m, 3H), 8.10-8.13 (m, 2H), 8.31 (s, 1H) and 8.87 (br s, 2H) ppm; MS (ES⁺) 323.99

Compound I-72 3-(5-cyclohexyl-1,3,4-oxadiazol-2-yl)-5-(4-(ethylsulfonyl)piperazin-1-yl)pyrazin-2-amine; 1H NMR (400.0 MHz, DMSO) d 1.24 (3H, t), 1.38-1.47 (3H, m), 1.60 (2H, m), 1.66 (2H, m), 1.79 (2H, m), 2.06 (2H, m), 3.10 (2H, q), 6.89 (2H, br s), 8.22 (1H, s) ppm; MS (ES⁺) 422.03

Compound I-83 4-(5-amino-6-(5-phenyl-1,3,4-oxadiazol-2-yl)pyrazin-2-yl)-N,N-dimethylpiperazine-1-sulfonamide; MS (ES⁺) 430.2

Compound I-87 5-(4-(1-methyl-1H-imidazol-4-ylsulfonyl)piperazin-1-yl)-3-(5-phenyl-1,3,4-oxadiazol-2-yl)pyrazin-2-amine; MS (ES+) 467.2

Compound I-90 5-(4-(furan-3-ylsulfonyl)piperazin-1-yl)-3-(5-phenyl-1,3,4-oxadiazol-2-yl)pyrazin-2-amine; MS (ES+) 453.1

Compound I-92 5-(4-(cyclopentylsulfonyl)piperazin-1-yl)-3-(5-phenyl-1,3,4-oxadiazol-2-yl)pyrazin-2-amine; MS (ES+) 455.2

Compound I-96 3-(5-phenyl-1,3,4-oxadiazol-2-yl)-5-(4-(thiophen-2-ylsulfonyl)piperazin-1-yl)pyrazin-2-amine; MS (ES+) 469.1

Compound I-98 3-(5-phenyl-1,3,4-oxadiazol-2-yl)-5-(4-(thiophen-3-ylsulfonyl)piperazin-1-yl)pyrazin-2-amine; MS (ES+) 469.1

Compound I-99 5-(4-(benzylsulfonyl)piperazin-1-yl)-3-(5-phenyl-1,3,4-oxadiazol-2-yl)pyrazin-2-amine; MS (ES+) 477.2

Compound I-101 6-(5-phenyl-1,3,4-oxadiazol-2-yl)pyrazin-2-yl)piperazin-1-yl)(phenyl)methanone; MS (ES+) 427.2

For compounds I-178 to I-258 below, please see Tables 7 and 8 for analytical data.

Compound I-178 1-(4-(5-amino-6-(5-phenyl-1,3,4-oxadiazol-2-yl)pyrazin-2-yl)piperazin-1-yl)-2-(2-methoxyethoxy)ethanone Compound I-179 1-(4-(5-amino-6-(5-phenyl-1,3,4-oxadiazol-2-yl)pyrazin-2-yl)piperazin-1-yl)-2-methoxyethanone Compound I-180 1-(4-(5-amino-6-(5-phenyl-1,3,4-oxadiazol-2-yl)pyrazin-2-yl)piperazin-1-yl)ethanone Compound I-183 (4-(5-amino-6-(5-phenyl-1,3,4-oxadiazol-2-yl)pyrazin-2-yl)piperazin-1-yl)(pyridin-3-yl)methanone Compound I-187 (4-(5-amino-6-(5-phenyl-1,3,4-oxadiazol-2-yl)pyrazin-2-yl)piperazin-1-yl)(pyridin-2-yl)methanone Compound I-189 (4-(5-amino-6-(5-phenyl-1,3,4-oxadiazol-2-yl)pyrazin-2-yl)piperazin-1-yl)(cyclobutyl)methanone Compound I-190 1-(4-(5-amino-6-(5-phenyl-1,3,4-oxadiazol-2-yl)pyrazin-2-yl)piperazin-1-yl)-2-methylpropan-1-one Compound I-194 (4-(5-amino-6-(5-phenyl-1,3,4-oxadiazol-2-yl)pyrazin-2-yl)piperazin-1-yl)(cyclopentyl)methanone Compound I-195 1-(4-(5-amino-6-(5-phenyl-1,3,4-oxadiazol-2-yl)pyrazin-2-yl)piperazin-1-yl)-2-phenoxyethanone Compound I-196 3-(5-phenyl-1,3,4-oxadiazol-2-yl)-5-(4-(phenylsulfonyl)piperazin-1-yl)pyrazin-2-amine Compound I-197 1-(4-(5-amino-6-(5-phenyl-1,3,4-oxadiazol-2-yl)pyrazin-2-yl)piperazin-1-yl)-2-phenylethanone Compound I-198 1-(4-(5-amino-6-(5-phenyl-1,3,4-oxadiazol-2-yl)pyrazin-2-yl)piperazin-1-yl)-2,2-dimethylpropan-1-one Compound I-202 5-(4-(2,6-difluorophenylsulfonyl)piperazin-1-yl)-3-(5-phenyl-1,3,4-oxadiazol-2-yl)pyrazin-2-amine Compound I-203 (4-(5-amino-6-(5-phenyl-1,3,4-oxadiazol-2-yl)pyrazin-2-yl)piperazin-1-yl)(2,6-difluorophenyl)methanone Compound I-216 (4-(5-amino-6-(5-phenyl-1,3,4-oxadiazol-2-yl)pyrazin-2-yl)piperazin-1-yl)(morpholino)methanone Compound I-218 4-(5-amino-6-(5-phenyl-1,3,4-oxadiazol-2-yl)pyrazin-2-yl)-N,N-dimethylpiperazine-1-carboxamide Compound I-221 2-methoxyethyl 4-(5-amino-6-(5-phenyl-1,3,4-oxadiazol-2-yl)pyrazin-2-yl)piperazine-1-carboxylate Compound I-223 (4-(5-amino-6-(5-phenyl-1,3,4-oxadiazol-2-yl)pyrazin-2-yl)piperazin-1-yl)(pyrrolidin-1-yl)methanone Compound I-225 methyl 4-(5-amino-6-(5-phenyl-1,3,4-oxadiazol-2-yl)pyrazin-2-yl)piperazine-1-carboxylate Compound I-231 (4-(5-amino-6-(5-phenyl-1,3,4-oxadiazol-2-yl)pyrazin-2-yl)piperazin-1-yl)(piperidin-1-yl)methanone Compound I-232 ethyl 4-(5-amino-6-(5-phenyl-1,3,4-oxadiazol-2-yl)pyrazin-2-yl)piperazine-1-carboxylate Compound I-246 but-2-ynyl 4-(5-amino-6-(5-phenyl-1,3,4-oxadiazol-2-yl)pyrazin-2-yl)piperazine-1-carboxylate Compound I-251 (4-(5-amino-6-(5-phenyl-1,3,4-oxadiazol-2-yl)pyrazin-2-yl)piperazin-1-yl)(cyclohexyl)methanone Compound I-255 benzyl 4-(5-amino-6-(5-phenyl-1,3,4-oxadiazol-2-yl)pyrazin-2-yl)piperazine-1-carboxylate Compound I-258 (4-(5-amino-6-(5-phenyl-1,3,4-oxadiazol-2-yl)pyrazin-2-yl)piperazin-1-yl)(2,6-dimethylphenyl)methanone Example 15

5-(1-(ethylsulfonyl)-1,2,3,6-tetrahydropyridin-4-yl)-3-(5-phenyl-1,3,4-oxadiazol-2-yl)pyrazin-2-amine
(Compound I-28)

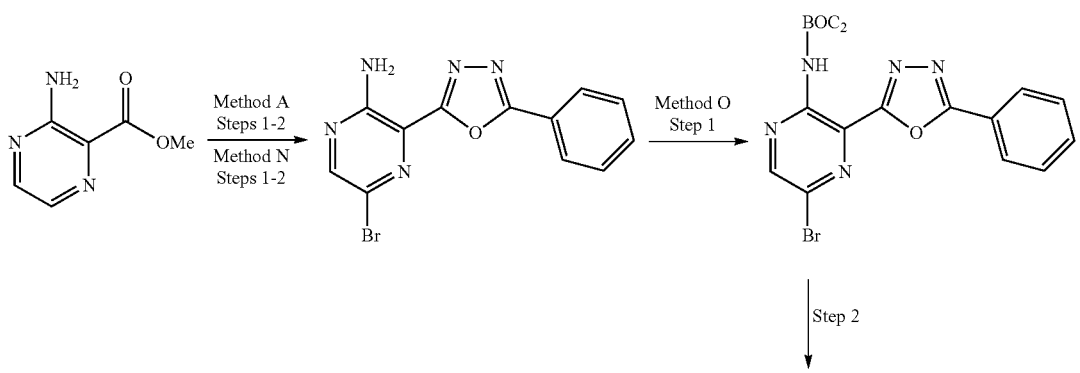

Scheme XV

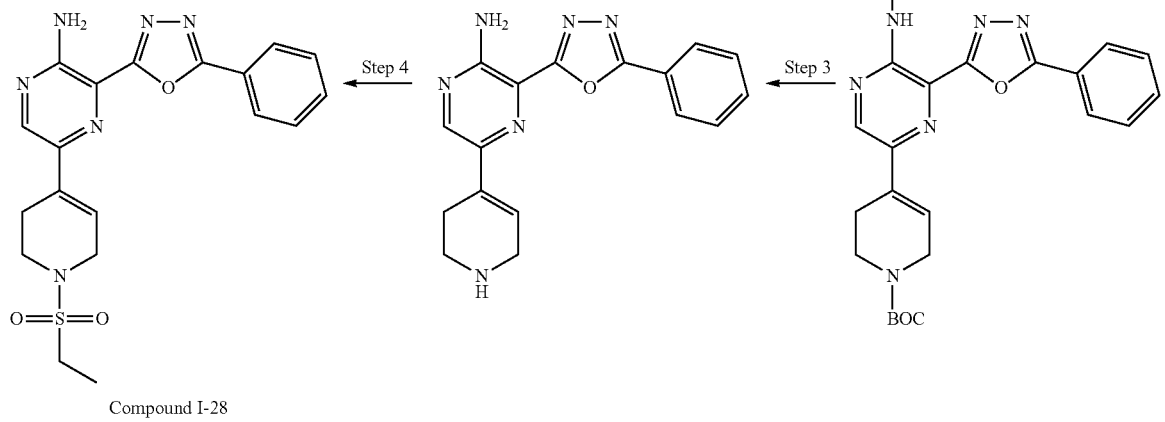

Compound I-28

Compound I-28 was prepared using Method A, Steps 1-2 followed by Method N, Steps 1-2 followed by Method O, Steps 1-4.

Method O: Step 1: Tert-butyl N-[5-bromo-3-(5-phenyl-1,3,4-oxadiazol-2-yl)pyrazin-2-yl]-N-tert-butoxycarbonyl-carbamate 5-bromo-3-(5-phenyl-1,3,4-oxadiazol-2-yl)pyrazin-2-amine (3.8348 g, 12.05 mmol) was suspended in DCM (57.29 mL) and THF (57.29 mL) and DMAP (147.2 mg, 1.205 mmol) was added followed by BOC anhydride (7.890 g, 8.305 mL, 36.15 mmol) in portions. The reaction was allowed to stir at RT. After 1 hour the reaction was treated with triethylamine (2.52 mL, 18.08 mmol) and the mixture allowed to stir. Analysis showed SM still remaining therefore a further 0.1 eq of DMAP was added followed by 5 g of BOC anhydride (1.9 eq) and the reaction left to stir at RT for 2 hours. The solvent was removed in vacuo and the mixture redissolved in DCM, washed with NaHCO$_3$ and brine, dried over MgSO$_4$, filtered and concentrated to give a brown oil which was purified on silica gel by flash column chromatography (0-25% EtOAc/Petrol) to afford the title compound as a pale yellow solid (3.96 g, 63% Yield).
MS (ES$^+$) 519.95

Method O: Step 2: tert-butyl 4-(5-(bis(tert-butoxycarbonyl)amino)-6-(5-phenyl-1,3,4-oxadiazol-2-yl)pyrazin-2-yl)-5,6-dihydropyridine-1(2H)-carboxylate Tert-butyl N-[5-bromo-3-(5-phenyl-1,3,4-oxadiazol-2-yl)pyrazin-2-yl]-N-tert-butoxycarbonyl-carbamate (2.4633 g, 4.752 mmol) was dissolved in DMF (19.24 mL) and tert-butyl 4-(4,4,5,5-tetramethyl-1,3,2-dioxaborolan-2-yl)-3,6-dihydro-2H-pyridine-1-carboxylate (2.204 g, 7.128 mmol) and Pd(PPh$_3$)$_2$Cl$_2$ (196.6 mg, 0.4752 mmol) were added followed by Na$_2$CO$_3$ (7.130 mL of 2 M, 14.26 mmol) and the reaction heated at 100° C. under nitrogen for 15 minutes. The reaction mixture was allowed to cool to RT and the solvent removed in vacuo. The mixture was diluted with EtOAc/water and the organic layer washed with water (×4) followed by brine (×3). After drying over MgSO$_4$, the reaction was filtered and evaporated to dryness to give a dark brown oil which was purified on silica gel by flash column chromatography (0-40% EtOAc/Petrol) to afford the title compound (2.40 g, 81% Yield).

1H NMR (400.0 MHz, DMSO) d 1.02 (27H, m), 2.67 (2H, m), 3.60 (2H, m), 4.13 (2H, m), 6.88 (1H, m), 7.70 (2H, m), 8.15 (2H, m), 8.87 (1H, m) ppm Method O: Step 3: 3-(5-phenyl-1,3,4-oxadiazol-2-yl)-5-(1,2,3,6-tetrahydropyridin-4-yl)pyrazin-2-amine Tert-butyl 4-(5-(bis(tert-butoxycarbonyl)amino)-6-(5-phenyl-1,3,4-oxadiazol-2-yl)pyrazin-2-yl)-5,6-dihydropyridine-1(2H)-carboxylate (2.4 g, 3.867 mmol) was dissolved in DCM (40 mL) and treated with TFA (8 mL, 103.8 mmol). The reaction was allowed to stir overnight and then the solvent was removed in vacuo. The mixture was azeotroped with DCM (×3) and dried under vacuum to give the desired product as an orange solid (1.89 g, 100% Yield).

1H NMR (400.0 MHz, DMSO) d 2.83 (br d, 2H), 3.39 (br d, 2H), 3.91 (br d, 2H), 6.66 (s, 1), 7.66-7.73 (m, 3H), 8.11-8.14 (m, 2H), 8.63 (s, 1H) and 8.86 (s, 1H) ppm; MS (ES$^+$) 321.0

Method O: Step 4: 5-(1-(ethylsulfonyl)-1,2,3,6-tetrahydropyridin-4-yl)-3-(5-phenyl-1,3,4-oxadiazol-2-yl)pyrazin-2-amine 3-(5-phenyl-1,3,4-oxadiazol-2-yl)-5-(1,2,3,6-tetrahydropyridin-4-yl)pyrazin-2-amine (50 mg, 0.1151 mmol) was dissolved in DCM (3 mL) and Et$_3$N (34.94 mg, 48.13 µL, 0.3453 mmol) followed by ethanesulfonyl chloride (16.28 mg, 12.00 µL, 0.1266 mmol) were added. The reaction was allowed to stir for 30 mins and then diluted with dichloromethane and washed with water. The aqueous layer was extracted further with dichloromethane and the organics washed with saturated aqueous NaHCO$_3$, dried over MgSO$_4$ and concentrated in vacuo. The resultant residue was purified on silica gel by flash column chromatography (0-5% MeOH/DCM) to afford the title compound (47.47 mg, 60% Yield).

1H NMR (400.0 MHz, DMSO) d 1.24 (t, J=7.4 Hz, 3H), 2.74 (br d, 2H), 3.15 (q, 2H), 3.50 (t, 2H), 4.00 (br d, 2H), 6.68 (br s, 1H), 7.67-7.69 (m, 5H), 8.14 (d, 2H) and 8.58 (s, 1H) ppm; MS (ES$^+$) 413.0

The following compounds were all prepared using the same method or a similar method to the one described for Compound I-28 in Example 15 above.

Compound I-41 3-(5-phenyl-1,3,4-oxadiazol-2-yl)-5-(1,2,3,6-tetrahydropyridin-4-yl)pyrazin-2-amine; 1H NMR (400.0 MHz, DMSO) d 2.83 (br d, 2H), 3.39 (br d, 2H), 3.91 (br d, 2H), 6.66 (s, 1H), 7.66-7.73 (m, 3H), 8.11-8.14 (m, 2H), 8.63 (s, 1H) and 8.86 (s, 1H) ppm; MS (ES$^+$) 321

Compound I-54 5-(1-(ethylsulfonyl)-1,2,3,6-tetrahydropyridin-4-yl)-3-(5-phenyl-1,3,4-oxadiazol-2-yl)pyrazin-2-amine; MS (ES$^+$) 413

Compound I-84 4-(5-amino-6-(5-phenyl-1,3,4-oxadiazol-2-yl)pyrazin-2-yl)-N,N-dimethyl-5,6-dihydropyridine-1(2H)-sulfonamide; MS (ES$^+$) 427.1

Compound I-100 5-(1-(benzylsulfonyl)-1,2,3,6-tetrahydropyridin-4-yl)-3-(5-phenyl-1,3,4-oxadiazol-2-yl)pyrazin-2-amine; MS (ES$^+$) 474.2

Compound I-102 3-(5-phenyl-1,3,4-oxadiazol-2-yl)-5-(1-(phenylsulfonyl)-1,2,3,6-tetrahydropyridin-4-yl)pyrazin-2-amine; MS (ES$^+$) 460.1

Compound I-103 (4-(5-amino-6-(5-phenyl-1,3,4-oxadiazol-2-yl)pyrazin-2-yl)-5,6-dihydropyridin-1(2H)-yl)(phenyl)methanone; MS (ES$^+$) 424.2

Compound I-115 but-2-ynyl 4-(5-amino-6-(5-phenyl-1,3,4-oxadiazol-2-yl)pyrazin-2-yl)-5,6-dihydropyridine-1(2H)-carboxylate; MS (ES$^+$) 416.2

Compound I-120 5-(1-(1-methyl-1H-imidazol-4-ylsulfonyl)-1,2,3,6-tetrahydropyridin-4-yl)-3-(5-phenyl-1,3,4-oxadiazol-2-yl)pyrazin-2-amine; MS (ES$^+$) 464.1

Compound I-121 3-(5-phenyl-1,3,4-oxadiazol-2-yl)-5-(1-(thiophen-3-ylsulfonyl)-1,2,3,6-tetrahydropyridin-4-yl)pyrazin-2-amine; MS (ES$^+$) 466.1

Compound I-122 5-(1-(cyclopropylsulfonyl)-1,2,3,6-tetrahydropyridin-4-yl)-3-(5-phenyl-1,3,4-oxadiazol-2-yl)pyrazin-2-amine; MS (ES$^+$) 424.1

Compound I-123 5-(1-(furan-3-ylsulfonyl)-1,2,3,6-tetrahydropyridin-4-yl)-3-(5-phenyl-1,3,4-oxadiazol-2-yl)pyrazin-2-amine; MS (ES$^+$) 450.1

Compound I-124 3-(5-phenyl-1,3,4-oxadiazol-2-yl)-5-(1-(propylsulfonyl)-1,2,3,6-tetrahydropyridin-4-yl)pyrazin-2-amine; MS (ES$^+$) 426.2

Compound I-125 1-(4-(5-amino-6-(5-phenyl-1,3,4-oxadiazol-2-yl)pyrazin-2-yl)-5,6-dihydropyridin-1(2H)-yl)ethanone; MS (ES$^+$) 362.2

Compound I-126 1-(4-(5-amino-6-(5-phenyl-1,3,4-oxadiazol-2-yl)pyrazin-2-yl)-5,6-dihydropyridin-1(2H)-yl)-2-phenoxyethanone; MS (ES$^+$) 454.2

Compound I-127 (4-(5-amino-6-(5-phenyl-1,3,4-oxadiazol-2-yl)pyrazin-2-yl)-5,6-dihydropyridin-1(2H)-yl)(cyclopentyl)methanone; MS (ES$^+$) 416.2

Compound I-128 (4-(5-amino-6-(5-phenyl-1,3,4-oxadiazol-2-yl)pyrazin-2-yl)-5,6-dihydropyridin-1(2H)-yl)(cyclobutyl)methanone; MS (ES$^+$) 402.2

Compound I-129 (4-(5-amino-6-(5-phenyl-1,3,4-oxadiazol-2-yl)pyrazin-2-yl)-5,6-dihydropyridin-1(2H)-yl)(pyridin-3-yl)methanone; MS (ES$^+$) 425.2

Compound I-130 1-(4-(5-amino-6-(5-phenyl-1,3,4-oxadiazol-2-yl)pyrazin-2-yl)-5,6-dihydropyridin-1(2H)-yl)-2-methoxyethanone; MS (ES$^+$) 392.2

Compound I-131 1-(4-(5-amino-6-(5-phenyl-1,3,4-oxadiazol-2-yl)pyrazin-2-yl)-5,6-dihydropyridin-1(2H)-yl)-2-ethylbutan-1-one; MS (ES$^+$) 418.2

Compound I-132 (4-(5-amino-6-(5-phenyl-1,3,4-oxadiazol-2-yl)pyrazin-2-yl)-5,6-dihydropyridin-1(2H)-yl)(pyridin-2-yl)methanone; MS (ES$^+$) 425.2

Compound I-133 (4-(5-amino-6-(5-phenyl-1,3,4-oxadiazol-2-yl)pyrazin-2-yl)-5,6-dihydropyridin-1(2H)-yl)(2,6-difluorophenyl)methanone; MS (ES$^+$) 460.2

Compound I-134 1-(4-(5-amino-6-(5-phenyl-1,3,4-oxadiazol-2-yl)pyrazin-2-yl)-5,6-dihydropyridin-1(2H)-yl)-2-(dimethylamino)ethanone; MS (ES$^+$) 405.2

Compound I-135 1-(4-(5-amino-6-(5-phenyl-1,3,4-oxadiazol-2-yl)pyrazin-2-yl)-5,6-dihydropyridin-1(2H)-yl)-2-(2-methoxyethoxy)ethanone; MS (ES$^+$) 436.2

Compound I-163 Tert-butyl 4-(5-amino-6-(5-phenyl-1,2,4-oxadiazol-3-yl)pyrazin-2-yl)-5,6-dihydropyridine-1(2H)-carboxylate; 1H NMR (400.0 MHz, DMSO) d 1.44 (9H, s), 2.60 (2H, m), 3.57 (2H, m), 4.06 (2H, m), 6.70 (1H, s), 7.30 (2H, br s), 7.69 (2H, m), 7.77 (1H, m), 8.25 (2H, m), 8.51 (1H, s) ppm: MS (ES$^+$) 421.02

For compounds I-192 to I-257 below, please see Tables 7 and 8 for analytical data.

Compound I-192 1-(4-(5-amino-6-(5-phenyl-1,3,4-oxadiazol-2-yl)pyrazin-2-yl)-5,6-dihydropyridin-1(2H)-yl)-2-methylpropan-1-one Compound I-201 1-(4-(5-amino-6-(5-phenyl-1,3,4-oxadiazol-2-yl)pyrazin-2-yl)-5,6-dihydropyridin-1(2H)-yl)-2-phenylethanone Compound I-217 (4-(5-amino-6-(5-phenyl-1,3,4-oxadiazol-2-yl)pyrazin-2-yl)-5,6-dihydropyridin-1(2H)-yl)(morpholino)methanone Compound I-220 4-(5-amino-6-(5-phenyl-1,3,4-oxadiazol-2-yl)pyrazin-2-yl)-N,N-dimethyl-5,6-dihydropyridine-1(2H)-carboxamide Compound I-222 3-(5-phenyl-1,3,4-oxadiazol-2-yl)-5-(1-(pyridin-3-ylsulfonyl)-1,2,3,6-tetrahydropyridin-4-yl)pyrazin-2-amine Compound I-224 2-methoxyethyl 4-(5-amino-6-(5-phenyl-1,3,4-oxadiazol-2-yl)pyrazin-2-yl)-5,6-dihydropyridine-1(2H)-carboxylate Compound I-226 (4-(5-amino-6-(5-phenyl-1,3,4-oxadiazol-2-yl)pyrazin-2-yl)-5,6-dihydropyridin-1(2H)-yl)(pyrrolidin-1-yl)methanone Compound I-228 methyl 4-(5-amino-6-(5-phenyl-1,3,4-oxadiazol-2-yl)pyrazin-2-yl)-5,6-dihydropyridine-1(2H)-carboxylate Compound I-236 (4-(5-amino-6-(5-phenyl-1,3,4-oxadiazol-2-yl)pyrazin-2-yl)-5,6-dihydropyridin-1(2H)-yl)(piperidin-1-yl)methanone Compound I-238 ethyl 4-(5-amino-6-(5-phenyl-1,3,4-oxadiazol-2-yl)pyrazin-2-yl)-5,6-dihydropyridine-1(2H)-carboxylate Compound I-245 3-(5-phenyl-1,3,4-oxadiazol-2-yl)-5-(1-(thiophen-2-ylsulfonyl)-1,2,3,6-tetrahydropyridin-4-yl)pyrazin-2-amine Compound I-257 benzyl 4-(5-amino-6-(5-phenyl-1,3,4-oxadiazol-2-yl)pyrazin-2-yl)-5,6-dihydropyridine-1(2H)-carboxylate Compound I-285 [4-[5-amino-6-(5-phenyl-1,3,4-oxadiazol-2-yl)pyrazin-2-yl]-3,6-dihydro-2H-pyridin-1-yl]-cyclopropyl-methanone 1H NMR (400.0 MHz, DMSO) d 0.74-0.78 (m, 4H), 1.99 (br s, 0.5H), 2.09 (br s, 0.5H), 2.61 (br s, 1H), 2.68 (br s, 1H), 3.73 (br s, 1H), 3.93 (br s, 1H), 4.19 (br s, 1H), 4.47 (br s, 1H), 6.67 (br s, 1H), 7.63-7.70 (m, 5H), 8.13 (d, 2H) and 8.59 (s, 1H) ppm; MS (ES$^+$) 389.16

Compound I-301 1-[4-[5-amino-6-(5-phenyl-1,3,4-oxadiazol-2-yl)pyrazin-2-yl]-3,6-dihydro-2H-pyridin-1-yl]propan-1-one 1H NMR (400.0 MHz, DMSO) d 1.04 (t, 3H), 2.36-2.45 (m, 2H), 2.60 (br s, 1H), 2.70 (br s, 1H), 3.65-3.72 (m, 2H), 4.17 (s, 1H), 4.21 (s, 1H), 6.65 (s, 1H), 7.62-7.69 (m, 5H), 8.11-8.13 (d, 2H) and 8.56 (s, 1H) ppm; MS (ES$^+$) 377.17

Example 16

3-(1H-benzo[d]imidazol-2-yl)-5-(4-(ethylsulfonyl)piperazin-1-yl)pyrazin-2-amine (Compound I-16)

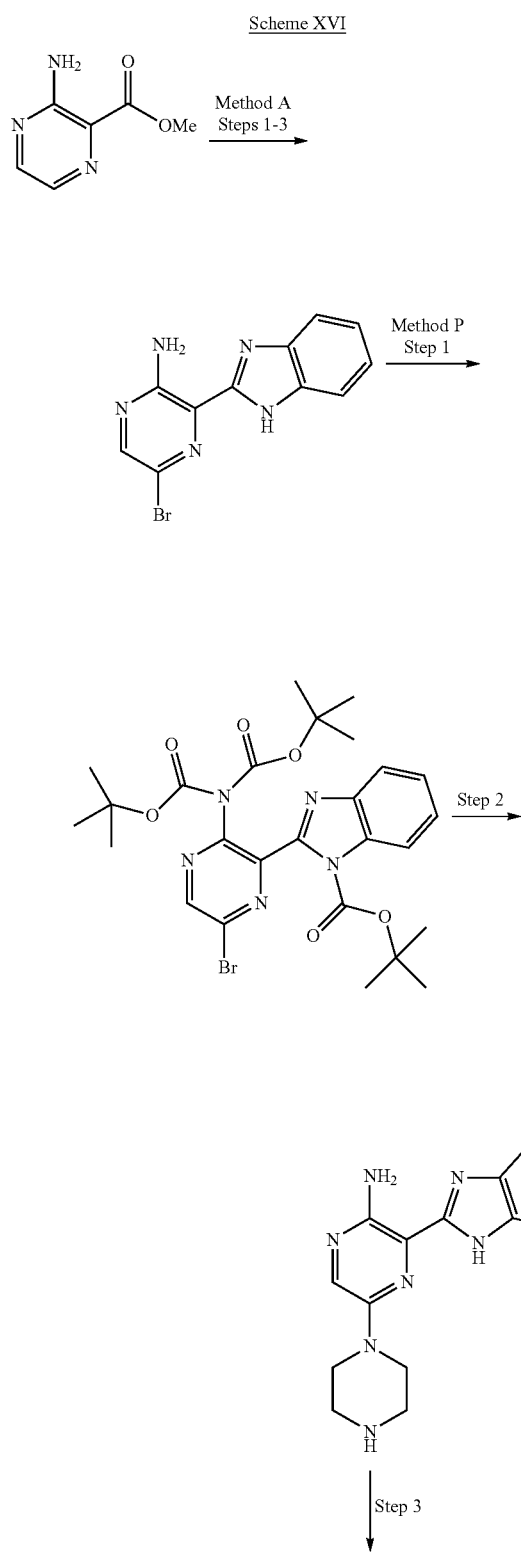

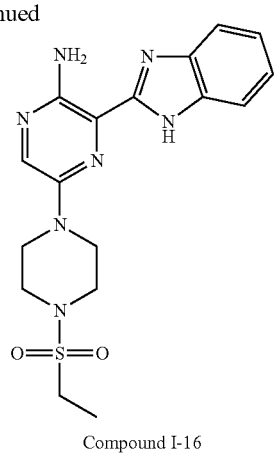

Compound I-16

Compound I-16 was prepared using Method A, Steps 1-3 followed by Method P, Steps 1-3.

Method P: Step 1: Tert-butyl 2-(3-(bis(tert-butoxycarbonyl)amino)-6-bromopyrazin-2-yl)-1H-benzo[d]imidazole-1-carboxylate 3-(1H-benzimidazol-2-yl)-5-bromo-pyrazin-2-amine (5 g, 17.23 mmol) was dissolved in acetonitrile (70 mL) and THF (120 mL) and treated with a few crystals of DMAP followed by addition of BOC anhydride (16.92 g, 17.81 mL, 77.54 mmol) in 4 portions over 15 minutes. The reaction was allowed to stir at RT overnight and concentrated to an oil, then redissolved and concentrated from DCM twice. The resultant residue was purified on silica gel by flash column chromatography (5-30% EtOAc/Petroleum ether) to afford the title compound (9.94 g, 98% Yield). 1H NMR (400.0 MHz, DMSO) d 1.10 (27H, m), 7.45 (1H, m), 7.52 (1H, m), 7.75 (1H, m), 8.09 (1H, m) and 9.10 (1H, s) ppm; MS (ES+) 591.90

Method P: Step 2: 3-(1H-benzo[d]imidazol-2-yl)-5-(piperazin-1-yl)pyrazin-2-amine Tert-butyl 2-[3-[bis(tert-butoxycarbonyl)amino]-6-bromo-pyrazin-2-yl]benzimidazole-1-carboxylate (12 g, 20.32 mmol) was dissolved in NMP (30 mL) followed by addition of DIPEA (5.252 g, 7.078 mL, 40.64 mmol) and piperazine (12.25 g, 142.2 mmol). The reaction was heated to 100° C. for 4 hours and diluted with EtOAc, washed with water, followed by brine and concentrated. The resultant residue was purified on silica gel by flash column chromatography (0-50% MeOH/EtOAc followed by 3% NH4OH in MeOH) to afford the BOC-protected product. This was dissolved in DCM/methanol and HCl (4M in dioxane) (50.80 mL of 4 M, 203.2 mmol) was added and the mixture stirred overnight at RT. The reaction was concentrated to a solid and redissolved in EtOAc, washed with sat. aqueous NaHCO3 and brine. The organic layer was dried over MgSO4 and concentrated to a give a solid which was slurried in DCM and triturated by slow addition of ether to give the desired product as an orange solid (7.07 g, 85% Yield). 1H NMR (400.0 MHz, DMSO) d 2.95 (4H, m), 3.52 (4H, m), 7.10 (2H, m), 7.55 (1H, m), 7.65 (1H, m), 8.15 (1H, m) and 12.61 (1H, br s) ppm; MS (ES+) 296.02

Method P: Step 3: 3-(1H-benzo[d]imidazol-2-yl)-5-(4-(ethylsulfonyl)piperazin-1-yl)pyrazin-2-amine 3-(1H-benzo[d]imidazol-2-yl)-5-(piperazin-1-yl)pyrazin-2-amine (50 mg, 0.169 mmol) was dissolved in DCM (3 mL)

and Et₃N (70.0 µL, 0.507 mmol) followed by ethanesulfonyl chloride (17.6 µL, 0.186 mmol) were added. The reaction was allowed to stir for 30 mins and then diluted with dichloromethane and washed with water. The aqueous layer was extracted further with dichloromethane and the organics washed with saturated aqueous NaHCO₃, dried over MgSO₄ and concentrated in vacuo. The resultant residue was purified on silica gel by flash column chromatography (0-5% MeOH/DCM) to afford the title compound (42.6 mg, 65% Yield). MS (ES⁺) 388.0

The following compounds were all prepared using the same method or a similar method to the one described for Compound I-16 in Example 16 above.

Compound I-39 (S)-5-(3-aminopyrrolidin-1-yl)-3-(1H-benzo[d]imidazol-2-yl)pyrazin-2-amine 1H NMR (400.0 MHz, DMSO) d 1.7-1.75 (1H,m), 2.05-2.1 (1H,m), 3.35-3.4 (1H,m), 3.4-3.5 (1H,m), 3.55-3.65 (3H, m), 7.02 (2H,s), 7.3-7.4 (2H,m), 7.55 (1H,d), 7.65-7.7 (2H, m), 12.5 (1H,vbrs) ppm; MS (ES⁺) 296

Compound I-40 3-(1H-benzo[d]imidazol-2-yl)-5-(piperazin-1-yl)pyrazin-2-amine

1H NMR (400.0 MHz, DMSO) d 2.9-2.95 (4H,m), 3.4-3.5 (4H,m), 7.3-7.4 (4H,m), 7.6 (1H,d), 7.7 (1H,d), 7.95 (1H,s), 12.7 (1H,vbrs) ppm; MS (ES⁺) 296

Compound I-80 3-(1H-benzo[d]imidazol-2-yl)-5-(4-(thiophen-3-ylsulfonyl)piperazin-1-yl)pyrazin-2-amine; MS (ES⁺) 441.1

Compound I-85 (S)-N-(1-(5-amino-6-(1H-benzo[d]imidazol-2-yl)pyrazin-2-yl)pyrrolidin-3-yl)propane-2-N,N-dimethylsulfamide; MS (ES⁺) 402.2

Compound I-86 3-(1H-benzo[d]imidazol-2-yl)-5-(4-(methylsulfonyl)piperazin-1-yl)pyrazin-2-amine; MS (ES⁺) 373.1

Compound I-88 4-(5-amino-6-(1H-benzo[d]imidazol-2-yl)pyrazin-2-yl)-N,N-dimethylpiperazine-1-sulfonamide; MS (ES⁺) 402.2

Compound I-91 3-(1H-benzo[d]imidazol-2-yl)-5-(4-(1-methyl-1H-imidazol-4-ylsulfonyl)piperazin-1-yl)pyrazin-2-amine; MS (ES⁺) 439.2

Compound I-95 3-(1H-benzo[d]imidazol-2-yl)-5-(4-(propylsulfonyl)piperazin-1-yl)pyrazin-2-amine; MS (ES⁺) 401.2

Compound I-97 3-(1H-benzo[d]imidazol-2-yl)-5-(4-(isopropylsulfonyl)piperazin-1-yl)pyrazin-2-amine; MS (ES⁺) 401.2

Compound I-104 3-(1H-benzo[d]imidazol-2-yl)-5-(4-(thiophen-2-ylsulfonyl)piperazin-1-yl)pyrazin-2-amine; MS (ES⁺) 441.1

Compound I-106 3-(1H-benzo[d]imidazol-2-yl)-5-(4-(benzylsulfonyl)piperazin-1-yl)pyrazin-2-amine; MS (ES⁺) 449.2

Compound I-107 (S)-N-(1-(5-amino-6-(1H-benzo[d]imidazol-2-yl)pyrazin-2-yl)pyrrolidin-3-yl)benzenesulfonamide; MS (ES⁺) 435.2

Compound I-108 (S)-N-(1-(5-amino-6-(1H-benzo[d]imidazol-2-yl)pyrazin-2-yl)pyrrolidin-3-yl)benzamide; MS (ES⁺) 399.2

Compound I-110 3-(1H-benzo[d]imidazol-2-yl)-5-(4-(phenylsulfonyl)piperazin-1-yl)pyrazin-2-amine; MS (ES⁺) 435.2

Compound I-111 (S)-N-(1-(5-amino-6-(1H-benzo[d]imidazol-2-yl)pyrazin-2-yl)pyrrolidin-3-yl)-2,2-dimethylpropanamide; MS (ES⁺) 379.2

Compound I-112 (4-(5-amino-6-(1H-benzo[d]imidazol-2-yl)pyrazin-2-yl)piperazin-1-yl)(cyclohexyl)methanone; MS (ES⁺) 405.2

For compounds I-174 to I-275, please see Tables 7 and 8 for analytical data.

Compound I-174 (4-(5-amino-6-(1H-benzo[d]imidazol-2-yl)pyrazin-2-yl)piperazin-1-yl)(cyclobutyl)methanone Compound I-175 1-(4-(5-amino-6-(1H-benzo[d]imidazol-2-yl)pyrazin-2-yl)piperazin-1-yl)-2-ethylbutan-1-one Compound I-176 (4-(5-amino-6-(1H-benzo[d]imidazol-2-yl)pyrazin-2-yl)piperazin-1-yl)(pyridin-2-yl)methanone Compound I-177 (4-(5-amino-6-(1H-benzo[d]imidazol-2-yl)pyrazin-2-yl)piperazin-1-yl)(2,6-difluorophenyl)methanone Compound I-181 (S)-N-(1-(5-amino-6-(1H-benzo[d]imidazol-2-yl)pyrazin-2-yl)pyrrolidin-3-yl)-2-(2-methoxyethoxy)ethanamide Compound I-182 (S)-N-(1-(5-amino-6-(1H-benzo[d]imidazol-2-yl)pyrazin-2-yl)pyrrolidin-3-yl)-2-methoxyethanamide Compound I-184 (S)-N-(1-(5-amino-6-(1H-benzo[d]imidazol-2-yl)pyrazin-2-yl)pyrrolidin-3-yl)-2-(dimethylamino)ethanamide Compound I-185 (S)-N-(1-(5-amino-6-(1H-benzo[d]imidazol-2-yl)pyrazin-2-yl)pyrrolidin-3-yl)ethanamide Compound I-188 (S)-N-(1-(5-amino-6-(1H-benzo[d]imidazol-2-yl)pyrazin-2-yl)pyrrolidin-3-yl)pyridine-3-carboxamide Compound I-193 (S)-N-(1-(5-amino-6-(1H-benzo[d]imidazol-2-yl)pyrazin-2-yl)pyrrolidin-3-yl)pyridine-2-carboxamide Compound I-199 1-(4-(5-amino-6-(1H-benzo[d]imidazol-2-yl)pyrazin-2-yl)piperazin-1-yl)-2-methylpropan-1-one Compound I-204 (S)-N-(1-(5-amino-6-(1H-benzo[d]imidazol-2-yl)pyrazin-2-yl)pyrrolidin-3-yl)cyclopentanecarboxamide Compound I-205 (S)-N-(1-(5-amino-6-(1H-benzo[d]imidazol-2-yl)pyrazin-2-yl)pyrrolidin-3-yl)-2-phenoxyethanamide Compound I-208 (4-(5-amino-6-(1H-benzo[d]imidazol-2-yl)pyrazin-2-yl)piperazin-1-yl)(phenyl)methanone Compound I-211 (S)-N-(1-(5-amino-6-(1H-benzo[d]imidazol-2-yl)pyrazin-2-yl)pyrrolidin-3-yl)-2-ethylbutanamide Compound I-264 1-(4-(5-amino-6-(1H-benzo[d]imidazol-2-yl)pyrazin-2-yl)piperazin-1-yl)-2-(2-methoxyethoxy)ethanone Compound I-265 1-(4-(5-amino-6-(1H-benzo[d]imidazol-2-yl)pyrazin-2-yl)piperazin-1-yl)-2-methoxyethanone Compound I-266 2-methoxyethyl 4-(5-amino-6-(1H-benzo[d]imidazol-2-yl)pyrazin-2-yl)piperazine-1-carboxylate Compound I-267 (4-(5-amino-6-(1H-benzo[d]imidazol-2-yl)pyrazin-2-yl)piperazin-1-yl)(pyrrolidin-1-yl)methanone Compound I-268 methyl 4-(5-amino-6-(1H-benzo[d]imidazol-2-yl)pyrazin-2-yl)piperazine-1-carboxylate Compound I-269 3-(1H-benzo[d]imidazol-2-yl)-5-(4-(furan-3-ylsulfonyl)piperazin-1-yl)pyrazin-2-amine Compound I-270 (4-(5-amino-6-(1H-benzo[d]imidazol-2-yl)pyrazin-2-yl)piperazin-1-yl)(piperidin-1-yl)methanone Compound I-271 ethyl 4-(5-amino-6-(1H-benzo[d]imidazol-2-yl)pyrazin-2-yl)piperazine-1-carboxylate Compound I-272 but-2-ynyl 4-(5-amino-6-(1H-benzo[d]imidazol-2-yl)pyrazin-2-yl)piperazine-1-carboxylate Compound I-273 1-(4-(5-amino-6-(1H-benzo[d]imidazol-2-yl)pyrazin-2-yl)piperazin-1-yl)-2-phenoxyethanone Compound I-274 benzyl 4-(5-amino-6-(1H-benzo[d]imidazol-2-yl)pyrazin-2-yl)piperazine-1-carboxylate Compound I-275 (4-(5-amino-6-(1H-benzo[d]imidazol-2-yl)pyrazin-2-yl)piperazin-1-yl)(2,6-dimethylphenyl)methanone Compound I-295 3-(1H-benzimidazol-2-yl)-5-(2-ethylsulfonyl-1,3,3a,4,6,6a-hexahydropyrrolo[3,4-c]pyrrol-5-yl)pyrazin-2-amine MS (ES⁺) 414.2

Example 17

3-amino-6-(1-(ethylsulfonyl)-1,2,3,6-tetrahydropyridin-4-yl)-N-(2-methylpyridin-4-yl)pyrazine-2-carboxamide (Compound I-166)

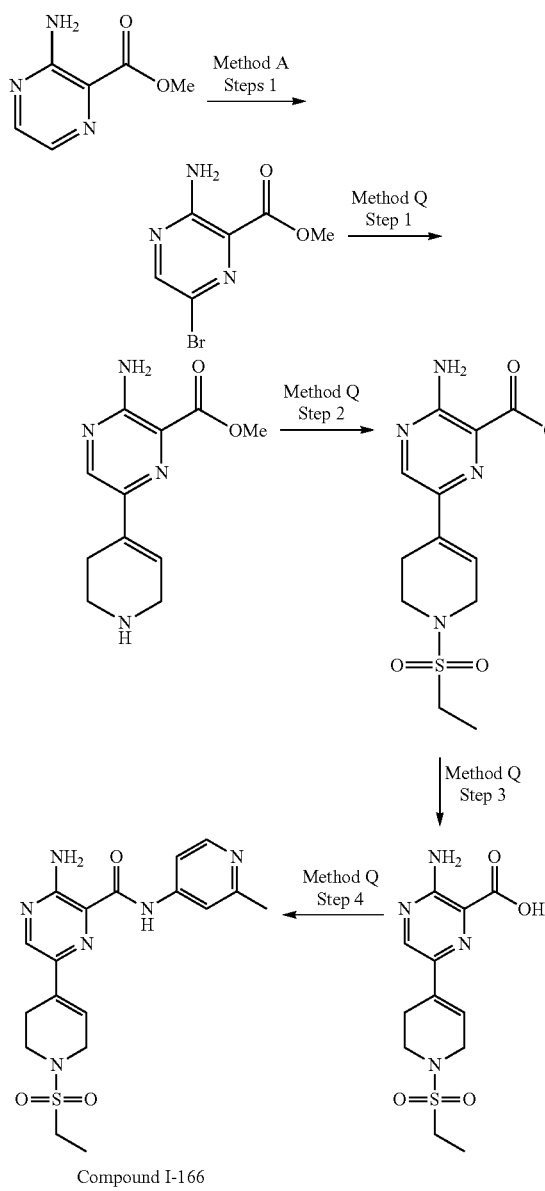

Compound I-166

Compound I-166 was prepared using Method A, Step 1 followed by Method Q, Steps 1-4.

Method Q: Step 1: Methyl 3-amino-6-(1,2,3,6-tetrahydropyridin-4-yl)pyrazine-2-carboxylate A mixture of methyl 3-amino-6-bromo-pyrazine-2-carboxylate (6 g, 25.86 mmol), tert-butyl-4-(4,4,5,5-tetramethyl-1,3,2-dioxaborolan-2-yl)-3,6-dihydro-2H-pyridine-1-carboxylate (7.996 g, 25.86 mmol), Na₂CO₃ (38.79 mL of 2 M, 77.58 mmol) and dichloropalladium; triphenylphosphane (544.5 mg, 0.7758 mmol) was stirred in DME (120.0 mL) at 100° C. for 5 hours. After this time water and EtOAc were added and the organics separated, dried and concentrated in vacuo. The residue was redissolved in DCM (20 mL) and TFA (20 mL) and the resulting solution stirred at ambient temperature for 2 hours. After this time saturated NaHCO₃ was added and the organics separated, dried and concentrated. The solid was then triturated with MeOH, filtered and washed with MeOH to give the desired product as a yellow solid (4.15 g, 69%). 1H NMR (400.0 MHz, DMSO) d 2.43 (3H, s), 3.41 (2H, m), 3.80-4.02 (5H, m), 6.52 (1H, s), 7.33 (2H, s), 8.52 (1H, s) ppm; MS (ES⁺) 234.97

Method Q: Step 2: Methyl 3-amino-6-(1-(ethylsulfonyl)-1,2,3,6-tetrahydropyridin-4-yl)pyrazine-2-carboxylate A solution of methyl 3-amino-6-(1,2,3,6-tetrahydropyridin-4-yl)pyrazine-2-carboxylate (4.15 g, 17.72 mmol) and N-ethyl-N-isopropyl-propan-2-amine (4.580 g, 6.173 mL, 35.44 mmol) in DMF (68.89 mL) was treated with ethanesulfonyl chloride (2.506 g, 1.847 mL, 19.49 mmol) and allowed to stir at ambient temperature for 16 hours. The reaction mixture was treated with water and the resulting precipitate collected and washed with water (5.5 g, 95% Yield). MS (ES⁺) 327.01

Method Q: Step 3: 3-amino-6-(1-(ethylsulfonyl)-1,2,3,6-tetrahydropyridin-4-yl)pyrazine-2-carboxylic acid A solution of methyl 3-amino-6-(1-ethylsulfonyl-3,6-dihydro-2H-pyridin-4-yl)pyrazine-2-carboxylate (5.5 g, 16.85 mmol) in MeOH (30 mL) was treated with a solution of NaOH (8.425 mL of 2 M, 16.85 mmol) in H₂O (30 mL). The resulting mixture was heated to 60° C. for 2 hours. After this time the solution was allowed to cool, neutralised with HCl and the resultant precipitate filtered (3.6 g, 65% Yield). 1H NMR (400.0 MHz, DMSO) d 1.20 (3H, t), 2.65 (2H, br s), 3.11 (2H, q), 3.44 (2H, m), 3.94 (2H, m), 6.60 (1H, m), 7.51 (2H, br s), 7.95 (1H, s), 8.52 (1H, s) ppm; MS (ES⁺) 312.97

Method Q: Step 4: 3-amino-6-(1-(ethylsulfonyl)-1,2,3,6-tetrahydropyridin-4-yl)-N-(2-methylpyridin-4-yl)pyrazine-2-carboxamide A solution of 3-amino-6-(1-ethylsulfonyl-3,6-dihydro-2H-pyridin-4-yl)pyrazine-2-carboxylic acid (79.87 mg, 0.255 mmol), CDI (82.92 mg, 0.511 mmoles), triethylamine (107 uL, 0.767 mmoles), and DMAP (1.56 mg, 0.012 mmol) was treated with 2-methylpyridin-4-amine (55.30 mg, 0.511 mmol). The reaction was allowed to stir at 100° C. for 16 hours, filtered and purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were collected, and freeze-dried to give the title compound (30.4 mg, 21% Yield). 1H NMR (400.0 MHz, DMSO) d 11.10 (s, 1H), 8.69-8.67 (m, 2H), 8.25-8.22 (m, 2H), 7.72 (s, 2H), 6.77

(d, J=3.3 Hz, 1H), 3.99 (d, J=2.9 Hz, 2H), 3.48 (t, J=5.7 Hz, 2H), 3.16 (q, J=7.4 Hz, 2H), 2.79 (s, 2H), 2.68 (s, 3H) and 1.25 (t, J=7.3 Hz, 3H) ppm; MS (ES⁺) 403.0

The following compounds were all prepared using the same method or a method similar to the one described for Compound I-166 in Example 17 above.

Compound I-165 3-amino-6-(1-(ethylsulfonyl)-1,2,3,6-tetrahydropyridin-4-yl)-N-(2-methoxypyridin-3-yl)pyrazine-2-carboxamide;

MS (ES+) 419

Compound I-167 3-amino-6-(1-(ethylsulfonyl)-1,2,3,6-tetrahydropyridin-4-yl)-N-(4-methylpyridin-2-yl)pyrazine-2-carboxamide

MS (ES+) 403

Compound I-168 3-amino-N-(1,3-dimethyl-1H-pyrazol-5-yl)-6-(1-(ethylsulfonyl)-1,2,3,6-tetrahydropyridin-4-yl)pyrazine-2-carboxamide

MS (ES+) 406

Compound I-169 3-amino-6-(1-(ethylsulfonyl)-1,2,3,6-tetrahydropyridin-4-yl)-N-(1H-indazol-3-yl)pyrazine-2-carboxamide

MS (ES+) 428

Compound I-170 3-amino-6-(1-(ethylsulfonyl)-1,2,3,6-tetrahydropyridin-4-yl)-N-(pyrazin-2-yl)pyrazine-2-carboxamide

MS (ES+) 390

Compound I-171 3-amino-6-(1-(ethylsulfonyl)-1,2,3,6-tetrahydropyridin-4-yl)-N-(pyridin-2-yl)pyrazine-2-carboxamide

MS (ES+) 389

Compound I-172 3-amino-N-(1H-benzo[d]imidazol-2-yl)-6-(1-(ethylsulfonyl)-1,2,3,6-tetrahydropyridin-4-yl)pyrazine-2-carboxamide

MS (ES+) 428

Example 18

3-(5-(3-aminophenyl)-4H-1,2,4-triazol-3-yl)-5-(4-(ethylsulfonyl)piperazin-1-yl)pyrazin-2-amine (Compound I-57)

SCHEME XVIII

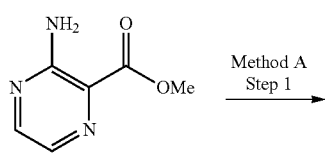

-continued

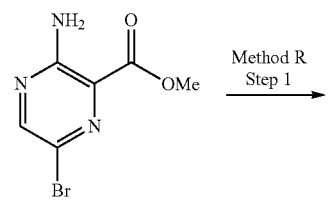

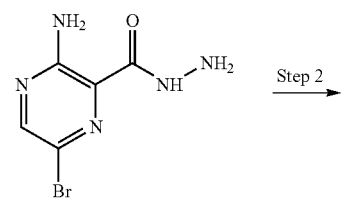

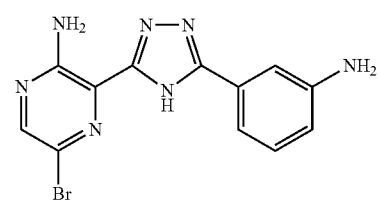

Step 3

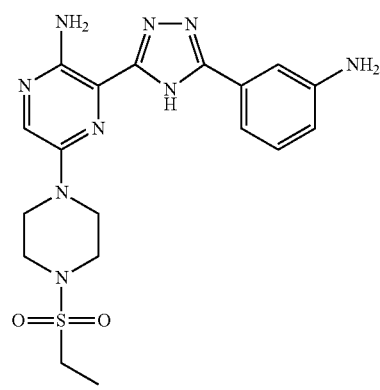

Compound I-57

Compound I-57 was prepared using Method A, Step 1 followed by Method R, Steps 1-3.

Method R: Step 1:
3-amino-6-bromopyrazine-2-carbohydrazide

A mixture of methyl 3-amino-6-bromo-pyrazine-2-carboxylate (5 g, 21.55 mmol) and hydrazine hydrate (5.397 g, 5.245 mL, 107.8 mmol) were heated to 100° C. for 1.5 hours. Water was added and the product collected by filtration, washed with methanol and dried to give 3-amino-6-bromo-pyrazine-2-carbohydrazide as a yellow solid (5.02 g, 100.4% Yield). MS (ES+) 233.78

Method R: Step 2: 3-(5-(3-aminophenyl)-4H-1,2,4-triazol-3-yl)-5-bromopyrazin-2-amine

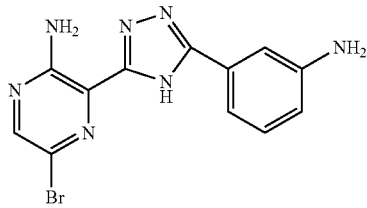 [SMILES: Nc1cccc(-c2nnc(-c3nc(Br)cnc3N)[nH]2)c1]

A mixture of 3-amino-6-bromo-pyrazine-2-carbohydrazide (5 g, 21.55 mmol), 3-aminobenzamidine dihydrochloride (4.484 g, 21.55 mmol) and NaOEt (4.399 g, 64.65 mmol) were combined in DMF (50.00 mL) and heated to 100° C. in the microwave for 20 min. Water was added and the precipitate collected. Used without further purification. Assumed 100% Yield.
MS (ES+) 334.02

Method R: Step 3: 3-(5-(3-aminophenyl)-4H-1,2,4-triazol-3-yl)-5-(4-(ethylsulfonyl)piperazin-1-yl)pyrazin-2-amne

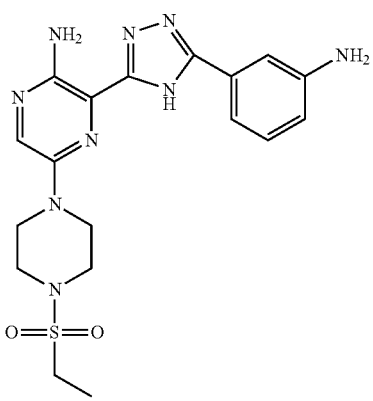 [SMILES: CCS(=O)(=O)N1CCN(c2cnc(N)c(-c3nnc(-c4cccc(N)c4)[nH]3)n2)CC1]

3-[5-(3-aminophenyl)-4H-1,2,4-triazol-3-yl]-5-bromopyrazin-2-amine (220 mg, 0.6623 mmol) was heated in neat 1-ethanesulfonyl piperazine (590.4 mg, 3.312 mmol) in the microwave at 190° C. for 2 hours. The reaction was treated with EtOAc and H₂O, the two layers separated and the organics dried and concentrated to give a yellow oil which was purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were collected, passed through a sodium bicarbonate cartridge and freeze-dried to give the title compound as a yellow solid (23.9 mg, 8% Yield). 1H NMR (400.0 MHz, DMSO) d 8.38 (s, 2H), 8.04 (s, 1H), 7.33 (s, 2H), 7.24 (s, 1H), 7.09 (s, 1H), 6.96 (s, 1H), 6.60 (s, 1H), 3.55 (s, 4H), 3.28 (s, 4H), 3.08 (d, J=5.7 Hz, 2H) and 1.20 (s, 3H) ppm; MS (ES+) 430.0

Example 19

5-(4-(ethylsulfonyl)piperazin-1-yl)-3-(imidazo[2,1-b]thiazol-6-yl)pyrazin-2-amine (Compound I-62)

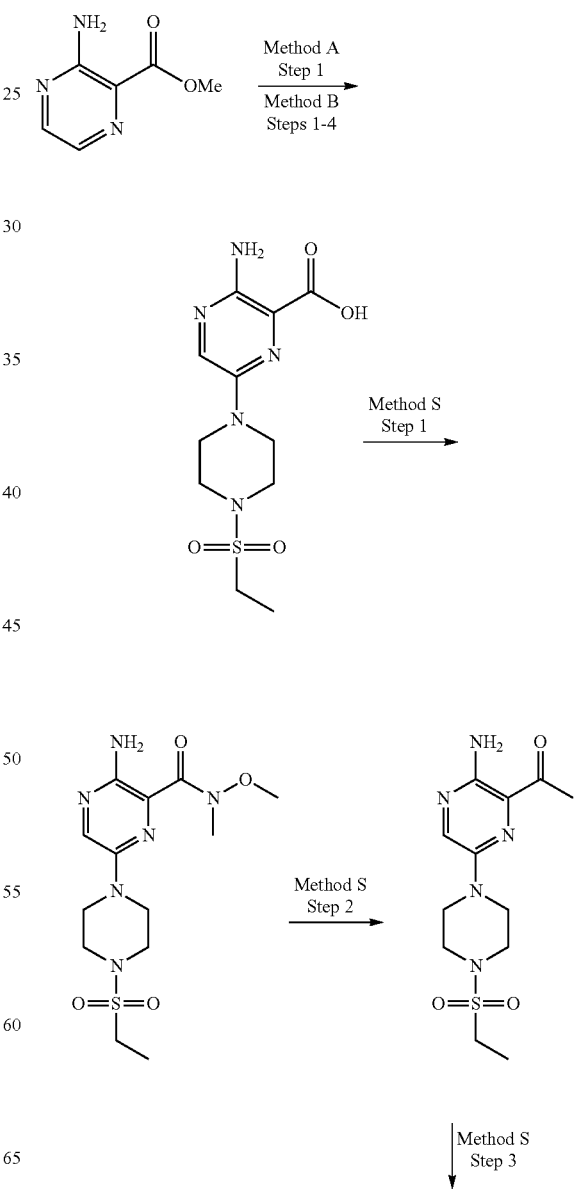

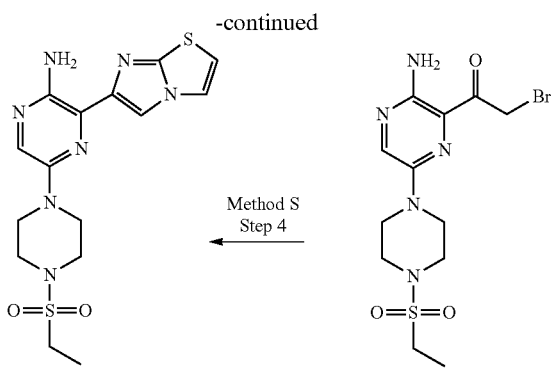

Compound I-62

Compound I-62 was prepared using Method A, Step 1 followed by Method B, Steps 1-4 followed by Method S, Steps 1-4.

Method S: Step 1: 3-amino-6-(4-(ethylsulfonyl)piperazin-1-yl)-N-methoxy-N-methylpyrazine-2-carboxamide A mixture of 3-amino-6-(4-ethylsulfonylpiperazin-1-yl)pyrazine-2-carboxylic acid (1 g, 3.171 mmol), N-methoxymethanamine hydrochloride (371.2 mg, 3.805 mmol) and triethylamine (705.9 mg, 972.3 µL 6.976 mmol) were dissolved in DMF (10 mL) and treated with TBTU (1.527 g, 4.756 mmol). The mixture was allowed to stir at ambient temperature for 1 hour. The reaction was treated with water, extracted with EtOAc (4×), and the organics separated, dried (MgSO$_4$) and concentrated. The resultant residue was purified on silica gel by flash column chromatography (0-100% EtOAc/Petrol) to afford the title compound as a yellow solid (864 mg, 76% Yield). 1H NMR (400.0 MHz, DMSO) d 1.21 (t, 3H), 3.10 (q, 2H), 3.27-3.30 (m, 4H), 3.34 (s, 3H), 3.38-3.40 (m, 4H), 3.68 (s, 3H), 5.87 (br s, 2H) and 7.99 (s, 1H) ppm; MS (ES$^+$) 359.0

Method S: Step 2: 1-(3-amino-6-(4-(ethylsulfonyl)piperazin-1-yl)pyrazin-2-yl)ethanone 3-amino-6-(4-(ethylsulfonyl)piperazin-1-yl)-N-methoxy-N-methylpyrazine-2-carboxamide (864 mg, 2.411 mmol) was dissolved in THF (10 mL) and cooled to −20° C. under nitrogen. MeMgBr (2.411 mL of 3 M, 7.233 mmol) was added dropwise and the reaction was left to stir at this temperature for 15 minutes after which time the reaction was allowed to slowly warm to ambient temperature. A further MeMgBr (803.7 µL of 3 M, 2.411 mmol) was added and analysis showed after 10 minutes showed no SM remaining. The mixture was quenched with 10 mL 1M HCl, stirred for 5 mins and then extracted with EtOAc (3×), dried (MgSO$_4$), filtered and the solvent removed in vacuo to give the product as an orange solid (510 mg, 68% Yield). 1H NMR (400.0 MHz, DMSO) d 1.23 (t, 3H), 2.54 (s, 3H), 3.11 (q, 2H), 3.30-3.32 (m, 4H), 3.47-3.49 (m, 4H), 7.42 (br s, 2H) and 8.34 (s, 1H) ppm; MS (ES$^+$) 314.0

Method S: Step 3: 1-(3-amino-6-(4-(ethylsulfonyl)piperazin-1-yl)pyrazin-2-yl)-2-bromoethanone A solution of 1-(3-amino-6-(4-(ethylsulfonyl)piperazin-1-yl)pyrazin-2-yl)ethanone (510 mg, 1.627 mmol) in AcOH (2 mL) and HBr in AcOH (0.5 mL of 33% w/v, 2.039 mmol) was treated with pyridinium tribromide (544.5 mg, 1.708 mmol) and the mixture allowed to stir at ambient temperature for 2 hours. The reaction was poured into ether (50 mL), partitioned between EtOAc/water and extract with EtOAc (3×). The mixture was dried (MgSO$_4$), filtered, evaporated down and the resultant residue was purified on silica gel by flash column chromatography (0-100% EtOAc/Petrol) to afford the title compound as a orange oil (68 mg, 11% Yield). 1H NMR (400.0 MHz, DMSO) d 1.23 (t, 3H), 3.12 (q, 2H), 3.31 (m, 4H), 3.52 (m, 4H), 4.86 (s, 2H), 7.21 (s, 1H), 8.34 (s, 1H) ppm; MS (ES$^+$) 393.91

Method S: Step 4: 5-(4-(ethylsulfonyl)piperazin-1-yl)-3-(imidazo[2,1-b]thiazol-6-yl)pyrazin-2-amine 1-[3-amino-6-(4-ethylsulfonylpiperazin-1-yl)pyrazin-2-yl]-2-bromo-ethanone (35 mg, 0.08922 mmol) was suspended in EtOH (2 mL) and 2 aminothiazole (8.935 mg, 0.08922 mmol) was added. The mixture was heated at reflux for 4 hours and then allowed to cool to ambient temperature. The solution was filtered through a 0.45 µnm PTFE filter and the solvent removed under a stream of nitrogen. The resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected and freeze-dried to give the title compound (55 mg, 10% Yield). 1H NMR (400.0 MHz, DMSO) d 1.14 (t, J=7.3 Hz, 3H), 3.01 (q, J=7.4 Hz, 2H), 3.21-3.23 (m, 4H), 3.34-3.36 (m, 4H), 7.28 (d, J=4.4 Hz, 1H), 7.67 (s, 1H), 7.89 (d, J=4.4 Hz, 1H) and 8.23 (s, 1H) ppm; MS (ES$^+$) 394.0

Example 20

5-(4-(ethylsulfonyl)piperazin-1-yl)-3-(6-phenylpyrimidin-4-yl)pyrazin-2-amine (Compound I-74)

SCHEME XX

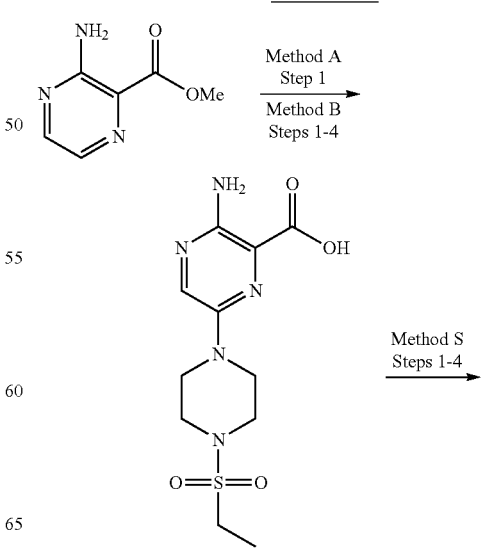

-continued

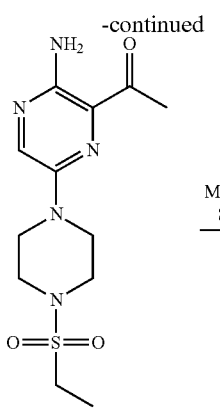

Method T
Step 1

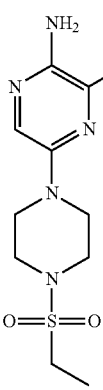

Method T
Step 2

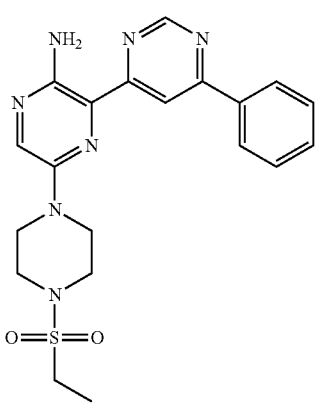

Compound I-74

Compound I-74 was prepared using Method A, Step 1 followed by Method B, Steps 1-4 followed by Method S, Steps 1-2 followed by Method T, Steps 1-2.

Method T: Step 1: (E)-1-(3-amino-6-(4-(ethylsulfonyl)piperazin-1-yl)pyrazin-2-yl)-3-phenylprop-2-en-1-one A solution of NaOH in methanol (191.5 µl, of 10% w/v, 0.4787 mmol) was added to a solution of 1-(3-amino-6-(4-(ethylsulfonyl)piperazin-1-yl)pyrazin-2-yl)ethanone (150 mg, 0.4787 mmol) and benzaldehyde (50.80 mg, 48.66 µL, 0.4787 mmol) in methanol (4 mL) (1 mL of dichloromethane was added to aid solubility). The reaction mixture was allowed to stir overnight at RT and then filtered and washed with a small amount of methanol. The bright orange coloured solid was taken through crude to the next stage. (104.6 mg, 54% Yield). 1H NMR (400.0 MHz, DMSO) d 1.21 (t, 3H), 3.13 (q, 2H), 3.35-3.37 (m, 4H), 3.54-3.57 (m, 4H), 7.47-7.51 (m, 3H), 7.55 (br s, 2H), 7.72 (d, 1H), 7.79-7.81 (m, 2H), 8.28 (d, 1H), 8.41 (s, 1H) ppm; MS (ES$^+$) 402.01

Method T: Step 2: 5-(4-(ethylsulfonyl)piperazin-1-yl)-3-(6-phenylpyrimidin-4-yl)pyrazin-2-amine A mixture of 1-(3-amino-6-(4-(ethylsulfonyl)piperazin-1-yl)pyrazin-2-yl)-3-phenylprop-2-en-1-one (45 mg, 0.1121 mmol), formamidine hydrochloride (9.026 mg, 0.1121 mmol) and NaOH (4.932 mg, 0.1233 mmol) were heated at reflux for 1 hour. The reaction mixture was allowed to cool to ambient temperature and the solvent removed in vacuo. The resultant residue was purified by reverse phase preparative HPLC [Waters Sunfire C18, 10 uM, 100A column, gradient 10%-95% B, (solvent A: 0.05% TFA in water, solvent B: CH$_3$CN) over 16 minutes at 25 mL/min]. The fractions were collected and freeze-dried to give the title compound (73 mg, 4% Yield). 1H NMR (400.0 MHz, DMSO) d 1.25 (t, 3H), 3.12 (q, 2H), 3.36-3.38 (m, 4H), 3.56-3.59 (m, 4H), 7.15 (br s, 2H), 7.60-7.61 (m, 3H), 8.25-8.26 (m, 3H), 8.76 (s, 1H) and 9.31 (s, 1H) ppm; MS (ES$^+$) 426.0

Compound I-73 was also prepared using Method A, Step 1 followed by Method B, Steps 1-4 followed by Method S, Steps 1-2 followed by Method T, Step 1.

Compound I-73 (E)-1-(3-amino-6-(4-(ethylsulfonyl)piperazin-1-yl)pyrazin-2-yl)-3-phenylprop-2-en-1-one; 1H NMR (400.0 MHz, DMSO) d 1.21 (t, 3H), 3.13 (q, 2H), 3.35-3.37 (m, 4H), 3.54-3.57 (m, 4H), 7.47-7.51 (m, 3H), 7.55 (br s, 2H), 7.72 (d, 1H), 7.79-7.81 (m, 2H), 8.28 (d, 1H), 8.41 (s, 1H) ppm; MS (ES$^+$) 402.01

Example 21

3-(1-(4-aminophenyl)-1H-1,2,3-triazol-4-yl)-5-(4-(ethylsulfonyl)piperazin-1-yl)pyrazin-2-amine (Compound I-160)

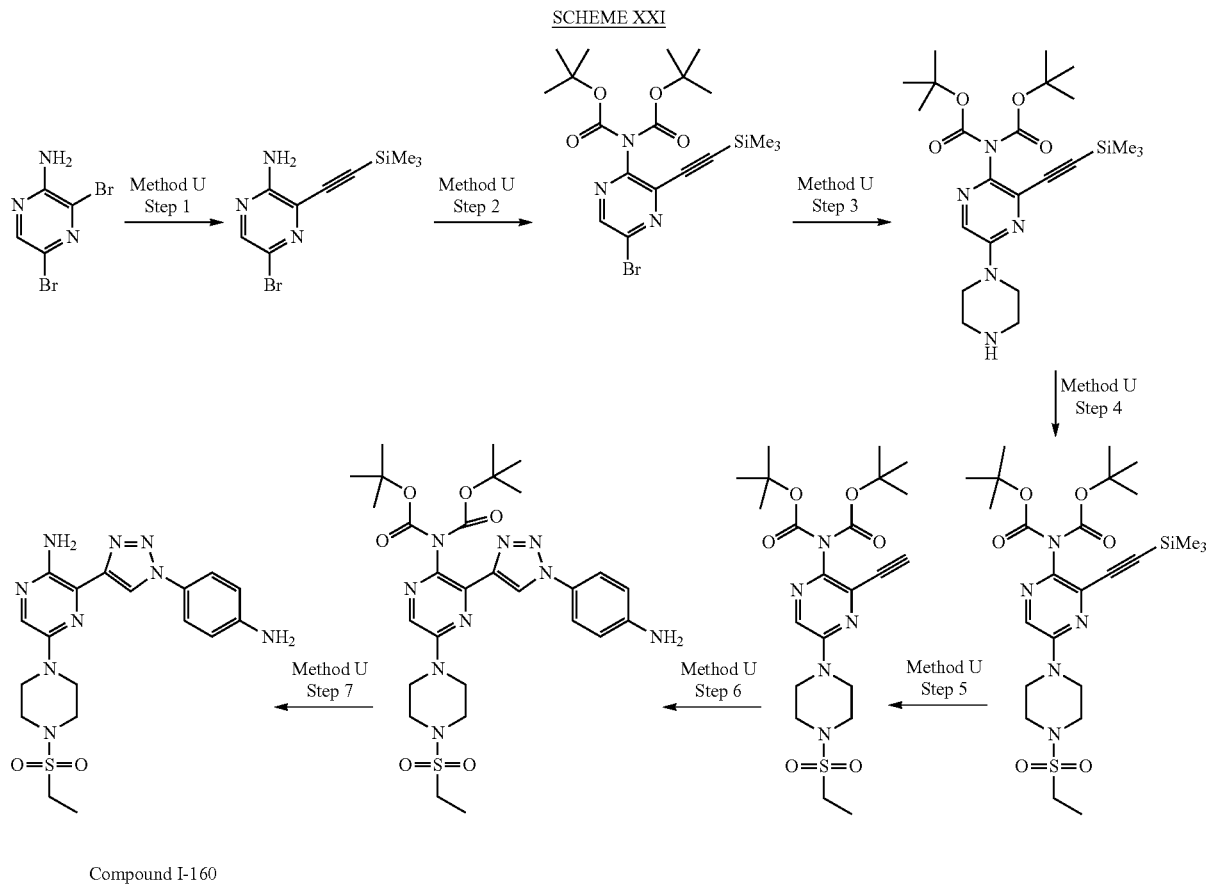

Compound I-160

Compound I-160 was prepared using Method U, Steps 1-7.

Method U: Step 1: 5-bromo-3-((trimethylsilyl)ethynyl)pyrazin-2-amine

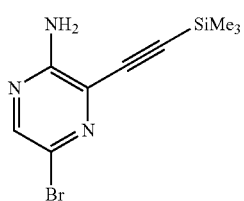 [SMILES: C[Si](C)(C)C#Cc1nc(Br)cnc1N]

(Trimethylsilyl)acetylene (1.845 g, 2.655 mL, 18.78 mmol) was added dropwise to a solution of 3,5-dibromopyrazin-2-amine (5 g, 19.77 mmol), triethylamine (10.00 g, 13.77 mL, 98.85 mmol), Copper(I) iodide (451.7 mg, 2.372 mmol) and Pd(PPh$_3$)$_4$(1.142 g, 0.9885 mmol) in DMF (25.00 mL) and the resulting solution stirred at ambient temperature for 30 minutes. The reaction was diluted with EtOAc and water and the layers separated. The aqueous layer was extracted further with EtOAc and the combined organics washed with water, dried (MgSO$_4$) and concentrated in vacuo. The mixture was purified on silica gel by flash column chromatography (0-15% EtOAc/Petrol) to afford the product as a yellow solid (3.99 g, 75% Yield). 1H NMR (400.0 MHz, DMSO) d 0.30 (s, 9H), 8.06 (s, 1H) ppm; MS (ES$^+$) 271.82

Method U: Step 2: Tert-butyl N-tert-butoxycarbonyl-N-[5-bromo-3-((trimethylsilyl)ethynyl)pyrazin-2-yl] carbamate 5-bromo-3-(2-trimethylsilylethynyl)pyrazin-2-amine (480 mg, 1.776 mmol) was dissolved in DCM (15 mL) and treated with BOC anhydride (1.163 g, 1.224 mL, 5.328 mmol) followed by DMAP (21.70 mg, 0.1776 mmol). The mixture was allowed to stir at ambient temperature overnight. The reaction was washed with NaHCO$_3$, extracted with DCM (3×), dried (MgSO$_4$), filtered and concentrated. The resultant brown oil was purified (ISCO Companion™, 40 g column, 0-10% EtOAc/Petrol) to afford the product as a colourless oil (641 mg, 77% Yield).

1H NMR (400.0 MHz, DMSO) d 0.00 (s, 9H), 1.11 (s, 18H) and 8.63 (s, 1H) ppm

Method U: Step 3: Tert-butyl N-tert-butoxycarbonyl-5-(piperazin-1-yl)-3-((trimethylsilyl)ethynyl)pyrazin-2-ylcarbamate Tert-butyl N-tert-butoxycarbonyl-N-[5-bromo-3-((trimethylsilyl)ethynyl)pyrazin-2-yl]carbamate (640 mg, 1.360 mmol) was dissolved in DMF (5 mL) and treated with piperazine (351.4 mg, 4.080 mmol). The reaction was allowed to heat at 100° C. for 15 minutes and then allowed to cool to ambient temperature and diluted with EtOAc/water. The aqueous layer was extracted with EtOAc and the combined organics washed with water (2×) and brine (2×). This was dried (MgSO$_4$), filtered and concentrated. The residue was purified by column chromatography (ISCO Companion™, 12 g column, 0-100% EtOAc/Petrol to 10% MeOH/DCM/1% NH$_4$OH) to afford the title compound as a yellow oil (494 mg, 76% Yield). 1H NMR (400.0 MHz, DMSO) d 0.03 (s, 9H), 1.18 (s, 18H), 2.99 (m, 4H), 3.29 (m, 4H) and 7.88 (s, 1H) ppm; MS (ES$^+$) 476.08

Method U: Step 4: Tert-butyl N-tert-butoxycarbonyl-5-(4-(ethylsulfonyl)piperazin-1-yl)-3-((trimethylsilyl)ethynyl)pyrazin-2-ylcarbamate Ethanesulfonyl chloride (147.0 mg, 108.3 µL, 1.143 mmol) was added slowly to a stirred solution of tert-butyl N-tert-butoxycarbonyl-5-(piperazin-1-yl)-3-((trimethylsilyl)ethynyl)pyrazin-2-ylcarbamate (494 mg, 1.039 mmol) and DIPEA (161.2 mg, 217.3 µL, 1.247 mmol) in DMF (5 mL) at ambient temperature. The reaction was allowed to stir for 5 minutes and then partitioned between EtOAc/water. The aqueous layer was extracted with EtOAc (3×) and the combined organics washed with brine, dried (MgSO$_4$), filtered and concentrated to give the product as a terracotta oil (645 mg, quantitative yield). MS (ES$^+$) 590.05

Method U: Step 5: Tert-butyl N-tert-butoxycarbonyl-N-[5-(4-ethylsulfonylpiperazin-1-yl)-3-ethynyl-pyrazin-2-yl]carbamate Tert-butyl N-tert-butoxycarbonyl-5-(4-(ethylsulfonyl)piperazin-1-yl)-3-((trimethylsilyl)ethynyl)pyrazin-2-ylcarbamate (589 mg, 1.037 mmol) was dissolved in anhydrous MeOH (10 mL) and treated with K$_2$CO$_3$ (14.33 mg, 0.1037 mmol). The reaction was allowed to stir at ambient temperature for 45 minutes. The solvent was removed in vacuo and the residue redissolved in DCM and washed with water followed by brine. The solution was dried (MgSO$_4$), filtered and concentrated and the residue was purified by column chromatography (ISCO Companion™, 24 g column, 0-100% EtOAc/Petrol) to afford the title compound as an orange solid (287 mg, 60% Yield). 1H NMR (400.0 MHz, DMSO) d 1.23 (t, J=7.4 Hz, 3H), 1.38 (s, 18H), 3.11 (q, 2H), 3.26-3.34 (m, 4H), 3.69-3.71 (m, 4H), 4.65 (s, 1H) and 8.27 (s, 1H) ppm; MS (ES$^+$) 396.0

Method U: Step 6: Tert-butyl N-tert-butoxycarbonyl-3-(1-(4-aminophenyl)-1H-1,2,3-triazol-4-yl)-5-(4-(ethylsulfonyl)piperazin-1-yl)pyrazin-2-ylcarbamate A mixture of tert-butyl N-tert-butoxycarbonyl-N-[5-(4-ethylsulfonylpiperazin-1-yl)-3-ethynyl-pyrazin-2-yl]carbamate (50 mg, 0.1009 mmol) and 4-Azidoaniline hydrochloride (17.32 mg, 0.1009 mmol) were suspended in t-BuOH (1 mL)/Water (1.000 mL). The reaction was treated with (+)-Sodium L-ascorbate (1.999 mg, 0.01009 mmol) followed by CuSO$_4$.5H$_2$O (0.2519 mg, 0.1103 µL, 0.001009 mmol) and the mixture allowed to stir at ambient temperature for 16 hours. The reaction was treated with DIPEA (13.04 mg, 17.57 µL, 0.1009 mmol) and allowed to heat to 40° C. for 5 hours and then cooled to ambient temperature. The mixture was partitioned between EtOAc/NaHCO$_3$ and the aqueous layer extracted with EtOAc (2×), dried (MgSO$_4$), filtered and concentrated. The material was used crude in the next step (quantitative yield assumed). MS (ES$^+$) 630.00

Method U: Step 7: 3-(1-(4-aminophenyl)-1H-1,2,3-triazol-4-yl)-5-(4-(ethylsulfonyl)piperazin-1-yl)pyrazin-2-amine Tert-butyl N-tert-butoxycarbonyl-3-(1-(4-aminophenyl)-1H-1,2,3-triazol-4-yl)-5-(4-(ethylsulfonyl)piperazin-1-yl)pyrazin-2-ylcarbamate (64 mg, 0.1016 mmol) was dissolved in DCM (5 mL) and treated with TFA (500 µL, 6.490 mmol). The reaction was allowed to stir at ambient temperature overnight and then the solvent removed in vacuo. The resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected and freeze-dried to give the title compound (24.3 mg, 30% Yield). 1H NMR (400.0 MHz, DMSO) d 1.24 (t, J=7.4 Hz, 3H), 3.11 (q, J=7.4 Hz, 2H), 3.30-3.33 (m, 4H), 3.50-3.52 (m, 4H), 6.77 (d, J=8.6 Hz, 2H), 7.67 (d, J=8.8 Hz, 2H), 7.88 (s, 1H) and 9.09 (s, 1H) ppm; MS (ES$^+$) 430.0

Example 22

3-([1,2,4]triazolo[1,5-a]pyridin-2-yl)-5-(1-(ethylsulfonyl)-1,2,3,6-tetrahydropyridin-4-yl)pyrazin-2-amine (Compound I-276)

SCHEME XXII

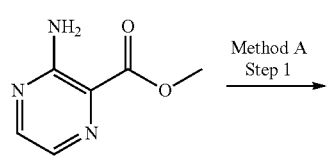

217

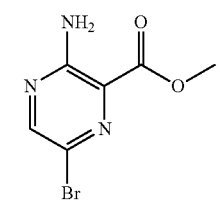 Method V Step 1 → 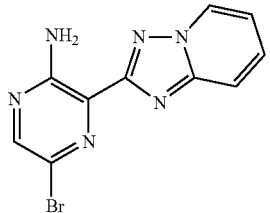 Method V Step 2 →

-continued

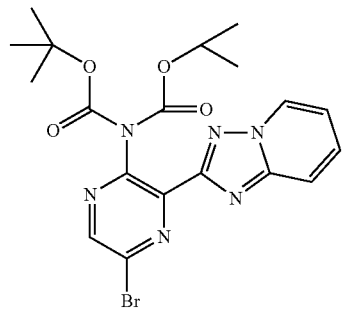

Method V Step 3 ↓

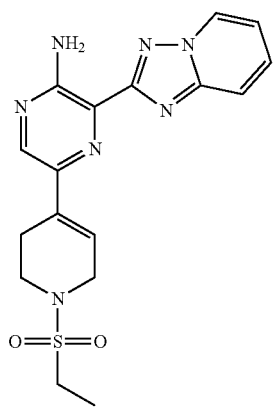

Compound I-276

← Method V Step 5 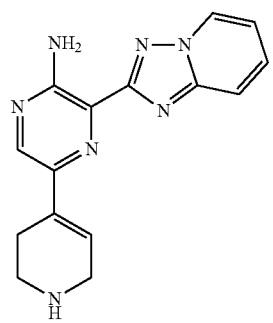 ← Method V Step 4 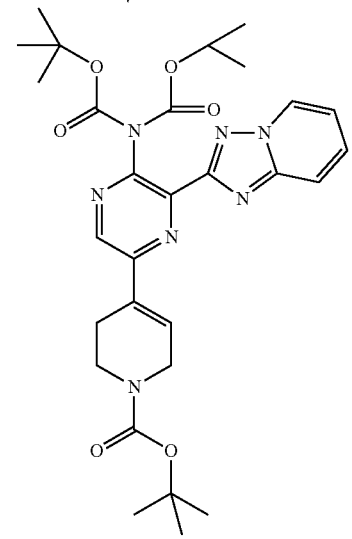

Compound I-276 was prepared using Method A, Step 1 followed by Method V, Steps 1-5.

Method V: Step 1: 3-([1,2,4]triazolo[1,5-a]pyridin-2-yl)-5-bromopyrazin-2-amine A mixture of pyridin-1-ium-1,2-diamine (185 mg, 0.7805 mmol), methyl 3-amino-6-bromo-pyrazine-2-carboxylate (217.3 mg, 0.9366 mmol) and NaOH (49.96 mg, 1.249 mmol) in EtOH (7 mL) were heated at 80° C. After 1 hour further methyl 3-amino-6-bromo-pyrazine-2-carboxylate (50 mg, 0.2155 mmol) was added and the reaction allowed to heat for a further 1.5 hours. The reaction was allowed to cool to ambient temperature and the solvent removed in vacuo. The mixture was partitioned between DCM/Water and the layers separated. The organics were dried (MgSO$_4$), filtered and concentrated to give the product as an off-white solid (134 mg, 59% Yield). 1H NMR (400.0 MHz, DMSO) d 7.34 (td, J=6.9, 2.7 Hz, 1H), 7.77-7.81 (m, 1H), 7.87 (br s, 2H), 7.97 (d, 1H), 8.31 (s, 1H) and 9.09 (d, 1H) ppm; MS (ES$^+$) 292.8

Method V: Step 2: Tert-butyl N-tert-butoxycarbonyl-3-([1,2,4]triazolo[1,5-a]pyridin-2-yl)-5-bromopyrazin-2-ylcarbamate A solution of 3-([1,2,4]triazolo[1,5-a]pyridin-2-yl)-5-bromopyrazin-2-amine (168 mg, 0.5771 mmol) in DCM (15 mL) was treated with BOC anhydride (377.8 mg, 397.7 μL, 1.731 mmol) followed by DMAP (7.050 mg, 0.05771 mmol). The mixture was allowed to stir at ambient temperature for 16 hours. Analysis showed SM remaining therefore further BOC anhydride (377.8 mg, 397.7 μL, 1.731 mmol) and DMAP (7.050 mg, 0.05771 mmol) were added and the mixture allowed to stir for a further 16 hours. The reaction was washed with NaHCO$_3$, extracted with DCM (3×), dried (MgSO$_4$), filtered and concentrated. The residue was purified by column chromatography (ISCO Companion™, 24 g column, 0-100% EtOAc/Petrol) to afford the title compound as a white solid (167 mg, 59% Yield). 1H NMR (400.0 MHz, DMSO) d 1.28 (s, 18H), 7.38-7.42 (m, 1H), 7.82-7.86 (m, 1H), 7.99-8.02 (m, 1H), 9.06 (s, 1H) and 9.05-9.10 (m, 1H) ppm; MS (ES$^+$) 493.0

Method V: Step 3: Tert-butyl 4-(6-([1,2,4]triazolo[1,5-a]pyridin-2-yl)-5-(bis(tert-butoxycarbonyl)amino)pyrazin-2-yl)-5,6-dihydropyridine-1(2H)-carboxylate Tert-butyl N-tert-butoxycarbonyl-3-([1,2,4]triazolo[1,5-a]pyridin-2-yl)-5-bromopyrazin-2-ylcarbamate (92 mg, 0.1872 mmol) was dissolved in DMF (1.5 mL) and treated with tert-butyl 4-(4,4,5,5-tetramethyl-1,3,2-dioxaborolan-2-yl)-3,6-dihydro-2H-pyridine-1-carboxylate (86.83 mg, 0.2808 mmol), PdCl$_2$(PPh$_3$)$_2$ (13.14 mg, 0.01872 mmol) and K$_2$CO$_3$ (280.8 μL of 2 M, 0.5616 mmol). The mixture was allowed to heat at 100° C. for 1 hour and then allowed to cool to ambient temperature. The reaction was treated with EtOAc/water, the organics separated, washed with water (2×) followed by brine (2×), dried (MgSO₄), filtered and concentrated to a brown oil. The residue was purified by column chromatography (ISCO Companion™, 12 g column, 0-100% EtOAc/Petrol) to afford the title compound as a white solid (77 mg, 69% Yield). MS (ES⁺) 594.0

Method V: Step 4: 3-([1,2,4]triazolo[1,5-a]pyridin-2-yl)-5-(1,2,3,6-tetrahydropyridin-4-yl)pyrazin-2-amine Tert-butyl 4-[5-(bis(tert-butoxycarbonyl)amino)-6-([1,2,4]triazolo[1,5-a]pyridin-2-yl)pyrazin-2-yl]-3,6-dihydro-2H-pyridine-1-carboxylate (77 mg, 0.1297 mmol) was dissolved in DCM (1.6 mL) and treated with TFA (400 µL, 5.192 mmol). The mixture was allowed to stir at ambient temperature for 2 hours and the solvent removed in vacuo. The mixture was azeotroped with DCM (3×) and Ether (3×) and dried under vacuum to furnish the product as a yellow solid (104 mg, quantitative yield). MS (ES⁺) 294.0

Method V: Step 5: 3-([1,2,4]triazolo[1,5-a]pyridin-2-yl)-5-(1-(ethylsulfonyl)-1,2,3,6-tetrahydropyridin-4-yl)pyrazin-2-amine 5-(1,2,3,6-tetrahydropyridin-4-yl)-3-([1,2,4]triazolo[1,5-a]pyridin-2-yl)pyrazin-2-amine (82 mg, 0.1291 mmol) was dissolved in DCM (4 mL) and treated with triethylamine (78.38 mg, 108.0 µL, 0.7746 mmol) followed by ethanesulfonyl chloride (18.26 mg, 13.46 µL, 0.1420 mmol). The reaction mixture was allowed to stir at ambient temperature for 1 hour when analysis showed SM remaining. The mixture was treated with further ethanesulfonyl chloride (16.60 mg, 12.23 µL, 0.1291 mmol) and stirred for a further hour. The reaction was diluted with DCM, washed with water and the aqueous layer extracted further with dichloromethane (2×). The combined organics were washed with saturated aqueous NaHCO₃, dried (MgSO₄) and concentrated in vacuo. The resultant residue was purified by column chromatography (ISCO Companion™, 12 g column, 0-2.5% MeOH/DCM) to afford the title compound which was freeze-dried to give a yellow solid (9 mg, 17% Yield). 1H NMR (400.0 MHz, DMSO) d 1.24 (t, J=7.4 Hz, 3H), 2.71 (br s, 2H), 3.14 (q, J=7.3 Hz, 2H), 3.48 (t, J=5.7 Hz, 2H), 3.98 (d, J=2.9 Hz, 2H), 6.62 (br s, 1H), 7.30-7.33 (m, 1H), 7.72 (br s, 2H), 7.75-7.79 (m, 1H), 7.98 (d, J=8.8 Hz, 1H), 8.40 (s, 1H) and 9.11 (d, J=6.7 Hz, 1H) ppm; MS (ES⁺) 386.0

Example 23

3-(benzofuran-2-yl)-5-(4-(ethylsulfonyl)piperazin-1-yl)pyrazin-2-amine (Compound I-29)

SCHEME XXIII

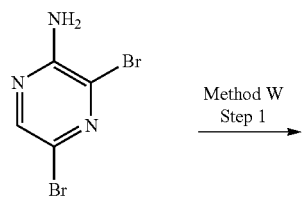

Compound I-29

Compound I-29 was prepared using Method W, Steps 1-3.

Method W: Step 1: 3-(benzofuran-2-yl)-5-bromopyrazin-2-amine

A solution of 3,5-dibromopyrazin-2-amine (200 mg, 0.7908 mmol), benzofuran-2-ylboronic acid (140.9 mg, 0.8699 mmol), NaHCO₃ (199.3 mg, 2.372 mmol) and palladium; triphenylphosphane (91.38 mg, 0.07908 mmol) in dimethoxyethane (2.000 mL) and water (1.000 mL) was heated at 120° C. in the microwave for 10 minutes. The reaction was diluted with EtOAc/Water and the layers separated. The aqueous layer was extracted further with EtOAc (2×), dried (MgSO₄) and concentrated in vacuo. The mixture was purified on silica gel by flash column chromatography (0-20% EtOAc/Petrol) to afford the product as a bright yellow solid (191 mg, 83% Yield). MS (ES⁺) 291.89

Method W: Step 2: Tert-butyl 3-(benzofuran-2-yl)-5-bromopyrazin-2-ylcarbamate

A solution of 3-(benzofuran-2-yl)-5-bromo-pyrazin-2-amine (179 mg, 0.6170 mmol) was treated with di-tert-butyl-dicarbonate (404.0 mg, 425.3 µL, 1.851 mmol) and 4-(dimethylamino)pyridine (7.538 mg, 0.06170 mmol) in dichloromethane (5 mL) and the reaction mixture allowed to stir overnight at ambient temperature. The reaction was diluted with DCM (10 mL) and washed with 1N HCl (1×), sat aqueous NaHCO₃ (1×) and brine (1×), dried (MgSO₄) and concentrated in vacuo. The material was used crude in the next step (235 mg, 98% Yield).

Method W: Step 3: 3-(benzofuran-2-yl)-5-(4-(ethylsulfonyl)piperazin-1-yl)pyrazin-2-amine A solution of tert-butyl N-[3-(benzofuran-2-yl)-5-bromopyrazin-2-yl]carbamate, 1-ethylsulfonylpiperazine (164.5 mg, 0.9228 mmol) and 2-methoxyethanol (3 mL) were heated at 100° C. for 3 hours. The reaction mixture was allowed to cool to RT, treated with HCl in dioxane (384.5 µL of 4 M, 1.538 mmol) and allowed to stir at RT for 3 hours. The mixture was concentrated in vacuo and the resultant residue was purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were collected and freeze-dried to give the title compound as an orange solid (15.5 mg, 12% Yield). 1H NMR (DMSO) d 1.24 (3H, t), 3.11 (2H, q), 3.45 masked signal, 3.51 (4H, m), 6.12 (2H, br s), 7.30 (1H, m), 7.34 (1H, m), 7.47 (1H, s), 7.71 (2H, m), 7.98 (1H, s) ppm; MS (ES⁺) 388.01

Example 24

5-(4-(ethylsulfonyl)piperazin-1-yl)-3-(5-phenyloxazol-2-yl)pyrazin-2-amine (Compound I-36)

SCHEME XXIV

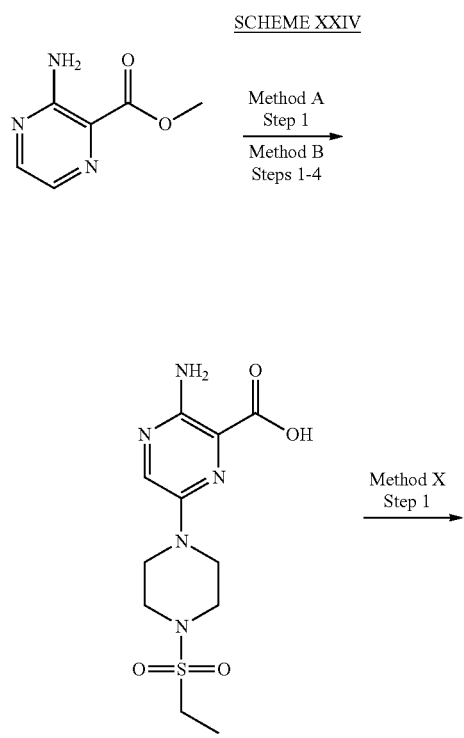

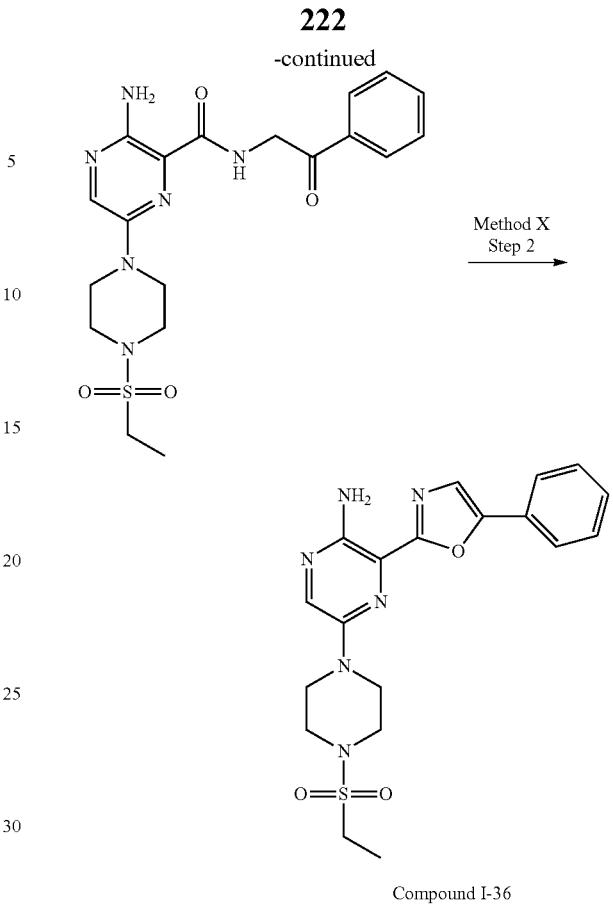

Compound I-36

Compound I-36 was prepared using Method A, Step 1 followed by Method B, Steps 1-4 followed by Method X, Steps 1-2.

Method X: Step 1: 3-amino-6-(4-(ethylsulfonyl)piperazin-1-yl)-N-(2-oxo-2-phenylethyl)pyrazine-2-carboxamide 2-amino-1-phenyl-ethanone hydrochloride (136.1 mg, 0.7928 mmol) was added to a solution of 3-amino-6-(4-ethylsulfonylpiperazin-1-yl)pyrazine-2-carboxylic acid (250 mg, 0.7928 mmol) and DIPEA (512.3 mg, 690.4 µL, 3.964 mmol) in CH₂Cl₂ (3.332 mL) and DMF (833.2 µL) and the resulting solution stirred at room temperature for 1 hour. The reaction was diluted with EtOAc/water and the layers separated. The aqueous layer was extracted further with EtOAc (2×) and the combined organics washed with water (3×), dried (MgSO₄) and concentrated in vacuo. The mixture was purified on silica gel by flash column chromatography (100% EtOAc) to afford the product (229 mg, 67% Yield). 1H NMR (CDCl₃) d 1.28 (3H, t), 3.06 (2H, q), 3.51-3.53 (4H, m), 3.56-3.59 (4H, m), 4.95 (2H, d), 6.2 (2H, br s), 7.56 (2H, m), 7.68 (1H, m), 8.05 (3H, m), 8.65 (1H, m) ppm; MS (ES⁺) 433.0

Method X: Step 2: 5-(4-(ethylsulfonyl)piperazin-1-yl)-3-(5-phenyloxazol-2-yl)pyrazin-2-amine 3-amino-6-(4-ethylsulfonylpiperazin-1-yl)-N-phenacyl-pyrazine-2-carboxamide (80 mg, 0.1850 mmol) in H₂SO₄ (1.5 mL) was stirred at ambient temperature for 16 hours. The reaction was neutralised by addition of NaHCO₃ solution and then extracted with EtOAc (3×), combined organics dried (MgSO$_4$) and concentrated in vacuo. The resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected and freeze-dried to give the title compound as an orange solid (4.5 mg, 6% Yield). 1H NMR (DMSO) d 1.25 (3H, t), 3.11 (2H, q), 3.35 masked signal, 3.54 (4H, m), 7.00 (2H, br s), 7.42 (1H, m), 7.53 (2H, m), 7.84 (2H, m), 7.99 (1H, s), 8.14 (1H, s) ppm; MS (ES$^+$) 415.0

Example 25

5-(4-(ethylsulfonyl)piperazin-1-yl)-3-(5-methyl-1,2,4-oxadiazol-3-yl)pyrazin-2-amine (Compound I-38)

Method Y: Step 2: (E)-3-amino-6-bromo-N'-hydroxypyrazine-2-carboximidamide 3-amino-6-bromo-pyrazine-2-carbonitrile (4.5958 g, 23.09 mmol) was dissolved in MeOH (91.92 mL), cooled to 0° C. and treated with hydroxylamine hydrochloride (1.605 g, 23.09 mmol) and triethylamine (2.336 g, 3.218 mL, 23.09 mmol). The reaction was allowed to warm to ambient temperature, stirred for 48 hours and then evaporated to dryness. Methanol (a minimum amount) was added, the mixture sonicated, filtered and washed with MeOH to give the product as a brown solid 5.27 g, 98% Yield). 1H NMR (400.0 MHz, DMSO) d 5.88 (s, 2H), 7.64 (br s, 2H), 8.14 (s, 1H) and 10.38 (s, 1H) ppm; MS (ES$^+$) 233.75

SCHEME XXV

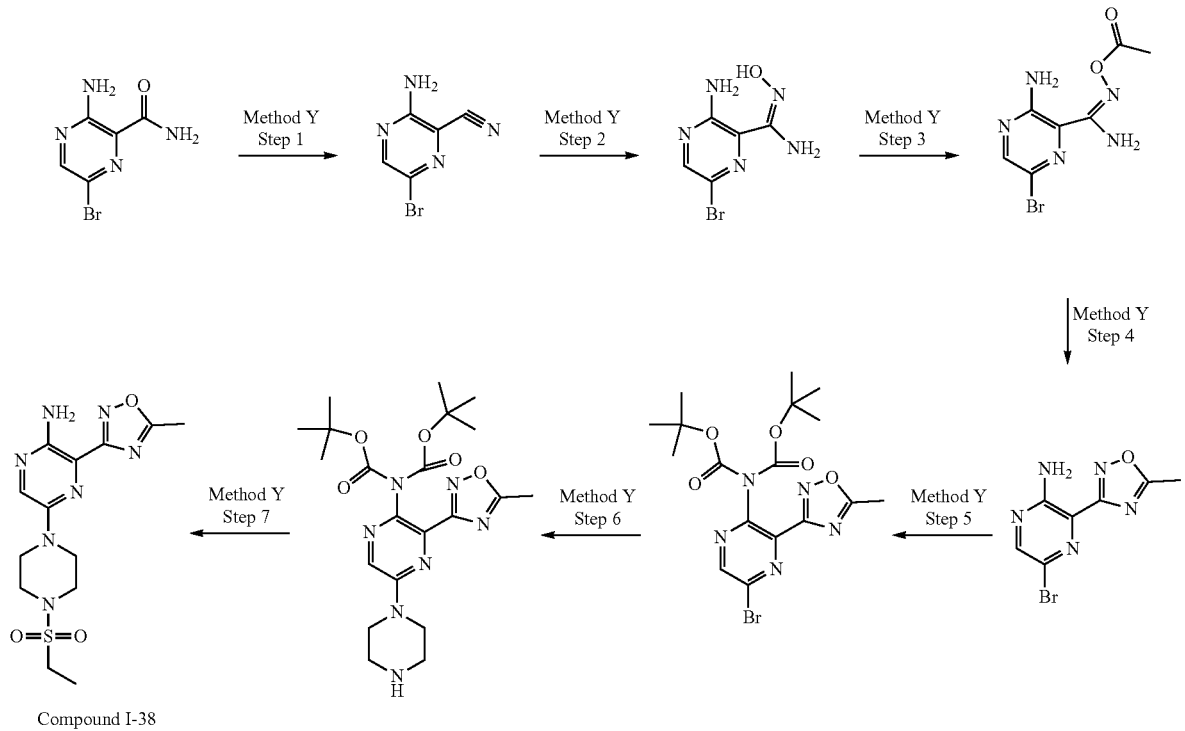

Compound I-38 was prepared using Method Y, Steps 1-7.

Method Y: Step 1:
3-amino-6-bromopyrazine-2-carbonitrile 3-amino-6-bromo-pyrazine-2-carboxamide (500 mg, 2.304 mmol) was dissolved in pyridine (5 mL) and treated with POCl$_3$ (666 µL, 7.145 mmol) dropwise at 0° C. After the addition was complete the reaction was allowed to warm to ambient temperature and stirred for 1.5 hours. The solvent was removed in vacuo and the reaction carefully treated with NaHCO$_3$ to basify. The mixture was diluted with EtOAc and the layers separated. The aqueous layer was further extracted with EtOAc (1×) and the combined organics washed with brine (1×), 0.1 M HCl (1×) and water (1×), dried (MgSO$_4$), filtered and concentrated to furnish the product as a brown solid (197 mg, 43% Yield). 1H NMR (DMSO) d 7.62 (2H, br s), 8.45 (1H, s) ppm Method Y: Step 3: (E)-3-amino-6-bromo-N-(ethanoyloxy)pyrazine-2-carboximidamide A suspension of 3-amino-6-bromo-N'-hydroxypyrazine-2-carboximidamide (5.2697 g, 22.71 mmol) in DCM (68.46 mL) and triethylamine (2.528 g, 3.482 mL, 24.98 mmol) was treated with acetyl chloride (1.961 g, 1.776 mL, 24.98 mmol) and allowed to stir at ambient temperature for 15 minutes. The solvent and volatile reagents were removed in vacuo and the residue triturated from MeOH/ether. The resultant precipitate was isolated by filtration to furnish the product as a brown solid (8.40 g, quantitative yield). 1H NMR (400.0 MHz, DMSO) d 2.18 (3H, s), 6.90 (2H, br s), 7.78 (2H, br s), 8.29 (1H, s) ppm; MS (ES$^+$) 275.78

Method Y: Step 4: 5-bromo-3-(5-methyl-1,2,4-oxadiazol-3-yl)pyrazin-2-amine

A mixture of (E)-3-amino-6-bromo-N-(ethanoyloxy)pyrazine-2-carboximidamide (8.405 g, 22.71 mmol) and AcOH (30 mL) was heated to 70° C. for 2 hours. The reaction mixture was allowed to cool, diluted with water and then neutralised with solid NaHCO$_3$. The resultant dark coloured precipitate was filtered off (3.83 g, 66% Yield). 1H NMR (400.0 MHz, DMSO) d 2.68 (s, 3H), 7.31 (br s, 2H) and 8.34 (s, 1H) ppm; MS (ES$^+$) 258.80

Method Y: Step 5: Tert-butyl N-[5-bromo-3-(5-methyl-1,2,4-oxadiazol-3-yl)pyrazin-2-yl]-N-tert-butoxycarbonyl-carbamate BOC anhydride (1.355 g, 1.426 mL, 6.210 mmol) and DMAP (25.29 mg, 0.2070 mmol) were added to a solution of 5-bromo-3-(5-methyl-1,2,4-oxadiazol-3-yl)pyrazin-2-amine (530 mg, 2.070 mmol) in DCM (7.918 mL) and the reaction mixture allowed to stir overnight at ambient temperature. The mixture was diluted with DCM and washed with water (1×), 1N HCl (1×), saturated NaHCO$_3$ (1×), dried over MgSO$_4$ and concentrated in vacuo. The resultant residue was purified on silica gel by flash column chromatography (0-30% EtOAc/Petrol) to afford the product as a beige solid (686 mg, 73% Yield). 1H NMR (400.0 MHz, CDCl$_3$) d 1.37 (18H, s), 2.73 (3H, s), 8.74 (1H, s) ppm

Method Y: Step 6: Tert-butyl N-[3-(5-methyl-1,2,4-oxadiazol-3-yl)-5-piperazin-1-yl-pyrazin-2-yl]-N-tert-butoxycarbonyl-carbamate A mixture of tert-butyl N-[5-bromo-3-(5-methyl-1,2,4-oxadiazol-3-yl)pyrazin-2-yl]-N-tert-butoxycarbonyl-carbamate (200 mg, 0.4383 mmol) in DMF (1.562 mL) was treated with piperazine (377.5 mg, 4.383 mmol) and the reaction mixture heated at 100° C. for 30 minutes. The reaction was allowed to cool to RT and diluted with EtOAc/Water and the layers separated. The organic layer was washed with water (3×), dried (MgSO$_4$), filtered and concentrated in vacuo. The material was used crude in the next step (150 mg, 67% Yield). 1H NMR (400.0 MHz, CDCl$_3$) d 1.37 (18H, s), 2.73 (3H, s), 3.14 (4H, m) ppm; MS (ES$^+$) 462.14

Method Y: Step 7: 5-(4-(ethylsulfonyl)piperazin-1-yl)-3-(5-methyl-1,2,4-oxadiazol-3-yl)pyrazin-2-amine Ethanesulfonyl chloride (41.38 mg, 30.49 μL, 0.3218 mmol) was added to a solution of tert-butyl N-tert-butoxycarbonyl-N-[3-(5-methyl-1,2,4-oxadiazol-3-yl)-5-piperazin-1-yl-pyrazin-2-yl]carbamate (150 mg, 0.2925 mmol) and triethylamine (59.20 mg, 81.54 μL, 0.5850 mmol) in dichloromethane (5.818 mL) at 0° C. and the resulting solution stirred at ambient temperature for 1.5 hours. The reaction was treated with HCl in dioxane (365.8 μL of 4 M, 1.463 mmol) and allowed to stir at ambient temperature overnight. The reaction was concentrated in vacuo and the resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected and freeze-dried to give the title compound (19.8 mg, 12% Yield).

1H NMR (DMSO) d 1.23 (3H, t), 2.70 (3H, s), 3.08-3.13 (2H, q), 3.31 (4H, m), 3.48 (4H, m), 6.50 (2H, br s), 8.17 (1H, s) ppm; MS (ES$^+$) 353.99

Example 26

3-(benzo[b]thiophen-2-yl)-5-(4-(ethylsulfonyl)piperazin-1-yl)pyrazin-2-amine (Compound I-59)

SCHEME XXVI

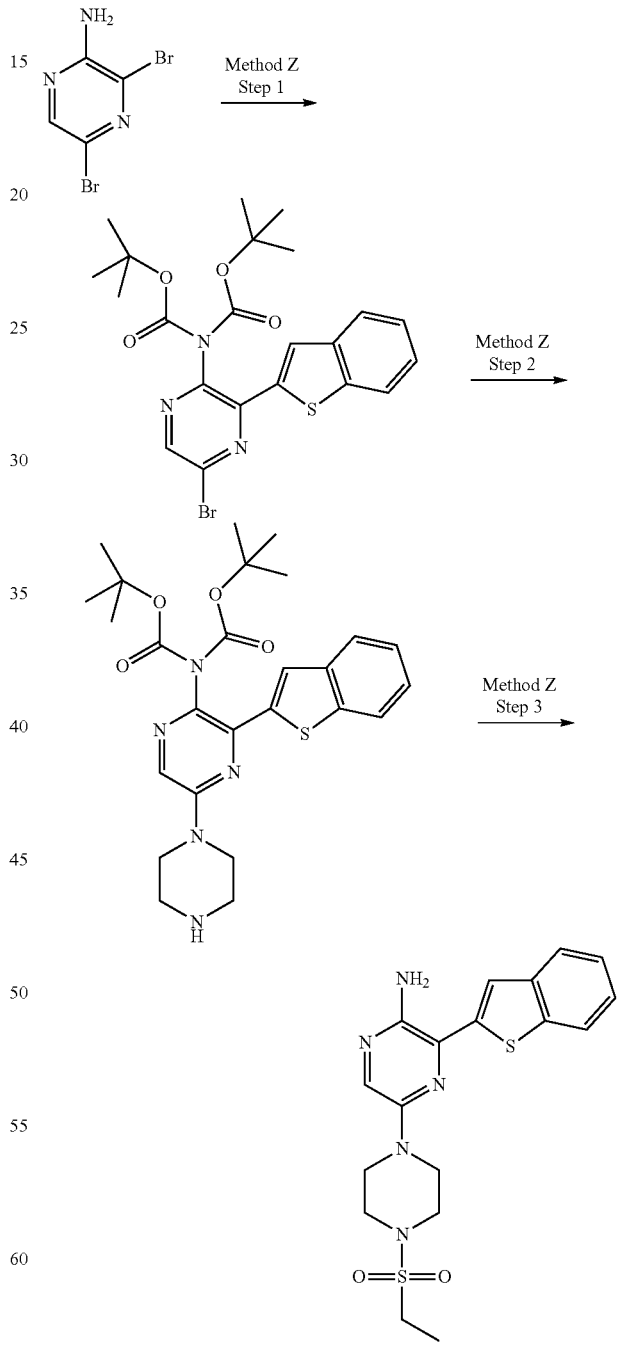

Compound I-59

Compound I-59 was prepared using Method Z, Steps 1-3.

Method Z: Step 1: Tert-butyl N-[3-(benzothiophen-2-yl)-5-bromo-pyrazin-2-yl]-N-tert-butoxycarbonyl-carbamate A mixture of 3,5-dibromopyrazin-2-amine (200 mg, 0.7908 mmol), benzothiophen-2-ylboronic acid (140.8 mg, 0.7908 mmol), NaHCO$_3$ (199.3 mg, 2.372 mmol) and palladium; triphenylphosphane (45.69 mg, 0.03954 mmol) in dimethoxyethane (2.000 mL) and water (1.000 mL) was heated at 120° C. in the microwave for 10 minutes. The reaction was diluted with EtOAc/water and the layers separated. The aqueous layer was extracted further with EtOAc (2×), dried (MgSO$_4$) and concentrated in vacuo. The residue was taken up in DCM (5.0 mL), treated with BOC anhydride (517.7 mg, 544.9 µL, 2.372 mmol) and DMAP (9.661 mg, 0.07908 mmol) and allowed to stir overnight at ambient temperature. The reaction was concentrated in vacuo and the resultant residue was purified on silica gel by flash column chromatography (0-10% EtOAc/Petrol) to afford the product as a bright yellow solid (302 mg, 75% Yield). 1H NMR (DMSO) d 1.33 (18H, s), 7.42 (2H, m), 7.89 (2H, m), 8.06 (1H, s), 8.49 (1H, s) ppm; MS (ES$^+$) 507.79

Method Z: Step 2: Tert-butyl N-[3-(benzothiophen-2-yl)-5-piperazin-1-yl-pyrazin-2-yl]-N-tert-butoxycarbonyl-carbamate Tert-butyl N-[3-(benzothiophen-2-yl)-5-bromo-pyrazin-2-yl]-N-tert-butoxycarbonyl-carbamate (100 mg, 0.1975 mmol) was dissolved in DMF (781.2 µL) and treated with piperazine (170.1 mg, 1.975 mmol) and the reaction mixture heated at 100° C. for 30 minutes. The reaction was allowed to cool to ambient temperature and diluted with EtOAc/water and the layers separated. The organic layer was washed with water (3×), dried (MgSO$_4$) and concentrated in vacuo. The material was used crude in the next step (92 mg, 91% Yield). 1H NMR (DMSO) d 1.23 (18H, s), 2.98 (4H, m), 3.59 (2H, m), 3.63 (2H, m), 7.29 (2H, m), 7.74 (3H, m), 7.89 (1H, s) ppm; MS (ES$^+$) 511.98

Method Z: Step 3: 3-(benzo[b]thiophen-2-yl)-5-(4-(ethylsulfonyl)piperazin-1-yl)pyrazin-2-amine Ethanesulfonyl chloride (25.43 mg, 18.74 µL, 0.1978 mmol) was added to a solution of tert-butyl N-[3-(benzothiophen-2-yl)-5-piperazin-1-yl-pyrazin-2-yl]-N-tert-butoxycarbonyl-carbamate (92 mg, 0.1798 mmol) and triethylamine (36.39 mg, 50.12 µL, 0.3596 mmol) in dichloromethane (3.965 mL) at 0° C. and the resulting solution stirred at room temperature for 1.5 hours. The reaction was then treated with HCl in dioxane (224.8 µL of 4 M, 0.8990 mmol) and allowed to stir at ambient temperature overnight. The mixture was concentrated in vacuo and the resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected, passed through a sodium bicarbonate cartridge and freeze-dried to give the title compound as a yellow solid (14.4 mg, 20% Yield). 1H NMR (DMSO) d 1.24 (3H, t), 2.51 (2H, q), 3.30 masked signal, 3.52 (4H, m), 5.91 (2H, br s), 7.36-7.40 (2H, m), 7.84-7.86 (1H, m), 7.92 (1H, s), 7.95 (1H, m), 8.06 (1H, s) ppm; MS (ES$^+$) 404.02

Example 27

5-(4-(ethylsulfonyl)piperazin-1-yl)-3-(1H-indol-2-yl)pyrazin-2-amine (Compound I-61)

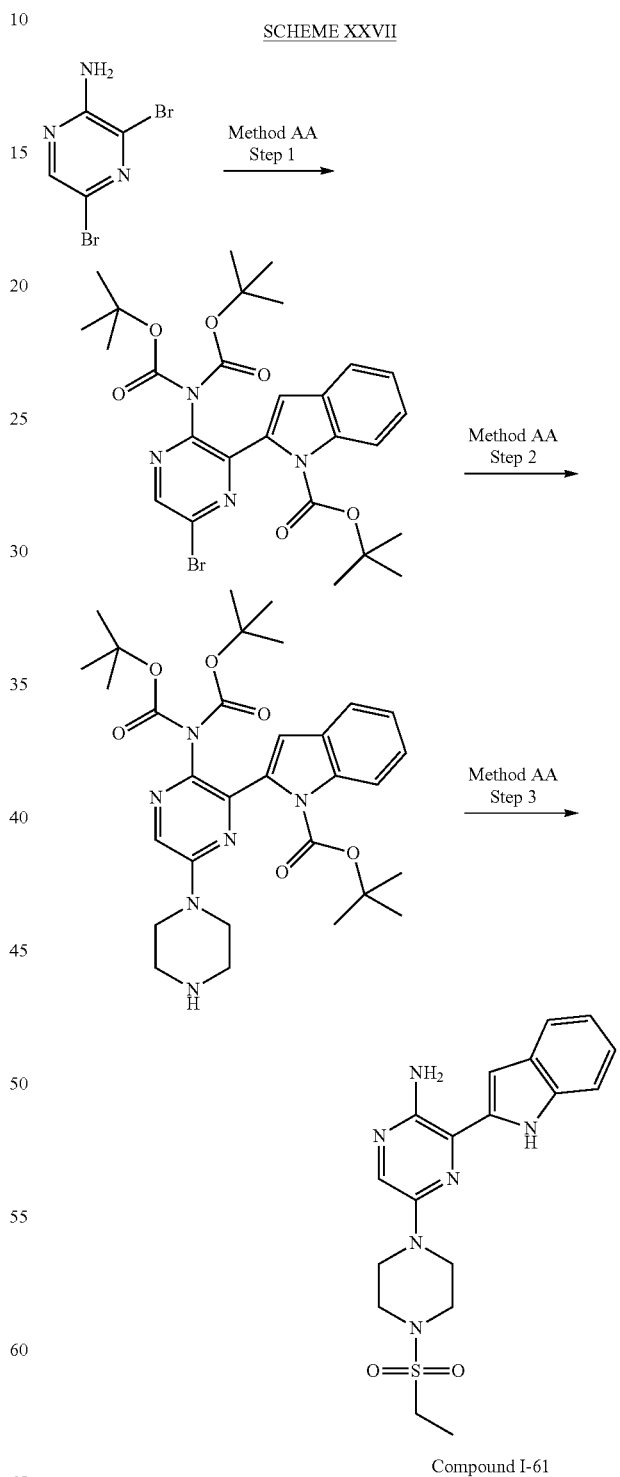

SCHEME XXVII

Compound I-61

Compound I-61 was prepared using Method AA, Steps 1-3.

Method AA: Step 1: Tert-butyl 2-(3-(bis(tert-butoxycarbonyl)amino)-6-bromopyrazin-2-yl)-1H-indole-1-carboxylate A mixture of 3,5-dibromopyrazin-2-amine (200 mg, 0.7908 mmol), tert-butyl 2-(4,4,5,5-tetramethyl-1,3,2-dioxaborolan-2-yl)indole-1-carboxylate (271.4 mg, 0.7908 mmol), NaHCO$_3$ (199.3 mg, 2.372 mmol) and palladium; triphenylphosphane (45.69 mg, 0.03954 mmol) in dimethoxyethane (2.000 mL) and water (1.000 mL) was heated at 120° C. in the microwave for 10 minutes. The reaction was diluted with EtOAc/water and the layers separated. The aqueous layer was extracted further with EtOAc (2×), dried (MgSO$_4$) and concentrated in vacuo. The residue was taken up in DCM (5 mL), treated with BOC anhydride (517.7 mg, 544.9 µL, 2.372 mmol) and DMAP (9.661 mg, 0.07908 mmol) and allowed to stir overnight at ambient temperature. The reaction was concentrated in vacuo and the resultant residue was purified on silica gel by flash column chromatography (0-10% EtOAc/Petrol) to afford the product as a bright yellow solid (254 mg, 55% Yield). 1H NMR (DMSO) d 1.33 (18H, s), 1.53 (9H, s), 6.90 (1H, s), 7.26 (1H, m), 7.38 (1H, m), 7.58 (1H, m), 8.21 (1H, m) 8.56 (1H, s); MS (ES$^+$) 590.89

Method AA: Step 2: Tert-butyl 2-(3-(bis(tert-butoxycarbonyl)amino)-6-(piperazin-1-yl)pyrazin-2-yl)-1H-indole-1-carboxylate A mixture of tert-butyl 2-[3-[bis(tert-butoxycarbonyl)amino]-6-bromo-pyrazin-2-yl]indole-1-carboxylate (100 mg, 0.1696 mmol) and piperazine (146.1 mg, 1.696 mmol) in DMF (2 mL) was heated at 100° C. for 30 minutes and then allowed to cool to ambient temperature. The reaction was diluted with EtOAc/water and the organic layer washed further with water (2×), dried (MgSO$_4$) and concentrated in vacuo. The material was used crude in the next step (quantitative yield assumed). MS (ES$^+$) 595.09

Method AA: Step 3: 5-(4-(ethylsulfonyl)piperazin-1-yl)-3-(1H-indol-2-yl)pyrazin-2-amine Ethanesulfonyl chloride (43.25 mg, 31.87 µL, 0.3364 mmol) was added to a solution of tert-butyl 2-[3-(bis(tert-butoxycarbonyl)amino)-6-piperazin-1-yl-pyrazin-2-yl]indole-1-carboxylate (100 mg, 0.1682 mmol) and triethylamine (18.72 mg, 25.79 µL, 0.1850 mmol) in DCM (2 mL) at 0° C. and the reaction mixture allowed to stir at ambient temperature for 30 minutes. The reaction was then treated with HCl in dioxane (210.2 µL of 4 M, 0.8410 mmol) and allowed to stir at ambient temperature overnight. The mixture was concentrated in vacuo and the resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected, passed through a sodium bicarbonate cartridge and freeze-dried to give the title compound as a yellow solid (5.5 mg, 8% Yield). 1H NMR (DMSO) d 1.25 (3H, t), 3.12 (2H, q), 3.30 masked signal, 3.59 (4H, m), 5.66 (2H, br s), 7.00-7.04 (1H, m), 7.14-7.18 (2H, m), 7.51 (1H, m), 7.58 (1H, m), 7.81 (1H, s), 11.25 (1H, br s) ppm; MS (ES$^+$) 386.87

Example 28

5-(4-(ethylsulfonyl)piperazin-1-yl)-3-(3-phenylisoxazol-5-yl)pyrazin-2-amine (Compound I-162)

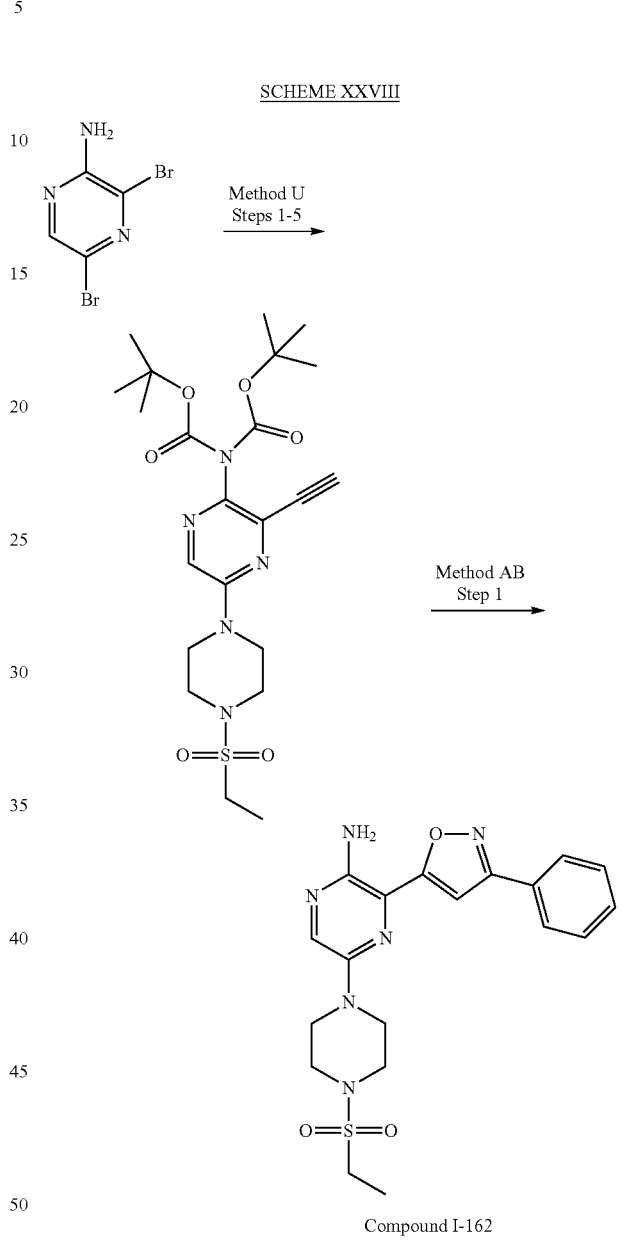

Compound I-162

Compound I-162 was prepared using Method U, Steps 1-5 followed by Method AB, Step 1.

Method AB: Step 1: 5-(4-(ethylsulfonyl)piperazin-1-yl)-3-(3-phenylisoxazol-5-yl)pyrazin-2-amine Triethylamine (10.21 mg, 14.06 µL, 0.1009 mmol) was added to a solution of tert-butyl N-tert-butoxycarbonyl-N-[5-(4-ethylsulfonylpiperazin-1-yl)-3-ethynyl-pyrazin-2-yl]carbamate (50 mg, 0.1009 mmol) and N-hydroxybenzimidoyl chloride (15.70 mg, 0.1009 mmol) in THF (4 mL) and the reaction mixture allowed to stir at ambient temperature for 1 hour. After this time the reaction mixture was heated under reflux for 3 hours and allowed to cool to RT. The reaction was treated with HCl in dioxane (126.1 μL of 4 M, 0.5045 mmol), allowed to stir overnight at ambient temperature, concentrated in vacuo and the resultant residue was purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were collected and freeze-dried to give the title compound as an orange solid (9.9 mg, 18% Yield). 1H NMR (DMSO) d 1.03 (3H, t), 2.90 (2H, q), 3.11 (4H, m), 3.33 (4H, m), 5.88 (2H, br s), 7.34-7.36 (4H, m), 7.77 (2H, m), 7.92 (1H, s) ppm; MS (ES⁺) 414.98

Example 29

3-(1H-benzo[d]imidazol-2-yl)-5-(1-phenyl-1,2,3,6-tetrahydropyridin-4-yl)pyrazin-2-amine (Compound I-159)

SCHEME XXIX

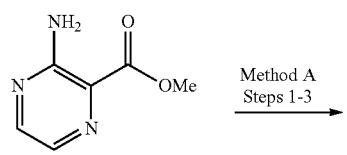

Method A
Steps 1-3

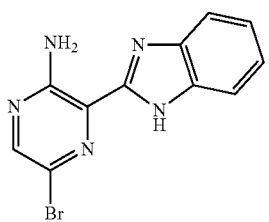

Method AC
Step 1

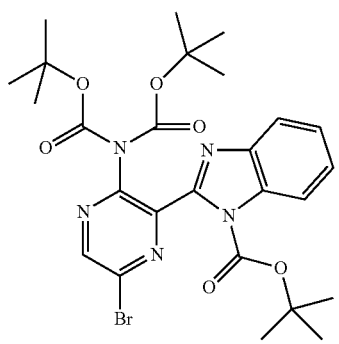

Method AC
Step 2

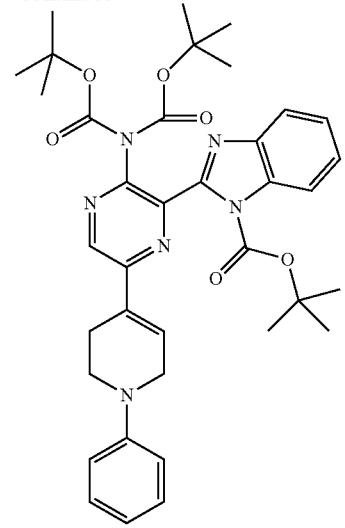

Method AC
Step 3

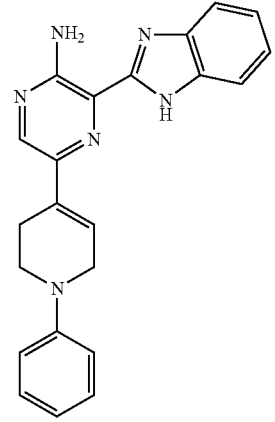

Compound I-159

Compound I-159 was prepared using Method A, Steps 1-3 followed by Method AC, Steps 1-3.

Method AC: Step 1: tert-butyl 2-(3-(bis(tert-butoxycarbonyl)amino)-6-bromopyrazin-2-yl)-1H-benzo[d]imidazole-1-carboxylate 3-(1H-benzimidazol-2-yl)-5-bromo-pyrazin-2-amine (8.0443 g, 27.73 mmol) was dissolved in acetonitrile (100.6 mL) and THF (100.6 mL) and treated with DMAP (338.8 mg, 2.773 mmol) followed by portionwise addition of BOC anhydride (27.24 g, 28.67 mL, 124.8 mmol). The reaction was allowed to stir at ambient temperature overnight. The mixture was concentrated in vacuo, diluted with DCM and washed with NaHCO₃ (3×). The aqueous layer was further extracted with DCM (2×) and the combined organics washed with brine, dried (MgSO₄), filtered and concentrated in vacuo. The resultant residue was purified by column chromatography (ISCO Companion™, 330 g column, 0-30% EtOAc/Petrol) to afford the title compound which was freeze-dried to give a yellow solid (13.05 g, 80% Yield). 1H NMR (400.0 MHz, DMSO) d 1.26 (s, 18H), 1.45 (s, 9H), 7.45-7.56 (m, 2H), 7.79-7.81 (m, 1H), 8.02-8.04 (m, 1H) and 9.08 (s, 1H) ppm; MS (ES⁺) 592.09

Method AC: Step 2: Tert-butyl 2-(3-(bis(tert-butoxy-carbonyl)amino)-6-(1-phenyl-1,2,3,6-tetrahydropyridin-4-yl)pyrazin-2-yl)-1H-benzo[d]imidazole-1-carboxylate A mixture of tert-butyl 2-[3-[bis(tert-butoxycarbonyl)amino]-6-bromo-pyrazin-2-yl]benzimidazole-1-carboxylate (100 mg, 0.1694 mmol), 1-phenyl-4-(4,4,5,5-tetramethyl-1,3,2-dioxaborolan-2-yl)-3,6-dihydro-2H-pyridine (58 mg, 0.2034 mmol), 4-ditert-butylphosphanyl-N,N-dimethyl-aniline; dichloropalladium (2 mg, 0.002825 mmol) and K$_2$CO$_3$ (28 mg, 0.2026 mmol) in toluene (1000 μL) and water (120 μL) were heated to 100° C. overnight. The reaction was diluted with DCM, washed with water followed by 1M NaOH, dried (MgSO$_4$) and concentrated in vacuo. The material was used crude in the next step (quantitative yield assumed).

MS (ES$^+$) 669.02

Method AC: Step 3: 3-(1H-benzo[d]imidazol-2-yl)-5-(1-phenyl-1,2,3,6-tetrahydropyridin-4-yl)pyrazin-2-amine A solution of tert-butyl 2-(3-(bis(tert-butoxycarbonyl)amino)-6-(1-phenyl-1,2,3,6-tetrahydropyridin-4-yl)pyrazin-2-yl)-1H-benzo[d]imidazole-1-carboxylate (100 mg, 0.1495 mmol) in DCM (1 mL) was treated with TFA (1 mL, 12.98 mmol) and allowed to stir at ambient temperature for 40 minutes. The reaction was concentrated in vacuo and the resultant residue was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected, passed through a sodium bicarbonate cartridge and freeze-dried to give the title compound as a pale brown solid (8.0 mg, 14% Yield). 1H NMR (400.0 MHz, DMSO) d 2.84 (2H, m), 3.53 (2H, m), 3.94 (2H, m), 6.76-6.90 (3H, m), 7.20-7.69 (6H, m), 7.70-9.39 (4H, m), 12.88 (1H, m) ppm; MS (ES$^+$) 369.02

Example 30

3-(1H-benzo[d]imidazol-2-yl)-5-(1-(thiazol-2-yl)-1,2,3,6-tetrahydropyridin-4-yl)pyrazin-2-amine (Compound I-164)

SCHEME XXX

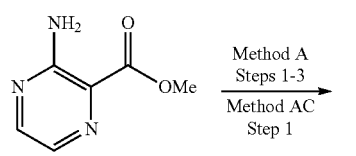

Method A Steps 1-3
Method AC Step 1

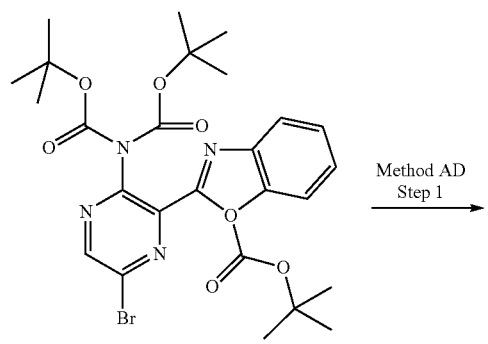

Method AD Step 1

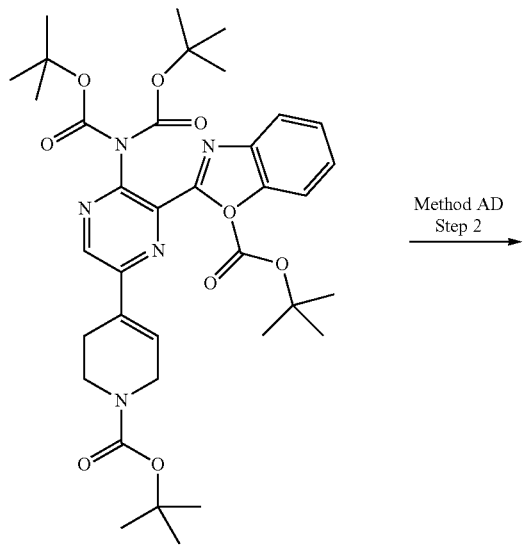

Method AD Step 2

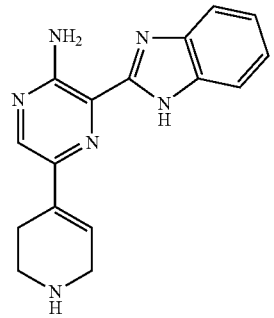

Method AD Step 3

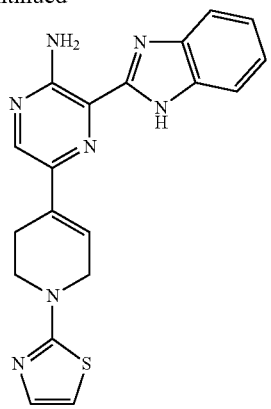

Compound I-164

Compound I-164 was prepared using Method A, Steps 1-3 followed by Method AC, Step 1 followed by Method AD, Steps 1-3.

Method AD: Step 1: Tert-butyl 2-(3-(bis(tert-butoxycarbonyl)amino)-6-(1-(tert-butoxycarbonyl)-1,2,3,6-tetrahydropyridin-4-yl)pyrazin-2-yl)-1H-benzo[d]imidazole-1-carboxylate A mixture of tert-butyl 2-[3-[bis(tert-butoxycarbonyl)amino]-6-bromo-pyrazin-2-yl]benzimidazole-1-carboxylate (1.7068 g, 1.734 mmol), tert-butyl 4-(4,4,5,5-tetramethyl-1,3,2-dioxaborolan-2-yl)-3,6-dihydro-2H-pyridine-1-carboxylate (643.5 mg, 2.081 mmol), 4-ditert-butylphosphanyl-N,N-dimethyl-aniline; dichloropalladium (12.28 mg, 0.01734 mmol) and $K_2CO_3$ (479.3 mg, 3.468 mmol) in toluene (9.216 mL) and water (1.024 mL) was heated to 100° C. for 16 hours. The reaction mixture was allowed to cool to RT and partitioned between DCM and water. The organic layer was washed with 1M NaOH solution, dried ($Na_2SO_4$), filtered and concentrated in vacuo to give a brown oil. This was purified by column chromatography (ISCO Companion™, 40 g column, 0-20% EtOAc/Petrol) to afford the title compound as a yellow oil (1.028 g, 60% Yield). MS ($ES^+$) 693.38

Method AD: Step 2: 3-(1H-benzo[d]imidazol-2-yl)-5-(1,2,3,6-tetrahydropyridin-4-yl)pyrazin-2-amine A solution of tert-butyl 2-(3-(bis(tert-butoxycarbonyl)amino)-6-(1-(tert-butoxycarbonyl)-1,2,3,6-tetrahydropyridin-4-yl)pyrazin-2-yl)-1H-benzo[d]imidazole-1-carboxylate (1.7248 g, 2.490 mmol) in DCM (17.25 mL) was treated with TFA (5 mL, 64.90 mmol) and left to stir at ambient temperature for 4 hours. The reaction mixture was concentrated in vacuo and triturated from MeOH/Toluene and the resultant orange solid was filtered off (622 mg, 48% Yield). 1H NMR (400.0 MHz, DMSO) d 2.90 (2H, m), 3.41 (2H, m), 3.96 (2H, m), 6.80 (1H, m), 7.09-7.30 (4H, m), 7.82 (2H, br s), 8.52 (1H, s) ppm; MS ($ES^+$) 293.03

Method AD: Step 3: 3-(1H-benzo[d]imidazol-2-yl)-5-(1-(thiazol-2-yl)-1,2,3,6-tetrahydropyridin-4-yl)pyrazin-2-amine A solution of 3-(1H-benzo[d]imidazol-2-yl)-5-(1,2,3,6-tetrahydropyridin-4-yl)pyrazin-2-amine (100 mg, 0.1922 mmol) in DMSO (2.000 mL) was treated with triethylamine (58.35 mg, 80.37 μL, 0.5766 mmol) and 2-chlorothiazole (27.57 mg, 0.2306 mmol) and heated in the microwave for 40 minutes at 160° C. The reaction mixture was filtered and purified by reverse phase preparative HPLC [Waters Sunfire C18, 10 uM, 100A column, gradient 10%-95% B (solvent A: 0.05% TFA in water, solvent B: $CH_3CN$) over 16 minutes at 25 mL/min]. The fractions were collected, passed through a sodium bicarbonate cartridge and freeze-dried to give the title compound (20.6 mg, 15% Yield). 1H NMR (400.0 MHz, DMSO) d 2.89 (s, 2H), 3.80 (t, J=5.7 Hz, 2H), 4.21 (d, J=2.5 Hz, 2H), 6.86 (s, 1H), 6.94-6.96 (m, 1H), 7.28-7.31 (m, 3H), 7.69 (s, 2H) and 8.41 (s, 1H) ppm; MS ($ES^+$) 376.0

Example 31

5-(1-(ethylsulfonyl)-1,2,3,6-tetrahydropyridin-4-yl)-3-(5-methyl-1H-benzo[d]imidazol-2-yl)pyrazin-2-amine (Compound I-157)

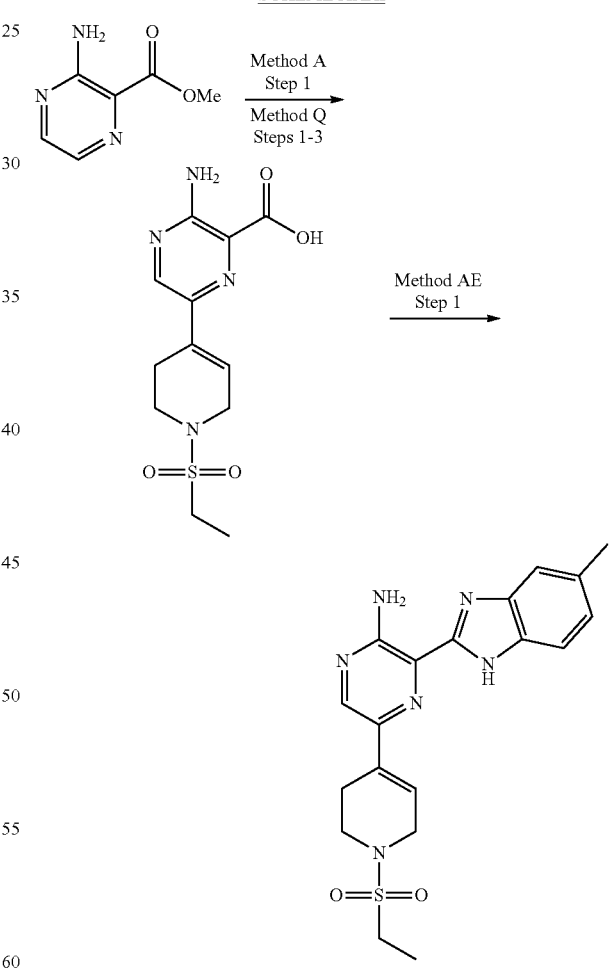

SCHEME XXXI

Compound I-157

Compound I-157 was prepared using Method A, Step 1 followed by Method Q, Steps 1-3 followed by Method AE, Step 1.

237

Method AE: Step 1: 5-(1-(ethylsulfonyl)-1,2,3,6-tetrahydropyridin-4-yl)-3-(5-methyl-1H-benzo[d]imidazol-2-yl)pyrazin-2-amine

A mixture of 3-amino-6-(1-ethylsulfonyl-3,6-dihydro-2H-pyridin-4-yl)pyrazine-2-carboxylic acid (100 mg, 0.320 mmol), 4-methylbenzene-1,2-diamine (39.12 mg, 0.320 mmol), diethoxyphosphorylformonitrile (47.83 uL, 0.320 mmol) and triethylamine (44.63 uL, 0.320 mmol) in DME (1 mL) were heated in a microwave at 170° C. for 90 min. After this time the reaction mixture was filtered and purified by reverse phase preparative HPLC [Waters Sunfire C18, 10 uM, 100A column, gradient 10%-95% B (solvent A: 0.05% TFA in water, solvent B: $CH_3CN$) over 16 minutes at 25 mL/min]. The fractions were collected, and freeze-dried to give the title compound (46.8 mg, 21% Yield). 1H NMR (400.0 MHz, DMSO) d 8.34 (s, 1H), 7.57 (d, J=8.1 Hz, 1H), 7.46 (s, 1H), 7.11 (d, J=8.0 Hz, 1H), 6.78 (s, 1H), 4.00 (d, J=2.8 Hz, 2H), 3.50 (t, J=5.7 Hz, 2H), 3.16 (q, J=7.4 Hz, 2H), 2.78 (s, 2H), 2.46 (s, 3H) and 1.25 (t, J=7.4 Hz, 3H) ppm; MS ($ES^+$) 399
The following compounds were all prepared using the same method or a method similar to the one described for Compound I-157 in Example 31 above.

Compound I-152 3-(6,7-dimethyl-1H-benzo[d]imidazol-2-yl)-5-(1-(ethylsulfonyl)-1,2,3,6-tetrahydropyridin-4-yl)pyrazin-2-amine 1H NMR (400.0 MHz, DMSO) d 12.68 (s, 1H), 8.33 (s, 1H), 7.32 (d, J=7.1 Hz, 1H), 7.11 (d, J=8.2 Hz, 1H), 6.79 (s, 1H), 4.00 (d, J=2.7 Hz, 2H), 3.50 (t, J=5.7 Hz, 2H), 3.16 (q, J=7.4 Hz, 2H), 2.79 (s, 2H), 2.54 (s, 3H), 2.36 (s, 3H) and 1.25 (t, J=7.3 Hz, 3H) ppm; MS ($ES^+$) 413

Compound I-153 3-(6,7-difluoro-1H-benzo[d]imidazol-2-yl)-5-(1-(ethylsulfonyl)-1,2,3,6-tetrahydropyridin-4-yl)pyrazin-2-amine); MS ($ES^+$) 421

Compound I-154 3-(5,6-dimethyl-1H-benzo[d]imidazol-2-yl)-5-(1-(ethylsulfonyl)-1,2,3,6-tetrahydropyridin-4-yl)pyrazin-2-amine); MS ($ES^+$) 413

Compound I-155 5-(1-(ethylsulfonyl)-1,2,3,6-tetrahydropyridin-4-yl)-3-(4-fluoro-1H-benzo[d]imidazol-2-yl)pyrazin-2-amine); MS ($ES^+$) 403

Compound I-156 3-(5-tert-butyl-1H-benzo[d]imidazol-2-yl)-5-(1-(ethylsulfonyl)-1,2,3,6-tetrahydropyridin-4-yl)pyrazin-2-amine); MS ($ES^+$) 441
For compounds I-191 and I-192 below, please see Tables 7 and 8 for analytical data.

Compound I-191 4-(5-amino-6-(1H-benzo[d]imidazol-2-yl)pyrazin-2-yl)-5,6-dihydropyridin-1(2H)-yl)(pyridin-3-yl)methanone Compound I-192 1-(4-(5-amino-6-(5-phenyl-1,3,4-oxadiazol-2-yl)pyrazin-2-yl)-5,6-dihydropyridin-1(2H)-yl)-2-methylpropan-1-one

Example 32

1-[5-amino-6-(5-phenyl-1,3,4-oxadiazol-2-yl)pyrazin-2-yl]-3,6-dihydro-2H-pyridine-4-carboxylic acid (Compound I-288)

SCHEME XXXII

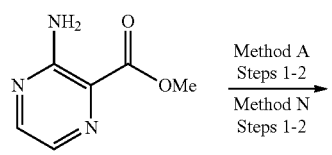

Method A
Steps 1-2
Method N
Steps 1-2

238

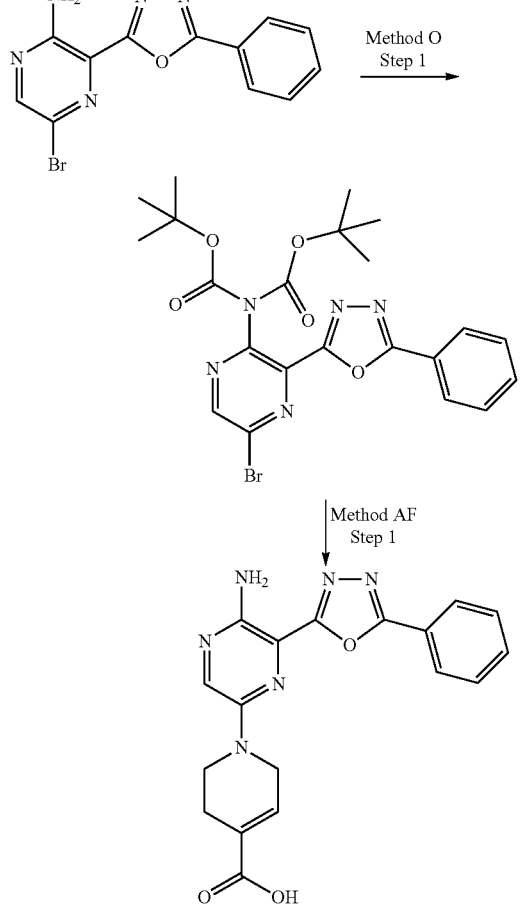

Compound I-288

Compound I-288 was prepared using Method A, Steps 1-2, followed by Method N Steps 1-2 followed by Method O Step 1 and Method AF Step 1.

Method AF: Step 1: 1-[5-amino-6-(5-phenyl-1,3,4-oxadiazol-2-yl)pyrazin-2-yl]-3,6-dihydro-2H-pyridine-4-carboxylic acid

A mixture of 1,2,3,6-tetrahydropyridine-4-carboxylic acid (36.18 mg, 0.2846 mmol) and tert-butyl N-tert butoxycarbonyl-5-bromo-3-(5-phenyl-1,3,4-oxadiazol-2-yl)pyrazin-2-ylcarbamate (80 mg, 0.1423 mmol) and $Et_3N$ (43.20 mg, 59.50 μL, 0.4269 mmol) in DMF (800.3 μL) were heated at 100° C. in the microwave for 20 mins. The reaction mixture was diluted with ethylacetate, washed with water and concentrated to an oil. The oil was dissolved in $CH_2Cl_2$ (10 mL) and TFA (162.3 mg, 109.7 μL, 1.423 mmol) added and the resulting solution stirred at room temperature for 1 hr. The reaction mixture was concentrated in vacuo to leave an oil which was purified by reverse phase preparative HPLC [Waters Sunfire C18, 10 uM, 100A column, gradient 10%-95% B (solvent A: 0.05% TFA in water, solvent B: $CH_3CN$) over 16 minutes at 25 mL/min]. The fractions were collected, and freeze-dried to give the product (15 mg, 20% yield) 1H NMR (400 MHz, MeOD) d 1.70-1.75 (m, 2H), 2.85 (t, 2H), 3.35-3.4 (m, 2H), 6.25 (br s, 1H), 6.65 (d, 1H), 6.7-6.8 (m, 4H) and 7.25-7.4 (m, 4H); MS ($ES^+$) 365.1

The following compounds were all prepared using the method described for Compound I-288 in Example 32 above.

Compound I-290 3-(5-phenyl-1,3,4-oxadiazol-2-yl)-5-(4-thiazol-2-yl-3,6-dihydro-2H-pyridin-1-yl)pyrazin-2-amine 1H NMR (400 MHz, MeOD) d 1.95-2.0 (m, 2H), 3.0 (t, 2H), 3.35-3.4 (m, 2H), 5.95-6.0 (m, 1H), 6.65 (d, 1H), 6.7-6.8 (m, 4H) and 7.25-7.35 (m, 4H) ppm; MS (ES+) 404.18

Example 33

N-(1-(5-amino-6-(5-phenyl-1,3,4-oxadiazol-2-yl)pyrazin-2-yl)azetidin-3-yl)ethanamide (Compound I-282)

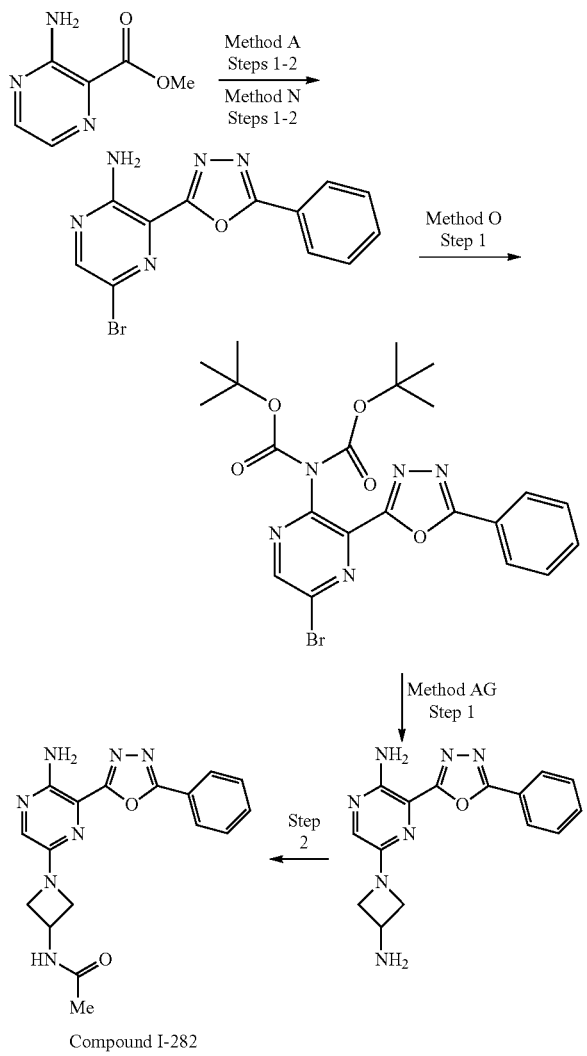

Compound I-282

Compound I-282 was prepared using Method A, Steps 1-2, followed by Method N Steps 1-2 followed by Method O Step 1 and Method AH Steps 1-2.

Method AG: Step 1: 5-(3-aminoazetidin-1-yl)-3-(5-phenyl-1,3,4-oxadiazol-2-yl)pyrazin-2-amine A mixture of tert-butyl N-tert butoxycarbonyl-5-bromo-3-(5-phenyl-1,3,4-oxadiazol-2-yl)pyrazin-2-ylcarbamate (200 mg, 0.3858 mmol) and tert-butyl N-(azetidin-3-yl)carbamate (66.44 mg, 0.3858 mmol) and DIPEA (99.72 mg, 134.4 μL, 0.7716 mmol) in DMF (5 mL) was heated at 90° C. After this time, the reaction mixture was cooled to room temperature and diluted with ethylacetate (5 mL), washed with water (5 mL) and concentrated in vacuo to leave a solid. The solid was dissolved in dichloromethane (10 mL) and trifluoroacetic acid (1.319 g, 891.2 μL, 11.57 mmol) was added and the resulting solution stirred at room temperature for 1 hr. The reaction mixture was concentrated in vacuo to leave an oil. The oil was redissolved in dichloromethane and concentrated in vacuo to leave the product, which was used crude in the next step.

Method AG: Step 2: N-[1-[5-amino-6-(5-phenyl-1,3,4-oxadiazol-2-yl)pyrazin-2-yl]azetidin-3-yl]acetamide Acetyl chloride (12.69 mg, 11.49 μL, 0.1616 mmol) was added to a solution of 5-(3-aminoazetidin-1-yl)-3-(5-phenyl-1,3,4-oxadiazol-2-yl)pyrazin-2-amine (50 mg, 0.1616 mmol) and DIPEA (27.15 mg, 36.59 μL, 0.2101 mmol in CH$_2$Cl$_2$ (5 mL) and the resulting solution stirred at room temperature for 20 mins. After this time, the reaction mixture was washed with saturated aqueous NaHCO$_3$ solution (1×5 mL), dried over MgSO$_4$ and concentrated in vacuo to leave a solid. The product was purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected, and freeze-dried to give the product (12.5 mg, 21% yield); 1H NMR (400 MHz, CDCl$_3$) d 1.98 (s, 3H), 3.4 (q, 1H), 3.7-3.76 (m, 2H), 4.4-4.45 (m, 2H), 4.75-4.85 (m, 1H), 6.2 (s, 2H), 7.5-7.6 (m, 3H), 7.7 (s, 1H) and 8.2-8.3 (m, 2H) ppm; MS (ES+) 352.1

The following compounds were all prepared using a similar method to the one described for Compound I-282 in Example 34 above Compound I-302 N-[1-[5-amino-6-(5-phenyl-1,3,4-oxadiazol-2-yl)pyrazin-2-yl]azetidin-3-yl]ethanesulfonamide 1H NMR (400 MHz, DMSO) d 1.3 (t, 3H), 3.1 (q, 2H), 3.8-3.85 (m, 2H), 4.35-4.42 (m, 3H), 7.0 (m, 2H), 7.7-7.8 (m, 3H), 7.8-7.85 (m, 2H) and 8.05-8.1 (m, 2H); MS (ES+) 402.2

Example 34

5-(2-ethylsulfonyl-1,3,3a,4,6,6a-hexahydropyrrolo[3,4-c]pyrrol-5-yl)-3-(5-phenyl-1,3,4-oxadiazol-2-yl)pyrazin-2-amine (Compound I-305)

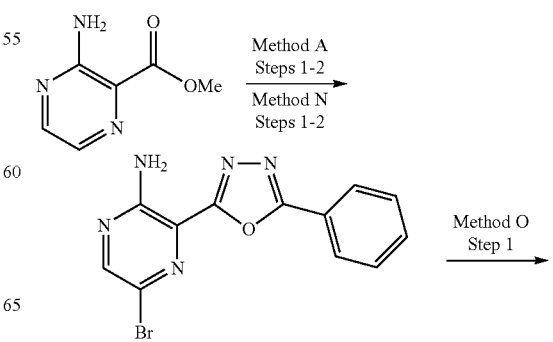

241

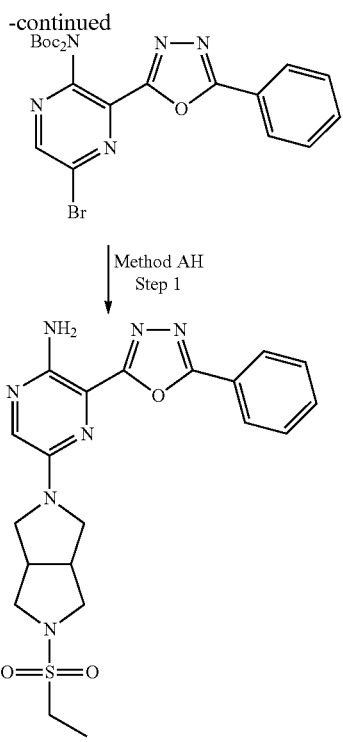

Compound I-305

Compound I-305 was prepared using Method A, Steps 1-2, followed by Method N Steps 1-2 followed by Method O Step 1 and followed by Method AI Step 1.

242

Method AH: Step 1: 5-(2-ethylsulfonyl-1,3,3a,4,6,6a-hexahydropyrrolo[3,4-c]pyrrol-5-yl)-3-(5-phenyl-1,3,4-oxadiazol-2-yl)pyrazin-2-amine 2-ethylsulfonyl-3,3a,4,5,6,6a-hexahydro-1H-pyrrolo[3,4-c]pyrrole (36.34 mg, 0.1779 mmol) and $Et_3N$ (54.01 mg, 74.39 µL, 0.5337 mmol) were added to a solution of tert-butyl N-tert butoxycarbonyl-5-bromo-3-(5-phenyl-1,3,4-oxadiazol-2-yl)pyrazin-2-ylcarbamate (100 mg, 0.1779 mmol) in DMF (2 mL) and the resulting solution heated at 100° C. for 2 h. The reaction mixture was cooled to room temperature and diluted with ethyl acetate (5 mL) and washed successively with water (2×5 mL) followed by brine (1×5 mL). The organic layer was concentrated in vacuo to leave a solid. The solid was dissolved in $CH_2Cl_2$ (10 mL) and trifluoroacetic acid (405.7 mg, 274.1 µL, 3.558 mmol) was added. The reaction mixture was stirred at room temperature for 1 h and the reaction mixture then concentrated in vacuo to an oil. The oil was redissolved in $CH_2Cl_2$ (20 ml) and concentrated in vacuo to leave a solid. The solid was purified by reverse phase preparative HPLC [Waters Sunfire C18, 10 uM, 100A column, gradient 10%-95% B (solvent A: 0.05% TFA in water, solvent B: $CH_3CN$) over 16 minutes at 25 mL/min]. The fractions were collected, and freeze-dried to give the product (34.4 mg, 40% yield); 1H NMR (400 MHz, DMSO) d 1.25 (t, 3H), 3.1-3.2 (m, 4H), 3.25-3.3 (m, 2H), 3.4-3.45 (m, 2H), 3.5-3.7 (m, 4H), 6.75 (s, 2H), 7.6-7.65 (m, 3H) and 8.05-8.1 (m, 2H) ppm; MS ($ES^+$) 442.1

Example 35

5-[4-(2-methylsulfonylethyl)piperazin-1-yl]-3-(5-phenyl-1,34-oxadiazol-2-yl)pyrazin-2-amine (Compound I-296)

SCHEME XXXV

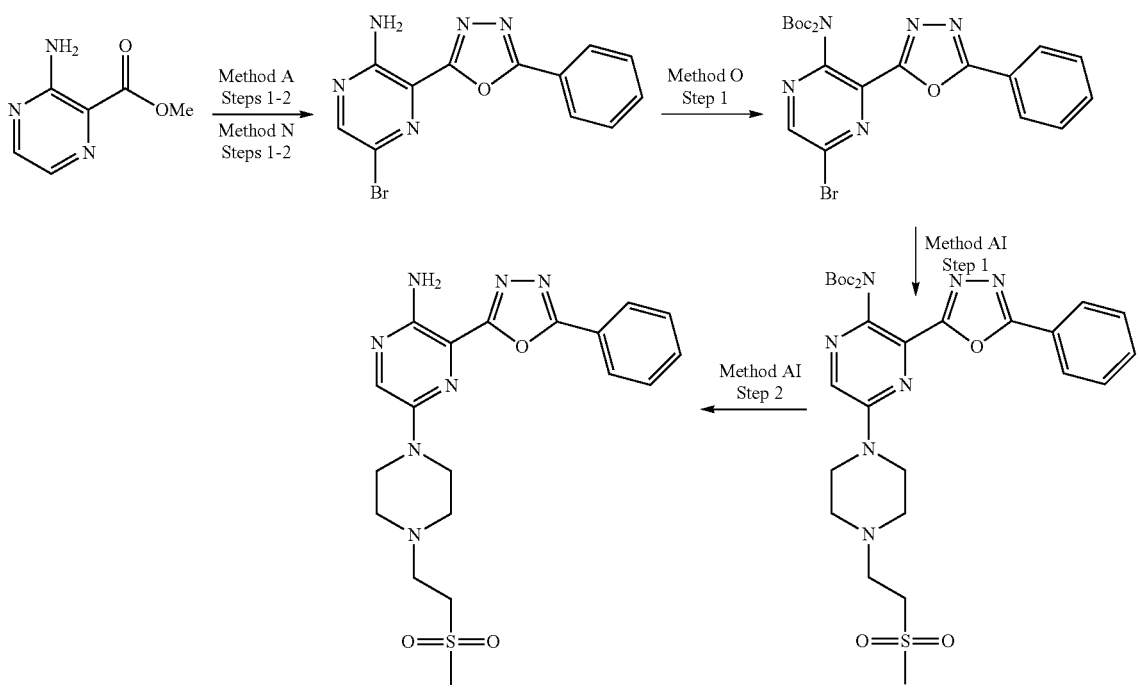

Compound I-296

Compound I-296 was prepared using Method A, Steps 1-2, followed by Method N Steps 1-2 followed by Method O Step 1 and followed by Method AJ Steps 1-2.

Method AI: Step 1: tert-butyl N-tert-butoxylcarbonyl-5-(4-(2-(methylsulfonyl)ethyl)piperazin-1-yl)-3-(5-phenyl-1,3,4-oxadiazol-2-yl)pyrazin-2-ylcarbamate tert-butyl N-tert butoxycarbonyl-5-bromo-3-(5-phenyl-1,3,4-oxadiazol-2-yl)pyrazin-2-ylcarbamate (75 mg, 0.13 mmol) was dissolved in DMF (1 mL) and 1-(2-(methylsulfonyl)ethyl)piperazine (77 mg, 0.40 mmol) was added. The reaction mixture was heated at 100° C. in a sealed tube overnight. The reaction mixture was cooled to room temperature and partitioned between $CH_2Cl_2$ and water and the layers separated using a phase separation cartridge. The organic layer was concentrated in vacuo to give the product (84.01 mg, 0.13 mmol)

Method AI: Step 2: 5-[4-(2-methylsulfonylethyl)piperazin-1-yl]-3-(5-phenyl-1,3,4-oxadiazol-2-yl)pyrazin-2-amine tert-butyl N-tert-butoxylcarbonyl-5-(4-(2-(methylsulfonyl)ethyl)piperazin-1-yl)-3-(5-phenyl-1,3,4-oxadiazol-2-yl)pyrazin-2-ylcarbamate (84.01 mg, 0.13 mmol) was dissolved in $CH_2Cl_2$ (10 mL) and trifluoroacetic acid (2 mL) added and the reaction mixture stirred at room temperature overnight. The reaction mixture was concentrated in vacuo and purified by reverse phase preparative HPLC [Waters Sunfire C18, 10 uM, 100A column, gradient 10%-95% B (solvent A: 0.05% TFA in water, solvent B: $CH_3CN$) over 16 minutes at 25 mL/min]. The product was passed through a bicarbonate cartridge and the cartridge washed with methanol and the filtrate concentrated in vacuo to leave a solid. The solid was taken up in acetonitrile and water and freeze dried to give the product (20.6 mg, 34% yield); 1H NMR (400 MHz, DMSO) d 2.60 (m, 5H), 2.77 (m, 2H), 3.06 (s, 3H), 3.31 (m, 2H), 3.36 masked signal, 3.56 (m, 4H), 6.90 (br s, 2H), 7.64-7.68 (m, 3H), 8.11 (m, 2H) and 8.25 (s, 1H) ppm; MS (ES$^+$) 430.2

The following compounds were all prepared using the method described for Compound I-296 in Example 36 above Compound I-298 3-[4-[5-amino-6-(5-phenyl-1,3,4-oxadiazol-2-yl)pyrazin-2-yl]piperazin-1-yl]propanenitrile 1H NMR (400 MHz, DMSO) d 2.60-2.66 (m, 6H), 2.75 (m, 2H), 3.46 (m, 4H), 6.90 (br s, 2H), 7.64-7.68 (m, 3H), 8.11 (m, 2H) and 8.24 (s, 1H) ppm; MS (ES$^+$) 377.2

Compound I-300 5-(4-benzylpiperazin-1-yl)-3-(5-phenyl-1,3,4-oxadiazol-2-yl)pyrazin-2-amine 1H NMR (400 MHz, DMSO) d 3.31 masked signal, 3.46 (m, 4H) 3.55 (m, 2H), 6.88 (br s, 2H), 7.27 (m, 1H), 7.36 (m, 4H), 7.64-7.68 (m, 3H), 8.11 (m, 2H) and 8.23 (s, 1H) ppm; MS (ES$^+$) 414.2

Compound I-303 2-[4-[5-amino-6-(5-phenyl-1,3,4-oxadiazol-2-yl)pyrazin-2-yl]piperazin-1-yl]-1-morpholinoethanone 1H NMR (400 MHz, DMSO) d 2.59 (m, 4H), 3.24 (s, 2H), 3.46 (m, 6H) 3.56 (m, 6H), 6.90 (br s, 2H), 7.64-7.68 (m, 3H), 8.11 (m, 2H) and 8.23 (s, 1H) ppm; MS (ES$^+$) 451.3

Compound I-306 2-[4-[5-amino-6-(5-phenyl-1,3,4-oxadiazol-2-yl)pyrazin-2-yl]piperazin-1-yl]ethanol 1H NMR (400 MHz, DMSO) d 2.46 (m, 2H), 2.59 (m, 4H), 3.46 (m, 4H), 3.56 (m, 2H), 4.47 (t, 1H), 6.90 (br s, 2H), 7.64-7.69 (m, 3H), 8.11 (m, 2H) and 8.24 (s, 1H) ppm Example 36

1-[5-amino-6-(1H-benzimidazol-2-yl)pyrazin-2-yl]pyridin-4-one (Compound I-286)

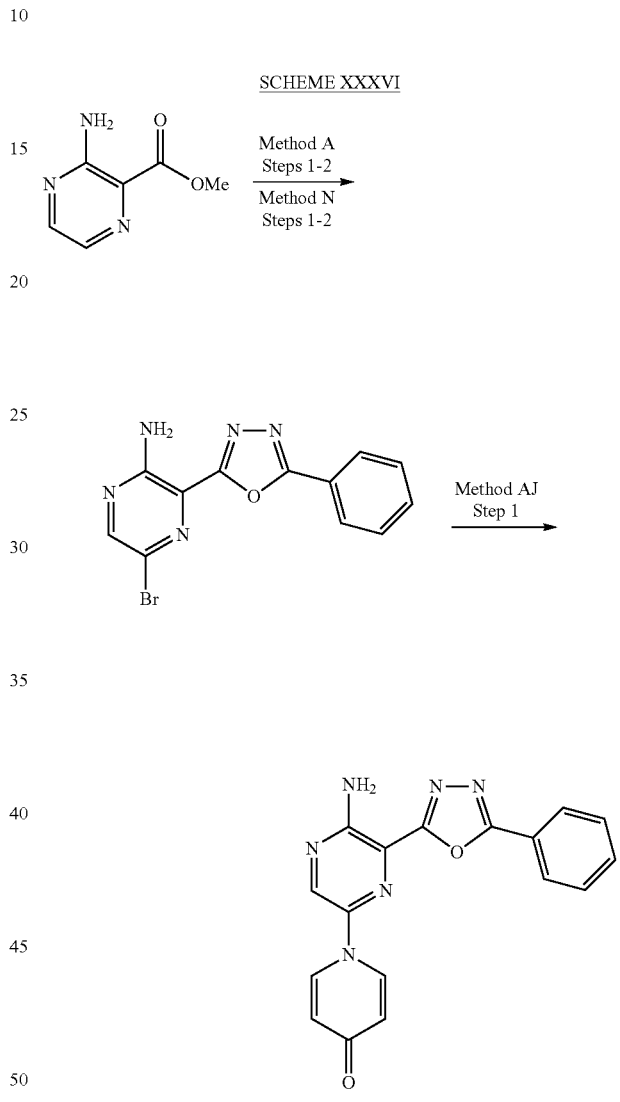

Compound I-286

Compound I-286 was prepared using Method A, Steps 1-2, Method N Steps 1-2 followed by Method AK step 1.

Method AJ: Step 1: 1-[5-amino-6-(5-phenyl-1,3,4-oxadiazol-2-yl)pyrazin-2-yl]pyridin-4-one To a solution of 5-bromo-3-(5-phenyl-1,3,4-oxadiazol-2-yl)pyrazin-2-amine (150.0 mg, 0.4715 mmol) in DMF (3.000 mL) was added copper (5.992 mg, 0.09430 mmol) and cesium carbonate (307.2 mg, 0.9430 mmol) followed by pyridin-4-ol (448.4 mg, 4.715 mmol) and the reaction mixture heated at 160° C. in the microwave for 1 h. The reaction mixture was filtered and washed with DMF (2 mL). Ethyl acetate and water were added to the filtrate and the layers separated. The aqueous layer was extracted further with ethyl acetate (3×5 mL) and the combined organic extracts were washed with water (3×5 mL). The organic extracts were dried over Na$_2$SO$_4$, filtered and concentrated in vacuo. The material was triturated with a mixture of methanol and ether to leave the product. (42.6 mg, 25% yield); 1H NMR (400 MHz, DMSO) d 6.33 (d, 2H), 7.69 (s, 2H), 8.15-8.18 (m, 2H), 8.35 (d, 2H) and 8.78 (s, 1H) ppm; MS (ES$^+$) 333.11

Example 37

2-[5-amino-6-(1H-benzimidazol-2-yl)pyrazin-2-yl]isoindolin-1-one (Compound I-304)

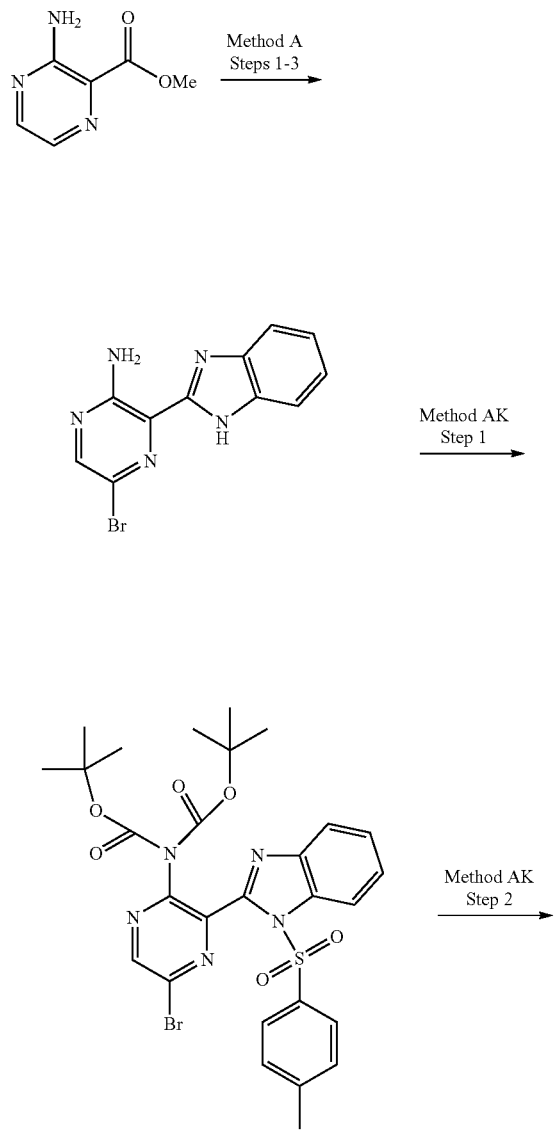

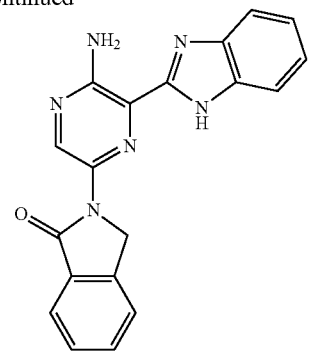

Compound I-304

Compound I-304 was prepared using Method A, Steps 1-3, followed by Method AL Steps 1-2.

Method AK: Step 1: tert-butyl N-tert-butoxycarbonyl-5-bromo-3-(1-tosyl-1H-benzo[d]imidazol-2-yl)pyrazin-2-ylcarbamate Sodium hydride (496.4 mg, 551.6 μL, 12.41 mmol) was added to a solution of 3-(1H-benzimidazol-2-yl)-5-bromopyrazin-2-amine (3 g, 10.34 mmol) THF (20 mL) at 0° C. The resulting suspension was stirred for 5 mins and 4-methylbenzenesulfonylchloride (2.168 g, 11.37 mmol) was added. The reaction was stirred for a further 30 mins and then quenched with saturated NH$_4$Cl aqueous solution and extracted with ethylacetate (3×50 mL). The organic layer was washed with water (1×20 mL) and concentrated in vacuo to a solid. The solid was dissolved in THF (15 mL) and di-tert-butyl dicarbonate (5.190 g, 5.463 mL, 23.78 mmol) and DMAP (126.3 mg, 1.034 mmol) were added. The mixture was stirred overnight at room temperature and then concentrated in vacuo to leave an oil. The oil was dissolved in CH$_2$Cl$_2$ and the product precipitated by slow addition of ether and isolated by filtration (3.1 g, 47% yield);
1H NMR (400 MHz, DMSO) d 1.75 (m, 18H), 2.15 (s, 3H), 7.70-7.80 (m, 4H), 7.90 (m, 1H), 8.00 (m, 1H), 8.20 (m, 2H) and 8.60 (s, 1H); MS (ES$^+$) 646.20

Method AK: Step 2: 2-[5-amino-6-(1H-benzimidazol-2-yl)pyrazin-2-yl]isoindolin-1-one C28H30BrN5O6S (100 mg, 0.1552 mmol), isoindolin-1-one (31.00 mg, 0.2328 mmol), (5-diphenylphosphanyl-9,9-dimethyl-xanthen-4-yl)-diphenyl-phosphane (13.47 mg, 0.02328 mmol), 1,5-diphenylpenta-1,4-dien-3-one palladium (7.106 mg, 0.007760 mmol) and cesium carbonate (101.1 mg, 0.3104 mmol) were heated in dioxane (3 mL) at 70° C. for 1 hr. The reaction mixture was cooled to room temperature and diluted with ethyl acetate (10 mL) and washed with water (1×10 mL) and brine (1×10 mL), dried over MgSO$_4$ and concentrated in vacuo. The residue was dissolved in CH$_2$Cl$_2$ (10 mL) and trifluoroacetic acid (353.9 mg, 239.1 μL, 3.104 mmol) added and the reaction mixture stirred at room temperature for 1 h. The reaction mixture was concentrated in vacuo and the residue purified by reverse phase preparative HPLC [Waters Sunfire C18, 10 uM, 100A column, gradient 10%-95% B (solvent A: 0.05% TFA in water, solvent B: CH$_3$CN) over 16 minutes at 25 mL/min]. The fractions were collected, and freeze-dried to give the product (7.5 mg, 13.4% yield); 1H NMR (400 MHz, MeOD) d 5.25 (s, 2H), 7.3-7.35 (m, 2H), 7.55-7.6 (m, 1H), 7.63-7.7 (m, 4H), 7.9 (d, 1H) and 9.22 (s, 1H) ppm; MS (ES$^+$) 343.1

Example 38

5-(1-ethylsulfonyl-3,6-dihydro-2H-pyridin-4-yl)-3-(5-phenyl-1,2,4-oxadiazol-3-yl)pyrazin-2-amine (Compound I-307)

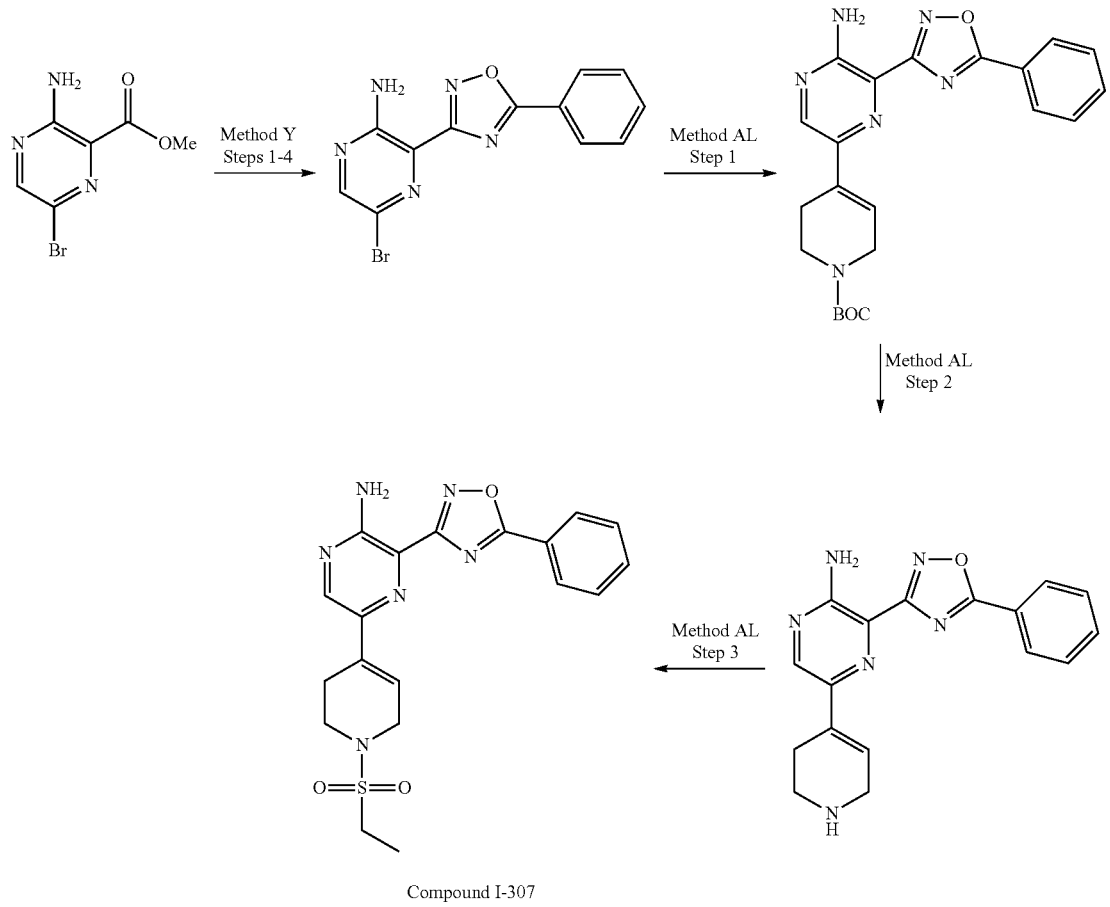

Compound I-307

Compound I-307 was prepared using Method Y, Steps 1-4 followed by Method AM steps 1-3.

Method AL: Step 1: tert-butyl 4-(5-amino-6-(5-phenyl-1,2,4-oxadiazol-3-yl)pyrazin-2-yl)-5,6-dihydropyridine-1(2H)-carboxylate 5-bromo-3-(5-phenyl-1,2,4-oxadiazol-3-yl)pyrazin-2-amine (150 mg, 0.4715 mmol), tert-butyl-4-(4,4,5,5-tetramethyl-1,3,2-dioxaborolan-2-yl)-3,6-dihydro-2H-pyridine-1-carboxylate (189.5 mg, 0.6130 mmol) and sodium carbonate (707.0 µL of 2 M, 1.414 mmol) in DMF (1.500 mL) were heated to 120° C. for 45 min in the microwave. After this time the reaction mixture was diluted with water (5 mL) and ethyl acetate (5 mL) and the layers separated. Organic layer washed with water (3×5 mL), dried (MgSO$_4$) and concentrated in vacuo to leave the title compound as a yellow/orange solid (175.6 mg, 88% yield). 1H NMR (400 MHz, DMSO) d 1.44 (s, 9H), 2.60 (m, 2H), 3.57 (m, 2H), 4.06 (m, 2H), 6.70 (s, 1H), 7.30 (br s, 2H), 7.69 (m, 2H), 7.77 (m, 1H), 8.25 (m, 2H) and 8.51 (1H, s) ppm; MS (ES$^+$) 421.02

Method AL: Step 2: 3-(5-phenyl-1,2,4-oxadiazol-3-yl)-5-(1,2,3,6-tetrahydropyridin-4-yl)pyrazin-2-amine A solution of HCl in dioxane (505.5 µL of 4 M, 2.022 mmol) was added to a solution of tert-butyl 4-[5-amino-6-(5-phenyl-1,2,4-oxadiazol-3-yl)pyrazin-2-yl]-3,6-dihydro-2H-pyridine-1-carboxylate (170 mg, 0.4043 mmol) in methanol (5 mL) at rt and the reaction mixture stirred at room temperature for 48 h. The reaction mixture was concentrated in vacuo to give the title compound (129 mg, 99% yield); MS (ES$^+$) 321.03

Method AL: Step 3: 5-(1-ethylsulfonyl-3,6-dihydro-2H-pyridin-4-yl)-3-(5-phenyl-1,2,4-oxadiazol-3-yl)pyrazin-2-amine Ethanesulfonyl chloride (62.13 mg, 45.78 µL, 0.4832 mmol) and triethyl amine (122.2 mg, 168.3 µL, 1.208 mmol) were added to a solution of 3-(5-phenyl-1,2,4-oxadiazol-3-yl)-5-(1,2,3,6-tetrahydropyridin-4-yl)pyrazin-2-amine (129 mg, 0.4027 mmol) in dichloromethane (5 mL) at 0° C. and the resulting solution stirred at room temperature for 2 h. The reaction mixture was concentrated in vacuo and purified by reverse phase preparative HPLC [Waters Sunfire C18, 10 uM, 100A column, gradient 10%-95% B (solvent A: 0.05% TFA in water, solvent B: CH₃CN) over 16 minutes at 25 mL/min]. The fractions were collected, and freeze-dried. The solid was taken up in dichloromethane (5 mL) and washed with saturated aqueous NaHCO₃ solution (2×5 mL), dried over MgSO₄ and concentrated in vacuo to leave the product (65 mg, 40% yield) 1H NMR (400 MHz, DMSO) d 1.24 (t, 3H), 2.68 (m, 2H), 3.13 (q, 2H), 3.48 (m, 2H), 3.99 (m, 2H), 6.63 (m, 1H), 7.29 (br s, 2H), 7.68 (m, 2H), 7.77 (m, 1H), 8.26 (m, 2H) and 8.52 (1H, s) ppm; MS (ES⁺) 412.97

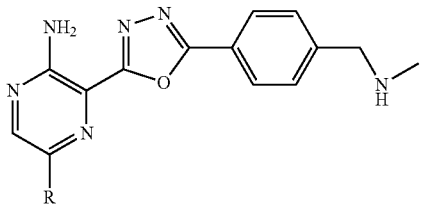

III

Illustrated below are exemplary methods for the preparation of compounds of formula III.

Procedure for the Preparation of Bromo Intermediate:

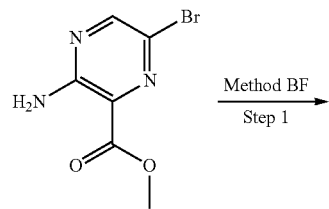

Method BF
Step 1

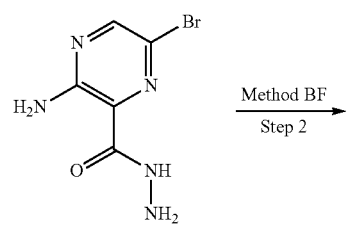

Method BF
Step 2

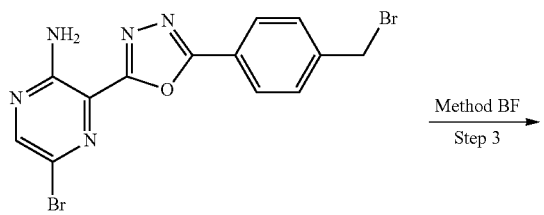

Method BF
Step 3

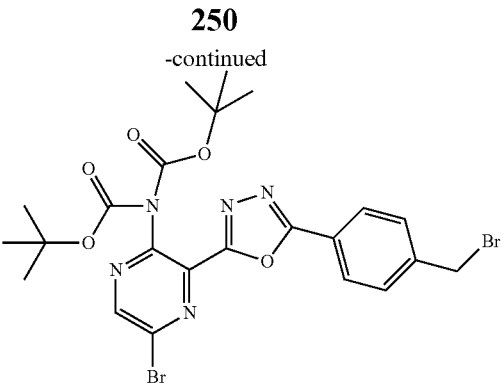

Method BF:

Step 1: 3-Amino-6-bromopyrazine-2-carbohydrazide

To a suspension of methyl 3-amino-6-bromo-pyrazine-2-carboxylate (2.5 g, 10.8 mmol) in EtOH (50 mL) was added hydrazine hydrate (3.2 g, 3.1 mL, 64.6 mmol) and the reaction mixture was heated at 70° C. for 1.5 h forming a thick yellow solid. The solid was isolated by filtration, washed with water (20 mL) and ethanol (40 mL). The solid was dried under high vacuum to yield 3-amino-6-bromo-pyrazine-2-carbohydrazide (2.35 g, 94%) as a light yellow solid. ¹H NMR (400 MHz, DMSO-d₆) δ 9.78 (s, 1H), 8.31 (s, 1H), 7.62 (s, 2H), 4.53 (d, =3.5 Hz, 2H). LC/MS m/z 233.1 [M+H]⁺.

Step 2: 5-Bromo-3-(5-(4-(bromomethyl)phenyl)-1,3,4-oxadiazol-2-yl)pyrazin-2-amine To a suspension of 3-amino-6-bromo-pyrazine-2-carbohydrazide (200 mg, 0.86 mmol) and 4-(bromomethyl)benzoic acid (185 mg, 0.86 mmol) in MeCN (4 mL) at room temperature was added dibromo(triphenyl)phosphorane (1.7 g, 4.14 mmol) and the resulting reaction mixture was stirred for 1 h. The reaction mixture was diluted with acetonitrile (2 mL) and DIPEA (668 mg, 900 µL, 5.2 mmol) was added dropwise and the suspension was allowed to stir overnight. The suspension was filtered, washed with CH₃CN and hexane, and air dried to provide 5-bromo-3-(5-(4-(bromomethyl)phenyl)-1,3,4-oxadiazol-2-yl)pyrazin-2-amine (240 mg, 68%) as a yellow solid. ¹H NMR (400 MHz, DMSO-d₆) δ 8.45 (s, 1H), 8.11 (d, J=8.1 Hz, 2H), 7.72 (d, J=8.2 Hz, 2H), 4.82 (s, 2H). LC/MS m/z 412.1 [M+H]⁺.

Step 3: tert-Butyl N-[5-bromo-3-[5-[4-(bromomethyl)phenyl]-1,3,4-oxadiazol-2-yl]pyrazin-2-yl]-N-tert-butoxycarbonyl-carbamate To a solution of 5-bromo-3-[5-[4-(bromomethyl)phenyl]-1,3,4-oxadiazol-2-yl]pyrazin-2-amine (240 mg, 0.58 mmol) in THF (10 mL) was added DIPEA (302 mg, 407 µL, 2.3 mmol) followed by the addition of di-tert-butyl dicarbonate (637 mg, 671 µL, 2.9 mmol) and 4-dimethylaminopyridine (7 mg, 0.06 mmol). The reaction mixture was stirred at 45° C. overnight. The reaction mixture was concentrated in vacuo and purified by silica gel column chromatography using 10-70% ethyl acetate in hexane to yield tert-butyl N-[5-bromo-3-[5-[4-(bromomethyl)phenyl]-1,3,4-oxadiazol-2-yl]pyrazin-2-yl]-N-tert-butoxycarbonyl-carbamate (120 mg, 34%) as a white solid. ¹H NMR (400 MHz, DMSO-d₆) δ 9.16 (s, 1H), 8.12 (d, J=8.2 Hz, 2H), 7.74 (d, J=8.2 Hz, 2H), 4.83 (s, 2H), 1.29 (s, 18H).

Procedures for the Preparation of Amine Intermediates.

We have provided several methods for preparing amine intermediates. The methods provided herein involve the use of nitrogen-protecting groups and deprotecting agents that are used under a variety of conditions. One of skill in the art would understand that the methods provided herein (e.g., Methods BG, BG-1, BG-2, BH, BH-1 BI,) can be applied to a variety of amines and are not limited to the specific examples shown herein. In general, suitable amine protecting groups that could be used include, but are not limited to, [F-moc, Boc, Cbz, Bn, Ts]. Suitable solvents for these reactions include, but are not limited to [dioxane, DMF, H$_2$O, EtOAc, CH$_2$Cl$_2$]. Suitable deprotecting groups include, but are not limited to, [Piperidine, TFA, HCl, H$_2$/Pd—C, BBr$_3$, HBr—AcOH].

Amine Intermediate

Example 1

1-(2,7-Diazaspiro[4.4]nonan-2-yl)propan-1-one

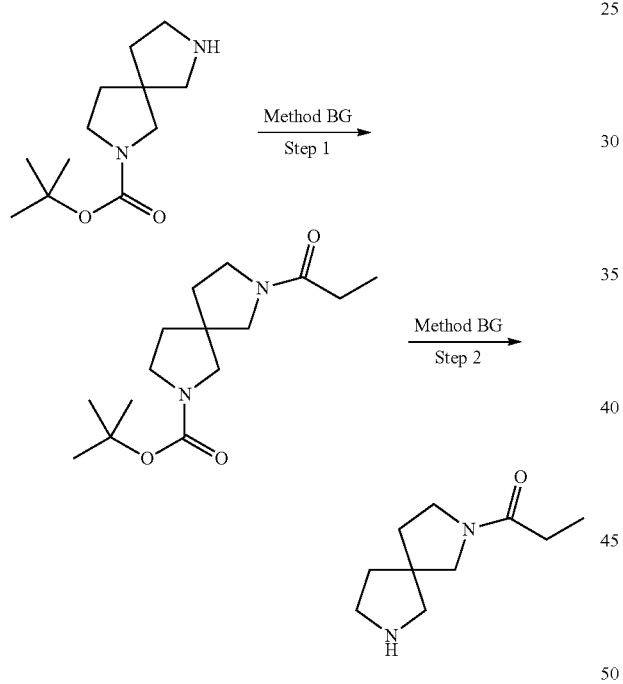

Method BG:

Step 1: tert-Butyl 7-propionyl-2,7-diazaspiro[4.4]nonane-2-carboxylate

To a solution of tert-butyl 3,7-diazaspiro[4.4]nonane-3-carboxylate (127 mg, 0.56 mmol) in anhydrous DCM (1 mL), cooled in an ice water bath was added Et$_3$N (57 mg, 78 μL, 0.56 mmol), followed by the addition of propanoyl chloride (57 mg, 54 μL, 0.62 mmol) as a solution in DCM (0.2 mL). The reaction mixture was stirred for 20 minutes, diluted with DCM and was washed with 1M HCl (×2) and brine (×1). The organic layer was dried over Na$_2$SO$_4$, filtered and concentrated under reduced pressure to yield tert-butyl 3-propanoyl-3,7-diazaspiro[4.4]nonane-7-carboxylate (154 mg, 97%) as an orange oil. $^1$H NMR (400 MHz, CDCl$_3$) δ 3.73-3.11 (m, 8H), 2.34-2.17 (m, 2H), 1.97-1.70 (m, 4H), 1.46 (s, 9H), 1.16 (t, J=7.4 Hz, 3H). LC/MS m/z 283.5 [M+H]$^+$.

Step 2:
1-(2,7-Diazaspiro[4.4]nonan-2-yl)propan-1-one

To a solution of tert-butyl 3-propanoyl-3,7-diazaspiro[4.4]nonane-7-carboxylate (153 mg, 0.54 mmol) in DCM (0.5 mL) was added a solution of hydrogen chloride (1.4 mL of 4 M, 5.4 mmol) in dioxane. The reaction mixture was stirred at room temperature for 1 h. The solvents were removed under reduced pressure and the crude product was dried on the high vacuum for 1 h to yield 1-(3,7-diazaspiro[4.4]nonan-3-yl)propan-1-one as an off white gum. LC/MS m/z 183.3 [M+H]$^+$.

The following amines were prepared using the procedure described above.

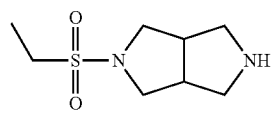

2-Ethylsulfonyl-3,3a,4,5,6,6a-hexahydro-1H-pyrrolo[3,4-c]pyrrole. LC/MS m/z 205.3 [M+H]$^+$.

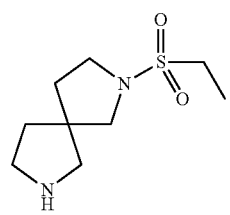

2-(Ethylsulfonyl)-2,7-diazaspiro[4.4]nonane.

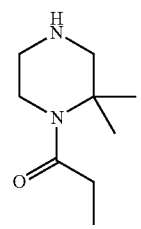

1-(2,2-Dimethylpiperazin-1-yl)propan-1-one. LC/MS m/z 171.5 [M+H]$^+$.

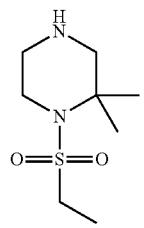

1-(Ethylsulfonyl)-2,2-dimethylpiperazine. LC/MS m/z 207.1 [M+H]$^+$.

253

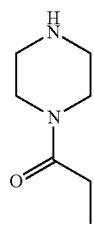

1-(piperazin-1-yl)propan-1-one. LC/MS m/z 143.3 [M+H]⁺.

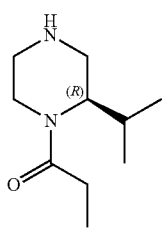

tert-Butyl (3R)-3-isopropyl-4-propanoyl-piperazine-1-carboxylate. LC/MS m/z 185.3 [M+H]⁺.

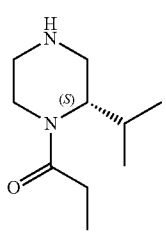

tert-Butyl (3S)-3-isopropyl-4-propanoyl-piperazine-1-carboxylate. LC/MS m/z 185.3 [M+H]⁺.

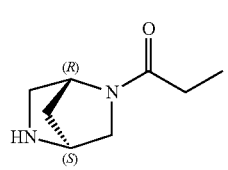

1-[(1S,4R)-2,5-Diazabicyclo[2.2.1]heptan-5-yl]propan-1-one.

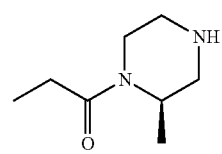

1-[(2R)-2-Methylpiperazin-1-yl]propan-1-one.

254

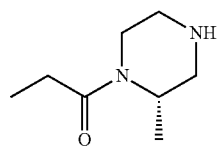

1-[(2S)-2-Methylpiperazin-1-yl]propan-1-one.

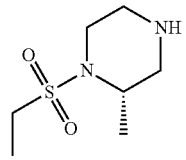

(2S)-1-Ethylsulfonyl-2-methyl-piperazine.

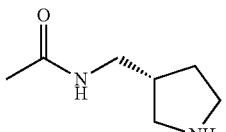

N-[[(3R)-Pyrrolidin-3-yl]methyl]acetamide. LC/MS m/z 143.1 [M+H]⁺.

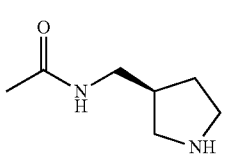

N-[[(3S)-Pyrrolidin-3-yl]methyl]acetamide. LC/MS m/z 143.3 [M+H]⁺.

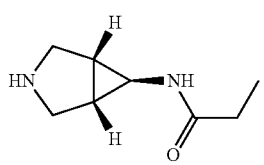

N-((1R,6S)-3-Azabicyclo[3.1.0]hexan-6-yl)propionamide. LC/MS m/z 155.3 [M+H]⁺.

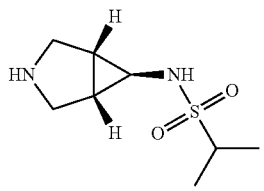

N-((1R,6S)-3-Azabicyclo[3.1.0]hexan-6-yl)propane-2-sulfonamide. LC/MS m/z 205.3 [M+H]⁺.

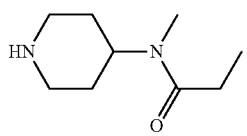

N-Methyl-N-(piperidin-4-yl)propionamide. LC/MS m/z 171.3 [M+H]⁺.

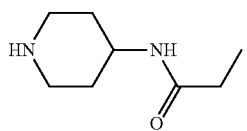

N-(Piperidin-4-yl)propionamide. LC/MS m/z 157.3 [M+H]⁺.

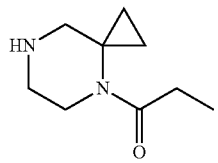

1-(4,7-Diazaspiro[2.5]octan-4-yl)propan-1-one. LC/MS m/z 169.1 [M+H]⁺.

Amine Intermediate

Example 2

(R)-N-Ethylpyrrolidine-2-carboxamide

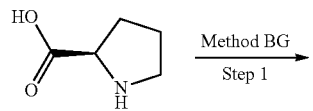

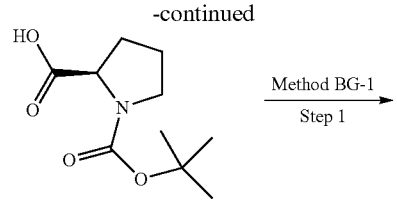

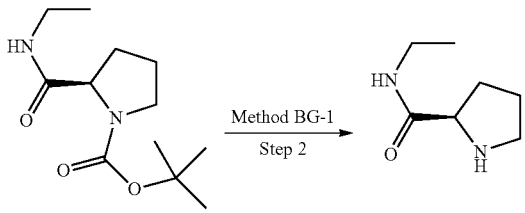

Method BG-1:

Step 1: (R)-tert-Butyl 2-(ethylcarbamoyl)pyrrolidine-1-carboxylate

To a solution of (2R)-1-tert-butoxycarbonylpyrrolidine-2-carboxylic acid (810 mg, 3.8 mmol) and HATU (1.40 g, 3.8 mmol) in DMF (7.5 mL) was added ethanamine (3.8 mL of 2 M, 7.5 mmol) followed by DIEA (1.0 g, 1.4 mL, 8.0 mmol) at room temperature. The reaction mixture was stirred at room temperature for 16 h. The reaction mixture was diluted with EtOAc and washed sequentially with 1M HCl, saturated NaHCO₃ and brine solution. The organic layer was dried (Na₂SO₄) filtered and concentrated under reduced pressure to obtain tert-butyl (2R)-2-(ethylcarbamoyl)pyrrolidine-1-carboxylate (624 mg, 68%). LC/MS m/z 243.4 [M+H]⁺.

Step 2: (R)-N-Ethylpyrrolidine-2-carboxamide

To tert-butyl (2R)-2-(ethylcarbamoyl)pyrrolidine-1-carboxylate (561 mg, 2.3 mmol) was added hydrogen chloride (580 µL of 4 M, 2.3 mmol) in dioxane at room temperature under an atmosphere of nitrogen. The reaction mixture was stirred for 3 h. The solvent was removed under reduced pressure to obtain (2R)-N-ethylpyrrolidine-2-carboxamide (225 mg, 54%). LC/MS m/z 143.2 [M+H]⁺.

The following amines were prepared using the procedure described above.

(S)-N-Ethylpyrrolidine-2-carboxamide.

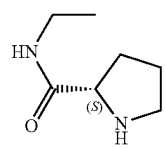

(S)-N-Ethylpyrrolidine-2-carboxamide. LC/MS m/z 143.2 [M+H]⁺.

Amine Intermediate

Example 3

(S)-Pyrrolidin-3-yl ethylcarbamate

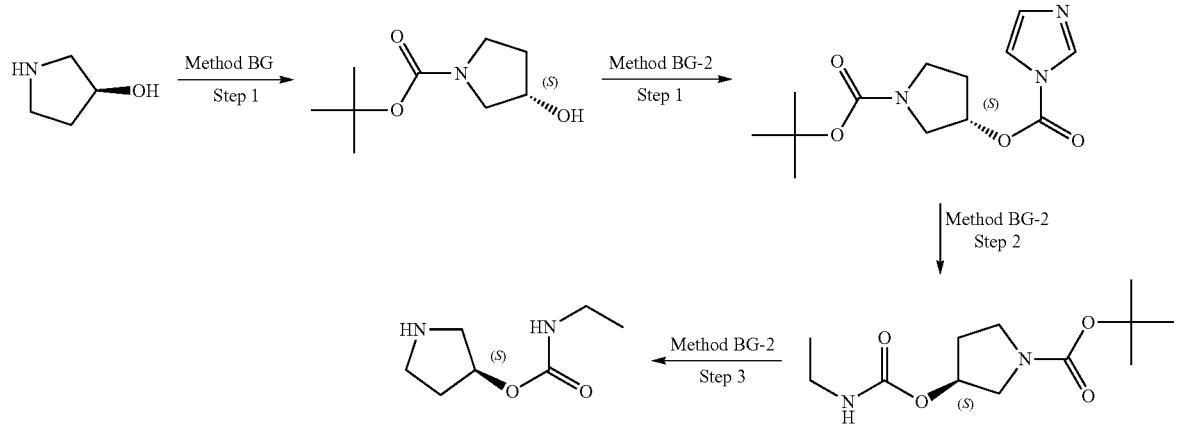

Method BG-2:

Step 1: (S)-1-(tert-Butoxycarbonyl)pyrrolidin-3-yl 1H-imidazole-1-carboxylate

To a solution of tert-butyl (3S)-3-hydroxypyrrolidine-1-carboxylate (360 mg, 1.9 mmol) in THF (8 mL) was added triethylamine (253 mg, 349 μL, 2.5 mmol) followed by the addition of CDI (374 mg, 2.3 mmol) portionwise. The reaction mixture was heated at 50° C. for 3 h, cooled to room temperature and diluted with EtOAc. The organic layer was washed with 1 M HCl solution, dried over MgSO$_4$, filtered and concentrated under reduced pressure. The crude material was purified via silica gel column chromatography using 20 to 100% EtOAc in hexanes to obtain (S)-1-(tert-butoxycarbonyl)pyrrolidin-3-yl 1H-imidazole-1-carboxylate (345 mg, 64%). $^1$HNMR (400 MHz, CDCl$_3$) δ 8.14 (s, 1H), 7.42 (d, J=1.2 Hz, 1H), 7.09 (s, 1H), 4.46 (s, 1H), 3.66 (dd, J=33.8, 10.7 Hz, 1H), 3.56-3.29 (m, 2H), 2.25 (s, 1H), 2.04-1.87 (m, 2H), 1.48 (t, J=4.0 Hz, 9H). LC/MS m/z 282.4 [M+H]$^+$.

Step 2: tert-Butyl (3S)-3-(Ethylcarbamoyloxy)pyrrolidine-1-carboxylate

To a solution of [(3S)-1-tert-butoxycarbonylpyrrolidin-3-yl]imidazole-1-carboxylate (173 mg, 0.61 mmol) in THF (2.5 mL) at room temperature under an atmosphere of nitrogen was added a solution of ethanamine (369 mg, 461 μL of 2 M, 0.9 mmol) in THF followed by the addition of DIEA (119 mg, 161 μL, 0.9 mmol). The reaction mixture was heated at 60° C. for 1.5 h, cooled to room temperature and diluted with EtOAc. The organic layer was washed with 5 mL of 1M HCl solution, dried over MgSO$_4$, filtered and concentrated under reduced pressure to obtain tert-butyl (3S)-3-(ethylcarbamoyloxy)pyrrolidine-1-carboxylate. LC/MS m/z 259.2 [M+H]$^+$.

Step 3: (S)-Pyrrolidin-3-yl ethylcarbamate

Crude tert-butyl (S)-3-(ethylcarbamoyloxy)pyrrolidine-1-carboxylate from step 2 was treated with hydrogen chloride (461 μL of 4 M, 1.8 mmol) in dioxane. The reaction mixture was stirred for 1.5 h at room temperature. The solvent was removed under reduced pressure to obtain (S)-pyrrolidin-3-yl ethylcarbamate (88 mg, 73%). $^1$H NMR (400 MHz, DMSO-d$_6$) δ 9.56-8.98 (m, 2H), 4.38 (s, 1H), 3.29-3.05 (m, 4H), 3.03-2.94 (m, 2H), 1.95-1.75 (m, 3H), 1.29 (dd, J=13.8, 6.6 Hz, 1H), 1.01 (t, J=7.2 Hz, 1H). LC/MS m/z 159.4 [M+H]$^+$.

Amine Intermediate

Example 4

(3aS,6aR)-1,2,3,3a,4,5,6,6a-Octahydrocyclopenta[c]pyrrol-4-ol

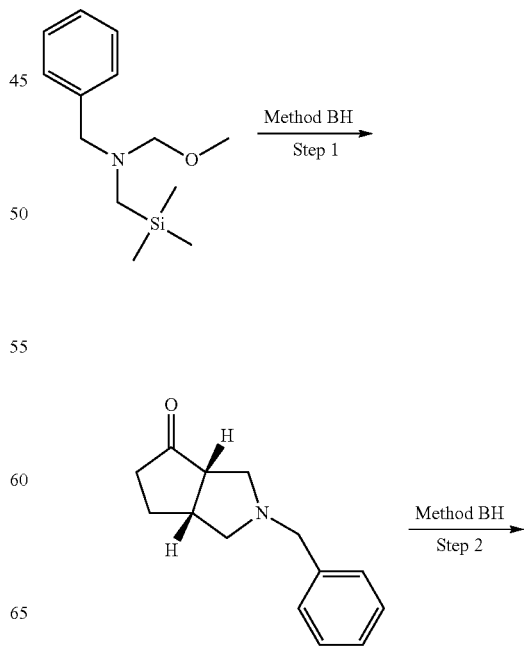

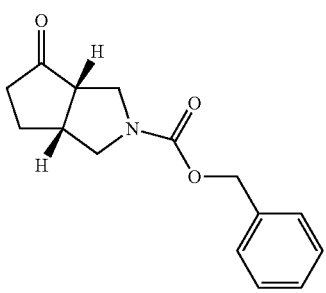

Method BH
Step 3

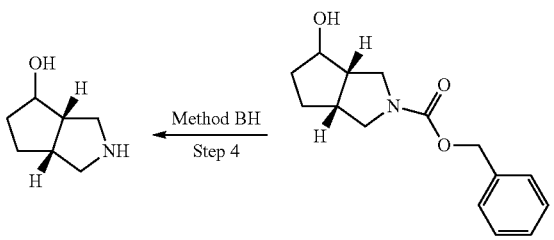

Method BH:

Step 1: (3aS,6aR)-2-Benzylhexahydrocyclopenta[c]pyrrol-4(5H)-one

A round bottom flask purged with argon was charged with N-benzyl-1-methoxy-N-(trimethylsilylmethyl)methanamine (31.2 g, 131.4 mmol) and cyclopent-2-ene-1-one (9.0 g, 9.2 mL, 109.5 mmol). The reaction mixture was cooled to 0° C. and a solution of trifluoroacetic acid (1.25 g, 847 µL, 11.0 mmol) in DCM (11 mL) was added to it. The reaction mixture was stirred at 0° C. for 4 h, warmed to room temperature and stirred for 18 h. The reaction was quenched by the addition of saturated sodium bicarbonate and the layers were separated. The aqueous layer was extracted with DCM and the combined organic layers was washed with brine, dried over sodium sulfate and concentrated under reduced pressure. The crude material was purified via silica gel column chromatography using 40 to 80% EtOAc in hexanes to obtain (3aR,6aS)-2-benzyl-1,3,3a,4,5,6a-hexahydrocyclopenta[c]pyrrol-6-one (19.8 g, 84%) as a light yellow oil.
LC/MS m/z 216.5 [M+H]$^+$.

Step 2: (3aS,6aR)-Benzyl 4-oxohexahydrocyclopenta[c]pyrrole-2(1H)-carboxylate

A solution of (3aR,6aS)-2-benzyl-1,3,3a,4,5,6a-hexahydrocyclopenta[c]pyrrol-6-one (19.8 g, 92 mmol) in dichloromethane (770 mL) was treated with benzyl chloroformate (26.7 g, 22.3 mL, 156 mmol) at room temperature. The reaction mixture was stirred overnight at room temperature. The solvent was removed under reduced pressure and the crude material obtained was purified using silica gel column chromatography using 40 to 99% EtOAc in hexanes to obtain benzyl(3aR,6aS)-6-oxo-1,3,3a,4,5,6a-hexahydrocyclopenta[c]pyrrole-2-carboxylate (11.2 g, 43.19 mmol, 47%) as a light yellow oil. NMR (400 MHz, CDCl$_3$) δ 7.41-7.23 (m, 5H), 5.11 (d, J=4.2 Hz, 2H), 3.82-3.52 (m, 3H), 3.29-3.14 (m, J=5.6 Hz, 1H), 3.13-2.93 (m, J=11.1, 6.8 Hz, 1H), 2.81-2.68 (m, J=8.6, 3.6 Hz, 1H), 2.37 (t, J=7.8 Hz, 2H), 2.26-2.10 (m, 1H), 1.86 (s, 1H). LC/MS m/z 260.1 [M+H]$^+$.

Step 3: (3aS,6aR)-Benzyl 4-hydroxyhexahydrocyclopenta[c]pyrrole-2(1H)-carboxylate A solution of benzyl (3aR,6aS)-6-oxo-1,3,3a,4,5,6a-hexahydrocyclopenta[c]pyrrole-2-carboxylate (850 mg, 3.3 mmol) in THF (10 mL) was added dropwise to a suspension of lithium borohydride (86 mg, 4 mmol) in THF (5 mL) at −78° C. The reaction mixture was allowed to warm to room temperature and was stirred overnight. The reaction mixture was then cooled to 0° C. and quenched with H$_2$O$_2$ (30% in H$_2$O) and then poured onto H$_2$O. The aqueous layer was extracted with EtOAc (2×) and the combined organic layer was washed with brine, dried over Na$_2$SO$_4$, filtered and concentrated under reduced pressure to obtain benzyl (3aR,6aS)-6-hydroxy-3,3a,4,5,6,6a-hexahydro-1H-cyclopenta[c]pyrrole-2-carboxylate (850 mg, 99%) as a colorless oil. LC/MS m/z 262.1 [M+H]$^+$.

Step 4: (3aS,6aR)-Octahydrocyclopenta[c]pyrrol-4-ol

A mixture of benzyl (3aR,6aS)-6-hydroxy-3,3a,4,5,6,6a-hexahydro-1H-cyclopenta[c]pyrrole-2-carboxylate (850 mg, 3.3 mmol) and Pd/C (200 mg) in THF (5.000 mL) was hydrogenated at 25-30 psi in a Parr shaker. After 12 h, the reaction mixture was diluted with MeOH and filtered through a plug of celite. The solvents were removed under reduced pressure to obtain (3aS,6aR)-1,2,3,3a,4,5,6,6a-octahydrocyclopenta[c]pyrrol-4-ol in quantitative yield.
LC/MS m/z 128.1 [M+H]$^+$.

Amine Intermediate

Example 5

2-(Isopropylsulfonyl)-2,6-diazaspiro[3.4]octane

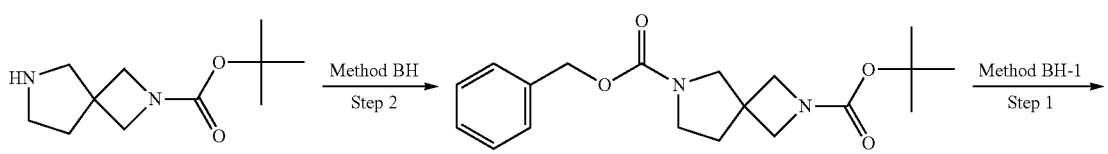

-continued

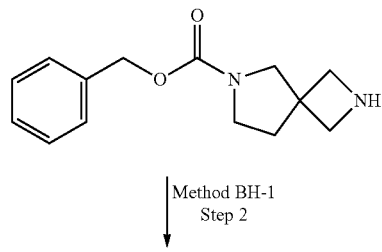

Method BH-1
Step 2

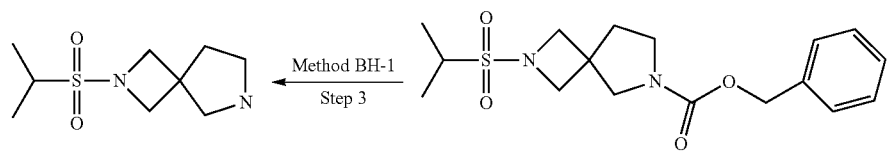

Method BH-1:

Step 1: Benzyl 2,6-diazaspiro[3.4]octane-6-carboxylate

A solution of 6-benzyl 2-tert-butyl 2,6-diazaspiro[3.4]octane-2,6-dicarboxylate (705 mg, 2.0 mmol) in DCM (1 mL) was treated with hydrogen chloride (5 mL of 4 M, 20 mmol) in dioxane. The reaction mixture was stirred at room temperature for 1 h. The solvent was removed under reduced pressure to obtain benzyl 2,7-diazaspiro[3.4]octane-7-carboxylate. LC/MS m/z 247.3 [M+H]$^+$.

Step 2: Benzyl 2-(isopropylsulfonyl)-2,6-diazaspiro[3.4]octane-6-carboxylate A solution of benzyl 2,7-diazaspiro[3.4]octane-7-carboxylate (192 mg, 0.68 mmol) in DCM (1 mL) was treated with triethylamine (137 mg, 189 μL, 1.36 mmol) and isopropylsulfonyl chloride (107 mg, 84 μL, 0.75 mmol) at 0° C. The reaction mixture was stirred for 20 minutes. The reaction mixture was diluted with DCM and washed with 1N HCl and brine. The organic layer was dried over Na$_2$SO$_4$ filtered and concentrated under reduced pressure to obtain benzyl 2-isopropylsulfonyl-2,6-diazaspiro[3.4]octane-6-carboxylate (230 mg, 96%) as a colorless oil.

LC/MS m/z 353.3 [M+H]$^+$.

Step 3: 2-(Isopropylsulfonyl)-2,6-diazaspiro[3.4]octane

A solution of benzyl 2-isopropylsulfonyl-2,6-diazaspiro[3.4]octane-6-carboxylate (230 mg, 0.65 mmol) in AcOH (2 mL) was treated with Pd (7.0 mg, 0.06 mmol) (10% on activated carbon) and stirred under an atmosphere of hydrogen for 1.5 h. The reaction mixture was diluted with DCM, filtered and washed with 1N HCl and brine. The organic layer was dried over Na$_2$SO$_4$, filtered and concentrated to obtain 2-isopropylsulfonyl-2,6-diazaspiro[3.4]octane in quantitative yield. LC/MS m/z 219.3 [M+H]$^+$.

Amine Intermediate

Example 5

8-(Ethylsulfonyl)-3,8-diazabicyclo[3.2.1]octane.

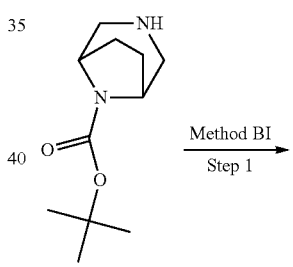

Method BI
Step 1

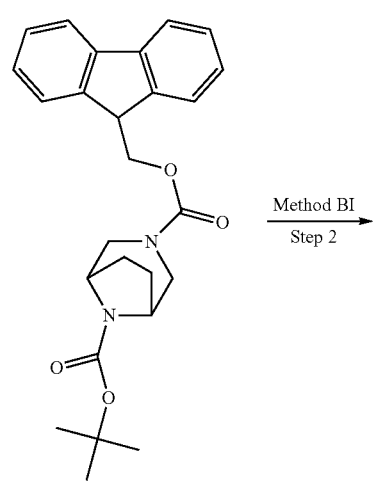

Method BI
Step 2

263
-continued

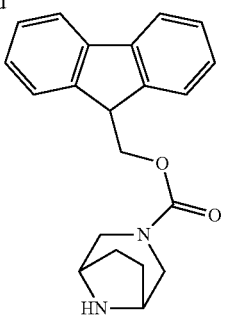

Method BI
Step 3

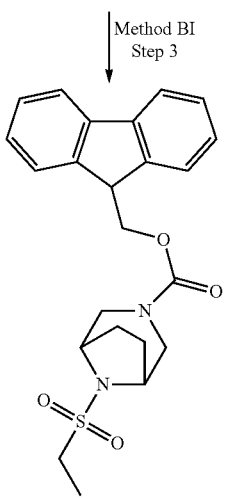

Method BI
Step 4

Method BI:

Step 1: 3-(9H-Fluoren-9-yl)methyl 8-tert-butyl 3,8-diazabicyclo[3.2.1]octane-3,8-dicarboxylate A solution of tert-butyl 3,8-diazabicyclo[3.2.1]octane-8-carboxylate (105 mg, 0.5 mmol) in dichloromethane (3 mL) and triethylamine (100 mg, 138 µL, 1.0 mmol) was treated with 9H-fluoren-9-ylmethyl carbonochloridate (128.0 mg, 0.5 mmol). The reaction mixture was stirred for 1 h. The reaction mixture was washed with 1 N HCl, water, 50% saturated bicarbonate and brine. The organic layer was dried over Na$_2$SO$_4$, filtered and concentrated to obtain a solution of 3-(9H-fluoren-9-yl)methyl 8-tert-butyl 3,8-diazabicyclo[3.2.1]octane-3,8-dicarboxylate in DCM (2 mL), which was used directly for the next step. LC/MS m/z 435.5 [M+H]$^+$.

Step 2: (9H-Fluoren-9-yl)methyl 3,8-diazabicyclo[3.2.1]octane-3-carboxylate

A solution of 3-(9H-fluoren-9-yl)methyl 8-tert-butyl 3,8-diazabicyclo[3.2.1]octane-3,8-dicarboxylate in DCM (2 mL) from the step 1 was treated dropwise with TFA (2.2 g, 1.5 mL, 19.5 mmol) at room temperature and the reaction mixture was stirred for 1 h. The solvents were removed under reduced pressure and the crude material was dissolved in 1 N HCl (2 mL) and washed with ether. The solution was basified with saturated bicarbonate solution and the aqueous layer was extracted with DCM. The organic layer was dried over Na$_2$SO$_4$, filtered and concentrated to obtain a solution of (9H-fluoren-9-yl)methyl 3,8-diazabicyclo[3.2.1]octane-3-carboxylate in DCM (2 mL), which was used directly for the next step. LC/MS m/z 335.5 [M+H]$^+$.

264

Step 3: (9H-Fluoren-9-yl)methyl 8-(ethylsulfonyl)-3,8-diazabicyclo[3.2.1]octane-3-carboxylate To the solution of (9H-fluoren-9-yl)methyl 3,8-diazabicyclo[3.2.1]octane-3-carboxylate in DCM (2 mL) from step 2 was added triethylamine (100 mg, 138 µL, 1.0 mmol) and ethanesulfonyl chloride (190 mg, 140 µL, 1.4 mmol). The reaction mixture was stirred for 16 h. The reaction mixture was washed with 50% saturated bicarbonate solution and brine. The organic layer was dried over Na$_2$SO$_4$, filtered and concentrated in vacuo to obtain (9H-fluoren-9-yl)methyl 8-(ethylsulfonyl)-3,8-diazabicyclo[3.2.1]octane-3-carboxylate, which was used directly for the next step. LC/MS m/z 427.5 [M+H]$^+$.

Step 4:
8-(Ethylsulfonyl)-3,8-diazabicyclo[3.2.1]octane

Crude 9H-fluoren-9-ylmethyl 8-ethylsulfonyl-3,8-diazabicyclo[3.2.1]octane-3-carboxylate obtained from step 3 was dissolved in DMF (500 µL) and treated with piperidine (4 mg, 5 µL, 0.05 mmol). The reaction mixture was stirred for 2 h at room temperature. The reaction mixture was diluted with methanol/DCM and treated with carbonate resin. The reaction mixture was filtered and concentrated under reduced pressure to yield 8-ethylsulfonyl-3,8-diazabicyclo[3.2.1]octane which was used directly in the next step without further purification.

LC/MS m/z 205.3 [M+H]$^+$.

Example 32

5-(1-(2-Aminoethylsulfonyl)-1,2,3,6-tetrahydropyridin-4-yl)-3-(1H-benzo[d]imidazol-2-yl)pyrazin-2-amine (Compound I-313)

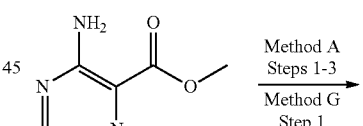

Method A
Steps 1-3

Method G
Step 1

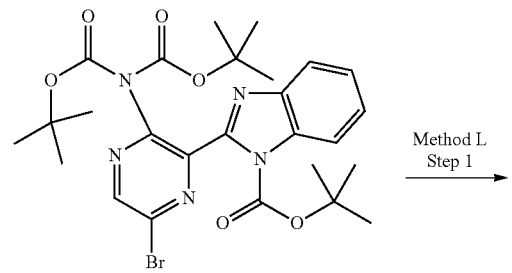

Method L
Step 1

265
-continued

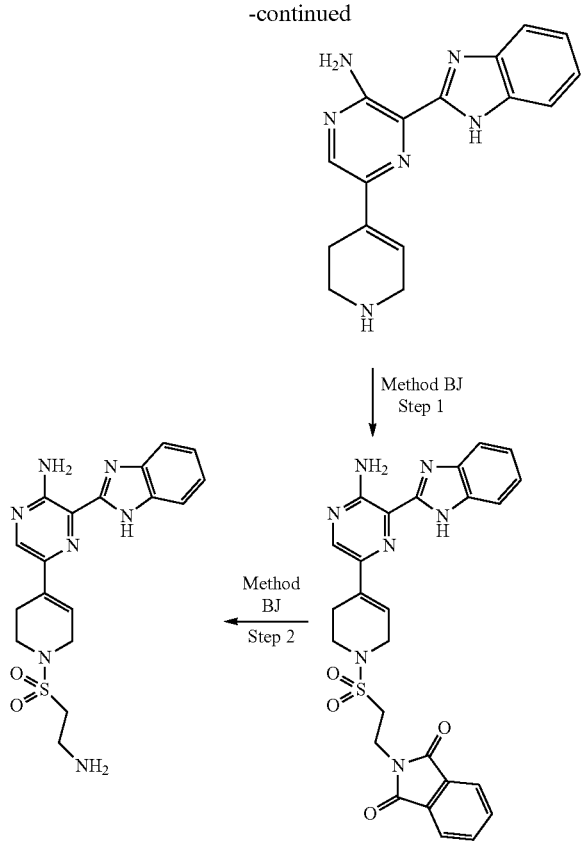

Compound I-313 was prepared using Method A, Steps 1-3 followed by Method G, Step 1 followed by Method L, Steps 1-2, followed by Method BJ, Steps 1-2.

Method BJ: Step 1: 2-(2-(4-(5-Amino-6-(1H-benzo[d]imidazol-2-yl)pyrazin-2-yl)-5,6-dihydropyridin-1(2H)-ylsulfonyl)ethyl)isoindoline-1,3-dione To a solution of 3-(1H-benzimidazol-2-yl)-5-(1,2,3,6-tetrahydropyridin-4-yl)pyrazin-2-amine (73 mg, 0.25 mmol) and triethylamine (51 mg, 70 µL, 0.50 mmol) in DMSO (1 mL) at 0° C. was added 2-(1,3-dioxoisoindolin-2-yl)ethanesulfonyl chloride (68 mg, 0.25 mmol). The reaction mixture was warmed to room temperature, stirred for 3 h and then partitioned between EtOAc and water. The aqueous layer was extracted with EtOAc, dried (MgSO$_4$), filtered and concentrated. The crude material was dissolved in DMSO and purified by prep HPLC to obtain: 2-(2-(4-(5-amino-6-(1H-benzo[d]imidazol-2-yl)pyrazin-2-yl)-5,6-dihydropyridin-1(2H)-ylsulfonyl)ethyl)isoindoline-1,3-dione (23 mg, 17%). LC/MS m/z 530.0 [M+H]$^+$.

Method BJ: Step 2: 5-(1-(2-Aminoethylsulfonyl)-1,2,3,6-tetrahydropyridin-4-yl)-3-(1H-benzo[d]imidazol-2-yl)pyrazin-2-amine To a suspension of 2-(2-(4-(5-amino-6-(1H-benzo[d]imidazol-2-yl)pyrazin-2-yl)-5,6-dihydropyridin-1(2H)-ylsulfonyl)ethyl)isoindoline-1,3-dione (24 mg, 0.045 mmol) in ethanol (240 µL) was added hydrazine (1.5 mg, 1.4 µL, 0.045 mmol), and the reaction mixture was heated at 80° C. for 2 h. The reaction mixture was cooled to room temperature and was dissolved in 0.5 ml of DMSO and purified via reverse

266 phase HPLC using 1 to 99% MeOH in H2O 2O (0.05% HCl as modifier) to obtain 5-(1-(2-aminoethylsulfonyl)-1,2,3,6-tetrahydropyridin-4-yl)-3-(1H-benzo[d]imidazol-2-yl)pyrazin-2-amine (4 mg, 18%). $^1$HNMR (400 MHz, MeOD) δ 8.59 (s, 1H), 8.12-8.03 (m, 2H), 7.78 (dd, J=6.1, 3.2 Hz, 2H), 7.16 (s, 1H), 4.43 (d, J=2.1 Hz, 2H), 3.95 (t, J=5.6 Hz, 2H), 3.81-3.67 (m, 4H), 3.12 (s, 2H). LC/MS m/z 400.0 [M+H]$^+$.

Compound I-331 was prepared using the method described for Compound I-313 in Example 32 above.

Compound I-331: 5-(1-(3-aminopropylsulfonyl)-1,2,3,6-tetrahydropyridin-4-yl)-3-(1H-benzo[d]imidazol-2-yl)pyrazin-2-amine. $^1$H NMR (400 MHz, MeOD) δ 8.31 (s, 1H), 7.81 (dd, J=6.1, 3.1 Hz, 2H), 7.52 (dd, J=6.2, 3.2 Hz, 2H), 6.90 (s, 1H), 4.12 (s, 2H), 3.63 (t, J=5.6 Hz, 2H), 3.26 (t, J=7.3 Hz, 2H), 3.18-3.10 (m, 2H), 2.83 (d, J=1.5 Hz, 2H), 2.32-2.05 (m, 2H). LC/MS m/z 414.2 [M+H]$^+$.

Example 33

4-(4-(5-Amino-6-(1H-benzo[d]imidazol-2-yl)pyrazin-2-yl)-5,6-dihydropyridin-1(2H)-yl)-4-oxobutanoic acid. (Compound I-324)

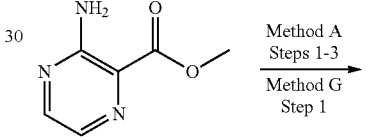

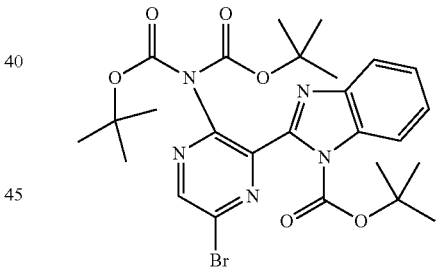

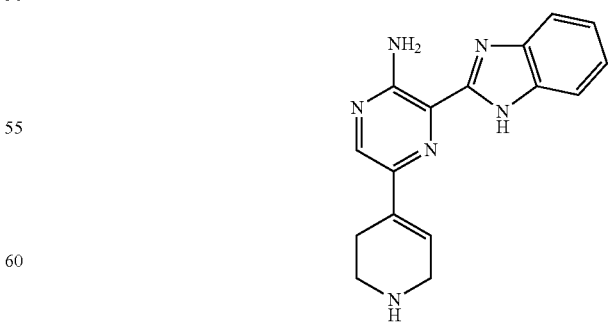

267
-continued

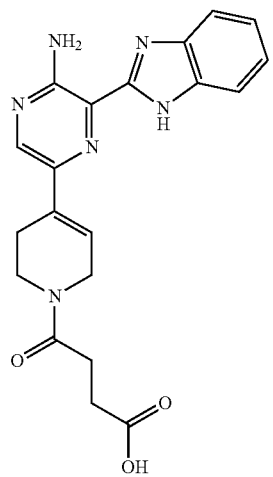

Compound I-324 was prepared using Method A, Steps 1-3 followed by Method G, Step 1 followed by Method L, Steps 1-2, followed by Method BK, Step 1.

Method BK: Step 1: 4-(4-(5-Amino-6-(1H-benzo[d]imidazol-2-yl)pyrazin-2-yl)-5,6-dihydropyridin-1(2H)-yl)-4-oxobutanoic acid To a solution of 3-(1H-benzimidazol-2-yl)-5-(1,2,3,6-tetrahydropyridin-4-yl)pyrazin-2-amine (50 mg, 0.12 mmol) in DCM (2 mL) at 0° C. was added methyl 4-chloro-4-oxobutanoate (19 mg, 15 µL, 0.12 mmol) followed by the addition of triethylamine (50 mg, 69 µL, 0.5 mmol). The reaction mixture was stirred at room temperature for 2 h and then partitioned between EtOAc and water. The aqueous layer was extracted with EtOAc, dried (MgSO$_4$), filtered and concentrated. The crude material was dissolved in DMSO and purified by reverse phase HPLC using 1-99% MeOH in H$_2$O to obtain methyl 4-(4-(5-amino-6-(1H-benzo[d]imidazol-2-yl)pyrazin-2-yl)-5,6-dihydropyridin-1(2H)-yl)-4-oxobutanoate, which was re-dissolved in THF (1.0 mL), treated with NaOH (996 µL of 2.5 M, 2.5 mmol) and stirred for 18 h at room temperature. The reaction mixture was then acidified with conc. HCl till pH7 and extracted with DCM. The organic layer was dried (MgSO$_4$), filtered and concentrated. The crude material was purified via reverse phase HPLC using 1-99% MeOH in H$_2$O (0.05% HCl modifier) to obtain 4-(4-(5-amino-6-(1H-benzo[d]imidazol-2-yl)pyrazin-2-yl)-5,6-dihydropyridin-1(2H)-yl)-4-oxobutanoic acid (5 mg, 11%). $^1$H NMR (400 MHz, MeOD) δ 8.24 (s, 1H), 7.66 (d, J=4.1 Hz, 2H), 7.27 (dd, J=6.0, 3.1 Hz, 2H), 6.68 (d, J=7.9 Hz, 1H), 4.34 (s, 1H), 4.27 (s, 1H), 3.84 (t, J=5.6 Hz, 2H), 2.85 (s, 1H), 2.80-2.65 (m, 3H), 2.56-2.47 (m, 2H). LC/MS m/z 393.0 [M+H]$^+$.

268

Example 34

1-(4-(5-Amino-6-(1H-benzo[d]imidazol-2-yl)pyrazin-2-yl)-5,6-dihydropyridin-1(2H)-yl)-3-(methylamino)propan-1-one (Compound I-346)

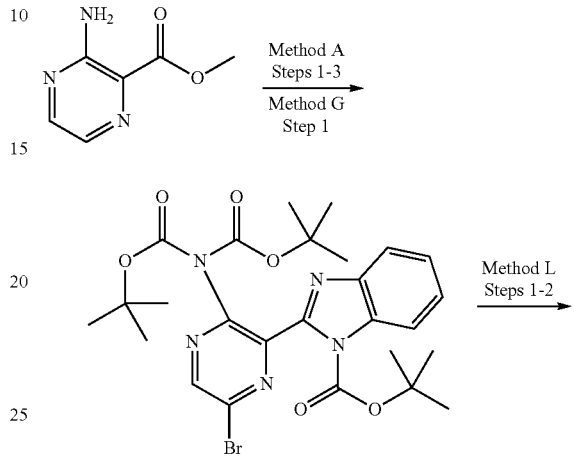

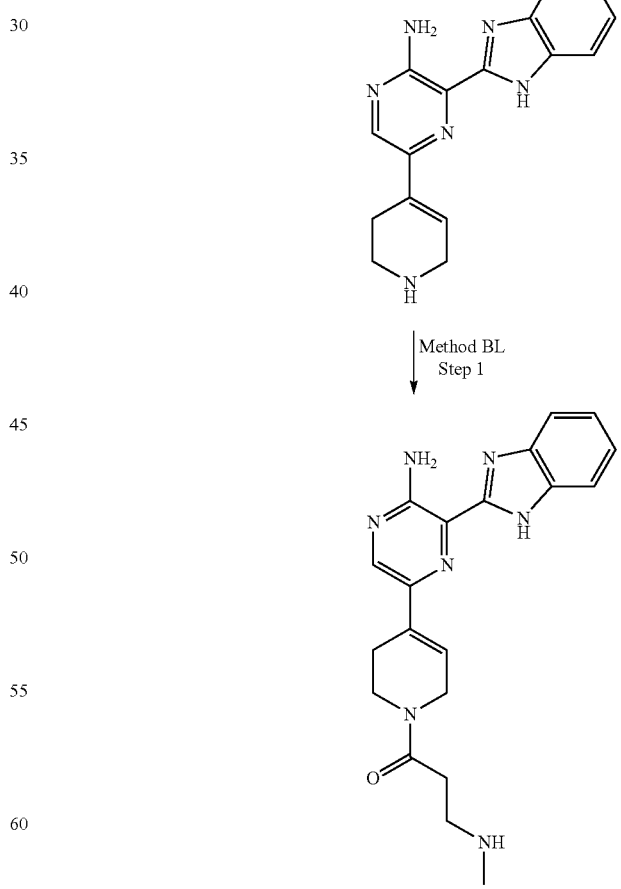

Compound I-346 was prepared using Method A, Steps 1-3 followed by Method G, Step 1 followed by Method L, Steps 1-2, followed by Method BL, Step 1.

Method BL: Step 1: 1-(4-(5-amino-6-(1H-benzo[d]imidazol-2-yl)pyrazin-2-yl)-5,6-dihydropyridin-1(2H)-yl)-3-(methylamino)propan-1-one To a solution of 3-[tert-butoxycarbonyl(methyl)amino]propanoic acid (14 mg, 0.07 mmol) in DMSO (445 µL) was added HATU (26 mg, 0.07 mmol) followed by the addition of Example 35

5-(4-(Ethylamino)cyclohex-1-enyl)-3-(5-phenyl-1,3,4-oxadiazol-2-yl)pyrazin-2-amine (Compound I-314)

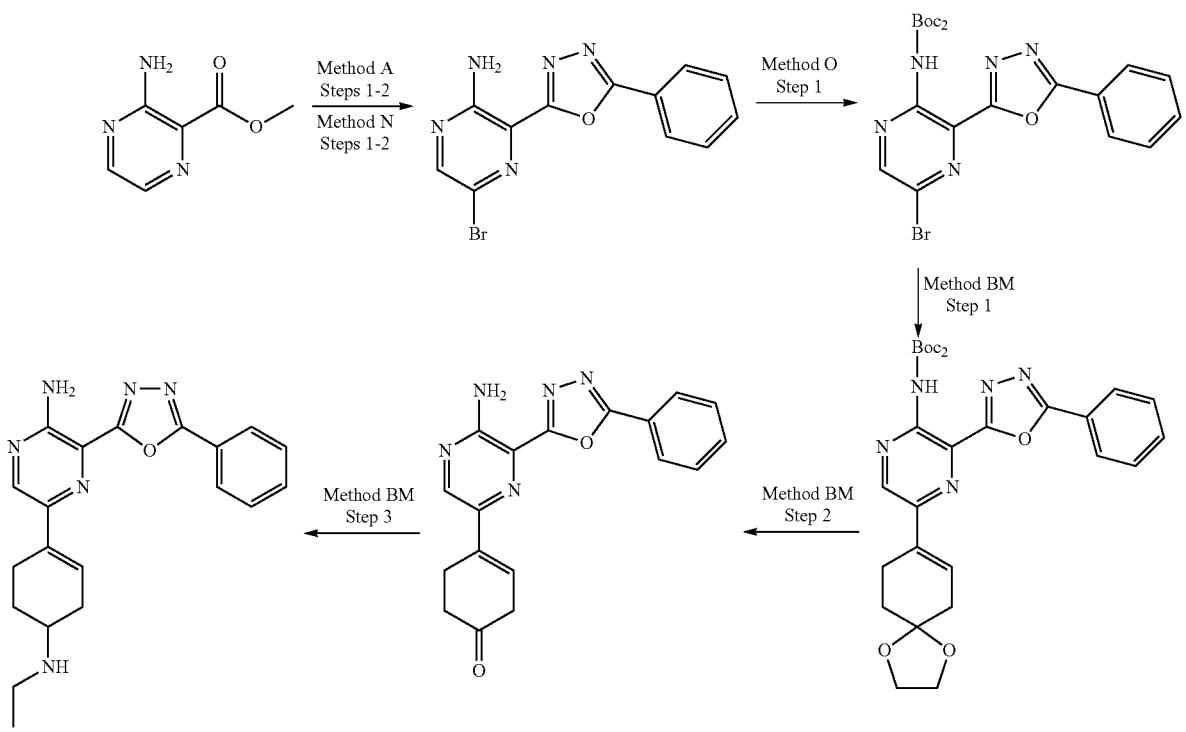

triethylamine (28 mg, 38 µL, 0.27 mmol) and 3-(1H-benzimidazol-2-yl)-5-(1,2,3,6-tetrahydropyridin-4-yl)pyrazin-2-amine (20 mg, 0.07 mmol) at room temperature. The reaction mixture was stirred at room temperature for 18 h and then partitioned between EtOAc and water. The aqueous layer was extracted with EtOAc, dried ($Na_2SO_4$), filtered and concentrated. To the crude material was added 1:1 DCM:TFA (3 ml) and it was stirred for 1 h. The solvents were evaporated under reduced pressure and the crude material obtained was dissolved in DMSO and purified by reverse phase chromatography using 1-99% MeOH in $H_2O$ (0.05% HCl modifier) to obtain 1-(4-(5-amino-6-(1H-benzo[d]imidazol-2-yl)pyrazin-2-yl)-5,6-dihydropyridin-1(2H)-yl)-3-(methylamino)propan-1-one (2 mg, 7%). $^1$H NMR (400 MHz, MeOD) δ 8.31 (d, J=15.9 Hz, 1H), 7.81 (dd, J=6.1, 3.1 Hz, 2H), 7.52 (dd, J=6.0, 3.1 Hz, 2H), 6.88 (d, J=20.4 Hz, 1H), 4.33 (dd, J=13.5, 2.6 Hz, 2H), 3.85 (dt, J=39.3, 5.6 Hz, 2H), 2.95 (dt, J=24.1, 6.0 Hz, 2H), 2.82 (s, 1H), 2.75 (s, 4H). LC/MS m/z 378.0 [M+H]$^+$.

Compound I-338 was prepared using the method described for Compound I-346 in Example 34 above.

Compound I-338 3-amino-1-(4-(5-amino-6-(1H-benzo[d]imidazol-2-yl)pyrazin-2-yl)-5,6-dihydropyridin-1(2H)-yl)propan-1-one. $^1$H NMR (400 MHz, MeOD) δ 8.26 (d, J=16.6 Hz, 1H), 7.68 (dd, J=5.9, 3.2 Hz, 2H), 7.31 (dd, J=6.0, 3.1 Hz, 2H), 6.73 (d, J=36.2 Hz, 1H), 4.30 (dd, J=22.0, 2.6 Hz, 2H), 3.84 (dt, J=44.5, 5.7 Hz, 2H), 3.25-3.20 (m, 2H), 2.93-2.72 (m, 4H). LC/MS m/z 364.5 [M+H]$^+$.

Compound I-314 was prepared using Method A, Steps 1-2 followed by Method N, Step 1-2 followed by Method O, Step 1, followed by Method BM, Steps 1-3.

Method BM: Step 1: tert-Butyl N-tert-butoxycarbonyl-N-[5-(1,4-dioxaspiro[4.5]dec-7-en-8-yl)-3-(5-phenyl-1,3,4-oxadiazol-2-yl)pyrazin-2-yl]carbamate.

A solution of tert-butyl N-[5-bromo-3-(5-phenyl-1,3,4-oxadiazol-2-yl)pyrazin-2-yl]-N-tert-butoxycarbonyl-carbamate (250 mg, 0.48 mmol), 2-(1,4-dioxaspiro[4.5]dec-7-en-8-yl)-4,4,5,5-tetramethyl-1,3,2-dioxaborolane (128 mg, 0.48 mmol), 4-ditert-butylphosphanyl-N,N-dimethylaniline; dichloropalladium (3.5 mg, 0.005 mmol) and $K_2CO_3$ (133 mg, 0.96 mmol) in toluene (2 mL) and water (250.0 µL) was heated to 80° C. for 18 h. The reaction mixture was cooled to room temperature and diluted with DCM (30 ml) and water (30 ml). The layers were separated and the organic layer was washed with 1M NaOH solution, dried ($Na_2SO_4$), filtered and concentrated. The crude material was purified via silica gel column chromatography using 0-30% EtOAc/Hexanes to obtain tert-butyl N-tert-butoxycarbonyl-N-[5-(1,4-dioxaspiro[4.5]dec-7-en-8-yl)-3-(5-phenyl-1,3,4-oxadiazol-2-yl)pyrazin-2-yl]carbamate (180 mg, 65%) as a yellow solid. LC/MS m/z 478.26 [M+H-Boc]$^+$.

Method BM: Step 2: 4-[5-Amino-6-(5-phenyl-1,3,4-oxadiazol-2-yl)pyrazin-2-yl]cyclohex-3-en-1-one.

A solution of tert-butyl N-tert-butoxycarbonyl-N-[5-(1,4-dioxaspiro[4.5]dec-7-en-8-yl)-3-(5-phenyl-1,3,4-oxadiazol- 2-yl)pyrazin-2-yl]carbamate in (40 mg, 0.069 mmol) AcOH (832 mg, 788 μL, 13.85 mmol) and H$_2$O (50 mg, 50 μL, 2.8 mmol) was heated at 80° C. for 2 h. The reaction mixture was diluted with 10 ml of EtOAc and pH was adjusted to 8 with 1N NaOH. The reaction mixture was washed with 20 ml of NaHCO$_3$. The layers were separated and the organic layer was washed with brine, dried over Na$_2$SO$_4$, filtered and concentrated to obtain 4-[5-amino-6-(5-phenyl-1,3,4-oxadiazol-2-yl)pyrazin-2-yl]cyclohex-3-en-1-one (19 mg, 82%), which was used as crude for the next step. LC/MS m/z 334.0 [M+H]$^+$.

Method BM: Step 3: 5-[4-(Ethylamino)cyclohexen-1-yl]-3-(5-phenyl-1,3,4-oxadiazol-2-yl)pyrazin-2-amine To a solution of 4-[5-amino-6-(5-phenyl-1,3,4-oxadiazol-2-yl)pyrazin-2-yl]cyclohex-3-en-1-one (15 mg, 0.045 mmol) in DCE (500 μL) was added a solution of ethaneamine (34 μL, of 2 M, 0.07 mmol) in THF and the reaction mixture was stirred for 5 min. Thereafter Na(OAc)$_3$BH (15 mg, 0.07 mmol) was added followed by addition of AcOH (3 mg, 3 μL, 0.05 mmol) and the reaction mixture was stirred for 2 h at room temperature. The crude material was dissolved in DMSO and purified via reverse phase HPLC using 1-99 MeOH/H2O (0.05% HCl modifier) to obtain 5-[4-(ethylamino)cyclohexen-1-yl]-3-(5-phenyl-1,3,4-oxadiazol-2-yl)pyrazin-2-amine (2 mg, 9%) as yellow solid. $^1$H NMR (400 MHz, DMSO-d$_6$) δ 8.84 (s, 1H), 8.56 (s, 1H), 8.12 (d, J=7.9 Hz, 2H), 7.68 (d, J=7.0 Hz, 3H), 7.60 (s, 1H), 6.58 (s, 1H), 3.05 (dd, J=13.2, 6.6 Hz, 2H), 2.76 (m, 3H), 2.38 (m, 1H), 2.27 (d, J=10.9 Hz, 1H), 1.78 (m, 1H), 1.26 (t, J=7.2 Hz, 3H). LC/MS m/z 363.05 [M+H]$^+$.

Example 36

Ethyl 2-(5-amino-6-(5-phenyl-1,3,4-oxadiazol-2-yl)pyrazin-2-yl)cyclopropanecarboxylate (Compound I-337)

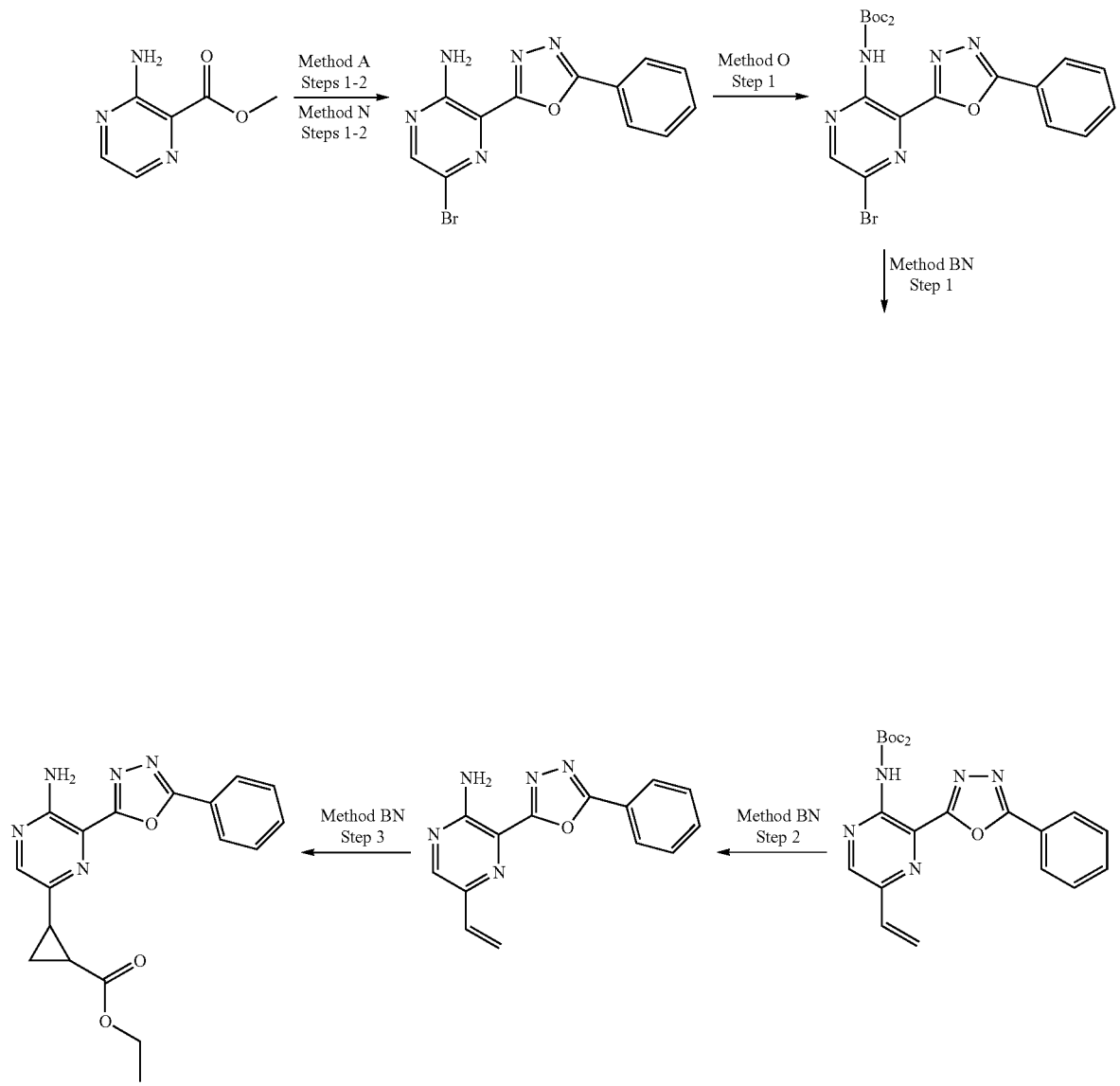

Compound I-337 was prepared using Method A, Steps 1-2 followed by Method N, Step 1-2 followed by Method O, Step 1, followed by Method BN, Steps 1-3.

Method BN: Step 1: tert-Butyl N-tert-butoxycarbonyl-N-[3-(5-phenyl-1,3,4-oxadiazol-2-yl)-5-vinyl-pyrazin-2-yl]carbamate To a solution of tert-butyl N-[5-bromo-3-(5-phenyl-1,3,4-oxadiazol-2-yl)pyrazin-2-yl]-N-tert-butoxycarbonyl-carbamate (500 mg, 0.96 mmol) in toluene (2 mL) and ethanol (2 mL) was added pyridine; 2,4,6-trivinyl-1,3,5,2,4,6-trioxatriborinane (290 mg, 1.2 mmol), $K_2CO_3$ (533 mg, 4 mmol) and $Pd(PPh_3)_4$ (112 mg, 0.1 mmol). The reaction mixture was heated at 60° C. under an atmosphere of nitrogen for 1 h. The reaction mixture was filtered, concentrated and the crude material obtained was purified via silica gel column chromatography using EtOAc/hex gradient to obtain tert-butyl N-tert-butoxycarbonyl-N-[3-(5-phenyl-1,3,4-oxadiazol-2-yl)-5-vinyl-pyrazin-2-yl]carbamate (449 mg, 100%).

Method BN: Step 2: 3-(5-Phenyl-1,3,4-oxadiazol-2-yl)-5-vinyl-pyrazin-2-amine.

To a solution of tert-butyl N-tert-butoxycarbonyl-N-[3-(5-phenyl-1,3,4-oxadiazol-2-yl)-5-vinyl-pyrazin-2-yl]carbamate (138 mg, 0.3 mmol) in DCM (0.7 mL) at room temperature under an atmosphere of $N_2$ was added TFA (338 mg, 228 μL, 3 mmol) and reaction mixture was stirred for 20 minutes. The reaction mixture was diluted with DCM and slowly quenched with satd. $NaHCO_3$. The layers were separated and the organic layer was dried over $Na_2SO_4$, filtered and concentrated to yield 3-(5-phenyl-1,3,4-oxadiazol-2-yl)-5-vinyl-pyrazin-2-amine (67 mg, 85%) as a yellow solid. LC/MS m/z 266.4 [M+H]+.

Method BN: Step 3: Ethyl 2-[5-amino-6-(5-phenyl-1,3,4-oxadiazol-2-yl)pyrazin-2-yl]cyclopropanecarboxylate.

To a vial charged with 3-(5-phenyl-1,3,4-oxadiazol-2-yl)-5-vinyl-pyrazin-2-amine (26 mg, 0.01 mmol) under an atmosphere of nitrogen at room temperature was slowly added a solution of ethyl 2-diazoacetate (34 mg, 31 μL, 0.1 mmol) in toluene (350 μL) over a period of 10 min. The reaction mixture was heated at 110° C. for 1 h. The reaction mixture was cooled to room temperature and the solvent was removed under reduced pressure. The crude material was dissolved in DMSO (1 mL), filtered and purified via reverse phase column chromatography using 10 to 99% MeOH—$H_2O$ (TFA modifier) to obtain ethyl 2-[5-amino-6-(5-phenyl-1,3,4-oxadiazol-2-yl)pyrazin-2-yl]cyclopropanecarboxylate. $^1$H NMR (400.0 MHz, $CDCl_3$) δ 8.23-8.15 (m, 3H), 7.59-7.50 (m, 3H), 4.19 (q, J=7.1 Hz, 2H), 2.64 (dd, J=6.2, 12.7 Hz, 1H), 2.25 (dd, J=5.5, 12.4 Hz, 1H), 1.66-1.61 (m, 2H) and 1.39-1.24 (m, 3H) ppm; LC/MS m/z 352.2 [M+H]+.

Example 37

3-(5-Phenyl-1,3,4-oxadiazol-2-yl)-5-(2,7-diazaspiro[4.4]nonan-2-yl)pyrazin-2-amine (Compound I-340)

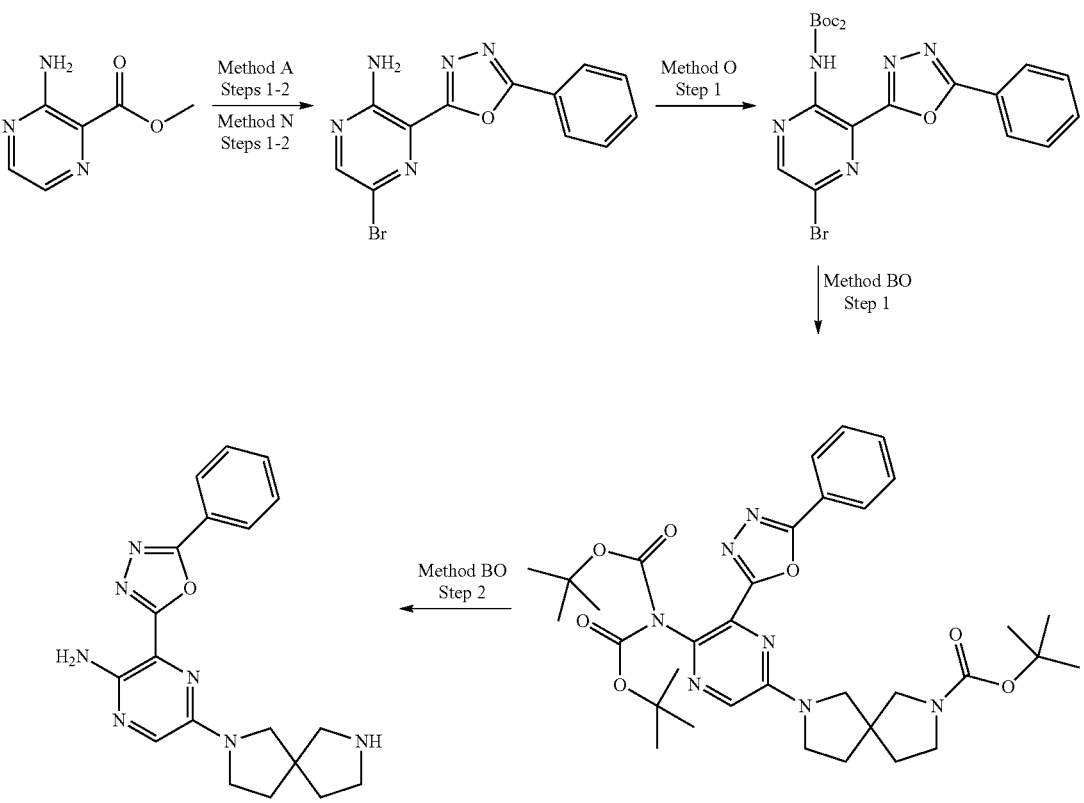

Compound I-340 was prepared using Method A, Steps 1-2 followed by Method N, Steps 1-2 followed by Method O, Step 1, followed by Method BO Steps 1-2.

Method BO: Step 1: tert-Butyl 7-[5-[bis(tert-butoxycarbonyl)amino]-6-(5-phenyl-1,3,4-oxadiazol-2-yl)pyrazin-2-yl]-3,7-diazaspiro[4.4]nonane-3-carboxylate.

A mixture of tert-butyl N-[5-bromo-3-(5-phenyl-1,3,4-oxadiazol-2-yl)pyrazin-2-yl]-N-tert-butoxycarbonyl-carbamate (70 mg, 0.14 mmol), tert-butyl 3,7-diazaspiro[4.4]nonane-3-carboxylate (31 mg, 0.14 mmol) and DIEA (35 mg, 47 μL, 0.27 mmol) in DMF (1 mL) was heated at 90° C. for 2 h. The reaction mixture was allowed to cool to room temperature and diluted with EtOAc. The organic layer was washed with brine (2×), dried over $Na_2SO_4$, filtered and concentrated under reduced pressure. The crude material was purified by flash chromatography using 0-35% EtOAc in hexanes to yield tert-butyl 7-[5-[bis(tert-butoxycarbonyl)amino]-6-(5-phenyl-1,3,4-oxadiazol-2-yl)pyrazin-2-yl]-3,7-diazaspiro[4.4]nonane-3-carboxylate (56 mg, 62%) as a yellow solid. $^1$H NMR (400 MHz, DMSO-$d_6$) δ 8.15-8.04 (m, 3H), 7.71-7.60 (m, J=7.5 Hz, 3H), 3.74-3.62 (m, 2H), 3.59-3.53 (m, 2H), 3.39 (s, 2H), 2.89 (s, 1H), 2.73 (s, 1H), 2.10-1.99 (m, 2H), 1.98-1.84 (m, 2H), 1.41 (d, J=7.3 Hz, 9H), 1.29 (s, 18H). LC/MS m/z 664.7 [M+H]$^+$.

Method BO: Step 2: 3-(5-Phenyl-1,3,4-oxadiazol-2-yl)-5-(2,7-diazaspiro[4.4]nonan-2-yl)pyrazin-2-amine tert-Butyl 7-[5-[bis(tert-butoxycarbonyl)amino]-6-(5-phenyl-1,3,4-oxadiazol-2-yl)pyrazin-2-yl]-3,7-diazaspiro[4.4]nonane-3-carboxylate (50.9 mg, 0.07668 mmol) was treated with a solution of hydrogen chloride (192 μL, of 4 M, 0.77 mmol) in dioxane. The reaction mixture was stirred for 2 h at room temperature. The solvent was removed under reduced pressure and the residue was dissolved in DMF and purified by reverse phase HPLC using (1-99% ACN/$H_2O$ (5 mM HCl)) to yield 3-(5-phenyl-1,3,4-oxadiazol-2-yl)-5-(2,7-diazaspiro[4.4]nonan-2-yl)pyrazin-2-amine. $^1$H NMR (400 MHz, DMSO-$d_6$) δ 9.34 (s, 2H), 8.25-7.99 (m, 2H), 7.89 (s, 1H), 7.66 (d, J=6.6 Hz, 3H), 3.60-3.47 (m, 4H); 3.36-3:25 (m, 2H), 3.18 (tt, J=12.1, 6.0 Hz, 2H), 2.19-1.83 (m, J=17.8, 12.7, 5.9 Hz, 4H); LC/MS m/z 364.1 [M+H]$^+$.

The following compounds were all prepared using the method described for Compound I-340 in Example 37 above.

Compound I-318: (3aR,6aS)-2-[5-Amino-6-(5-phenyl-1,3,4-oxadiazol-2-yl)pyrazin-2-yl]-3,3a,4,5,6,6a-hexahydro-1H-cyclopenta[c]pyrrol-6-ol. LC/MS m/z 365.1 [M+H]$^+$.

Example 38

(3aS,6aR)-2-(5-Amino-6-(5-phenyl-1,3,4-oxadiazol-2-yl)pyrazin-2-yl)hexahydrocyclopenta[c]pyrrol-4(5H)-one (Compound I-319)

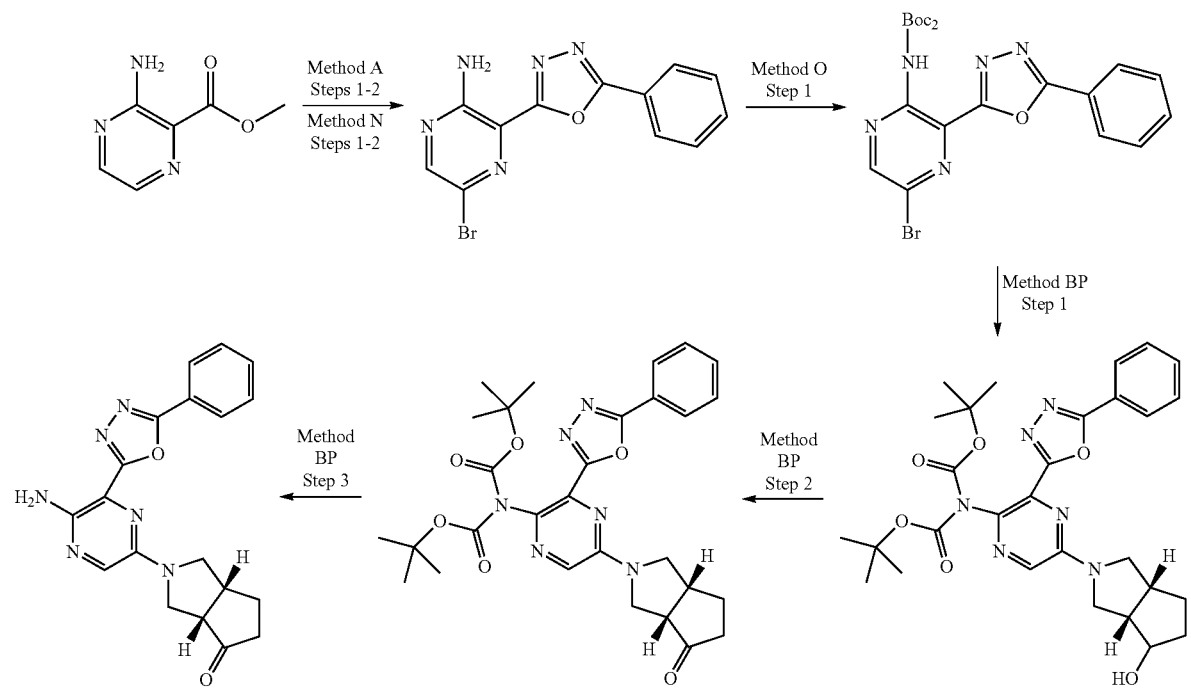

Compound I-319 was prepared using Method A, Steps 1-2 followed by Method N, Steps 1-2 followed by Method O, Step 1, followed by Method BP Steps 1-3.

Method BP: Step 1: tert-Butyl N-[5-[(3aR,6aS)-6-hydroxy-3,3a,4,5,6,6a-hexahydro-1H-cyclopenta[c]pyrrol-2-yl]-3-(5-phenyl-1,3,4-oxadiazol-2-yl)pyrazin-2-yl]-N-tert-butoxycarbonyl-carbamate A solution of tert-butyl N-[5-bromo-3-(5-phenyl-1,3,4-oxadiazol-2-yl)pyrazin-2-yl]-N-tert-butoxycarbonyl-carbamate (115 mg, 0.22 mmol), (3aS,6aR)-1,2,3,3a,4,5,6,6a-octahydrocyclopenta[c]pyrrol-4-ol (73 mg, 0.57 mmol) and triethyl amine (34 mg, 46 μL, 0.33 mmol) in DMF was heated to 90° C. for 90 minutes. The solvent was removed under reduced pressure and the crude material was purified by silica gel column chromatography using 5-60% EtOAc in DCM to yield tert-butyl N-[5-[(3aR,6aS)-6-hydroxy-3,3a,4,5,6,6a-hexahydro-1H-cyclopenta[c]pyrrol-2-yl]-3-(5-phenyl-1,3,4-oxadiazol-2-yl)pyrazin-2-yl]-N-tert-butoxycarbonyl-carbamate (104 mg, 83%). LC/MS m/z 465.5 [M+H-Boc]⁺.

Method BP: Step 2: tert-Butyl N-[5-[(3aR,6aS)-6-oxo-1,3,3a,4,5,6a-hexahydrocyclopenta[c]pyrrol-2-yl]-3-(5-phenyl-1,3,4-oxadiazol-2-yl)pyrazin-2-yl]-N-tert-butoxycarbonyl-carbamat A solution of tert-butyl N-[5-[(3aR,6aS)-6-hydroxy-3,3a,4,5,6,6a-hexahydro-1H-cyclopenta[c]pyrrol-2-yl]-3-(5-phenyl-1,3,4-oxadiazol-2-yl)pyrazin-2-yl]-N-tert-butoxycarbonyl-carbamate (104 mg, 0.18 mmol) in DCM (1 mL) at 0° C. was treated with a solution of Dess-Martin periodinane (921 µL 0.3 M, 0.28 mmol) in DCM. The reaction mixture was warmed to room temperature and stirred overnight. The solvent was evaporated under reduced pressure and the crude material was purified by silica gel column chromatography using 5-60% EtOAc in DCM to yield tert-butyl N-[5-[(3aR,6aS)-6-oxo-1,3,3a,4,5,6a-hexahydrocyclopenta[c]pyrrol-2-yl]-3-(5-phenyl-1,3,4-oxadiazol-2-yl)pyrazin-2-yl]-N-tert-butoxycarbonyl-carbamate (57 mg, 55%) as a yellow solid. LC/MS m/z 463.5 [M+H-Boc]⁺.

Method BP: Step 3: (3aR,6aS)-2-[5-phenyl-1,3,4-oxadiazol-2-yl)pyrazin-2-yl]-1,3,3a,4,5,6a-hexahydrocyclopenta[c]pyrrol-6-one A solution of tert-butyl N-[5-[(3aR,6aS)-6-oxo-1,3,3a,4,5,6a-hexahydrocyclopenta[c]pyrrol-2-yl]-3-(5-phenyl-1,3,4-oxadiazol-2-yl)pyrazin-2-yl]-N-tert-butoxycarbonyl-carbamate (57 mg, 0.10 mmol) in DCM (1 mL) was treated with TFA (1.5 g, 1 mL, 13 mmol) The reaction mixture was stirred at room temperature for 1 h. The solvents were evaporated and the residue was dissolved in DMF and purified by reverse phase column chromatography to obtain (3aR,6aS)-2-[5-amino-6-(5-phenyl-1,3,4-oxadiazol-2-yl)pyrazin-2-yl]-1,3,3a,4,5,6a-hexahydrocyclopenta[c]pyrrol-6-one. LC/MS m/z 363.1 [M+H]⁺

Example 39

1-(7-(5-Amino-6-(5-(4-((methylamino)methyl)phenyl)-1,3,4-oxadiazol-2-yl)pyrazin-2-yl)-2,7-diazaspiro[4.4]nonan-2-yl)propan-1-one (Compound I-342)

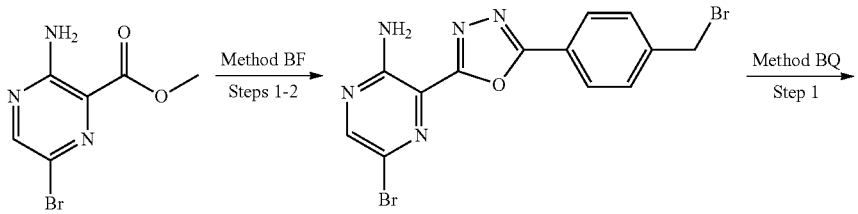

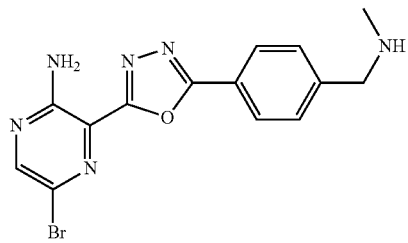

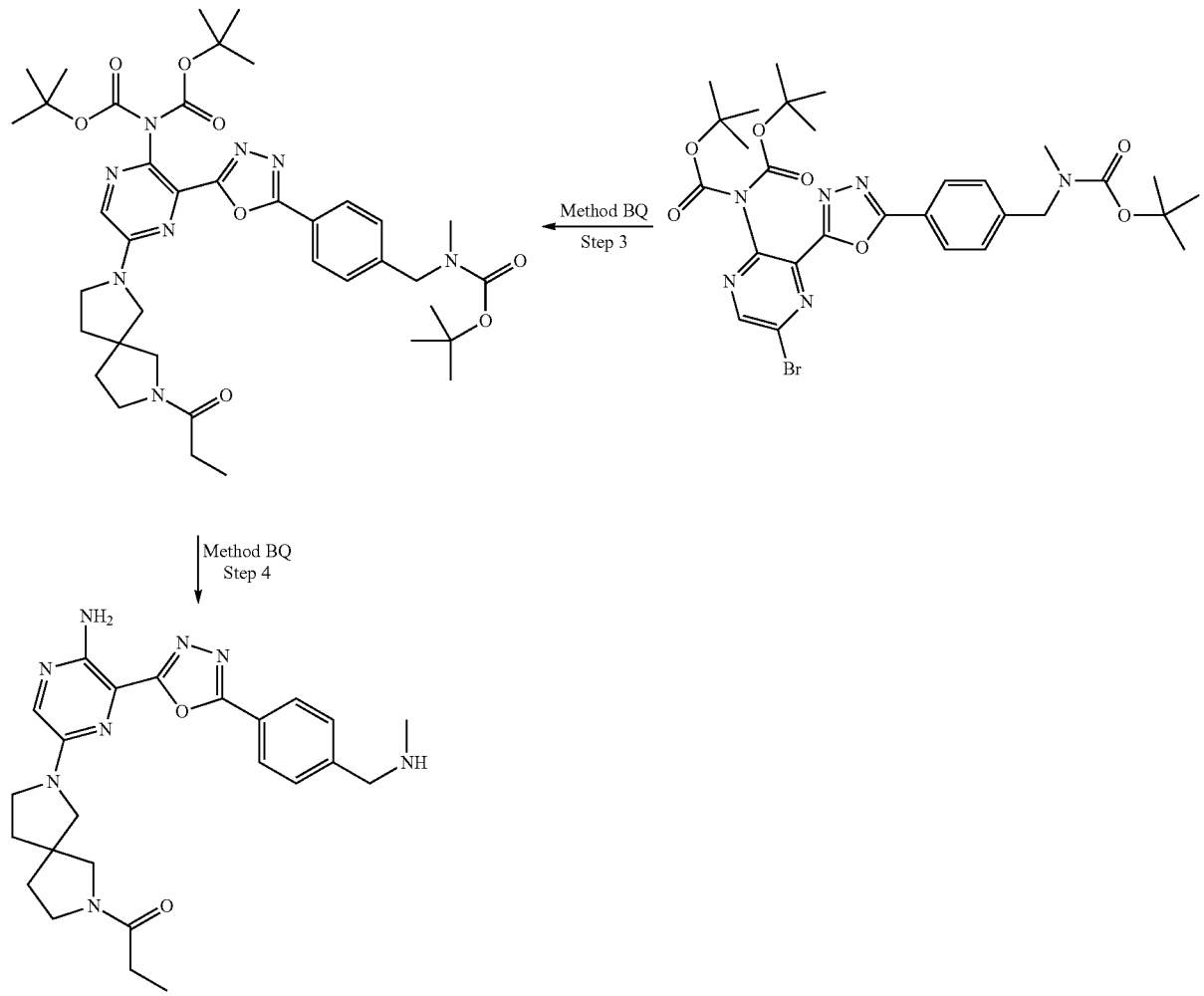

Compound I-342 was prepared using Method BF, Steps 1-2 followed by Method BQ, Steps 1-4

Method BQ: Step 1: 5-Bromo-3-(5-(4-((methylamino)methyl)phenyl)-1,3,4-oxadiazol-2-yl)pyrazin-2-amine A suspension of 5-bromo-3-[5-[4-(bromomethyl)phenyl]-1,3,4-oxadiazol-2-yl]pyrazin-2-amine (2 g, 4.9 mmol) and Na$_2$CO$_3$ (1.55 g, 14.60 mmol) in tetrahydrofuran (30 mL) was treated with methanamine (3.6 mL of 2 M, 7.3 mmol) in THF. The reaction mixture was heated at 60° C. for 1 h. The reaction was cooled, diluted with water and the organic layer was extracted with dichloromethane. The organic layer was dried over Na$_2$SO$_4$, filtered and concentrated in vacuo to yield 5-bromo-3-(5-(4-((methylamino)methyl)phenyl)-1,3,4-oxadiazol-2-yl)pyrazin-2-amine (1.7 g, 97%) as a yellow solid, which was used without purification in the next step. LC/MS m/z 363.5 [M+H]$^+$.

Method BQ: Step 2: tert-Butyl N-[[4-[5-[3-[bis(tert-butoxycarbonyl)amino]-6-bromo-pyrazin-2-yl]-1,3,4-oxadiazol-2-yl]phenyl]methyl]-N-methyl-carbamate To a solution of 5-bromo-3-(5-(4-((methylamino)methyl)phenyl)-1,3,4-oxadiazol-2-yl)pyrazin-2-amine (2.1 g, 5.8 mmol) and DMAP (71 mg, 0.58 mmol) in tetrahydrofuran (62 mL) was added a solution of tert-butoxycarbonyl tert-butyl carbonate (6.3 g, 6.7 mL, 29 mmol) in tetrahydrofuran (12 mL). The reaction mixture was heated at 45° C. for 16 h, cooled to room temperature and concentrated in vacuo. The crude material was purified using silica gel column chromatography (10-40% ethyl acetate/hexane) to obtain tert-butyl N-[[4-[5-[3-[bis(tert-butoxycarbonyl)amino]-6-bromo-pyrazin-2-yl]-1,3,4-oxadiazol-2-yl]phenyl]methyl]-N-methyl-carbamate (2.6 g, 67% yield) as a white foam. $^1$H NMR (400 MHz, DMSO-d$_6$) δ 9.15 (s, 1H), 8.12 (d, J=8.1 Hz, 2H), 7.50 (d, J=8.1 Hz, 2H), 4.50 (s, 2H), 2.84 (s, 3H), 1.28 (s, 27H). LC/MS m/z 663.5 [M+H]$^+$.

Method BQ: Step 3: tert-Butyl N-[[4-[5-[3-[bis(tert-butoxycarbonyl)amino]-6-(3-propanoyl-3,7-diazaspiro[4.4]nonan-7-yl)pyrazin-2-yl]-1,3,4-oxadiazol-2-yl]phenyl]methyl]-N-methyl-carbamate To a solution of tert-butyl N-[[4-[5-[3-[bis(tert-butoxycarbonyl)amino]-6-bromo-pyrazin-2-yl]-1,3,4-oxadiazol-2-yl]phenyl]methyl]-N-methyl-carbamate (153 mg, 0.23 mmol) and 1-(3,7-diazaspiro[4.4]nonan-3-yl)propan-1-one (101 mg, 0.46 mmol) in DMF (2 mL) was added Et$_3$N (70 mg, 97 µL, 0.70 mmol). The reaction vessel was sealed and heated at 90° C. for 40 minutes. The reaction mixture was cooled to room temperature, diluted with EtOAc and washed with brine (2×). The organic layer was dried over Na$_2$SO$_4$, filtered and concentrated under reduced pressure. The crude material was purified by silica gel column chromatography using 0-60% EtOAc in DCM to yield tert-butyl N-[[4-[5-[3[bis(tert-butoxycarbonyl)amino]-6-(3-propanoyl-3,7-diazaspiro[4.4]nonan-7-yl)pyrazin-2-yl]-1,3,4-oxadiazol-2-yl]phenyl]methyl]-N-methyl-carbamate (133 mg, 75%). LC/MS m/z 763.9 [M+H]$^+$.

Method BQ: Step 4: 1-(7-(5-Amino-6-(5-(4-((methylamino)methyl)phenyl)-1,3,4-oxadiazol-2-yl)pyrazin-2-yl)-2,7-diazaspiro[4.4]nonan-2-yl)propan-1-one A solution of tert-butyl N-[[4-[5-[3-[bis(tert-butoxycarbonyl)amino]-6-(3-propanoyl-3,7-diazaspiro[4.4]nonan-7-yl)pyrazin-2-yl]-1,3,4-oxadiazol-2-yl]phenyl]methyl]-N-methyl-carbamate (129 mg, 0.17 mmol) in dioxane (0.3 mL) was treated with a solution of hydrogen chloride (423 µL of 4 M, 1.7 mmol) in dioxane and the reaction mixture was allowed to stir for 40 minutes. The solvents were removed under reduced pressure and the residue was dissolved in DMF (1 mL) and purified by reverse phase HPLC using (10-99% ACN/H$_2$O (5 mM HCl modifier)) to yield 1-(7-(5-amino-6-(5-(4-((methylamino)methyl)phenyl)-1,3,4-oxadiazol-2-yl)pyrazin-2-yl)-2,7-diazaspiro[4.4]nonan-2-yl)propan-1-one. $^1$H NMR (400 MHz, DMSO-d$_6$) d 9.44 (s, 2H), 8.13 (dd, J=8.3, 2.4 Hz, 2H), 7.91 (t, J=4.5 Hz, 1H), 7.81 (d, J=7.5 Hz, 2H), 4.26-4.20 (m, 2H), 3.58 (dt, J=13.6, 6.8 Hz, 3H), 3.51-3.29 (m, 5H), 2.57 (t, J=5.3 Hz, 3H), 2.24 (dt, J=15.1, 7.5 Hz, 2H), 1.94 (ddt, J=32.7, 13.2, 6.6 Hz, 4H), 0.99 (dd, J=16.5, 7.5 Hz, 3H). LC/MS m/z 463.5 [M+H]$^+$.

The following compounds were all prepared using the method described for Compound I-342 in Example 39 above.

Compound I-332: 5-(2-Ethylsulfonyl-1,3,3a,4,6,6a-hexahydropyrrolo[3,4-c]pyrrol-5-yl)-3-[5-[4-(methylaminomethyl)phenyl]-1,3,4-oxadiazol-2-yl]pyrazin-2-amine. $^1$H NMR (400 MHz, DMSO-d$_6$) d 9.57 (d, J=4.9 Hz, 2H), 8.13 (d, J=8.2 Hz, 2H), 7.95 (s, 1H), 7.83 (d, J=8.2 Hz, 2H), 4.23 (t, J=5.8 Hz, 2H), 3.65 (dd, J=10.2, 6.9 Hz, 2H), 3.58 (dd, J=9.8, 7.2 Hz, 2H), 3.43 (dd, J=10.5, 3.0 Hz, 2H), 3.21 (dd, J=10.0, 3.7 Hz, 2H), 3.13 (dt, J=11.0, 5.5 Hz, 4H), 2.57 (t, J=5.3 Hz, 3H), 1.22 (t, J=7.4 Hz, 3H). LC/MS m/z 485.5 [M+H]$^+$.

Compound I-330: 5-(3-Ethylsulfonyl-3,7-diazaspiro[4.4]nonan-7-yl)-3-[5-[4-(methylaminomethyl)phenyl]-1,3,4-oxadiazol-2-yl]pyrazin-2-amine. $^1$H NMR (400 MHz, DMSO-d$_6$) d 9.45 (s, 2H), 8.13 (d, J=8.1 Hz, 2H), 7.91 (s, 1H), 7.81 (d, J=8.0 Hz, 2H), 4.26-4.21 (m, 2H), 3.58 (t, J=6.9 Hz, 2H), 3.54-3.46 (m, 2H), 3.44 (t, J=6.8 Hz, 2H), 3.30 (q, J=9.6 Hz, 2H), 3.16 (q, J=7.3 Hz, 2H), 2.57 (t, J=5.2 Hz, 3H), 2.09-1.90 (m, 4H), 1.23 (dd, J=13.1, 5.7 Hz, 3H). LC/MS m/z 499.2 [M+H]$^+$.

Compound I-329: 1-[4-[5-Amino-6-[5-[4-(methylaminomethyl)phenyl]-1,3,4-oxadiazol-2-yl]pyrazin-2-yl]-2,2-dimethyl-piperazin-1-yl]propan-1-one. $^1$H NMR (400 MHz, DMSO-d$_6$) δ 9.34 (s, 2H), 8.14 (d, J=7.8 Hz, 3H), 7.80 (d, J=8.2 Hz, 2H), 4.24 (t, J=5.8 Hz, 2H), 3.81-3.76 (m, 2H), 3.71 (s, 2H), 3.62 (t, J=5.3 Hz, 2H), 2.58 (t, J=5.3 Hz, 3H), 2.34 (q, J=7.4 Hz, 2H), 1.43 (s, 6H), 0.98 (t, J=7.3 Hz, 3H). LC/MS m/z 451.5 [M+H]$^+$.

Compound I-328: 5-(4-Ethylsulfonyl-3,3-dimethyl-piperazin-1-yl)-3-[5-[4-(methylaminomethyl)phenyl]-1,3,4-oxadiazol-2-yl]pyrazin-2-amine. $^1$H NMR (400 MHz, DMSO-d$_6$) δ 9.15 (s, 2H), 8.27 (s, 1H), 8.17 (d, J=8.1 Hz, 2H), 7.77 (d, J=8.2 Hz, 2H), 4.25 (t, J=5.7 Hz, 2H), 3.60-3.54 (m, 4H, partially obscured by H$_2$O peak), 3.44 (s, 2H, partially obscured by H$_2$O peak), 3.14 (q, J=7.3 Hz, 2H), 2.60 (t, J=5.2 Hz, 3H), 1.48 (s, 6H), 1.24 (t, J=7.3 Hz, 3H). LC/MS m/z 487.3 [M+H]$^+$ Compound I-344: 8-[5-Amino-6-[5-[4-(methylaminomethyl)phenyl]-1,3,4-oxadiazol-2-yl]pyrazin-2-yl]-2-methyl-2,8-diazaspiro[4.5]decan-1-one. $^1$H NMR (400 MHz, DMSO-d$_6$) δ 9.29 (s, 2H), 8.28 (s, 1H), 8.14 (d, J=8.2 Hz, 2H), 7.78 (d, J=8.2 Hz, 2H), 4.24 (s, 2H), 4.10 (d, J=12.8 Hz, 2H), 3.32 (t, J=6.8 Hz, 2H), 3.00 (t, J=12.4 Hz, 2H), 2.75 (s, 3H), 2.58 (t, J=4.8 Hz, 3H), 2.00 (t, J=6.8 Hz, 2H), 1.77 (t, J=11.5 Hz, 2H), 1.47 (d, J=13.2 Hz, 2H). LC/MS m/z 449.5 [M+H]$^+$.

Compound I-341: 5-(8-Ethylsulfonyl-3,8-diazabicyclo[3.2.1]octan-3-yl)-3-[5-[4-(methylaminomethyl)phenyl]-1,3,4-oxadiazol-2-yl]pyrazin-2-amine. $^1$H NMR (400 MHz, DMSO-d$_6$) δ 9.25 (s, 2H), 8.16 (d, J=8.3 Hz, 3H), 7.78 (d, J=8.2 Hz, 2H), 4.32 (s, 2H), 4.25 (t, J=5.7 Hz, 2H), 3.99 (d, J=10.5 Hz, 2H), 3.19 (q, J=7.1 Hz, 2H), 3.02 (d, J=11.3 Hz, 2H), 2.59 (t, J=5.2 Hz, 3H), 1.98-1.87 (m, 2H), 1.87-1.78 (m, 2H), 1.25 (t, J=7.2 Hz, 3H). LC/MS m/z 485.5 [M+H]$^+$.

Compound I-334: 1-[(1S,4R)-2-[5-Amino-6-[5-[4-(methylaminomethyl)phenyl]-1,3,4-oxadiazol-2-yl]pyrazin-2-yl]-2,5-diazabicyclo[2.2.1]heptan-5-yl]propan-1-one. $^1$H NMR (400 MHz, MeOD) δ 8.27 (d, J=8.1 Hz, 2H), 7.86 (s, 1H), 7.77 (d, J=8.2 Hz, 2H), 5.09-4.94 (m, 2H), 4.33 (s, 2H), 3.82-3.64 (m, 2H), 3.63-3.44 (m, 2H), 2.79 (s, 3H), 2.49 (ddd, J=45.5, 15.6, 7.7 Hz, 1H), 2.32-1.96 (m, 3H), 1.10 (dt, J=36.9, 7.5 Hz, 3H). LC/MS m/z 435.54 [M+H]$^+$.

Compound I-315: 1-[(2R)-4-[5-Amino-6-[5-[4-(methylaminomethyl)phenyl]-1,3,4-oxadiazol-2-yl]pyrazin-2-yl]-2-methyl-piperazin-1-yl]propan-1-one. $^1$H NMR (400 MHz, MeOD) δ 8.28 (d, J=8.2 Hz, 2H), 8.08 (s, 1H), 7.76 (d, J=8.2 Hz, 2H), 4.53-4.36 (m, 1H), 4.33 (s, 2H), 4.27-4.04 (m, 2H), 3.99-3.89 (m, 1H), 3.69-3.55 (m, 1H), 3.19 (d, J=11.7 Hz, 1H), 3.12-2.86 (m, 1H), 2.79 (s, 3H), 2.59-2.39 (m, 2H), 1.34 (d, J=41.1 Hz, 3H), 1.16 (t, J=7.1 Hz, 3H). LC/MS m/z 435.54 [M+H]$^+$.

Compound I-321: 5-Isoindolin-2-yl-3-[5-[4-(methylaminomethyl)phenyl]-1,3,4-oxadiazol-2-yl]pyrazin-2-amine. $^1$H NMR (400 MHz, DMSO-d$_6$) δ 9.44 (s, 2H), 8.17 (d, J=8.1 Hz, 2H), 8.05 (s, 1H), 7.83 (d, J=8.2 Hz, 2H), 7.45 (dd, J=5.3, 3.2 Hz, 2H), 7.33 (dd, J=5.5, 3.1 Hz, 2H), 4.84 (s, 4H), 4.25 (t, J=5.7 Hz, 2H), 2.59 (t, J=5.2 Hz, 31-I). LC/MS m/z 400.5 [M+H]$^+$.

Compound I-345: 5-[(3S)-4-Ethylsulfonyl-3-methyl-piperazin-1-yl]-3-[5-[4-(methylaminomethyl)phenyl]-1,3,4-oxadiazol-2-yl]pyrazin-2-amine. $^1$H NMR (400 MHz, DMSO-d$_6$) δ 9.25 (d, J=5.0 Hz, 2H), 8.28 (s, 1H), 8.17 (d, J=8.2 Hz, 2H), 7.78 (d, J=8.2 Hz, 2H), 4.25 (t, J=5.7 Hz, 2H), 4.17 (d, J=12.1 Hz, 1H), 4.09 (dd, J=8.4, 4.2 Hz, 1H), 4.01 (d, J=12.6 Hz, 1H), 3.40-3.30 (m, 2H), 3.21-3.09 (m, 2H), 3.09-

3.00 (m, 1H), 2.86 (td, J=12.0, 3.2 Hz, 1H), 2.59 (t, J=5.3 Hz, 3H), 1.31 (d, J=6.7 Hz, 3H), 1.23 (t, J=7.3 Hz, 3H). LC/MS m/z 473.3 [M+H]+.

Compound I-347: 1-[(2R)-4-[5-Amino-6-[5-[4-(methylaminomethyl)phenyl]-1,3,4-oxadiazol-2-yl]pyrazin-2-yl]-2-methyl-piperazin-1-yl]propan-1-one. 1H NMR (400 MHz, DMSO-d6) δ 9.32 (d, J=4.2 Hz, 2H), 8.28 (s, 1H), 8.16 (d, J=8.1 Hz, 2H), 7.79 (d, J=8.1 Hz, 2H), 4.44-4.29 (m, 1H), 4.25 (t, J=5.8 Hz, 2H), 4.21-4.11 (m, 1H), 4.02 (d, J=11.4 Hz, 1H), 3.90-3.76 (m, 2H), 2.99 (s, 2H), 2.90-2.64 (m, 1H), 2.59 (t, J=5.3 Hz, 3H), 2.43-2.22 (m, 2H), 1.27 (s, 1H), 1.22-1.09 (m, 1H), 1.02 (t, J=7.2 Hz, 3H). LC/MS m/z 438.34 [M+H]+.

Compound I-323: N-[[(3S)-1-[5-Amino-6-[5-[4-(methylaminomethyl)phenyl]-1,3,4-oxadiazol-2-yl]pyrazin-2-yl]pyrrolidin-3-yl]methyl]acetamide. 1H NMR (400 MHz, DMSO-d6) d 9.17 (s, 2H), 8.15 (d, J=8.0 Hz, 2H), 8.04 (t, J=5.5 Hz, 1H), 7.90 (s, 1H), 7.77 (d, J=8.2 Hz, 2H), 4.25 (t, J=5.9 Hz, 2H), 3.59 (dd, J=20.4, 10.2 Hz, 2H), 3.44 (dd, J=17.2, 7.3 Hz, 1H), 3.22-3.01 (m, 3H), 2.63-2.53 (m, 3H), 2.46-2.39 (m, 1H), 2.06 (dd, J=12.3, 5.4 Hz, 1H), 1.88 (d, J=26.8 Hz, 3H), 1.73 (dd, J=12.6, 7.1 Hz, 1H). LC/MS m/z 423.5 [M+H]+.

Compound I-317: N-[[(3R)-1-[5-Amino-6-[5-[4-(methylaminomethyl)phenyl]-1,3,4-oxadiazol-2-yl]pyrazin-2-yl]pyrrolidin-3-yl]methyl]acetamide. 1H NMR (400 MHz, DMSO-d6) d 9.06 (s, 2H), 8.15 (d, J=8.2 Hz, 2H), 8.04 (s, 1H), 7.90 (s, 1H), 7.76 (d, J=8.2 Hz, 2H), 4.25 (s, 2H), 3.58 (dd, J=20.3, 10.4 Hz, 2H), 3.44 (dd, J=17.0, 6.9 Hz, 1H), 3.14 (s, 3H), 2.60 (d, J=5.3 Hz, 3H), 2.33 (s, 1H), 2.06 (d, J=6.8 Hz, 1H), 1.84 (s, 3H), 1.73 (dd, J=11.9, 7.3 Hz, 1H). LC/MS m/z 423.5 [M+H]+.

Compound I-316: 3-[5-[4-(Methylaminomethyl)phenyl]-1,3,4-oxadiazol-2-yl]-5-(3-phenylpyrrolidin-1-yl)pyrazin-2-amine. LC/MS m/z 428.2 [M+H]+.

Compound I-322: 5-(4-Ethylpiperazin-1-yl)-3-[5-[4-(methylaminomethyl)phenyl]-1,3,4-oxadiazol-2-yl]pyrazin-2-amine. 1H NMR (400 MHz, DMSO-d6) δ 10.78 (s, 1H), 9.38 (s, 2H), 8.34 (s, 1H), 8.17 (d, J=8.2 Hz, 2H), 7.80 (d, J=8.2 Hz, 2H), 4.37-4.15 (m, 3H), 3.59 (d, J=12.5 Hz, 3H), 3.36-3.24 (m, 3H), 3.20-3.04 (m, 3H), 2.58 (t, J=5.3 Hz, 3H), 1.30 (t, J=7.2 Hz, 3H). LC/MS m/z 395.0 [M+H]+.

Compound I-327: 1-[4-[5-Amino-6-[5-[4-(methylaminomethyl)phenyl]-1,3,4-oxadiazol-2-yl]pyrazin-2-yl]piperazin-1-yl]propan-1-one. NMR (400 MHz, DMSO-d6) δ 9.33 (s, 2H), 8.27 (s, 1H), 8.16 (d, J=8.1 Hz, 2H), 7.80 (d, J=8.1 Hz, 2H), 4.24 (t, J=5.4 Hz, 2H), 3.62 (s, 4H), 3.46 (d, J=21.5 Hz, 4H), 2.58 (t, J=5.3 Hz, 3H), 2.39 (q, J=7.3 Hz, 2H), 1.02 (t, J=7.4 Hz, 3H). LC/MS m/z 423.5 [M+H]+.

Compound I-325: 5-(4-Ethylsulfonylpiperazin-1-yl)-3-[5-[4-(methylaminomethyl)phenyl]-1,3,4-oxadiazol-2-yl]pyrazin-2-amine. 1H NMR (400 MHz, DMSO-d6) δ 9.24 (s, 2H), 8.28 (s, 1H), 8.17 (d, J=8.0 Hz, 2H), 7.78 (d, J=8.2 Hz, 2H), 4.25 (t, J=5.8 Hz, 2H), 3.59-3.51 (m, 4H), 3.42-3.30 (m, 4H), 3.12 (q, J=7.4 Hz, 2H), 2.59 (t, J=5.2 Hz, 3H), 1.24 (t, J=7.3 Hz, 3H). LC/MS m/z 459.5 [M+H]+.

Compound I-333: 1-[(2R)-4-[5-Amino-6-[5-[4-(methylaminomethyl)phenyl]-1,3,4-oxadiazol-2-yl]pyrazin-2-yl]-2-isopropyl-piperazin-1-yl]propan-1-one. 1H NMR (400 MHz, DMSO-d6) δ 9.30 (s, 2H), 8.25 (s, 1H), 8.13 (d, J=8.1 Hz, 2H), 7.79 (d, J=8.2 Hz, 2H), 4.50-4.38 (m, 2H), 4.31-4.21 (m, 3H), 4.12 (dd, J=8.6, 6.4 Hz, 1H), 3.85 (d, J=13.4 Hz, 0.6H), 3.65 (d, J=10.9 Hz, 0.4H), 3.26 (t, J=11.4 Hz, 0.6H), 2.87 (ddd, J=15.2, 9.2, 5.6 Hz, 1H), 2.81-2.65 (m, 1.5H), 2.58 (t, J=5.2 Hz, 3H), 2.48-2.26 (m, 3H), 2.25-2.00 (m, 1H), 1.14-0.99 (m, 6H), 0.80 (d, J=6.6 Hz, 1.2H), 0.74 (d, J=6.7 Hz, 1.8H). LC/MS m/z 465.7 [M+H]+.

Compound I-326: 1-[(2S)-4-[5-Amino-6-[5-[4-(methylaminomethyl)phenyl]-1,3,4-oxadiazol-2-yl]pyrazin-2-yl]-2-isopropyl-piperazin-1-yl]propan-1-one. 1H NMR (400 MHz, DMSO-d6) δ 9.30 (s, 2H), 8.25 (s, 1H), 8.13 (d, J=8.1 Hz, 2H), 7.79 (d, J=8.2 Hz, 2H), 4.50-4.38 (m, 2H), 4.31-4.21 (m, 3H), 4.12 (dd, J=8.6, 6.4 Hz, 1H), 3.85 (d, J=13.4 Hz, 0.6H), 3.65 (d, J=10.9 Hz, 0.4H), 3.26 (t, J=11.4 Hz, 0.6H), 2.87 (ddd, J=15.2, 9.2, 5.6 Hz, 1H), 2.81-2.65 (m, 1.5H), 2.58 (t, J=5.2 Hz, 3H), 2.48-2.26 (m, 3H), 2.25-2.00 (m, 1H), 1.14-0.99 (m, 6H), 0.80 (d, J=6.6 Hz, 1.2H), 0.74 (d, J=6.7 Hz, 1.8H). LC/MS m/z 465.5 [M+H]+.

Compound I-343: 3-[5-[4-(Aethylaminomethyl)phenyl]-1,3,4-oxadiazol-2-yl]-5-pyrrolidin-1-yl-pyrazin-2-amine. 1H NMR (400 MHz, DMSO-d6) δ 9.00 (s, 2H), 8.15 (d, J=8.2 Hz, 2H), 7.91 (s, 1H), 7.74 (d, J=8.2 Hz, 2H), 4.26 (s, 2H), 3.47 (t, J=6.3 Hz, 4H), 2.63 (s, 3H), 1.97 (t, J=6.4 Hz, 4H). LC/MS m/z 428.2 [M+H]+.

Compound I-348: (2S)-1-[5-Amino-6-[5-[4-(methylaminomethyl)phenyl]-1,3,4-oxadiazol-2-yl]pyrazin-2-yl]-N-ethyl-pyrrolidine-2-carboxamide. 1H NMR (400 MHz, DMSO-d6) δ 8.85 (s, 2H), 8.19 (d, J=8.1 Hz, 2H), 8.00 (t, J=5.7 Hz, 1H), 7.87 (s, 1H), 7.73 (d, J=8.2 Hz, 2H), 4.36-4.22 (m, 3H), 3.52-3.39 (m, 2H), 3.05 (dtd, J=19.9, 13.4, 6.3 Hz, 2H), 2.64 (dd, J=13.5, 8.3 Hz, 3H), 2.25-2.14 (m, 1H), 2.04-1.92 (m, 3H), 0.91 (t, J=7.1 Hz, 3H).

Compound I-352: [(2S)-1-[5-Amino-6-[5-[4-(methylaminomethyl)phenyl]-1,3,4-oxadiazol-2-yl]pyrazin-2-yl]pyrrolidin-2-yl]methanol. NMR (400 MHz, DMSO-d6) δ 8.87 (s, 2H), 8.16 (d, J=8.2 Hz, 2H), 7.99 (s, 1H), 7.73 (d, J=8.2 Hz, 2H), 6.69 (s, 2H), 4.26 (t, J=5.7 Hz, 2H), 4.05-3.99 (m, 1H), 3.64-3.55 (m, 3H), 3.44-3.32 (m, 2H), 2.62 (t, J=5.1 Hz, 3H), 1.98-1.92 (m, 3H); LC/MS m/z 382.4 [M+H]+.

Compound I-356: [(2R)-1-[5-Amino-6-[5-[4-(methylaminomethyl)phenyl]-1,3,4-oxadiazol-2-yl]pyrazin-2-yl]pyrrolidin-2-yl]methanol. 1H NMR (400 MHz, DMSO-d6) δ 9.34 (s, 2H), 8.14 (d, J=8.1 Hz, 1H), 7.98 (t, J=5.8 Hz, 2H), 7.80 (d, J=8.2 Hz, 1H), 7.67 (d, J=8.2 Hz, 1H), 4.26-4.17 (m, 3H), 4.09-3.97 (m, 1H), 3.66-3.49 (m, 2H), 3.45-3.32 (m, 1H), 3.31-3.22 (m, 1H), 2.57 (dd, J=11.3, 5.6 Hz, 3H), 1.99-1.90 (m, 3H); LC/MS m/z 382.2 [M+H]+.

Compound I-357: (2R)-1-[5-Amino-6-[5-[4-(methylaminomethyl)phenyl]-1,3,4-oxadiazol-2-yl]pyrazin-2-yl]-N-ethyl-pyrrolidine-2-carboxamide. 1H NMR (400 MHz, DMSO-d6) δ 9.03 (s, 2H), 8.18 (d, J=8.1 Hz, 2H), 8.02 (t, J=4.9 Hz, 1H), 7.87 (s, 1H), 7.76 (d, J=8.2 Hz, 2H), 4.37-4.21 (m, 3H), 3.13-2.95 (M, 2H), 2.61 (t, J=5.3 Hz, 3H), 2.27-2.12 (m, 2H), 2.07-1.90 (m, 4H), 0.91 (t, J=7.2 Hz, 3H); LC/MS m/z 423.2 [M+H]+.

Compound I-361: 3-[5-[4-(Methylaminomethyl)phenyl]-1,3,4-oxadiazol-2-yl]-5-[(2S)-2-methylpyrrolidin-1-yl]pyrazin-2-amine. 1H NMR (400 MHz, DMSO-d6) δ 8.85 (s, 2H), 8.14 (d, J=8.1 Hz, 2H), 7.92 (s, 1H), 7.73 (d, J=8.2 Hz, 2H), 4.26 (s, 2H), 4.14 (s, 1H), 2.67 (s, 1H), 2.62 (t, J=5.3 Hz, 3H), 2.45 (s, 1H), 2.33 (s, 1H), 2.06 (s, 3H), 1.70 (s, 1H), 1.24 (d, J=6.1 Hz, 3H). LC/MS m/z 366.4 [M+H]+.

Compound I-362: 3-[5-[4-(Methylaminomethyl)phenyl]-1,3,4-oxadiazol-2-yl]-5-[(2R)-2-methylpyrrolidin-1-yl]pyrazin-2-amine. 1H NMR (400 MHz, DMSO-d6) δ 8.85 (s, 2H), 8.14 (d, J=8.2 Hz, 2H), 7.92 (s, 1H), 7.73 (d, J=8.1 Hz, 2H), 4.26 (s, 2H), 4.15 (s, 1H), 2.67 (s, 1H), 2.62 (t, J=5.3 Hz, 3H), 2.33 (s, 1H), 2.06 (s, 3H), 1.70 (s, 1H), 1.24 (d, J=6.2 Hz, 3H). LC/MS m/z 366.2 [M+H]+.

Compound I-359: (R)-1-(4-(5-Amino-6-(5-(4-((methylamino)methyl)phenyl)-1,3,4-oxadiazol-2-yl)pyrazin-2-yl)-3-methylpiperazin-1-yl)propan-1-one. 1H NMR (400 MHz, MeOD) δ 8.27 (d, J=8.3 Hz, 1H), 8.15 (d, J=3.7 Hz, 1H), 7.76 (d, J=8.3 Hz, 2H), 4.63-4.39 (m, 1H), 4.33 (s, 2H), 4.07 (m, 2H), 3.82 (dd, J=42.9, 13.5 Hz, 2H), 3.71-3.36 (m, 3H), 3.09 (m, 1H), 2.79 (s, 3H), 2.57-2.44 (m, 2H), 1.36-1.07 (m, 8H). LC/MS m/z 437.5 [M+H]+.

Compound I-360: 8-(5-Amino-6-(5-(4-((methylamino)methyl)phenyl)-1,3,4-oxadiazol-2-yl)pyrazin-2-yl)-2,8-diazaspiro[4.5]decan-1-one; 1HNMR (400 MHz, DMSO-d6) δ 9.40 (d, J=4.5 Hz, 2H), 8.28 (s, 1H), 8.14 (d, J=8.1 Hz, 2H), 7.80 (d, J=8.2 Hz, 2H), 7.63 (s, 1H), 4.23 (t, J=5.8 Hz, 2H), 4.10 (d, J=13.1 Hz, 2H), 3.21 (t, J=6.7 Hz, 2H), 3.00 (t, J=11.5

Hz, 2H), 2.57 (t, J=5.3 Hz, 3H), 2.04 (t, J=6.7 Hz, 2H), 1.76 (td, J=12.8, 4.1 Hz, 2H), 1.48 (d, J=13.2 Hz, 2H); LC/MS m/z 435.5 [M+H]$^+$.

Compound I-363: 1-(7-(5-Amino-6-(5-(4-((methylamino)methyl)phenyl)-1,3,4-oxadiazol-2-yl)pyrazin-2-yl)-4,7-diazaspiro[2.5]octan-4-yl)propan-1-one; $^1$H NMR (400 MHz, DMSO-d$_6$) δ 9.39 (s, 2H), 8.20 (s, 1H), 8.16 (d, J=8.1 Hz, 2H), 7.80 (d, J=8.1 Hz, 2H), 4.29-4.17 (m, J=5.8 Hz, 4H), 3.82-3.45 (m, 4H), 3.34 (s, 3H), 2.58 (t, J=5.3 Hz, 3H), 1.23 (s, 1H), 1.11-0.97 (m, 7H). LC/MS m/z 449.3 [M+H]$^+$.

Compound I-364: 1-(1-(5-Amino-6-(5-(4-((methylamino)methyl)phenyl)-1,3,4-oxadiazol-2-yl)pyrazin-2-yl)piperidin-4-yl)pyrrolidin-2-one; $^1$HNMR (400 MHz, DMSO-d$_6$) δ 9.40 (d, J=4.6 Hz, 2H), 8.28 (s, 1H), 8.15 (d, J=8.2 Hz, 2H), 7.80 (d, J=8.2 Hz, 2H), 4.30 (d, J=12.9 Hz, 2H), 4.24 (t, J=5.8 Hz, 2H), 4.04-3.92 (m, 1H), 3.31 (t, J=6.9 Hz, 2H), 2.88 (t, J=11.5 Hz, 2H), 2.57 (t, J=5.3 Hz, 3H), 2.24 (t, J=8.0 Hz, 2H), 1.96-1.84 (m, 2H), 1.77-1.65 (m, 4H); LC/MS m/z 449.3 [M+H]$^+$.

Compound I-365: N-(1-(5-Amino-6-(5-(4-((methylamino)methyl)phenyl)-1,3,4-oxadiazol-2-yl)pyrazin-2-yl)piperidin-4-yl)-N-methylpropionamide; $^1$H NMR (400 MHz, DMSO-d$_6$) δ 9.41 (s, 2H), 8.28 (d, J=5.1 Hz, 1H), 8.15 (d, J=8.0 Hz, 2H), 7.80 (d, J=7.7 Hz, 2H), 4.31 (d, J=12.6 Hz, 3H), 4.24 (t, J=5.7 Hz, 2H), 2.88 (dd, J=24.8, 12.7 Hz, 2H), 2.80 (s, 2H), 2.69 (s, 1H), 2.57 (t, J=5.3 Hz, 3H), 2.44-2.38 (m, J=7.4 Hz, 1H), 2.31 (dd, J=14.6, 7.2 Hz, 1H), 1.89-1.67 (m, J=14.0, 10.5 Hz, 3H), 1.57 (d, J=10.5 Hz, 1H), 1.04-0.95 (m, J=11.4, 7.4 Hz, 3H). LC/MS m/z 451.3 [M+H]$^+$.

Compound I-366: N-(1-(5-Amino-6-(5-(4-((methylamino)methyl)phenyl)-1,3,4-oxadiazol-2-yl)pyrazin-2-yl)piperidin-4-yl)propionamide. $^1$HNMR (400 MHz, DMSO-d$_6$) δ 8.24 (s, 1H), 8.03 (d, J=8.1 Hz, 2H), 7.74 (d, J=7.7 Hz, 1H), 7.58 (d, J=8.2 Hz, 2H), 6.85 (s, 2H), 4.10 (d, J=13.0 Hz, 2H), 3.87-3.65 (m, 3H), 2.95 (t, J=11.1 Hz, 2H), 2.29 (s, 3H), 2.10-2.02 (m, 2H), 1.84 (d, J=10.2 Hz, 2-H), 1.46 (dd, J=20.2, 10.9 Hz, 2H), 0.99 (t, J=7.6 Hz, 3H). LC/MS m/z 437.5 [M+H]$^+$.

Compound I-368: 5-(2-(Isopropylsulfonyl)-2,6-diazaspiro[3.4]octan-6-yl)-3-(5-(4-((methylamino)methyl)phenyl)-1,3,4-oxadiazol-2-yl)pyrazin-2-amine; $^1$H NMR (400 MHz, DMSO) δ 9.14 (s, 2H), 8.16 (d, J=8.1 Hz, 2H), 7.93 (s, 1H), 7.77 (d, J=8.2 Hz, 2-H), 4.25 (t, J=5.8 Hz, 2H), 3.94 (d, J=7.8 Hz, 2H), 3.86 (d, J=7.8 Hz, 2H), 3.68 (s, 2H), 3.52 (t, J=6.8 Hz, 2H), 3.31-3.20 (m, 1H), 2.60 (t, J=5.2 Hz, 3H), 2.22 (t, J=6.8 Hz, 2H), 1.25 (d, J=6.8 Hz, 6H); LC/MS m/z 499.1 [M+H]$^+$.

Compound I-358: N-[(1S,5R)-3-[5-amino-6-[5-[4-(methylaminomethyl)phenyl]-1,3,4-oxadiazol-2-yl]pyrazin-2-yl]-3-azabicyclo[3.1.0]hexan-6-yl]propanamide; $^1$H NMR (400 MHz, DMSO) d 9.11 (s, 2H), 8.17 (d, J=8.1 Hz, 2H), 7.99 (d, J=3.6 Hz, 1H), 7.91 (s, 1H), 7.77 (d, J=8.2 Hz, 2H), 4.25 (t, J=5.8 Hz, 3H), 3.83 (d, J=10.0 Hz, 2H), 3.41 (d, J=9.1 Hz, 2H), 2.60 (t, J=5.2 Hz, 3H), 2.05 (d, J=7.6 Hz, 2H), 1.79 (s, 2H), 0.99 (t, J=7.5 Hz, 3H); LC/MS m/z 435.5 [M+H]$^+$.

Compound I-369: N-[1S,5R)-3-[5-Amino-6-[5-[4-(methylaminomethyl)phenyl]-1,3,4-oxadiazol-2-yl]pyrazin-2-yl]-3-azabicyclo[3.1.0]hexan-6-yl]ethanesulfonamide; $^1$H NMR (400 MHz, DMSO) d 9.03 (s, 2H), 8.17 (d, J=8.3 Hz, 2H), 7.91 (s, 1H), 7.76 (d, J=8.3 Hz, 2H), 7.56 (s, 1H), 6.76 (s, 2H), 4.24-4.22 (m, 2H), 3.82 (d, J=10.0 Hz, 2H), 3.43 (s, 2H), 3.11 (t, J=7.3 Hz, 2H), 2.61 (t, J=5.1 Hz, 3H), 2.33 (s, 1H), 1.96 (s, 2H), 1.21 (t, J=7.3 Hz, 3H); LC/MS m/z 471.3 [M+H]$^+$.

Compound I-370: N-[(1S,5R)-3-[5-Amino-6-[5-[4-(methylaminomethyl)phenyl]-1,3,4-oxadiazol-2-yl]pyrazin-2-yl]-3-azabicyclo[3.1.0]hexan-6-yl]propane-2-sulfonamide; 1H NMR (400 MHz, DMSO) d 9.05 (s, 2H), 8.16 (d, J=9.4 Hz, 2H), 7.91 (s, 1H), 7.76 (d, J=8.2 Hz, 2H), 7.55 (s, 1H), 4.25 (t, J=5.8 Hz, 2H), 3.81 (d, J=10.2 Hz, 2H), 3.42 (d, J=9.8 Hz, 2H), 3.38-3.31 (m, 1H), 2.61 (t, J=5.3 Hz, 3H), 2.33 (s, 1H), 1.96 (s, 2H), 1.24 (d, J=5.2 Hz, 6H); LC/MS m/z 485.5 [M+H]$^+$.

Compound I-371: (3S)-1-[5-Amino-6-[5-[4-(methylaminomethyl)phenyl]-1,3,4-oxadiazol-2-yl]pyrazin-2-yl]pyrrolidin-3-ol; LC/MS m/z 368.1 [M+H]$^+$.

Compound I-372: [(3S)-1-[5-Amino-6-[5-[4-(methylaminomethyl)phenyl]-1,3,4-oxadiazol-2-yl]pyrazin-2-yl]pyrrolidin-3-yl]N-ethylcarbamate; $^1$H NMR (400 MHz, DMSO-d$_6$) d 8.21 (s, 1H), 8.04 (d, J=8.1 Hz, 2H), 7.92 (d, J=15.9 Hz, 1H), 7.62 (t, J=7.1 Hz, 2H), 7.19 (t, J=5.5 Hz, 0.5H), 6.72 (s, 1.5H), 5.27 (s, 1H), 3.82 (s, 2H), 3.75-3.46 (m, 3H), 3.00 (dt, J=13.3, 6.8 Hz, 2H), 2.34 (s, 3H), 2.28-2.17 (m, 1.5H), 2.16-2.04 (m, 1.5H), 1.13 (t, J=7.0 Hz, 0.5H), 0.99 (t, J=7.2 Hz, 3H), 0.82 (d, J=6.9 Hz, 0.5H). LC/MS m/z 439.14 [M+H]$^+$.

Compound I-373: [(3S)-1-[5-Amino-6-[5-[4-(methylaminomethyl)phenyl]-1,3,4-oxadiazol-2-yl]pyrazin-2-yl]pyrrolidin-3-yl]N-(2-methoxyethyl)carbamate. LC/MS m/z 469.2 [M+H]$^+$.

Example 40

[(3aR,6aS)-2-[5-Amino-6-[5-[4-(methylaminomethyl)phenyl]-1,3,4-oxadiazol-2-yl]pyrazin-2-yl]-3,3a,4,5,6,6a-hexahydro-1H-cyclopenta[c]pyrrol-6-yl]methanesulfonate (Compound I-320)

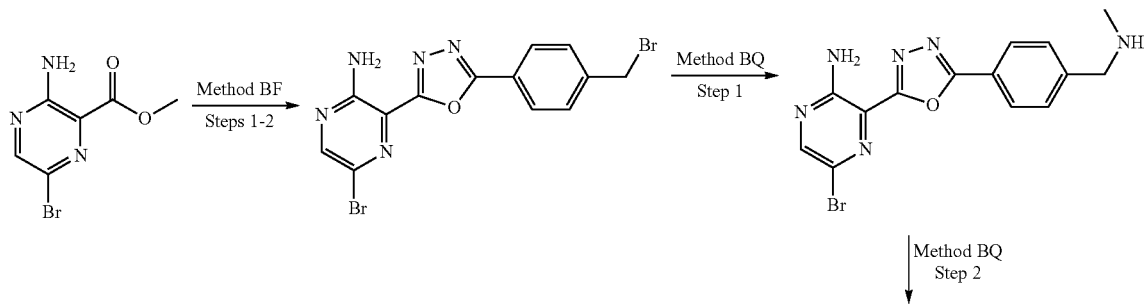

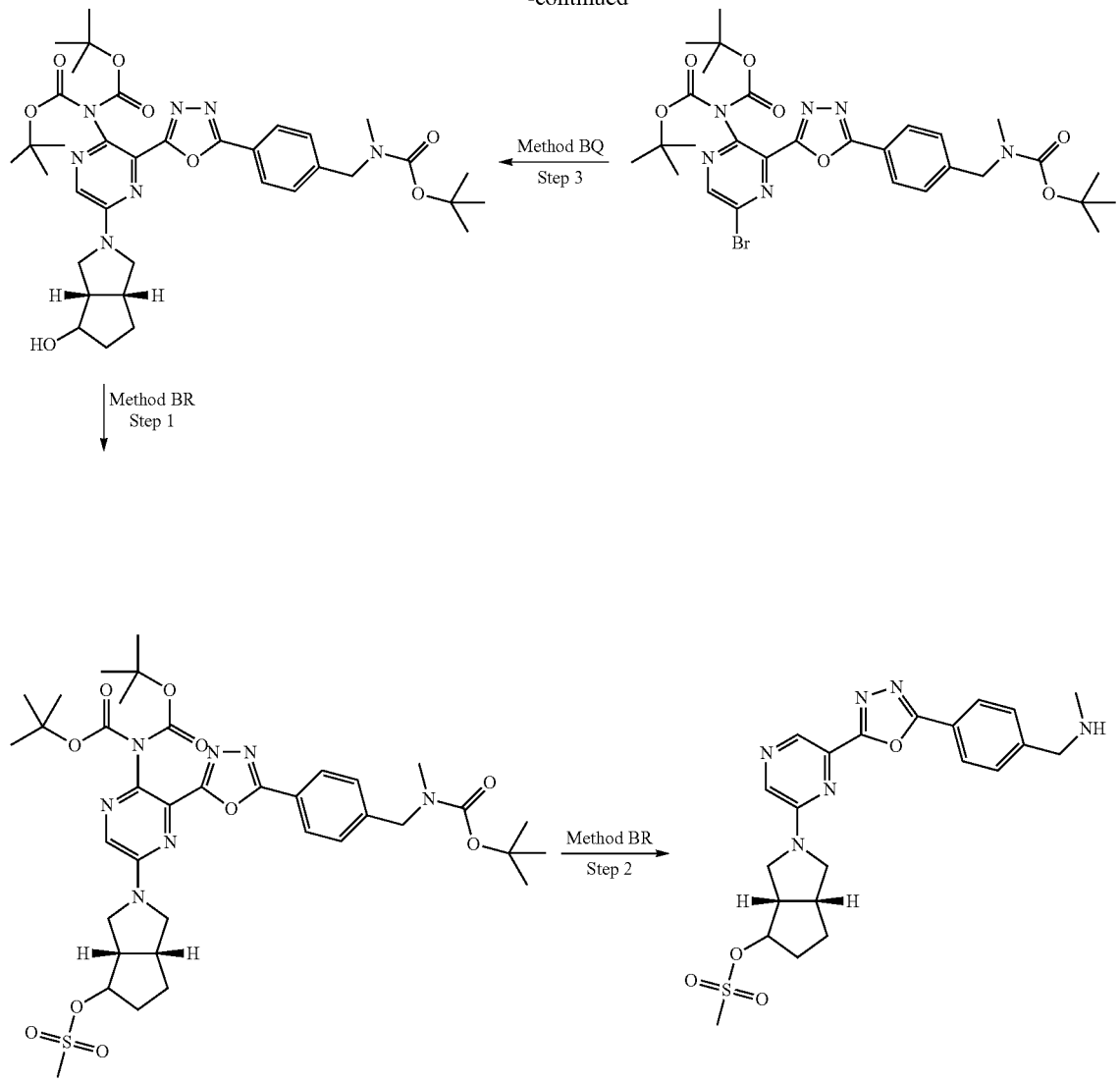

Compound I-320 was prepared using Method BF, Steps 1-2, followed by Method BQ Steps 1-3, followed by Method BR Steps 1-2.

Method BR: Step 1: [(3aR,6aS)-2-[5-[bis(tert-Butoxycarbonyl)amino]-6-[5-[4-[[tert-butoxycarbonyl-methyl)amino]methyl]phenyl]-1,3,4-oxadiazol-2-yl]pyrazin-2-yl]-3,3a,4,5,6,6a-hexahydro-1H-cyclopenta[c]pyrrol-6-yl]methanesulfonate To a solution of tert-butyl N-[[4-[5-[6-[(3aR,6aS)-6-hydroxy-3,3a,4,5,6,6a-hexahydro-1H-cyclopenta[c]pyrrol-2-yl]-3-[bis(tert-butoxycarbonyl)amino]pyrazin-2-yl]-1,3,4-oxadiazol-2-yl]phenyl]methyl]-N-methyl-carbamate (70 mg, 0.10 mmol) and DMAP (1.2 mg, 0.01 mmol) in DCM at 0° C. was added triethylamine (11 mg, 15 µL, 0.11 mmol) followed by the addition of methane sulfonyl chloride (12 mg, 8 µL, 0.10 mmol). The reaction mixture was warmed to room temperature over a period of 1.5 h and used directly in the next step.

Method BR: Step 2: [(3aR,6aS)-2-[5-Amino-6-[5-[4-(methylaminomethyl)phenyl]-1,3,4-oxadiazol-2-yl]pyrazin-2-yl]-3,3a,4,5,6,6a-hexahydro-1H-cyclopenta[c]pyrrol-6-yl]methanesulfonate To the crude reaction mixture from step 1 was added TFA (1 mL). The reaction mixture was stirred for 30 minutes at room temperature. The solvent was evaporated and the crude material was redissolved in DMSO and purified via reverse phase HPLC to obtain [(3aR,6aS)-2-[5-amino-6-[5-[4-(methylaminomethyl)phenyl]-1,3,4-oxadiazol-2-yl]pyrazin-2-yl]-3,3a,4,5,6,6a-hexahydro-1H-cyclopenta[c]pyrrol-6-yl]methanesulfonate (8 mg, 23%). LC/MS m/z 486.2 [M+H]$^+$.

Example 41

N-((3aS,6aR)-2-(5-Amino-6-(5-(4-((methylamino)methyl)phenyl)-1,3,4-oxadiazol-2-yl)pyrazin-2-yl)octahydrocyclopenta[c]pyrrol-4-yl)ethanesulfonamide (Compound I-354)

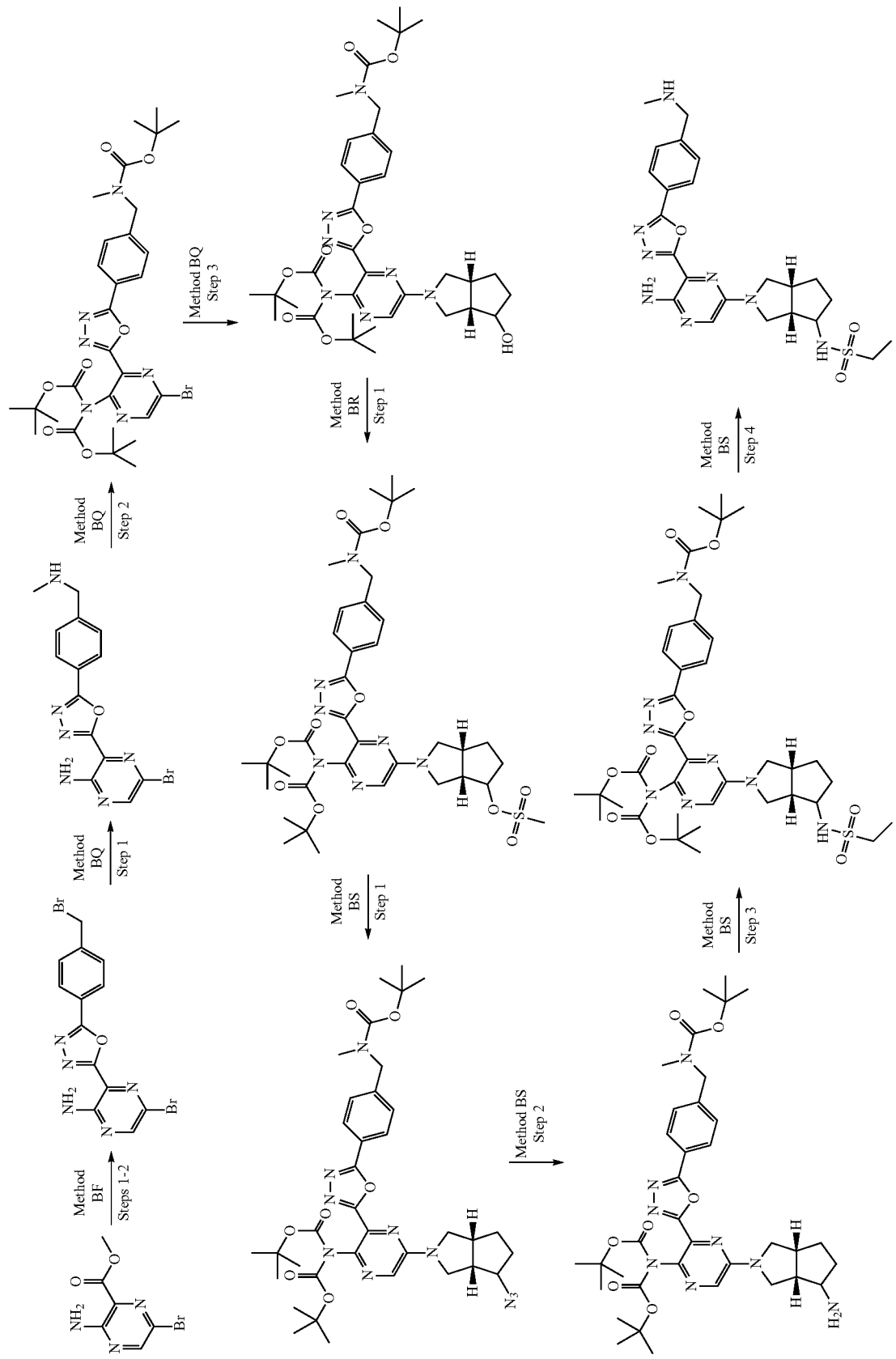

Compound I-354 was prepared using Method BF, Steps 1-2, followed by Method BQ Steps 1-3, followed by Method BR Step 1, followed by Method BS Steps 1-4.

Method BS: Step 1: tert-Butyl N-[[4-[5-[6-[(3aR, 6aS)-6-azido-3,3a,4,5,6,6a-hexahydro-1H-cyclopenta[c]pyrrol-2-yl]-3-[bis(tert-butoxycarbonyl) amino]pyrazin-2-yl]-1,3,4-oxadiazol-2-yl]phenyl] methyl]-N-methyl-carbamate A solution of [(3aR,6aS)-2-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]-3,3a,4,5,6,6a-hexahydro-1H-cyclopenta[c]pyrrol-6-yl] methanesulfonate (460 mg, 0.58 mmol) and sodium azide (190 mg, 573 µL, 2.9 mmol) in DMF (4 mL) was heated at 70° C. for 48 h. The solvent was removed under reduced pressure and the residue was dissolved in EtOAc. The organic layer was washed with $H_2O$, followed by washing with brine. The organic layer was dried over $Na_2SO_4$, filtered and concentrated under reduced pressure to obtain tert-butyl N-[[4-[5-[6-[(3aR,6aS)-6-azido-3,3a,4,5,6,6a-hexahydro-1H-cyclopenta[c]pyrrol-2-yl]-3-[bis(tert-butoxycarbonyl)amino] pyrazin-2-yl]-1,3,4-oxadiazol-2-yl]phenyl]methyl]-N-methyl-carbamate (401 mg, 93%). LC/MS m/z 733.7 [M+H]+.

Method BS: Step 2: tert-Butyl N-[[4-[5-[6-[(3aR, 6aS)-6-amino-3,3a,4,5,6,6a-hexahydro-1H-cyclopenta[c]pyrrol-2-yl]-3-[bis(tert-butoxycarbonyl) amino]pyrazin-2-yl]-1,3,4-oxadiazol-2-yl]phenyl] methyl]-N-methyl-carbamate A flask charged with tert-butyl N-[[4-[5-[6-[(3aR,6aS)-6-azido-3,3a,4,5,6,6a-hexahydro-1H-cyclopenta[c]pyrrol-2-yl]-3-[bis(tert-butoxycarbonyl)amino]pyrazin-2-yl]-1,3,4-oxadiazol-2-yl]phenyl]methyl]-N-methyl-carbamate (400 mg, 0.55 mmol) and Pd/C (108 mg, 1.0 mmol) was flushed under $N_2$ followed by evacuating under vacuum. EtOH (3 mL) was added under inert atmosphere followed by evacuating under vacuum. The reaction mixture was stirred for 4.5 h under an atmosphere of $H_2$. The reaction mixture was filtered and the solvent was evaporated under reduced pressure to obtain tert-butyl N-[[4-[5-[6-[(3aR,6aS)-6-amino-3,3a,4,5,6, 6a-hexahydro-1H-cyclopenta[c]pyrrol-2-yl]-3-[bis(tert-butoxycarbonyl)amino]pyrazin-2-yl]-1,3,4-oxadiazol-2-yl] phenyl]methyl]-N-methyl-carbamate (300 mg, 78%). LC/MS m/z 707.5 [M+H]+.

Method BS: Step 3: tert-Butyl N-[[4-[5-[6-[(3aR, 6aS)-6-(ethylsulfonylamino)-3,3a,4,5,6,6a-hexahydro-1H-cyclopenta[c]pyrrol-2-yl]-3-[bis(tert-butoxycarbonyl)amino]pyrazin-2-yl]-1,3,4-oxadiazol-2-yl] phenyl]methyl]-N-methyl-carbamate To a solution of tert-butyl N-[[4-[5-[6-[(3aR,6aS)-6-amino-3,3a,4,5,6,6a-hexahydro-1H-cyclopenta[c]pyrrol-2-yl]-3-[bis(tert-butoxycarbonyl)amino]pyrazin-2-yl]-1,3,4-oxadiazol-2-yl]phenyl]methyl]-N-methyl-carbamate (150 mg, 0.22 mmol) and triethylamine (24 mg, 33 µL, 0.23 mmol) in DCM (1 mL) at 0° C. was added ethanesulfonyl chloride (29 mg, 21 µL, 0.22 mmol). The reaction mixture was stirred for 30 min. The solvent was evaporated and the crude material was purified via silica gel column chromatography using 10 to 70% EtOAc in DCM to obtain tert-butyl N-[[4-[5-[6-[(3aR, 6aS)-6-(ethylsulfonylamino)-3,3a,4,5,6,6a-hexahydro-1H-cyclopenta[c]pyrrol-2-yl]-3-[bis(tert-butoxycarbonyl) amino]pyrazin-2-yl]-1,3,4-oxadiazol-2-yl]phenyl]methyl]-N-methyl-carbamate (110 mg, 650%). LC/MS m/z 799.5 [M+H]+.

Method BS: Step 4: N-[(3aR,6aS)-2-[5-Amino-6-[5-[4-(methylaminomethyl)phenyl]-1,3,4-oxadiazol-2-yl]pyrazin-2-yl]-3,3a,4,5,6,6a-hexahydro-1H-cyclopenta[c]pyrrol-6-yl]ethanesulfonamide A solution of tert-butyl N-[[4-[5-[6-[(3aR,6aS)-6-(ethylsulfonylamino)-3,3a,4,5,6,6a-hexahydro-1H-cyclopenta[c] pyrrol-2-yl]-3-[bis(tert-butoxycarbonyl)amino]pyrazin-2-yl]-1,3,4-oxadiazol-2-yl]phenyl]methyl]-N-methyl-carbamate (110 mg, 0.14 mmol) in DCM (1 mL) was treated with TFA (1.0 g, 676 µL, 8.8 mmol). The reaction mixture was stirred for 1 hour. The solvent was evaporated and the residue was purified via reverse phase HPLC using 10 to 99% ACN in water (5 mM HCl modifier) to obtain N-[(3aR,6aS)-2-[5-amino-6-[5-[4-(methylaminomethyl)phenyl]-1,3,4-oxadiazol-2-yl]pyrazin-2-yl]-3,3a,4,5,6,6a-hexahydro-1H-cyclopenta[c]pyrrol-6-yl]ethanesulfonamide. LC/MS m/z 499.2 [M+H]+

Compound I-355: was prepared using the method described for Compound I-354 in Example 41 above.

Compound I-355: N-((3aS,6aR)-2-(5-Amino-6-(5-(4-((methylamino)methyl)phenyl)-1,3,4-oxadiazol-2-yl)pyrazin-2-yl)octahydrocyclopenta[c]pyrrol-4-yl) propionamide. LC/MS m/z 463.2 [M+H]+.

Example 42

1-(7-(5-Amino-6-(5-(4-((methylamino)methyl)phenyl)-1,3,4-oxadiazol-2-yl)pyrazin-2-yl)-2,7-diazaspiro[4.4]nonan-2-yl)propan-1-one (Compound I-349)

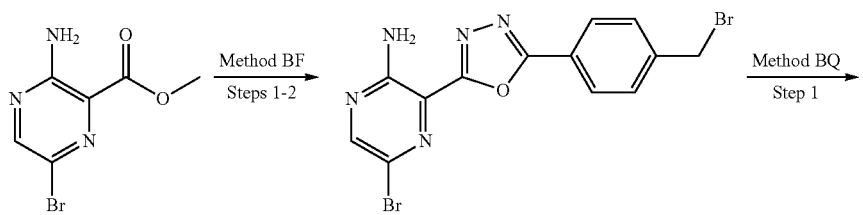

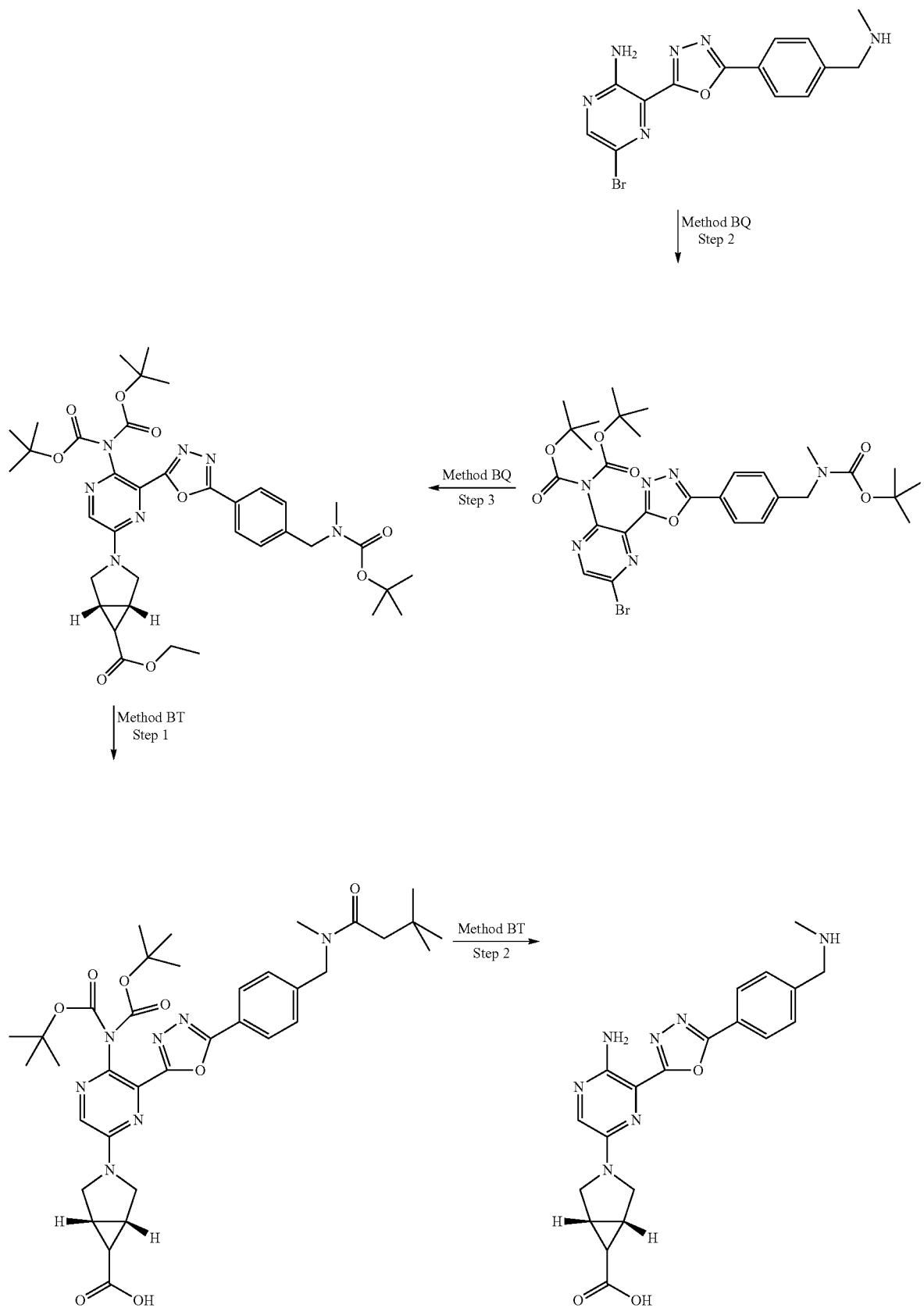

Compound I-349 was prepared using Method BF, Steps 1-2 followed by Method BQ, Steps 1-3, followed by the Method BT, Steps 1-2.

Method BT: Step 1: (1R,5S)-3-[5-[bis(tert-Butoxycarbonyl)amino]-6-[5-[4-[[tert-butoxycarbonyl(methyl)amino]methyl]phenyl]-1,3,4-oxadiazol-2-yl]pyrazin-2-yl]-3-azabicyclo[3.1.0]hexane-6-carboxylic acid To a solution of ethyl (1R,5S)-3-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]-3-azabicyclo[3.1.0]hexane-6-carboxylate (270 mg, 0.37 mmol) in of 2:1 THF: MeOH (1 mL) was added NaOH (550 µL, of 1 M, 0.55 mmol). The reaction mixture was stirred for 30 minutes at room temperature. The solvent was evaporated to obtain (1R,5S)-3-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]-3-azabicyclo[3.1.0]hexane-6-carboxylic acid, which was used for the next step without further purification.

Method BT: Step 2: (1R,5S)-3-[5-Amino-6-[5-[4-(methylaminomethyl)phenyl]-1,3,4-oxadiazol-2-yl]pyrazin-2-yl]-3-azabicyclo[3.1.0]hexane-6-carboxylic acid.

To a solution of (1R,5S)-3-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]-3-azabicyclo[3.1.0]hexane-6-carboxylic acid (30 mg, 0.04 mmol) in DCM (0.3 mL) was added TFA (500 µL, 6.50 mmol) and reaction was stirred at room temperature for 2 h. The solvent was removed under reduced pressure and the residue was dissolved in DMSO, filtered and purified via reverse phase HPLC using a gradient of 10 to 99% MeOH—H$_2$O (TFA modifier) to obtain (1R,5S)-3-[5-amino-6-[5-[4-(methylaminomethyl)phenyl]-1,3,4-oxadiazol-2-yl]pyrazin-2-yl]-3-azabicyclo[3.1.0]hexane-6-carboxylic acid. LC/MS m/z 408.4 [M+H]$^+$. $^1$H NMR (400 MHz, DMSO-d$_6$) δ 12.23 (s, 1H), 8.85 (s, 2H), 8.17 (d, J=8.2 Hz, 2H), 7.91 (s, 1H), 7.73 (d, J=8.2 Hz, 2H), 6.77 (s, 2H), 4.26 (t, J=5.7 Hz, 2H), 3.87 (d, J=10.4 Hz, 2H), 3.47-3.46 (m, 2H), 2.63 (t, J=5.2 Hz, 3H), 2.19 (s, 2H), 1.49 (t, J=2.9 Hz, 1H).

Example 43

1-(7-(5-Amino-6-(5-(4-((methylamino)methyl)phenyl)-1,3,4-oxadiazol-2-yl)pyrazin-2-yl)-2,7-diazaspiro[4.4]nonan-2-yl)propan-1-one (Compound I-351

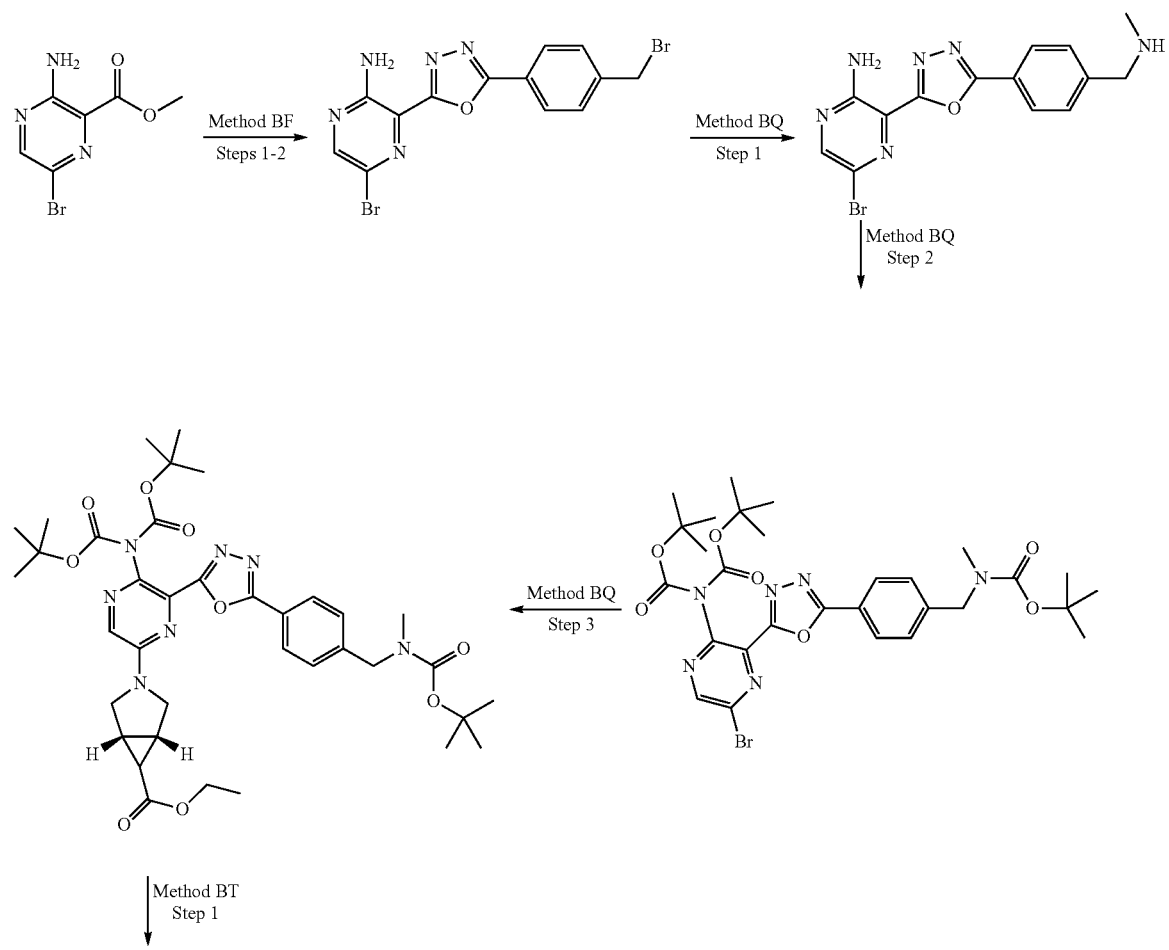

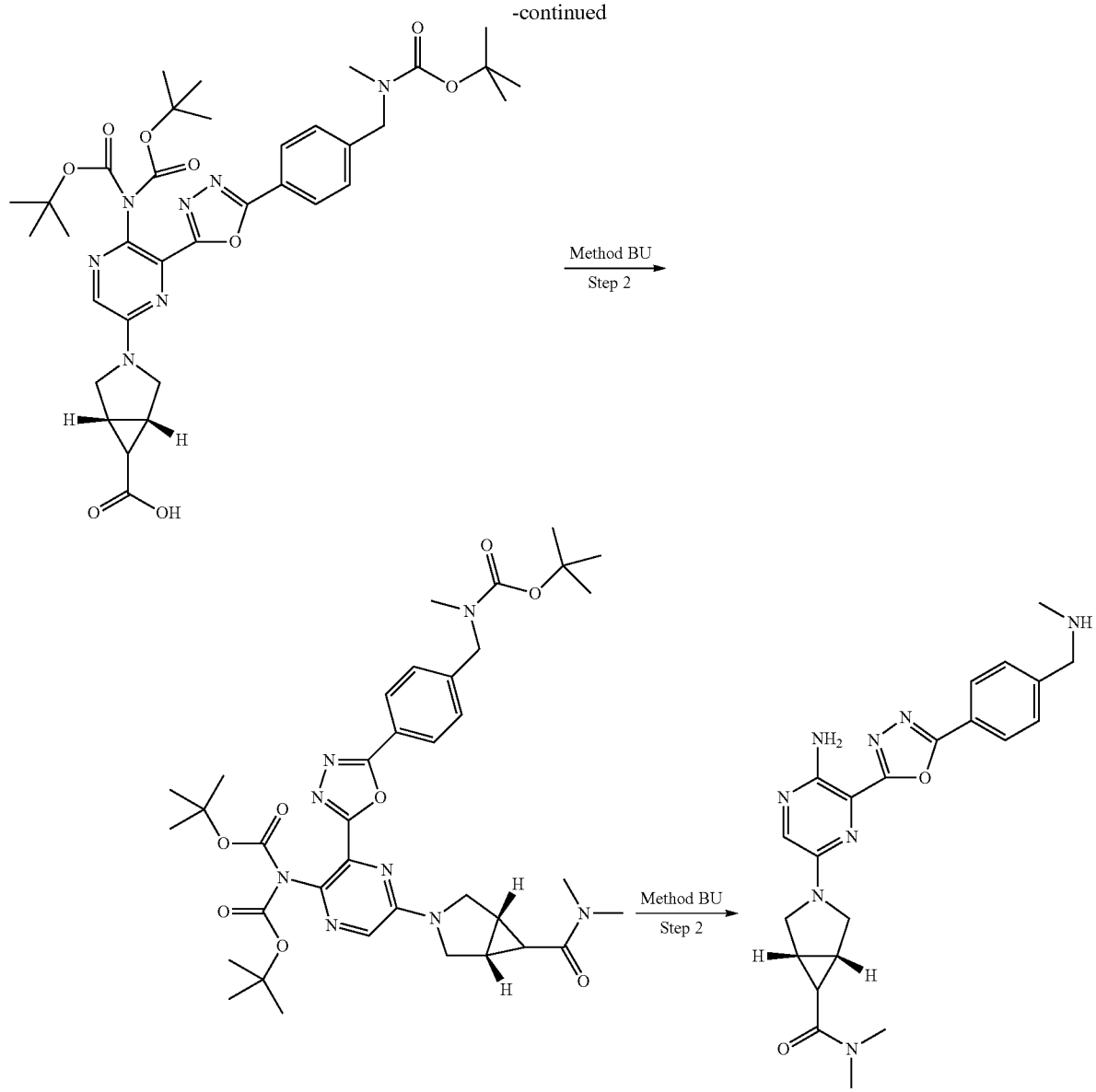

Compound I-351 was prepared using Method BF, Steps 1-2 followed by Method BQ, Step 1-3, followed by the Method BT, Step 1, followed by Method BU, Steps 1-2.

Method BU: Step 1: tert-Butyl N-[[4-[5-[3-[bis(tert-butoxycarbonyl)amino]-6-[(1R,5S)-6-(dimethylcarbamoyl)-3-azabicyclo[3.1.0]hexan-3-yl]pyrazin-2-yl]-1,3,4-oxadiazol-2-yl]phenyl]methyl]-N-methyl-carbamate To a solution of (1R,5S)-3-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]-3-azabicyclo[3.1.0]hexane-6-carboxylic acid (127 mg, 0.18 mmol) and HATU (68 mg, 0.18 mmol) in DMF (720 µL) at room temperature was added DIEA (49 mg, 66 µL, 0.38 mmol) followed by the addition of a solution of N-methylmethanamine (253 mg, 270 µL of 2 M, 0.54 mmol) in THF. The reaction mixture was stirred at room temperature for 1.5 h. The reaction mixture was diluted with ethyl acetate and washed with brine solution. The organics were separated, dried over MgSO₄, filtered and concentrated under reduced pressure. The crude material was purified via silica gel column chromatography using 2 to 15% MeOH in DCM to obtain tert-butyl N-[[4-[5-[3-[bis(tert-butoxycarbonyl)amino]-6-[(1R,5S)-6-(dimethylcarbamoyl)-3-azabicyclo[3.1.0]hexan-3-yl]pyrazin-2-yl]-1,3,4-oxadiazol-2-yl]phenyl]methyl]-N-methyl-carbamate (81 mg, 61%).

Method BU: Step 2: (1R,5S)-3-[5-Amino-6-[5-[4-(methylaminomethyl)phenyl]-1,3,4-oxadiazol-2-yl]pyrazin-2-yl]-N,N-dimethyl-3-azabicyclo[3.1.0]hexane-6-carboxamide.

A solution of tert-butyl N-[[4-[5-[3-[bis(tert-butoxycarbonyl)amino]-6-[(1R,5S)-6-(dimethylcarbamoyl)-3-azabicyclo[3.1.0]hexan-3-yl]pyrazin-2-yl]-1,3,4-oxadiazol-2-yl]phenyl]methyl]-N-methyl-carbamate (75 mg, 0.1 mmol) in 0.8 mL of 50% TFA-DCM mixture was stirred under an atmosphere of nitrogen at room temperature for 1 h. The solvents were evaporated and the crude material was purified via reverse phase HPLC using 10 to 99% methanol in water (TFA modifier) to obtain (1R,5S)-3-[5-amino-6-[5-[4-(methylaminomethyl)phenyl]-1,3,4-oxadiazol-2-yl]pyrazin-2-yl]-N,N-dimethyl-3-azabicyclo[3.1.0]hexane-6-carboxamide. $^1$H NMR (400 MHz, DMSO-$d_6$) δ 8.87 (s, 2H), 8.16 (d, J=8.2 Hz, 2H), 7.91 (s, 1H), 7.73 (d, J=8.2 Hz, 2H), 6.76 (s, 2H), 4.26 (t, J=5.7 Hz, 2H), 3.86 (d, J=10.2 Hz, 2H), 3.49-3.46 (m, 2H), 3.10 (s, 3H), 2.84 (s, 3H), 2.63 (t, J=5.2 Hz, 3H), 2.09 (s, 2H), 1.90 (t, J=3.1 Hz, 1H). LC/MS m/z 435.2 [M+H]$^+$.

Compound I-350 was prepared using the method described for Compound I-351 in Example 43 above.

Compound I-350: (1R,5S)-3-[5-Amino-6-[5-[4-(methylaminomethyl)phenyl]-1,3,4-oxadiazol-2-yl]pyrazin-2-yl]-N-ethyl-3-azabicyclo[3.1.0]hexane-6-carboxamide. $^1$H NMR (400 MHz, DMSO-$d_6$) δ 8.86 (s, 2H), 8.17 (d, J=8.1 Hz, 2H), 8.00 (t, J=5.4 Hz, 1H), 7.95-7.88 (m, 1H), 7.73 (d, J=8.2 Hz, 2H), 6.77 (s, 2H), 4.26 (t, J=5.6 Hz, 2H), 3.85 (t, J=11.5 Hz, 2H), 3.09 (dt, J=14.0, 7.0 Hz, 2H), 2.64 (dd, J=14.4, 9.4 Hz, 4H), 2.33 (s, 1H), 2.19 (s, 1H), 1.52 (dd, J=9.1, 6.2 Hz, 1H), 1.01 (t, J=7.2 Hz, 2H). LC/MS m/z 435.4 [M+H]$^+$.

Example 44

1-(7-(5-Amino-6-(5-(4-((methylamino)methyl)phenyl)-1,3,4-oxadiazol-2-yl)pyrazin-2-yl)-2,7-diazaspiro[4.4]nonan-2-yl)propan-1-one (Compound I-335)

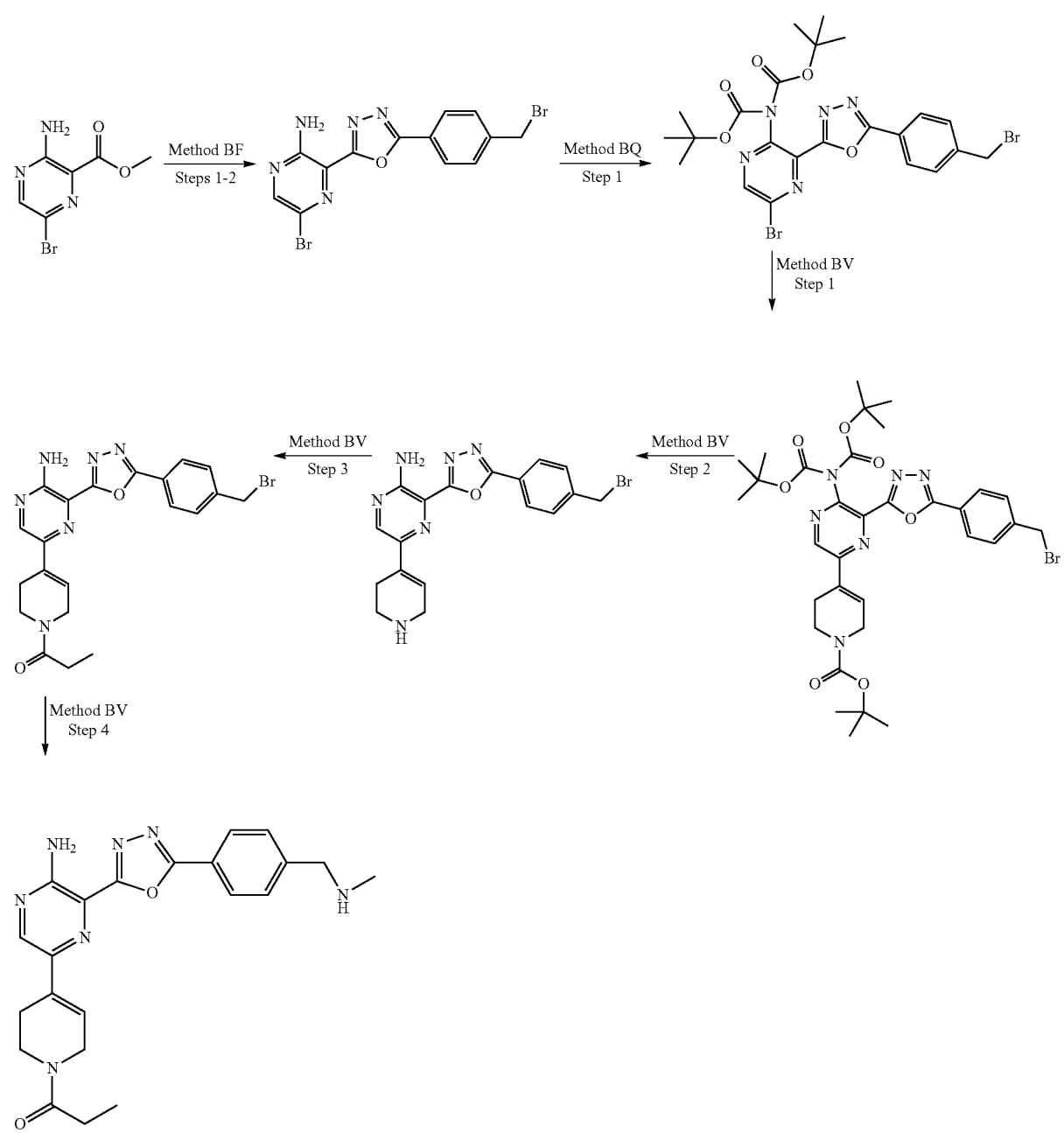

Compound I-335 was prepared using Method BF, Steps 1-3 followed by Method BV, Steps 1-4.

Method BV: Step 1: tert-Butyl 4-[5-[bis(tert-butoxycarbonyl)amino]-6-[5-[4-(bromomethyl)phenyl]-1,3,4-oxadiazol-2-yl]pyrazin-2-yl]-3,6-dihydro-2H-pyridine-1-carboxylate To a solution of tert-butyl N-[5-bromo-3-[5-[4-(bromomethyl)phenyl]-1,3,4-oxadiazol-2-yl]pyrazin-2-yl]-N-tert-butoxycarbonyl-carbamate (500 mg, 0.82 mmol) in toluene (4.4 mL)/water (484 μL) was added tert-butyl 4-(4,4,5,5-tetramethyl-1,3,2-dioxaborolan-2-yl)-3,6-dihydro-2H-pyridine-1-carboxylate (304 mg, 1.0 mmol) followed by the addition of 4-ditert-butylphosphanyl-N,N-dimethyl-aniline; dichloropalladium (58 mg, 0.082 mmol) and $K_2CO_3$ (226 mg, 1.6 mmol). The reaction mixture was heated at 60° C. for 3 h. The reaction mixture was partitioned between DCM and saturated aqueous $NaHCO_3$, the layers were separated and the aqueous layer was extracted with DCM. The combined organics were dried over $Na_2SO_4$, filtered and concentrated to brown oil. The crude material was purified by silica gel column chromatography using 0-20% EtOAc in hexanes to yield tert-butyl 4-[5-[bis(tert-butoxycarbonyl)amino]-6-[5-[4-(bromomethyl)phenyl]-1,3,4-oxadiazol-2-yl]pyrazin-2-yl]-3,6-dihydro-2H-pyridine-1-carboxylate (350 mg, 60%). $^1$HNMR (400 MHz, $CDCl_3$) δ 8.74 (s, 1H), 8.22 (d, J=33.8 Hz, 2H), 7.59 (d, J=8.2 Hz, 2H), 6.92 (s, 1H), 4.54 (s, 2H), 4.24 (s, 2H), 3.73 (t, J=5.5 Hz, 2H), 2.79 (d, J=0.8 Hz, 2H), 1.37 (s, 18H), 1.24 (s, 9H).

Method BV: Step 2: 3-[5-[4-(Bromomethyl)phenyl]-1,3,4-oxadiazol-2-yl]-5-(1,2,3,6-tetrahydropyridin-4-yl)pyrazin-2-amine tert-Butyl-4-[5-[bis(tert-butoxycarbonyl)amino]-6-[5-[4-(bromomethyl)phenyl]-1,3,4-oxadiazol-2-yl]pyrazin-2-yl]-3,6-dihydro-2H-pyridine-1-carboxylate (54 mg, 0.07 mmol) was treated with a solution of 4 M hydrogen chloride (376 μL of 4 M, 1.5 mmol) in dioxane and stirred at room temperature for 1 h. The solvent was removed under reduced pressure to yield 3-[5-[4-(bromomethyl)phenyl]-1,3,4-oxadiazol-2-yl]-5-(1,2,3,6-tetrahydropyridin-4-yl)pyrazin-2-amine as an off white solid, which was used in the next step without further purification. LC/MS m/z 415.5 [M+H]$^+$.

Method BV: Step 3: 1-[4-[5-Amino-6-[5-[4-(bromomethyl)phenyl]-1,3,4-oxadiazol-2-yl]pyrazin-2-yl]-3,6-dihydro-2H-pyridin-1-yl]propan-1-one.

To a solution of 3-[5-[4-(bromomethyl)phenyl]-1,3,4-oxadiazol-2-yl]-5-(1,2,3,6-tetrahydropyridin-4-yl)pyrazin-2-amine (34 mg, 0.07 mmol) in anhydrous DCM (500 μL) cooled in an ice water bath under an atmosphere of nitrogen was added DIEA (49 mg, 66 μL, 0.38 mmol) followed by the dropwise addition of a solution of propanoyl chloride (8 mg, 7 μL, 0.08 mmol) in DCM (0.2 mL). The reaction mixture was stirred for 15 minutes. The reaction mixture was diluted with DCM and washed three times with 1M aqueous HCl solution, twice with saturated aqueous $NaHCO_3$ solution and then twice with a solution of brine. The layers were separated and the organic layer was dried over $Na_2SO_4$, filtered and concentrated to dryness under reduced pressure to yield 1-[4-[5-amino-6-[5-[4-(bromomethyl)phenyl]-1,3,4-oxadiazol-2-yl]pyrazin-2-yl]-3,6-dihydro-2H-pyridin-1-yl]propan-1-one (20 mg, 57%). LC/MS m/z 471.3 [M+H]$^+$.

Method BV: Step 4: 1-[4-[5-Amino-6-[5-[4-(methylaminomethyl)phenyl]-1,3,4-oxadiazol-2-yl]pyrazin-2-yl]-3,6-dihydro-2H-pyridin-1-yl]propan-1-one A solution of 1-[4-[5-amino-6-[5-[4-(bromomethyl)phenyl]-1,3,4-oxadiazol-2-yl]pyrazin-2-yl]-3,6-dihydro-2H-pyridin-1-yl]propan-1-one (20 mg, 0.04 mmol) and a solution of methanamine (107 μL of 2 M, 0.21 mmol) in THF was heated at 65° C. for 6 h. The reaction mixture was allowed to cool to room temperature and the solvents were evaporated under reduced pressure. The crude material obtained was dissolved in DMF (1 mL), filtered and purified by mass directed reverse phase LC/MS (1-99% $ACN/H_2O$ (5 mM HCl)) to yield 1-[4-[5-amino-6-[5-[4-(methylaminomethyl)phenyl]-1,3,4-oxadiazol-2-yl]pyrazin-2-yl]-3,6-dihydro-2H-pyridin-1-yl]propan-1-one (9 mg, 45%). $^1$H NMR (400 MHz, DMSO-$d_6$) δ 9.28 (s, 2H), 8.58 (s, 1H), 8.18 (d, J=7.7 Hz, 2H), 7.80 (d, J=8.0 Hz, 2H), 7.63 (s, 2H), 6.66 (s, 1H), 4.30-4.13 (m, 4H), 3.70 (dt, J=16.2, 5.4 Hz, 2H), 2.71 (s, 1H), 2.59 (t, J=5.2 Hz, 4H), 2.41 (dt, J=21.8, 7.3 Hz, 2H), 1.03 (q, J=7.0 Hz, 3H). LC/MS m/z 420.5 [M+H]$^+$.

Compound I-339 was prepared using the method described for Compound I-335 in Example 44 above.

Compound I-339: 5-(1-Ethylsulfonyl-3,6-dihydro-2H-pyridin-4-yl)-3-[5-[4-(methylaminomethyl)phenyl]-1,3,4-oxadiazol-2-yl]pyrazin-2-amine. LC/MS m/z 456.1 [M+H]$^+$.

Example 45

3-(5-(4-((Methylamino)methyl)phenyl)-1,3,4-oxadiazol-2-yl)-5-(4-methylcyclohex-1-enyl)pyrazin-2-amine. (Compound I-336)

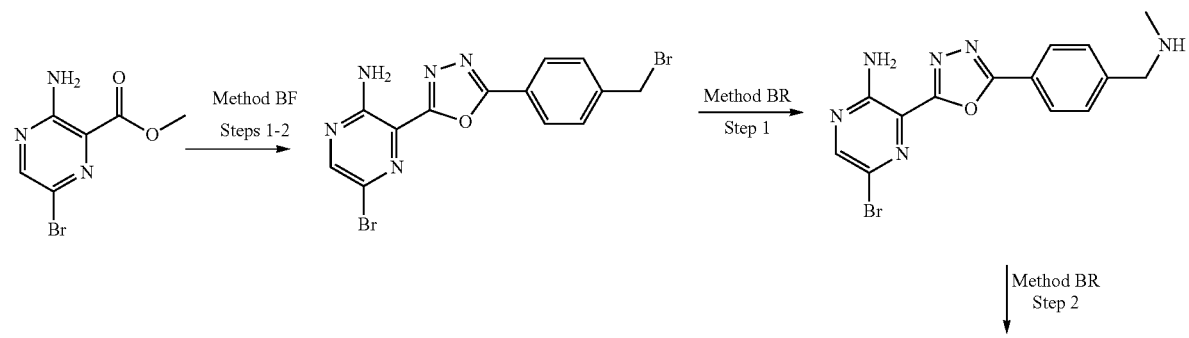

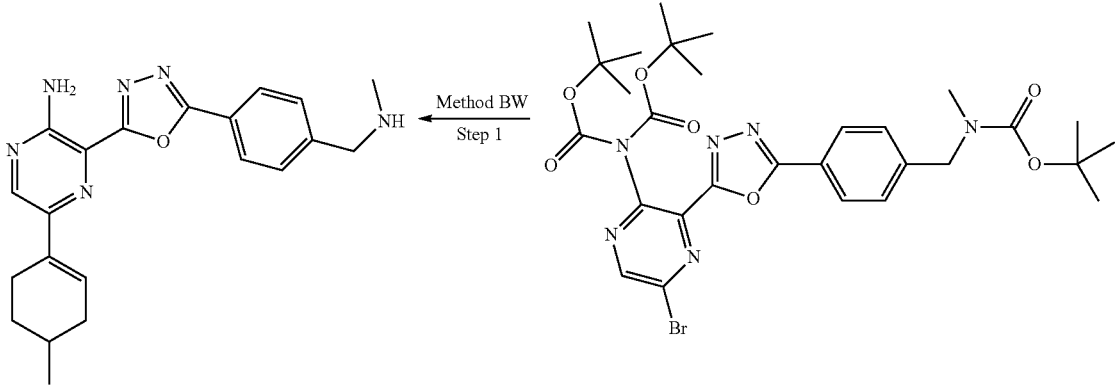

Compound I-336 was prepared using Method BF, Steps 1-2 followed by Method BR, Steps 1-2, followed by Method BW, Step 1.

Method BW: Step 1: 3-(5-(4-((Methylamino)methyl) phenyl)-1,3,4-oxadiazol-2-yl)-5-(4-methylcyclohex-1-enyl)pyrazin-2-amine A suspension of tert-butyl N [[4-[5-[3-[bis(tert-butoxycarbonyl)amino]-6-bromo-pyrazin-2-yl]-1,3,4-oxadiazol-2-yl]phenyl]methyl]-N-methyl-carbamate (70 mg, 0.11 mmol), 4-ditert-butylphosphanyl-N,N-dimethyl-aniline; dichloropalladium (0.75 mg, 0.001 mmol) and $K_2CO_3$ (29 mg, 0.2 mmol) in toluene (630 µL) and water (70 µL) was heated to 80° C. for 18 h. The reaction mixture was cooled to room temperature and diluted with DCM (30 ml) and water (30 ml). The layers were separated and the organic layer was washed with 1M NaOH solution, dried over ($Na_2SO_4$), filtered and concentrated to dryness. The crude material obtained was stirred in 1:1 DCM:TFA mixture (3 mL) for 1 h. The solvents were evaporated under reduced pressure and the crude material was purified by reverse phase chromatography using 1 to 99% MeOH in water (0.05% HCl) to obtain 3-(5-(4-((methylamino)methyl)phenyl)-1,3,4-oxadiazol-2-yl)-5-(4-methylcyclohex-1-enyl)pyrazin-2-amine. $^1$H NMR (400 MHz, MeOD) δ 8.33-8.21 (m, 3H), 7.79-7.68 (m, 2H), 6.65 (s, 1H), 4.32 (d, J=5.3 Hz, 2H), 3.78-3.61 (m, 2H), 3.34 (d, J=5.4 Hz, 1H), 2.78 (d, J=5.3 Hz, 3H), 2.71 (d, J=14.9 Hz, 1H), 2.42 (ddd, J=22.1, 18.2, 5.7 Hz, 2H), 2.00-1.83 (m, 2H), 1.82-1.69 (m, 1H), 1.40 (dt, J=16.6, 4.6 Hz, 1H), 1.05 (t, J=5.9 Hz, 3H). LC/MS m/z 377.0[M+H]$^+$.

Example 46

N-(4-(5-Amino-6-(5-(4-((methylamino)methyl)phenyl)-1,3,4-oxadiazol-2-yl)pyrazin-2-yl)cyclohex-3-enyl)propionamide. (Compound I-367)

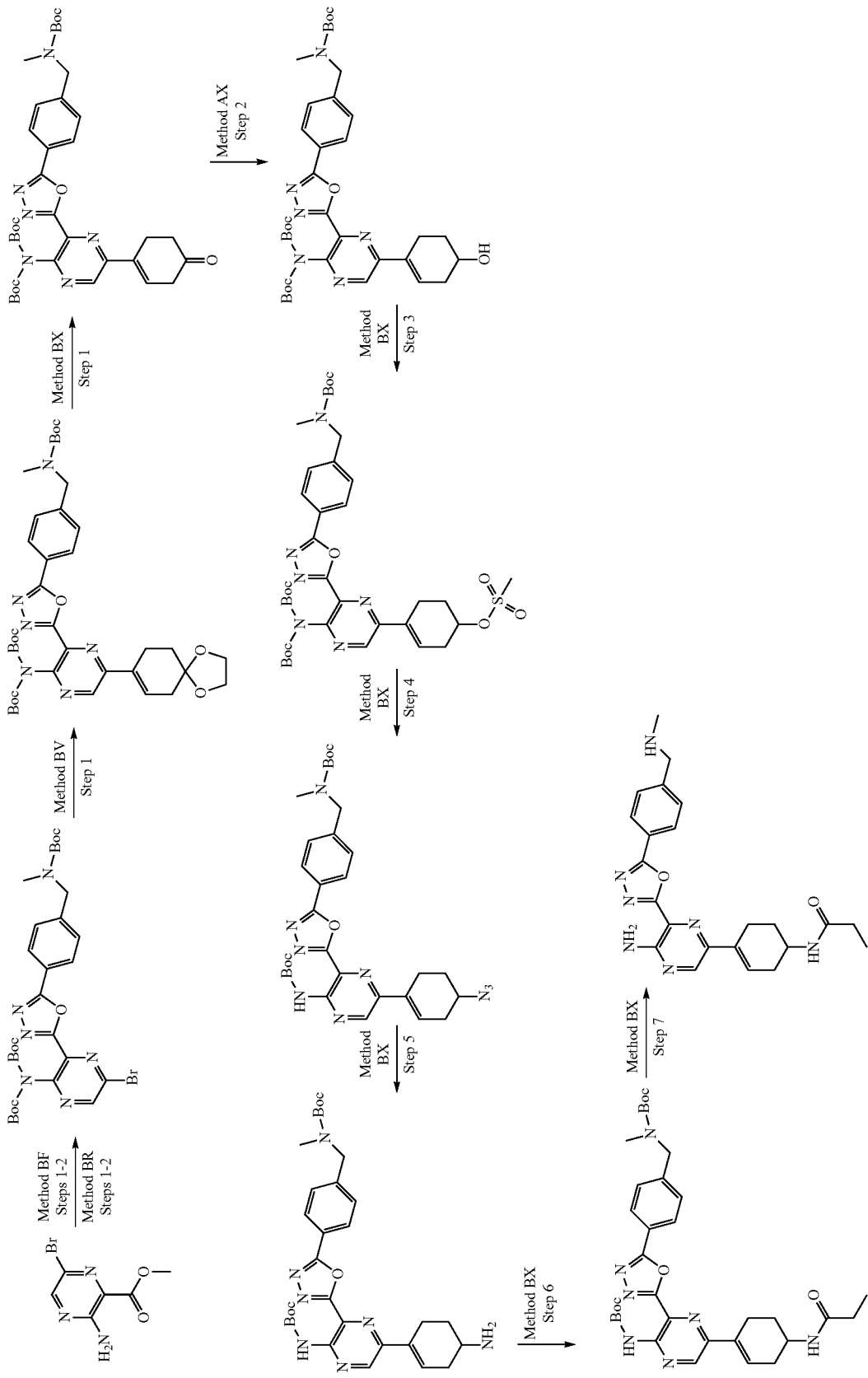

Compound I-367 was prepared using Method BF, Steps 1-2 followed by Method BR, Steps 1-2, followed by Method BV, Step 1, followed by Method BX, Steps 1-5.

Method BX: Step 1: tert-Butyl N-[[4-[5-[3-[bis(tert-butoxycarbonyl)amino]-6-(4-oxocyclohex-1-yl)pyrazin-2-yl]-1,3,4-oxadiazol-2-yl]phenyl]methyl]-N-methyl-carbamate To a solution of tert-butyl N-[[4-[5-[3-[bis(tert-butoxycarbonyl)amino]-6-(1,4-dioxaspiro[4.5]dec-7-en-8-yl)pyrazin-2-yl]-1,3,4-oxadiazol-2-yl]phenyl]methyl]-N-methyl-carbamate (680 mg, 0.94 mmol) in THF (2.0 mL) was added 1 M aqueous HCl (1.9 mL of 1 M, 1.9 mmol) and the reaction mixture was heated at 60° C. for 6 h. The reaction was cooled to room temperature and diluted with EtOAc, the layers were separated and the organic layer was washed once with aqueous $NaHCO_3$, then once with brine, dried over $Na_2SO_4$, filtered and concentrated to dryness to yield tert-butyl N-[[4-[5-[3-[bis(tert-butoxycarbonyl)amino]-6-(4-oxocyclohexen-1-yl)pyrazin-2-yl]-1,3,4-oxadiazol-2-yl]phenyl]methyl]-N-methyl-carbamate (487 mg, 76%) and was used without further purification. LC/MS m/z 677.5 $[M+H]^+$.

Method BX: Step 2: tert-Butyl N-[[4-[5-[3-[bis(tert-butoxycarbonyl)amino]-6-(4-hydroxycyclohexen-1-yl)pyrazin-2-yl]-1,3,4-oxadiazol-2-yl]phenyl]methyl]-N-methyl-carbamate A solution of tert-butyl N-[[4-[5-[3-[bis(tert-butoxycarbonyl)amino]-6-(4-oxocyclohexen-1-yl)pyrazin-2-yl]-1,3,4-oxadiazol-2-yl]phenyl]methyl]-N-methyl-carbamate (431 mg, 0.64 mmol) in MeOH (2 mL) was cooled in an ice water bath. Sodium boranuide (27 mg, 0.70 mmol) was added and the reaction mixture was stirred for 40 minutes at 0° C. upon which the ice bath was removed. After stirring at room temperature for 8 h, the reaction mixture was quenched with water and aq. $NaHCO_3$ and diluted with EtOAc. The layers were separated and the aqueous layer was extracted once more with EtOAc. The combined organic layer was dried over $Na_2SO_4$, filtered and concentrated. The crude material was purified by silica gel column chromatography using 0-40% EtOAc in DCM to yield tert-butyl N-[[4-[5-[3-[bis(tert-butoxycarbonyl)amino]-6-(4-hydroxycyclohexen-1-yl)pyrazin-2-yl]-1,3,4-oxadiazol-2-yl]phenyl]methyl]-N-methyl-carbamate (126 mg, 41%). $^1$H NMR (400 MHz, DMSO-$d_6$) δ 9.04 (s, 1H), 8.11 (d, J=8.0 Hz, 2H), 7.49 (d, J=8.1 Hz, 2H), 7.01 (s, 1H), 4.81 (d, J=3.8 Hz, 1H), 4.49 (s, 2H), 3.93-3.86 (m, 1H), 2.83 (s, 5H), 2.64-2.53 (m, J=19.3 Hz, 2H), 1.97-1.90 (m, J=12.4 Hz, 1H), 1.71 (dd, J=14.0, 8.7 Hz, 1H), 1.45 (s, 3H), 1.36 (s, 6H), 1.26 (s, 18H); LC/MS m/z 579.9 $[M+H]^+$.

Method BX: Step 3: [4-[5-[bis(tert-Butoxycarbonyl)amino]-6-[5-[4-[[tert-butoxycarbonylmethyl)amino]methyl]phenyl]-1,3,4-oxadiazol-2-yl]pyrazin-2-yl]cyclohex-3-en-1-yl]methanesulfonate To a solution of tert-butyl N-[[4-[5-[3-[bis(tert-butoxycarbonyl)amino]-6-(4-hydroxycyclohexen-1-yl)pyrazin-2-yl]-1,3,4-oxadiazol-2-yl]phenyl]methyl]-N-methyl-carbamate (124 mg, 0.18 mmol) in anhydrous DCM (2 mL) was added DMAP (2 mg, 0.02 mmol), followed by the addition of $Et_3N$ (20 mg, 28 µL, 0.20 mmol) under an atmosphere of nitrogen. The reaction mixture was cooled in an ice water bath and then treated with a solution of methanesulfonyl chloride (22 mg, 15 µL, 0.19 mmol) in DCM (0.1 mL) dropwise. The reaction mixture was stirred for 45 minutes and then partitioned between DCM/1M aqueous HCl. The layers were separated and the organic layer was washed twice with aqueous 1M HCl, once with aqueous $NaHCO_3$, then brine solution. The organic layer was dried over $Na_2SO_4$, filtered and concentrated to dryness under reduced pressure to yield [4-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]cyclohex-3-en-1-yl]methanesulfonate (138 mg, 100%) and was used without any further purification in the next step. LC/MS m/z 757.5 $[M+H]^+$.

Method BX: Step 4: tert-Butyl N-[[4-[5-[6-(4-azidocyclohexen-1-yl)-3-(tert-butoxycarbonylamino)pyrazin-2-yl]-1,3,4-oxadiazol-2-yl]phenyl]methyl]-N-methyl-carbamate To a solution of [4-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]cyclohex-3-en-1-yl]methanesulfonate (138 mg, 0.18 mmol) in anhydrous DMF (1 mL) was added sodium azide (59 mg, 0.91 mmol) and the reaction mixture was heated at 70° C. under an atmosphere of nitrogen for 15 h. The reaction mixture was cooled to room temperature, quenched with water and diluted with EtOAc. An aqueous saturated brine solution was added, the layers were separated and the organic layer was washed twice more with an aqueous saturated brine solution. The organic layer was dried over $Na_2SO_4$, filtered and concentrated under reduced pressure to a brown oil to provide tert-butyl N-[[4-[5-[6-(4-azidocyclohexen-1-yl)-3-(tert-butoxycarbonylamino)pyrazin-2-yl]-1,3,4-oxadiazol-2-yl]phenyl]methyl]-N-methyl-carbamate (103 mg, 94%), which was used without any further purification in the next step. LC/MS m/z 604.7 $[M+H]^+$.

Method BX: Step 5: tert-Butyl N-[[4-[5-[6-(4-aminocyclohexen-1-yl)-3-(tert-butoxycarbonylamino)pyrazin-2-yl]-1,3,4-oxadiazol-2-yl]phenyl]methyl]-N-methyl-carbamate To a solution of tert-butyl N-[[4-[5-[6-(4-azidocyclohexen-1-yl)-3-(tert-butoxycarbonylamino)pyrazin-2-yl]-1,3,4-oxadiazol-2-yl]phenyl]methyl]-N-methyl-carbamate (103 mg, 0.17 mmol) in anhydrous THF (1.5 mL) was added triphenylphosphine (67 mg, 0.26 mmol) and the reaction mixture was stirred at room temperature for 1 h. Water (61 µL, 3.41 mmol) was added after 1 h, and the reaction mixture was heated at 65° C. for 3 h. The reaction mixture was allowed to cool to room temperature and was partitioned between EtOAc/aqueous brine. The layers were separated and the aqueous layer was extracted once more with EtOAc. The combined organics were dried over $Na_2SO_4$, filtered and concentrated to dryness. The crude material was purified by silica gel column chromatography using 20% MeOH in EtOAc to yield tert-butyl N-[[4-[5-[6-(4-aminocyclohexen-1-yl)-3-(tert-butoxycarbonylamino)pyrazin-2-yl]-1,3,4-oxadiazol-2-yl]phenyl]methyl]-N-methyl-carbamate (21 mg, 21%). LC/MS m/z 578.3 $[M+H]^+$.

Method BX: Step 6: tert-Butyl N-[[4-[5-[3-(tert-butoxycarbonylamino)-6-[4-(propanoylamino)cyclohexen-1-yl]pyrazin-2-yl]-1,3,4-oxadiazol-2-yl]phenyl]methyl]-N-methyl-carbamate To a solution of tert-butyl N-[[4-[5-[6-(4-aminocyclohexen-1-yl)-3-(tert-butoxycarbonylamino)pyrazin-2-yl]-1,3, 4-oxadiazol-2-yl]phenyl]methyl]-N-methyl-carbamate (20 mg, 0.03 mmol) in anhydrous DCM (200 µL) was added Et₃N (5 mg, 7 µL, 0.05 mmol) and the reaction mixture was cooled in an ice water bath. A solution of propanoyl chloride (3.843 mg, 3.625 µL, 0.04154 mmol) in DCM (0.1 mL) was added dropwise to the above reaction mixture. The reaction mixture was diluted with DCM and washed once with water. The organic layer was dried over Na₂SO₄, filtered and concentrated under reduced pressure. The crude material was purified by silica gel column chromatography using 10% MeOH in EtOAc to yield tert-butyl N-[[4-[5-[3-(tert-butoxycarbonylamino)-6-[4-(propanoylamino)cyclohexen-1-yl]pyrazin-2-yl]-1,3,4-oxadiazol-2-yl]phenyl]methyl]-N-methyl-carbamate (21 mg, 96%).

LC/MS m/z 634.3 [M+H]⁺.

Method BX: Step 7: N-(4-(5-Amino-6-(5-(4-((methylamino)methyl)phenyl)-1,3,4-oxadiazol-2-yl)pyrazin-2-yl)cyclohex-3-enyl)propionamide To a solution of tert-butyl N-[[4-[5-[3-[bis(tert-butoxycarbonyl)amino]-6-[4-(propanoylamino)cyclohexen-1-yl] pyrazin-2-yl]-1,3,4-oxadiazol-2-yl]phenyl]methyl]-N-methyl-carbamate (21 mg, 0.03 mmol) in DCM (220 µL) was added TFA (326 mg, 220 µL, 2.9 mmol) and the reaction mixture was stirred for 40 minutes at room temperature. The reaction mixture was concentrated under reduced pressure. The residue was dissolved in DMF (1 mL) and purified by Gilson reverse phase HPLC using (5-99% ACN/H₂O (5 mM HCl)) to yield N-(4-(5-Amino-6-(5-(4-((methylamino)methyl)phenyl)-1,3,4-oxadiazol-2-yl)pyrazin-2-yl)cyclohex-3-enyl)propionamide. ¹H NMR (400 MHz, MeOD) d 8.41 (s, 1H), 8.31 (d, J=8.4 Hz, 2H), 7.77 (d, J=8.3 Hz, 2H), 6.64 (s, 1H), 4.34 (s, 2H), 4.11-3.98 (m, 1H), 2.81 (s, 4H), 2.63 (d, J=17.8 Hz, 2H), 2.26 (q, J=7.7 Hz, 3H), 2.15-2.04 (m, 1H), 1.78 (dd, J=11.3, 5.0 Hz, 1H), 1.18 (t, J=7.6 Hz, 3H). LC/MS m/z 434.2 [M+H]⁺.

Example 42

1-(4-(5-Amino-6-(5-(4-((methylamino)methyl)phenyl)-1,3,4-oxadiazol-2-yl)pyrazin-2-yl)piperidin-1-yl)propan-1-one (Compound I-353)

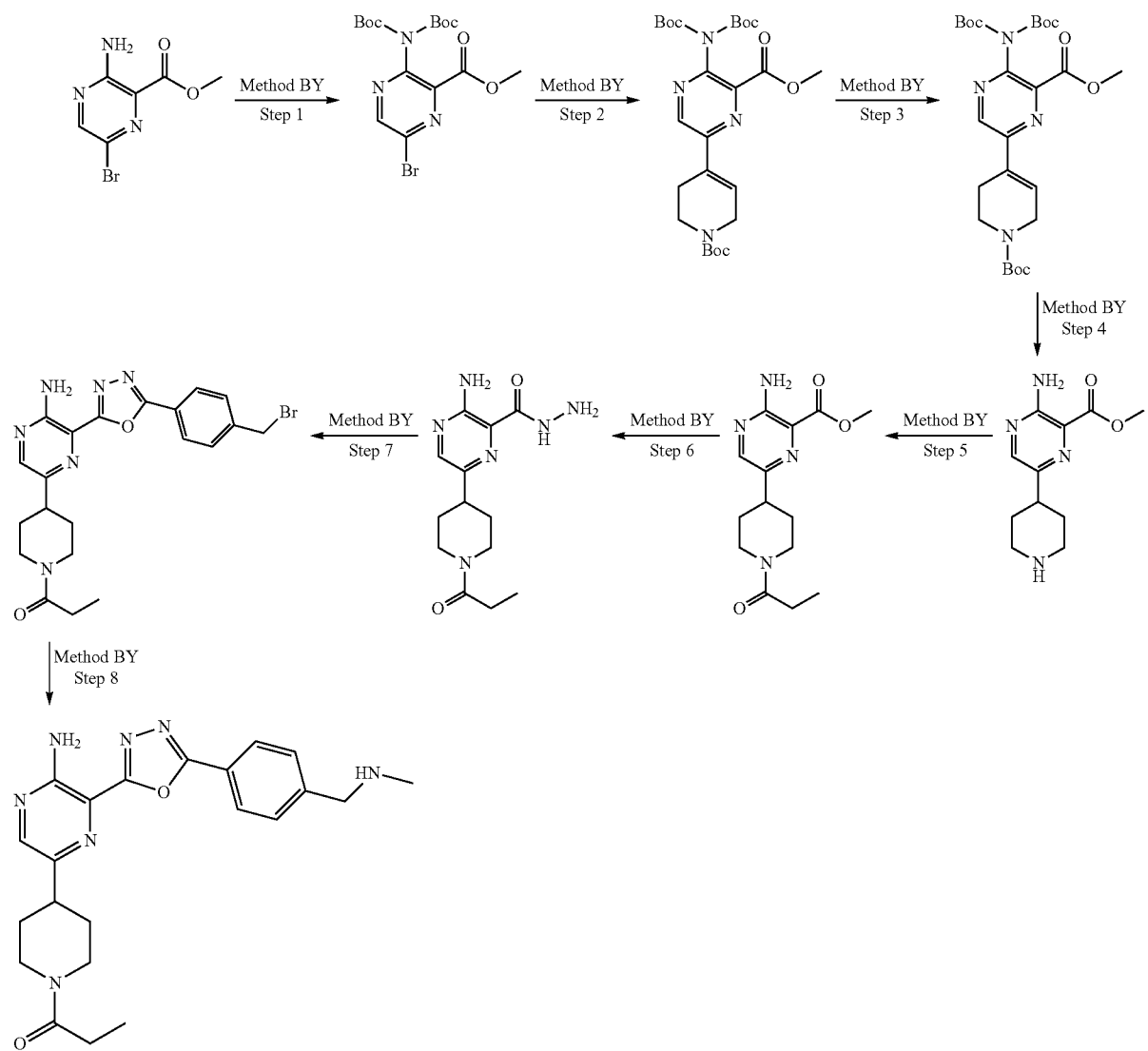

Compound I-353 was prepared using Method BY Steps 1-8.

Method BY: Step 1: Methyl 3-[bis(tert-butoxycarbonyl)amino]-6-bromo-pyrazine-2-carboxylate Methyl 3-amino-6-bromo-pyrazine-2-carboxylate (3 g, 12.93 mmol) and DMAP (158.0 mg, 1.3 mmol) were suspended in dichloromethane (45 mL) and treated dropwise with a solution of di-tert-butyl dicarbonate (11.3 g, 11.9 mL, 51.72 mmol) in dichloromethane (10 mL). The reaction mixture was stirred for 30 minutes, then washed with 0.2 N HCl, 50% saturated sodium bicarbonate solution, dried over $Na_2SO_4$, filtered and concentrated in vacuo. The crude product was purified by silica gel column chromatography using 10-30% ethyl acetate/hexane to obtain methyl 3-[bis(tert-butoxycarbonyl)amino]-6-bromo-pyrazine-2-carboxylate (5.40 g, 97%) as a white solid. $^1H$ NMR (400 MHz, DMSO-$d_6$) δ 9.11 (s, 1H), 3.90 (s, 3H), 1.35 (s, 18H). LC/MS m/z 434.5 $[M+H]^+$.

Method BY: Step 2: Methyl 3-[bis(tert-butoxycarbonyl)amino]-6-(1-tert-butoxycarbonyl-3,6-dihydro-2H-pyridin-4-yl)pyrazine-2-carboxylate A suspension of tert-butyl 4-(4,4,5,5-tetramethyl-1,3,2-dioxaborolan-2-yl)-3,6-dihydro-2H-pyridine-1-carboxylate (858 mg, 2.8 mmol), 4-ditert-butylphosphanyl-N,N-dimethyl-aniline; dichloropalladium (164 mg, 0.23 mmol), methyl 3-[bis(tert-butoxycarbonyl)amino]-6-bromo-pyrazine-2-carboxylate (1.0 g, 2.3 mmol), and $Na_2CO_3$ (490 mg, 4.6 mmol) under an atmosphere of nitrogen in toluene (15 mL) and water (2 mL) was heated to 95° C. for 2 h. The reaction mixture was diluted with ethyl acetate, washed with 1N HCl, 50% saturated sodium bicarbonate solution, and brine. The organic layer was dried over anhydrous $Na_2SO_4$, filtered, and concentrated. The crude product was purified via silica gel column chromatography using 10-50% ethyl acetate/hexane to provide methyl 3-[bis(tert-butoxycarbonyl)amino]-6-(1-tert-butoxycarbonyl-3,6-dihydro-2H-pyridin-4-yl)pyrazine-2-carboxylate (1.2 g, 97%) as a amber oil. $^1H$ NMR (400 MHz, DMSO-$d_6$) δ 9.03 (s, 1H), 6.97 (s, 1H), 4.12 (s, 2H), 3.89 (s, 3H), 3.57 (t, J=5.2 Hz, 2H), 2.61 (s, 2H), 1.43 (s, 9H), 1.34 (s, 18H). LC/MS m/z 535.5 $[M+H]^+$.

Method BY: Step 3: Methyl 3-[bis(tert-butoxycarbonyl)amino]-6-(1-tert-butoxycarbonyl-4-piperidyl)pyrazine-2-carboxylate A solution of methyl 3-[bis(tert-butoxycarbonyl)amino]-6-(1-tert-butoxycarbonyl-3,6-dihydro-2H-pyridin-4-yl)pyrazine-2-carboxylate (700 mg, 1.3 mmol) in methanol (28 mL) was stirred with 10% Pd/C (wet) (557 mg, 0.26 mmol) at 35° C. under an atmosphere of hydrogen for 16 h. The reaction mixture was filtered, concentrated in vacuo, and purified via silica gel column chromatography using 10-70% ethyl acetate/hexane to provide methyl 3-[bis(tert-butoxycarbonyl)amino]-6-(1-tert-butoxycarbonyl-4-piperidyl)pyrazine-2-carboxylate (285 mg) as an light orange sticky solid. $^1H$ NMR (400 MHz, $CDCl_3$) δ 8.52 (s, 1H), 4.28 (bs, 2H), 3.97 (s, 3H), 3.06 (t, J=12.0 Hz, 1H), 2.86 (t, J=12.0 Hz, 2H), 1.98 (d, J=12.5 Hz, 2H), 1.79 (qd, J=12.6, 3.9 Hz, 2H), 1.48 (s, 9H), 1.41 (s, 18H). LC/MS m/z 537.7 $[M+H]^+$.

Method BY: Step 4: Methyl 3-amino-6-(4-piperidyl)pyrazine-2-carboxylate

To a solution of methyl 3-[bis(tert-butoxycarbonyl)amino]-6-(1-tert-butoxycarbonyl-4-piperidyl)pyrazine-2-carboxylate (285 mg) in DCM (7 mL) was added TFA (3 mL) dropwise. The reaction mixture was stirred at room temperature for 1 h, then diluted with acetonitrile and concentrated in vacuo. The reaction mixture was diluted with ethyl acetate, washed with 50% saturated sodium bicarbonate solution (2×20 mL), water, and brine. The product was not able to be extracted from aqueous layer with ethyl acetate, and was taken forward directly to the subsequent acylation step using Schotten-Baumen conditions LC/MS m/z 237.1 $[M+H]^+$.

Method BY: Step 5: Methyl 3-amino-6-(1-propionylpiperidin-4-yl)pyrazine-2-carboxylate To a rapidly stirring biphasic solution of methyl 3-amino-6-(4-piperidyl)pyrazine-2-carboxylate (135 mg, 0.57 mmol) in 50% saturated sodium bicarbonate and dichloromethane (20 mL) at 25° C. was added propanoyl chloride (79 mg, 75 μL, 0.86 mmol) dropwise. The reaction was stirred at room temperature for 30 minutes. The organic layer was separated, dried over $Na_2SO_4$, filtered, and concentrated in vacuo to provide methyl 3-amino-6-(1-propionylpiperidin-4-yl)pyrazine-2-carboxylate (111 mg, 66%). $^1H$ NMR (400 MHz, DMSO-$d_6$) δ 8.25 (s, 1H), 7.19 (s, 2H), 4.51 (d, J=12.9 Hz, 1H), 3.95 (d, J=13.6 Hz, 1H), 3.84 (s, 3H), 3.08 (t, J=12.2 Hz, 1H), 2.88 (ddd, J=15.5, 7.9, 3.7 Hz, 1H), 2.61 (t, J=11.7 Hz, 1H), 2.34 (q, J=7.5 Hz, 2H), 1.80 (t, J=13.7 Hz, 2H), 1.69-1.39 (m, 2H), 1.00 (t, J=7.4 Hz, 3H). LC/MS m/z 293.5 [M+H]

Method BY: Step 6: 3-amino-6-(1-propionylpiperidin-4-yl)pyrazine-2-carbohydrazide Methyl 3-amino-6-(1-propanoyl-4-piperidyl)pyrazine-2-carboxylate (110 mg, 0.38 mmol) was suspended in EtOH (2 mL) and hydrazine hydrate (94 mg, 92 μL, 1.9 mmol) was added and the reaction mixture was heated at 70° C. for 1.5 h, followed by 16 h heating at 35° C. forming a thick yellow solid. The solid was isolated by filtration, washed with water (20 mL) and ethanol (40 mL). The solid was dried under high vacuum to yield 3-amino-6-(1-propionylpiperidin-4-yl)pyrazine-2-carbohydrazide (105 mg, 95%) as a light yellow solid. $^1H$ NMR (400 MHz, DMSO-$d_6$) δ 9.70 (s, 1H), 8.12 (s, 1H), 7.27 (bs, 2H), 4.57-4.43 (m, 3H), 3.94 (d, J=13.6 Hz, 1H), 3.33 (bs, 2H), 3.13-2.97 (m, 1H), 2.90-2.76 (m, 1H), 2.58 (t, J=11.7 Hz, 1H), 2.34 (q, J=7.4 Hz, 2H), 1.83-1.70 (m, 3H), 1.69-1.55 (m, 1H), 1.01 (t, J=7.4 Hz, 3H). LC/MS m/z 293.3 $[M+H]^+$.

Method BY: Step 7: 1-[4-[5-Amino-6-[5-[4-(bromomethyl)phenyl]-1,3,4-oxadiazol-2-yl]pyrazin-2-yl]-1-piperidyl]propan-1-one Dibromo(triphenyl)phosphorane (682 mg, 1.6 mmol) was added to a suspension of 3-amino-6-(1-propanoyl-4-piperidyl)pyrazine-2-carbohydrazide (105 mg, 0.36 mmol) and 4-(bromomethyl)benzoic acid (77 mg, 0.36 mmol) in MeCN (2 mL) at room temperature and the resulting solution was stirred for 1 h under an atmosphere of nitrogen. DIPEA (278.5 mg, 375.3 μL, 2.155 mmol) was added dropwise and the solution was stirred for 2 h. The reaction mixture was diluted with ethyl acetate, washed with 50% saturated sodium bicarbonate solution (2×20 mL), water, and brine. The solution was dried over anhydrous $Na_2SO_4$, filtered, concentrated in vacuo to obtain 1-[4-[5-amino-6-[5-[4-(bromomethyl)phenyl]-1,3,4-oxadiazol-2-yl]pyrazin-2-yl]-1-piperidyl]propan-1-one, which was taken to the next step without further purification.

LC/MS m/z 472.5 $[M+H]^+$.

Method BY: Step 8: 1-(4-(5-Amino-6-(5-(4-((methylamino)methyl)phenyl)-1,3,4-oxadiazol-2-yl)pyrazin-2-yl)piperidin-1-yl)propan-1-one A solution of 1-[4-[5-amino-6-[5-[4-(bromomethyl)phenyl]-1,3,4-oxadiazol-2-yl]pyrazin-2-yl]-1-piperidyl]propan- 1-one and Na₂CO₃ (114 mg, 1.1 mmol) in tetrahydrofuran was treated with a solution of methylamine (1.3 mL of 2 M, 2.5 mmol) in THF and heated at 65° C. for 30 minutes. The reaction mixture was diluted with ethyl acetate, washed with 50% saturated sodium bicarbonate solution (2×20 mL), water, and brine. The solution was dried over anhydrous Na₂SO₄, filtered, and concentrated in vacuo. The crude material was purified via reverse phase HPLC (1-50% CH3CN/5 mM HCl) to provide 1-(4-(5-amino-6-(5-(4-((methylamino) methyl)phenyl)-1,3,4-oxadiazol-2-yl)pyrazin-2-yl)piperidin-1-yl)propan-1-one.

$^1$H NMR (400 MHz, DMSO-d₆) δ 9.16 (s, 2H), 8.29 (s, 1H), 8.17 (d, J=8.1 Hz, 2H), 7.78 (d, J=8.1 Hz, 2H), 4.56 (d, J=12.5 Hz, 1H), 4.25 (t, J=5.7 Hz, 2H), 4.00 (d, J=13.3 Hz, 1H), 3.14 (t, J=12.5 Hz, 1H), 2.98 (t, J=11.9 Hz, 1H), 2.67 (t, J=11.9 Hz, 1H), 2.60 (t, J=5.2 Hz, 3H), 2.37 (q, J=7.5 Hz, 2H), 1.91 (t, J=12.1 Hz, 2H), 1.64 (ddd, J=33.0, 20.8, 11.9 Hz, 2H), 1.02 (t, J=7.4 Hz, 3H). LC/MS m/z 422.5 [M+H]⁺.

Example 43

(2-(5-Amino-6-(5-(4-((methylamino)methyl)phenyl)-1,3,4-oxadiazol-2-yl)pyrazin-2-yl)cyclopropyl) ((R)-3-aminopyrrolidin-1-yl)methanone (Compound I-374)

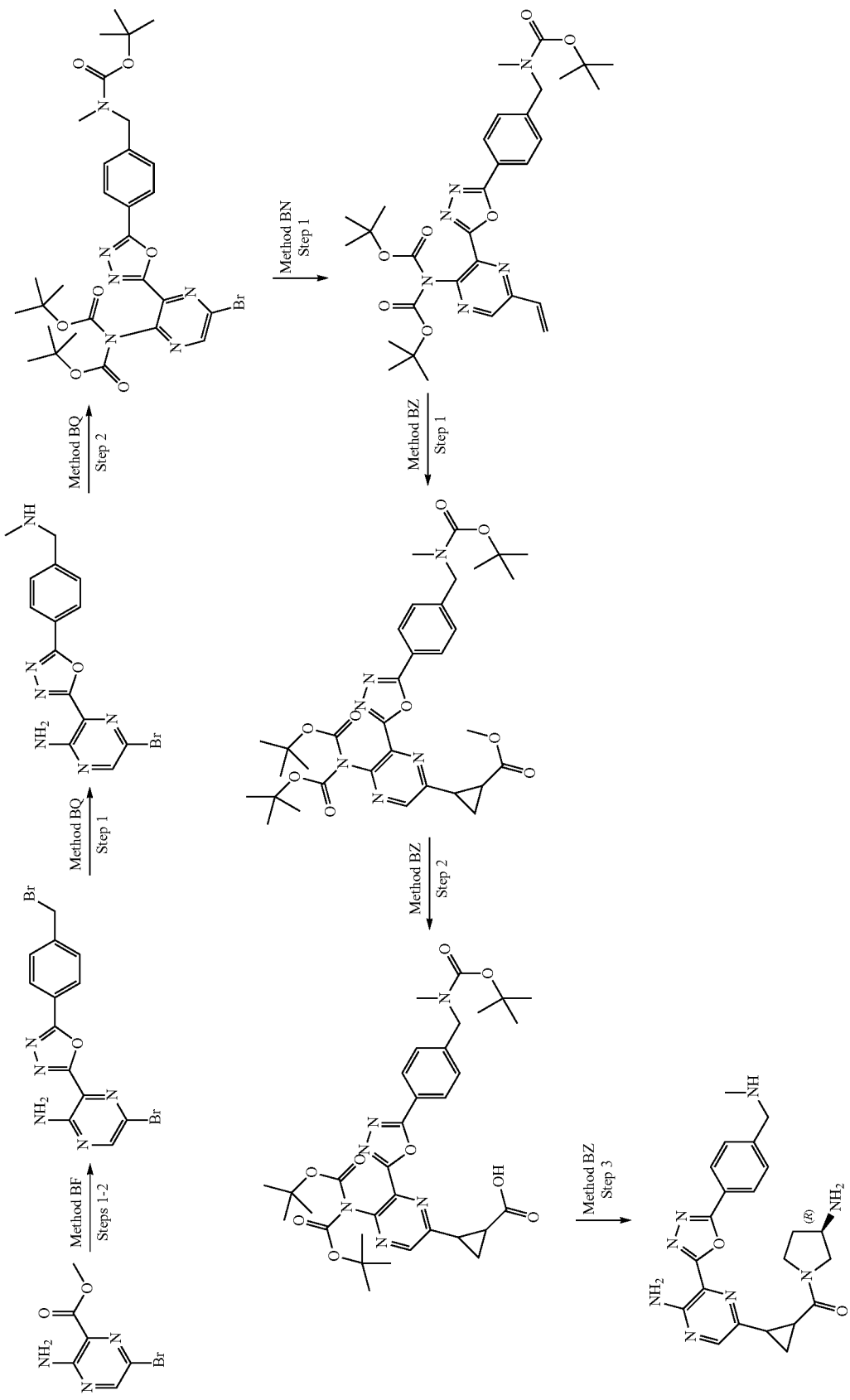

Compound I-374 was prepared using Method BF, Steps 1-2, followed by Method BQ Steps 1-2, followed by Method BN Step 1, followed by Method BZ Steps 1-4

Method BZ: Step 1: Ethyl 2-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]cyclopropanecarboxylate To a solution of tert-butyl N-[[4-[5-[3-[bis(tert-butoxycarbonyl)amino]-6-vinyl-pyrazin-2-yl]-1,3,4-oxadiazol-2-yl]phenyl]methyl]-N-methyl-carbamate (850 mg, 1.4 mmol) in toluene (0.2 mL) at 110° C. was added a solution of ethyl 2-diazoacetate (637 mg, 587 µL, 5.6 mol) in toluene (0.7 mL) slowly over a period of 30 minutes. The reaction mixture showed incomplete conversion to product, when stirred at room temperature, so another 4 equivalents of ethyl 2-diazoacetate (637 mg, 587 µL, 5.6 mmol) was added and the reaction mixture was heated at 110° C. for 20 minutes. The reaction mixture was cooled to room temperature and the solvent was evaporated under reduced pressure. The residue obtained was purified via silica gel column chromatography using 5 to 100% EtOAc in hexanes to yield ethyl 2-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]cyclopropanecarboxylate (921 mg, 1.326 mmol, 94.96%). LC/MS m/z 595.6 [M+H-Boc]$^+$.

Method BZ: Step 2: 2-[5-[bis(tert-Butoxycarbonyl)amino]-6-[5-[4-[[tert-butoxycarbonyl(methyl)amino]methyl]phenyl]-1,3,4-oxadiazol-2-yl]pyrazin-2-yl]cyclopropanecarboxylic acid To a solution of ethyl 2-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]cyclopropanecarboxylate (825 mg, 1.2 mmol) in THF:MeOH solvent mixture (3.2 mL:1.6 mL) at room temperature was added aqueous NaOH (594 µL, of 4 M, 2.37 mmol) and reaction mixture was heated at 50° C. for 20 minutes. The reaction mixture was cooled to room temperature and diluted with EtOAc and washed with 1M HCl solution. The layers were separated and the organic layer was washed with brine, dried over Na$_2$SO$_4$, filtered and concentrated to obtain 2-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]cyclopropanecarboxylic acid. $^1$H NMR (400 MHz, DMSO-d$_6$) δ 10.19 (s, 1H), 8.73 (s, 1H), 8.07 (d, J=8.2 Hz, 2H), 7.47 (t, J=6.7 Hz, 2H), 4.49 (s, 2H), 2.83 (s, 5H), 1.91 (s, 2H), 1.49-1.33 (m, 27H). LC/MS m/z 567.6 [M+H]$^+$. (less 1 Boc)

Method BZ: Step 3: [2-[5-Amino-6-[5-[4-(methylaminomethyl)phenyl]-1,3,4-oxadiazol-2-yl]pyrazin-2-yl]cyclopropyl]-[(3R)-3-aminopyrrolidin-1-yl]methanone To a solution of 2-[5-[bis(tert-butoxycarbonyl)amino]-6-[5-[4-[[tert-butoxycarbonyl(methyl)amino]methyl]phenyl]-1,3,4-oxadiazol-2-yl]pyrazin-2-yl]cyclopropanecarboxylic acid (100 mg, 0.15 mmol) and tert-butyl N-[(3R)-pyrrolidin-3-yl]carbamate (31 mg, 0.17 mmol) in DMF (0.6 mL) at room temperature was added HATU (57 mg, 0.15 mmol) followed by the addition of DIEA (48 mg, 65 µL, 0.37 mmol) and reaction mixture was stirred at room temperature overnight. The reaction mixture was diluted with EtOAc and washed with 1M HCl solution, and then with brine. The layers were separated and the organic layer was dried over Na$_2$SO$_4$, filtered and concentrated to obtain tert-butyl N-[[4-[5-[3-[bis(tert-butoxycarbonyl)amino]-6-[2-[(3R)-3-(tert-butoxycarbonylamino)pyrrolidine-1-carbonyl]cyclopropyl]pyrazin-2-yl]-1,3,4-oxadiazol-2-yl]phenyl]methyl]-N-methyl-carbamate, which was dissolved in of 50% TFA-DCM (1 mL) mixture and stirred for 25 minutes at room temperature. The reaction mixture was concentrated under reduced pressure. The crude material was dissolved in DMSO (1 mL), filtered and purified using reverse phase HPLC (10 to 99% MeOH in H$_2$O with HCl modifier) to obtain [2-[5-amino-6-[5-[4-(methylaminomethyl)phenyl]-1,3,4-oxadiazol-2-yl]pyrazin-2-yl]cyclopropyl]-[(3R)-3-aminopyrrolidin-1-yl]methanone. LC/MS m/z 435.4 [M+H]$^+$.

The following compounds were all prepared using the method described for Compound I-374 in Example 43 above.

Compound I-375: 2-[5-Amino-6-[5-[4-(methylaminomethyl)phenyl]-1,3,4-oxadiazol-2-yl]pyrazin-2-yl]-N-ethyl-cyclopropanecarboxamide. LC/MS m/z 394.05 [M+H]$^+$.

Compound I-376: 2-[5-Amino-6-[5-[4-(methylaminomethyl)phenyl]-1,3,4-oxadiazol-2-yl]pyrazin-2-yl]-N-(2,3-dihydroxypropyl)cyclopropanecarboxamide. LC/MS m/z 440.2 [M+H]$^+$.

Compound I-377: 245-Amino-6-[5-[4-(methylaminomethyl)phenyl]-1,3,4-oxadiazol-2-yl]pyrazin-2-yl]-N-(2-methoxyethyl)-N-methyl-cyclopropanecarboxamide. $^1$H NMR (400 MHz, DMSO-d$_6$) δ 9.23 (s, 2H), 8.26 (s, 0.3H, minor), 8.18 (d, J=8.1 Hz, 2H), 8.12 (d, J=5.1 Hz, 1H, minor), 7.79 (d, J=8.1 Hz, 2H), 7.47 (bs, 1H), 4.25 (t, J=5.8 Hz, 2H), 3.54-3.46 (m, 1H), 3.43 (s, 1H), 3.25 (s, 1H), 3.16 (d, J=8.6 Hz, 1H), 3.08-2.93 (m, 1H), 2.88 (s, 1H), 2.71 (dt, J=15.5, 7.6 Hz, 1H), 2.60 (dd, J=13.9, 8.7 Hz, 4H), 2.41 (dd, J=14.6, 8.1 Hz, 1H), 2.33 (s, 0.5H, minor), 2.21 (dd, J=14.3, 8.3 Hz, 1H), 1.74 (dd, J=12.0, 5.6 Hz, 1H), 1.52-1.42 (m, 1H), 1.27 (dd, J=9.0, 4.1 Hz, 1H). LC/MS m/z 438.22 [M+H]$^+$.

Tables 7 and 8 below include some analytical data for some compounds of the instant disclosure.

TABLE 7

| Cmpd No. | LCMS ES+ | LCMS Rt (min) |
|---|---|---|
| I-174 | 378.2 | 1.09 |
| I-175 | 394.23 | 1.17 |
| I-176 | 401.18 | 0.98 |
| I-177 | 436.16 | 1.14 |
| I-178 | 440.2 | 0.97 |
| I-179 | 396.17 | 0.96 |
| I-180 | 366.16 | 0.95 |
| I-181 | 412.2 | 0.97 |
| I-182 | 368.18 | 0.95 |
| I-183 | 429.17 | 0.97 |
| I-184 | 381.21 | 0.89 |
| I-185 | 338.17 | 0.91 |
| I-186 | 378.2 | 0.88 |
| I-187 | 429.17 | 1.01 |
| I-188 | 401.18 | 0.95 |
| I-189 | 406.19 | 1.15 |
| I-190 | 394.19 | 1.10 |
| I-191 | 398.17 | 1.00 |
| I-192 | 391.18 | 1.15 |
| I-193 | 401.18 | 1.08 |
| I-194 | 420.21 | 1.21 |
| I-195 | 458.19 | 1.18 |
| I-196 | 464.14 | 1.25 |
| I-197 | 442.19 | 1.17 |
| I-198 | 408.21 | 1.2 |
| I-199 | 366.2 | 1.05 |
| I-200 | 375.19 | 1.15 |
| I-201 | 439.18 | 1.20 |
| I-202 | 500.12 | 1.25 |
| I-203 | 464.16 | 1.18 |

TABLE 7-continued

| Cmpd No. | LCMS ES+ | LCMS Rt (min) |
|---|---|---|
| I-204 | 392.21 | 1.11 |
| I-205 | 430.19 | 1.14 |
| I-206 | 389.2 | 1.21 |
| I-207 | 440.14 | 1.14 |
| I-208 | 400.18 | 1.11 |
| I-209 | 384.21 | 1.07 |
| I-210 | 433.14 | 1.25 |
| I-211 | 394.23 | 1.12 |
| I-212 | 398.22 | 1.10 |
| I-213 | 411.19 | 1.17 |
| I-214 | 377.2 | 1.19 |
| I-215 | 433.15 | 1.17 |
| I-216 | 437.2 | 1.01 |
| I-217 | 434.19 | 1.05 |
| I-218 | 395.19 | 1.04 |
| I-219 | 378.13 | 0.92 |
| I-220 | 392.18 | 1.09 |
| I-221 | 426.18 | 1.10 |
| I-222 | 462.13 | 1.14 |
| I-223 | 421.2 | 1.12 |
| I-224 | 423.17 | 1.14 |
| I-225 | 382.15 | 1.11 |
| I-226 | 418.19 | 1.16 |
| I-227 | 406.19 | 1.03 |
| I-228 | 379.14 | 1.16 |
| I-229 | 371.19 | 0.93 |
| I-230 | 412.2 | 0.89 |
| I-231 | 435.22 | 1.21 |
| I-232 | 396.17 | 1.19 |
| I-233 | 441.14 | 0.99 |
| I-234 | 364.18 | 1.06 |
| I-235 | 405.2 | 1.02 |
| I-236 | 432.21 | 1.26 |
| I-237 | 402.18 | 0.97 |
| I-238 | 393.16 | 1.24 |
| I-239 | 397.2 | 1.0 |
| I-240 | 406.16 | 1.05 |
| I-241 | 434.13 | 1.12 |
| I-242 | 358.15 | 0.98 |
| I-243 | 395.18 | 1.12 |
| I-244 | 351.15 | 1.12 |
| I-245 | 467.09 | 1.27 |
| I-246 | 420.17 | 1.22 |
| I-247 | 411.22 | 1.09 |
| I-248 | 432.17 | 1.12 |
| I-249 | 404.21 | 1.21 |
| I-250 | 365.16 | 1.19 |
| I-251 | 434.22 | 1.26 |
| I-252 | 396.17 | 1.10 |
| I-253 | 454.16 | 1.13 |
| I-254 | 389.16 | 1.23 |
| I-255 | 458.19 | 1.33 |
| I-256 | 410.22 | 1.15 |
| I-257 | 455.18 | 1.37 |
| I-258 | 456.21 | 1.24 |
| I-259 | 403.22 | 1.25 |
| I-260 | 434.19 | 1.22 |
| I-261 | 427.18 | 1.32 |
| I-262 | 432.21 | 1.13 |
| I-263 | 425.2 | 1.23 |
| I-264 | 412.2 | 0.95 |
| I-265 | 368.18 | 0.94 |
| I-266 | 398.19 | 1.05 |
| I-267 | 393.21 | 1.06 |
| I-268 | 354.16 | 1.05 |
| I-269 | 426.13 | 1.12 |
| I-270 | 407.22 | 1.14 |
| I-271 | 368.18 | 1.12 |
| I-272 | 392.18 | 1.17 |
| I-273 | 430.19 | 1.14 |
| I-274 | 430.19 | 1.27 |
| I-275 | 428.21 | 1.18 |
| I-295 | 414.2 | 3.5 |

TABLE 8

| Cmpd No. | LCMS ES+ | LCMS Rt (min) | HNMR |
|---|---|---|---|
| I-276 | 386 | 3 | H NMR (400.0 MHz, DMSO) d 1.24 (t, J = 7.4 Hz, 3H), 2.71 (br s, 2H), 3.14 (q, J = 7.3 Hz, 2H), 3.48 (t, J = 5.7 Hz, 2H), 3.98 (d, J = 2.9 Hz, 2H), 6.62 (br s, 1H), 7.30-7.33 (m, 1H), 7.72 (br s, 2H), 7.75-7.79 (m, 1H), 7.98 (d, J = 8.8 Hz, 1H), 8.40 (s, 1H), and 9.11 (d, J = 6.7 Hz, 1H) ppm |
| I-277 | 379 | 3.70 | 3.57-3.59 (m, 4H), 3/65-3.67 (m, 4H), 6.91-6.94 (m, 1H), 7.23-7.26 (m, 3H), 7.64 (br s, 2H), 8.07 (2, 1H) |
| I-278 | 433.05 | 3.38 | dmso d6 1.64 (1H, m), 2.00 (1H, m), 2.17 (6H, s), 2.60 (1H, m), 2.72 (2H, m), 3.25 (2H, m), 3.41 (3H, m), 3.61 (1H, m), 3.95 (2H, m), 6.74 (1H, s), 7.29 (2H, m), 7.62 (1H, d), 7.75 (1H, d), 8.36 (1H, s) |
| I-279 | 419.03 | 3.05 | dmso d6 1.85 (2H, s), 2.74 (2H, s), 2.88 (2H, s), 2.99 (2H, s), 3.40 (6H, m), 3.90 (2H, s), 6.76 (1H, s), 7.28 (2H, m), 7.62 (1H, d), 7.76 (1H, d), 8.36 (1H, s) |
| I-280 | 405.03 | 3.05 | DMSO D6 2.73 (6H, m), 3.17 (4H, m), 3.42 (2H, m), 3.96 (2H, s), 6.75 (1H, s), 7.29 (2H, m), 7.62 (1H, d), 7.75 (1H, d), 8.36 (1H, s) |
| I-281 | 348 | 3.29 | MeOH 2.5 (3H, s), 4.15-4.2 (2H, m), 4.4-4.45 (2H, m), 5.05 (2H, s), 7.25 (1H, d), 7.52 (1H, s), 7.6 (1H, d), 8.2 (1H, s), 8.8 (1H, s) |
| I-282 | 352.1 | 2.93 | CHCl3 1.98 (3H, s), 3.4 (1H, q), 3.7-3.76 (2H, m), .4.-4.45 (2H, m), 4.75-4.85 (2H, m), 6.2 (2H, s), 7.5-7.6 (3H, m), 7.7 (1H, s), 8.2-8.3 (2H, m) |
| I-283 | 434.16 | 3.62 | (DMSO) 1.24 (3H, t), 3.11 (2H, q), 3.33 (4H, masked signal), 3.56 (4H, m), 6.97 (2H, br s), 7.53-7.58 (1H, m), 7.69-7.75 (1H, m), 7.86-7.90 (1H, m), 7.96-7.98 *1H, m), 8.29 (1H, s) |
| I-284 | 361.21 | 3.62 | H NMR (400.0 MHz, DMSO) d 0.75-0.78 (m, 4H), 2.00-2.05 (m, 1H), 2.67 (s, 1H), 2.80 (s, 1H), 3.75 (s, 1H), 3.94 (s, 1H), 4.21 (s, 1H), 4.47 (s, 1H), 6.78 (s, 1H), 7.24 (s, 2H), 7.62 (d, 1H), 7.76 (d, 1H), 8.37 (d, 1H) and 12.85 (s, 1H) ppm |
| I-285 | 389.16 | 3.67 | H NMR (400.0 MHz, DMSO) d 0.74-0.78 (m, 4H), 1.99 (br s, 0.5H), 2.09 (br s, 0.5H), 2.61 (br s, 1H), 2.68 (br s, 1H), 3.73 (br s, 1H), 3.93 (br s, 1H), 4.19 (br s, 1H), 4.47 (br s, 1H), 6.67 (br s, 1H), 7.63-7.70 (m, 5H), 8.13 (d, 2H) and 8.59 (s, 1H) ppm |
| I-286 | 333.11 | 2.97 | H NMR (400.0 MHz, DMSO) d 6.33 (d, J = 7.8 Hz, 2H), 7.69 (s, 2H), 8.15-8.18 (m, 2H), 8.35 (d, J = 7.9 Hz, 2H) and 8.78 (s, 1H) ppm |
| I-287 | 430.2 | 3.72 | (DMSO) 1.24 (3H, t), 2.70 (3H, s), 3.10 (2H, q), 3.30 (4H—hidden by water signal) 3.54 (4H, m), 6.96 (2H, br s), 7.45-7.50 (2H, m), 7.57 (1H, m), 8.03 (1H, m), 8.28 (1H, s) |
| I-288 | 365.1 | 3 | MeOH 1.7-1.75 (2H, m), 2.85 (2H, t), 3.35-3.4 (2H, m), 6.25 (1H, brs), 6.65 (1H, d), 6.7-6.8 (4H, m), 7.25-7.4 (4H, m), |
| I-289 | 452.12 | 3.45 | (DMSO) 1.23 (3H, t), 3.10 (2H, q), 3.32 (4H, m), 3.52 (4H, m), 6.98 (2H, br s), 7.45 (1H, m), 7.77-7.85 (1H, m), 8.31 (1H, s) |
| I-290 | 404.18 | 3.64 | MeOH 1.95-2.0 (2H, m), 3.0 (2H, t), 3.35-3.4 (2H, m), 5.95-6.0 (1H, m), 6.65 (1H, d), 6.7-6.8 (4H, m), 7.25-7.35 (4H, m), |
| I-291 | 399.14 | 3.62 | H NMR (400.0 MHz, DMSO) d 0.99-1.03 (m, 3H), 1.69-1.79 (m, 2H), 2.80 (br s, 2H), 3.10-3.20 (m, 2H), 3.49-3.50 (m, 2H), 3.95 (s, 2H), 6.79 (s, 1H), 7.24-7.34 (m, 2H), 7.62 (d, 1H), 7.76 (d, 1H), 8.37 (s, 1H) and 12.85 (s, 1H) ppm |
| I-292 | 434.12 | 3.59 | (DMSO) 1.24 (3H, m), 3.11 (2H, t), 3.56 (4H, m), 6.96 (2H, br s), 7.50 (2H, m), 8.18 (2H, m), 8.28 (1H, s)<br>4H of piperazine hidden by water peak |
| I-293 | 363.22 | 3.7 | H NMR (400.0 MHz, DMSO) d 1.04-1.07 (m, 6H), 2.67 (br s, 1H), 2.73 (br s, 1H), 2.89-3.04 (m, 1H), 3.75 (s, 2H), 4.20 (s, 1H), 4.30 (s, 1H), 6.76 (br s, 1H), 7.24-7.33 (m, 2H), 7.62 |

TABLE 8-continued

| Cmpd No. | LCMS ES+ | LCMS Rt (min) | HNMR |
|---|---|---|---|
| | | | (d, 1H), 7.76 (d, 1H), 8.36 (s, 1H) and 12.84 (s, 1H) ppm |
| I-294 | 436.11 | 3.6 | (DMSO) 1.23 (3H, t), 2.63 (3H, s), 3.10 (2H, q), 3.30 (4H, masked signal with water peak), 3.54 (4H, m), 6.92 (2H, br s), 7.19 (1H, d), 7.87 (1H, d), 8.27 (1H, s) |
| I-296 | | | H NMR (400.0 MHz, DMSO) d 2.60 (m, 5H), 2.77 (m, 2H), 3.06 (s, 3H), 3.31 (m, 2H), 3.36 masked signal, 3.56 (m, 4H), 6.90 (br s, 2H), 7.64-7.68 (m, 3H), 8.11 (m, 2H), 8.25 (s, 1H) |
| I-297 | 406.15 | 3.27 | (DMSO) 1.24 (3H, t), 3.11 (2H, q), 3.30 (4H, masked signal), 3.52 (4H, m), 6.85 (1H, m), 6.95 (2H, b r s), 7.47 (1H, m), 8.12 (1H, m), 8.27 (1H, s) |
| I-298 | | | H NMR (400.0 MHz, DMSO) d 2.60-2.66 (m, 6H), 2.75 (m, 2H), 3.46 (m, 4H), 6.90 (br s, 2H), 7.64-7.68 (m, 3H), 8.11 (m, 2H), 8.24 (s, 1H) |
| I-299 | 434.15 | 3.48 | (DMSO) 1.24 (3H, t), 3.11 (2H, t), 3.30 (4H, masked signal), 3.53 (4H, m), 6.97 (2H, br s), 7.47-7.56 (2H, m), 7.75 (1H, m), 8.11 (1H, m), 8.29 (1H, s) |
| I-300 | | | H NMR (400.0 MHz, DMSO) d 3.31 masked signal, 3.46 (m, 4H), 3.55 (m, 2H), 6.88 (br s, 2H), 7.27 (m, 1H), 7.36 (m, 4H), 7.64-7.68 (m, 3H), 8.11 (m, 2H), 8.23 (s, 1H) |
| I-301 | 377.17 | 3.59 | H NMR (400.0 MHz, DMSO) d 1.04 (t, 3H), 2.36-2.45 (m, 2H), 2.60 (br s, 1H), 2.70 (br s, 1H), 3.65-3.72 (m, 4H), 4.17 (s, 1H), 4.21 (s, 1H), 6.65 (s, 1H), 7.62-7.69 (m, 5H), 8.11-8.13 (d, 2H) and 8.56 (s, 1H) ppm |
| I-302 | 402.2 | 3.17 | DMSO 1.3 (3H, t), 3.1 (2H, q), 3.8-3.85 (2H, m), 4.35-4.42 (3H, m), 7.0 (2H, m), 7.7-7.8 (3H, m), 7.8-7.85 (2H, m), 8.05-8.1 (2H, m) |
| I-303 | | | H NMR (400.0 MHz, DMSO) d 2.59 (m, 4H), 3.24 (s, 2H), 3.46 (m, 6H), 3.56 (m, 6H), 6.90 (br s, 2H), 7.64-7.68 (m, 3H), 8.11 (m, 2H), 8.23 (s, 1H) |
| I-304 | 343.1 | 3.6 | MeOH 5.25 (2H, s), 7.3-7.35 (2H, m), 7.55-7.6 (1H, m), 7.63-7.7 (4H, m), 7.9 (1H, d), 9.22 (1H, s), |
| I-305 | 442.1 | 3.42 | DMSO 1.25 (3H, t), 3.1-3.2 (4H, m), 3.25-3.3 (2H, m), 3.4-3.45 (2H, m), 3.5-3.7 (4H, m), 6.75 (2H, s), 7.6-7.65 (3H, m), 8.05-8.1 (2H, m) |
| I-306 | | | H NMR (400.0 MHz, DMSO) d 2.46 (m, 2H), 2.59 (m, 4H), 3.46 (m, 4H), 3.56 (m, 2H), 4.47 (t, 1H), 6.90 (br s, 2H), 7.64-7.69 (m, 3H), 8.11 (m, 2H), 8.24 (s, 1H) |
| I-307 | 412.97 | 3.55 | (DMSO) 1.24 (3H, t) 2.68 (2H, m), 3.13 (2H, q), 3.48 (2H, m), 3.99 (2H, m), 6.63 (1H, m), 7.29 (2H, br s), 7.68 (2H, m), 7.77 (1H, m), 8.26 (2H, m), 8.52 (1H, s) |
| I-308 | 464 | 3.54 | H NMR (400.0 MHz, CDCl3) d 7.83 (d, J = 8.0 Hz, 1H), 7.64 (s, 1H), 7.54-7.43 (m, 3H), 7.35-7.32 (m, 3H), 7.28-7.24 (m, 3H), 7.04 (d, J = 8.0 Hz, 1H), 3.14-3.11 (m, 4H), 2.93 (q, J = 7.4 Hz, 2H), 2.76 (t, J = 5.0 Hz, 4H) and 1.37 (t, J = 7.4 Hz, 3H) ppm |
| I-309 | 349.19 | 3.57 | H NMR (400.0 MHz, DMSO) d 1.01-1.06 (m, 3H), 2.33-2.47 (m, 2H), 2.67 (s, 1H), 2.76 (s, 1H), 3.67-3.75 (m, 2H), 4.19-4.23 (m, 2H), 6.76 (d, 1H), 7.24-7.33 (m, 2H), 7.62 (d, 1H), 7.76 (d, 1H), 8.36 (d, 1H) and 12.84 (s, 1H) ppm |
| I-310 | 305.1 | 3.09 | DMSO 6.45 (1H, t), 6.55 (1H, d), 7.3-7.35 (2H, m), 7.5-7.55 (1H, m), 7.6-7.7 (2H, brs), 8.05-8.1 (1H, m), 8.55 (1H, s), 13.15 (1H, vbrs) |
| I-311 | 305.15 | 2.97 | H NMR (400.0 MHz, DMSO) d 6.34 (d, J = 7.8 Hz, 2H), 7.26-7.37 (m, 2H), 7.62 (d, 1H), 7.80 (d, 1H), 8.56 (d, J = 7.8 Hz, 2H), 8.64 (s, 1H) and 13.17 (s, 1H) ppm |
| I-312 | 422.1 | 3.45 | (DMSO) 1.24 (3H, t), 3.11 (2H, q), 3.34 (4H, m), 3.55 (4H, m), 6.93 (2H, br s), 7.35 (1H, m), 7.94 (1H, dd), 8.01 (1H, dd), 8.27 (1H, s) |

Examples 32

Cellular ATR Inhibition Assay

Compounds were screened for their ability to inhibit intracellular ATR using an immunofluorescence microscopy assay to detect phosphorylation of the ATR substrate histone H2AX in hydroxyurea treated cells. HT29 cells were plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds were then added to the cell media from a final concentration of 25 μM in 3-fold serial dilutions and the cells were incubated at 37° C. in 5% $CO_2$. After 15 min, hydroxyurea (Sigma H8627) was added to a final concentration of 2 mM.

After 45 min of treatment with hydroxyurea, the cells were washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells were then washed once in wash buffer and blocked for 30 min at room temperature in 10% goat serum (Sigma G9023) diluted in wash buffer (block buffer). To detect H2AX phosphorylation levels, the cells were then incubated for 1 h at room temperature in primary antibody (mouse monoclonal anti-phosphorylated histone H2AX Ser139 antibody; Upstate 05-636) diluted 1:250 in block buffer. The cells were then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells were then washed five times in wash buffer and finally 100 ul PBS was added to each well before imaging.

Cells were imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification was then calculated for each well using BD Image Data Explorer software (BD Biosciences Version 2.2.15). Phosphorylated H2AX-positive nuclei were defined as Hoechst-positive regions of interest containing Alexa Fluor 488 intensity at 1.75-fold the average Alexa Fluor 488 intensity in cells not treated with hydroxyurea. The percentage of H2AX positive nuclei was finally plotted against concentration for each compound and IC50s for intracellular ATR inhibition were determined using Prism software (GraphPad Prism version 3.0cx for Macintosh, GraphPad Software, San Diego Calif., USA). Compound I-27 was found to have an IC50 value of <1 uM. Compounds I-24 and I-26 were found to have an IC50 value of ≧1 uM but <5 uM. Compounds I-25 and I-28 were found to have an IC50 value of ≧5 uM but <10 uM. Compound I-16 was found to have an IC50 value of ≧10 uM but <30 uM.

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry*, 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 33

ATR Inhibition Assay

Test compounds were screened for their ability to inhibit ATR kinase using a radioactive-phosphate incorporation assay. Assays were carried out in a mixture of 50 mM Tris/HCl (pH 7.5), 10 mM $MgCl_2$ and 1 mM DTT. Final substrate concentrations were 10 µM [γ-33P]ATP (3 mCi 33 P ATP/mmol ATP, Perkin Elmer) and 800 µM target peptide (ASELPASQPQPFSAKKK). Assays were carried out at 25° C. in the presence of 5 nM full-length ATR. An assay stock buffer solution was prepared containing all of the reagents listed above, with the exception of ATP and the test compound of interest. 13.5 µL of the stock solution was placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate was pre-incubated for 10 minutes at 25° C. and the reaction initiated by addition of 15 µL [γ-33P]ATP (final concentration 10 µM).

The reaction was stopped after 24 hours by the addition of 30 µL 0.1M phosphoric acid containing 2 mM ATP. A multiscreen phosphocellulose filter 96-well plate (Millipore, Cat no. MAPHN0B50) was pretreated with 100 µL 0.2M phosphoric acid prior to the addition of 45 µL of the stopped assay mixture. The plate was washed with 5×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Below is a chart showing the Ki value of compounds of the disclosure.
Compounds with a Ki value of ≦100 nM are marked with "+++." Compounds with a Ki value >100 nM but ≦1 uM are marked with "++." Compounds with a Ki value >1 uM but <10 uM are marked with "+."

| Cmpd No. | ATR Ki |
|---|---|
| I-1 | + |
| I-2 | + |
| I-3 | ++ |
| I-4 | ++ |
| I-5 | + |
| I-6 | ++ |
| I-7 | ++ |
| I-8 | ++ |
| I-9 | + |
| I-10 | ++ |
| I-11 | + |
| I-12 | + |
| I-13 | + |
| I-14 | + |
| I-15 | ++ |
| I-16 | ++ |
| I-17 | ++ |
| I-18 | +++ |
| I-19 | ++ |
| I-20 | ++ |
| I-21 | + |
| I-22 | ++ |
| I-23 | +++ |
| I-24 | +++ |
| I-25 | +++ |
| I-26 | +++ |
| I-27 | +++ |
| I-28 | +++ |
| I-29 | ++ |
| I-30 | ++ |
| I-31 | + |
| I-32 | + |
| I-33 | + |
| I-34 | + |
| I-35 | + |
| I-36 | ++ |
| I-37 | + |
| I-38 | + |
| I-39 | + |
| I-40 | + |
| I-41 | ++ |
| I-42 | + |
| I-43 | ++ |
| I-44 | + |
| I-45 | + |
| I-46 | ++ |
| I-47 | + |
| I-48 | ++ |
| I-49 | + |
| I-50 | + |
| I-51 | + |
| I-52 | + |
| I-53 | ++ |
| I-54 | +++ |
| I-55 | ++ |
| I-56 | ++ |
| I-57 | ++ |
| I-58 | +++ |
| I-59 | ++ |
| I-60 | +++ |
| I-61 | + |
| I-62 | + |
| I-63 | ++ |
| I-64 | + |
| I-65 | + |
| I-66 | ++ |
| I-67 | +++ |
| I-68 | ++ |
| I-69 | ++ |
| I-70 | + |
| I-71 | +++ |
| I-72 | + |
| I-73 | + |
| I-74 | ++ |
| I-75 | + |
| I-76 | ++ |
| I-77 | + |
| I-78 | ++ |
| I-79 | +++ |
| I-80 | ++ |
| I-81 | + |
| I-82 | +++ |
| I-83 | ++ |
| I-84 | +++ |
| I-85 | + |
| I-86 | ++ |
| I-87 | ++ |
| I-88 | ++ |
| I-89 | +++ |
| I-90 | ++ |
| I-91 | ++ |

| Cmpd No. | ATR Ki |
|---|---|
| I-92 | ++ |
| I-93 | +++ |
| I-94 | +++ |
| I-95 | ++ |
| I-96 | ++ |
| I-97 | ++ |
| I-98 | ++ |
| I-99 | ++ |
| I-100 | +++ |
| I-101 | ++ |
| I-102 | +++ |
| I-103 | +++ |
| I-104 | ++ |
| I-105 | +++ |
| I-106 | ++ |
| I-107 | ++ |
| I-108 | ++ |
| I-109 | + |
| I-110 | ++ |
| I-111 | ++ |
| I-112 | ++ |
| I-113 | + |
| I-114 | + |
| I-115 | +++ |
| I-116 | ++ |
| I-117 | ++ |
| I-118 | ++ |
| I-119 | ++ |
| I-120 | +++ |
| I-121 | +++ |
| I-122 | +++ |
| I-123 | +++ |
| I-124 | +++ |
| I-125 | +++ |
| I-126 | +++ |
| I-127 | +++ |
| I-128 | +++ |
| I-129 | +++ |
| I-130 | +++ |
| I-131 | +++ |
| I-132 | +++ |
| I-133 | +++ |
| I-134 | ++ |
| I-135 | +++ |
| I-136 | +++ |
| I-137 | ++ |
| I-138 | +++ |
| I-139 | +++ |
| I-140 | ++ |
| I-141 | + |
| I-142 | + |
| I-143 | + |
| I-144 | ++ |
| I-145 | ++ |
| I-146 | + |
| I-147 | + |
| I-148 | + |
| I-149 | ++ |
| I-150 | + |
| I-151 | + |
| I-152 | ++ |
| I-153 | +++ |
| I-154 | ++ |
| I-155 | +++ |
| I-156 | + |
| I-157 | +++ |
| I-158 | ++ |
| I-159 | ++ |
| I-160 | ++ |
| I-161 | ++ |
| I-162 | ++ |
| I-163 | ++ |
| I-164 | +++ |
| I-165 | +++ |
| I-166 | ++ |
| I-167 | +++ |
| I-168 | ++ |
| I-169 | +++ |
| I-170 | ++ |
| I-171 | ++ |
| I-172 | +++ |
| I-173 | ++ |
| I-174 | + |
| I-175 | + |
| I-176 | ++ |
| I-177 | ++ |
| I-178 | ++ |
| I-179 | ++ |
| I-180 | ++ |
| I-181 | + |
| I-182 | + |
| I-183 | ++ |
| I-184 | + |
| I-185 | ++ |
| I-186 | ++ |
| I-187 | ++ |
| I-188 | ++ |
| I-189 | ++ |
| I-190 | ++ |
| I-191 | ++ |
| I-192 | +++ |
| I-193 | ++ |
| I-194 | ++ |
| I-195 | + |
| I-196 | ++ |
| I-197 | ++ |
| I-198 | ++ |
| I-199 | + |
| I-200 | +++ |
| I-201 | +++ |
| I-202 | ++ |
| I-203 | ++ |
| I-204 | ++ |
| I-205 | ++ |
| I-206 | ++ |
| I-207 | ++ |
| I-208 | ++ |
| I-209 | + |
| I-210 | +++ |
| I-211 | + |
| I-212 | + |
| I-213 | ++ |
| I-214 | ++ |
| I-215 | +++ |
| I-216 | ++ |
| I-217 | +++ |
| I-218 | ++ |
| I-219 | ++ |
| I-220 | +++ |
| I-221 | ++ |
| I-222 | +++ |
| I-223 | ++ |
| I-224 | +++ |
| I-225 | ++ |
| I-226 | +++ |
| I-227 | ++ |
| I-228 | +++ |
| I-229 | ++ |
| I-230 | + |
| I-231 | ++ |
| I-232 | ++ |
| I-233 | ++ |
| I-234 | ++ |
| I-235 | ++ |
| I-236 | +++ |
| I-237 | + |
| I-238 | +++ |
| I-239 | + |
| I-240 | ++ |
| I-241 | +++ |
| I-242 | + |
| I-243 | ++ |
| I-244 | ++ |
| I-245 | +++ |

| Cmpd No. | ATR Ki |
|---|---|
| I-246 | ++ |
| I-247 | + |
| I-248 | ++ |
| I-249 | ++ |
| I-250 | ++ |
| I-251 | ++ |
| I-252 | + |
| I-253 | ++ |
| I-254 | ++ |
| I-255 | + |
| I-256 | ++ |
| I-257 | ++ |
| I-258 | ++ |
| I-259 | +++ |
| I-260 | + |
| I-261 | ++ |
| I-262 | ++ |
| I-263 | +++ |
| I-264 | + |
| I-265 | + |
| I-266 | + |
| I-267 | + |
| I-268 | + |
| I-269 | ++ |
| I-270 | + |
| I-271 | + |
| I-272 | + |
| I-273 | + |
| I-274 | + |
| I-275 | + |
| I-276 | + |
| I-277 | ++ |
| I-278 | ++ |
| I-279 | ++ |
| I-280 | ++ |
| I-281 | + |
| I-282 | + |
| I-283 | ++ |
| I-284 | +++ |
| I-285 | +++ |
| I-286 | +++ |
| I-287 | ++ |
| I-288 | ++ |
| I-289 | ++ |
| I-290 | ++ |
| I-291 | +++ |
| I-292 | ++ |
| I-293 | ++ |
| I-294 | +++ |
| I-295 | + |
| I-296 | ++ |
| I-297 | ++ |
| I-298 | + |
| I-299 | ++ |
| I-300 | + |
| I-301 | +++ |
| I-302 | ++ |
| I-303 | ++ |
| I-304 | ++ |
| I-305 | ++ |
| I-306 | + |
| I-307 | ++ |
| I-308 | ++ |
| I-309 | +++ |
| I-310 | +++ |
| I-311 | +++ |
| I-312 | ++ |
| I-313 | ++ |
| I-314 | ++ |
| I-315 | ++ |
| I-316 | +++ |
| I-317 | +++ |
| I-318 | +++ |
| I-319 | ++ |
| I-320 | +++ |
| I-321 | + |
| I-322 | ++ |
| I-323 | +++ |
| I-324 | ++ |
| I-325 | +++ |
| I-326 | +++ |
| I-327 | +++ |
| I-328 | ++ |
| I-329 | + |
| I-330 | + |
| I-331 | +++ |
| I-332 | + |
| I-333 | ++ |
| I-334 | ++ |
| I-335 | ++ |
| I-336 | ++ |
| I-337 | ++ |
| I-338 | ++ |
| I-339 | ++ |
| I-340 | + |
| I-341 | ++ |
| I-342 | ++ |
| I-343 | +++ |
| I-344 | +++ |
| I-345 | +++ |
| I-346 | ++ |
| I-347 | ++ |
| I-348 | + |
| I-349 | ++ |
| I-350 | ++ |
| I-351 | ++ |
| I-352 | ++ |
| I-353 | ++ |
| I-354 | ++ |
| I-355 | ++ |
| I-356 | ++ |
| I-357 | ++ |
| I-358 | ++ |
| I-359 | ++ |
| I-360 | ++ |
| I-361 | ++ |
| I-362 | ++ |
| I-363 | ++ |
| I-364 | ++ |
| I-365 | ++ |
| I-366 | ++ |
| I-367 | +++ |
| I-368 | ++ |
| I-369 | +++ |
| I-370 | ++ |
| I-371 | ++ |
| I-372 | ++ |
| I-373 | ++ |
| I-374 | + |
| I-375 | ++ |
| I-376 | ++ |
| I-377 | + |

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A compound of formula I:

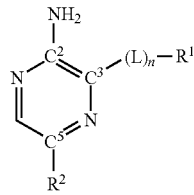

or a pharmaceutically acceptable salt thereof wherein:
$R^1$ is a 5-6 membered monocyclic aryl or heteroaryl ring having 0-4 heteroatoms independently selected from nitrogen, oxygen, or sulfur; wherein said monocyclic aryl or heteroaryl ring is optionally fused to another ring to form a 8-10 membered bicyclic aryl or heteroaryl ring having 0-6 heteroatoms independently selected from nitrogen, oxygen, or sulfur; $R^1$ is optionally substituted with 1-5 $J^1$ groups;
$C^2$, $C^3$ and $C^5$ are carbon;
$R^2$ is -Q or -Q-$Q^1$;
Q is a 3-7 membered monocyclic saturated or unsaturated non-aromatic ring having 0-4 heteroatoms independently selected from nitrogen, oxygen, or sulfur; each Q is independently and optionally substituted with 1-4 $J^Q$ groups; Q is substituted with zero to two occurrences of J;
Q is optionally fused to $Q^1$ to form a fused bicyclic ring Q-$Q^1$; or Q and $Q^1$ are optionally joined together at a carbon atom to form a spirocyclic bicyclic ring Q-$Q^1$; or Q and $Q^1$, taken together, form a bridged bicyclic ring Q-$Q^1$ wherein said bridge is 1-3 atoms long; Q-$Q^1$ can be optionally substituted with 1-2 J groups; wherein J can be bonded to either Q or $Q^1$;
$Q^1$ is a 3-8 membered monocyclic saturated or unsaturated ring having 0-4 heteroatoms independently selected from nitrogen, oxygen, or sulfur; each $Q^1$ is independently and optionally substituted with 1-4 $J^{Q1}$ groups;
J is halo, oxo, —CN, —$NO_2$, $V^1$—R", or —(V)$_m$—R*;
R" is H or a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each R" is optionally substituted with 1-5 J';
L is —C(O)NH— or —C(O)N($C_{1-6}$alkyl)-;
n is 0 or 1;
each $J^Q$ and $J^{Q1}$ is independently halo, oxo, —CN, —$NO_2$, V—R, or —(V)$_m$-$Q^2$;
$J^1$ is halo, —CN, —$NO_2$, V—R, or —($V^2$)$_m$-$Q^3$;
V is a $C_{1-10}$aliphatic chain wherein 0-3 methylene units are optionally and independently replaced with oxygen, nitrogen, sulfur, C(O), S(O), or S(O)$_2$; V is optionally substituted with 1-6 occurrences of $J^V$;
$V^1$ is a $C_{1-10}$aliphatic chain wherein 0-3 methylene units are optionally replaced with —NR'—, —O—, —S—, C(O), S(O), or S(O)$_2$; $V^1$ is optionally substituted with 1-6 occurrences of $J^{V1}$;
m is 0 or 1;
$V^2$ is a $C_{1-10}$aliphatic chain wherein 0-3 methylene units are optionally and independently replaced with oxygen, nitrogen, sulfur, C(O), S(O), or S(O)$_2$; V is optionally substituted with 1-6 occurrences of $J^{V2}$;
m is 0 or 1;
$Q^2$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^2$ is optionally substituted with 1-5 $J^{Q2}$;
$Q^3$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^3$ is optionally substituted with 1-5 $J^{Q3}$;
each $J^V$, $J^{V1}$, and $J^{V2}$ is independently halogen, CN, $NH_2$, $NO_2$, $C_{1-4}$aliphatic, NH($C_{1-4}$aliphatic) N($C_{1-4}$aliphatic)$_2$, OH, O($C_{1-4}$aliphatic), $CO_2H$, $CO_2$($C_{1-4}$aliphatic), C(O)$NH_2$, C(O)NH($C_{1-4}$aliphatic), C(O)N($C_{1-4}$aliphatic)$_2$,NHCO($C_{1-4}$aliphatic), N($C_{1-4}$aliphatic)CO ($C_{1-4}$aliphatic), $SO_2$($C_{1-4}$aliphatic), $NHSO_2$($C_{1-4}$aliphatic), or N($C_{1-4}$aliphatic)$SO_2$($C_{1-4}$aliphatic), wherein said $C_{1-4}$aliphatic is optionally substituted with halo;
each $J^{Q2}$ and $J^{Q3}$ is independently halo, oxo, CN, $NO_2$, X—R, or —(X)$_p$-$Q^4$,
p is 0 or 1;
X is $C_{1-10}$aliphatic; wherein 1-3 methylene units of said $C_{1-6}$aliphatic are optionally replaced with —NR, —O—, —S—, C(O), S(O)$_2$, or S(O); wherein X is optionally and independently substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2H$, $CO_2$($C_{1-4}$aliphatic), C(O)$NH_2$, C(O) NH($C_{1-4}$aliphatic), C(O)N($C_{1-4}$aliphatic)$_2$, SO($C_{1-4}$aliphatic), $SO_2$($C_{1-4}$aliphatic), $SO_2$NH($C_{1-4}$aliphatic), $SO_2$NH($C_{1-4}$aliphatic), NHC(O)($C_{1-4}$aliphatic), N($C_{1-4}$aliphatic)C(O)($C_{1-4}$aliphatic), wherein said $C_{1-4}$aliphatic is optionally substituted with 1-3 occurrences of halo;
$Q^4$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^4$ is optionally substituted with 1-5 $J^{Q4}$;
$J^{Q4}$ is halo, CN, or $C_{1-4}$alkyl wherein up to 2 methylene units are optionally replaced with O, N, S, C(O), S(O), or S(O)$_2$;
each R*, R', and R is independently H or $C_{1-4}$alkyl wherein said $C_{1-4}$alkyl is optionally substituted with 1-4 halo.
2. The compound of claim 1, wherein
$R^1$ is a 5-6 membered monocyclic aryl or heteroaryl ring having 0-3 heteroatoms independently selected from nitrogen, oxygen, or sulfur; wherein said monocyclic aryl or heteroaryl ring is optionally fused to another ring to form a 8-10 membered bicyclic aryl or heteroaryl ring having 0-4 heteroatoms independently selected from nitrogen, oxygen, or sulfur; $R^1$ is optionally substituted with 1-5 $J^1$ groups;
Q is a 3-7 membered monocyclic saturated or partially unsaturated non-aromatic ring having 0-4 heteroatoms independently selected from nitrogen, oxygen, or sulfur; Q can be optionally fused to $Q^1$; each Q is independently and optionally substituted with 1-4 $J^Q$ groups; Q is substituted with one to two occurrences of J;

$Q^1$ is a 5-8 membered monocyclic saturated or unsaturated ring having 0-4 heteroatoms independently selected from nitrogen, oxygen, or sulfur; each $Q^1$ is independently and optionally substituted with 1-4 $J^{Q1}$ groups;

J is fluoro oxo, —CN, —NO$_2$, $V^1$—R", or —(V)$_m$—R*;

L is —C(O)NH—;

each $J^Q$ and $J^{Q1}$ is independently halo, —CN, —NO$_2$, V—R, or —(V)$_m$-Q$^2$;

each $J^{Q2}$ and $J^{Q3}$ is independently halogen, NO$_2$, CN, or $C_{1-6}$aliphatic wherein up to 1 methylene unit is optionally replaced with N(R)$_2$, OR, SR, COR, CO$_2$R, CON(R)$_2$, SOR, SO$_2$R, SO$_2$N(R)$_2$, OCOR, NRCOR, NRCOOR, NRSOR, NRSO$_2$R, NRSO$_2$N(R)$_2$, OCON(R)$_2$, or NRCON(R)$_2$; wherein said $C_{1-6}$aliphatic is optionally substituted with 1-4 substituents selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$aliphatic), or haloC$_{1-4}$aliphatic;

each $J^V$ is independently NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$aliphatic), or haloC$_{1-4}$aliphatic.

3. The compound of claim 2, wherein

J is oxo or (V$^1$)—R";

$V^1$ is $C_{1-6}$ aliphatic chain wherein up to three methylene unit of the aliphatic chain may be optionally replaced with —NR'—, —O—, —S—, —C(O)—, —S(O)—, or —S(O)$_2$—; wherein the first or second methylene group away from the point of attachment is replaced with CO, SO, SO$_2$, S, or O;

R' is H or C$_{1-4}$alkyl;

R" is H or a 5-6 membered monocyclic ring containing 0-2 heteroatoms selected from O, N, or S; wherein said R" is optionally substituted with 1-3 occurrences of halo, C$_{1-3}$alkyl, CN, OH, O(C$_{1-3}$alkyl), NH$_2$, NH(C$_{1-3}$alkyl), N(C$_{1-3}$alkyl)$_2$, or acetyl.

4. The compound of claim 2, wherein $R^1$ is

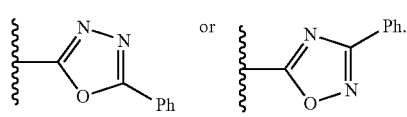 [SMILES: *c1nnc(-c2ccccc2)o1 ; "or" ; *c1nc(-c2ccccc2)no1]

5. The compound of claim 2, wherein Q is C$_{3-7}$ cycloalkyl, pyrrolidinyl, piperidinyl, piperazinyl, homopiperazinyl, homopiperidinyl, morpholinyl, or thiomorpholinyl.

6. The compound of claim 2, wherein Q is

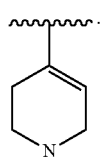

7. The compound of claim 2, wherein J is C$_{1-6}$aliphatic chain wherein up to 2 methylene units of C$_{1-6}$aliphatic optionally replaced with heteroatom selected from O, N, or S.

8. A compound of formula Ia:

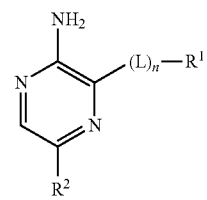

or a pharmaceutically acceptable salt thereof wherein:

$R^1$ is a 5-6 membered monocyclic aryl or heteroaryl ring having 0-4 heteroatoms independently selected from nitrogen, oxygen, or sulfur; wherein said monocyclic aryl or heteroaryl ring is optionally fused to another ring to form a 8-10 membered bicyclic aryl or heteroaryl ring having 0-6 heteroatoms independently selected from nitrogen, oxygen, or sulfur; $R^1$ is optionally substituted with 1-5 $J^1$ groups;

$R^2$ is -Q or -Q-Q$^1$;

Q is a 3-7 membered monocyclic saturated or unsaturated non-aromatic ring having 0-4 heteroatoms independently selected from nitrogen, oxygen, or sulfur; Q is optionally substituted with 1-4 $J^Q$ groups; Q is optionally substituted with 1-2 J groups;

$Q^1$ is a 3-8 membered monocyclic saturated or unsaturated ring having 0-4 heteroatoms independently selected from nitrogen, oxygen, or sulfur; each $Q^1$ is independently and optionally substituted with 1-4 $J^{Q1}$ groups;

Q is optionally fused to $Q^1$ to form a fused bicyclic ring Q-Q$^1$; or Q and $Q^1$ are optionally joined together at a carbon atom to form a spirocyclic bicyclic ring Q-Q$^1$; or Q and $Q^1$, taken together, form a bridged bicyclic ring Q-Q$^1$ wherein said bridge is 1-3 atoms long; Q-Q$^1$ can be optionally substituted with 1-2 J groups; wherein J can be bonded to either Q or $Q^1$;

each $J^Q$ and $J^{Q1}$ is independently halo, oxo, —CN, —NO$_2$, V—R, or —(V)$_m$-Q$^2$;

J is halo, oxo, —CN, —NO$_2$, $V^1$—R", or —(V)$_m$—R*;

L is —C(O)NH— or —C(O)N(C$_{1-6}$alkyl)—;

n is 0 or 1;

$J^1$ is halo, —CN, —NO$_2$, V—R, or —(V$^2$)$_m$-Q$^3$;

V is a C$_{1-10}$aliphatic chain wherein 0-3 methylene units are optionally replaced with —NR—, —O—, —S—, C(O), S(O), or S(O)$_2$; V is optionally substituted with 1-6 occurrences of $J^V$;

$V^1$ is a C$_{1-10}$aliphatic chain wherein 0-3 methylene units are optionally replaced with —NR'—, —O—, —S—, C(O), S(O), or S(O)$_2$; $V^1$ is optionally substituted with 1-6 occurrences of $J^{V1}$;

$V^2$ is a C$_{1-10}$aliphatic chain wherein 0-3 methylene units are optionally and independently replaced with —NR—, —O—, —S—, C(O), S(O), or S(O)$_2$; $V^2$ is optionally substituted with 1-6 occurrences of $J^{V2}$;

m is 0 or 1;

$Q^2$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^2$ is optionally substituted with 1-5 $J^{Q2}$;

$Q^3$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^3$ is optionally substituted with 1-5 $J^{Q3}$;

R" is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each R" is optionally substituted with 1-5 J';

each $J^V$, $J^{V1}$ and $J^{V2}$ is independently halogen, CN, $NH_2$, $NO_2$, $C_{1-4}$aliphatic, $NH(C_{1-4}$aliphatic), $N(C_{1-4}$aliphatic$)_2$, OH, $O(C_{1-4}$aliphatic), $CO_2H$, $CO_2(C_{1-4}$aliphatic), $C(O)NH_2$, $C(O)NH(C_{1-4}$aliphatic), $C(O)N(C_{1-4}$aliphatic$)_2$, $NHCO(C_{1-4}$aliphatic), $N(C_{1-4}$aliphatic)CO$(C_{1-4}$aliphatic), $SO_2(C_{1-4}$aliphatic), $NHSO_2(C_{1-4}$aliphatic), or $N(C_{1-4}$aliphatic)$SO_2(C_{1-4}$aliphatic), wherein said $C_{1-4}$-aliphatic is optionally substituted with halo;

each $J^{Q2}$, $J^{Q3}$, and J' is independently halo, oxo, CN, $NO_2$, X—R, or —(X)$_p$-$Q^4$, p is 0 or 1;

X is a $C_{1-10}$aliphatic; wherein 1-3 methylene units of said $C_{1-6}$aliphatic are optionally replaced with —NR, —O—, —S—, C(O), $S(O)_2$, or S(O); wherein X is optionally and independently substituted with 1-4 occurrences of $NH_2$, $NH(C_{1-4}$aliphatic), $N(C_{1-4}$aliphatic$)_2$, halogen, $C_{1-4}$aliphatic, OH, $O(C_{1-4}$aliphatic), $NO_2$, CN, $CO_2H$, $CO_2(C_{1-4}$aliphatic), $C(O)NH_2$, $C(O)NH(C_{1-4}$aliphatic), $C(O)N(C_{1-4}$aliphatic$)_2$, $SO(C_{1-4aliphatic})$, $SO_2(C_{1-4}$aliphatic), $SO_2NH(C_{1-4}$aliphatic), $SO_2N(C_{1-4}$aliphatic$)_2$, $NHC(O)(C_{1-4}$aliphatic), or $N(C_{1-4}$aliphatic)$C(O)(C_{1-4}$aliphatic), wherein said $C_{1-4}$aliphatic is optionally substituted with 1-3 occurrences of halo;

$Q^4$ is a 3-6 membered monocyclic ring containing 0-2 heteroatoms selected from O, N, or S; each $Q^4$ is optionally substituted with $J^{Q4}$;

$J^{Q4}$ is halo, CN, or $C_{1-4}$alkyl wherein up to 2 methylene units are optionally replaced with O, N, S, C(O), S(O), or $S(O)_2$;

each R*, R', and R is independently H or $C_{1-4}$alkyl wherein said $C_{1-4}$alkyl is optionally substituted with 1-4 halo.

9. The compound of claim 8, wherein each $J^Q$ and $J^{Q1}$ is independently halo, oxo, —CN, —$NO_2$, or V—R.

10. The compound of claim 8, wherein Q or $Q^1$ is substituted with 1-2 occurrences of J.

11. The compound of claim 10, wherein Q or $Q^1$ is substituted with zero occurrences of $J^Q$ and $J^{Q1}$ and Q is substituted with 1 occurrence of J.

12. The compound of claim 10, wherein
each J is independently oxo, $(V^1)$—R" or —(V)$_m$—R*;
each V and $V^1$ is independently a $C_{1-6}$ aliphatic chain wherein up to three methylene unit of the aliphatic chain may be optionally replaced with —NR'—, —O—, —S—, —C(O)—, —S(O)—, or —$S(O)_2$—; wherein the first or second methylene group away from the point of attachment is replaced with —C(O)—, —S(O)—, —$S(O)_2$—, —S—, or —O—;
each $J^V$ and $J^{V1}$ is independently halo or $C_{1-4}$alkyl;
R' is H or $C_{1-4}$alkyl;
R* is H or $C_{1-4}$alkyl;
R" is a 3-7 membered monocyclic ring containing 0-2 heteroatoms selected from O, N, or S; wherein said R" is optionally substituted with 1-3 occurrences of J';

J' is oxo, halo, $C_{1-3}$alkyl, halo$C_{1-3}$alkyl, CN, OH, $O(C_{1-3}$alkyl), $NH_2$, $NH(C_{1-3}$alkyl), $N(C_{1-3}$alkyl$)_2$, or acetyl.

13. The compound of claim 8, wherein Q contains sulfur, nitrogen, or oxygen as a ring member.

14. The compound of claim 13, wherein Q contains nitrogen as a ring member.

15. The compound of claim 14, wherein
said nitrogen of Q is substituted with one occurrence of $J^Q$;
$J^Q$ is phenyl, pyridyl, pyrimidyl, thiazolyl, $C_{1-6}$aliphatic, or benzyl; wherein $J^Q$ is optionally substituted with 1-3 occurrences of $J^{Q2}$;
$J^{Q2}$ is halo, halo$C_{1-6}$aliphatic, CN, $NO_2$, or $C_{1-6}$aliphatic, wherein 1-3 methylene units of said $C_{1-6}$aliphatic are optionally replaced with —NH—, —O—, —S—, C(O), $S(O)_2$, or S(O).

16. The compound of claim 8, wherein n is 1.

17. The compound of claim 16, wherein $R^1$ is a bicyclic ring.

18. The compound of claim 17, wherein said ring is a 8-9 membered heteroaryl containing 1-4 heteroatoms selected from O, N, or S.

19. The compound of claim 18, wherein said heteroatom is nitrogen.

20. The compound according to claim 18, wherein said ring is selected from benzimidazolyl, benzoxazolyl, indazolyl, benzothiazolyl, indolyl, benzotriazolyl, pyrrolopyridyl, imidazopyridyl, or triazolopyridyl.

21. The compound of claim 16, wherein $R^1$ is a monocyclic 5-6-membered ring.

22. The compound of claim 21, wherein $R^1$ is pyrazolyl, phenyl, pyridyl, or pyrazinyl.

23. The compound of claim 8, wherein n is 0.

24. The compound of claim 23, wherein $R^1$ is a 5-6 membered monocyclic heteroaryl ring having 1-4 heteroatoms independently selected from nitrogen, oxygen, or sulfur, or a 8-10 membered bicyclic heteroaryl ring having 1-6 heteroatoms independently selected from nitrogen, oxygen, or sulfur; each $R^1$ is optionally substituted with 1-5 $J^1$ groups.

25. The compound of claim 24, wherein $R^1$ is a 6-membered monocyclic ring selected from pyrimidyl or pyridyl.

26. The compound of claim 24, wherein $R^1$ is a monocyclic 5-membered heteroaryl ring containing 1-3 heteroatoms selected from oxygen, nitrogen, or sulfur; or $R^1$ is a 5-membered heteroaryl ring containing 1-2 heteroatoms selected from oxygen, nitrogen, or sulfur fused to a 6-membered aryl or heteroaryl ring containing 0-4 nitrogen atoms.

27. The compound of claim 23, wherein said ring heteroatom (shown as G) is located next to the carbon atom bonded to $C^3$ as shown below in formula II:

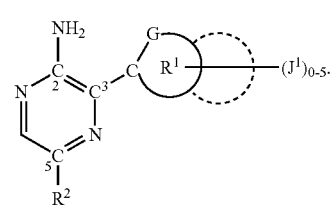

28. The compound of claim 27, wherein $R^1$ is a 5-membered ring optionally fused to another ring or a monocyclic 5-membered ring containing 1-3 heteroatoms selected from oxygen, nitrogen, or sulfur.

29. The compound of claim 28, wherein $R^1$ is a 5-membered ring and is selected from the following:

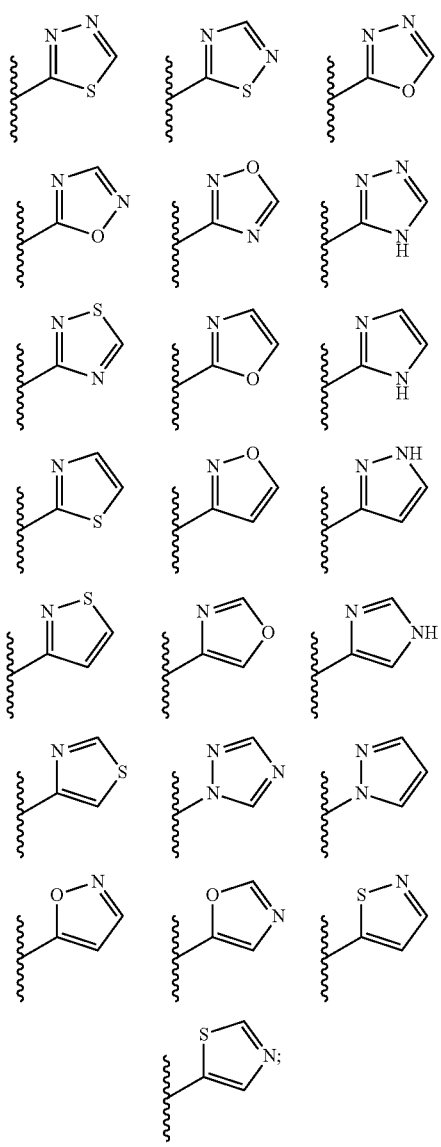

wherein each R¹ is optionally substituted with 1-2 occurrences of J¹.

30. The compound of claim 29, wherein R¹ is selected from the following:

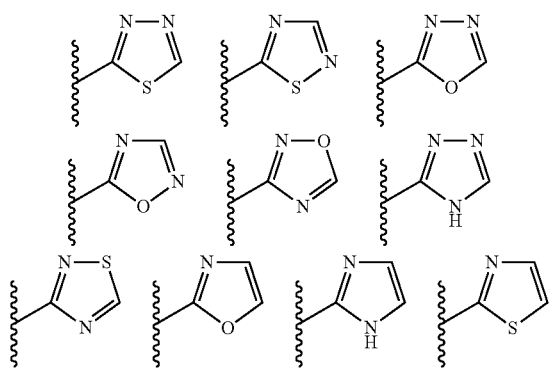

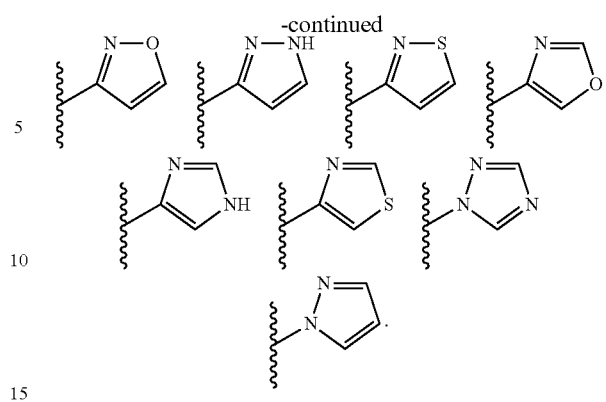

31. The compound of claim 30, wherein R¹ is,

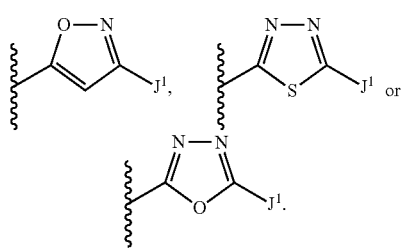

32. The compound of claim 31, wherein R¹ is

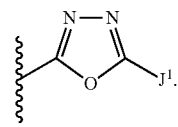

33. The compound of claim 32, wherein $J^1$ is $C_{1-4}$alkyl, cyclohexyl, phenyl, thienyl, furanyl, or NH-phenyl.

34. The compound of claim 33, wherein $J^1$ is phenyl.

35. The compound of claim 34, wherein the phenyl of $J^1$ is optionally substituted with 1-3 occurrences of $J^{Q3}$; wherein $J^{Q3}$ is selected from halo, CN, NO₂, X—R, or —(X)$_p$-Q⁴; p is 0-1; X is a $C_{1-10}$aliphatic wherein 1-3 methylene units of said $C_{1-6}$aliphatic are optionally replaced with —NR, —O—, —S—, C(O), S(O)₂, or S(O); R is H; and Q⁴ is a 3-6 membered monocyclic ring containing 0-2 heteroatoms selected from O or N, wherein X is optionally substituted with 1-3 occurrences of halo or CN.

36. The compound of claim 35, wherein $J^{Q3}$ is a $C_{1-10}$aliphatic chain wherein 1-2 methylene units of X are replaced with —O— or —NR—.

37. The compound of claim 35, wherein Q⁴ is an optionally substituted 3-6 membered cycloalkyl ring.

38. The compound of claim 35, wherein $J^{Q3}$ is halo, OH, NH₂, CH₂NH₂, CH(CH₃)NH₂, CH(CH₃)NHCH₃, C(CH₃)₂NH₂, CH₂CH₂NH₂, CH₂NHCH₃, CH₂N(CH₃)₂, CH(CH₃)NH₂, CH₂NHC(CH₃)₂, CH₂NHCH₂CHF₂, CH₂NHCH₂CH(CH₃)OH, CH₂NHCH₂C(CH₃)₂OH, CH₂NHCH₂CH(OH)-cyclopropyl, CH₂NHCH₂CH₂N(CH₃)₂, CH₂NHCH(CH₂CH₃)₃, CH₂NHCH₃, CH₂NHCH₂CH₃, CH₂NHCH₂CH₂CH₃, CH₂NH-cyclopropyl, CH₂NHCH₂CH₂OH, CH₂NHCH₂CH₂OCH₃, CH₂NHCH₂CH₂OCH₂CH₂OH, azetidinyl or pyrrolidinyl.

39. The compound of claim 23, wherein R¹ is selected from benzimidazolyl, imidazopyridyl, triazolopyridyl, benzofuranyl, or benzothiazolyl.

40. The compound of claim 39, wherein $R^1$ is selected from:

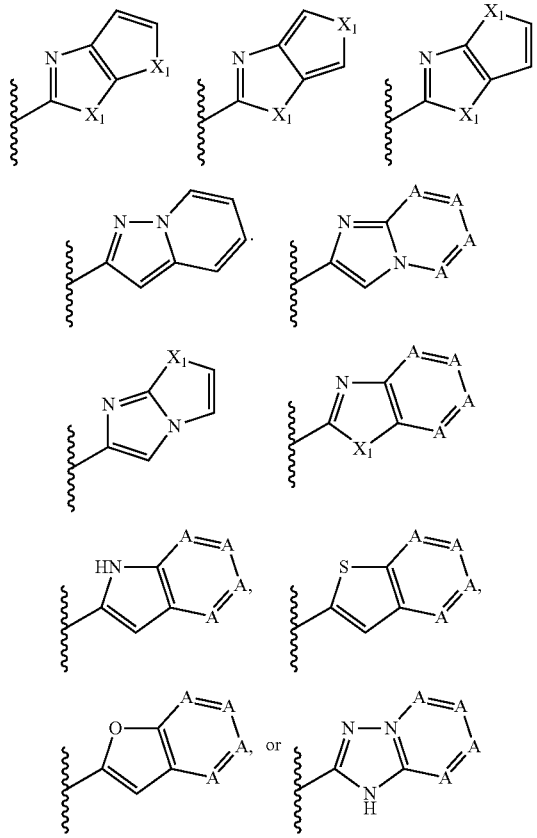

wherein each $R^1$ is optionally substituted with 1-2 occurrences of $J^1$;

A is C or N, provided that at least two occurrence of A are carbon; and $X_1$ is O, N, or S.

41. The compound of claim 40, wherein $R^1$ is

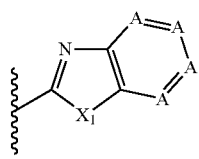

wherein each $R^1$ is optionally substituted with 1-2 occurrences of $J^1$; A is carbon or nitrogen; and $X_1$ is selected from O, N, or S.

42. The compound of claim 41, wherein $R^1$ is benzimidazolyl.

43. The compound of claim 8, wherein $R^2$ is Q.

44. The compound of claim 43, wherein Q is $C_{3-7}$ cycloalkyl, pyrrolidinyl, piperidinyl, piperazinyl, homopiperazinyl, homopiperidinyl, morpholinyl, or thiomorpholinyl.

45. The compound of claim 8, wherein Q is bonded through a carbon atom.

46. The compound of claim 45, wherein Q is

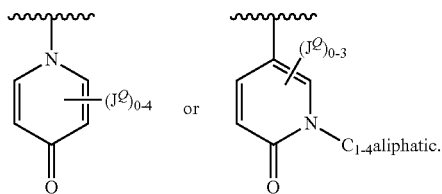

47. The compound of claim 45, wherein Q or Q-$Q^1$ is selected from the following:

$C_{3-8}$cycloaliphatic ring,

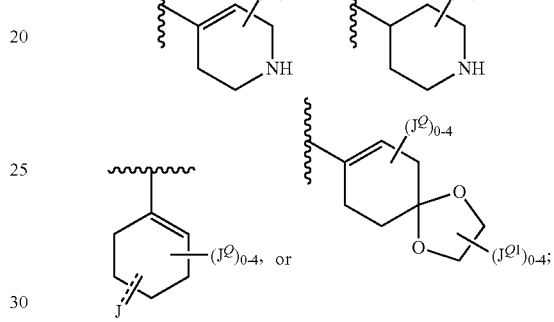

wherein said $C_{1-4}$aliphatic bonded to the pyridone is optionally substituted with halo, halo$C_{1-3}$alkyl, CN, OH, O($C_{1-3}$alkyl), $NH_2$, NH($C_{1-3}$alkyl), N($C_{1-3}$alkyl)$_2$, or acetyl.

48. The compound of claim 47, wherein Q is optionally substituted

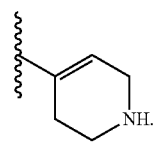 [SMILES: *C1=CCNCC1]

49. The compound of claim 45, wherein Q is

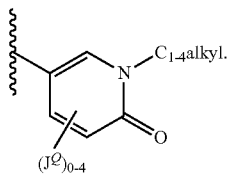

50. The compound of claim 8, wherein Q is bonded through a nitrogen atom.

51. The compound of claim 50, wherein Q is optionally substituted azetidinyl, pyrrolidinyl, piperidinyl, piperazinyl, homopiperazinyl, homopiperidinyl, morpholinyl, or thiomorpholinyl, wherein said Q is optionally fused to $Q^1$ to form a fused bicyclic ring Q-$Q^1$; or Q and $Q^1$ are optionally joined together at a carbon atom to form a spirocyclic bicyclic ring Q-$Q^1$; or Q and $Q^1$, taken together, form a bridged bicyclic ring Q-Q¹ wherein said bridge is 1-3 atoms long; Q-Q¹ can be optionally substituted with 1-2 J groups; wherein J can be bonded to either Q or Q¹.

52. The compound of claim 51, wherein Q is an optionally substituted group selected from the following:

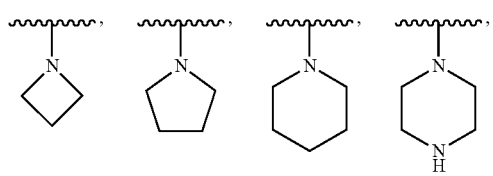

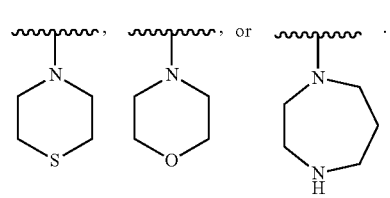

53. The compound of claim 52, wherein J is bonded in the position of Q as shown below:

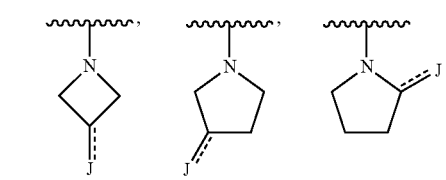

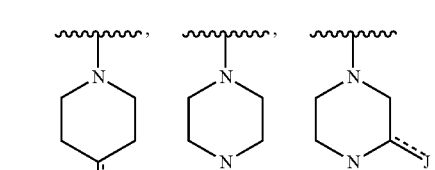

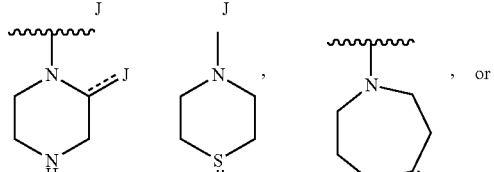

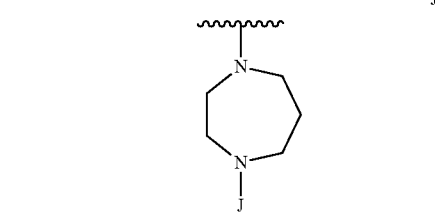

wherein Q is optionally substituted with 1-4 occurrences of $J^Q$.

54. The compound of claim 51, wherein Q and Q¹ together combine to form a bicyclic ring selected from the group consisting of

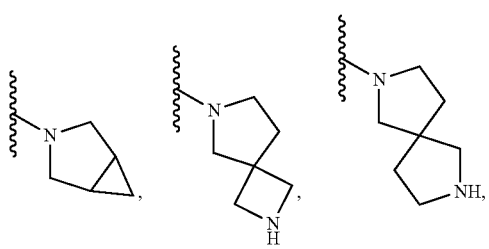

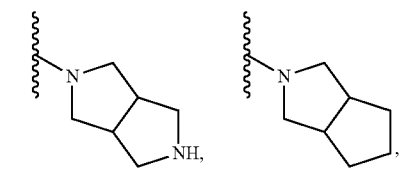

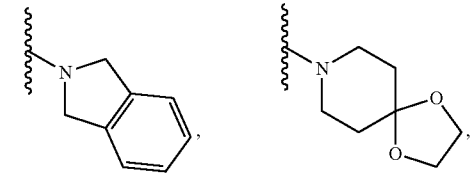

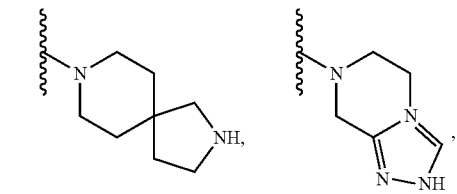

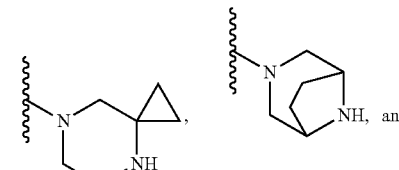

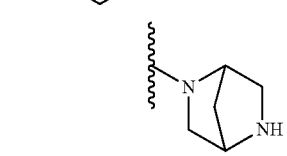

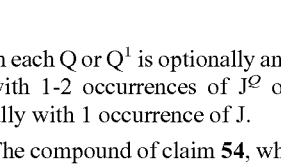

wherein each Q or Q¹ is optionally and independently substituted with 1-2 occurrences of $J^Q$ or $J^{Q1}$ respectively and optionally with 1 occurrence of J.

55. The compound of claim 54, wherein J is bonded in the position of Q or Q¹ as shown below:

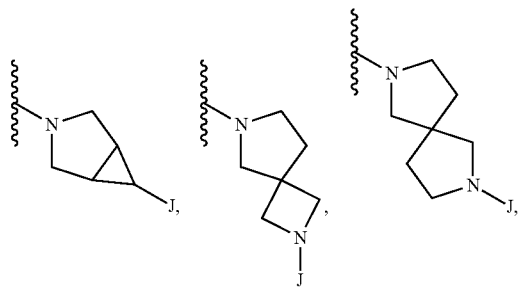

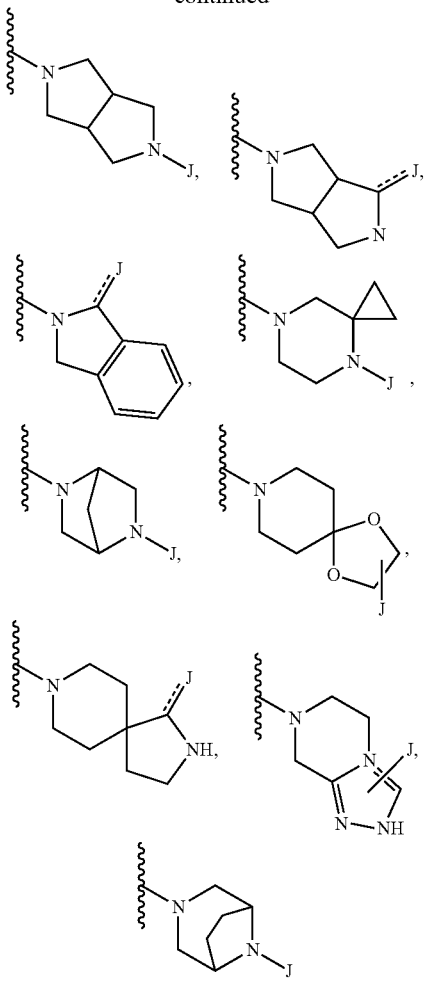

wherein Q is optionally substituted with 1-4 occurrences of $J^Q$ or $J^{Q1}$ respectively.

56. The compound of claim 23, wherein J is $C_{1-6}$aliphatic chain wherein up to 2 methylene units of $C_{1-6}$aliphatic optionally replaced with heteroatom selected from O, N, or S.

57. The compound of claim 8, wherein J is oxo, $V^1$—R", or —(V)$_m$—R*; wherein
each V and $V^1$ is independently a $C_{1-6}$ alkylidene chain wherein 0-3 methylene units are replaced with O, N, S, CO, SO, or $SO_2$;
R* is H or $C_{1-6}$alkyl;
m is 0 or 1; and
R" is a 3-7 membered saturated or unsaturated monocyclic ring having 0-3 heteroatoms independently selected from nitrogen, oxygen, or sulfur.

58. The compound of claim 57, wherein $R^2$ is piperazine or tetrahydropyridinyl; m is 0; J is oxo, $V^1$—R", or —(V)—R*, wherein R" is thiazolyl, pyridyl, pyrimidyl, phenyl; and R* is optionally substituted with halo, $O(C_{1-4}$alkyl), halo$C_{1-4}$alkyl, or CN.

59. The compound of claim 57, wherein
V is O, $O(C_{1-6}$alkyl), $(C_{1-4}$alkyl)O, C(O)O, C(O)O($C_{1-6}$alkyl), C(O)O($C_{1-6}$alkyl)O($C_{1-6}$alkyl), C(O)($C_{1-6}$alkyl), C(O)($C_{1-6}$alkyl)N, C(O)($C_{1-6}$alkyl)NH($C_{1-6}$alkyl), C(O)($C_{1-6}$alkyl)C(O)O, C(O)($C_{1-6}$alkyl)O, C(O)($C_{1-6}$alkyl)O($C_{1-6}$alkyl), C(O)($C_{1-6}$alkyl)NH($C_{1-6}$alkyl), C(O)($C_{1-6}$alkyl)O($C_{1-4}$alkyl)O($C_{1-6}$alkyl), C(O)NH, C(O)NH($C_{1-6}$alkyl), C(O)N($C_{1-6}$alkyl), NH, N($C_{1-6}$alkyl), N($C_{1-6}$alkyl)$_2$, NHC(O), NHC(O)$C_{1-6}$ alkyl, NHC(O)($C_{1-6}$alkyl)O, NHC(O)($C_{1-6}$alkyl)O($C_{1-6}$alkyl), NHC(O)($C_{1-6}$alkyl)O($C_{1-6}$alkyl)O($C_{1-6}$alkyl), NHC(O)($C_{1-6}$alkyl)NH($C_{1-6}$alkyl), C(O)N($C_{1-6}$alkyl)-, C(O)N($C_{1-6}$alkyl)$_2$, $SO_2$, $S(O)_2(C_{1-6}$alkyl)-, $S(O)_2(C_{1-6}$alkyl)NH, $S(O)_2$NH($C_{1-6}$alkyl)-, $S(O)_2$N($C_{1-6}$alkyl)$_2$, $NHSO_2$, or $NHSO_2$N($C_{1-6}$alkyl)$_2$;
R* is H or $C_{1-6}$alkyl; and
R" is $C_3$-$C_8$ cycloaliphatic, imidazolyl, thienyl, thiazolyl, furanyl, pyrazolyl, triazolyl, pyrrolyl, phenyl, pyridyl, pyrimidyl, pyrazinyl, pyrrolidinyl, piperidinyl, piperazinyl, homopiperidinyl, homopiperazinyl, morpholinyl, thiomorpholinyl, or tetrahydropyranyl.

60. The compound of claim 59, wherein
V is O, $OCH_2$, $CH_2O$, C(O), $C(O)CH_2$, $C(O)CH_2CH_2NH$, $C(O)CH_2CH_2NHCH_2$, $C(O)CH_2CH_2C(O)O$, $C(O)CH_2O$, $C(O)CH_2OCH_2$, $C(O)CH_2N(CH_3)CH_2$, $C(O)CH_2OCH_2CH_2OCH_2$, $C(O)CH(CH_3)CH_2$, $C(O)CH(CH_2CH_3)CH_2CH_2$, C(O)O, $C(O)OCH_2$, $C(O)OCH_2CH_2$, $C(O)OCH_2CH_2OCH_2$, $C(O)OCH_2C\equiv C-CH_2$, C(O)NH, $C(O)NHCH_2$, $C(O)N(CH_3)$—, $C(O)N(CH_3)CH_2$—, NH, $N(C_{1-6}$aliphatic), $N(CH_3)CH_2$, NHC(O), $NHC(O)CH_2$, $NHC(O)CH_2O$, $NHC(O)CH_2OCH_2$, $NHC(O)CH_2OCH_2CH_2OCH_2$, $NHC(O)CH_2N(CH_3)CH_2$, $NHC(O)C(CH_3)_2CH_2$, $NHC(O)CH(CH_2CH_3)CH_2CH_2$, $SO_2$, $S(O)_2CH_2$, $S(O)_2CH_2CH_2$, $S(O)_2CH_2CH_2NH$, $S(O)_2CH_2CH_2CH_2NH$, $S(O)_2CH_2CH_2CH_2$, $S(O)_2CH(CH_3)CH_2$, $S(O)_2N(CH_3)CH_2$, $NHSO_2$, or $NHSO_2N(CH_3)CH_2$;
R is H or $C_{1-6}$alkyl; and
$Q^2$ is cyclopropyl, cyclobutyl, cyclopentyl, cyclohexyl, phenyl, imidazolyl, thienyl, thiazolyl, furanyl, pyrazolyl, triazolyl, tetrazolyl, pyrrolyl, phenyl, pyridyl, pyrimidyl, pyrazinyl, pyrrolidinyl, piperidinyl, piperazinyl, homopiperidinyl, homopiperazinyl, morpholinyl, thiomorpholinyl, or tetrahydropyranyl; wherein said $Q^2$ is optionally substituted with $C_{1-6}$alkyl, CN, halo, halo$C_{1-4}$alkyl, NH($C_{1-4}$alkyl), N($C_{1-4}$alkyl)$_2$, or O($C_{1-6}$alkyl).

61. The compound of claim 23, wherein J is selected from $C_{1-6}$aliphatic, oxo, —OH, —O($C_{1-6}$aliphatic), CN, —C(O)($C_{1-6}$aliphatic), —C(O)(phenyl), —C(O)(benzyl), —C(O)$CH_2O$(phenyl), —C(O)$CH_2O(C_{1-6}$aliphatic), —C(O)$CH_2O$(benzyl), —C(O)(pyridyl), —C(O)(pyrrolidinyl), —C(O)(piperidinyl), —C(O)(piperazinyl), —C(O)(homopiperazinyl), —C(O)(morpholinyl), —C(O)(tetrahydropyranyl), —C(O)O($C_{1-6}$aliphatic), —C(O)O(phenyl), —C(O)O(benzyl), —C(O)$NH_2$, —C(O)NH($C_{1-6}$aliphatic), —C(O)N($C_{1-6}$aliphatic)$_2$, —C(O)NH(phenyl), —C(O)NH(benzyl), —$S(O)_2(C_{1-6}$aliphatic), —$S(O)_2$(phenyl), —$S(O)_2$(benzyl), —$S(O)_2$(pyridyl), —$S(O)_2$(furanyl), —$S(O)_2$(imidazolyl), —$S(O)_2$(thienyl), —$S(O)_2$NH($C_{1-6}$aliphatic), —$S(O)_2$N($C_{1-6}$aliphatic)$_2$, —$S(O)_2$NH(phenyl), —$S(O)_2$NH(benzyl), —NHC(O)($C_{1-6}$aliphatic), —NHC(O)(pyridyl), $NHS(O)_2N(C_{1-6}$aliphatic)$_2$, $NH_2$, NH($C_{1-6}$aliphatic), N($C_{1-6}$aliphatic)$_2$; wherein said phenyl, benzyl, pyrrolidinyl, piperidinyl, piperazinyl, morpholinyl, tetrahydropyranyl, or $C_{1-6}$aliphatic is optionally substituted with halo, $C_{1-3}$alkyl, CN, OH, O($C_{1-3}$alkyl), $NH_2$, NH($C_{1-3}$alkyl), N($C_{1-3}$alkyl)$_2$, acetyl, $SO_2(C_{1-3}$alkyl).

62. The compound of claim 61, wherein J is selected from, oxo, —OH, —NHC(O)($C_{1-4}$alkyl), —C(O)($C_{1-4}$alkyl), —C(O)$NH_2$, —C(O)NH($C_{1-4}$alkyl), —C(O)NH($C_{1-4}$alkyl)$_2$, —$S(O)_2(C_{1-4}$alkyl), —$S(O)_2$NH($C_{1-4}$alkyl), or —$S(O)_2$N($C_{1-4}$alkyl)$_2$.

63. The compound of claim 23, wherein J is selected from —C(O)CH₂(phenyl), NH₂, NH(C₁₋₃alkyl), N(C₁₋₃alkyl)₂, —NHS(O)₂(phenyl), —NHC(O)(phenyl), —NHC(O)(pyridyl), —C(O)CH₂O(phenyl), —C(O)CH₂O(C₁₋₃alkyl), —NHC(O)CH₂O(C₁₋₃alkyl), —NHC(O)CH₂O(phenyl), —C(O)CH₂N(C₁₋₃alkyl)₂, —NHC(O)CH₂N(C₁₋₃alkyl)₂, —C(O)CH₂O(C₁₋₃alkyl)O(C₁₋₃alkyl), —NHC(O)CH₂O(C₁₋₃alkyl)O(C₁₋₃alkyl), —C(O)O(C₁₋₃alkyl)O(C₁₋₃alkyl), phenyl, pyridyl, thiazolyl, CF₃, pyrimidiyl, wherein said phenyl, pyridyl, or pyrimidyl group is optionally substituted with halo, O(C₁₋₆aliphatic), CN, CF₃, C(O)(furanyl).

64. The compound of claim 1 selected from the following:

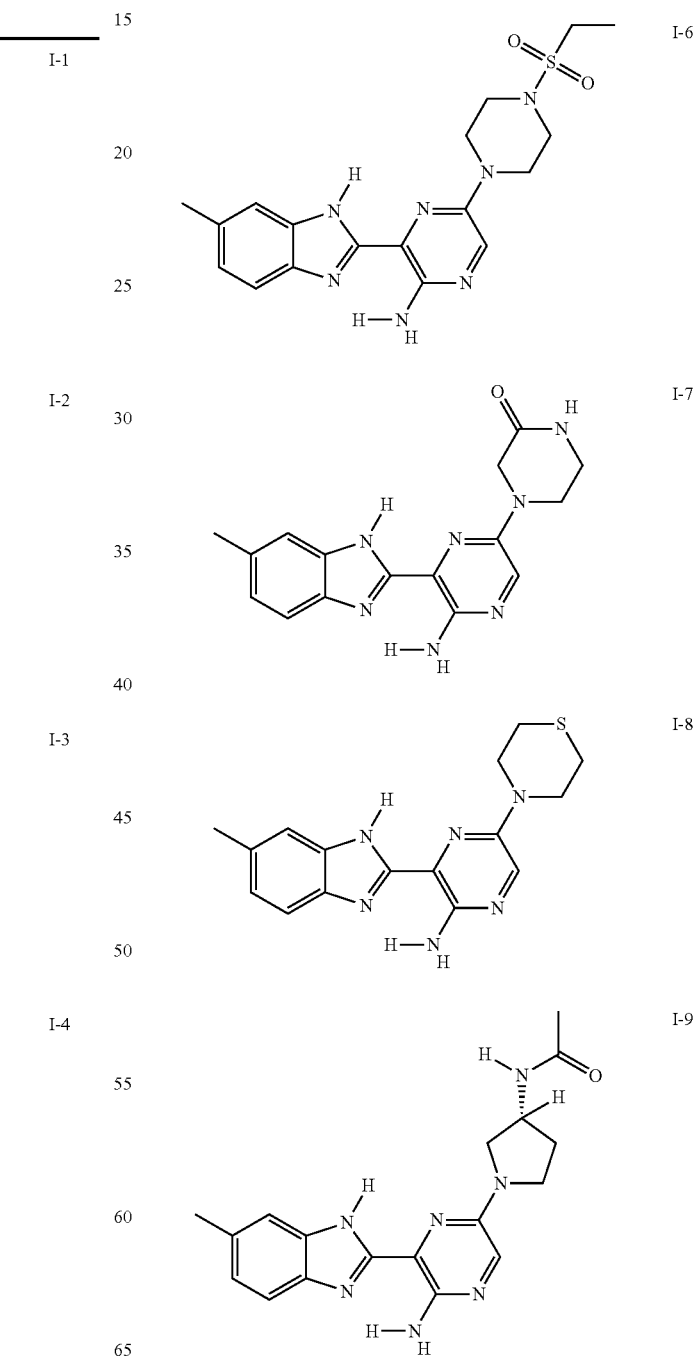

| 345 -continued | | 346 -continued | |
|---|---|---|---|
| 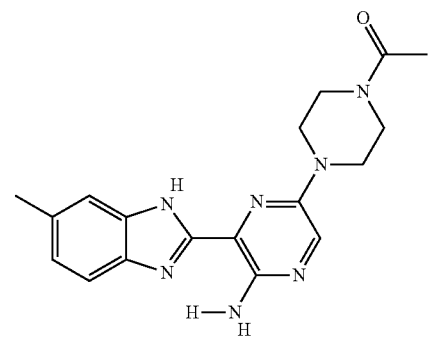 | I-10 | 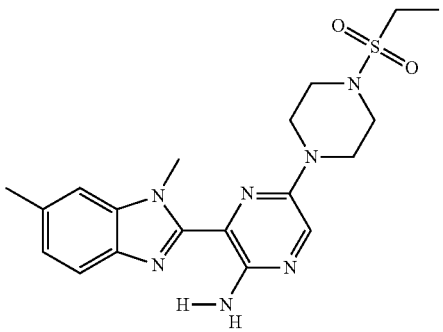 | I-15 |
| 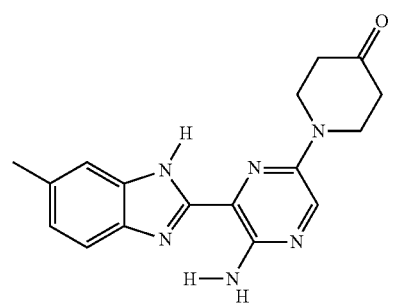 | I-11 | 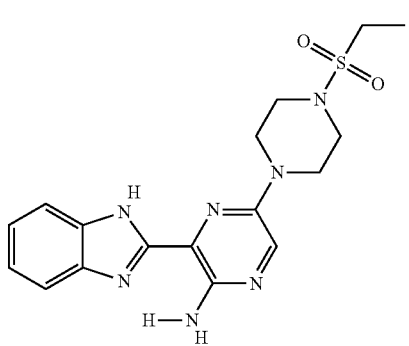 | I-16 |
| 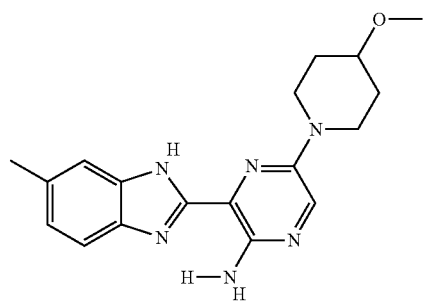 | I-12 | | |
| 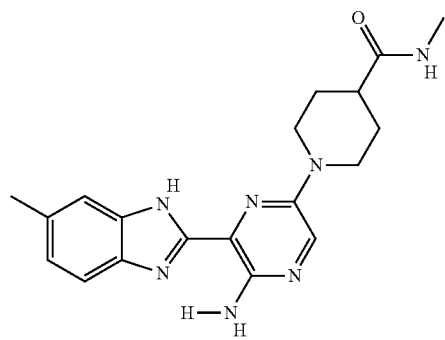 | I-13 | 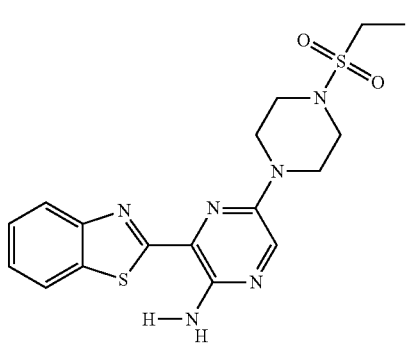 | I-17 |
| 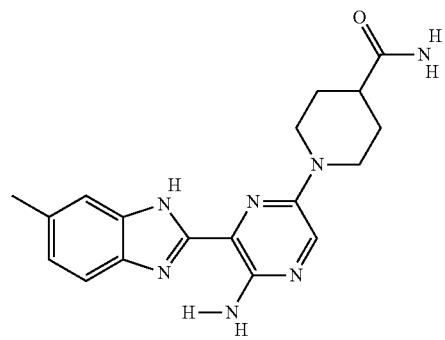 | I-14 | 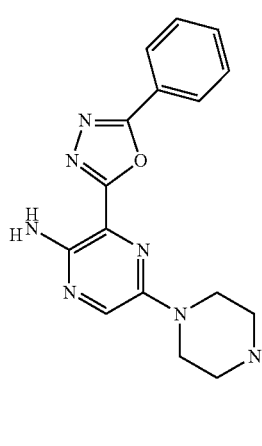 | I-18 |

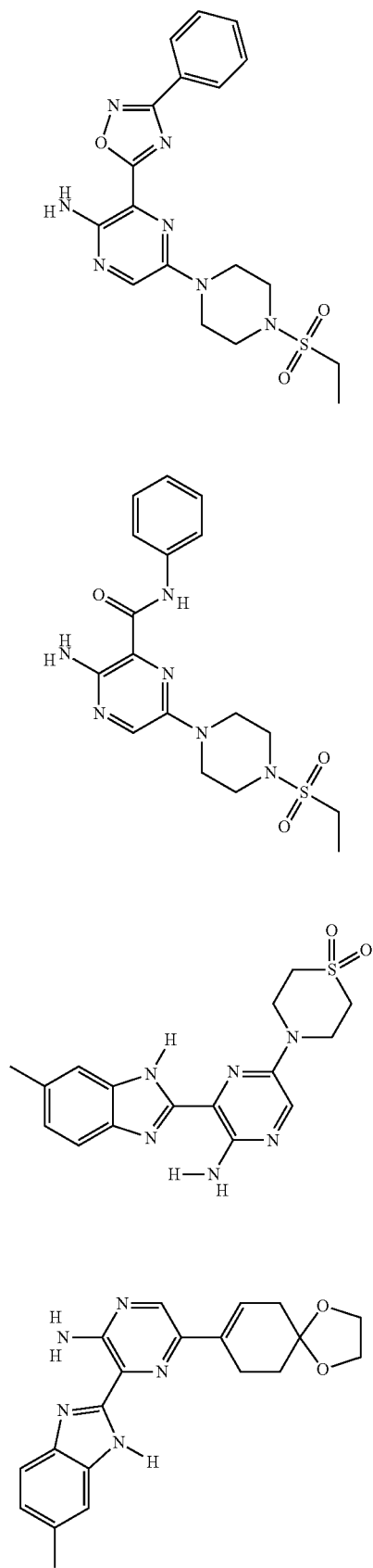
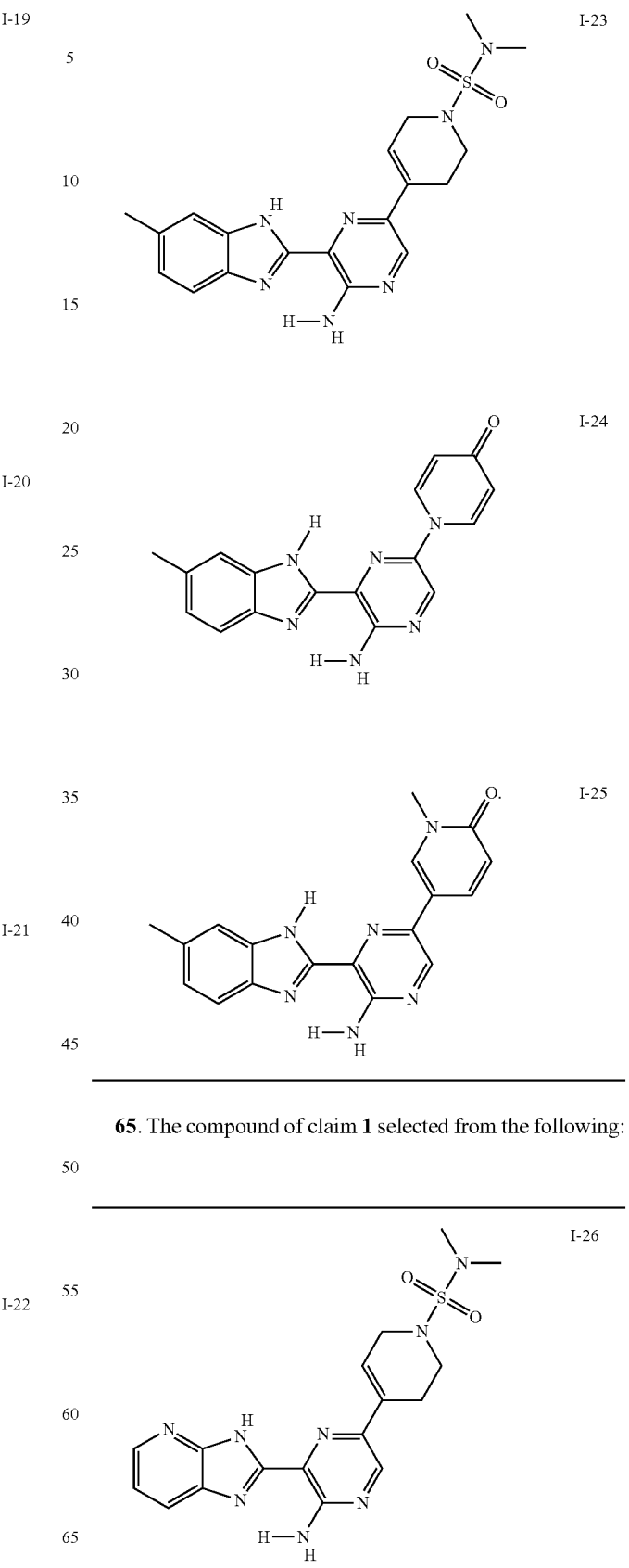
65. The compound of claim 1 selected from the following:

-continued
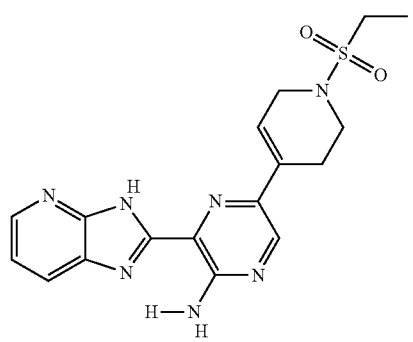
I-27
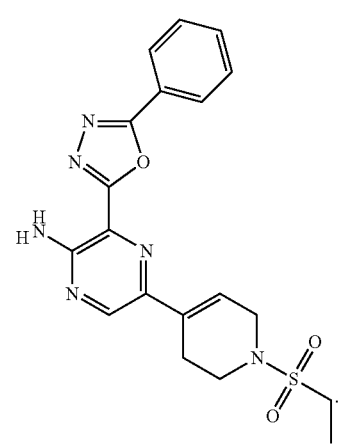
I-28
66. The compound of claim 1 selected from the following:
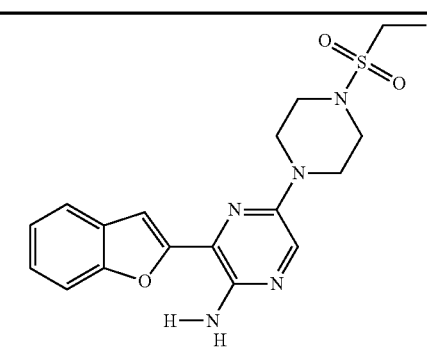
I-29
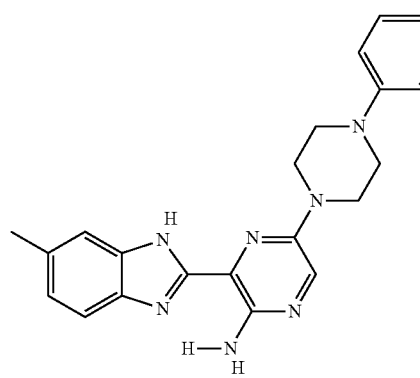
I-30
-continued
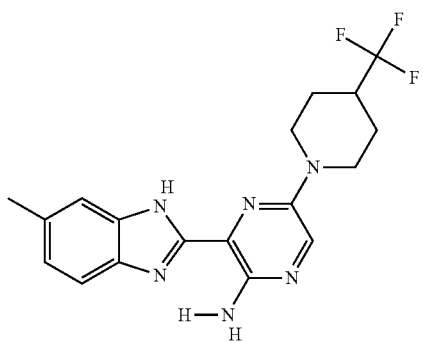
I-31
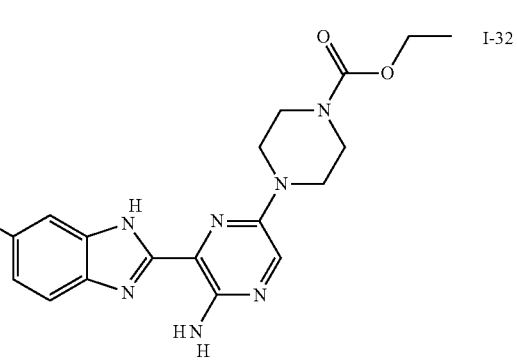
I-32
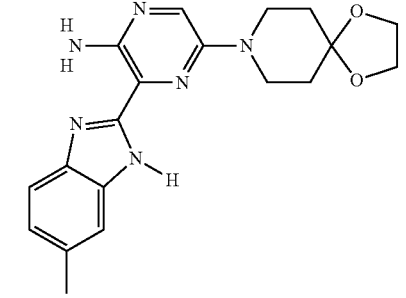
I-33
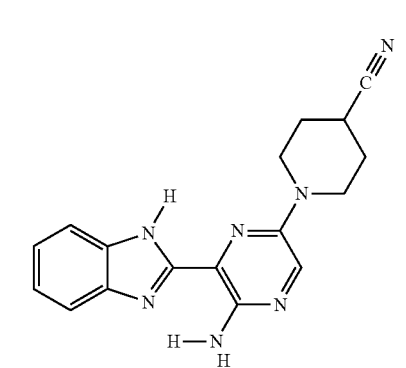
I-34

| 351 -continued | 352 -continued |
|---|---|
| 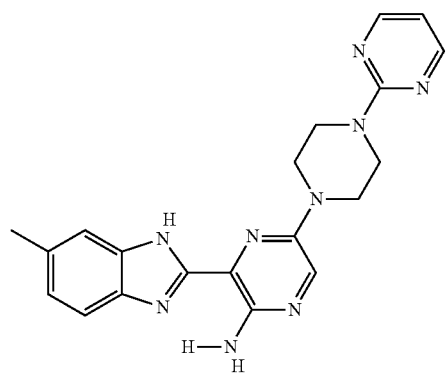 I-35 | 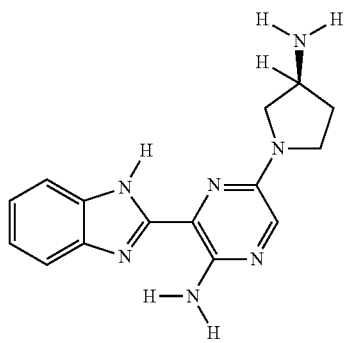 I-39 |
| 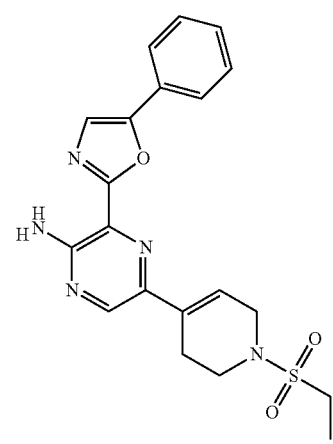 I-36 | 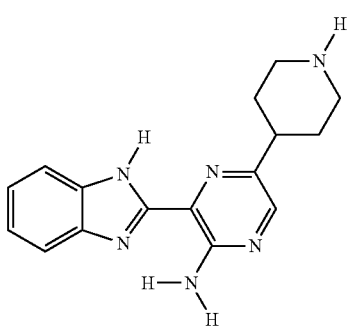 I-40 |
| 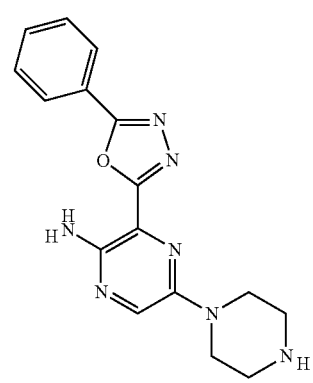 I-37 | 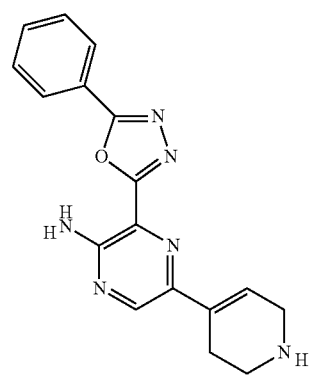 I-41 |
| 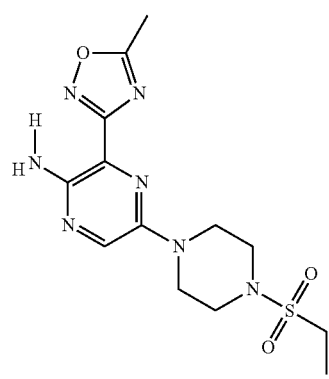 I-38 | 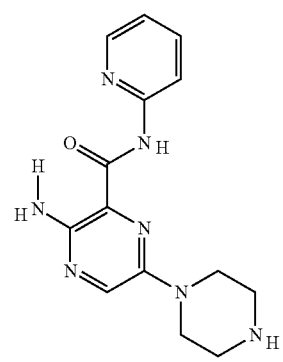 I-42 |

353
-continued
| | |
|---|---|
| 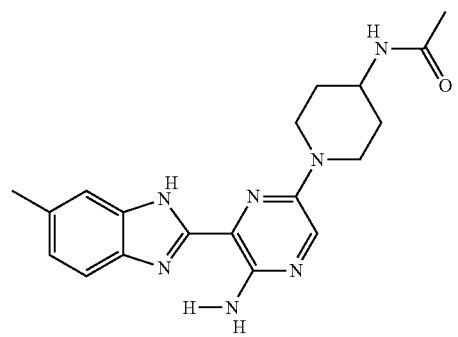 I-43 | 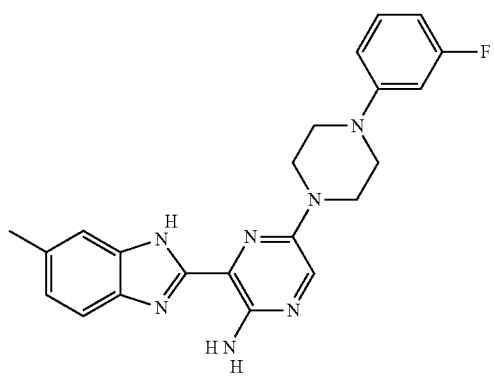 I-47 |
| 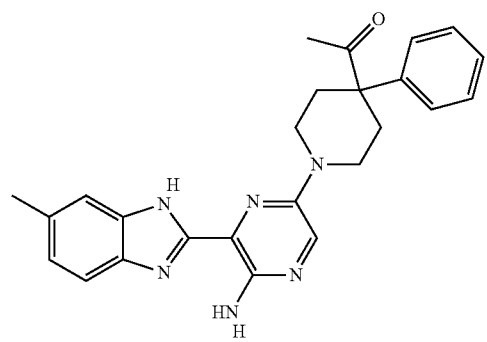 I-44 | 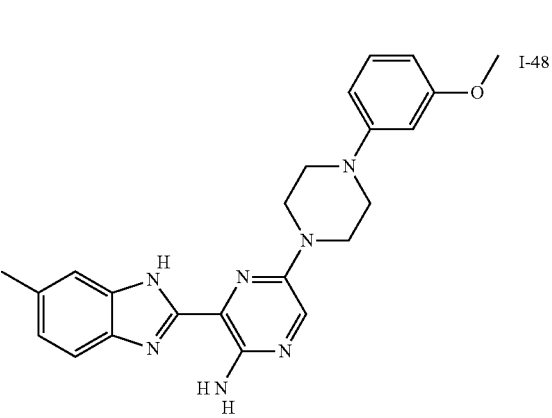 I-48 |
| 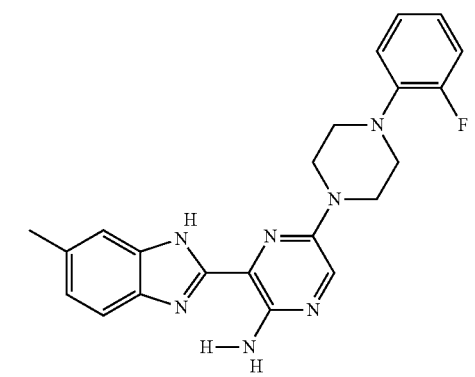 I-45 | 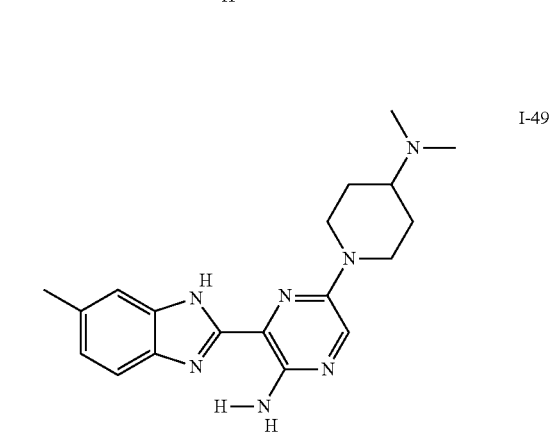 I-49 |
| 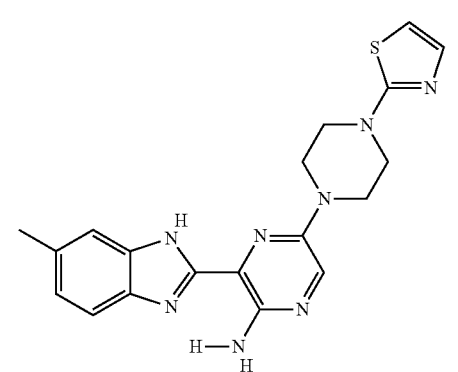 I-46 | 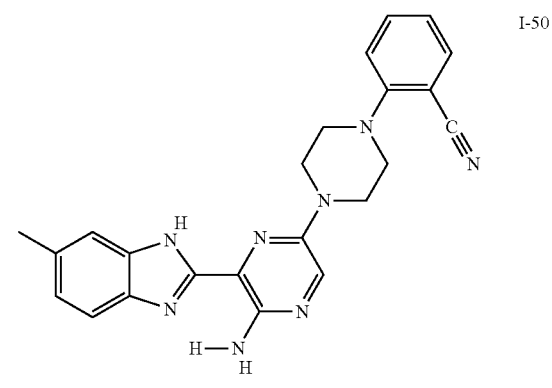 I-50 |
354
-continued

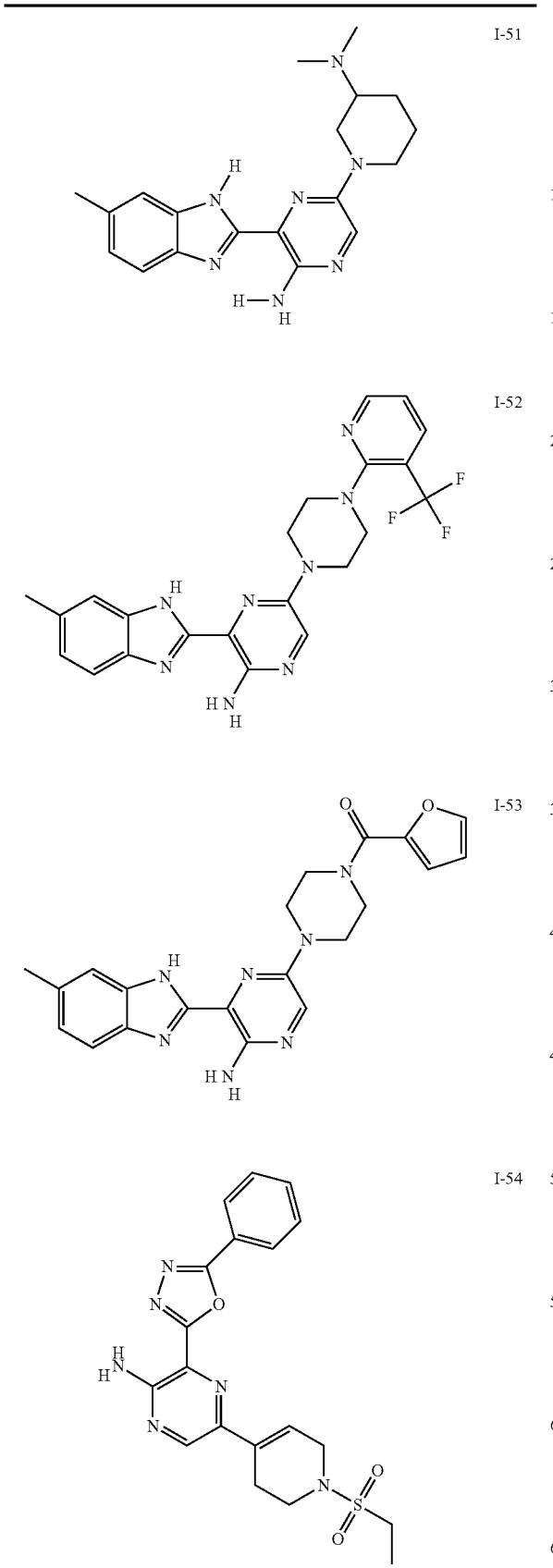
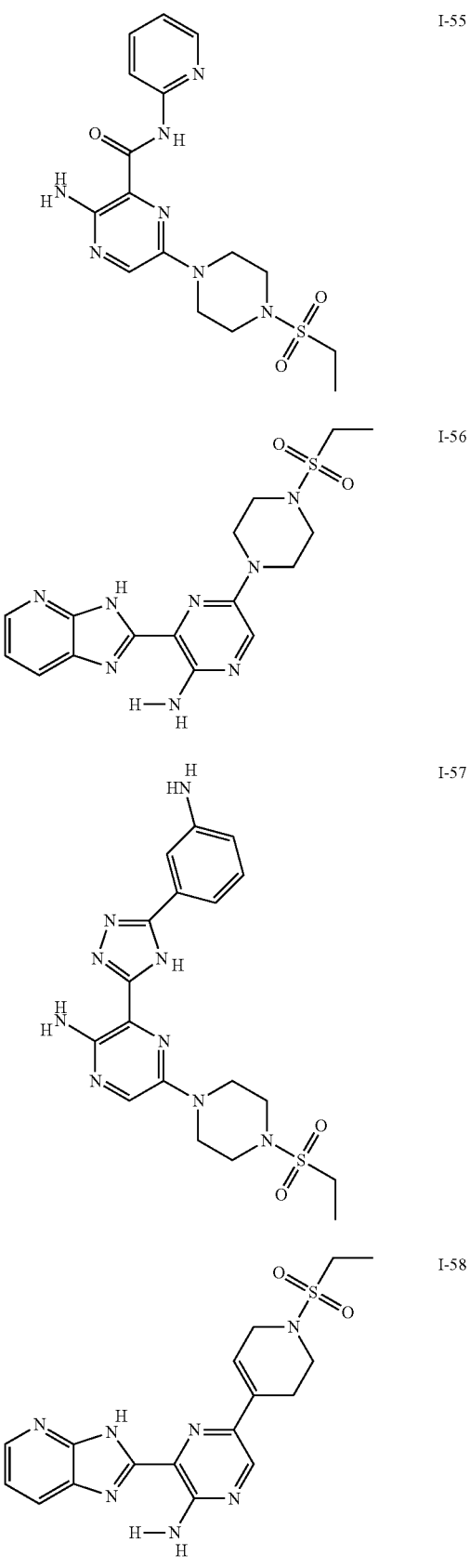

-continued
I-59
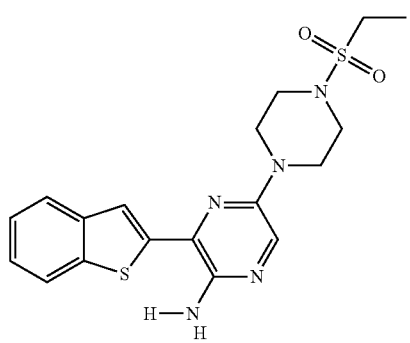
I-60
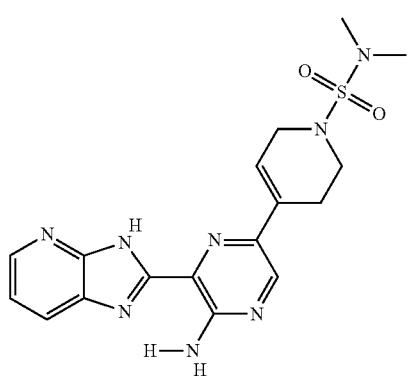
I-61
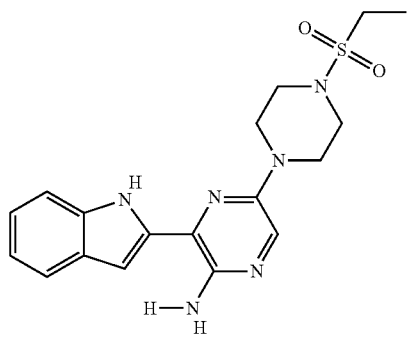
I-62
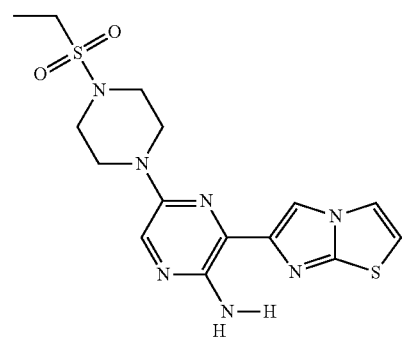
-continued
I-63
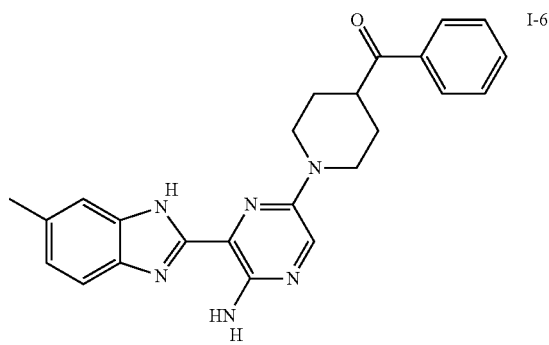
I-64
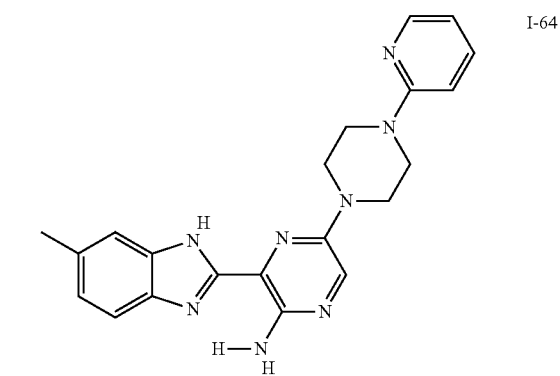
I-65
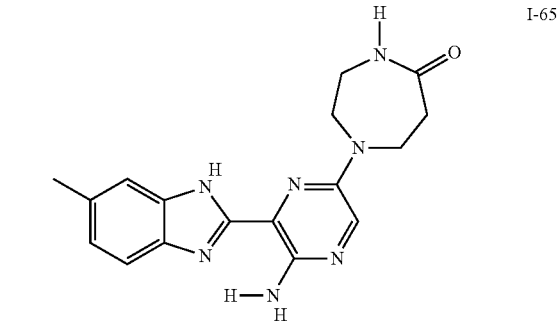
I-66
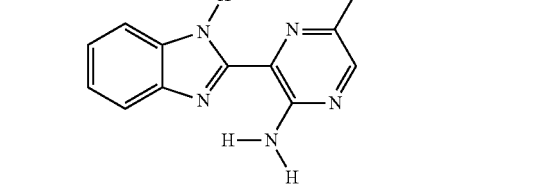

| 359 -continued | | 360 -continued | |
|---|---|---|---|
| 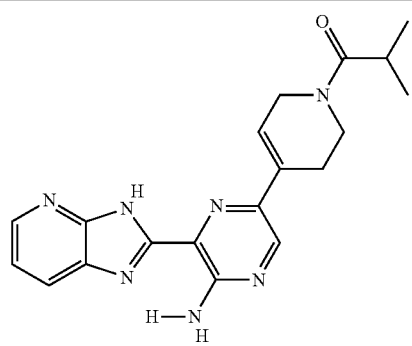 | I-67 | 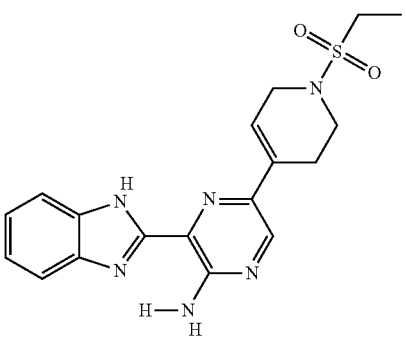 | I-71 |
| 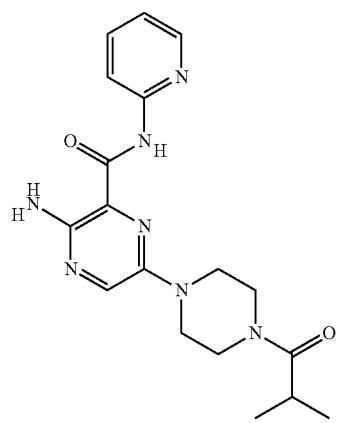 | I-68 | 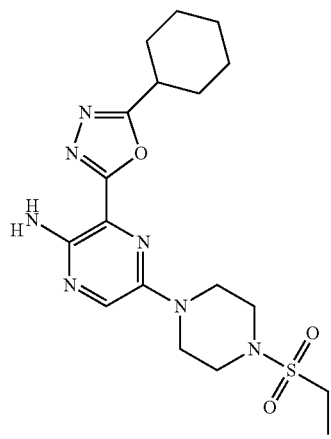 | I-72 |
| 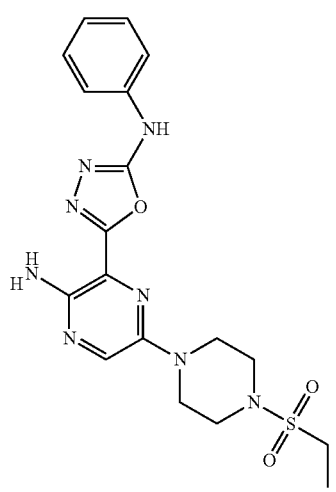 | I-69 | 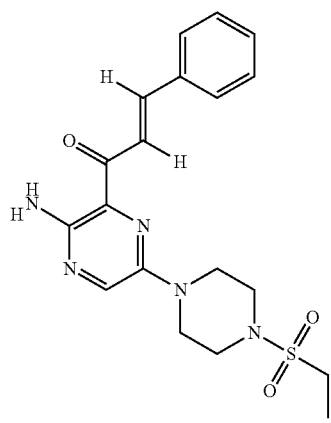 | I-73 |
| 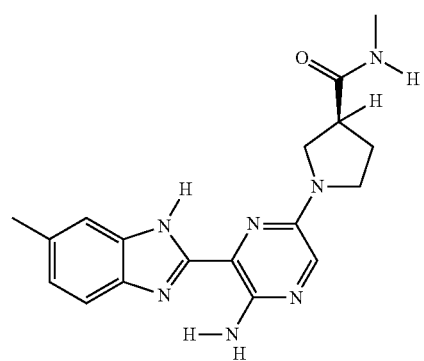 | I-70 | 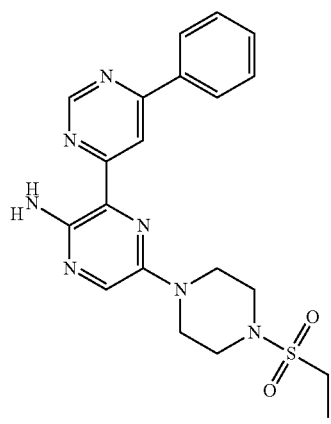 | I-74 |

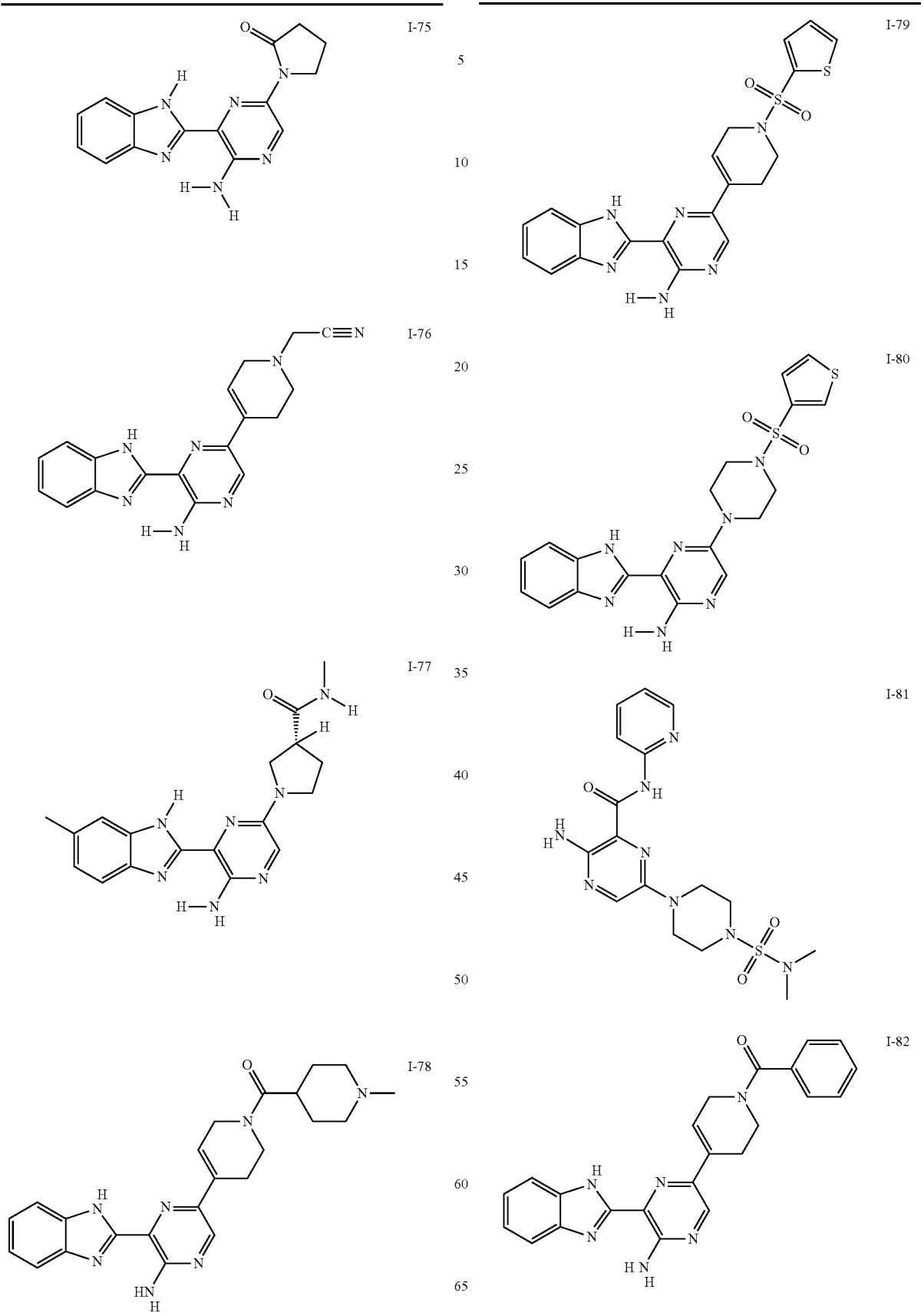

-continued
I-83
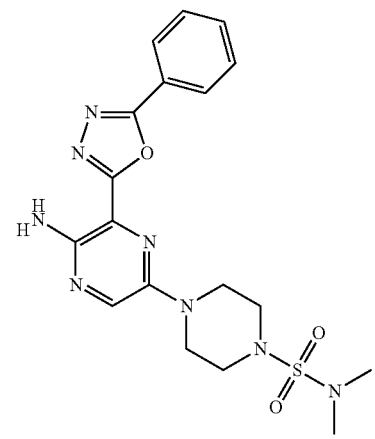
I-84
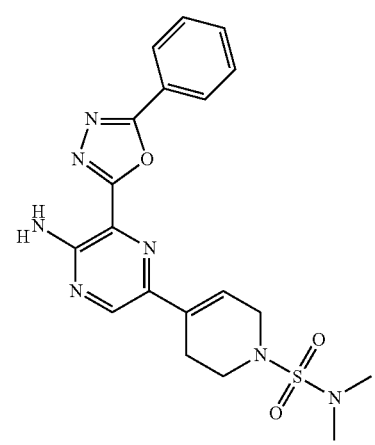
I-85
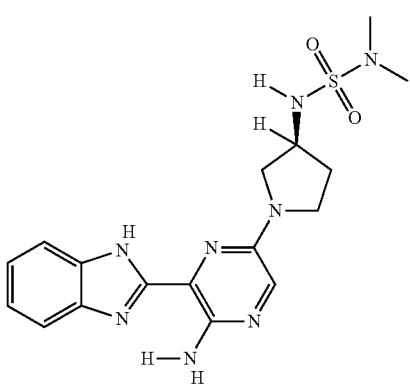
I-86
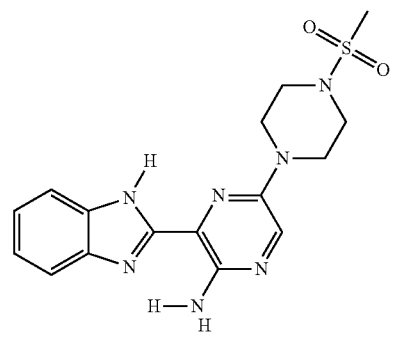
-continued
I-87
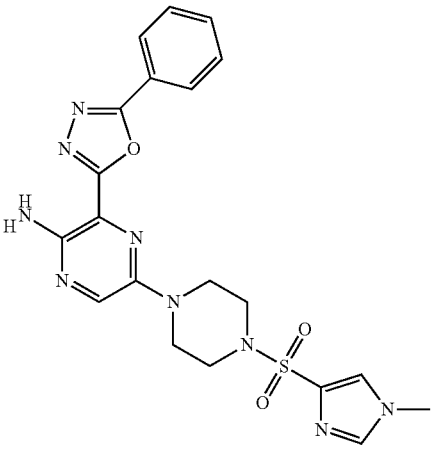
I-88
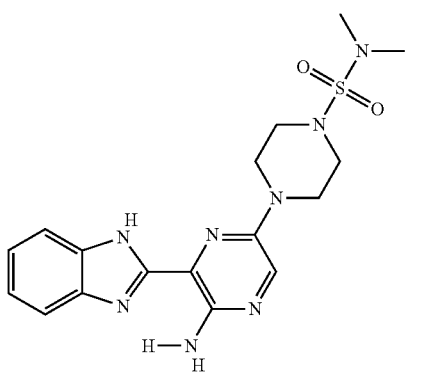
I-89
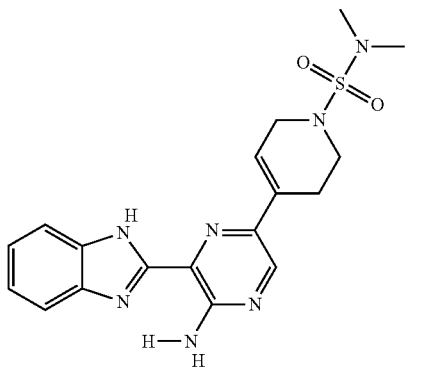
I-90
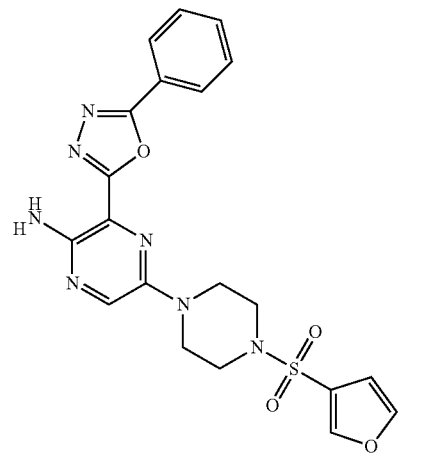

365
-continued
I-91
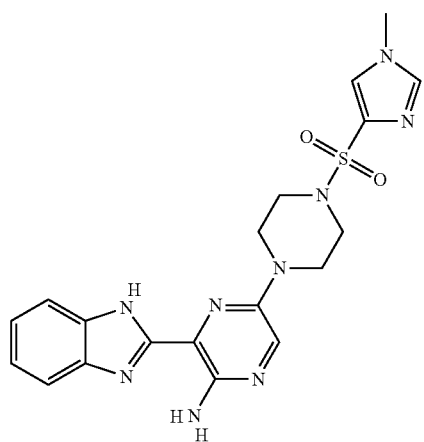
I-92
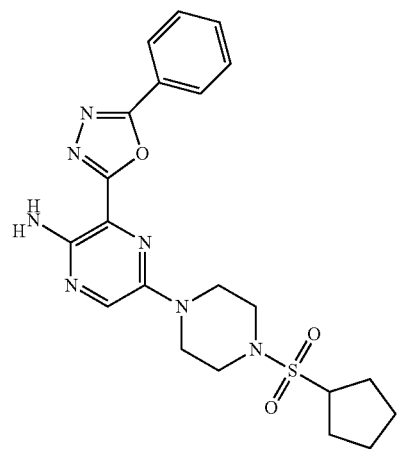
I-93
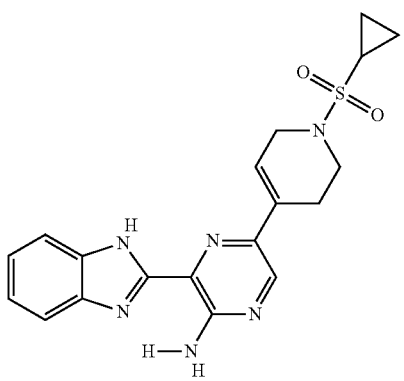
366
-continued
I-94
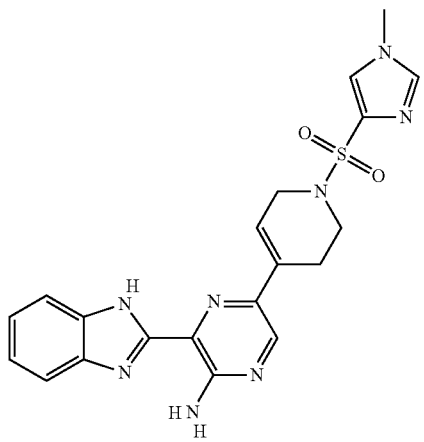
I-95
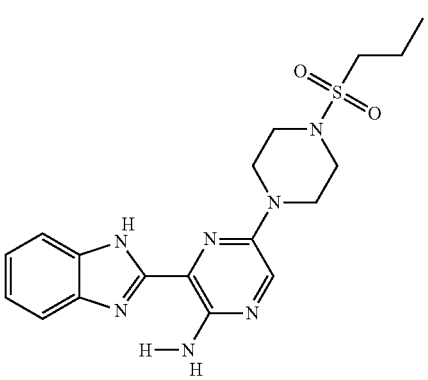
I-96
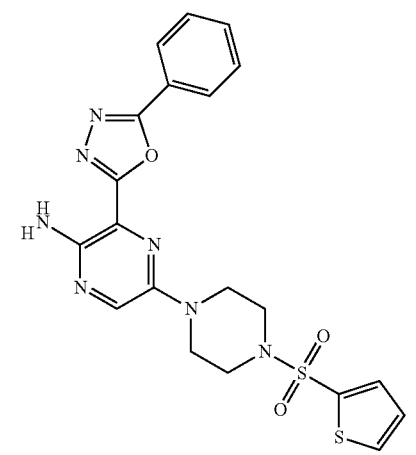
I-97
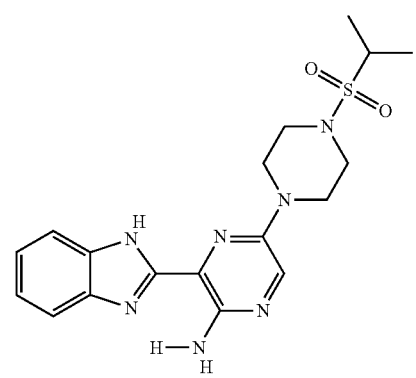

| 367 -continued | 368 -continued |
|---|---|
| 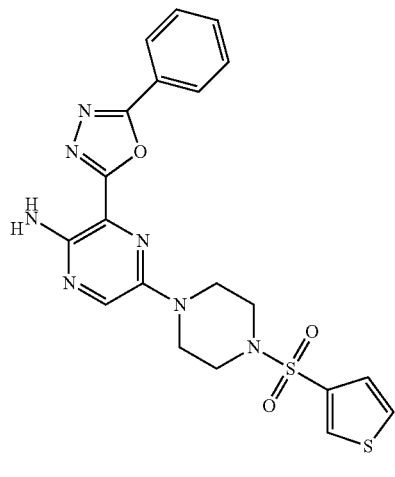 I-98 | 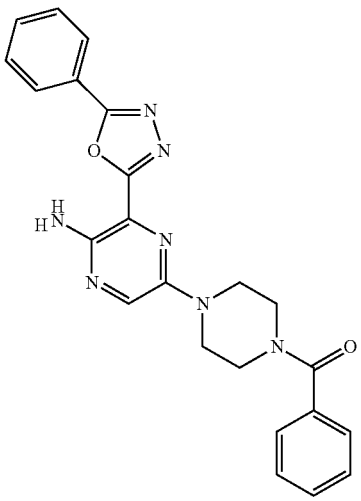 I-101 |
| 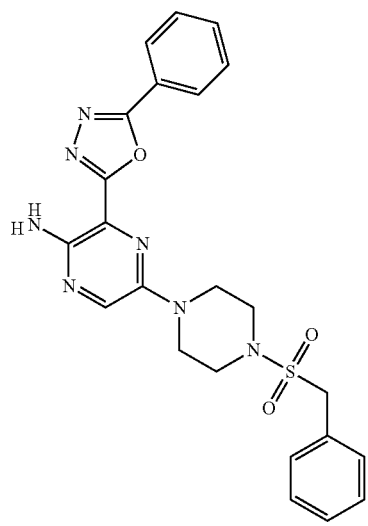 I-99 | 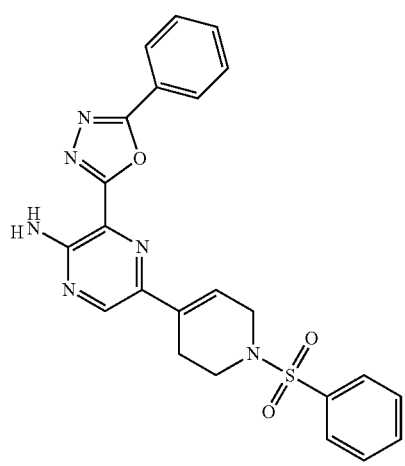 I-102 |
| 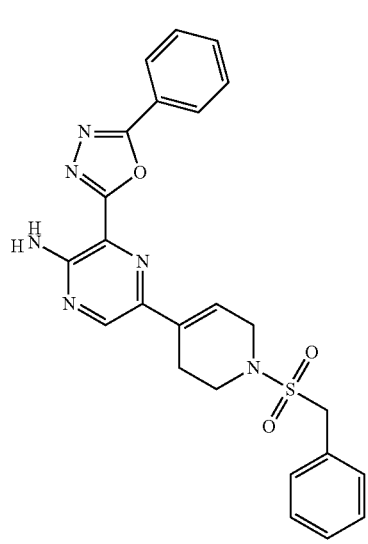 I-100 | 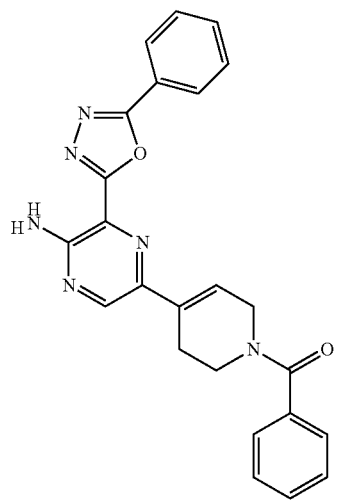 I-103 |

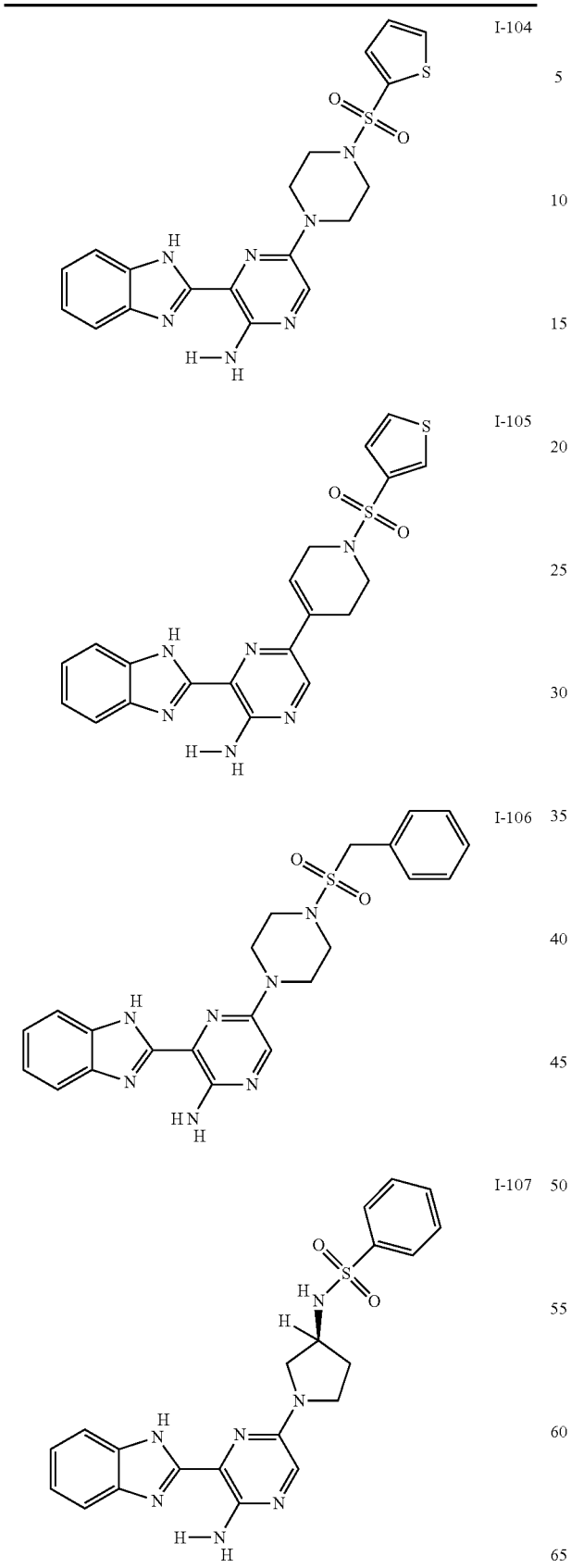
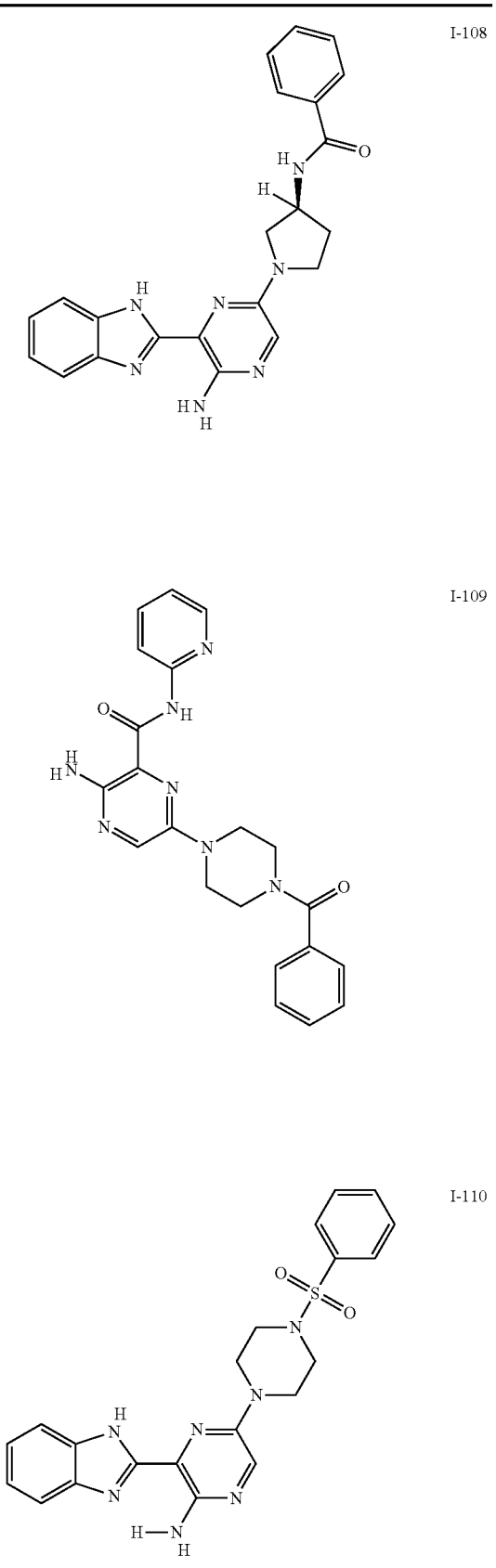

| 371 -continued | 372 -continued |
|---|---|
| I-111 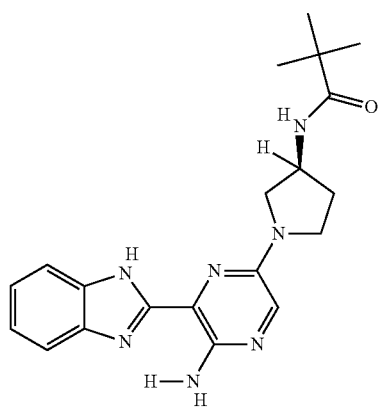 | I-114 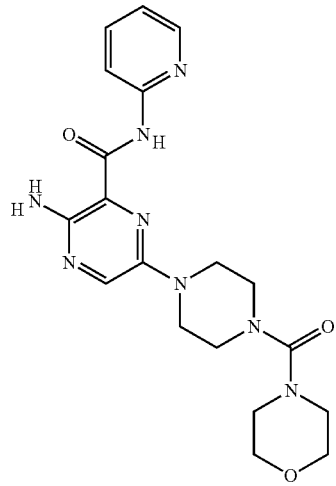 |
| I-112 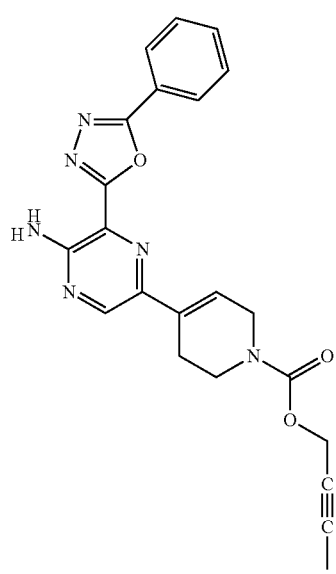 wait | |
| I-112 | I-115 |
| I-113 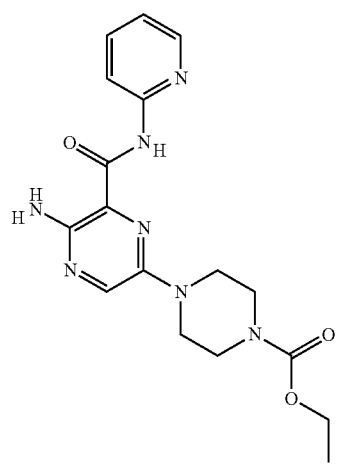 | I-116 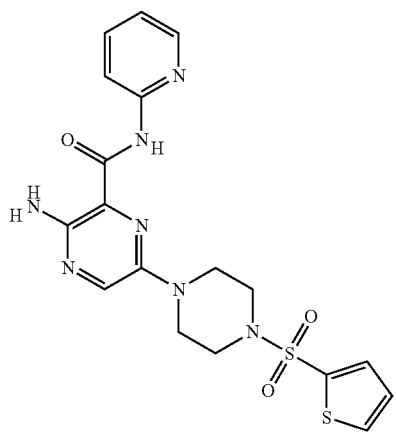 |

373
-continued
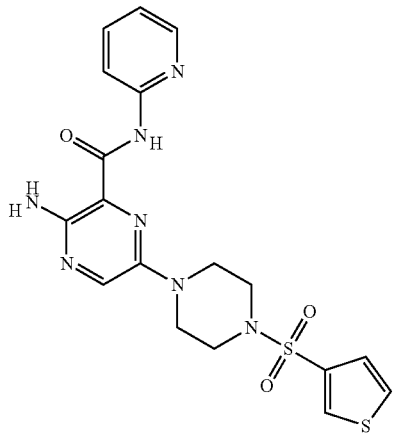
I-117
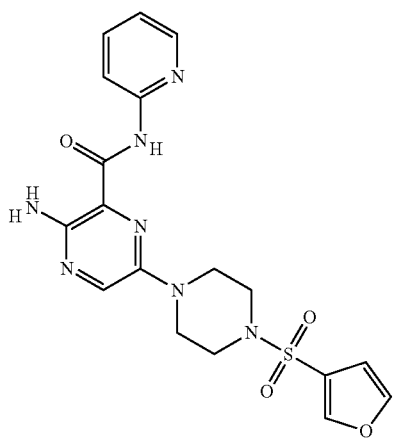
I-118
I-119
374
-continued
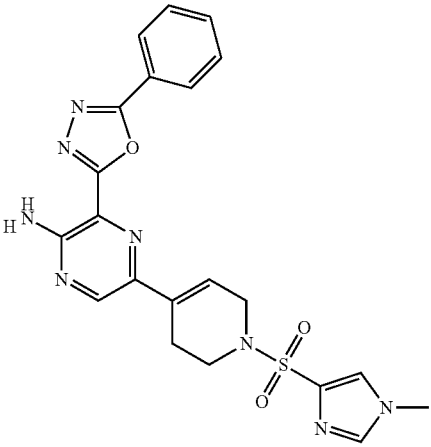
I-120
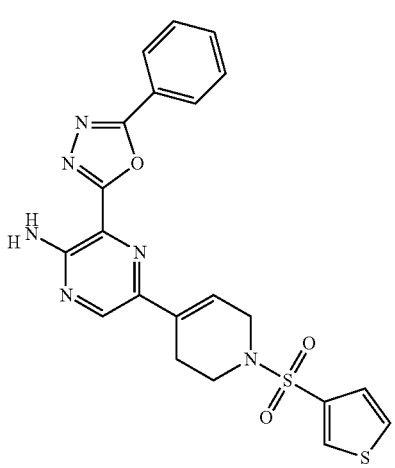
I-121
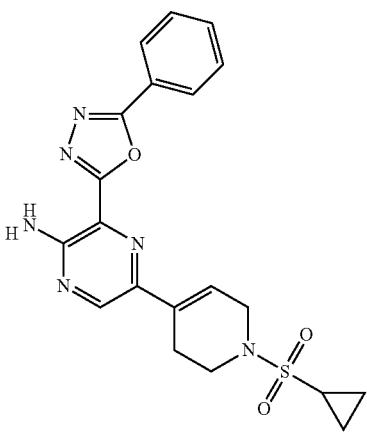
I-122

-continued
I-123
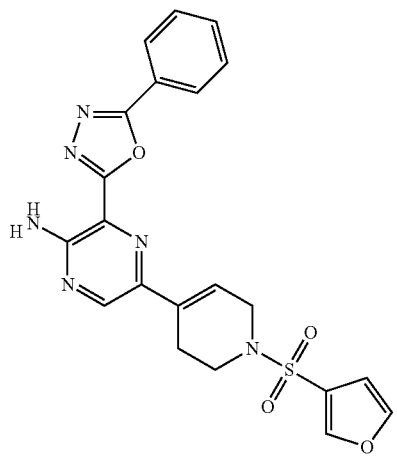
I-124
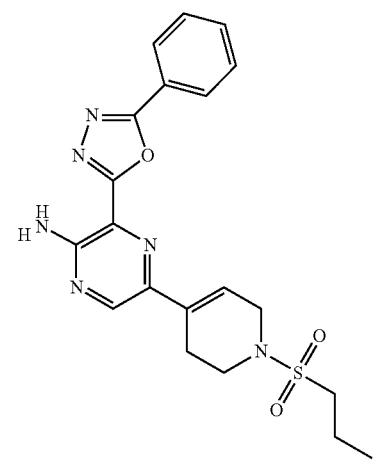
I-125
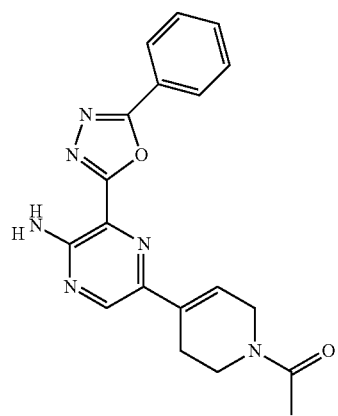
-continued
I-126
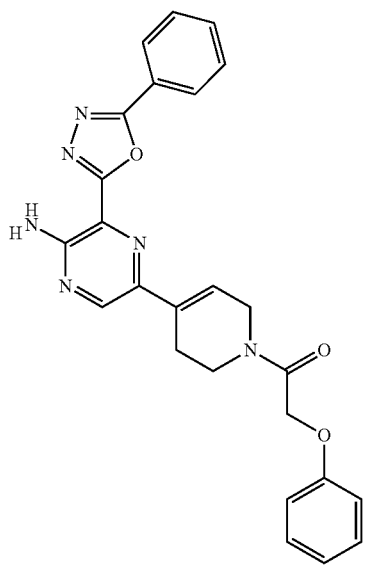
I-127
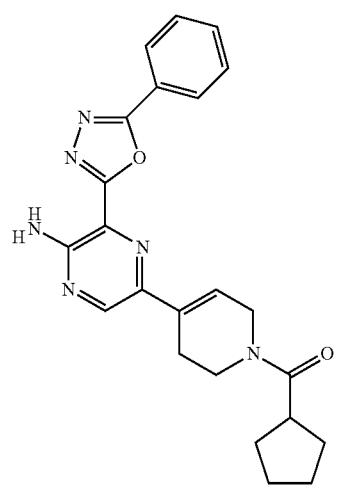
I-128
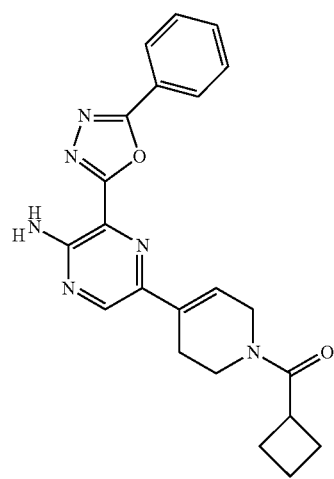

377
-continued
I-129
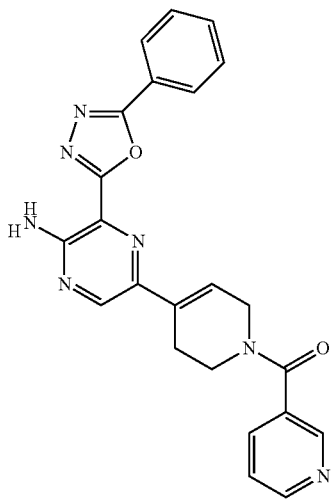
I-130
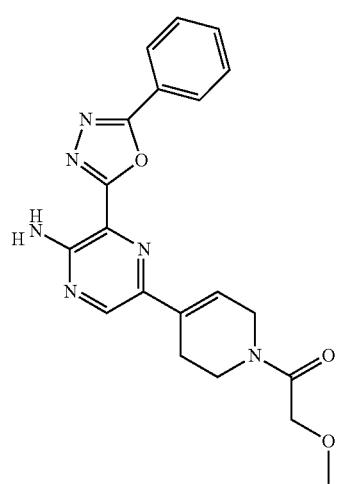
I-131
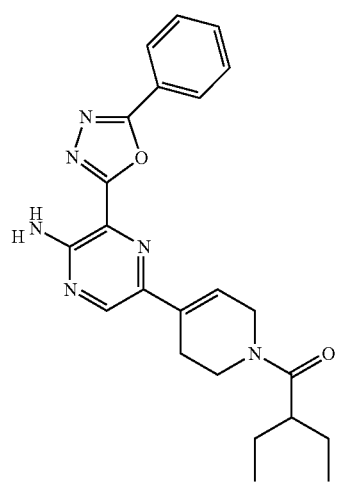
378
-continued
I-132
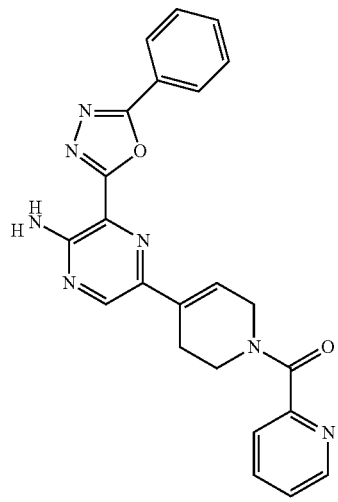
I-133
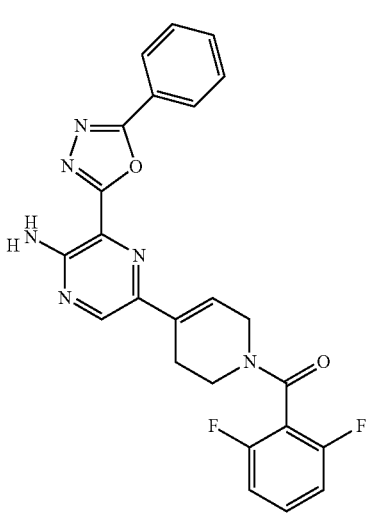
I-134
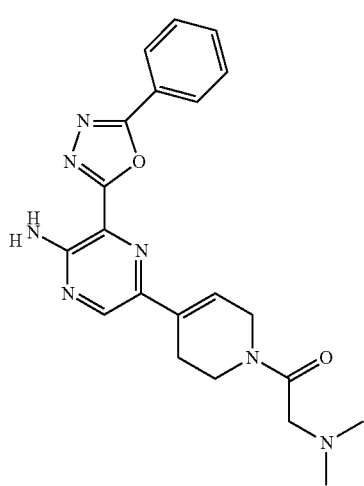

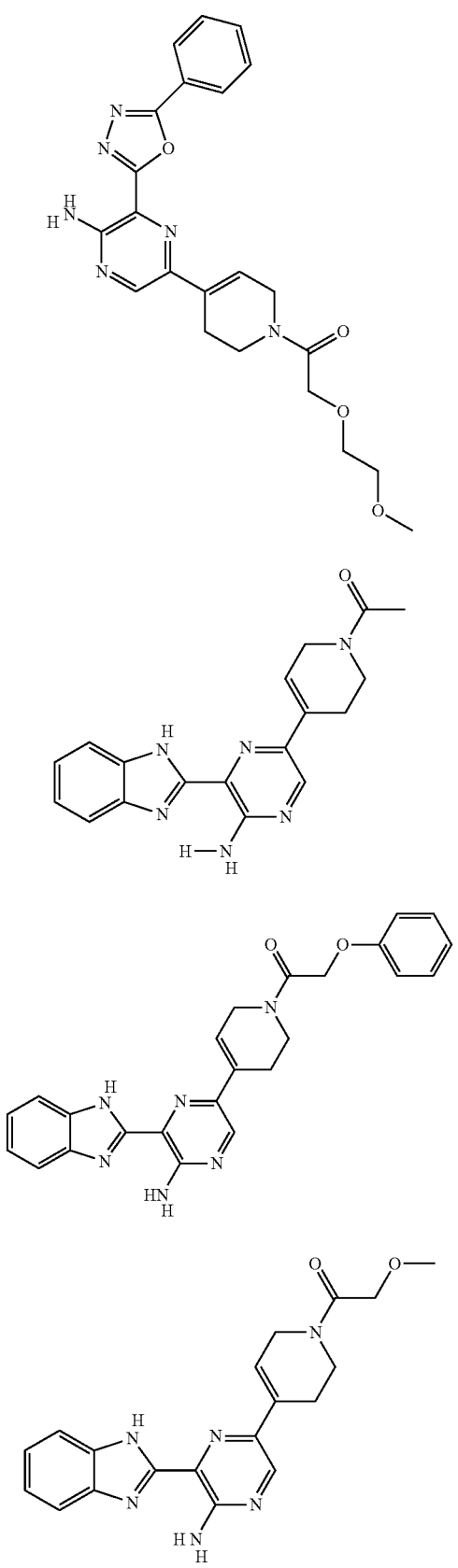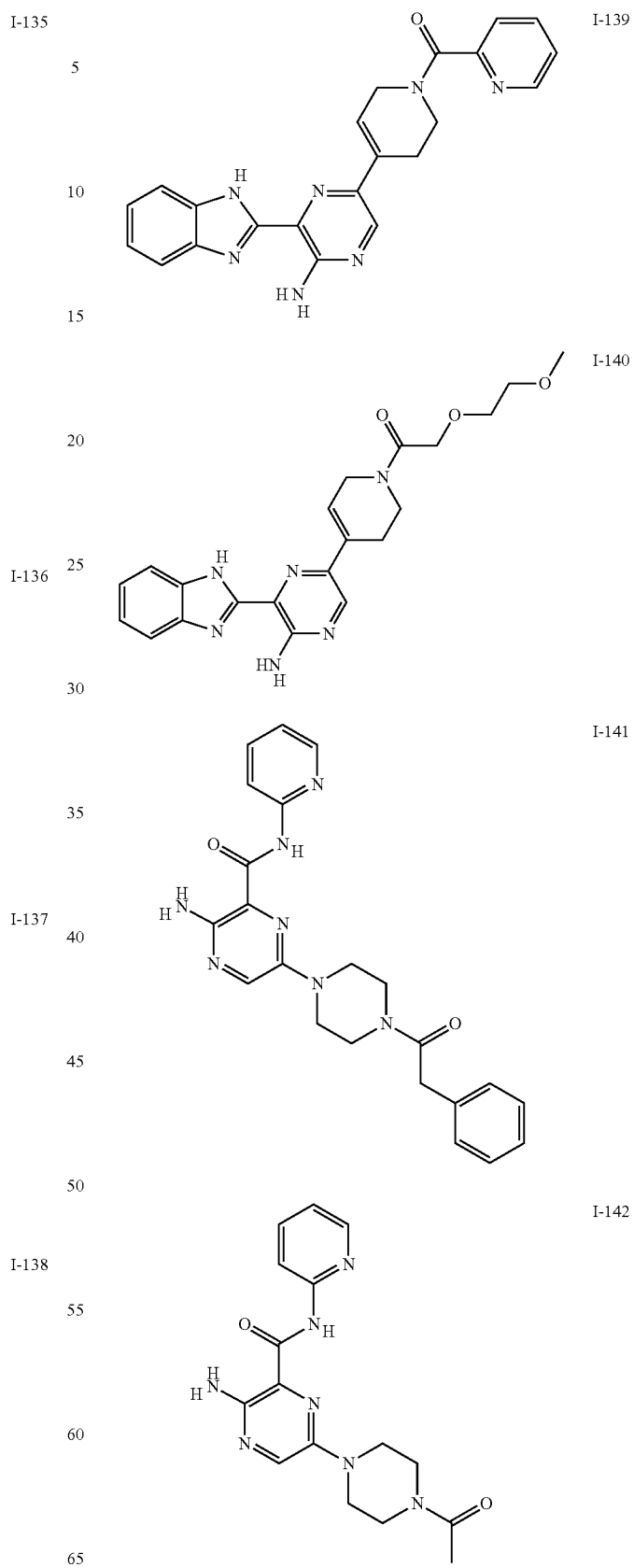

|  |  |
|---|---|
| I-143 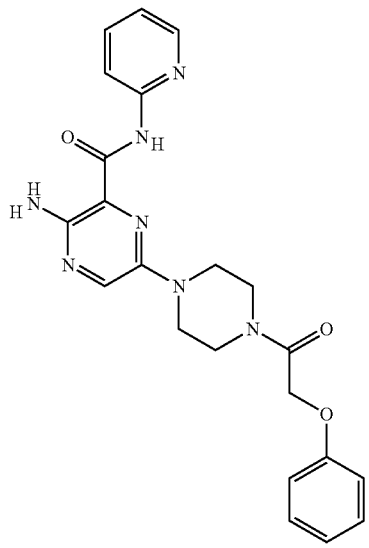 | I-146 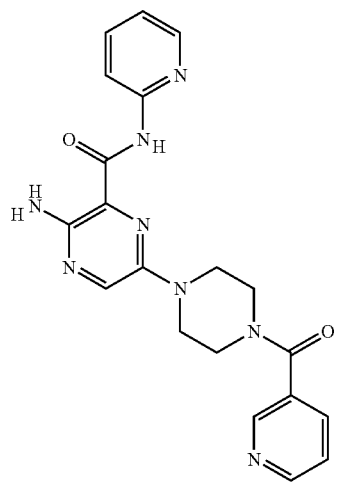 |
| I-144 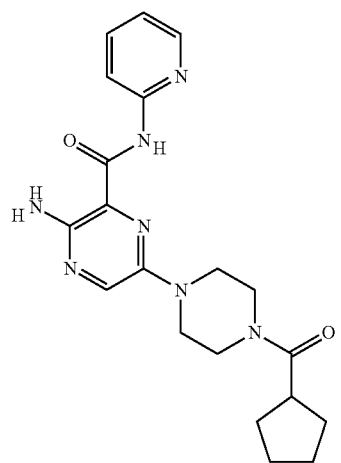 | I-147 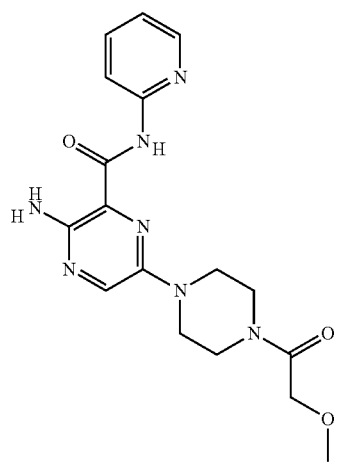 |
| I-145 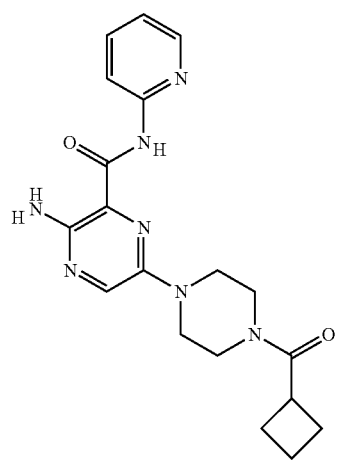 | I-148 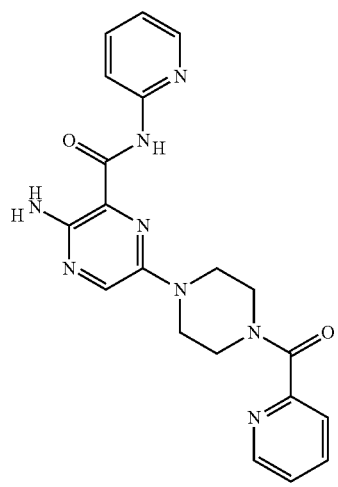 |

| 383 -continued | 384 -continued |
|---|---|
| 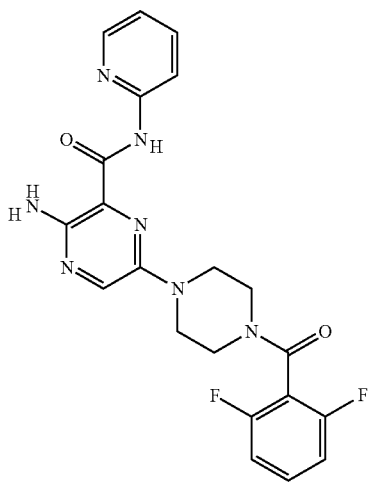 I-149 | 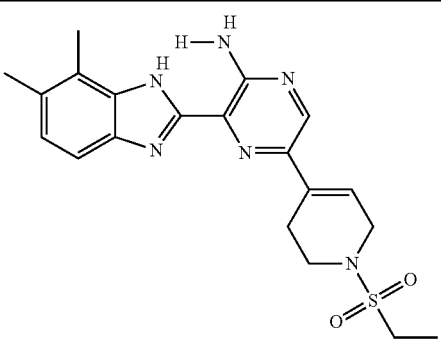 I-152 |
| | 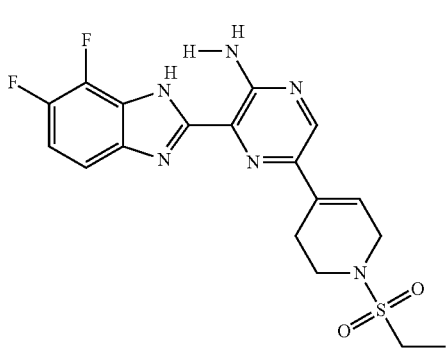 I-153 |
| I-150 | 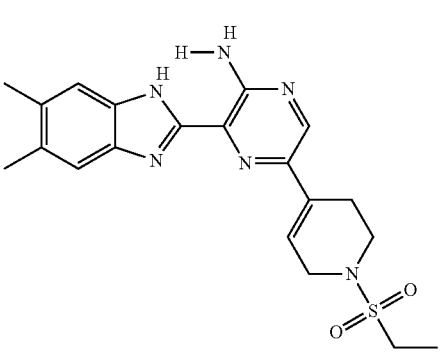 I-154 |
| I-151 | 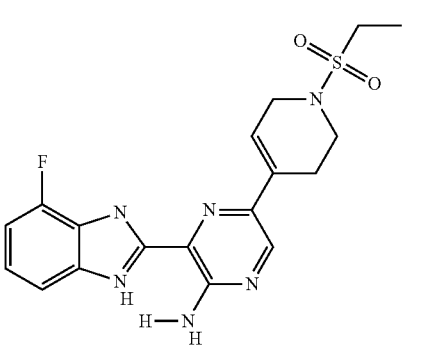 I-155 |

| 385 -continued | 386 -continued |
|---|---|
| 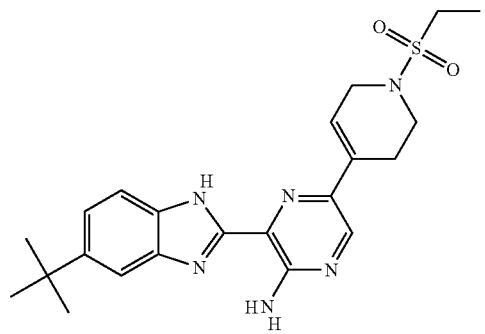 I-156 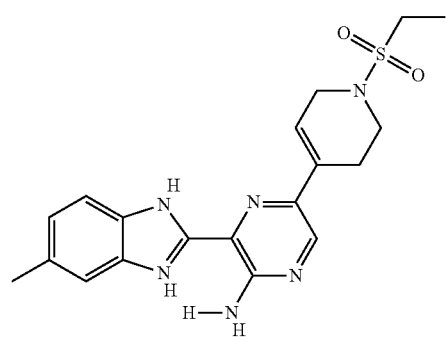 I-157 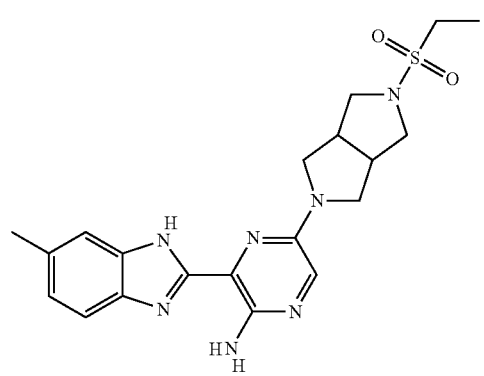 I-158 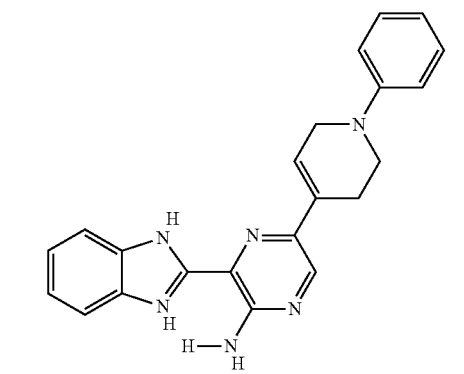 I-159 | 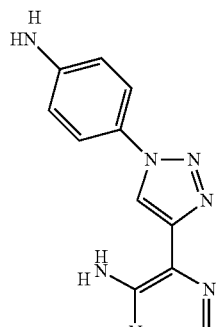 I-160 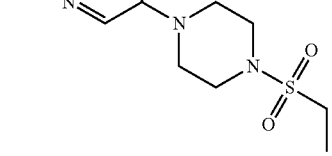 I-161 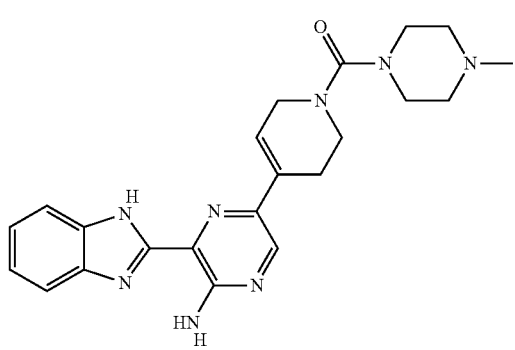 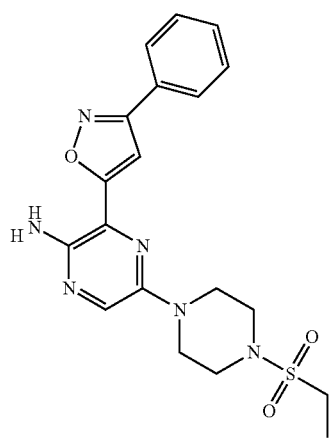 I-162 |

| 387 -continued | 388 -continued |
|---|---|
| 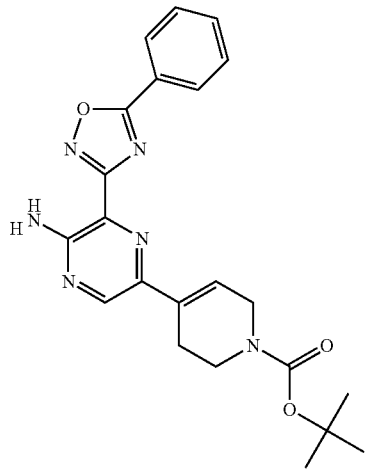 I-163 | 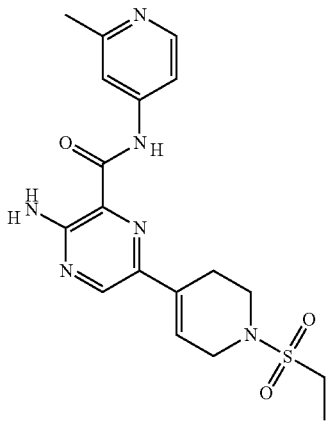 I-166 |
| 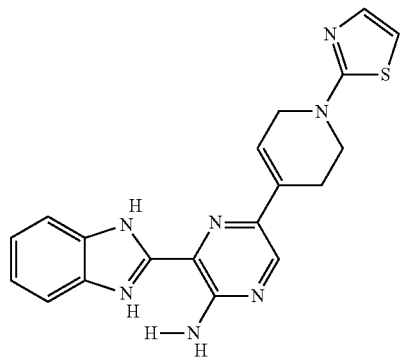 I-164 | 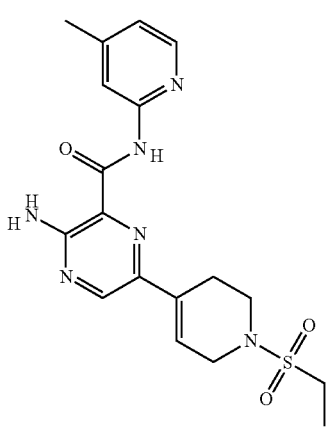 I-167 |
| 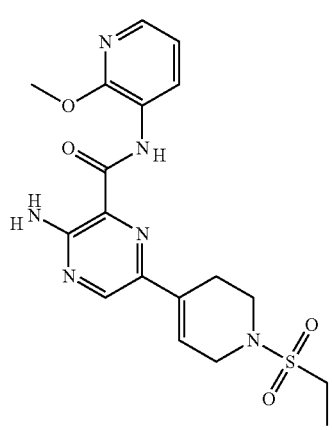 I-165 | 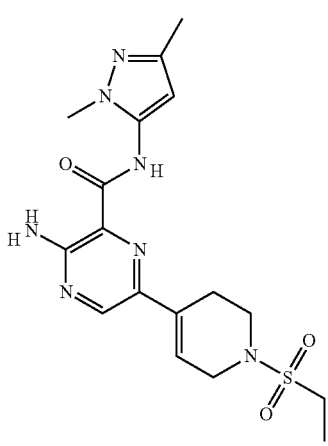 I-168 |

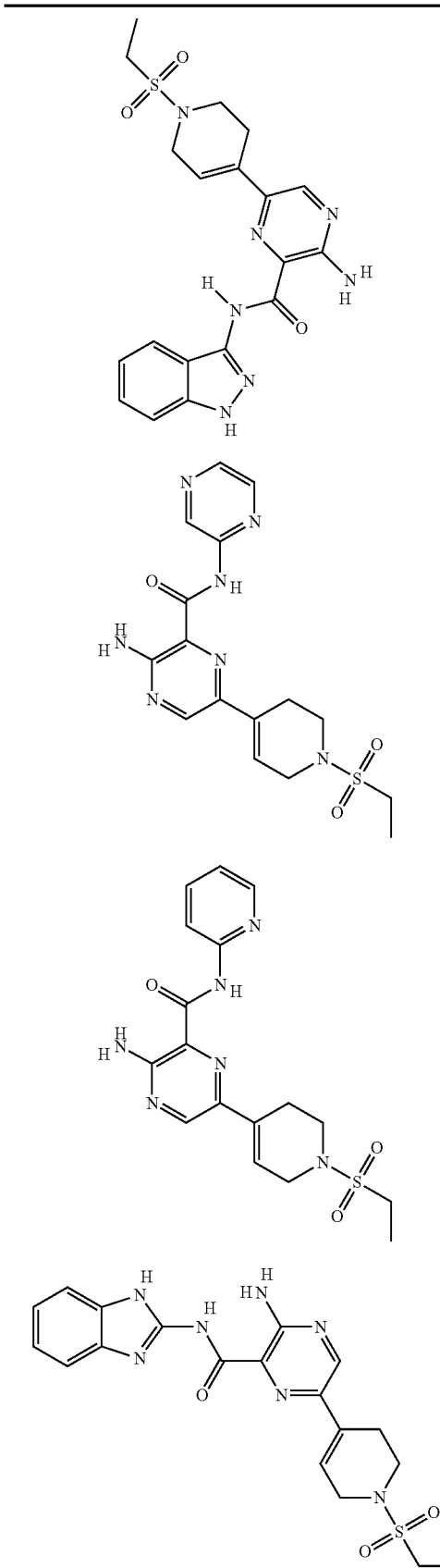
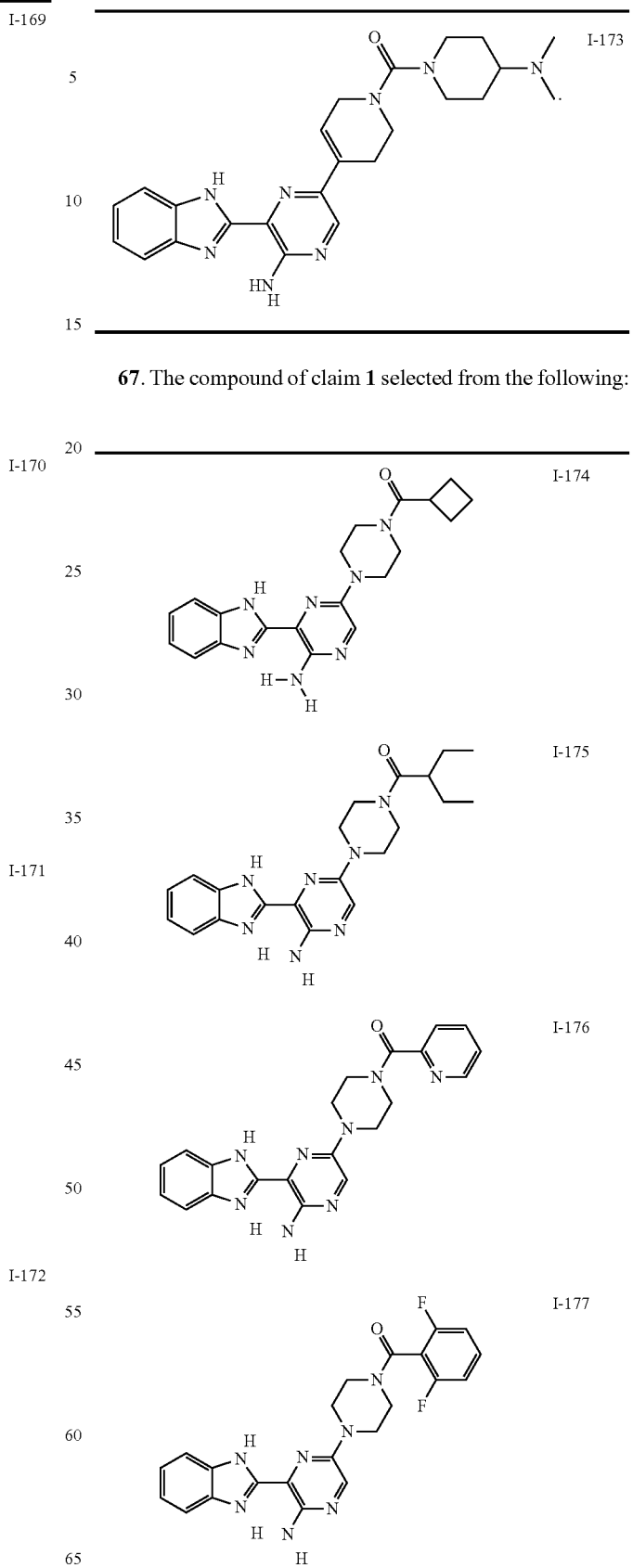
67. The compound of claim 1 selected from the following:

| 391 -continued | 392 -continued |
|---|---|
| I-178 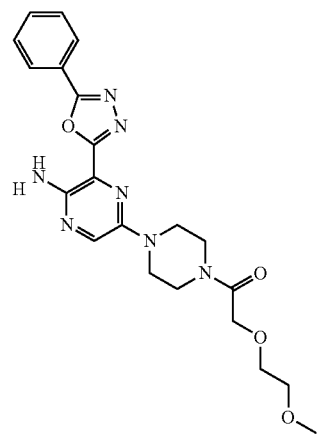 | I-182 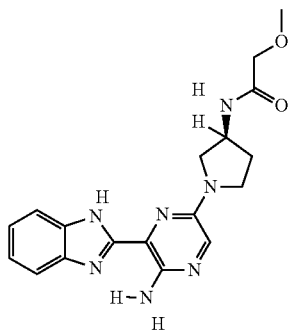 |
| I-179 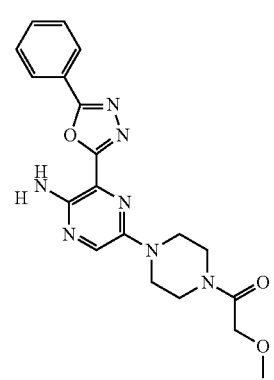 | I-183 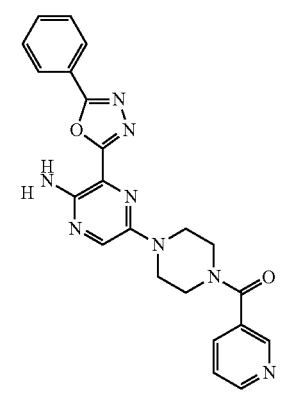 |
| I-180 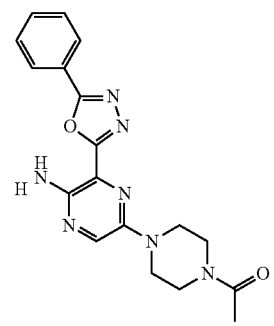 | I-184 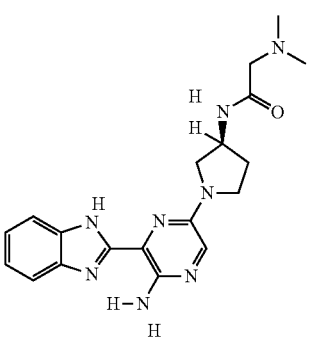 |
| I-181 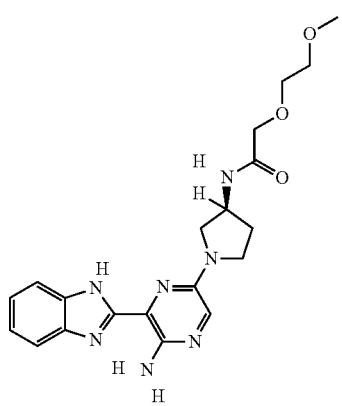 | I-185 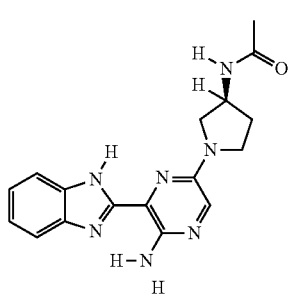 |
| | I-186 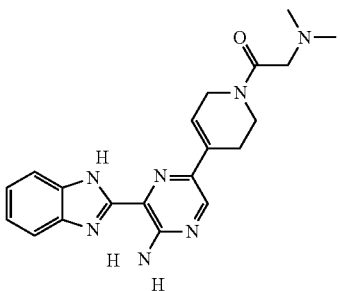 |

| 393 -continued | | 394 -continued | |
|---|---|---|---|
| 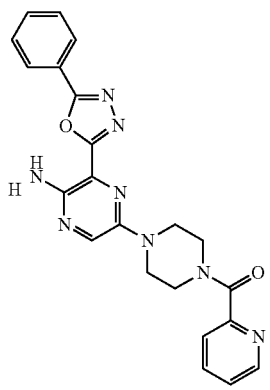 | I-187 | 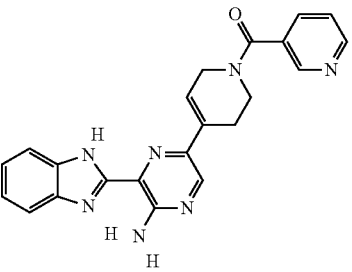 | I-191 |
| 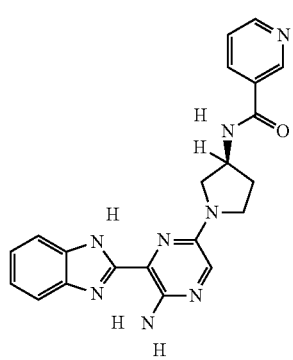 | I-188 | 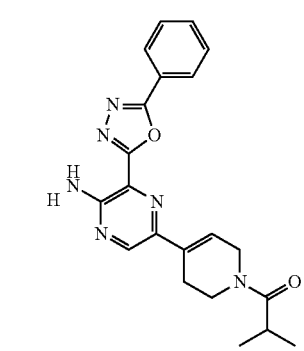 | I-192 |
| 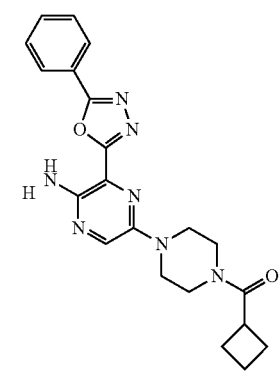 | I-189 | 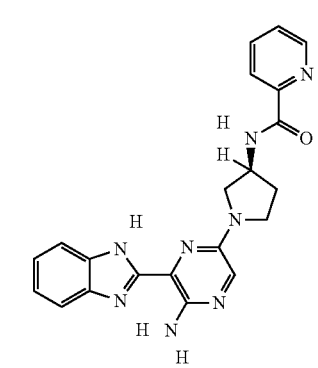 | I-193 |
| 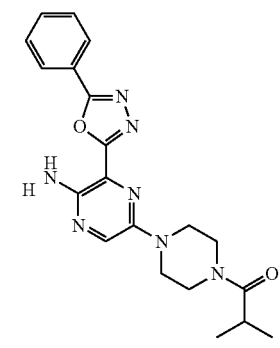 | I-190 | 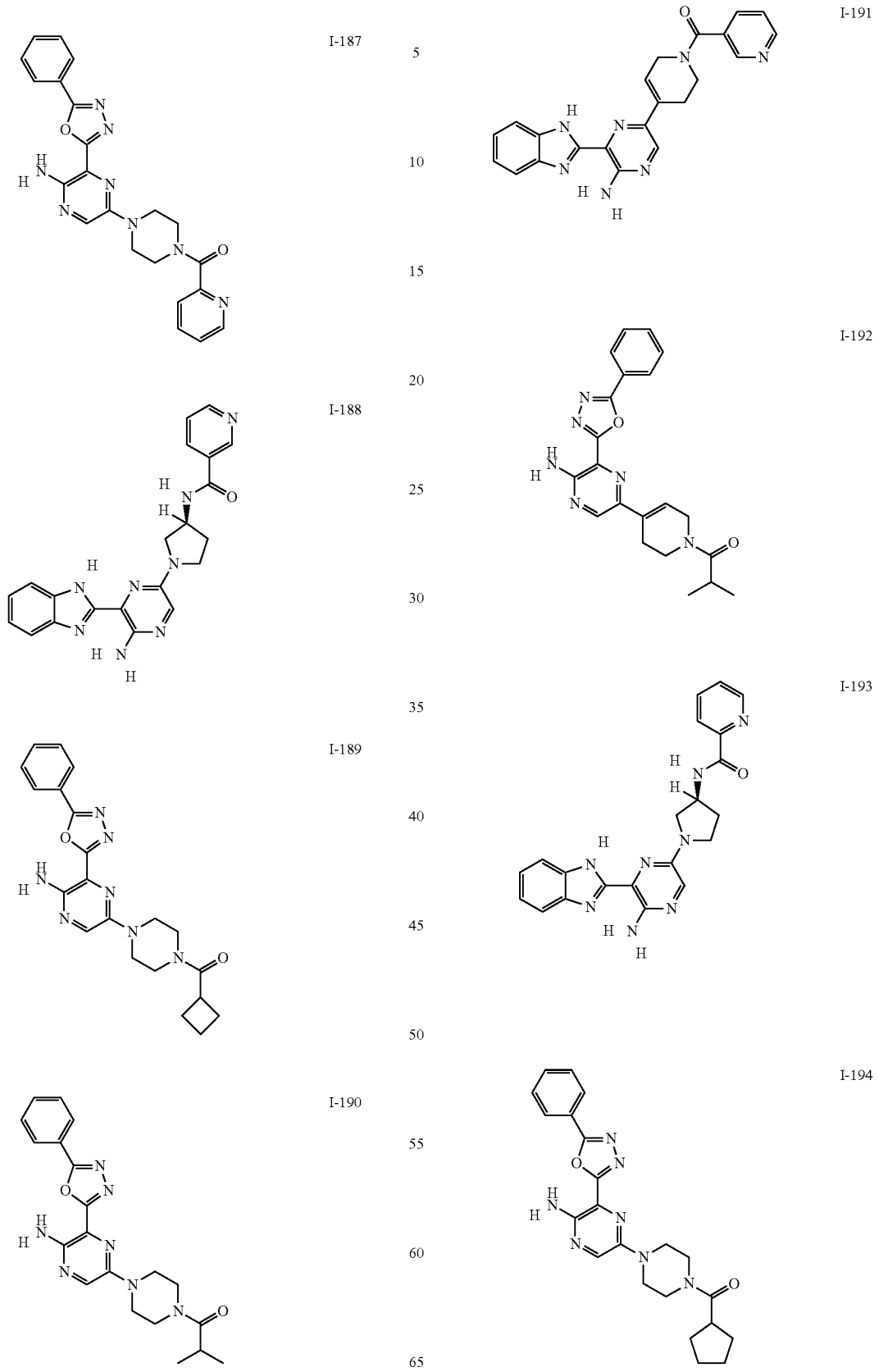 | I-194 |

| 395 -continued | 396 -continued |
|---|---|
| I-195 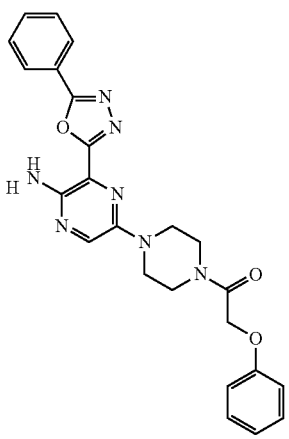 | I-199 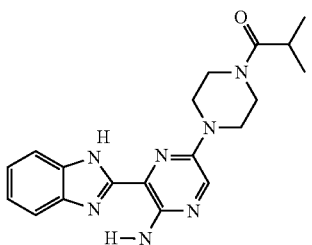 |
| I-196 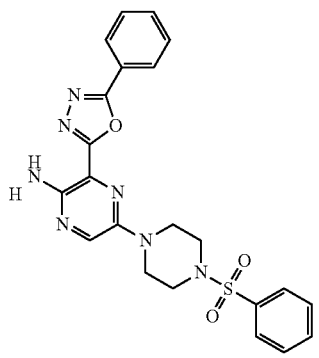 | I-200 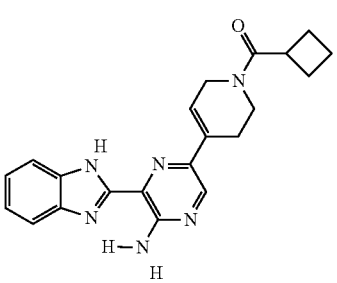 |
| I-197 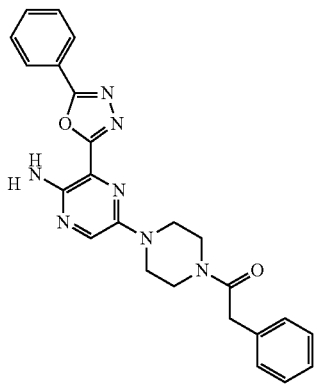 | I-201 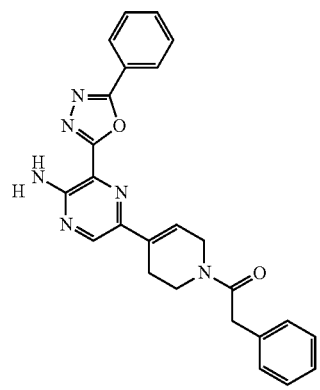 |
| I-198 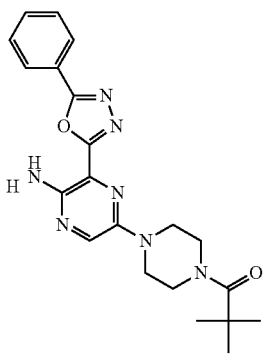 | I-202 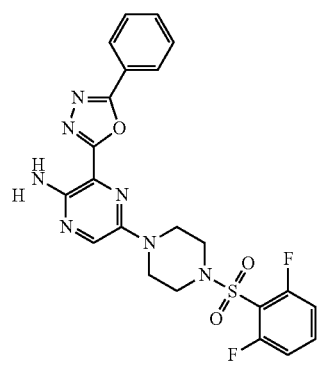 |

| 397 -continued | 398 -continued |
|---|---|
| 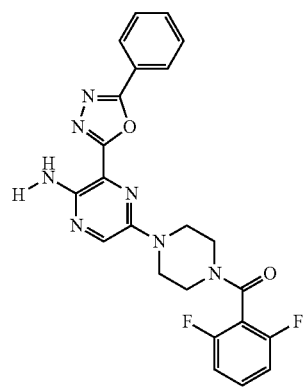 [SMILES: Nc1ncc(N2CCN(C(=O)c3c(F)cccc3F)CC2)nc1-c1nnc(-c2ccccc2)o1] I-203 | 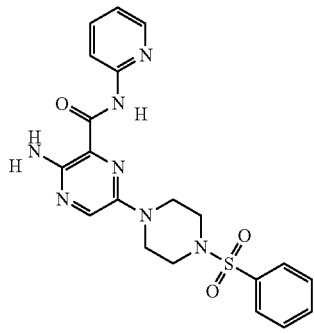 I-207 |
| 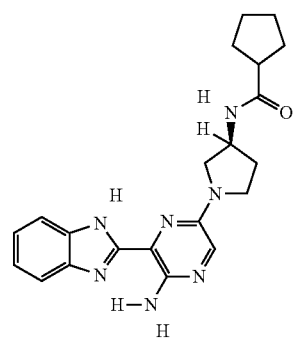 I-204 | 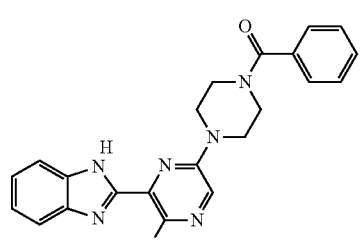 I-208 |
| 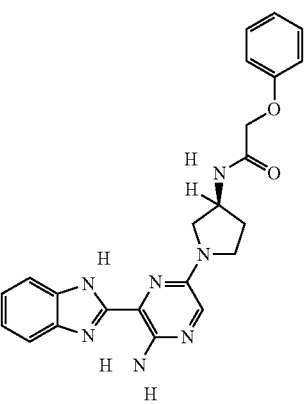 I-205 | 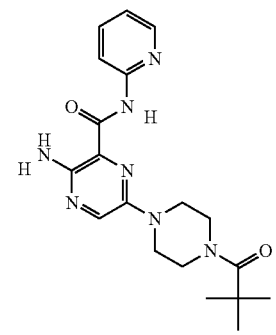 I-209 |
| | 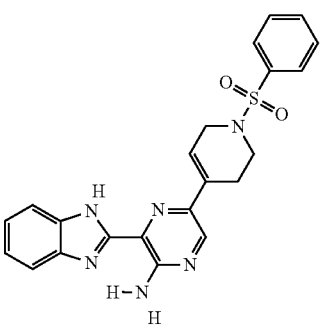 I-210 |
| 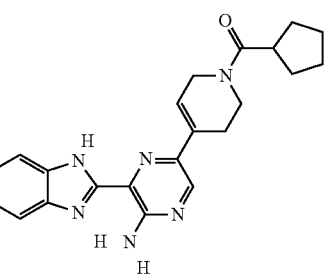 I-206 | 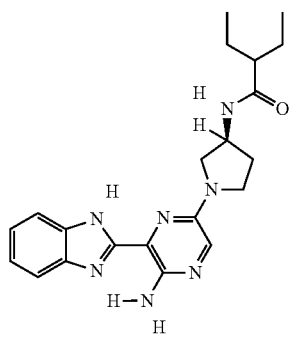 I-211 |

| 399 -continued | 400 -continued |
|---|---|
| 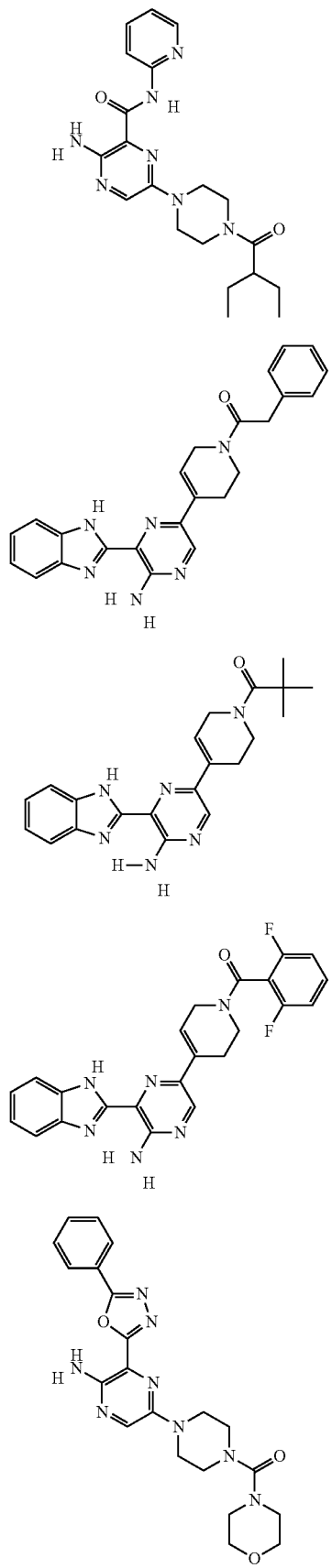 | 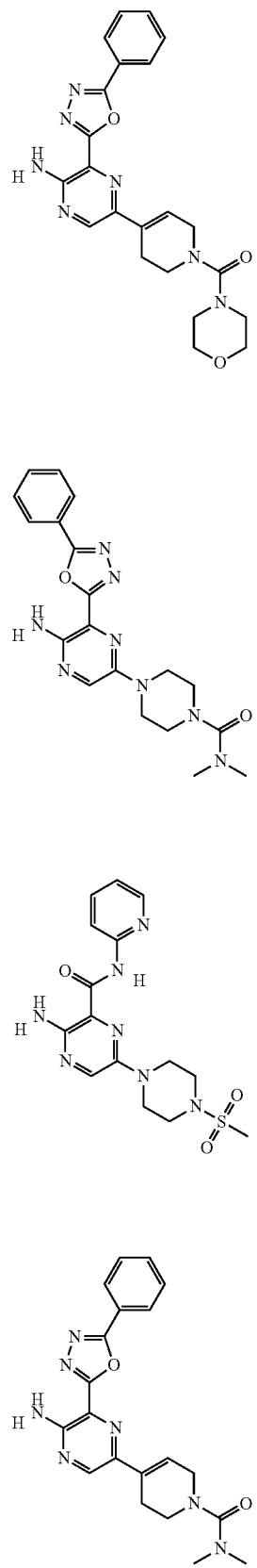 |
I-212
I-213
I-214
I-215
I-216
I-217
I-218
I-219
I-220

| 401 -continued | 402 -continued |
|---|---|
| I-221 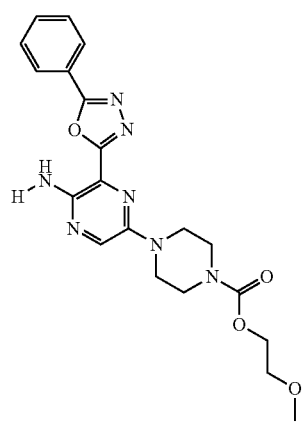 [SMILES: COCCOC(=O)N1CCN(c2cnc(N)c(-c3nnc(-c4ccccc4)o3)n2)CC1] | I-225 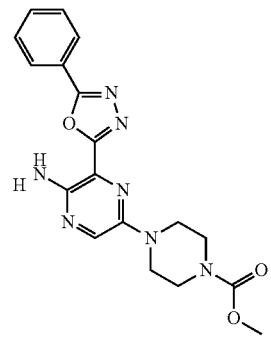 |
| I-222 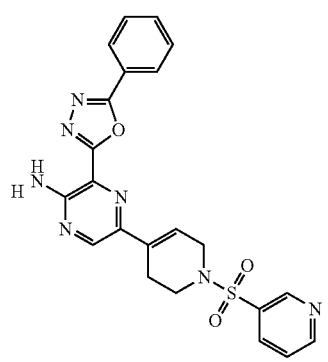 | I-226 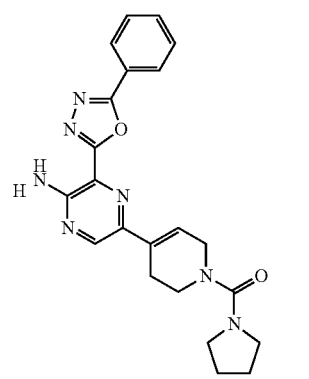 |
| I-223 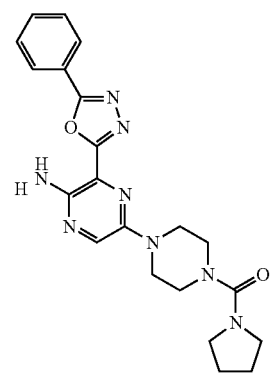 | I-227 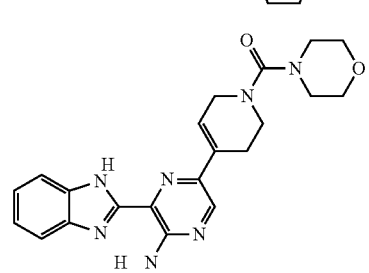 |
| I-224 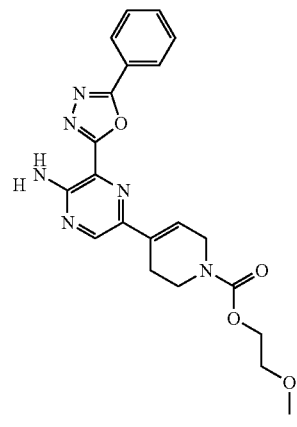 | I-228 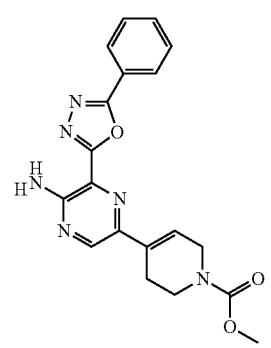 |
| | I-229 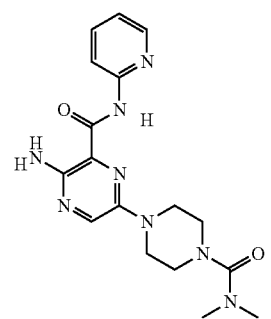 |

-continued
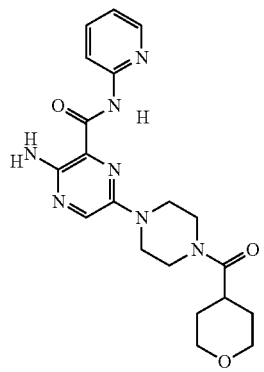
I-230
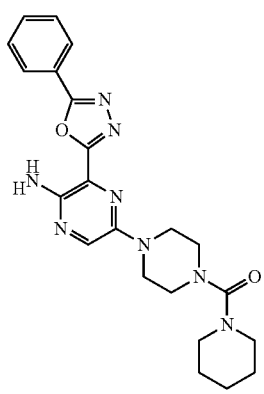
I-231
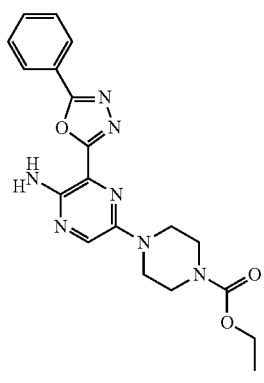
I-232
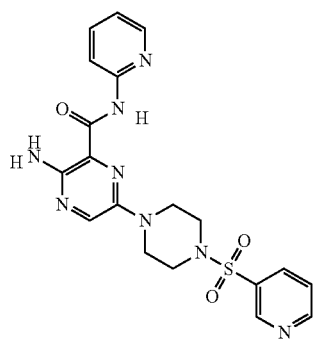
I-233
-continued
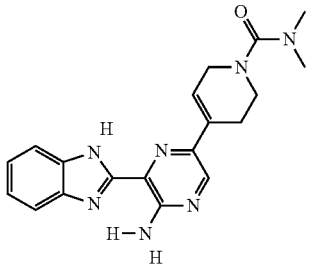
I-234
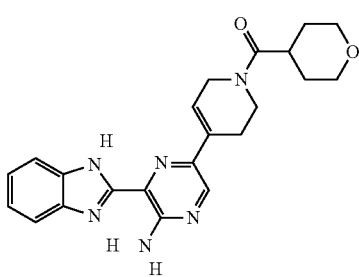
I-235
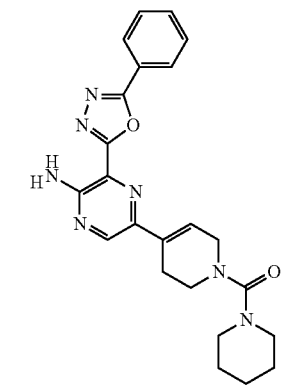
I-26
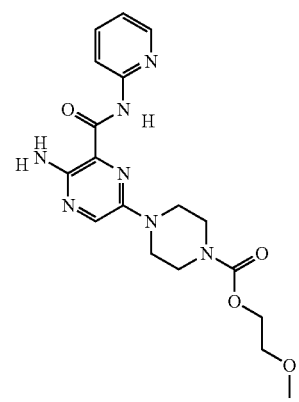
I-237

| | |
|---|---|
| 405 -continued | 406 -continued |
| I-238 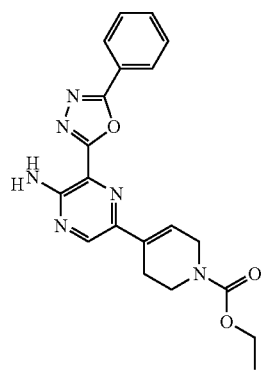 | I-242 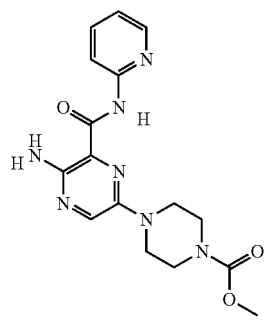 |
| I-239 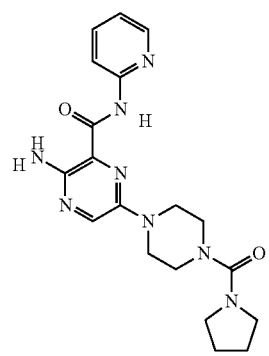 | I-243 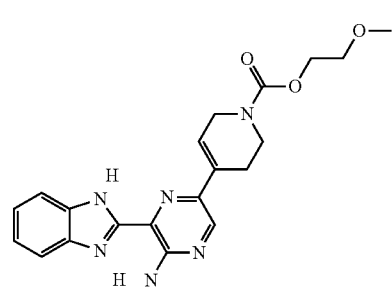 |
| I-240 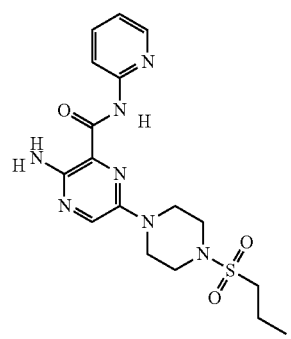 | I-244 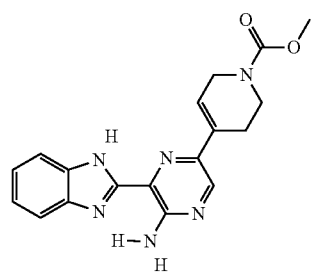 |
| I-241 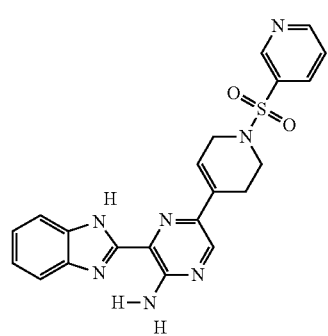 | I-245 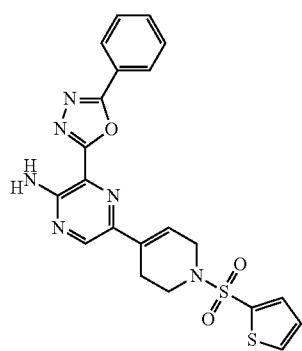 |

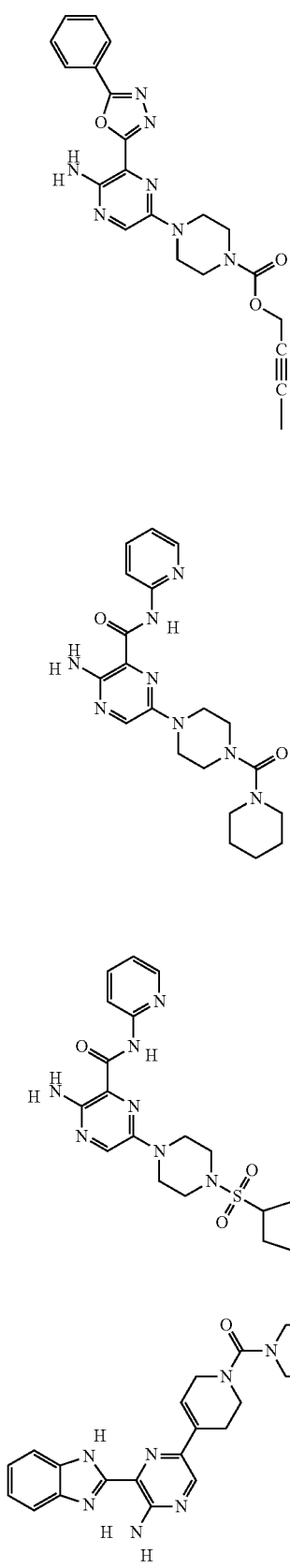
I-246
I-247
I-248
I-249
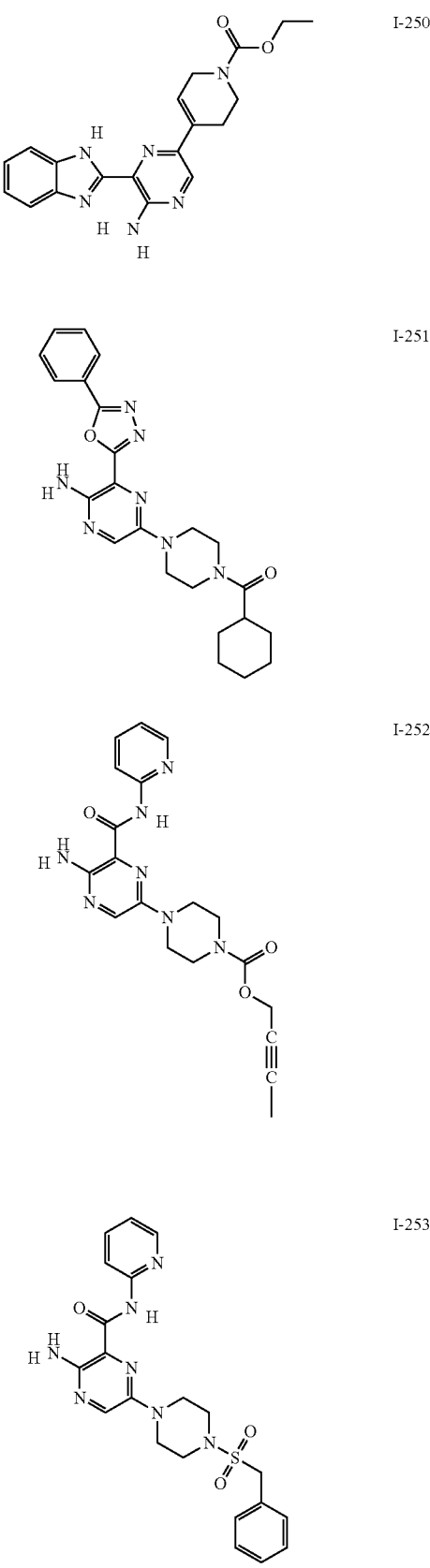
I-250
I-251
I-252
I-253

| | |
|---|---|
| I-254 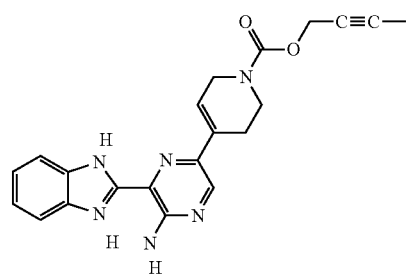 | I-258 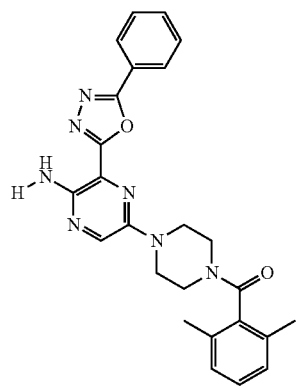 |
| I-255 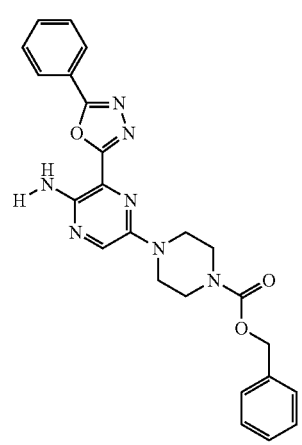 [SMILES: Nc1ncc(N2CCN(C(=O)OCc3ccccc3)CC2)nc1-c1nnc(-c2ccccc2)o1] | I-259 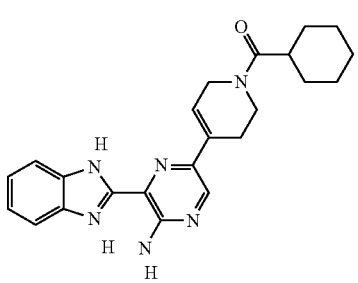 |
| I-256 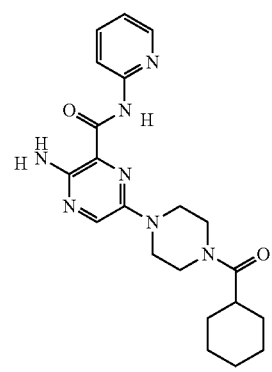 | I-260 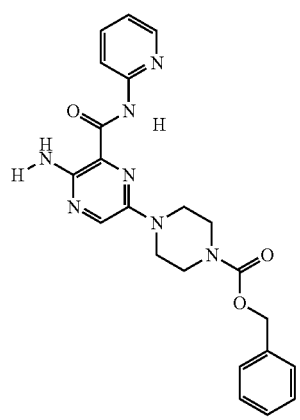 |
| I-257 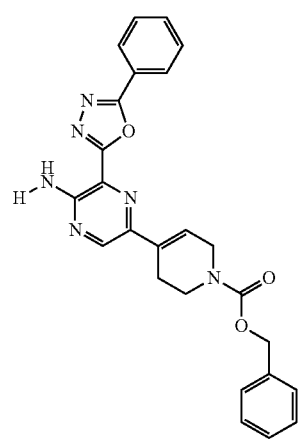 [SMILES: Nc1ncc(C2=CCN(C(=O)OCc3ccccc3)CC2)nc1-c1nnc(-c2ccccc2)o1] | I-261 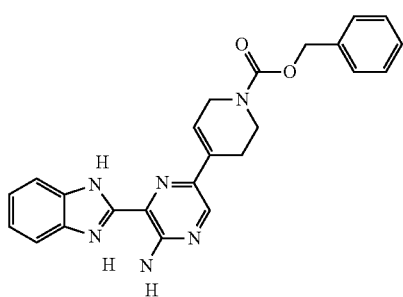 |

-continued
I-262
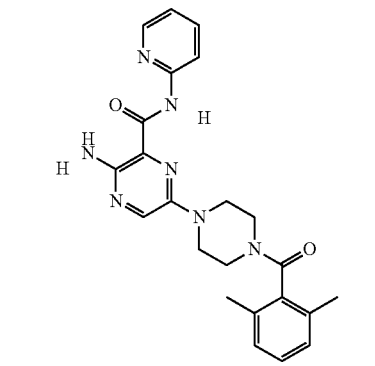
I-263
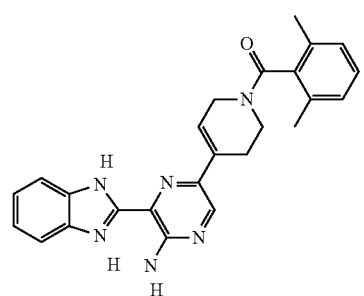
I-264
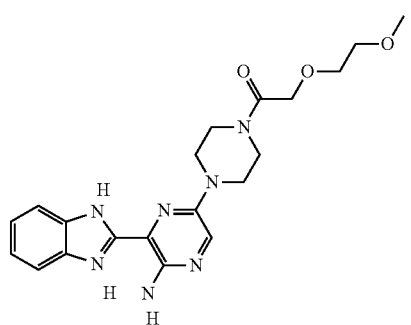
I-265
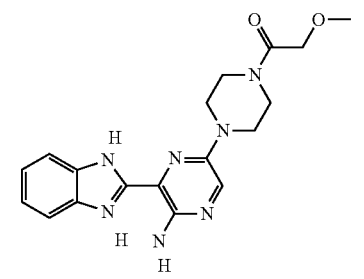
I-266
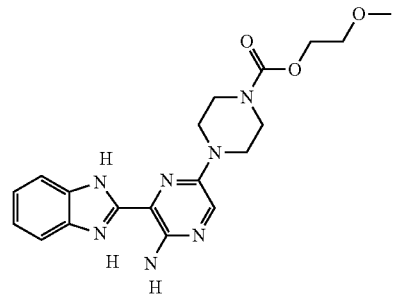
-continued
I-267
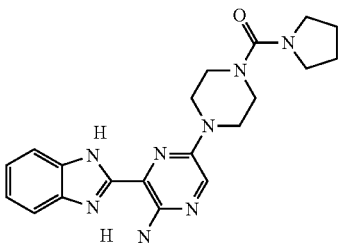
I-268
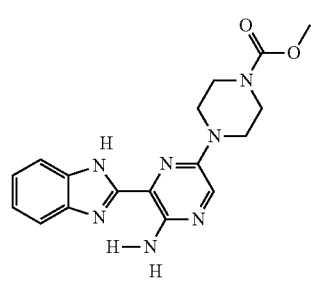
I-269
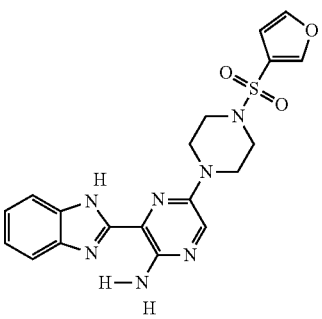
I-270
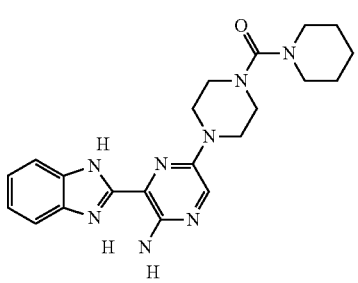
I-271
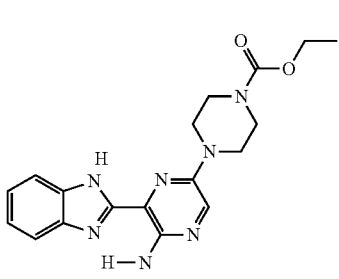

| | |
|---|---|
| I-272 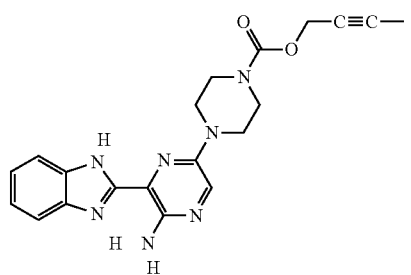 | I-277 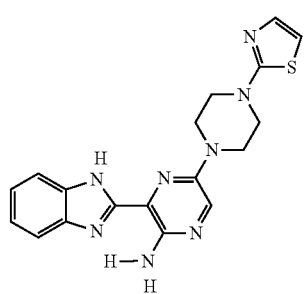 |
| I-273 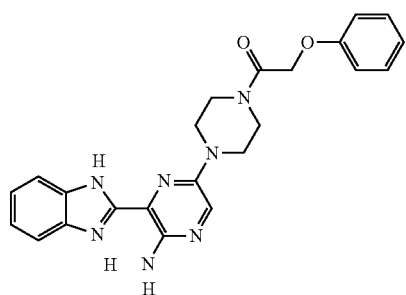 | I-278 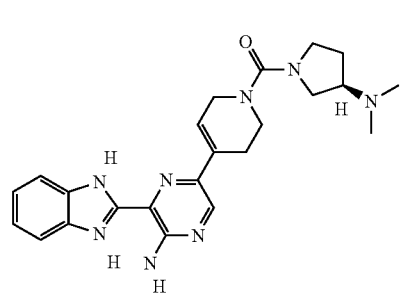 |
| I-274 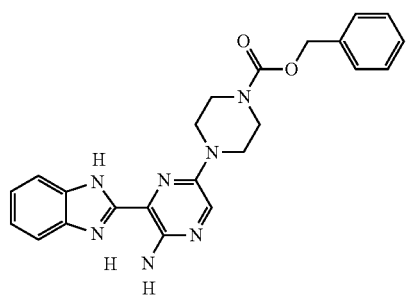 | I-279 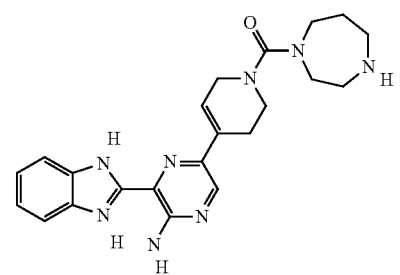 |
| I-25 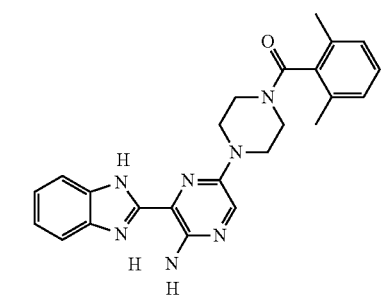 | I-280 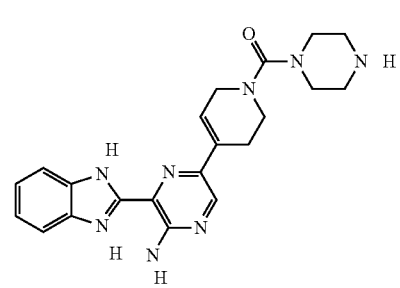 |
| I-276 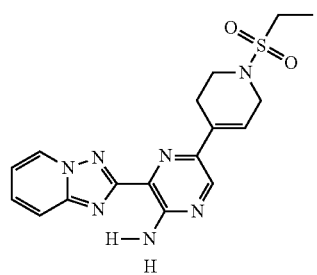 | I-281 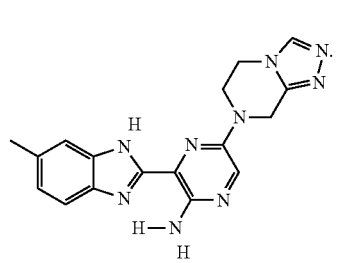 |

68. The compound of claim 1 selected from the following:
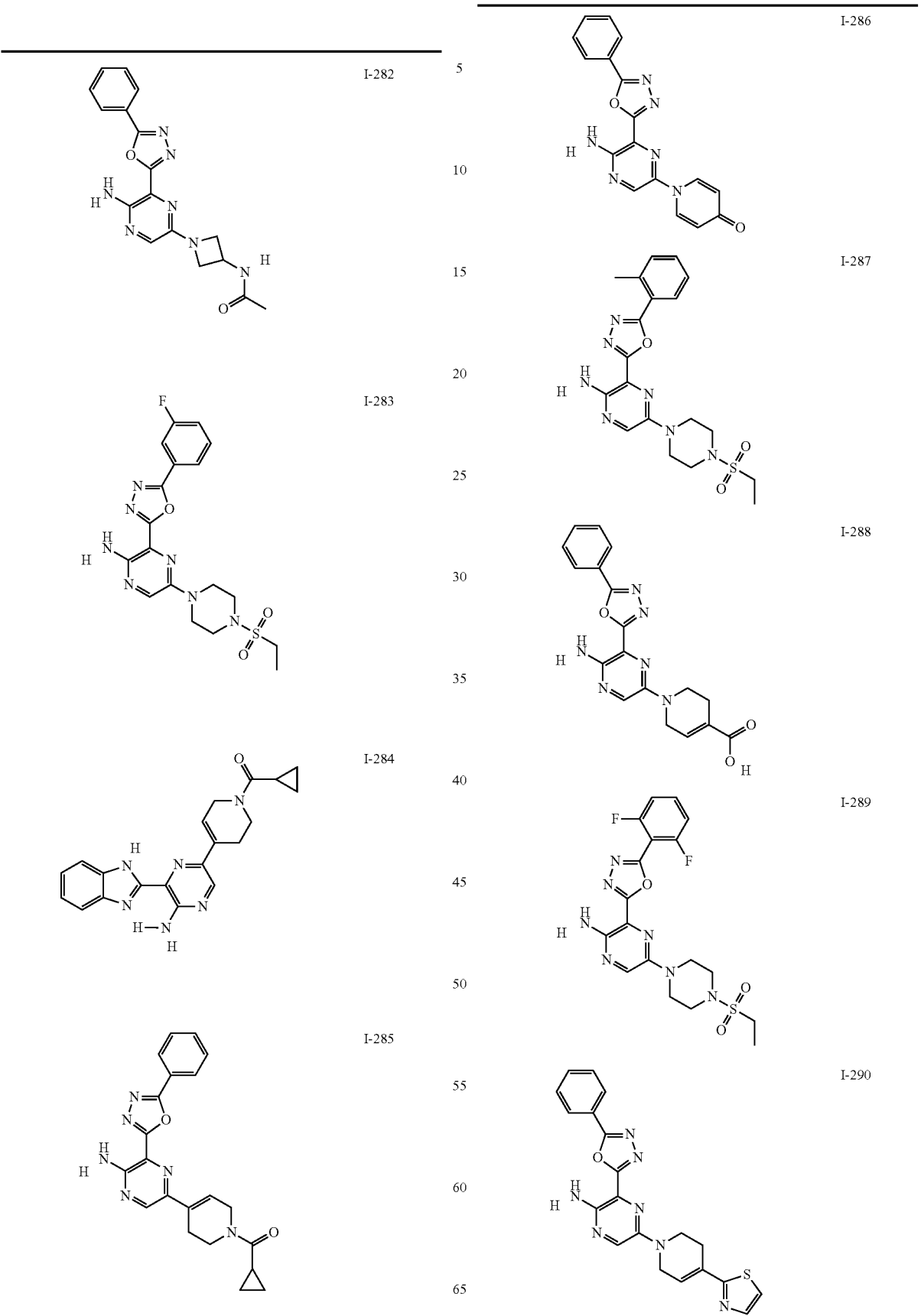

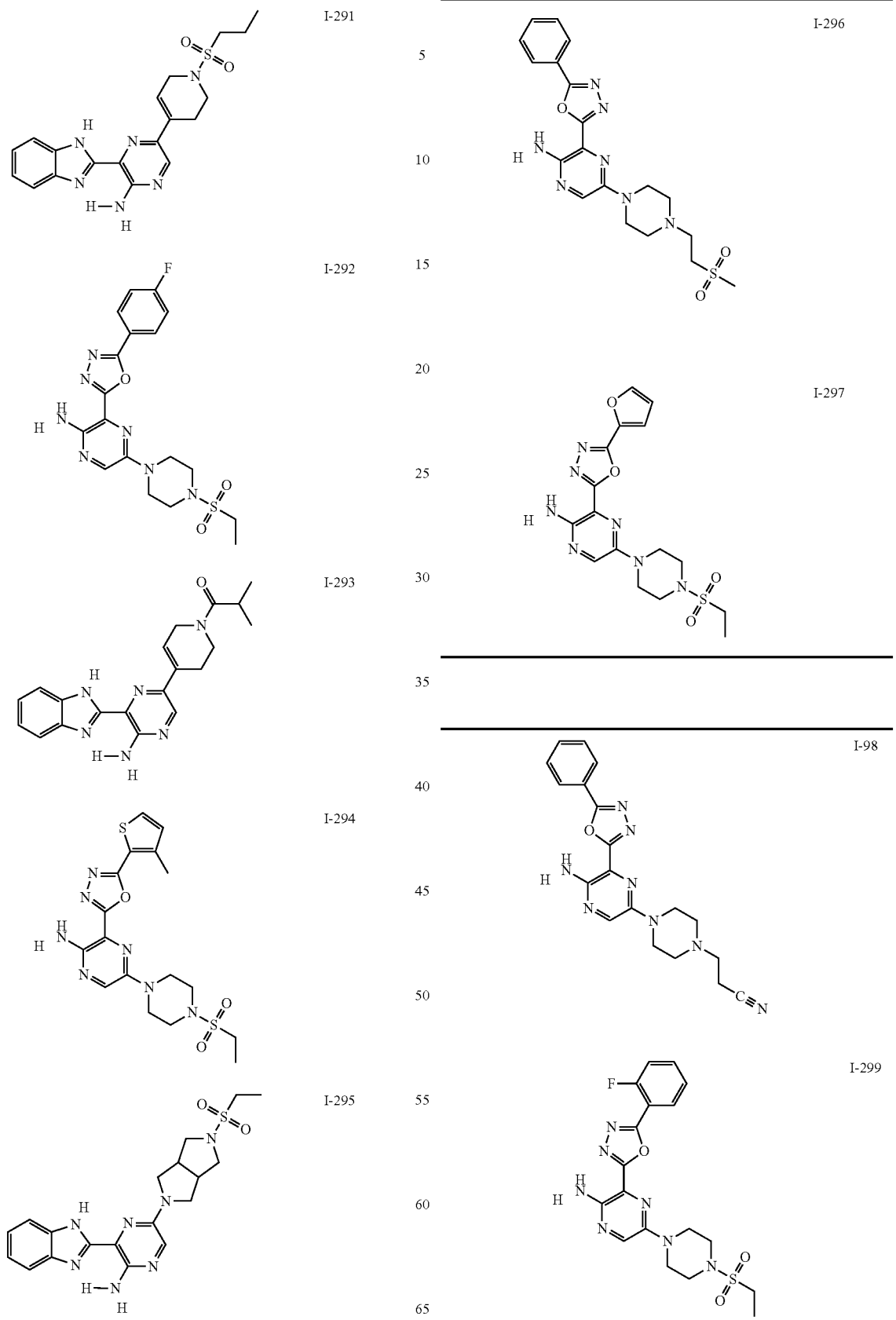

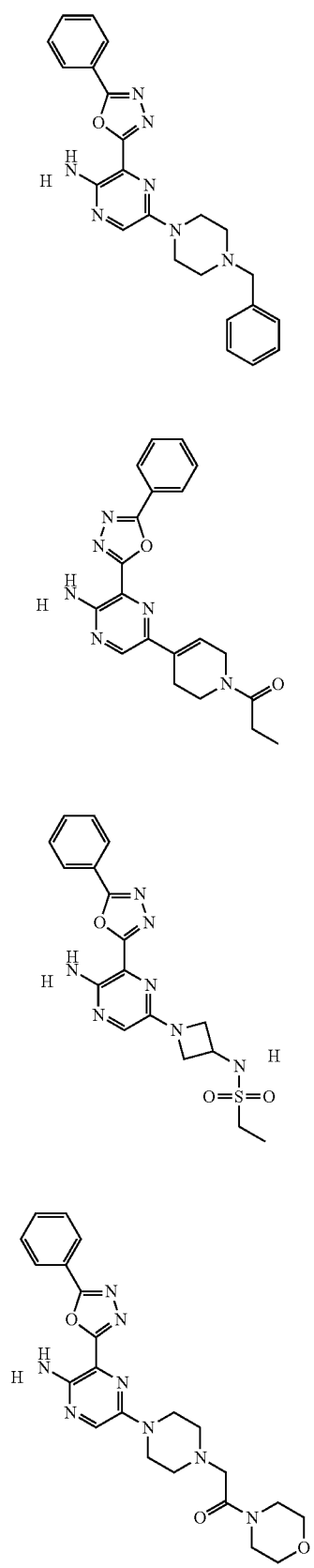

-continued
I-309
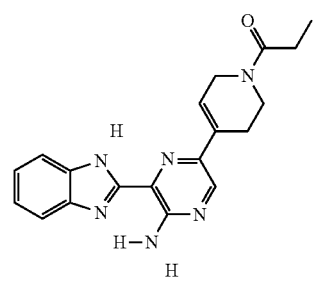
I-310
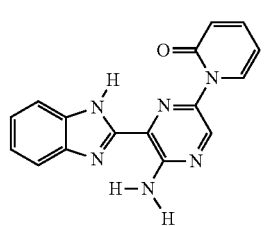 [SMILES: Nc1ncc(-n2ccccc2=O)nc1-c1nc2ccccc2[nH]1]
I-311
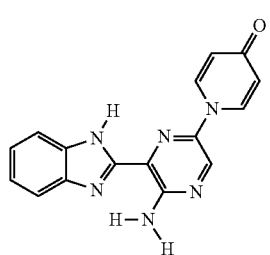 [SMILES: Nc1ncc(-n2ccc(=O)cc2)nc1-c1nc2ccccc2[nH]1]
I-312
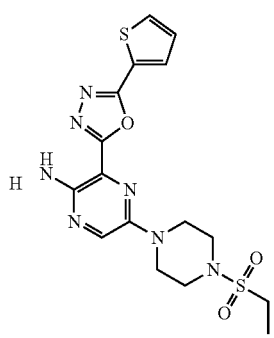
I-313
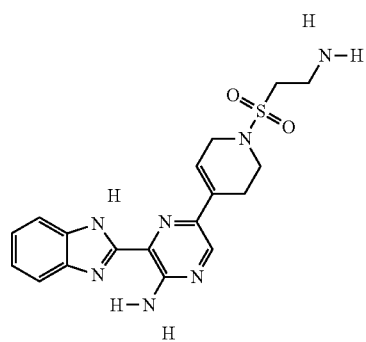
-continued
I-314
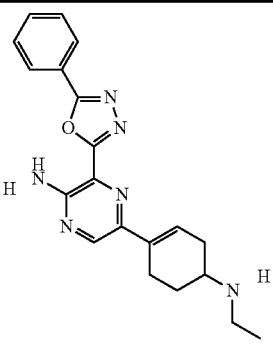
I-315
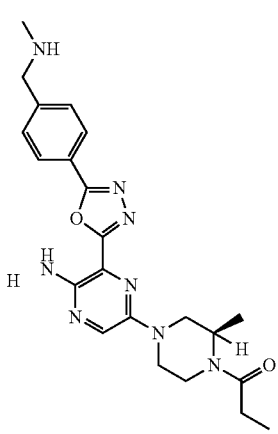
I-316
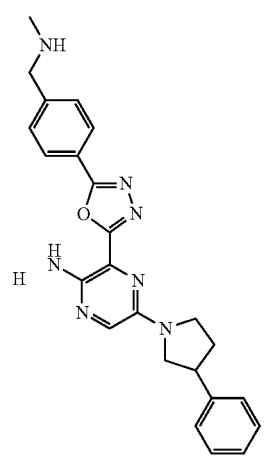
I-317
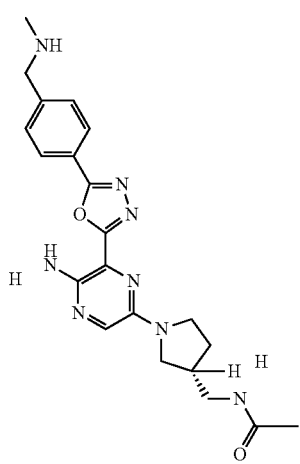

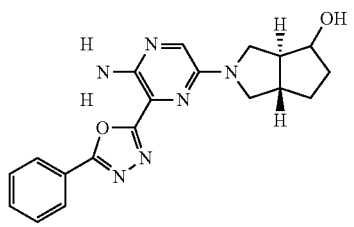 I-318
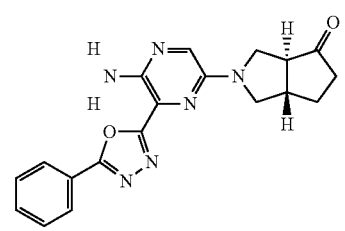 I-319
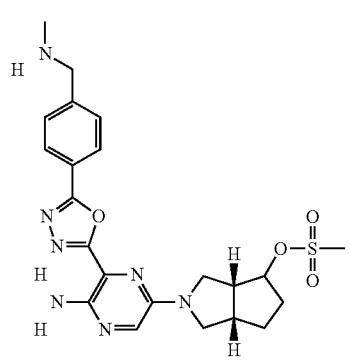 I-320
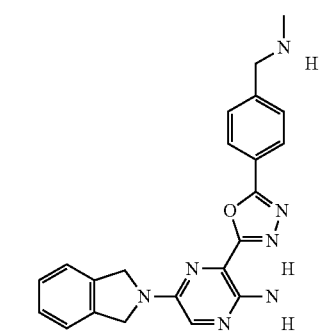 I-321
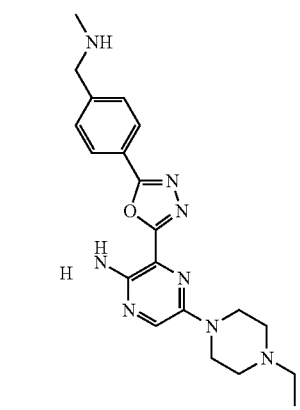 I-322
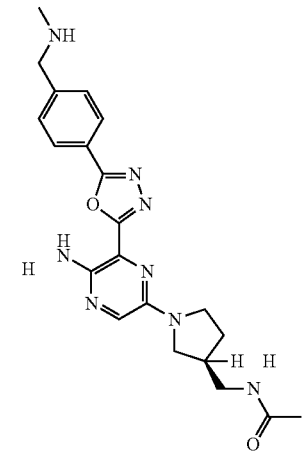 I-323
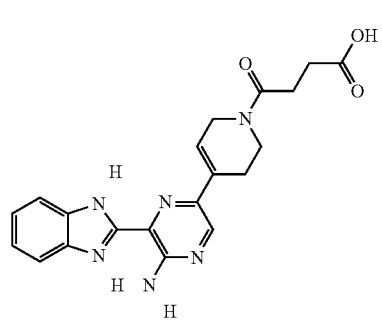 I-324
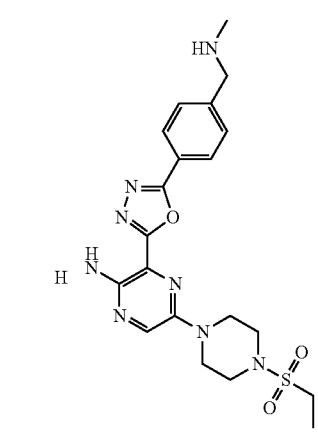 I-325
I-326

425
-continued
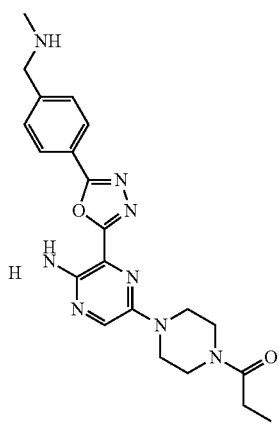
I-327
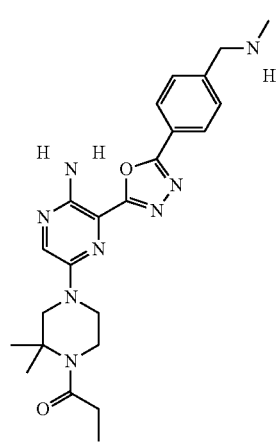
I-328
I-329
426
-continued
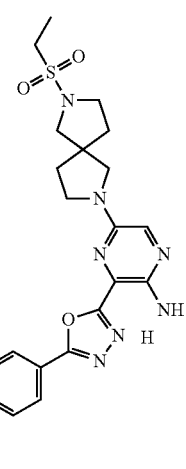
I-330
I-331
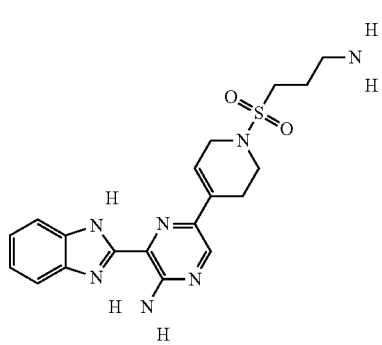
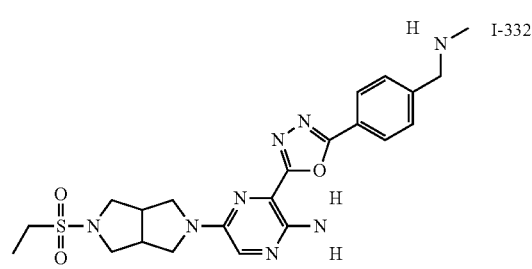
I-332
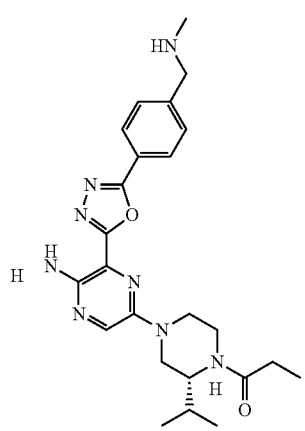
I-333

427
-continued
| | |
|---|---|
| 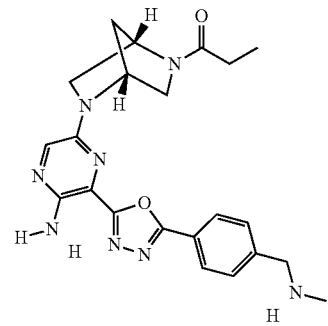 | I-334 |
| 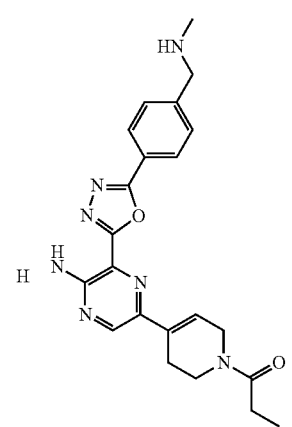 | I-335 |
| 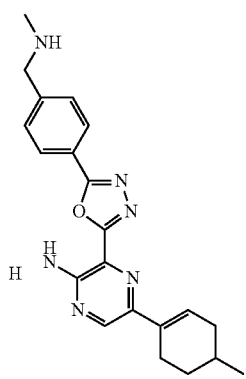 | I-336 |
| 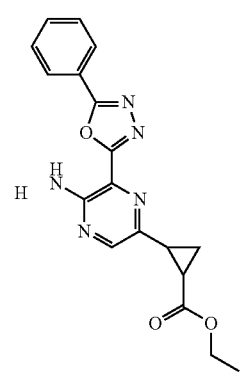 | I-337 |
428
-continued
| | |
|---|---|
| 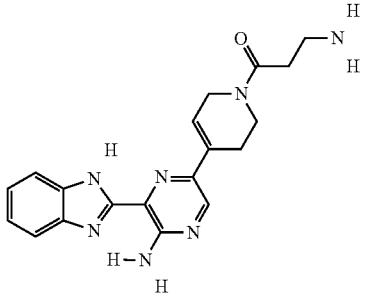 | I-338 |
| 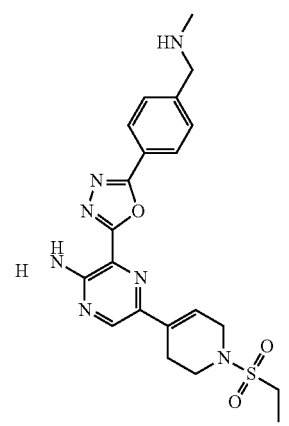 | I-339 |
| 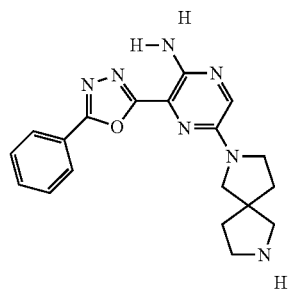 | I-340 |
| 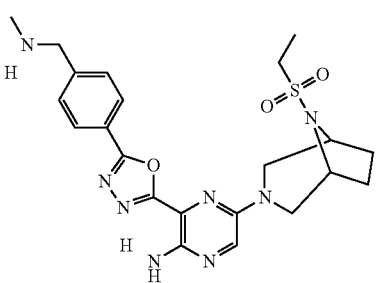 | I-341 |
| 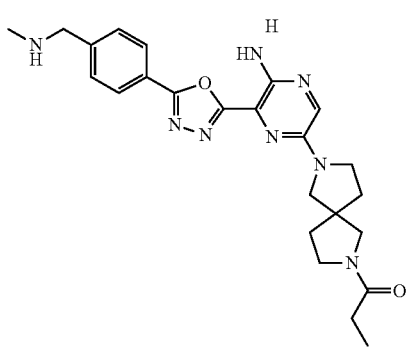 | I-342 |

I-343 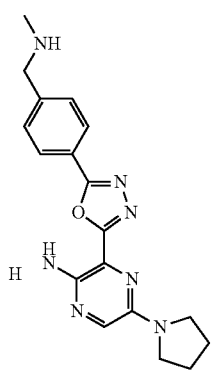
I-344 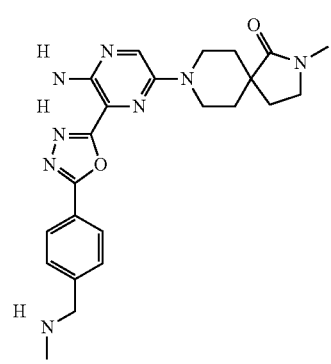
I-345 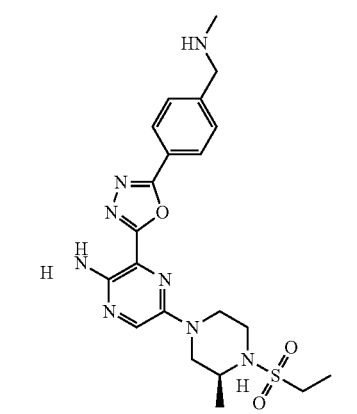
I-346 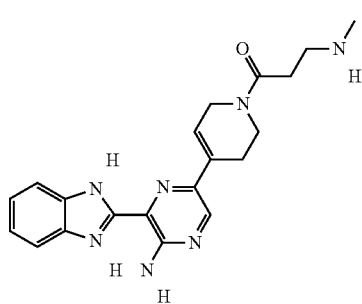
I-347 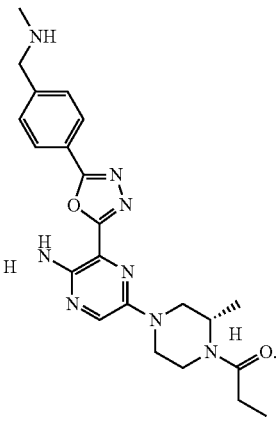
69. The compound of claim 1 selected from the following:
I-348 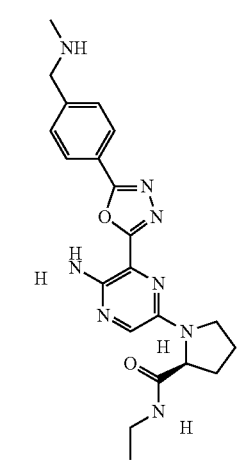
I-349 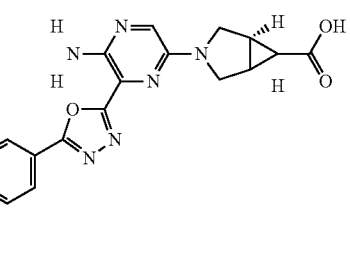
I-350 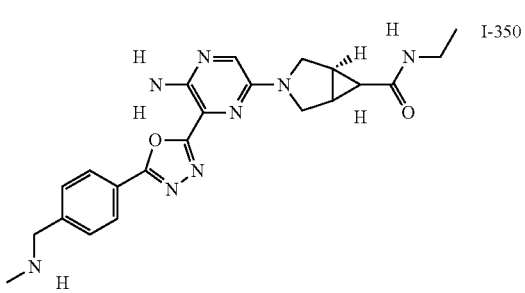

431
-continued
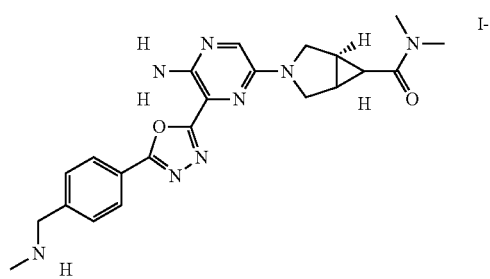
I-351
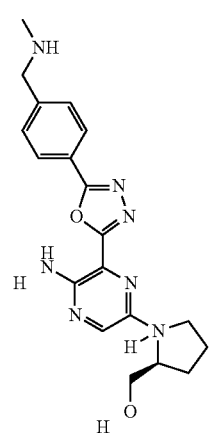
I-352
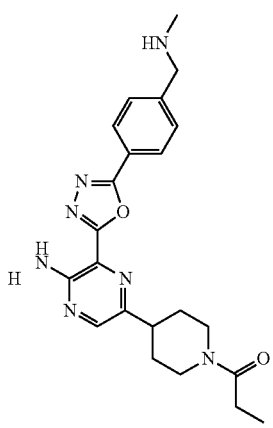
I-353
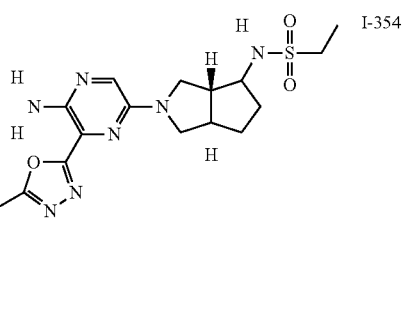
I-354
432
-continued
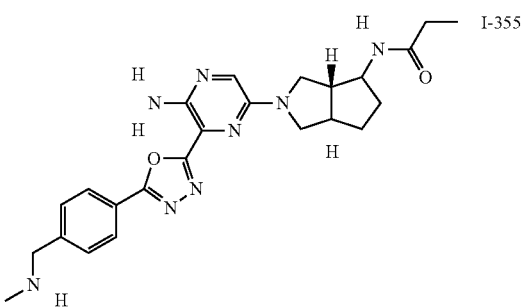
I-355
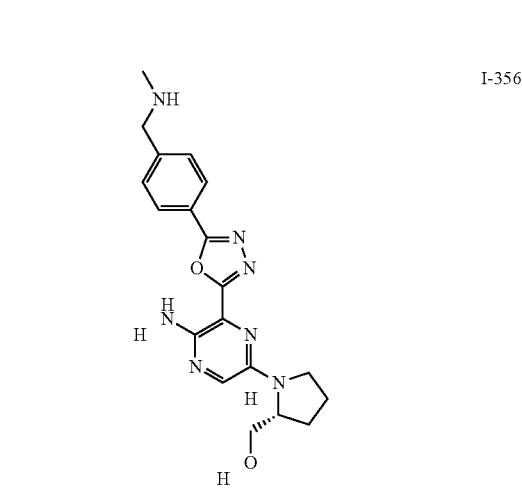
I-356
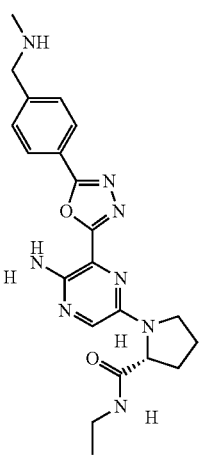
I-357
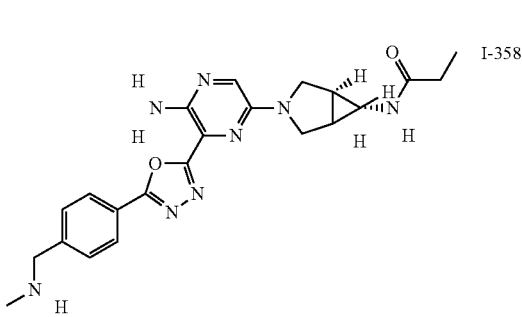
I-358

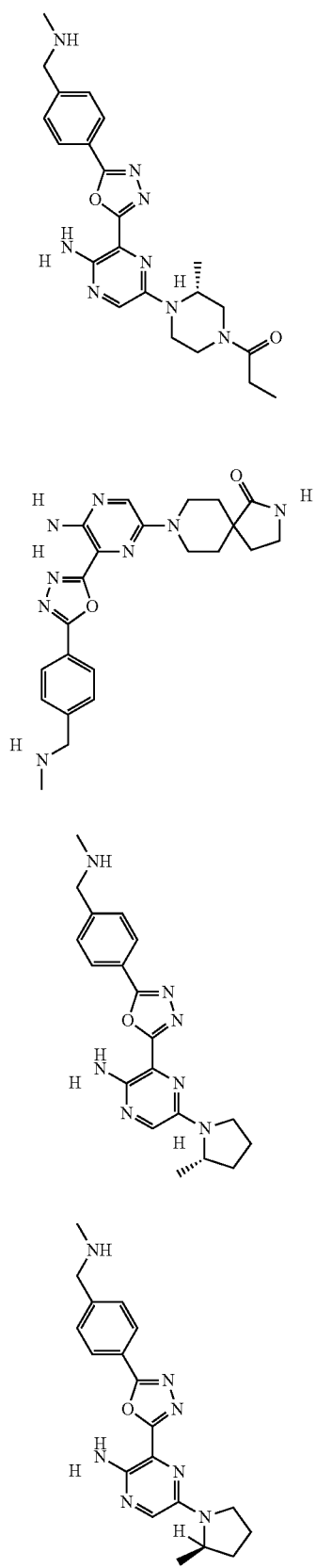
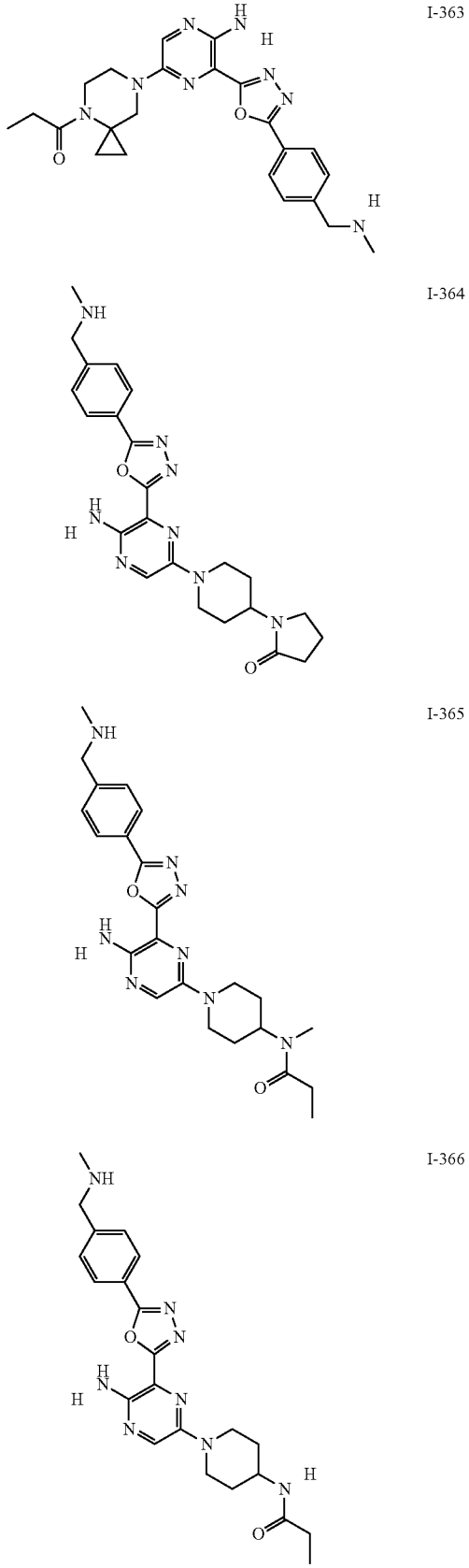

| 435 -continued | 436 -continued |
|---|---|
| I-37 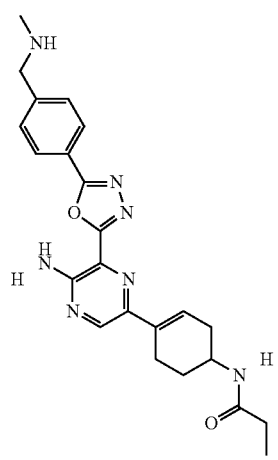 | I-371 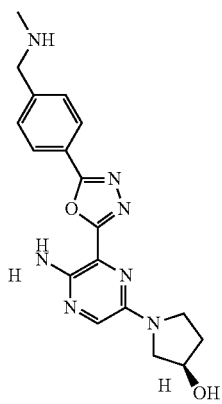 |
| I-368 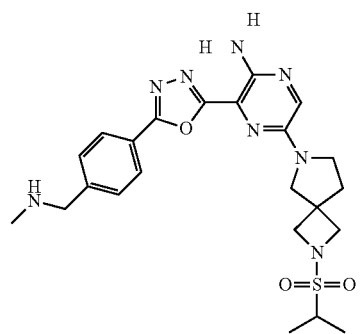 | I-372 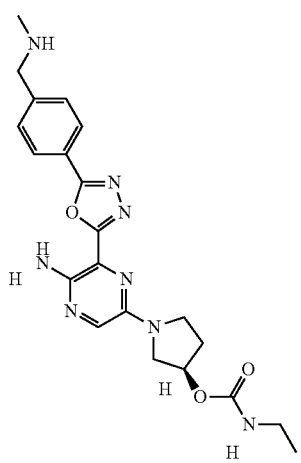 |
| I-369 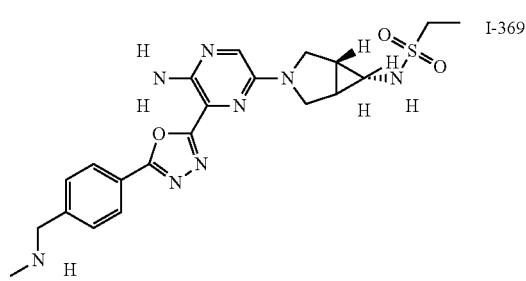 | I-373 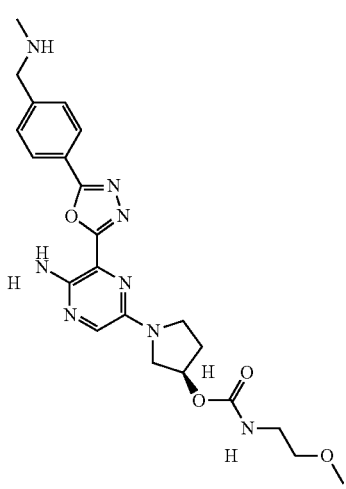 |
| I-370 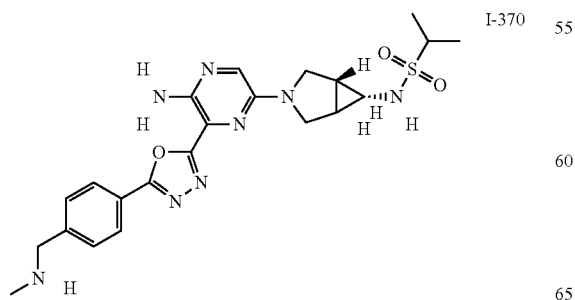 | |

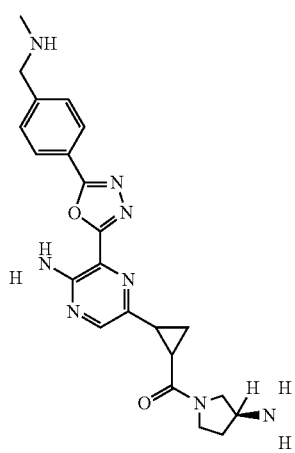
I-374
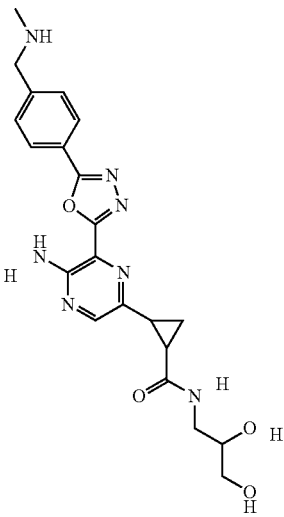
I-376
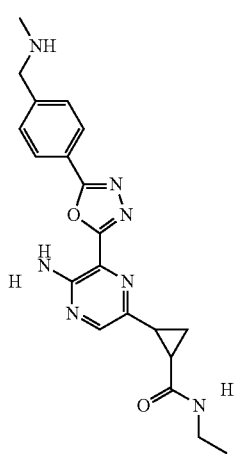
I-375
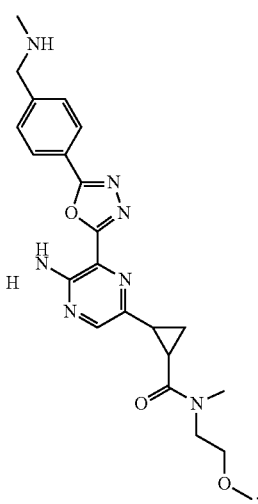
I-377
70. A composition comprising a compound of formula I wherein the variables are as defined in claim 1.
71. The compound of claim 31, wherein R¹ is
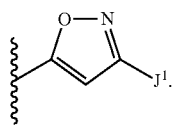
* * * * *

UNITED STATES PATENT AND TRADEMARK OFFICE
CERTIFICATE OF CORRECTION

PATENT NO.        : 8,410,112 B2                                          Page 1 of 1
APPLICATION NO.   : 13/104291
DATED             : April 2, 2013
INVENTOR(S)       : Charrier et al.

It is certified that error appears in the above-identified patent and that said Letters Patent is hereby corrected as shown below:

In the Claims

Claim 1
Column 330, line 27, after the term "each" and before the term "JQ2", please insert the term --J',--.
Column 330, line 28, please replace the "," with a --;--.

Signed and Sealed this
Twenty-fifth Day of February, 2014

Michelle K. Lee
*Deputy Director of the United States Patent and Trademark Office*